(12) United States Patent
Nielsen et al.

(10) Patent No.: US 11,634,718 B2
(45) Date of Patent: Apr. 25, 2023

(54) PRODUCTION OF MACROCYCLIC KETONES IN RECOMBINANT HOSTS

(71) Applicant: TAKASAGO INTERNATIONAL CORPORATION, Tokyo (JP)

(72) Inventors: Curt aimé Friis Nielsen, Reinach (CH); Jon Heal, Nottingham (GB); Johannes Haerle, Reinach (CH)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 16/760,710

(22) PCT Filed: Nov. 1, 2018

(86) PCT No.: PCT/EP2018/079960
§ 371 (c)(1),
(2) Date: Apr. 30, 2020

(87) PCT Pub. No.: WO2019/086583
PCT Pub. Date: May 9, 2019

(65) Prior Publication Data
US 2020/0347412 A1  Nov. 5, 2020

Related U.S. Application Data

(60) Provisional application No. 62/580,037, filed on Nov. 1, 2017.

(51) Int. Cl.
*C12N 9/00* (2006.01)
*C12N 9/02* (2006.01)
(Continued)

(52) U.S. Cl.
CPC ............ *C12N 15/52* (2013.01); *C12N 9/0008* (2013.01); *C12N 9/0071* (2013.01); *C12N 9/1029* (2013.01); *C12N 9/1096* (2013.01); *C12N 9/88* (2013.01); *C12N 9/93* (2013.01); *C12N 15/63* (2013.01); *C12P 7/26* (2013.01)

(58) Field of Classification Search
CPC ....... C12N 9/1096; C12N 9/88; C12N 9/0008; C12N 9/93; C12N 9/1029; C12N 9/0071; C12N 9/0042; C12N 15/80
See application file for complete search history.

(56) References Cited

U.S. PATENT DOCUMENTS 5,081,311 A  1/1992  Huellmann et al.
5,120,880 A  6/1992  Huellmann et al.
(Continued)

FOREIGN PATENT DOCUMENTS

CN  104357476 B  6/2017
EP  0400509 A1  12/1990
(Continued)

OTHER PUBLICATIONS

BCA1_YEAST. UniProtKB Database. 2016.*
(Continued)

*Primary Examiner* — Yong D Pak
(74) *Attorney, Agent, or Firm* — Sughrue Mion, PLLC

(57) ABSTRACT

The invention relates to recombinant microorganisms and methods for producing macrocyclic ketones and macrocyclic ketone precursors.

25 Claims, 23 Drawing Sheets

Specification includes a Sequence Listing.

(51) Int. Cl.
*C12N 9/10* (2006.01)
*C12N 9/88* (2006.01)
*C12P 7/26* (2006.01)
*C12N 15/52* (2006.01)
*C12N 15/63* (2006.01)

(56) References Cited

U.S. PATENT DOCUMENTS

| | | |
|---|---|---|
| 2003/0049822 A1 | 3/2003 | Wilson et al. |
| 2008/0148432 A1 | 6/2008 | Abad |
| 2015/0240267 A1* | 8/2015 | Anthony .......... C12P 5/00 435/160 |
| 2015/0353966 A1 | 12/2015 | Beardslee et al. |
| 2016/0298145 A1 | 10/2016 | Laplaza et al. |
| 2017/0016034 A1 | 1/2017 | Haushalter et al. |
| 2017/0029854 A1 | 2/2017 | Del Cardayre et al. |
| 2018/0258434 A1 | 9/2018 | Beardslee et al. |
| 2019/0010524 A1 | 1/2019 | Laplaza et al. |
| 2021/0310033 A1 | 10/2021 | Del Cardayre et al. |

FOREIGN PATENT DOCUMENTS

| | | |
|---|---|---|
| EP | 1258494 A1 | 11/2002 |
| EP | 1586652 A1 | 10/2005 |
| EP | 3330380 A1 | 6/2018 |
| JP | 2016-501040 A | 1/2016 |
| JP | 2016-501041 A | 1/2016 |
| JP | 2017-512485 A | 5/2017 |
| WO | 2006069610 A2 | 7/2006 |
| WO | 2007032522 A2 | 3/2007 |
| WO | 2007129770 A2 | 11/2007 |
| WO | 2011022651 A1 | 2/2011 |
| WO | 2012096686 A1 | 7/2012 |
| WO | 2013006730 A2 | 1/2013 |
| WO | 2015021045 A2 | 2/2015 |
| WO | 2015157719 A1 | 10/2015 |
| WO | 2016107920 A1 | 7/2016 |
| WO | 2016/207267 A1 | 12/2016 |

OTHER PUBLICATIONS

International Search Report (PCT/ISA/210) dated Jan. 9, 2019, from the International Searching Authority in application No. PCT/EP2018/079960.

Written Opinion (PCT/ISA/237) dated Jan. 9, 2019, from the International Searching Authority in application No. PCT/EP2018/079960.

Waché, Y.,et al: "Yeast as an efficient biocatalyst for the production of lipid-derived flavours and fragrances", Antonie Van Leeuwenhoek, vol. 89, No. 3-4, Apr. 25, 2006, pp. 405-416.

Werner, N., et al: "Biotechnological production of bio-based long-chain dicarboxylic acids with oleogenious yeasts", World Journal of Microbiology and Biotechnology, Rapid Communications of Oxford, GB, vol. 33, No. 11, (Oct. 5, 2017), pp. 1-9.

Sathesh-Prabu, C., et al, "Production of Long-Chain α,ω-Dicarboxylic Acids by Engineered *Escherichia coli* from Renewable Fatty Acids and Plant Oils", Journal of Agricultural and Food Chemistry, vol. 63, No. 37, Sep. 11, 2015, pp. 8199-8208.

Bowen, C., et al, "Engineering *Escherichia coli* for Conversion of Glucose to Medium-Chain ω-Hydroxy Fatty Acids and α,ω-Dicarboxylic Acids", ACS Synthetic Biology, vol. 5, No. 3, Dec. 21, 2015, pp. 200-206.

Werner, N., et al, "*Candida guilliermondii* as a potential biocatalyst for the production of long-chain α,ω-dicarboxylic acids", Biotechnology Letters, Kluwer Academic Publishers, Dordrecht, vol. 39, No. 3, Nov. 30, 2016, pp. 429-438.

Krishnaswamy, N.R., et al, "Textbook of neuro-oncology: Fascinating Organic Molecules from Nature", Jan. 1, 2005, Resonance, URL:https://link.springer.com/content/pdf/10.1007/s12045-013-0086-3.pdf pp. 673-683.

Xiao, K. et al, "Metabolic Engineering for Enhanced Medium Chain Omega Hydroxy Fatty Acid Production in *Escherichia coli*", Frontiers in Microbiology, vol. 9, Feb. 7, 2018, pp. 1-13.

Office Action dated Oct. 18, 2022 from the Japanese Patent Office in JP 2020-524565.

* cited by examiner

FIG. 1C

| Macrocyclic Ketone precursor | Macrocyclic Ketone Precursor Structure |
|---|---|
| 10-Methyldodecanoic acid<br>anteiso-Tridecanoic acid<br>CAS Number: 7416-57-1 | |
| 12-Methyltetradecanoic acid<br>anteiso-Pentadecanoic acid<br>CAS Number: 5502-94-3 | |
| (S)-12-Methyltetradecanoic acid<br>anteiso-Pentadecanoic acid<br>CAS Number: 5746-58-7 | |
| 14-Methylhexadecanoic acid<br>(anteiso-Heptadecanoic acid)<br>CAS Number: 5918-29-6 | |
| (S)-14-Methylhexadecanoate<br>CAS Number: 5746-59-8 | |
| 16-Methyloctadecanoic acid<br>Anteiso-Nonadecanoic acid<br>CAS Number: 17001-28-4 | |

FIG. 1D

| Name | Structure |
|---|---|
| (S)-16-Methyloctadecanoic acid<br>Anteiso-Nonadecanoic acid<br>CAS Number: 313691-81-5 | |
| Dodecane-1,12-dioic acid<br>CAS Number: 693-23-2 | 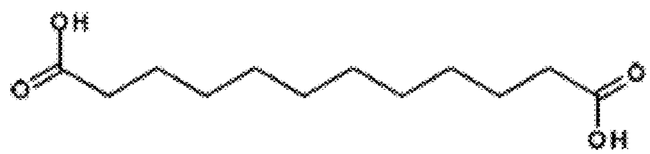 |
| (E)-2-Dodecenedioic acid<br>(E)-traumatic acid<br>CAS Number: 6402-36-4 | 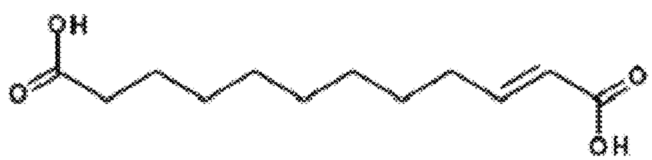 |
| 3-Dodecenedioic acid (double bond undefined)<br>CAS Number: 6790-25-6 | 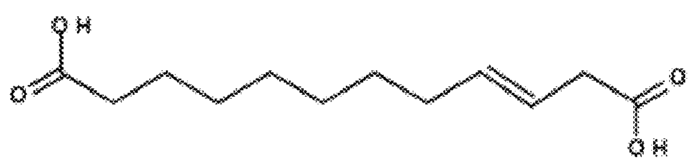 |
| Tetradecane-1,14-dioic acid<br>CAS Number: 821-38-5 | 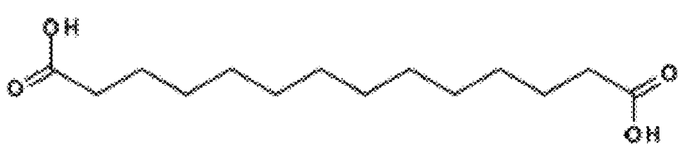 |

FIG. 1E

| | |
|---|---|
| 5-Tetradecenedioic acid, (5Z)- CAS Number: 128823-59-6 | |
| Hexadecane-1,16-dioic acid CAS Number: 505-54-4 | |
| 7-Hexadecenedioic acid, (7Z)- CAS Number: 253687-18-2 | |
| Octadecane-1,18-dioic acid CAS Number: 871-70-5 | |

| | |
|---|---|
| 9-Octadecenedioic acid, (9Z)- <br><br> CAS Number: 20701-68-2 |  |
| Eicosanedioic Acid <br><br> CAS Number: 2424-92-2 |  |
| 9-Eicosenedioic acid, (9Z)- <br><br> CAS Number: 253687-69-3 |  |

FIG. 1J

| | |
|---|---|
| (R)-3-Methylhexadecane-1,16-dioic acid | |
| (R)-14-Methylhexadecane-1,16-dioyl-CoA | |
| (R)-3-Methyloctadecane-1,18-dioic acid | |
| (R)-3-Methyloctadecane-1,18-dioyl-CoA | |
| Cyclopentadecanone, 3-methyl-, (3R)-<br><br>(R)-Muscone<br>l-Muscone<br>CAS Number: 10403-00-6 | |

SEQUENCE LISTING

<160> NUMBER OF SEQ ID NOS: 52

<210> SEQ ID NO 1
<211> LENGTH: 1566
<212> TYPE: DNA
<213> ORGANISM: Candida maltosa

<400> SEQUENCE: 1

```
atgatcgacg aaatcttgcc aaagttggtc caatactggt atatcgtttt gccaaccttg    60
ttgatcatca agcacgttgt ttcttacatc aacacccaaa gattgatgag aaagtttaga   120
gccaagccag ttaccaacgt tttgaatgat ggtttcttcg gtattccaaa cggtatcaag   180
gctatcaaag aaaagaacaa aggtagagcc caagaataca acgacgaaaa atttgctgct   240
ggtccaaaac ctaaagtcgg tacttatttg ttcaagttgt tcaccaagga tgtcttggtt   300
accaaagatc cagaaaacat taaggctatt tggccacccc aattcgaaga ttttttcattg   360 ggtaagagat ggacttctt caagccatta ttgggttacg gtattttcac cttggatggt   420
gaaggttgga acattctag agctatgtta agaccacaat cgccagaga caagttggt    480 catgttaagt tgattgaacc acacttccaa tctttgaaga agcacatcat taagaacaag   540
```

```
ggtcaattct tcgacatcca agaattattc ttcagattca ccgttgattc cgccaccgaa    600
tttttgtttg gtgaatcagt tgaatccttg aaggacgaat ctatcggtta tgaccaacaa    660
gactttgatt tcgacggtag aaagaatttt gctgaagcct taacaaggc  tcaagaatac    720 ttgggtacta gagcaatctt gcaatctttc tactggttgg ttaatggtgc cgatttcaaa    780
aagtctgttg ccgaagttca aagttcacc  gattactatg ttcaaaaggc tttggatgct    840
accccagaag aattggaaaa acattccggt tacattttct tgtacgaatt ggtccaacaa    900
accagagatc caaaggtttt gagagatcaa tcattgaaca ttttgttggc cggtagagat    960
acaactgctg gtttattgtc tttcgccttg tttgaattgg ctagaaatcc agaagtttgg   1020
tccagattga gagaagaaat tggtgataag ttcggtttgg atgaagatgc taccatcgaa   1080
ggtatttctt tcgaatcctt aaagcaatgc gaatacttga aggccgttgt taacgaatgt   1140
ttgagaatgt atccatccgt cccaagaaac tttagaattg ctacaaagca cactaccttg   1200
ccaagaggtg gtggtcctga tgtaaagat  ccaattttca tcaaaaaggg tgccgttgtt   1260
tcctacggta ttaactctac tcacttggac ccaatgtatt acggtccaga tgctagatta   1320
ttcaacccag atagatggtc taagccagaa acaaaaaagt tgggttgggc tttttttgcca  1380 ttcaatggtg gtccaagaat atgcttgggt caacaatttg ctttgacaga agctagttac   1440
gtcttggtca aatgatcca  aaacttcaaa gaattagaat tgactccaaa caccgtctac   1500
ccaccaagaa gattgactaa tttgaccatg tccttgtacg atggtgctta cattaaggtc   1560
aactaa                                                              1566

<210> SEQ ID NO 2
<211> LENGTH: 2041
<212> TYPE: DNA
<213> ORGANISM: Candida maltosa

<400> SEQUENCE: 2
atggccttgg acaagttgga cttgtacgtt attatagttt tggctgttgc tgttgccgct     60
tactttgcta agaatcaatt tttggatcaa ccacaagaca ctggtttctt gtctaatgat    120
actgctggtg gtaactccag agatattttg gaaactttga agaagaacaa caagaacacc    180
ttgttgttgt tcggttctca aactggtact gctgaagatt acgctaacaa gttgtccaga    240
gaaatccatt ctagattcgg tttgaaaact atggttgctg attcgctga  ttacgattgg    300 gataactttg gtgatattcc aaacgacatc ttggttttct tcatcgttgc tacttatggt    360
gaaggtgaac ctactgataa cgccgatgaa tttcatactt ggttgactga tgaagccgat    420
actttgtcta ctttgagata cactgttttc ggtttgggta actctaccta cgaattttac    480
aacgccattg gtagaaagtt cgatagatta ttggaagaaa agggtggtga agatttgcc   540 gattacggtg aaggtgatga tggtactggt actttggatg aagatttctt gacttggaag    600
gacaacgttt tcgataccct tgaagaacgac ttgaacttcg aagaaagaga attgaagtac    660
gaacctaacg tcaagttgac cgaaagagat gatttgaccg ttgatgattc cgaagttct    720 ttgggtgaac ctaacaagaa gtacatccaa tccgaagaaa ttgacttgac taagggtcca    780
ttcgatcata ctcatccata cttggctaag atcagtaaga ccagagaatt attcgcctcc    840
aaagaaagaa actgcgttca cgttgaattt gatgtctccg aatctaactt gaagtacact    900
actggtgatc atttggcagt ttggccatct aattctgacg aaaacattgc caagttcatc    960
aagtgctttg gtttggatga taagatcaac accgttttcg aattgaaggc tttggattcc   1020
acttaccaaa ttccattccc aaacccaatt acttacggtg ctgttgttag acatcacttg   1080
```

```
gaaatttctg gtccagtctc tagacaattc ttcttggcta ttgctggttt tgctccagac    1140
gaagaaacta agaaaacttt caccagaatc ggtaacgaca agcaagaatt tgctaacaag    1200
atcaccagaa aaaagttgaa cgttgctgac gctttgttgt ttgcttctaa tggtagacct    1260
tggtctgatg tcccattcga atttatcatt gaaaacgtcc cacacttgca acctagatat    1320
tactctatct cctcctcctc attgtctgaa aagcaaacca ttaacattac cgccgttgtt    1380
gaagtagaag aagaagctga cggtagagct gttactggtg ttgttactaa tttgttgaag    1440
aacatcgaaa ttgaacaaaa caagaccggt gaaaagccag ttgttcatta tgatttgtct    1500
ggtccaagaa acaagtttaa caaattcaag ttgccagtcc acgtcagaag atccaatttt    1560
aagttgccaa agaacactac cacccccagtt attttgattg gtccaggtac aggtgttgct    1620
ccattgagag ttttgttag agaaagagtt caacaagtta agaacggtgt taacgttggt    1680
aagaccgttt tgttttacgg ttgcagaaac gaacacgacg atttcttgta caaacaagaa    1740
tggtctgaat acgcctccgt tttaggtgaa aacttcgaaa tgtttaccgc cttctcaaga    1800
caagacccat ctaaaaaagt ttacgtccaa gataagatcg ccgaaaactc taaggttgtt    1860
aacgacttat tgaacgaagg tgccattatc tacgtttgtg gtgatgcttc aagaatggct    1920
agagatgttc aatctaccat tgctaagatc gttgccaagc acagagaaat tcaagaagat    1980
aaggctgtcg aattggtcaa gtcttggaaa gttcaaaaca gataccaaga agatgtttgg    2040
t                                                                   2041

<210> SEQ ID NO 3
<211> LENGTH: 1671
<212> TYPE: DNA
<213> ORGANISM: Humulus lupulus

<400> SEQUENCE: 3
atggaagatc tgaagccgag accagccagc tcctctccac tcacccctct ggggtttctg      60
gaaagagccg ccaccgtttta tggcgactgt acctccgtcg tttacgacgc cgtttcatac    120
acctggtccc agactcaccg ccgctgtctc tgtcttgcct cctccatcgc ctcactcggc     180
atcgaaaacg gccatgtcgt ctccgtcctc gccccaaacg tcccccaaat gtacgagctt     240
cacttcgccg ttcccatggc cggcgccatc ctcaacgccg tcaacctccg tctcgatgcc     300
cgcaccatct ccatcctcct ccatcacagc gaatcgaaac tcatcttcgt cgatcatctc     360
tctcgtgatc tcatcctcga agccatcgct ctgttcccga acaagcccc tgttcctcgc     420 ctcgttttta tggcggacga gtctgaatcg gtaatagtt cagagttggg gaaagaattc     480
ttctgcagtt ataaggatct gatcgataga ggggacccgg atttcaagtg ggtcatgcct     540
aaaagcgagt gggacccgat gattcttaac tacacttctg gaacgacgtc atcgccgaaa     600
ggggttgtcc attgtcaccg gggaatattt ataatgacag tcgactctct catcgattgg     660
ggagttccta acagccagt ttatctatgg actctgccca tgtttcacgc caatgggtgg     720
agctatcctt ggggtatggc ggcggtcggc gggaccaata tctgcctgcg taaattcgac     780
tctgaaataa tttacgatat gataaaacgg cacggcgtga cccacatgtg cggagccccc     840
gttgtactca acatgctctc caacgcgccg ggatcggaac cgctgaaaac aacggttcag     900
atcatgactg caggagctcc gccgcctcg gcggtgcttt tccggaccga gtcgctgggc     960
ttcgcggtga gccacggcta cgggcttacc gaaacggcgg ggttagtggt gtcgtgcgcg    1020
tggaagaaag agtggaacca tctcccggcg acggagagag cgaggctcaa gtcgagacaa    1080
```

-continued

| | |
|---|---|
| ggggtgggga cggtgatgca gaccaaaatc gatgtcgttg acccggtgac cggagccgcc | 1140 |
| gtgaagcgag acggatcaac gttgggcgag gttgttctga gaggcgggtc ggtcatgctc | 1200 |
| gggtacctaa aagacccaga aggaacggcg aaatccatga ccgcagacgg gtggttctac | 1260 |
| accggggacg ttggagtcat gcacccagat gggtatttgg agatcaaaga ccggtccaag | 1320 |
| gacgtcatca tcagcggcgg agagaatttg agcagcgtcg aggtggagtc aattctgtac | 1380 |
| agtcacccgg atattctgga ggcggcggtt gtggcccggc cagacgagtt ctgggggag | 1440 |
| acgccgtgtg ctttcgtgag cttgaagaaa ggtttaacga agaagccgac ggagaaggag | 1500 |
| atcgtggagt attgtcggag taagttgccg cgttacatgg tacccaaaac ggtggtgttt | 1560 |
| aaggaggagc ttcccaagac atcgactggg aaggttcaga aatttatact gagagatatg | 1620 |
| gccagaggta tgggctctgc aactgctgga gcgagccgga gccgaatgtg a | 1671 |

<210> SEQ ID NO 4
<211> LENGTH: 1656
<212> TYPE: DNA
<213> ORGANISM: Solanum tuberosum

<400> SEQUENCE: 4

| | |
|---|---|
| atggatgagc taaagccaac gccaccaaat tcaagtcctc ttactcctat taccttcttg | 60 |
| gaaagagctg ctactatcta tgccgattgc ccttccatcg tctacaacaa cacaactcac | 120 |
| aattggtccc aaacccattc tcgttgccta aaagttgctt catccattgc atcttttggt | 180 |
| attcaaagaa atcatgttgt ctccgttgtt gcccctaata tccctgccat gtatgagctt | 240 |
| cattttgctg ttcccatggc tggtgctgta ctcaacacca ttaatctccg tcttgatgca | 300 |
| cgtactatct ctgtactcct ccgtcacagc gaatctaaac tcctcttcgt tgattgtcaa | 360 |
| tccaaatccc taattctcga agctctgtcc ttatttccgc ctgaattcca ccgtccggtt | 420 |
| ctcgttctta tcgaggacga cgaattccca attccaaaaa ctgatgaatt tatcgctact | 480 |
| tatgaggaat tggttgaaag aggggattcg ggtttcaatt ggattcgccc gaaaagtgaa | 540 |
| tttgatccga ttgctatgaa ttacacttct ggaactacat ctgctccgaa aggtgtggtt | 600 |
| catagccata ggggtatttt cgttgtttcg ttggattcgt tgattgaatg gtccgttccg | 660 |
| aaacagccgg tttatttatg gacgctacct atgtttcatg caaacggatg gagttatcca | 720 |
| tggggaatgg ctgctgttgg tggaacgaat atctgtttga gaaaattcga tgccggaatc | 780 |
| atttatgact cgatcaacaa acatggtgtt actcatatct gcgctgctcc agtggtactc | 840 |
| aacatgttgt cgaattcccc tgacagtaag ccattaaaac ccctgtttta tataatgaca | 900 |
| gcaggatccc cacccctgc tgctgtcctg tttcgaacag agtcccttgg atttgtagtc | 960 |
| catcatggtt atggacttac agaaactggt ggattagtta tttcttgtac atggaaaaat | 1020 |
| cactggaata aatttccagc aaatgaaaga gcaaggctga atcaagaca aggggttagg | 1080 |
| acattaggga tggcggaagt ggacgtggtg atccagaat caggagtcag tgttaaacgg | 1140 |
| gacggatcaa cattaggaga aattgttcta aagggtgcct gtgtcatgtt gggttacttt | 1200 |
| aaagacccgg aaggaacgtc gaaatgcatg aaagatgatg ttggttttta cacaggggat | 1260 |
| gtggcagtta tgcatcctga tggatactta gaaattaaag acagatcaaa ggacgtgatc | 1320 |
| ataagtggtg gagagaattt gagcagtgta gaagtggaat cagtgttgta tacccatcca | 1380 |
| gcgattaacg aagcagcagt agtggcacgg ccagatgaat tctggggcga acaccgtgt | 1440 |
| gcatttgtta gtctgaatgg aaaacacaag gcgagtgaaa aagacattat tgagttttgt | 1500 |
| agagccaaat tgccacatta tatggtacca aagactgtca taattaaaca agagcttcca | 1560 |

```
aagacatcaa cagggaaaat tcagaagttc gtgcttagag acattgctaa aagtatgggg      1620
aaaagcaata gcagcaagaa ggtgagcaga atgtag                                1656

<210> SEQ ID NO 5
<211> LENGTH: 6156
<212> TYPE: DNA
<213> ORGANISM: Saccharomyces cerevisiae

<400> SEQUENCE: 5
atggacgctt actccacaag accattaacc ctatctcacg gttctttaga gcacgtgctt        60
ctggtaccaa ccgcttcatt tttcattgct tcgcaattac aagaacaatt taataaaatt       120
ttgcccgaac ccactgaagg gtttgctgca gatgacgagc ctaccacacc tgctgaacta       180
gtggggaaat tccttggcta cgtatcttct ctagtcgaac cttccaaggt cggtcaattc       240
gatcaggtct tgaacctttg cttaacagaa tttgaaaact gttatttaga aggcaatgac       300
attcacgcct tggctgctaa actattacag gaaaacgaca caactttagt gaagactaaa       360
gaactaatta aaaattatat taccgccaga ataatggcta agagaccatt tgacaaaaaa       420
tccaactctg ctctttttag ggccgtcggc gagggtaacg cacaattggt agccatttc        480 ggtggtcaag gtaacaccga cgactacttt gaagaattgc gtgatctata tcaaacttat       540
catgtcttag tgggagattt aatcaagttc tccgctgaaa ctttaagtga actgattaga       600
actactttag atgctgaaaa agtcttact caaggtttaa acatattgga atggttggag        660 aaccttcaa ataccccaga caaggactat ttactttcca ttccaatttc atgccccta        720 attggtgtca ttcaattggc tcactacgta gttactgcca agcttttggg tttcactcca       780
ggtgagttaa gatcttactt aaaaggtgct acaggtcact ctcaaggttt ggttactgct       840
gtcgccatag ctgagacgga ttcctgggaa tccttcttcg tctccgtaag aaaagcaatt       900
actgtattat tcttcatcgg tgttcgttgt tacgaagcat acccaaacac ttccctacca       960
ccatccatct tggaagattc cttggaaaac aatgaaggtg ttccatctcc aatgttgtcc      1020
atttccaatc taactcaaga acaagttcaa gactatgtaa ataagactaa ctctcatttg      1080
ccagctggta aacaagttga aatttctcta gtcaatggtg cgaagaatct agtcgtatcg      1140
ggcccaccac aatcattata tggttaaaac ttgactttaa gaaaggccaa ggccccatct      1200
ggactggatc aatcaagaat cccattcagc gaaagaaaat tgaagttctc caataggttc      1260
ttacctgttg catcaccatt ccattcccat ctattggttc cagcttcaga tttgattaac      1320 aaaagacttag tcaaaaacaa tgtcagcttt aacgctaaag atattcaaat ccccgtttac      1380 gacactttg atggttcaga tctaagagtc ctttcaggtt ccatttccga gagaatcgtc       1440
gactgcatca ttagattacc tgtcaaatgg gaaactacta cacaattcaa agccaccac       1500 atattagact ttggtccagg tggagcttcc ggtttaggtg ttttaaccca tcgtaataaa      1560
gatggtactg tgttcgtgt tatcgttgcc ggtactctcg acattaaccc agatgatgat      1620
tacggattca agcaagaaat ctttgatgtt actagtaatg gtttgaagaa aatccaaac     1680 tggttggaag aataccatcc aaaattaatt aagaacaaat caggcaaaat ttttgtcgaa      1740 acaaaattt ctaaattaat cggtagacca cctttattgg ttcctggtat gacaccatgt      1800
actgtttctc cagatttcgt agctgctacc acaaatgctg ttataccat tgagttggcc      1860 ggtggtggtt acttttccgc agcaggtatg accgccgcta ttgattctgt ggtttctcag      1920
atagaaaagg gtagtacctt cggtatcaac ttgatctacg tcaatccatt tatgttacaa      1980
```

```
tggggtattc cattaatcaa ggaactaaga agcaaaggtt atccaattca attcttgacc    2040
attggtgctg gtgtcccatc attggaagtt gctagtgaat acatagagac attaggtttg    2100
aagtacttgg gtttgaaacc aggttccatt gatgctattt cgcaagttat aaacattgct    2160
aaagcacatc caaacttccc aatagcttta caatggaccg gtggtagagg tggtggtcat    2220
cattctttcg aagatgccca cactccaatg ttacaaatgt actccaagat tagaagacat    2280
ccaaacatta tgttgatatt cggttctggt ttcggttctg ctgatgacac ttacccatac    2340
ttaaccggtg aatggtccac aaaattcgat tatccaccaa tgccattcga tggtttccta    2400
tttggttcga gggtcatgat tgctaaggaa gttaaaactt ctcctgatgc taagaagtgt    2460
attgctgctt gtactggtgt tcctgatgat aaatgggaac aaacctacaa gaagccaact    2520
ggtggtattg tcactgttcg ctctgaaatg ggtgaaccaa ttcacaaaat tgccactcgt    2580
ggtgttatgc tatggaagga attcgacgaa accatcttca acttaccaaa gaataagttg    2640
gtaccaactt tggaagcaaa gagagattac attatctcaa gattgaacgc cgatttccaa    2700
aaaccatggt ttgctaccgt caacggtcaa gcccgtgacc tagccacaat gacatacgaa    2760
gaagttgcaa agagattggt ggaattaatg ttcatcagat ctaccaactc ttggtttgat    2820
gtcacatgga gaacctttac tggtgatttc ctacgtcgtg tcgaagaacg tttcactaaa    2880
agtaagacat tgtctttaat ccaatcctat tctctactag acaagcctga tgaagctatt    2940
gaaaagtat ttaatgctta tcctgccgct agggaacagt tcttgaatgc gcaagatatt    3000
gatcactttt tgagcatgtg tcaaaatcca atgcaaaaac cagtgccttt tgttccagtt    3060
ttggatcgta gattcgagat tttttttcaaa aaagattcgt tatggcaatc tgagcacttg    3120
gaagccgtcg tcgaccaaga cgttcaaaga acatgtatcc tacatggacc tgttgcagca    3180
caattcacta aagtcatcga tgaaccaatt aagagcatta tggatggtat tcacgatggt    3240
cacatcaaaa agttactaca tcaatattac ggtgacgatg agtcaaagat tccagcagtt    3300
gagtactttg gtggtaaaag ccctgtagac gtacaaagtc aagttgattc ttcctctgta    3360
tctgaagact cagctgtttt taaggcaaca tcctctactg atgaagaaag ctggtttaag    3420
gctttggcgg gatccgaaat taactggaga catgcaagtt tcttatgttc ctttatcact    3480
caagataaaa tgtttgtttc taacccaatt agaaaagttt tcaagccaag ccaaggaatg    3540
gttgttgaga tttccaacgg caatacttct tcaaagactg ttgtcactct ttcagaacct    3600
gttcaaggtg aattgaaacc aactgttatt ttgaagttgt tgaaggagaa cataatccaa    3660
atggaaatga ttgagaacag aactatggat ggtaagcccg tcagcttgcc attgttgtac    3720
aacttcaacc cagataatgg ttttgctcca atctctgaag ttatggagga cagaaaccaa    3780
agaattaagg aaatgtactg gaaattatgg attgatgagc cttccaattt ggactttgac    3840
ccaagagatg tcattaaggg caaagatttc gagatcaccg ctaaagaagt ttatgacttt    3900
acacacgctg ttggaaacaa ttgtgaagac ttcgtttcta gacctgatag aacgatgttg    3960
gccccaatgg actttgctat tgttgtcgga tggagagcca tcatcaaggc cattttccct    4020
aatacggtcg atggtgactt attgaagttg gttcatttgt ctaacggcta caagatgatt    4080
cctggcgcta agccactgca agttggtgat gttgtttcaa ctactgctgt tattgaatct    4140
gtcgtcaacc aacctacagg aaagattgtc gatgtggtag gtacattatc gagaaatggc    4200
aagcctgtca tggaagtcac ctcctcattc ttctacagag gcaactatac tgactttgaa    4260
aacactttcc aaaagactgt tgaacctgtt tatcaaatgc acatcaaaac ttctaaagat    4320
atagctgtct tgcgctctaa ggagtggttc caattggacg atgaagactt cgatctgtta    4380
```

```
aacaaaactt tgactttcga aactgaaact gaagttactt tcaagaatgc taacatcttc    4440
tcttcagtga aatgttttgg cccaattaaa gttgaattgc caaccaaaga aaccgtggag    4500
atcggtattg tcgattacga agccggtgcc tctcacggta accctgttgt tgatttcttg    4560
aagagaaacg gttccacatt ggaacaaaag gtcaatctag aaaatcctat tccaattgca    4620
gtacttgatt cgtacactcc aagtaccaac gaaccatacg ctagagtttc tggtgatttg    4680
aatccaattc acgtttcacg tcattttgcc tcttacgcaa acttgccagg tactatcacg    4740
cacggtatgt tttcttctgc ttccgtccgt gctttgattg aaaactgggc tgctgacagt    4800
gtttcatcca gggtacgtgg ctacacttgt caatttgttg acatggtttt gcctaacact    4860
gctttgaaaa catcgattca acatgttggt atgatcaatg gtagaaaatt gataaagttt    4920
gaaactagaa atgaagatga cgttgtagtt ttgactggtg aagccgaaat tgaacaacct    4980
gttactacct tcgttttcac tggtcaaggt tcacaagaac aaggtatggg tatggactta    5040
tacaaaactt ctaaagctgc tcaagatgtt tggaatagag ctgacaacca tttcaaggac    5100
acttatggtt tctctatctt agacattgtc attaacaacc cagttaactt aacaattcac    5160
ttcggtggtg aaaagggtaa gaggatcaga gaaaactatt ctgctatgat ctttgagact    5220
atcgtggatg aaaattgaa gactgaaaaa attttcaagg aaattaatga gcacagtact    5280
tcttacacat ttagatctga aaaggtttta ttgtctgcta ctcaatttac acaaccagct    5340
ttaactttga tggaaaaagc tgcttttcgaa gacttgaaat ctaaaggttt gatcccagcc    5400
gatgctactt tgctggtcta ctctttaggt gagtatgctg ctttggcctc tttggctgat    5460
gttatgtcta tcgaatcttt agttgaagtt gtgttctaca gaggtatgac tatgcaagtt    5520
gctgttccaa gagatgagtt gggcagatcc aactatggta tgattgccat taacccaggt    5580
agagtcgctg catcattctc tcaagaagct ttgcaatatg ttgttgagag agttggtaag    5640
agaaccggct ggttggttga aatcgtcaac tacaacgttg aaaaccaaca atatgttgca    5700
gctggtgatc taagagcttt agacaccgtt accaatgttc taaacttcat caaattacaa    5760
aaaattgata ttattgaact acaaaagtcc ttatctttgg aagaagttga aggtcatttg    5820
tttgagatca ttgacgaagc ttccaagaaa tctgctgtca agcctcgccc acttaaattg    5880
gagagaggtt tgcttgtat cccattagtt ggtatttctg ttcctttcca ttccacctac    5940
ttgatgaatg gtgttaaacc attcaagagt tccttgaaga agaatatcat aaaagaaaat    6000
gtgaaggttg ctagattggc cggaaagtac attccaaact tgactgcaaa accattccag    6060
gttactaagg aatatttcca ggacgtttat gatttgactg gctccgaacc tatcaaggaa    6120
atcatcgaca actgggaaaa gtatgaacaa tcctaa                             6156
```

<210> SEQ ID NO 6
<211> LENGTH: 6156
<212> TYPE: DNA
<213> ORGANISM: Saccharomyces cerevisiae

<400> SEQUENCE: 6

```
atggacgctt actccacaag accattaacc ctatctcacg gttctttaga gcacgtgctt      60
ctggtaccaa ccgcttcatt tttcattgct tcgcaattac aagaacaatt taataaaatt     120
ttgcccgaac ccactgaagg gtttgctgca gatgacgagc ctaccacacc tgctgaacta     180
gtggggaaat ccttggcta cgtatcttct ctagtcgaac cttccaaggt cggtcaattc     240
gatcaggtct tgaacctttg cttaacagaa tttgaaaact gttatttaga aggcaatgac    300
```

```
attcacgcct tggctgctaa actattacag gaaaacgaca caactttagt gaagactaaa    360
gaactaatta aaaattatat taccgccaga ataatggcta agagaccatt tgacaaaaaa    420
tccaactctg ctcttttag ggccgtcggc gagggtaacg cacaattggt agccattttc     480
ggtggtcaag gtaacaccga cgactacttt gaagaattgc gtgatctata tcaaacttat    540
catgtcttag tgggagattt aatcaagttc tccgctgaaa ctttaagtga actgattaga    600
actactttag atgctgaaaa agtctttact caaggtttaa acatattgga atggttggag    660
aacccttcaa ataccccaga caaggactat ttactttcca ttccaatttc atgcccctta    720
attggtgtca ttcaattggc tcactacgta gttactgcca agcttttggg tttcactcca    780
ggtgagttaa gatcttactt aaaaggtgct acaggtcact ctcaaggttt ggttactgct    840
gtcgccatag ctgagacgga ttcctgggaa tccttcttcg tctccgtaag aaaagcaatt    900
actgtattat tcttcatcgg tgttcgttgt tacgaagcat acccaaacac ttccctacca    960
ccatccatct tggaagattc cttggaaaac aatgaaggtg ttccatctcc aatgttgtcc    1020
atttccaatc taactcaaga acaagttcaa gactatgtaa ataagactaa ctctcatttg    1080
ccagctggta aacaagttga aatttctcta gtcaatggtg cgaagaatct agtcgtatcg    1140
ggcccaccac aatcattata tggtttaaac ttgactttaa gaaaggccaa ggccccatct    1200
ggactggatc aatcaagaat cccattcagc gaaagaaaat tgaagttctc caataggttc    1260
ttacctgttg catcaccatt ccattcccat ctattggttc cagcttcaga tttgattaac    1320
aaagacttag tcaaaaacaa tgtcagcttt aacgctaaag atattcaaat ccccgtttac    1380
gacactttg atggttcaga tctaagagtc ctttcaggtt ccatttccga gagaatcgtc    1440
gactgcgcaa ttagattacc tgtcaaatgg gaaactacta cacaattcaa agccacccac    1500
atattagact ttggtccagg tggagcttcc ggtttaggtg ttttaaccca tcgtaataaa    1560
gatggtactg gtgttcgtgt tatcgttgcc ggtactctcg acattaaccc agatgatgat    1620
tacgattca agcaagaaat ctttgatgtt actagtaatg gtttgaagaa aaatccaaac    1680
tggttggaag aataccatcc aaaattaatt aagaacaaat caggcaaaat ttttgtcgaa    1740
acaaaatttt ctaaattaat cggtagacca ccttttattgg ttcctggtat gacaccatgt    1800
actgtttctc cagatttcgt agctgctacc acaaatgctg gttataccat tgagttggcc    1860
ggtggtggtt actttccgc agcaggtatg accgccgcta ttgattctgt ggtttctcag    1920
atagaaaagg gtagtacctt cggtatcaac ttgatctacg tcaatccatt tatgttacaa    1980
tggggtattc cattaatcaa ggaactaaga agcaaaggtt atccaattca attcttgacc    2040
attggtgctg gtgtcccatc attggaagtt gctagtgaat acatagagac attaggttg     2100
aagtacttgg gtttgaaacc aggttccatt gatgctattt cgcaagttat aaacattgct    2160
aaagcacatc caaacttccc aatagctta caatggaccg gtggtagagg tggtggtcat     2220
cattctttcg aagatgccca cactccaatg ttacaaatgt actccaagat tagaagacat    2280
ccaaacatta tgttgatatt cggttctggt ttcggttctg ctgatgacac ttacccatac    2340
ttaaccggtg aatggtccac aaaattcgat tatccaccaa tgccattcga tggtttccta    2400
tttggttcga gggtcatgat tgctaaggaa gttaaaactt ctcctgatgc taagaagtgt    2460
attgctgctt gtactggtgt tcctgatgat aaatgggaac aaacctacaa gaagccaact    2520
ggtggtattg tcactgttcg ctctgaaatg gtgaaccaa ttcacaaaat tgccactcgt     2580
ggtgttatgc tatggaagga attcgacgaa accatcttca acttaccaaa gaataagttg    2640
gtaccaactt tggaagcaaa gagagattac attatctcaa gattgaacgc cgatttccaa    2700
```

```
aaaccatggt tgctaccgt caacggtcaa gcccgtgacc tagccacaat gacatacgaa    2760
gaagttgcaa agagattggt ggaattaatg ttcatcagat ctaccaactc ttggtttgat    2820
gtcacatgga gaacctttac tggtgatttc ctacgtcgtg tcgaagaacg tttcactaaa    2880
agtaagacat tgtctttaat ccaatcctat tctctactag acaagcctga tgaagctatt    2940
gaaaaagtat ttaatgctta tcctgccgct agggaacagt tcttgaatgc gcaagatatt    3000
gatcactttt tgagcatgtg tcaaaatcca atgcaaaaac cagtgccttt tgttccagtt    3060
ttggatcgta gattcgagat ttttttcaaa aaagattcgt tatggcaatc tgagcacttg    3120
gaagccgtcg tcgaccaaga cgttcaaaga acatgtatcc tacatggacc tgttgcagca    3180
caattcacta agtcatcga tgaaccaatt aagagcatta tggatggtat tcacgatggt    3240
cacatcaaaa agttactaca tcaatattac ggtgacgatg agtcaaagat tccagcagtt    3300
gagtactttg gtggtgaaag ccctgtagac gtacaaagtc aagttgattc ttcctctgta    3360
tctgaagact cagctgtttt taaggcaaca tcctctactg atgaagaaag ctggtttaag    3420
gctttggcgg atccgaaat taactggaga catgcaagtt tcttatgttc ctttatcact    3480
caagataaaa tgtttgtttc taacccaatt agaaaagttt tcaagccaag ccaaggaatg    3540
gttgttgaga tttccaacgg caatacttct tcaaagactg ttgtcactct ttcagaacct    3600
gttcaaggtg aattgaaacc aactgttatt ttgaagttgt tgaaggagaa cataatccaa    3660
atggaaatga ttgagaacag aactatggat ggtaagcccg tcagcttgcc attgttgtac    3720
aacttcaacc cagataatgg ttttgctcca atctctgaag ttatggagga cagaaaccaa    3780
agaattaagg aaatgtactg gaaattatgg attgatgagc ctttcaattt ggactttgac    3840
ccaagagatg tcattaaggg caaagatttc gagatcaccg ctaaagaagt ttatgacttt    3900
acacacgctg ttggaaacaa ttgtgaagac ttcgtttcta gacctgatag aacgatgttg    3960
gccccaatgg actttgctat tgttgtcgga tggagagcca tcatcaaggc cattttccct    4020
aatacggtcg atggtgactt attgaagttg gttcatttgt ctaacggcta caagatgatt    4080
cctggcgcta agccactgca agttggtgat gttgtttcaa ctactgctgt tattgaatct    4140
gtcgtcaacc aacctacagg aaagattgtc gatgtgtag gtacattatc gagaaatggc    4200
aagcctgtca tggaagtcac ctcctcattc ttctacagag gcaactatac tgactttgaa    4260
aacactttcc aaaagactgt tgaacctgtt tatcaaatgc acatcaaaac ttctaaagat    4320
atagctgtct tgcgctctaa ggagtggttc caattggacg atgaagactt cgatctgtta    4380
aacaaaactt tgactttcga aactgaaact gaagttactt tcaagaatgc taacatcttc    4440
tcttcagtga aatgttttgg cccaattaaa gttgaattgc caaccaaaga aaccgtggag    4500
atcggtattg tcgattacga agccggtgcc tctcacggta accctgttgt tgatttcttg    4560
aagagaaacg ttccacatt ggaacaaaag gtcaatctag aaaatcctat tccaattgca    4620
gtacttgatt cgtacactcc aagtaccaac gaaccatacg ctagagtttc tggtgatttg    4680
aatccaattc acgtttcacg tcattttgcc tcttacgcaa acttgccagg tactatcacg    4740
cacggtatgt tttcttctgc ttccgtccgt gctttgattg aaaactgggc tgctgacagt    4800
gtttcatcca gggtacgtgg ctacacttgt caatttgttg acatggtttt gcctaacact    4860
gctttgaaaa catcgattca acatgttggt atgatcaatg gtagaaaatt gataaagttt    4920
gaaactagaa atgaagatga cgttgtagtt ttgactggtg aagccgaaat tgaacaacct    4980
gttactacct tcgttttcac tggtcaaggt tcacaagaac aaggtatggg tatggactta    5040
```

-continued

| | |
|---|---|
| tacaaaactt ctaaagctgc tcaagatgtt tggaatagag ctgacaacca tttcaaggac | 5100 |
| acttatggtt tctctatctt agacattgtc attaacaacc cagttaactt aacaattcac | 5160 |
| ttcggtggtg aaaagggtaa gaggatcaga gaaaactatt ctgctatgat ctttgagact | 5220 |
| atcgtggatg gaaaattgaa gactgaaaaa attttcaagg aaattaatga gcacagtact | 5280 |
| tcttacacat ttagatctga aaaaggttta ttgtctgcta ctcaatttac acaaccagct | 5340 |
| ttaactttga tggaaaaagc tgctttcgaa gacttgaaat ctaaaggttt gatcccagcc | 5400 |
| gatgctactt tgctggtca ctctttaggt gagtatgctg ctttggcctc tttggctgat | 5460 |
| gttatgtcta tcgaatcttt agttgaagtt gtgttctaca gaggtatgac tatgcaagtt | 5520 |
| gctgttccaa gagatgagtt gggcagatcc aactatggta tgattgccat taacccaggt | 5580 |
| agagtcgctg catcattctc tcaagaagct ttgcaatatg ttgttgagag agttggtaag | 5640 |
| agaaccggct ggttggttga atcgtcaac tacaacgttg aaaaccaaca atatgttgca | 5700 |
| gctggtgatc taagagcttt agacaccgtt accaatgttc taaacttcat caaattacaa | 5760 |
| aaaattgata ttattgaact acaaaagtcc ttatctttgg aagaagttga aggtcatttg | 5820 |
| tttgagatca ttgacgaagc ttccaagaaa tctgctgtca agcctcgccc acttaaattg | 5880 |
| gagagaggtt ttgcttgtat cccattagtt ggtatttctg ttccttcca ttccacctac | 5940 |
| ttgatgaatg gtgttaaacc attcaagagt ttcttgaaga agaatatcat aaaagaaaat | 6000 |
| gtgaaggttg ctagattggc cggaaagtac attccaaact tgactgcaaa accattccag | 6060 |
| gttactaagg aatatttcca ggacgtttat gatttgactg gctccgaacc tatcaaggaa | 6120 |
| atcatcgaca actgggaaaa gtatgaacaa tcctaa | 6156 |

<210> SEQ ID NO 7
<211> LENGTH: 6156
<212> TYPE: DNA
<213> ORGANISM: Saccharomyces cerevisiae

<400> SEQUENCE: 7

| | |
|---|---|
| atggacgctt actccacaag accattaacc ctatctcacg gttctttaga gcacgtgctt | 60 |
| ctggtaccaa ccgcttcatt tttcattgct tcgcaattac aagaacaatt taataaaatt | 120 |
| ttgcccgaac ccactgaagg gtttgctgca gatgacgagc ctaccacacc tgctgaacta | 180 |
| gtggggaaat ccttggcta cgtatcttct ctagtcgaac cttccaaggt cggtcaattc | 240 |
| gatcaggtct tgaacctttg cttaacagaa tttgaaaact gttatttaga aggcaatgac | 300 |
| attcacgcct tggctgctaa actattacag gaaaacgaca caactttagt gaagactaaa | 360 |
| gaactaatta aaaattatat taccgccaga ataatggcta agagaccatt tgacaaaaaa | 420 |
| tccaactctg ctcttttag ggccgtcggc gagggtaacg cacaattggt agccattttc | 480 |
| ggtggtcaag gtaacaccga cgactacttt gaagaattgc gtgatctata tcaaaacttat | 540 |
| catgtcttag tgggagattt aatcaagttc tccgctgaaa ctttaagtga actgattaga | 600 |
| actactttag atgctgaaaa agtctttact caaggtttaa acatattgga atggttggag | 660 |
| aaccccttcaa atacccccaga caaggactat ttactttcca ttccaatttc atgcccctta | 720 |
| attggtgtca ttcaattggc tcactacgta gttactgcca agcttttggg tttcactcca | 780 |
| ggtgagttaa gatcttactt aaaaggtgct acaggtcact ctcaaggttt ggttactgct | 840 |
| gtcgccatag ctgagacgga ttcctgggaa tccttcttcg tctccgtaag aaaagcaatt | 900 |
| actgtattat tcttcatcgg tgttcgttgt tacgaagcat acccaaacac ttccctacca | 960 |
| ccatccatct tggaagattc cttggaaaac aatgaaggtg ttccatctcc aatgttgtcc | 1020 |

```
atttccaatc taactcaaga acaagttcaa gactatgtaa ataagactaa ctctcatttg    1080
ccagctggta aacaagttga aatttctcta gtcaatggtg cgaagaatct agtcgtatcg    1140
ggcccaccac aatcattata tggtttaaac ttgactttaa gaaaggccaa ggccccatct    1200
ggactggatc aatcaagaat cccattcagc gaaagaaaat tgaagttctc caataggttc    1260
ttacctgttg catcaccagc acattccat  ctattggttc cagcttcaga tttgattaac    1320
aaagacttag tcaaaaacaa tgtcagcttt aacgctaaag atattcaaat ccccgtttac    1380
gacactttg  atggttcaga tctaagagtc ctttcaggtt ccatttccga gagaatcgtc    1440
gactgcatca ttagattacc tgtcaaatgg gaaactacta cacaattcaa agccacccac    1500
atattagact ttggtccagg tggagcttcc ggtttaggtg ttttaaccca tcgtaataaa    1560
gatggtactg tgttcgtgt  tatcgttgcc ggtactctcg acattaaccc agatgatgat    1620
tacggattca agcaagaaat ctttgatgtt actagtaatg gtttgaagaa aaatccaaac    1680
tggttggaag ataccatcc  aaaattaatt aagaacaaat caggcaaaat ttttgtcgaa    1740
acaaaatttt ctaaattaat cggtagacca cctttattgg ttcctggtat gacaccatgt    1800
actgtttctc cagatttcgt agctgctacc acaaatgctg ttataccat  tgagttggcc    1860
ggtggtggtt acttttccgc agcaggtatg accgccgcta ttgattctgt ggtttctcag    1920
atagaaaagg gtagtacctt cggtatcaac ttgatctacg tcaatccatt tatgttacaa    1980
tggggtattc cattaatcaa ggaactaaga agcaaaggtt atccaattca attcttgacc    2040
attggtgctg tgtcccatc  attggaagtt gctagtgaat acatagagac attaggtttg    2100
aagtacttgg gtttgaaacc aggttccatt gatgctattt cgcaagttat aaacattgct    2160
aaagcacatc caaacttccc aatagcttta caatggaccg gtggtagagg tggtggtcat    2220
cattctttcg aagatgccca cactccaatg ttacaaatgt actccaagat tagaagacat    2280
ccaaacatta tgttgatatt cggttctggt ttcggttctg ctgatgacac ttacccatac    2340
ttaaccggtg aatggtccac aaaattcgat tatccaccaa tgccattcga tggtttccta    2400
tttggttcga gggtcatgat tgctaaggaa gttaaaactt ctcctgatgc taagaagtgt    2460
attgctgctt gtactggtgt tcctgatgat aaatgggaac aaacctacaa gaagccaact    2520
ggtggtattg tcactgttcg ctctgaaatg ggtgaaccaa ttcacaaaat tgccactcgt    2580
ggtgttatgc tatggaagga attcgacgaa accatcttca acttaccaaa gaataagttg    2640
gtaccaactt tggaagcaaa gagagattac attatctcaa gattgaacgc cgatttccaa    2700
aaaccatggt ttgctaccgt caacggtcaa gcccgtgacc tagccacaat gacatacgaa    2760
gaagttgcaa agagattggt ggaattaatg ttcatcagat ctaccaactc ttggtttgat    2820
gtcacatgga gaacctttac tggtgatttc ctacgtcgtg tcgaagaacg tttcactaaa    2880
agtaagacat tgtctttaat ccaatcctat tctctactag acaagcctga tgaagctatt    2940
gaaaaagtat ttaatgctta tcctgccgct agggaacagt tcttgaatgc gcaagatatt    3000
gatcactttt tgagcatgtg tcaaaatcca atgcaaaaac cagtgccttt tgttccagtt    3060
ttggatcgta gattcgagat ttttttcaaa aaagattcgt tatggcaatc tgagcacttg    3120
gaagccgtcg tcgaccaaga cgttcaaaga acatgtatcc tacatggacc tgttgcagca    3180
caattcacta aagtcatcga tgaaccaatt aagagcatta tggatggtat tcacgatggt    3240
cacatcaaaa agttactaca tcaatattac ggtgacgatg agtcaaagat tccagcagtt    3300
agtactttg  gtggtgaaag ccctgtagac gtacaaagtc aagttgattc ttcctctgta    3360
```

```
tctgaagact cagctgtttt taaggcaaca tcctctactg atgaagaaag ctggtttaag      3420
gctttggcgg gatccgaaat taactggaga catgcaagtt tcttatgttc ctttatcact      3480
caagataaaa tgtttgtttc taacccaatt agaaaagttt tcaagccaag ccaaggaatg      3540
gttgttgaga tttccaacgg caatacttct tcaaagactg ttgtcactct ttcagaacct      3600
gttcaaggtg aattgaaacc aactgttatt ttgaagttgt tgaaggagaa cataatccaa      3660
atggaaatga ttgagaacag aactatggat ggtaagcccg tcagcttgcc attgttgtac      3720
aacttcaacc cagataatgg tttttgctcca atctctgaag ttatggagga cagaaaccaa      3780
agaattaagg aaatgtactg gaaattatgg attgatgagc ctttcaattt ggactttgac      3840
ccaagagatg tcattaaggg caaagatttc gagatcaccg ctaaagaagt ttatgacttt      3900
acacacgctg ttggaaacaa ttgtgaagac ttcgtttcta gacctgatag aacgatgttg      3960
gccccaatgg actttgctat tgttgtcgga tggagagcca tcatcaaggc cattttccct      4020
aatacggtcg atggtgactt attgaagttg gttcatttgt ctaacggcta caagatgatt      4080
cctggcgcta agccactgca agttggtgat gttgtttcaa ctactgctgt tattgaatct      4140
gtcgtcaacc aacctacagg aaagattgtc gatgtggtag gtacattatc gagaaatggc      4200
aagcctgtca tggaagtcac ctcctcattc ttctacagag gcaactatac tgactttgaa      4260
aacactttcc aaaagactgt tgaacctgtt tatcaaatgc acatcaaaac ttctaaagat      4320
atagctgtct tgcgctctaa ggagtggttc caattggacg atgaagactt cgatctgtta      4380
aacaaaactt tgactttcga aactgaaact gaagttactt tcaagaatgc taacatcttc      4440
tcttcagtga aatgttttgg cccaattaaa gttgaattgc caaccaaaga aaccgtggag      4500
atcggtattg tcgattacga agccggtgcc tctcacggta accctgttgt tgatttcttg      4560
aagagaaacg gttccacatt ggaacaaaag gtcaatctag aaaatcctat tccaattgca      4620
gtacttgatt cgtacactcc aagtaccaac gaaccatacg ctagagtttc tggtgatttg      4680
aatccaattc acgtttcacg tcattttgcc tcttacgcaa acttgccagg tactatcacg      4740
cacggtatgt tttcttctgc ttccgtccgt gctttgattg aaaactgggc tgctgacagt      4800
gtttcatcca gggtacgtgg ctacacttgt caatttgttg acatggtttt gcctaacact      4860
gctttgaaaa catcgattca acatgttggt atgatcaatg gtagaaaatt gataaagttt      4920
gaaactagaa atgaagatga cgttgtagtt ttgactggtg aagccgaaat tgaacaacct      4980
gttactacct tcgtttttcac tggtcaaggt tcacaagaac aaggtatggg tatggactta      5040
tacaaaactt ctaaagctgc tcaagatgtt tggaatagag ctgacaacca tttcaaggac      5100
acttatggtt tctctatctt agacattgtc attaacaacc cagttaactt aacaattcac      5160
ttcggtggtg aaaagggtaa gaggatcaga gaaaactatt ctgctatgat ctttgagact      5220
atcgtggatg gaaaattgaa gactgaaaaa attttcaagg aaattaatga gcacagtact      5280
tcttacacat ttagatctga aaaaggttta ttgtctgcta ctcaatttac acaaccagct      5340
ttaactttga tggaaaaagc tgctttcgaa gacttgaaat ctaaaggttt gatcccagcc      5400
gatgctactt tgctggtca ctctttaggt gagtatgctg ctttggcctc tttggctgat      5460
gttatgtcta tcgaatcttt agttgaagtt gtgttctaca gaggtatgac tatgcaagtt      5520
gctgttccaa gagatgagtt gggcagatcc aactatggta tgattgccat taacccaggt      5580
agagtcgctg catcattctc tcaagaagct ttgcaatatg ttgttgagag agttggtaag      5640
agaaccggct ggtggttga atcgtcaac tacaacgttg aaaaccaaca atatgttgca      5700
gctggtgatc taagagcttt agacaccgtt accaatgttc taaacttcat caaattacaa      5760
```

-continued

| | |
|---|---:|
| aaaattgata ttattgaact acaaaagtcc ttatctttgg aagaagttga aggtcatttg | 5820 |
| tttgagatca ttgacgaagc ttccaagaaa tctgctgtca agcctcgccc acttaaattg | 5880 |
| gagagaggtt ttgcttgtat cccattagtt ggtatttctg ttcctttcca ttccacctac | 5940 |
| ttgatgaatg gtgttaaacc attcaagagt tccttgaaga agaatatcat aaagaaaat | 6000 |
| gtgaaggttg ctagattggc cggaaagtac attccaaact tgactgcaaa accattccag | 6060 |
| gttactaagg aatatttcca ggacgtttat gatttgactg gctccgaacc tatcaaggaa | 6120 |
| atcatcgaca actgggaaaa gtatgaacaa tcctaa | 6156 |

<210> SEQ ID NO 8
<211> LENGTH: 6156
<212> TYPE: DNA
<213> ORGANISM: Saccharomyces cerevisiae

<400> SEQUENCE: 8

| | |
|---|---:|
| atggacgctt actccacaag accattaacc ctatctcacg gttctttaga gcacgtgctt | 60 |
| ctggtaccaa ccgcttcatt tttcattgct tcgcaattac aagaacaatt taataaaatt | 120 |
| ttgcccgaac ccactgaagg gtttgctgca atgacgagc ctaccacacc tgctgaacta | 180 |
| gtggggaaat tccttggcta cgtatcttct ctagtcgaac cttccaaggt cggtcaattc | 240 |
| gatcaggtct tgaacctttg cttaacagaa tttgaaaact gttatttaga aggcaatgac | 300 |
| attcacgcct tggctgctaa actattacag gaaaacgaca caactttagt gaagactaaa | 360 |
| gaactaatta aaaattatat taccgccaga ataatggcta agagaccatt tgacaaaaaa | 420 |
| tccaactctg ctcttttag ggccgtcggc gagggtaacg cacaattggt agccattttc | 480 |
| ggtggtcaag gtaacaccga cgactacttt gaagaattgc gtgatctata tcaaacttat | 540 |
| catgtcttag tgggagattt aatcaagttc tccgctgaaa ctttaagtga actgattaga | 600 |
| actactttag atgctgaaaa agtctttact caaggtttaa acatattgga atggttggag | 660 |
| aacccttcaa atacccccaga caaggactat ttactttcca ttccaatttc atgcccctta | 720 |
| attggtgtca ttcaattggc tcactacgta gttactgcca agcttttggg tttcactcca | 780 |
| ggtgagttaa gatcttactt aaaaggtgct acaggtcact ctcaaggttt ggttactgct | 840 |
| gtcgccatag ctgagacgga ttcctgggaa tccttcttcg tctccgtaag aaaaagcaatt | 900 |
| actgtattat tcttcatcgg tgttcgttgt tacgaagcat acccaaacac ttccctacca | 960 |
| ccatccatct tggaagattc cttggaaaac aatgaaggtg ttccatctcc aatgttgtcc | 1020 |
| atttccaatc taactcaaga acaagttcaa gactatgtaa ataagactaa ctctcatttg | 1080 |
| ccagctggta acaagttgaa atttctcta gtcaatggtg cgaagaatct agtcgtatcg | 1140 |
| ggcccaccac aatcattata tggtttaaac ttgactttaa gaaaggccaa ggccccatct | 1200 |
| ggactggatc aatcaagaat cccattcagc gaaagaaaat tgaagttctc caataggttc | 1260 |
| ttacctgttg catcaccagc acattccat ctattggttc cagcttcaga tttgattaac | 1320 |
| aaagacttag tcaaaaacaa tgtcagcttt aacgctaaag atattcaaat ccccgtttac | 1380 |
| gacacttttg atggttcaga tctaagagtc ctttcaggtt ccatttccga gagaatcgtc | 1440 |
| gactgcgcaa ttgattacc tgtcaaatgg gaaaactaca cacaattcaa agccacccac | 1500 |
| atattagact ttggtccagg tggagcttcc ggtttaggtg ttttaaccca tcgtaataaa | 1560 |
| gatggtactg tgttcgtgt tatcgttgcc ggtactctcg acattaaccc agatgatgat | 1620 |
| tacggattca agcaagaaat ctttgatgtt actagtaatg gtttgaagaa aaatccaaac | 1680 |

```
tggttggaag aataccatcc aaaattaatt aagaacaaat caggcaaaat ttttgtcgaa    1740
acaaaatttt ctaaattaat cggtagacca cctttattgg ttcctggtat gacaccatgt    1800
actgtttctc cagatttcgt agctgctacc acaaatgctg gttataccat tgagttggcc    1860
ggtggtggtt acttttccgc agcaggtatg accgccgcta ttgattctgt ggtttctcag    1920
atagaaaagg gtagtacctt cggtatcaac ttgatctacg tcaatccatt tatgttacaa    1980
tggggtattc cattaatcaa ggaactaaga agcaaaggtt atccaattca attcttgacc    2040
attggtgctg gtgtcccatc attggaagtt gctagtgaat acatagagac attaggtttg    2100
aagtacttgg gtttgaaacc aggttccatt gatgctattt cgcaagttat aaacattgct    2160
aaagcacatc caaacttccc aatagcttta caatggaccg gtggtagagg tggtggtcat    2220
cattctttcg aagatgccca cactccaatg ttacaaatgt actccaagat tagaagacat    2280
ccaaacatta tgttgatatt cggttctggt ttcggttctg ctgatgacac ttacccatac    2340
ttaaccggtg aatggtccac aaaattcgat tatccaccaa tgccattcga tggtttccta    2400
tttggttcga gggtcatgat tgctaaggaa gttaaaactt ctcctgatgc taagaagtgt    2460
attgctgctt gtactggtgt tcctgatgat aaatgggaac aaacctacaa gaagccaact    2520
ggtggtattg tcactgttcg ctctgaaatg ggtgaaccaa ttcacaaaat tgccactcgt    2580
ggtgttatgc tatggaagga attcgacgaa accatcttca acttaccaaa gaataagttg    2640
gtaccaactt tggaagcaaa gagagattac attatctcaa gattgaacgc cgatttccaa    2700
aaaccatggt ttgctaccgt caacggtcaa gcccgtgacc tagccacaat gacatacgaa    2760
gaagttgcaa agagattggt ggaattaatg ttcatcagat ctaccaactc ttggtttgat    2820
gtcacatgga gaacctttac tggtgatttc ctacgtcgtg tcgaagaacg tttcactaaa    2880
agtaagacat tgtctttaat ccaatccat tctctactag acaagcctga tgaagctatt    2940 gaaaagtat ttaatgctta tcctgccgct agggaacagt tcttgaatgc gcaagatatt    3000
gatcactttt tgagcatgtg tcaaaatcca atgcaaaaac cagtgccttt tgttccagtt    3060
ttggatcgta gattcgagat tttttttcaaa aaagattcgt tatggcaatc tgagcacttg    3120
gaagccgtcg tcgaccaaga cgttcaaaga acatgtatcc tacatggacc tgttgcagca    3180
caattcacta aagtcatcga tgaaccaatt aagagcatta tggatggtat tcacgatggt    3240
cacatcaaaa agttactaca tcaatattac ggtgacgatg agtcaaagat tccagcagtt    3300
gagtactttg gtggtgaaag ccctgtagac gtacaaagtc aagttgattc ttcctctgta    3360
tctgaagact cagctgtttt taaggcaaca tcctctactg atgaagaaag ctggtttaag    3420
gctttggcgg gatccgaaat taactggaga catgcaagtt tcttatgttc ctttatcact    3480
caagataaaa tgtttgtttc taacccaatt agaaaagttt tcaagccaag ccaaggaatg    3540
gttgttgaga tttccaacgg caatacttct tcaaagactg ttgtcactct ttcagaacct    3600
gttcaaggtg aattgaaacc aactgttatt ttgaagttgt tgaaggagaa cataatccaa    3660
atggaaatga ttgagaacag aactatggat ggtaagcccg tcagcttgcc attgttgtac    3720
aacttcaacc cagataatgg ttttgctcca atctctgaag ttatggagga cagaaaccaa    3780
agaattaagg aaaatgtactg gaaattatgg attgatgagc ctttcaattt ggactttgac    3840
ccaagagatg tcattaaggg caaagatttc gagatcaccg ctaaagaagt ttatgacttt    3900
acacacgctg ttggaaacaa ttgtgaagac ttcgtttcta gacctgatag aacgatgttg    3960
gccccaatgg actttgctat tgttgtcgga tggagagcca tcatcaaggc cattttccct    4020
aatacggtcg atggtgactt attgaagttg gttcatttgt ctaacggcta caagatgatt    4080
```

```
cctggcgcta agccactgca agttggtgat gttgtttcaa ctactgctgt tattgaatct    4140
gtcgtcaacc aacctacagg aaagattgtc gatgtggtag gtacattatc gagaaatggc    4200
aagcctgtca tggaagtcac ctcctcattc ttctacagag gcaactatac tgactttgaa    4260
aacactttcc aaaagactgt tgaacctgtt tatcaaatgc acatcaaaac ttctaaagat    4320
atagctgtct tgcgctctaa ggagtggttc caattggacg atgaagactt cgatctgtta    4380
aacaaaactt tgactttcga aactgaaact gaagttactt tcaagaatgc taacatcttc    4440
tcttcagtga aatgttttgg cccaattaaa gttgaattgc caaccaaaga aaccgtggag    4500
atcggtattg tcgattacga agccggtgcc tctcacggta accctgttgt tgatttcttg    4560
aagagaaacg gttccacatt ggaacaaaag gtcaatctag aaaatcctat tccaattgca    4620
gtacttgatt cgtacactcc aagtaccaac gaaccatacg ctagagtttc tggtgatttg    4680
aatccaattc acgtttcacg tcattttgcc tcttacgcaa acttgccagg tactatcacg    4740
cacggtatgt tttcttctgc ttccgtccgt gctttgattg aaaactgggc tgctgacagt    4800
gtttcatcca gggtacgtgg ctacacttgt caatttgttg acatggtttt gcctaacact    4860
gctttgaaaa catcgattca acatgttggt atgatcaatg gtagaaaatt gataaagttt    4920
gaaactagaa atgaagatga cgttgtagtt ttgactggtg aagccgaaat tgaacaacct    4980
gttactacct tcgttttcac tggtcaaggt tcacaagaac aaggtatggg tatggactta    5040
tacaaaactt ctaaagctgc tcaagatgtt tggaatagag ctgacaacca tttcaaggac    5100
acttatggtt tctctatctt agacattgtc attaacaacc cagttaactt aacaattcac    5160
ttcggtggtg aaaagggtaa gaggatcaga gaaaactatt ctgctatgat ctttgagact    5220
atcgtggatg gaaaattgaa gactgaaaaa attttcaagg aaattaatga gcacagtact    5280
tcttacacat ttagatctga aaaaggttta ttgtctgcta ctcaatttac acaaccagct    5340
ttaactttga tggaaaaagc tgcttttcga gacttgaaat ctaaaggttt gatcccagcc    5400
gatgctactt ttgctggtca ctctttaggt gagtatgctg ctttggcctc tttggctgat    5460
gttatgtcta tcgaatcttt agttgaagtt gtgttctaca gaggtatgac tatgcaagtt    5520
gctgttccaa gagatgagtt gggcagatcc aactatggta tgattgccat taacccaggt    5580
agagtcgctg catcattctc tcaagaagct ttgcaatatg ttgttgagag agttggtaag    5640
agaaccggct ggttggttga aatcgtcaac tacaacgttg aaaaccaaca atatgttgca    5700
gctggtgatc taagagcttt agacaccgtt accaatgttc taaacttcat caaattacaa    5760
aaaattgata ttattgaact acaaaagtcc ttatctttgg aagaagttga aggtcatttg    5820
tttgagatca ttgacgaagc ttccaagaaa tctgctgtca agcctcgccc acttaaattg    5880
gagagaggtt tgcttgtat cccattagtt ggtatttctg ttcctttcca ttccacctac    5940
ttgatgaatg gtgttaaacc attcaagagt ttcttgaaga agaatatcat aaaagaaaat    6000
gtgaaggttg ctagattggc cggaaagtac attccaaact tgactgcaaa accattccag    6060
gttactaagg aatatttcca ggacgtttat gatttgactg gctccgaacc tatcaaggaa    6120
atcatcgaca actgggaaaa gtatgaacaa tcctaa                              6156
```

<210> SEQ ID NO 9
<211> LENGTH: 6156
<212> TYPE: DNA
<213> ORGANISM: Saccharomyces cerevisiae

<400> SEQUENCE: 9

```
atggacgctt actccacaag accattaacc ctatctcacg gttctttaga gcacgtgctt    60
ctggtaccaa ccgcttcatt tttcattgct tcgcaattac aagaacaatt taataaaatt   120
ttgcccgaac ccactgaagg gtttgctgca gatgacgagc ctaccacacc tgctgaacta   180
gtggggaaat tccttggcta cgtatcttct ctagtcgaac cttccaaggt cggtcaattc   240
gatcaggtct tgaacctttg cttaacagaa tttgaaaact gttatttaga aggcaatgac   300
attcacgcct tggctgctaa actattacag gaaaacgaca caactttagt gaagactaaa   360
gaactaatta aaattatat accgccaga ataatggcta agagaccatt tgacaaaaaa   420
tccaactctg ctcttttag ggccgtcggc gagggtaacg cacaattggt agccattttc   480
ggtggtcaag gtaacaccga cgactacttt gaagaattgc gtgatctata tcaaacttat   540
catgtcttag tgggagattt aatcaagttc tccgctgaaa ctttaagtga actgattaga   600
actactttag atgctgaaaa agtctttact caaggtttaa acatattgga atggttggag   660
aacccttcaa atacccccaga caaggactat ttactttccg ctccaatttc atgcccctta   720
attggtgtca ttcaattggc tcactacgta gttactgcca agcttttggg tttcactcca   780
ggtgagttaa gatcttactt aaaaggtgct acaggtcact ctcaaggttt ggttactgct   840
gtcgccatag ctgagacgga ttcctgggaa tccttcttcg tctccgtaag aaaagcaatt   900
actgtattat tcttcatcgg tgttcgttgt tacgaagcat acccaaacac ttccctacca   960
ccatccatct tggaagattc cttggaaaac aatgaaggtg ttccatctcc aatgttgtcc  1020
atttccaatc taactcaaga acaagttcaa gactatgtaa ataagactaa ctctcatttg  1080
ccagctggta aacaagttga aatttctcta gtcaatggtg cgaagaatct agtcgtatcg  1140
ggcccaccac aatcattata tggtttaaac ttgactttaa gaaaggccaa ggccccatct  1200
ggactggatc aatcaagaat cccattcagc gaaagaaaat tgaagttctc caataggttc  1260
ttacctgttg catcaccatc ccattcccat ctattggttc cagcttcaga tttgattaac  1320
aaagacttag tcaaaaacaa tgtcagcttt aacgctaaag atattcaaat ccccgtttac  1380
gacactttg atggttcaga tctaagagtc ctttcaggtt ccatttccga gagaatcgtc  1440
gactgcatca ttagattacc tgtcaaatgg gaaactacta cacaattcaa agccaccccac  1500
atattagact ttggtccagg tggagcttcc ggtttaggtg ttttaaccca tcgtaataaa  1560
gatggtactg tgttcgtgt tatcgttgcc ggtactctcg acattaaccc agatgatgat  1620
tacggattca agcaagaaat cttttgatgtt actagtaatg gtttgaagaa aaatccaaac  1680
tggttggaag ataccatcc aaaattaatt aagaacaaat caggcaaaat ttttgtcgaa  1740
acaaaatttt ctaaattaat cggtagacca cctttattgg ttcctggtat gacaccatgt  1800
actgtttctc cagatttcgt agctgctacc acaaatgctg gttataccat tgagttggcc  1860
ggtggtggtt acttttccgc agcaggtatg accgccgcta ttgattctgt ggtttctcag  1920
atagaaaagg gtagtacctt cggtatcaac ttgatctacg tcaatccatt tatgttacaa  1980
tgggtattc cattaatcaa ggaactaaga agcaaaggtt atccaattca attcttgacc  2040
attggtgctg tgtcccatc attggaagtt gctagtgaat acatagagac attaggttg  2100
aagtacttgg gtttgaaacc aggttccatt gatgctattt cgcaagttat aaacattgct  2160
aaagcacatc caaacttccc aatagcttta caatggaccg gtggtagagg tggtggtcat  2220
cattctttcg aagatgccca cactccaatg ttacaaatgt actccaagat tagaagacat  2280
ccaaacatta tgttgatatt cggttctggt ttcggttctg ctgatgacac ttacccatac  2340
ttaaccggtg aatggtccac aaaattcgat tatccaccaa tgccattcga tggtttccta  2400
```

```
tttggttcga gggtcatgat tgctaaggaa gttaaaactt ctcctgatgc taagaagtgt    2460
attgctgctt gtactggtgt tcctgatgat aaatgggaac aaacctacaa gaagccaact    2520
ggtggtattg tcactgttcg ctctgaaatg ggtgaaccaa ttcacaaaat tgccactcgt    2580
ggtgttatgc tatggaagga attcgacgaa accatcttca acttaccaaa gaataagttg    2640
gtaccaactt tggaagcaaa gagagattac attatctcaa gattgaacgc cgatttccaa    2700
aaaccatggt ttgctaccgt caacggtcaa gcccgtgacc tagccacaat gacatacgaa    2760
gaagttgcaa agagattggt ggaattaatg ttcatcagat ctaccaactc ttggtttgat    2820
gtcacatgga gaacctttac tggtgatttc ctacgtcgtg tcgaagaacg tttcactaaa    2880
agtaagacat tgtcttttaat ccaatcctat tctctactag acaagcctga tgaagctatt    2940
gaaaaagtat ttaatgctta tcctgccgct agggaacagt tcttgaatgc gcaagatatt    3000
gatcactttt tgagcatgtg tcaaaatcca atgcaaaaac cagtgccttt tgttccagtt    3060
ttggatcgta gattcgagat tttttttcaaa aaagattcgt tatggcaatc tgagcacttg    3120
gaagccgtcg tcgaccaaga cgttcaaaga acatgtatcc tacatggacc tgttgcagca    3180
caattcacta aagtcatcga tgaaccaatt aagagcatta tggatggtat tcacgatggt    3240
cacatcaaaa agttactaca tcaatattac ggtgacgatg agtcaaagat tccagcagtt    3300
gagtactttg gtggtgaaag ccctgtagac gtacaaagtc aagttgattc ttcctctgta    3360
tctgaagact cagctgtttt taaggcaaca tcctctactg atgaagaaag ctggtttaag    3420
gctttggcgg gatccgaaat taactggaga catgcaagtt tcttatgttc ctttatcact    3480
caagataaaa tgtttgtttc taacccaatt agaaaagttt tcaagccaag ccaaggaatg    3540
gttgttgaga tttccaacgg caatacttct tcaaagactg ttgtcactct ttcagaacct    3600
gttcaaggtg aattgaaacc aactgttatt ttgaagttgt tgaaggagaa cataatccaa    3660
atggaaatga ttgagaacag aactatggat ggtaagcccg tcagcttgcc attgttgtac    3720
aacttcaacc cagataatgg ttttgctcca atctctgaag ttatggagga cagaaaccaa    3780
agaattaagg aaatgtactg gaaattatgg attgatgagc ctttcaattt ggactttgac    3840
ccaagagatg tcattaaggg caaagatttc gagatcaccg ctaaagaagt ttatgacttt    3900
acacacgctg ttggaaacaa ttgtgaagac ttcgtttcta gacctgatag aacgatgttg    3960
gccccaatgg actttgctat tgttgtcgga tggagagcca tcatcaaggc catttttccct    4020 aatacggtcg atggtgactt attgaagttg gttcatttgt ctaacggcta caagatgatt    4080
cctggcgcta agccactgca agttggtgat gttgtttcaa ctactgctgt tattgaatct    4140
gtcgtcaacc aacctacagg aaagattgtc gatgtggtag gtacattatc gagaaatggc    4200
aagcctgtca tggaagtcac ctcctcattc ttctacagag gcaactatac tgactttgaa    4260
aacactttcc aaaagactgt tgaacctgtt tatcaaatgc acatcaaaac ttctaaagat    4320
atagctgtct tgcgctctaa ggagtggttc caattggacg atgaagactt cgatctgtta    4380
aacaaaactt tgactttcga aactgaaact gaagttactt tcaagaatgc taacatcttc    4440
tcttcagtga atgttttggg cccaattaaa gttgaattgc aaccaaagaa accgtggag    4500 atcggtattg tcgattacga agccggtgcc tctcacggta accctgttgt tgatttcttg    4560
aagagaaacg gttccacatt ggaacaaaag gtcaatctag aaaatcctat tccaattgca    4620
gtacttgatt cgtacactcc aagtaccaac gaaccatacg ctagagtttc tggtgatttg    4680
aatccaattc acgtttcacg tcattttgcc tcttacgcaa acttgccagg tactatcacg    4740
```

| | |
|---|---|
| cacggtatgt tttcttctgc ttccgtccgt gctttgattg aaaactgggc tgctgacagt | 4800 |
| gtttcatcca gggtacgtgg ctacacttgt caatttgttg acatggtttt gcctaacact | 4860 |
| gctttgaaaa catcgattca acatgttggt atgatcaatg gtagaaaatt gataaagttt | 4920 |
| gaaactagaa atgaagatga cgttgtagtt ttgactggtg aagccgaaat tgaacaacct | 4980 |
| gttactacct tcgttttcac tggtcaaggt tcacaagaac aaggtatggg tatggactta | 5040 |
| tacaaaactt ctaaagctgc tcaagatgtt tggaatagag ctgacaacca tttcaaggac | 5100 |
| acttatggtt tctctatctt agacattgtc attaacaacc cagttaactt aacaattcac | 5160 |
| ttcggtggtg aaaagggtaa gaggatcaga gaaaactatt ctgctatgat ctttgagact | 5220 |
| atcgtggatg gaaaattgaa gactgaaaaa attttcaagg aaattaatga gcacagtact | 5280 |
| tcttacacat ttagatctga aaaggttta ttgtctgcta ctcaatttac acaaccagct | 5340 |
| ttaactttga tggaaaaagc tgctttcgaa gacttgaaat ctaaaggttt gatcccagcc | 5400 |
| gatgctactt tgctggtca ctctttaggt gagtatgctg ctttggcctc tttggctgat | 5460 |
| gttatgtcta tcgaatcttt agttgaagtt gtgttctaca gaggtatgac tatgcaagtt | 5520 |
| gctgttccaa gagatgagtt gggcagatcc aactatggta tgattgccat taacccaggt | 5580 |
| agagtcgctg catcattctc tcaagaagct ttgcaatatg ttgttgagag agttggtaag | 5640 |
| agaaccggct ggttggttga aatcgtcaac tacaacgttg aaaaccaaca atatgttgca | 5700 |
| gctggtgatc taagagcttt agacaccgtt accaatgttc taaacttcat caaattacaa | 5760 |
| aaaattgata ttattgaact acaaaagtcc ttatctttgg aagaagttga aggtcatttg | 5820 |
| tttgagatca ttgacgaagc ttccaagaaa tctgctgtca gcctcgccc acttaaattg | 5880 |
| gagagaggtt ttgcttgtat cccattagtt ggtatttctg ttcctttcca ttccacctac | 5940 |
| ttgatgaatg gtgttaaacc attcaagagt tccttgaaga agaatatcat aaaagaaaat | 6000 |
| gtgaaggttg ctagattggc cggaaagtac attccaaact tgactgcaaa accattccag | 6060 |
| gttactaagg aatatttcca ggacgtttat gatttgactg ctccgaacc tatcaaggaa | 6120 |
| atcatcgaca actgggaaaa gtatgaacaa tcctaa | 6156 |

<210> SEQ ID NO 10
<211> LENGTH: 6156
<212> TYPE: DNA
<213> ORGANISM: Saccharomyces cerevisiae

<400> SEQUENCE: 10

| | |
|---|---|
| atggacgctt actccacaag accattaacc ctatctcacg gttctttaga gcacgtgctt | 60 |
| ctggtaccaa ccgcttcatt tttcattgct tcgcaattac aagaacaatt taataaaatt | 120 |
| ttgcccgaac ccactgaagg gtttgctgca gatgacgagc ctaccacacc tgctgaacta | 180 |
| gtggggaaat tccttggcta cgtatcttct ctagtcgaac cttccaaggt cggtcaattc | 240 |
| gatcaggtct tgaacctttg cttaacagaa tttgaaaact gttatttaga aggcaatgac | 300 |
| attcacgcct tggctgctaa actattacag gaaaacgaca caactttagt gaagactaaa | 360 |
| gaactaatta aaaattatat taccgccaga ataatggcta agagaccatt tgacaaaaaa | 420 |
| tccaactctg ctcttttag ggccgtcggc gagggtaacg cacaattggt agccattttc | 480 |
| ggtggtgcag gtaacaccga cgactacttt gaagaattgc gtgatctata tcaaacttat | 540 |
| catgtcttag tgggagattt aatcaagttc tccgctgaaa ctttaagtga actgattaga | 600 |
| actactttag atgctgaaaa agtctttact caaggtttaa acatattgga atggttggag | 660 |
| aacccttcaa ataccccaga caaggactat ttactttcca ttccaatttc atgcccctta | 720 |

```
attggtgtca ttcaattggc tcactacgta gttactgcca agcttttggg tttcactcca     780
ggtgagttaa gatcttactt aaaaggtgct acaggtcact ctcaaggttt ggttactgct     840
gtcgccatag ctgagacgga ttcctgggaa tccttcttcg tctccgtaag aaaagcaatt     900
actgtattat tcttcatcgg tgttcgttgt tacgaagcat acccaaacac ttccctacca     960
ccatccatct tggaagattc cttggaaaac aatgaaggtg ttccatctcc aatgttgtcc    1020
atttccaatc taactcaaga acaagttcaa gactatgtaa ataagactaa ctctcatttg    1080
ccagctggta aacaagttga aatttctcta gtcaatggtg cgaagaatct agtcgtatcg    1140
ggcccaccac aatcattata tggtttaaac ttgactttaa gaaaggccaa ggccccatct    1200
ggactggatc aatcaagaat cccattcagc gaaagaaaat tgaagttctc caataggttc    1260
ttacctgttg catcaccagc acattcccat ctattggttc cagcttcaga tttgattaac    1320
aaagacttag tcaaaaacaa tgtcagcttt aacgctaaag atattcaaat ccccgtttac    1380
gacactttg atggttcaga tctaagagtc ctttcaggtt ccatttccga gagaatcgtc    1440
gactgcatca ttagattacc tgtcaaatgg gaaactacta cacaattcaa agccacccac    1500
atattagact ttggtccagg tggagcttcc ggtttaggtg ttttaaccca tcgtaataaa    1560
gatggtactg gtgttcgtgt tatcgttgcc ggtactctcg acattaaccc agatgatgat    1620
tacggattca agcaagaaat ctttgatgtt actagtaatg gtttgaagaa aaatccaaac    1680
tggttggaag aataccatcc aaaattaatt aagaacaaat caggcaaaat ttttgtcgaa    1740
acaaaatttt ctaaattaat cggtagacca cctttattgg ttcctggtat gacaccatgt    1800
actgtttctc cagatttcgt agctgctacc acaaatgctg gttataccat tgagttggcc    1860
ggtggtggtt actttttccgc agcaggtatg accgccgcta ttgattctgt ggtttctcag    1920
atagaaaagg gtagtacctt cggtatcaac ttgatctacg tcaatccatt tatgttacaa    1980
tggggtattc cattaatcaa ggaactaaga agcaaaggtt atccaattca attcttgacc    2040
attggtgctg gtgtcccatc attggaagtt gctagtgaat acatagagac attaggtttg    2100
aagtacttgg gtttgaaacc aggttccatt gatgctattt cgcaagttat aaacattgct    2160
aaagcacatc caaacttccc aatagcttta caatggaccg gtggtagagg tggtggtcat    2220
cattctttcg aagatgccca cactccaatg ttacaaatgt actccaagat tagaagacat    2280
ccaaacatta tgttgatatt cggttctggt ttcggttctg ctgatgacac ttacccatac    2340
ttaaccggtg aatggtccac aaaattcgat tatccaccaa tgccattcga tggtttccta    2400
tttggttcga gggtcatgat tgctaaggaa gttaaaactt ctcctgatgc taagaagtgt    2460
attgctgctt gtactggtgt tcctgatgat aaatgggaac aaacctacaa gaagccaact    2520
ggtggtattg tcactgttcg ctctgaaatg ggtgaaccaa ttcacaaaat tgccactcgt    2580
ggtgttatgc tatggaagga attcgacgaa accatcttca acttaccaaa gaataagttg    2640
gtaccaactt tggaagcaaa gagagattac attatctcaa gattgaacgc cgatttccaa    2700
aaaccatggt ttgctaccgt caacggtcaa gcccgtgacc tagccacaat gacatacgaa    2760
gaagttgcaa agagattggt ggaattaatg ttcatcagat ctaccaactc ttggtttgat    2820
gtcacatgga gaacctttac tggtgatttc ctacgtcgtg tcgaagaacg tttcactaaa    2880
agtaagacat tgtctttaat ccaatcctat tctctactag acaagcctga tgaagctatt    2940
gaaaaagtat ttaatgctta tcctgccgct agggaacagt tcttgaatgc gcaagatatt    3000
gatcactttt tgagcatgtg tcaaaatcca atgcaaaaac cagtgccttt tgttccagtt    3060
```

```
ttggatcgta gattcgagat ttttttcaaa aaagattcgt tatggcaatc tgagcacttg   3120
gaagccgtcg tcgaccaaga cgttcaaaga acatgtatcc tacatggacc tgttgcagca   3180
caattcacta aagtcatcga tgaaccaatt aagagcatta tggatggtat tcacgatggt   3240
cacatcaaaa agttactaca tcaatattac ggtgacgatg agtcaaagat tccagcagtt   3300
gagtactttg gtggtgaaag ccctgtagac gtacaaagtc aagttgattc ttcctctgta   3360
tctgaagact cagctgtttt taaggcaaca tcctctactg atgaagaaag ctggtttaag   3420
gctttggcgg gatccgaaat taactggaga catgcaagtt tcttatgttc ctttatcact   3480
caagataaaa tgtttgtttc taacccaatt agaaaagttt tcaagccaag ccaaggaatg   3540
gttgttgaga tttccaacgg caatacttct tcaaagactg ttgtcactct ttcagaacct   3600
gttcaaggtg aattgaaacc aactgttatt ttgaagttgt tgaaggagaa cataatccaa   3660
atggaaatga ttgagaacag aactatggat ggtaagcccg tcagcttgcc attgttgtac   3720
aacttcaacc cagataatgg ttttgctcca atctctgaag ttatggagga cagaaaccaa   3780
agaattaagg aaatgtactg gaaattatgg attgatgagc ctttcaattt ggactttgac   3840
ccaagagatg tcattaaggg caaagatttc gagatcaccg ctaagaagt ttatgactt    3900
acacacgctg ttgaaaacaa ttgtgaagac ttcgtttcta gacctgatag aacgatgttg   3960
gccccaatgg actttgctat tgttgtcgga tggagagcca tcatcaaggc catttttccct  4020
aatacggtcg atggtgactt attgaagttg gttcatttgt ctaacggcta caagatgatt   4080
cctggcgcta agccactgca agttggtgat gttgtttcaa ctactgctgt tattgaatct   4140
gtcgtcaacc aacctacagg aaagattgtc gatgtggtag gtacattatc gagaaatggc   4200
aagcctgtca tggaagtcac ctcctcattc ttctacagag gcaactatac tgactttgaa   4260
aacactttcc aaaagactgt tgaacctgtt tatcaaatgc acatcaaaac ttctaaagat   4320
atagctgtct tgcgctctaa ggagtggttc caattggacg atgaagactt cgatctgtta   4380
aacaaaactt tgactttcga aactgaaact gaagttactt tcaagaatgc taacatcttc   4440
tcttcagtga atgttttggg cccaattaaa gttgaattgc caaccaaaga aaccgtggag   4500
atcggtattg tcgattacga agccggtgcc tctcacggta accctgttgt tgatttcttg   4560
aagagaaacg gttccacatt ggaacaaaag gtcaatctag aaaatcctat tccaattgca   4620
gtacttgatt cgtacactcc aagtaccaac gaaccatacg ctagagtttc tggtgatttg   4680
aatccaattc acgtttcacg tcattttgcc tcttacgcaa acttgccagg tactatcacg   4740
cacggtatgt tttcttctgc ttccgtccgt gctttgattg aaaactgggc tgctgacagt   4800
gtttcatcca gggtacgtgg ctacacttgt caatttgttg acatggtttt gcctaacact   4860
gctttgaaaa catcgattca acatgttggt atgatcaatg gtagaaaatt gataaagttt   4920
gaaactagaa atgaagatga cgttgtagtt ttgactggtg aagccgaaat tgaacaacct   4980
gttactacct tcgttttcac tggtcaaggt tcacaagaac aaggtatggg tatggactta   5040
tacaaaactt ctaaagctgc tcaagatgtt tggaatagag ctgacaacca tttcaaggac   5100
acttatggtt tctctatctt agacattgtc attaacaacc cagttaactt aacaattcac   5160
ttcggtggta aaagggtaa gaggatcaga gaaaactatt ctgctatgat ctttgagact   5220
atcgtggatg gaaaattgaa gactgaaaaa attttcaagg aaattaatga gcacagtact   5280
tcttacacat ttagatctga aaaaggttta ttgtctgcta ctcaatttac acaaccagct   5340
ttaacttga tggaaaaagc tgcttttcgaa gacttgaaat ctaaaggttt gatcccagcc   5400
gatgctactt ttgctggtca ctctttaggt gagtatgctg cttttggcctc tttggctgat   5460
```

```
gttatgtcta tcgaatcttt agttgaagtt gtgttctaca gaggtatgac tatgcaagtt    5520
gctgttccaa gagatgagtt gggcagatcc aactatggta tgattgccat taacccaggt    5580
agagtcgctg catcattctc tcaagaagct ttgcaatatg ttgttgagag agttggtaag    5640
agaaccggct ggttggttga aatcgtcaac tacaacgttg aaaaccaaca atatgttgca    5700
gctggtgatc taagagcttt agacaccgtt accaatgttc taaacttcat caaattacaa    5760
aaaattgata ttattgaact acaaaagtcc ttatctttgg aagaagttga aggtcatttg    5820
tttgagatca ttgacgaagc ttccaagaaa tctgctgtca gcctcgccc acttaaattg    5880 gagagaggtt ttgcttgtat cccattagtt ggtatttctg ttcctttcca ttccacctac    5940
ttgatgaatg gtgttaaacc attcaagagt ttcttgaaga agaatatcat aaaagaaaat    6000
gtgaaggttg ctagattggc cggaaagtac attccaaact tgactgcaaa accattccag    6060
gttactaagg aatatttcca ggacgtttat gatttgactg gctccgaacc tatcaaggaa    6120
atcatcgaca actgggaaaa gtatgaacaa tcctaa                              6156

<210> SEQ ID NO 11
<211> LENGTH: 6156
<212> TYPE: DNA
<213> ORGANISM: Saccharomyces cerevisiae

<400> SEQUENCE: 11
atggacgctt actccacaag accattaacc ctatctcacg gttctttaga gcacgtgctt      60
ctggtaccaa ccgcttcatt tttcattgct tcgcaattac aagaacaatt taataaaatt     120
ttgcccgaac ccactgaagg gtttgctgca gatgacgagc ctaccacacc tgctgaacta     180
gtggggaaat tccttggcta cgtatcttct ctagtcgaac cttccaaggt cggtcaattc     240
gatcaggtct tgaacctttg cttaacagaa tttgaaaact gttatttaga aggcaatgac     300
attcacgcct ggctgctaa actattacag gaaaacgaca caactttagt gaagactaaa     360
gaactaatta aaaattatat taccgccaga ataatggcta agagaccatt tgacaaaaaa     420
tccaactctg ctcttttttag ggccgtcggc gagggtaacg cacaattggt agccattttc     480
ggtggtcaag gtaacaccga cgactacttt gaagaattgc gtgatctata tcaaacttat     540
catgtcttag tgggagattt aatcaagttc tccgctgaaa ctttaagtga actgattaga     600
actactttag atgctgaaaa agtctttact caaggtttaa acatattgga atggttggag     660 aaccctcaa atacccccaga caaggactat ttactttcca ttccaatttc atgcccctta     720
attggtgtca ttcaattggc tcactacgta gttactgcca gcttttgg tttcactcca     780 ggtgagttaa gatcttactt aaaaggtgct acaggtcact ctcaaggttt ggttactgct     840
gtcgccatag ctgagacgga ttcctgggaa tccttcttcg tctccgtaag aaaagcaatt     900
actgtattat tcttcgcagg tgttcgttgt tacgaagcat acccaaacac ttccctacca     960
ccatccatct tggaagattc cttggaaaac aatgaaggtg ttccatctcc aatgttgtcc    1020
atttccaatc taactcaaga acaagttcaa gactatgtaa ataagactaa ctctcatttg    1080
ccagctggta aacaagttga aatttctcta gtcaatggtg cgaagaatct agtcgtatcg    1140
ggcccaccac aatcattata tggtttaaac ttgactttaa gaaaggccaa ggccccatct    1200
ggactggatc aatcaagaat cccattcagc gaaagaaaat tgaagttctc caataggttc    1260
ttacctgttg catcaccatt ccattcccat ctattggttc cagcttcaga tttgattaac    1320
aaagacttag tcaaaaacaa tgtcagcttt aacgctaaag atattcaaat ccccgtttac    1380
```

```
gacactttg atggttcaga tctaagagtc ctttcaggtt ccatttccga gagaatcgtc    1440
gactgcatca ttagattacc tgtcaaatgg gaaactacta cacaattcaa agccacccac   1500
atattagact ttggtccagg tggagcttcc ggtttaggtg ttttaaccca tcgtaataaa   1560
gatggtactg gtgttcgtgt tatcgttgcc ggtactctcg acattaaccc agatgatgat   1620
tacggattca agcaagaaat cttttgatgtt actagtaatg gtttgaagaa aaatccaaac   1680
tggttggaag aataccatcc aaaattaatt aagaacaaat caggcaaaat ttttgtcgaa    1740
acaaaatttt ctaaattaat cggtagacca cctttattgg ttcctggtat gacaccatgt   1800
actgtttctc cagatttcgt agctgctacc acaaatgctg ttataccat tgagttggcc    1860 ggtggtggtt acttttccgc agcaggtatg accgccgcta ttgattctgt ggtttctcag   1920
atagaaaagg gtagtacctt cggtatcaac ttgatctacg tcaatccatt tatgttacaa   1980
tggggtattc cattaatcaa ggaactaaga agcaaaggtt atccaattca attcttgacc    2040
attggtgctg gtgtcccatc attggaagtt gctagtgaat acatagagac attaggtttg   2100
aagtacttgg gtttgaaacc aggttccatt gatgctattt cgcaagttat aaacattgct   2160
aaagcacatc caaacttccc aatagcttta caatggaccg gtggtagagg tggtggtcat   2220 cattcttcg aagatgccca cactccaatg ttacaaatgt actccaagat tagaagacat    2280
ccaaacatta tgttgatatt cggttctggt ttcggttctg ctgatgacac ttacccatac   2340
ttaaccggtg aatggtccac aaaattcgat tatccaccaa tgccattcga tggtttccta   2400
tttggttcga gggtcatgat tgctaaggaa gttaaaactt ctcctgatgc taagaagtgt   2460
attgctgctt gtactggtgt tcctgatgat aaatgggaac aaacctacaa gaagccaact   2520
ggtggtattg tcactgttcg ctctgaaatg ggtgaaccaa ttcacaaaat tgccactcgt   2580
ggtgttatgc tatggaagga attcgacgaa accatcttca acttaccaaa gaataagttg   2640
gtaccaactt tggaagcaaa gagagattac attatctcaa gattgaacgc cgatttccaa   2700
aaaccatggt ttgctaccgt caacggtcaa gcccgtgacc tagccacaat gacatacgaa   2760
gaagttgcaa agagattggt ggaattaatg ttcatcagat ctaccaactc ttggtttgat   2820
gtcacatgga gaacctttac tggtgatttc ctacgtcgtg tcgaagaacg tttcactaaa   2880
agtaagacat tgtctttaat ccaatcctat tctctactag acaagcctga tgaagctatt   2940
gaaaaagtat ttaatgctta tcctgccgct agggaacagt tcttgaatgc gcaagatatt   3000
gatcactttt tgagcatgtg tcaaaatcca atgcaaaaac cagtgccttt tgttccagtt   3060
ttggatcgta gattcgagat tttttttcaaa aaagattcgt tatggcaatc tgagcacttg   3120
gaagccgtcg tcgaccaaga cgttcaaaga acatgtatcc tacatggacc tgttgcagca   3180
caattcacta aagtcatcga tgaaccaatt aagagcatta tggatggtat tcacgatggt   3240
cacatcaaaa agttactaca tcaatattac ggtgacgatg agtcaaagat tccagcagtt   3300
gagtactttg gtggtgaaag ccctgtagac gtacaaagtc aagttgattc ttcctctgta   3360
tctgaagact cagctgtttt taaggcaaca tcctctactg atgaagaaag ctggtttaag   3420
gctttggcgg gatccgaaat taactggaga catgcaagtt tcttatgttc ctttatcact   3480
caagataaaa tgtttgtttc taacccaatt agaaagtttt caagccaag caaggaatg    3540 gttgttgaga tttccaacgg caatacttct tcaaagactg ttgtcactct ttcagaacct   3600
gttcaaggtg aattgaaacc aactgttatt tgaagttgt tgaaggagaa cataatccaa    3660
atggaaatga ttgagaacag aactatggat ggtaagcccg tcagcttgcc attgttgtac   3720
aacttcaacc cagataatgg ttttgctcca atctctgaag ttatggagga cagaaaccaa   3780
```

```
agaattaagg aaatgtactg gaaattatgg attgatgagc ctttcaattt ggactttgac   3840
ccaagagatg tcattaaggg caaagatttc gagatcaccg ctaaagaagt ttatgacttt   3900
acacacgctg ttggaaacaa ttgtgaagac ttcgtttcta gacctgatag aacgatgttg   3960
gccccaatgg actttgctat tgttgtcgga tggagagcca tcatcaaggc cattttccct   4020
aatacggtcg atggtgactt attgaagttg gttcatttgt ctaacggcta caagatgatt   4080
cctggcgcta agccactgca agttggtgat gttgtttcaa ctactgctgt tattgaatct   4140
gtcgtcaacc aacctacagg aaagattgtc gatgtggtag gtacattatc gagaaatggc   4200
aagcctgtca tggaagtcac ctcctcattc ttctacagag gcaactatac tgactttgaa   4260
aacactttcc aaaagactgt tgaacctgtt tatcaaatgc acatcaaaac ttctaaagat   4320
atagctgtct tgcgctctaa ggagtggttc caattggacg atgaagactt cgatctgtta   4380
aacaaaactt tgactttcga aactgaaact gaagttactt tcaagaatgc taacatcttc   4440
tcttcagtga aatgttttgg cccaattaaa gttgaattgc caaccaaaga aaccgtggag   4500
atcggtattg tcgattacga agccggtgcc tctcacggta accctgttgt tgatttcttg   4560
aagagaaacg gttccacatt ggaacaaaag gtcaatctag aaaatcctat tccaattgca   4620
gtacttgatt cgtacactcc aagtaccaac gaaccatacg ctagagtttc tggtgatttg   4680
aatccaattc acgtttcacg tcattttgcc tcttacgcaa acttgccagg tactatcacg   4740
cacggtatgt tttcttctgc ttccgtccgt gctttgattg aaaactgggc tgctgacagt   4800
gtttcatcca gggtacgtgg ctacacttgt caatttgttg acatggtttt gcctaacact   4860
gctttgaaaa catcgattca acatgttggt atgatcaatg gtagaaaatt gataaagttt   4920
gaaactagaa atgaagatga cgttgtagtt ttgactggtg aagccgaaat tgaacaacct   4980
gttactacct tcgttttcac tggtcaaggt tcacaagaac aaggtatggg tatggactta   5040
tacaaaactt ctaaagctgc tcaagatgtt tggaatagag ctgacaacca tttcaaggac   5100
acttatggtt tctctatctt agacattgtc attaacaacc cagttaactt aacaattcac   5160
ttcggtggtg aaaagggtaa gaggatcaga gaaaactatt ctgctatgat ctttgagact   5220
atcgtggatg gaaaattgaa gactgaaaaa atttttcaagg aaattaatga gcacagtact   5280
tcttacacat ttagatctga aaaaggttta ttgtctgcta ctcaatttac acaaccagct   5340
ttaactttga tggaaaaagc tgcttttcgaa gacttgaaat ctaaaggttt gatcccagcc   5400
gatgctactt tgctggtca ctctttaggt gagtatgctg ctttggcctc tttggctgat   5460
gttatgtcta tcgaatcttt agttgaagtt gtgttctaca gaggtatgac tatgcaagtt   5520
gctgttccaa gagatgagtt gggcagatcc aactatggta tgattgccat taacccaggt   5580
agagtcgctg catcattctc tcaagaagct ttgcaatatg ttgttgagag agttggtaag   5640
agaaccggct ggttggttga aatcgtcaac tacaacgttg aaaaccaaca atatgttgca   5700
gctggtgatc taagagcttt agacaccgtt accaatgttc taaacttcat caaattacaa   5760
aaaattgata ttattgaact acaaaagtcc ttatctttgg aagaagttga aggtcatttg   5820
tttgagatca ttgacgaagc ttccaagaaa tctgctgtca gcctcgccc acttaaattg   5880 gagagaggtt ttgcttgtat cccattagtt ggtatttctg ttccttttcca ttccacctac   5940 ttgatgaatg gtgttaaacc attcaagagt ttcttgaaga agaatatcat aaaagaaaat   6000
gtgaaggttg ctagattggc cggaaagtac attccaaact tgactgcaaa accattccag   6060
gttactaagg aatatttcca ggacgtttat gatttgactg gctccgaacc tatcaaggaa   6120
```

| | | | | | |
|---|---|---|---|---|---|
| atcatcgaca | actgggaaaa | gtatgaacaa | tcctaa | | 6156 |

<210> SEQ ID NO 12
<211> LENGTH: 6156
<212> TYPE: DNA
<213> ORGANISM: Saccharomyces cerevisiae

<400> SEQUENCE: 12

| | | | | | |
|---|---|---|---|---|---|
| atggacgctt | actccacaag | accattaacc | ctatctcacg | gttctttaga | gcacgtgctt | 60 |
| ctggtaccaa | ccgcttcatt | tttcattgct | tcgcaattac | aagaacaatt | taataaaatt | 120 |
| ttgcccgaac | ccactgaagg | gtttgctgca | gatgacgagc | ctaccacacc | tgctgaacta | 180 |
| gtggggaaat | tccttggcta | cgtatcttct | ctagtcgaac | cttccaaggt | cggtcaattc | 240 |
| gatcaggtct | tgaacctttg | cttaacagaa | tttgaaaact | gttatttaga | aggcaatgac | 300 |
| attcacgcct | tggctgctaa | actattacag | gaaaacgaca | caactttagt | gaagactaaa | 360 |
| gaactaatta | aaaattatat | taccgccaga | ataatggcta | agagaccatt | tgacaaaaaa | 420 |
| tccaactctg | ctcttttttag | ggccgtcggc | gagggtaacg | cacaattggt | agccattttc | 480 |
| ggtggtcaag | gtaacaccga | cgactacttt | gaagaattgc | gtgatctata | tcaaacttat | 540 |
| catgtcttag | tgggagattt | aatcaagttc | tccgctgaaa | ctttaagtga | actgattaga | 600 |
| actactttag | atgctgaaaa | agtctttact | caaggtttaa | acatattgga | atggttggag | 660 |
| aacccttcaa | atacccccaga | caaggactat | ttactttcca | ttccaatttc | atgcccctta | 720 |
| attggtgtca | ttcaattggc | tcactacgta | gttactgcca | agcttttggg | tttcactcca | 780 |
| ggtgagttaa | gatcttactt | aaaaggtgct | acaggtcact | ctcaaggttt | ggttactgct | 840 |
| gtcgccatag | ctgagacgga | ttcctgggaa | tccttcttcg | tctccgtaag | aaaagcaatt | 900 |
| actgtattat | tcttcgcagg | tgttcgttgt | tacgaagcat | acccaaacac | ttccctacca | 960 |
| ccatccatct | tggaagattc | cttggaaaac | aatgaaggtg | ttccatctcc | aatgttgtcc | 1020 |
| atttccaatc | taactcaaga | acaagttcaa | gactatgtaa | ataagactaa | ctctcatttg | 1080 |
| ccagctggta | aacaagttga | aatttctcta | gtcaatggtg | cgaagaatct | agtcgtatcg | 1140 |
| ggcccaccac | aatcattata | tggtttaaac | ttgactttaa | gaaaggccaa | ggccccatct | 1200 |
| ggactggatc | aatcaagaat | cccattcagc | gaaagaaaat | tgaagttctc | caataggttc | 1260 |
| ttacctgttg | catcaccatt | ccattcccat | ctattggttc | cagcttcaga | tttgattaac | 1320 |
| aaagacttag | tcaaaaacaa | tgtcagcttt | aacgctaaag | atattcaaat | ccccgtttac | 1380 |
| gacacttttg | atggttcaga | tctaagagtc | ctttcaggtt | ccatttccga | gagaatcgtc | 1440 |
| gactgcgcaa | ttagattacc | tgtcaaatgg | gaaactacta | cacaattcaa | agccacccac | 1500 |
| atattagact | tggtccagg | tggagcttcc | ggtttaggtg | ttttaaccca | tcgtaataaa | 1560 |
| gatggtactg | tgttcgtgt | tatcgttgcc | ggtactctcg | acattaaccc | agatgatgat | 1620 |
| tacggattca | gcaagaaat | ctttgatgtt | actagtaatg | gtttgaagaa | aaatccaaac | 1680 |
| tggttggaag | aataccatcc | aaaattaatt | aagaacaaat | caggcaaaat | ttttgtcgaa | 1740 |
| acaaaatttt | ctaaattaat | cggtagacca | cctttattgg | ttcctggtat | gacaccatgt | 1800 |
| actgtttctc | cagatttcgt | agctgctacc | acaaatgctg | gttataccat | tgagttggcc | 1860 |
| ggtggtggtt | acttttccgc | agcaggtatg | accgccgcta | ttgattctgt | ggtttctcag | 1920 |
| atagaaaagg | gtagtacctt | cggtatcaac | ttgatctacg | tcaatccatt | tatgttacaa | 1980 |
| tggggtattc | cattaatcaa | ggaactaaga | agcaaaggtt | atccaattca | attcttgacc | 2040 |
| attggtgctg | gtgtcccatc | attggaagtt | gctagtgaat | acatagagac | attaggttg | 2100 |

| | |
|---|---|
| aagtacttgg gtttgaaacc aggttccatt gatgctattt cgcaagttat aaacattgct | 2160 |
| aaagcacatc caaacttccc aatagcttta caatggaccg gtggtagagg tggtggtcat | 2220 |
| cattctttcg aagatgccca cactccaatg ttacaaatgt actccaagat tagaagacat | 2280 |
| ccaaacatta tgttgatatt cggttctggt ttcggttctg ctgatgacac ttacccatac | 2340 |
| ttaaccggtg aatggtccac aaaattcgat tatccaccaa tgccattcga tggtttccta | 2400 |
| tttggttcga gggtcatgat tgctaaggaa gttaaaactt ctcctgatgc taagaagtgt | 2460 |
| attgctgctt gtactggtgt tcctgatgat aaatgggaac aaacctacaa gaagccaact | 2520 |
| ggtggtattg tcactgttcg ctctgaaatg ggtgaaccaa ttcacaaaat tgccactcgt | 2580 |
| ggtgttatgc tatggaagga attcgacgaa accatcttca acttaccaaa gaataagttg | 2640 |
| gtaccaactt tggaagcaaa gagagattac attatctcaa gattgaacgc cgatttccaa | 2700 |
| aaaccatggt ttgctaccgt caacggtcaa gcccgtgacc tagccacaat gacatacgaa | 2760 |
| gaagttgcaa agagattggt ggaattaatg ttcatcagat ctaccaactc ttggtttgat | 2820 |
| gtcacatgga gaacctttac tggtgatttc ctacgtcgtg tcgaagaacg tttcactaaa | 2880 |
| agtaagacat tgtctttaat ccaatcctat tctctactag acaagcctga tgaagctatt | 2940 |
| gaaaagtat ttaatgctta tcctgccgct agggaacagt tcttgaatgc gcaagatatt | 3000 |
| gatcactttt tgagcatgtg tcaaaatcca atgcaaaaac cagtgccttt tgttccagtt | 3060 |
| ttggatcgta gattcgagat tttttcaaa aaagattcgt tatggcaatc tgagcacttg | 3120 |
| gaagccgtcg tcgaccaaga cgttcaaaga acatgtatcc tacatggacc tgttgcagca | 3180 |
| caattcacta agtcatcga tgaaccaatt aagagcatta tggatggtat tcacgatggt | 3240 |
| cacatcaaaa agttactaca tcaatattac ggtgacgatg agtcaaagat tccagcagtt | 3300 |
| gagtactttg gtggtgaaag ccctgtagac gtacaaagtc aagttgattc ttcctctgta | 3360 |
| tctgaagact cagctgtttt taaggcaaca tcctctactg atgaagaaag ctggtttaag | 3420 |
| gctttggcgg gatccgaaat taactggaga catgcaagtt tcttatgttc ctttatcact | 3480 |
| caagataaaa tgtttgtttc taacccaatt agaaaagttt tcaagccaag ccaaggaatg | 3540 |
| gttgttgaga tttccaacgg caatacttct tcaaagactg ttgtcactct ttcagaacct | 3600 |
| gttcaaggtg aattgaaacc aactgttatt ttgaagttgt tgaaggagaa cataatccaa | 3660 |
| atggaaatga ttgagaacag aactatggat ggtaagcccg tcagcttgcc attgttgtac | 3720 |
| aacttcaacc cagataatgg ttttgctcca atctctgaag ttatggagga cagaaaccaa | 3780 |
| agaattaagg aaatgtactg gaaattatgg attgatgagc ctttcaattt ggactttgac | 3840 |
| ccaagagatg tcattaaggg caaagatttc gagatcaccg ctaaagaagt ttatgacttt | 3900 |
| acacacgctg ttggaaacaa ttgtgaagac ttcgtttcta gacctgatag aacgatgttg | 3960 |
| gccccaatgg actttgctat tgttgtcgga tggagagcca tcatcaaggc cattttccct | 4020 |
| aatacggtcg atggtgactt attgaagttg gttcatttgt ctaacggcta caagatgatt | 4080 |
| cctggcgcta agccactgca agttggtgat gttgtttcaa ctactgctgt tattgaatct | 4140 |
| gtcgtcaacc aacctacagg aaagattgtc gatgtggtag gtacattatc gagaaatggc | 4200 |
| aagcctgtca tggaagtcac ctcctcattc ttctacagag gcaactatac tgactttgaa | 4260 |
| aacactttcc aaaagactgt tgaacctgtt tatcaaatgc acatcaaaac ttctaaagat | 4320 |
| atagctgtct tgcgctctaa ggagtggttc caattggacg atgaagactt cgatctgtta | 4380 |
| aacaaaactt tgactttcga aactgaaact gaagttactt tcaagaatgc taacatcttc | 4440 |

```
tcttcagtga aatgttttgg cccaattaaa gttgaattgc caaccaaaga aaccgtggag    4500
atcggtattg tcgattacga agccggtgcc tctcacggta accctgttgt tgatttcttg    4560
aagagaaacg gttccacatt ggaacaaaag gtcaatctag aaaatcctat tccaattgca    4620
gtacttgatt cgtacactcc aagtaccaac gaaccatacg ctagagtttc tggtgatttg    4680
aatccaattc acgtttcacg tcattttgcc tcttacgcaa acttgccagg tactatcacg    4740
cacggtatgt tttcttctgc ttccgtccgt gctttgattg aaaactgggc tgctgacagt    4800
gtttcatcca gggtacgtgg ctacacttgt caatttgttg acatggtttt gcctaacact    4860
gctttgaaaa catcgattca acatgttggt atgatcaatg gtagaaaatt gataaagttt    4920
gaaactagaa atgaagatga cgttgtagtt ttgactggtg aagccgaaat tgaacaacct    4980
gttactacct tcgttttcac tggtcaaggt tcacaagaac aaggtatggg tatggactta    5040
tacaaaactt ctaaagctgc tcaagatgtt tggaatagag ctgacaacca tttcaaggac    5100
acttatggtt tctctatctt agacattgtc attaacaacc cagttaactt aacaattcac    5160
ttcggtggtg aaaagggtaa gaggatcaga gaaaactatt ctgctatgat ctttgagact    5220
atcgtggatg gaaaattgaa gactgaaaaa attttcaagg aaattaatga gcacagtact    5280
tcttacacat ttagatctga aaaaggttta ttgtctgcta ctcaatttac acaaccagct    5340
ttaactttga tggaaaaagc tgctttcgaa gacttgaaat ctaaaggttt gatcccagcc    5400
gatgctactt ttgctggtca ctcttttaggt gagtatgctg ctttggcctc tttggctgat    5460
gttatgtcta tcgaatcttt agttgaagtt gtgttctaca gaggtatgac tatgcaagtt    5520
gctgttccaa gagatgagtt gggcagatcc aactatggta tgattgccat taacccaggt    5580
agagtcgctg catcattctc tcaagaagct ttgcaatatg ttgttgagag agttggtaag    5640
agaaccggct ggttggttga aatcgtcaac tacaacgttg aaaaccaaca atatgttgca    5700
gctggtgatc taagagcttt agacaccgtt accaatgttc taaacttcat caaattacaa    5760
aaaattgata ttattgaact acaaaagtcc ttatctttgg aagaagttga aggtcatttg    5820
tttgagatca ttgacgaagc ttccaagaaa tctgctgtca gcctcgccc acttaaattg    5880 gagagaggtt ttgcttgtat cccattagtt ggtatttctg ttcctttcca ttccacctac    5940
ttgatgaatg gtgttaaacc attcaagagt ttcttgaaga gaatatcat aaaagaaaat    6000 gtgaaggttg ctagattggc cggaaagtac attccaaact tgactgcaaa accattccag    6060
gttactaagg aatatttcca ggacgtttat gatttgactg gctccgaacc tatcaaggaa    6120
atcatcgaca actgggaaaa gtatgaacaa tcctaa                              6156
```

<210> SEQ ID NO 13
<211> LENGTH: 2187
<212> TYPE: DNA
<213> ORGANISM: Ondatra zibethicus

<400> SEQUENCE: 13

```
atgccagagg cgctgcttct caggtctgcc agctccatcc tgaggactgt gttcttaagc      60
agactgctac caggtgggcc tgggtgtgtt cgaaaactta gtttgaacct gcagtaccag     120
caaggaataa ggccgaatgt acaaagcagc tccttaactg atgggcgaac actctccaaa     180
gagtcctcaa ctcatggcct tgagttctca gctccagaga aggcctcacc gccagacacc     240
gcagaggaag cactctggac agctcgggca gatggaagag tgcgcctgcg cagggaaccc     300
ttctgcacgc agcctcccta tactgtgcac cggatgttct acgaggccct ggataagtac     360
gggagcctca gtgctctggg tgtcaagcgc agaaacaagt gggaacgcat ctcttactac     420
```

```
cagtactacg agattgcccg caaagtcgcc agaggcttcc tgaagcttgg cctggagcga      480
gcccacagcg tggggatcct cggcttcaac tccccagagt ggttcttctc tgcagtgggc      540
acagtgttcg caggggggcat tgtcactggc atctacacca ctagctccct gaagcctgc      600 cagtacatcc cccacgactg ccgtgccaac gtcattgtgg ttgacacaca gaagcagctg      660
gagaagatac tgaagatctg gaaagacttg ccacacctca aagcagtggt aatataccaa      720
gaaccccttc caaagaagat ggtcaacgtg tacacgatgg aagaactcat agaactggga      780
caagaagtgc ctgaggaggc cctggacacc atcattgaca cccagcagcc caaccagtgt      840
tgcgtgctgg tctacacatc cggcaccacc ggaaacccca agggcgtgat gttgagtcaa      900
gacaatatca catggacagc acggtacggc agtcaggctg ggacatcca gccagcagaa       960 gtccagcagg aggtagtagt cagctacttg cccctcagcc acattgctgc ccagatctac     1020
gacctgtgga ccggcatcca gtggggagcc caggtctgct ttgcagatcc tgatgcccta     1080
aaggggagcc tggtgaacac actgcgggag gtggagccca tcccacat gggggtgcct      1140 cgtgtgtggg agaagatcat ggaagggatc caggaggtgg cggctcagtc tggcttcatc     1200
cggcgcaaga tgctgctatg ggccatgtca gtgaccttgg aacagaacct cacttgccct     1260
agcaatgacc tgaagcccct tcacaagcaga ctggcggatt acctagtatt agccaaggtc     1320
cgtcaggctc tgggctttgc caagtgtcag aagaacttct acggagcagc ccccatgact     1380
gcagaaacac agcgcttctt tctgggcctt aacatccgcc tgtacgcagg ctacggcctc     1440
agcgagagca caggccccca cttcatgtcc agccccataca actaccgact gtacagttct     1500
ggcaagttga tccctggctg ccgggtgaag ctggtcaatc aggatgccaa cggcatcggt     1560
gagatctgcc tgtggggccg aaccatcttc atgggctatc tgaacatgga ggacaaaacg     1620
tgtgaggcca ttgactcgga aggctggcta cacacaggtg acatgggccg tctggattct     1680
gatggcttcc tctacatcac tgggcgcctc aaagagttaa tcatcactgc gggtgggggag     1740 aatgtgcccc cagtgcccat tgaggaggct gtgaagacgg agctgccat catcagtagt     1800 gccatgctga tagggaccaga ggaagttc ctgtccatgc tgctaactct gaagtgcacg      1860
ctggacccag agacatctga ccgacagac aacctgacga gcaagctgt ggagttctgc       1920 cagagggtgg gcagcggggc cagcaccgta tccgagattg tggggcagag agatgaggct     1980
gtgtatcagg ccatccagga agggatccag agggtgaacg cgaatgcagc agcccggccc     2040
taccacatcc agaagtgggc cattctcaaa cgtgacttct ccatttctgg tggagaactg     2100
ggccctacca tgaaactgaa acggctcaca gttctggaga agtacaaaga tatcatcgat     2160 tcctttttatc aagagcaaaa acagtag                                         2187
```

<210> SEQ ID NO 14
<211> LENGTH: 1182
<212> TYPE: DNA
<213> ORGANISM: Saccharomyces cerevisiae

<400> SEQUENCE: 14

```
atgttgcaga gacattcctt gaagttgggg aaattctcca tcagaacact cgctactggt       60
gccccattag atgcatccaa actaaaaatt actagaaacc caaatccatc caagccaaga      120
ccaaatgaag aattagtgtt cggccagaca ttcaccgatc atatgttgac cattccttgg      180
tcagccaaag aagggtgggg cactccacac atcaagcctt acggtaatct ttctcttgac      240
ccatctgctt gtgtattcca ttatgcattt gaattatttg aaggtttgaa agcctacaga      300
```

| | |
|---|---:|
| actcctcaaa atactatcac catgttccgt ccggataaga acatggcccg tatgaacaag | 360 |
| tctgccgcta gaatttgttt gccaactttc gaatctgaag aattgatcaa acttaccggg | 420 |
| aaattgatcg aacaagataa acacttggtt cctcaaggta atggttactc attatacatc | 480 |
| agaccaacaa tgattggtac atccaagggt ttaggtgttg cactccctc cgaggctctt | 540 |
| ctttatgtta ttacttctcc agtcggtcct tattataaga ctggtttcaa agccgtacgt | 600 |
| cttgaagcaa cagactatgc tacaagagct tggccaggtg gtgttggcga caaaaaattg | 660 |
| ggtgctaact atgccccatg catcttacct caactacaag ctgccaaaag agggtaccaa | 720 |
| caaaatctat ggttgttcgg cccagaaaag aacatcactg aggttggtac tatgaacgtg | 780 |
| ttcttcgttt tcctcaacaa agtcactggc aagaaggaat tggttaccgc tccattagat | 840 |
| ggtaccattt tagaaggtgt taccagagac tctgttttaa cattggctcg tgacaaaacta | 900 |
| gatcctcaag aatgggacat caacgagcgt tattacacta ttactgaagt cgccactaga | 960 |
| gcaaaacaag gtgaactatt gaagccttc ggttctggta ctgctgctgt cgtttcacct | 1020 |
| atcaaggaaa ttggctggaa caacgaagat attcatgttc cactattgcc tggtgaacaa | 1080 |
| tgtggtgcat tgaccaagca agttgctcaa tggattgctg atatccaata cggtagagtc | 1140 |
| aattatggta actggtcaaa aactgttgcc gacttgaact aa | 1182 |

<210> SEQ ID NO 15
<211> LENGTH: 1131
<212> TYPE: DNA
<213> ORGANISM: Saccharomyces cerevisiae

<400> SEQUENCE: 15

| | |
|---|---:|
| atgaccttgg caccsctaga cgcctccaaa gttaagataa ctaccacaca acatgcatct | 60 |
| aagccaaaac cgaacagtga gttagtgttt ggcaagagct tcacggacca catgttaact | 120 |
| gcggaatgga cagctgaaaa agggtggggt accccagaga ttaaaccta tcaaaatctg | 180 |
| tctttagacc cttccgcggt ggttttccat tatgcttttg agctattcga agggatgaag | 240 |
| gcttacagaa cggtggacaa caaaattaca atgtttcgtc cagatatgaa tatgaagcgc | 300 |
| atgaataagt ctgctcagag aatctgtttg ccaacgttcg acccagaaga gttgattacc | 360 |
| ctaattggga aactgatcca gcaagataag tgcttagttc ctgaaggaaa aggttactct | 420 |
| ttatatatca ggcctacatt aatcggcact acggccggtt tagggggttc cacgcctgat | 480 |
| agagccttgc tatatgtcat ttgctgccct gtgggtcctt attacaaaac tggatttaag | 540 |
| gcggtcagac tggaagccac tgattatgcc acaagagctt ggccaggagg ctgtggtgac | 600 |
| aagaaactag gtgcaaacta cgcccctgc gtcctgccac aattgcaagc tgcttcaagg | 660 |
| ggttaccaac aaaatttatg gctatttggt ccaataaca acattactga agtcggcacc | 720 |
| atgaatgctt ttttcgtgtt taaagatagt aaaacgggca agaaggaact agttactgct | 780 |
| ccactagacg gtaccatttt ggaaggtgtt actaggggatt ccatttaaaa tcttgctaaa | 840 |
| gaaagactcg aaccaagtga atggaccatt agtgaacgct acttcactat aggcgaagtt | 900 |
| actgagagat ccaagaacgg tgaactactt gaagcctttg gttctggtac tgctgcgatt | 960 |
| gtttctccca ttaaggaaat cggctggaaa ggcgaacaaa ttaatattcc gttgttgccc | 1020 |
| ggcgaacaaa ccggtccatt ggccaaagaa gttgcacaat ggattaatgg aatccaatat | 1080 |
| ggcgagactg agcatggcaa ttggtcaagg gttgttactg atttgaactg a | 1131 |

<210> SEQ ID NO 16
<211> LENGTH: 1908

```
<212> TYPE: DNA
<213> ORGANISM: Saccharomyces cerevisiae

<400> SEQUENCE: 16
atggcacctg ttacaattga aaagttcgta aatcaagaag aacgacacct tgtttccaac      60
cgatcagcaa caattccgtt tggtgaatac atatttaaaa gattgttgtc catcgatacg     120
aaatcagttt tcggtgttcc tggtgacttc aacttatctc tattagaata tctctattca     180
cctagtgttg aatcagctgg cctaagatgg gtcggcacgt gtaatgaact gaacgccgct     240
tatgcggccg acggatattc ccgttactct aataagattg gctgtttaat aaccacgtat     300
ggcgttggtg aattaagcgc cttgaacggt atagccggtt cgttcgctga aaatgtcaaa     360
gttttgcaca ttgttggtgt ggccaagtcc atagattcgc gttcaagtaa ctttagtgat     420
cggaacctac atcatttggt cccacagcta catgattcaa attttaaagg gccaaatcat     480
aaagtatatc atgatatggt aaaagataga gtcgcttgct cggtagccta cttggaggat     540
attgaaactg catgtgacca agtcgataat gttatccgcg atatttacaa gtattctaaa     600
cctggttata ttttgttcc tgcagatttt gcggatatgt ctgttacatg tgataatttg     660
gttaatgttc cacgtatatc tcaacaagat tgtatagtat acccttctga aaaccaattg     720
tctgacataa tcaacaagat tactagttgg atatattcca gtaaaacacc tgcgatcctt     780
ggagacgtac tgactgatag gtatggtgtg agtaactttt tgaacaagct tatctgcaaa     840
actgggattt ggaatttttc cactgttatg ggaaaatctg taattgatga gtcaaaccca     900
acttatatgg gtcaatataa tggtaaagaa ggtttaaaac aagtctatga acattttgaa     960
ctgtgcgact ggtcttgca ttttggagtc gacatcaatg aaattaataa tgggcattat    1020
acttttactt ataaaccaaa tgctaaaatc attcaatttc atccgaatta tattcgcctt    1080
gtggacacta ggcagggcaa tgagcaaatg ttcaaaggaa tcaattttgc ccctatttta    1140
aaagaactat acaagcgcat tgacgtttct aaactttctt tgcaatatga ttcaaatgta    1200
actcaatata cgaacgaaac aatgcggtta gaagatccta ccaatggaca atcaagcatt    1260
attacacaag ttcacttaca aaagacgatg cctaaatttt tgaaccctgg tgatgttgtc    1320
gtttgtgaaa caggctcttt tcaattctct gttcgtgatt tcgcgtttcc ttcgcaatta    1380
aaatatatat cgcaaggatt tttcctttcc attggcatgg cccttcctgc cgccctaggt    1440
gttggaattg ccatgcaaga ccactcaaac gctcacatca atggtggcaa cgtaaaagag    1500
gactataagc caagattaat tttgtttgaa ggtgacggtg cagcacagat gacaatccaa    1560
gaactgagca ccattctgaa gtgcaatatt ccactagaag ttatcatttg aacaataac    1620
ggctacacta ttgaaagagc catcatgggc cctaccaggt cgtataacga cgttatgtct    1680
tggaaatgga ccaaactatt tgaagcattc ggagacttcg acggaaagta tactaatagc    1740
actctcattc aatgtccctc taaattagca ctgaaattgg aggagcttaa gaattcaaac    1800
aaaagaagcg ggatagaact tttagaagtc aaattaggcg aattggattt ccccgaacag    1860
ctaaagtgca tggttgaagc agcggcactt aaaagaaata aaaaatag                 1908

<210> SEQ ID NO 17
<211> LENGTH: 1521
<212> TYPE: DNA
<213> ORGANISM: Saccharomyces cerevisiae

<400> SEQUENCE: 17
atgcctacct tgtatactga tatcgaaatc ccacaattga aaatctcttt aaagcaaccg      60
```

| | |
|---|---|
| ctagggttgt ttatcaacaa tgagttttgt ccatcatcag atggaaagac catcgaaact | 120 |
| gtgaacccag ctactggcga accgataaca tccttccaag cagctaacga aaaggatgta | 180 |
| gacaaagctg tgaaagctgc cagggctgct tttgataacg tttggtcgaa gacatcttct | 240 |
| gagcaacgtg gtatttatct ttcaaactta ttaaaactta ttgaggagga gcaagacaca | 300 |
| cttgccgcat tagagacttt agacgctgga aagccttacc attcaaatgc caaggtgat | 360 |
| ttggcacaaa ttttacagct taccagatat tttgctgggt ccgctgataa gtttgacaaa | 420 |
| ggtgcaacca taccattgac ttttaacaag tttgcatata ctctaaaagt tccttttggc | 480 |
| gttgttgctc aaatcgttcc atggaattat cctctagcta tggcttgttg gaaattgcaa | 540 |
| ggtgccttag cagccggtaa cacggttatc atcaaacctg ctgagaatac ctctctatct | 600 |
| ctactttatt ttgctacttt aattaaaaaa gcaggttttc cacctggtgt tgtcaatatc | 660 |
| gttcctggtt atggatcact tgtaggccaa gccctagcat ctcacatgga tatcgacaaa | 720 |
| atatctttta cgggaagcac caaggtcggt ggatttgtgt tggaagcttc cggccaatcg | 780 |
| aaccttaaag acgttacact agaatgcggt ggtaagtctc ctgctctcgt atttgaagat | 840 |
| gcagaccttg ataaggctat cgattggata gcagctggca ttttctacaa ttcaggacag | 900 |
| aattgtaccg caaactcaag agtttatgtt caaagttcga tctacgacaa gtttgttgaa | 960 |
| aagtttaaag aaactgcaaa gaaggagtgg gatgttgcag gaaaatttga tccgtttgat | 1020 |
| gagaaatgca tcgttggtcc agttatatca agtacacagt atgaccgcat caaaagttac | 1080 |
| atagaacgtg gtaaaaggga ggaaaagttg gacatgttcc agacctctga atttcctatt | 1140 |
| ggtggagcta aaggctactt cattccccca accatcttca ctgatgtccc gcaaacatcg | 1200 |
| aaactgttac aggatgagat atttggcccg gttgtggttg ttagcaagtt cacaaattat | 1260 |
| gatgacgctc tgaagctggc taatgatact tgctacgggc tcgcctctgc ggtcttcaca | 1320 |
| aaagatgtca agaaagcgca catgtttgct cgcgatatta agcaggaac tgtttggatc | 1380 |
| aactcatcta acgatgaaga tgttaccgtt ccttttggcg ggtttaaaat gagtggtatt | 1440 |
| ggtagagaac tggggcaaag tggtgttgat acctatcttc aaacaaaagc agttcacata | 1500 |
| aatctctctt tggacaacta a | 1521 |

<210> SEQ ID NO 18
<211> LENGTH: 1563
<212> TYPE: DNA
<213> ORGANISM: Saccharomyces cerevisiae

<400> SEQUENCE: 18

| | |
|---|---|
| atgctttctc gcacaagagc tgcagctccg aattccagaa tattcactag aagcttgtta | 60 |
| cgtctttatt ctcaagcacc attacgcgtt ccaattactc ttccaaatgg tttcacctac | 120 |
| gaacagccaa cagggttatt catcaatggt gaatttgttg cctcgaagca aagaaaacg | 180 |
| tttgacgtga tcaatccatc taacgaagaa aagataacaa ctgtatacaa ggctatggaa | 240 |
| gatgatgttg atgaagccgt tgcagcggct aaaaaagctt tgaaacgaa gtggtctatt | 300 |
| gtagagccgg aggttcgcgc taaagcttta ttcaatctcg ctgacttggt tgagaaacac | 360 |
| caagaaacac tggctgccat tgagtcaatg gataatggta agtcattgtt ttgtgcgcgc | 420 |
| ggtgacgtcg cttagtatc taaatacttg cgttcttgcg gtggttgggc agataaaatc | 480 |
| tacggtaacg ttattgacac aggtaaaaac cattttacct actcaattaa ggaaccatta | 540 |
| ggcgtttgcg gccaaataat cccttggaac ttcccttttat tgatgtggtc atggaaaatt | 600 |
| gggcctgctc tggctacagg taacaccgtc gtattgaaac ccgctgaaac aacaccttta | 660 |

```
tctgcccttt tcgcttccca gttgtgtcag gaagcaggca tacccgctgg tgtagtcaat      720
atccttccgg gttccggtag agttgttgga gaaagattga gtgcacaccc agacgtgaag      780
aagattgctt ttacaggctc tactgccacc ggccgccata ttatgaaggt cgctgccgat      840
actgtcaaga aagtcacttt ggagctggga ggtaaatcac caaatattgt gtttgctgac      900
gctgatctag ataaagccgt caagaacatt gccttcggta ttttttacaa ctctggtgaa      960
gtttgctgcg ctggttccag aatatacatt caagatacag tatacgagga ggtgttgcaa     1020
aaactaaagg attacaccga gtcactaaag gtcggtgacc catttgatga ggaagttttc     1080
caaggtgctc aaacatctga caaacagctg cataaaattt tagactatgt cgatgtagca     1140
aaatcagagg gggctcgtct tgtgactgga ggggccagac atggcagtaa aggttatttt     1200
gtcaagccaa cagtgtttgc tgatgtcaaa gaagatatga aattgttaa ggaggaagtg      1260 tttggtccca ttgtaactgt atccaagttt tctactgttg atgaagtgat tgctatggca     1320
aatgattctc aatatggggtt agccgcaggt attcacacta acgatattaa caaggctgtt     1380
gatgtgtcca aaagagtgaa agctggtact gtttggataa ataccctataa caacttccac    1440 caaaatgttc ctttcggtgg cttcggccag tcaggtattg gccgtgaaat gggtgaggct     1500
gctttaagta actacactca aacaaaatct gtcagaattg ccattgacaa gccaattcgt     1560
tga                                                                   1563

<210> SEQ ID NO 19
<211> LENGTH: 6702
<212> TYPE: DNA
<213> ORGANISM: Saccharomyces cerevisiae

<400> SEQUENCE: 19
atgagcgaag aaagcttatt cgagtcttct ccacagaaga tggagtacga aattacaaac       60
tactcagaaa gacatacaga acttccaggt catttcattg gcctcaatac agtagataaa      120
ctagaggagt ccccgttaag ggactttgtt aagagtcacg gtggtcacac ggtcatatcc      180
aagatcctga tagcaaataa tggtattgcc gccgtgaaag aaattagatc cgtcagaaaa      240
tgggcatacg agacgttcgg cgatgacaga accgtccaat tcgtcgccat ggccacccca      300
gaagatctgg aggccaacgc agaatatatc cgtatggccg atcaatacat tgaagtgcca      360
ggtggtacta taataacaa ctacgctaac gtagacttga tcgtagacat cgccgaaaga       420
gcagacgtag acgccgtatg ggctggctgg ggtcacgcct ccgagaatcc actattgcct      480
gaaaaattgt cccagtctaa gaggaaagtc atctttattg ggcctccagg taacgccatg      540
aggtctttag gtgataaaat ctcctctacc attgtcgctc aaagtgctaa agtcccatgt      600
attccatggt ctggtaccgg tgttgacacc gttcacgtgg acgagaaaac cggtctggtc      660
tctgtcgacg atgacatcta tcaaaagggt tgttgtacct ctcctgaaga tggtttacaa      720
aaggccaagc gtattggttt tcctgtcatg attaaggcat ccgaaggtgg tggtggtaaa      780
ggtatcagac aagttgaacg tgaagaagat ttcatcgctt ataccacca ggcagccaac      840 gaaattccag ctccccccat tttcatcatg aagttggccg gtagagcgcg tcacttggaa      900
gttcaactgc tagcagatca gtacggtaca aatatttcct tgttcggtag agactgttcc      960
gttcagagac gtcatcaaaa aattatcgaa gaagcaccag ttacaattgc caaggctgaa     1020
acatttcacg agatggaaaa ggctgccgtc agactgggga aactagtcgg ttatgtctct     1080
gccggtaccg tggagtatct atattctcat gatgatggaa aattctactt tttagaattg     1140
```

-continued

```
aacccaagat tacaagtcga gcatccaaca acggaaatgg tctccggtgt taacttacct    1200
gcagctcaat tacaaatcgc tatgggtatc cctatgcata gaataagtga cattagaact    1260
ttatatggta tgaatcctca ttctgcctca gaaatcgatt tcgaattcaa aactcaagat    1320
gccaccaaga aacaaagaag acctattcca aagggtcatt gtaccgcttg tcgtatcaca    1380
tcagaagatc caaacgatgg attcaagcca tcgggtggta ctttgcatga actaaacttc    1440
cgttcttcct ctaatgtttg gggttacttc tccgtgggta acaatggtaa tattcactcc    1500
ttttcggact ctcagttcgg ccatattttt gcttttggtg aaaatagaca agcttccagg    1560
aaacacatgg ttgttgccct gaaggaattg tccattaggg gtgatttcag aactactgtg    1620
gaatacttga tcaaactttt ggaaactgaa gatttcgagg ataacactat taccaccggt    1680
tggttggacg atttgattac tcataaaatg accgctgaaa agcctgatcc aactcttgcc    1740
gtcatttgcg gtgccgctac aaaggctttc ttagcatctg aagaagcccg ccacaagtat    1800
atcgaatcct tacaaagggg acaagttcta tctaaagacc tactgcaaac tatgttccct    1860
gtagatttta tccatgaggg taaaagatac aagttcaccg tagctaaatc cggtaatgac    1920
cgttacacat tatttatcaa tggttctaaa tgtgatatca tactgcgtca actatctgat    1980
ggtggtcttt tgattgccat aggcggtaaa tcgcatacca tctattggaa agaagaagtt    2040
gctgctacaa gattatccgt tgactctatg actactttgt tggaagttga aaacgatcca    2100
acccagttgc gtactccatc ccctggtaaa ttggttaaat tcttggtgga aaatggtgaa    2160
cacattatca agggccaacc atatgcagaa attgaagtta tgaaaatgca aatgcctttg    2220
gtttctcaag aaaatggtat cgtccagtta ttaaagcaac ctggttctac cattgttgca    2280
ggtgatatca tggctattat gactcttgac gatccatcca aggtcaagca cgctctacca    2340
tttgaaggta tgctgccaga ttttggttct ccagttatcg aaggaaccaa acctgcctat    2400
aaattcaagt cattagtgtc tactttggaa acatttttga agggttatga caaccaagtt    2460
attatgaacg cttccttgca acaattgata gaggttttga gaaatccaaa actgccttac    2520
tcagaatgga aactacacat ctctgctttta cattcaagat tgcctgctaa gctagatgaa    2580
caaatggaag agttagttgc acgttctttg agacgtggtg ctgttttccc agctagacaa    2640
ttaagtaaat tgattgatat ggccgtgaag aatcctgaat acaacccga caaattgctg    2700
ggcgccgtcg tggaaccatt ggcggatatt gctcataagt actctaacgg ttagaagcc    2760
catgaacatt ctatatttgt ccatttcttg gaagaatatt acgaagttga aaagttattc    2820
aatggtccaa atgttcgtga ggaaaatatc attctgaaat tgcgtgatga aaaccctaaa    2880
gatctagata aagttgcgct aactgttttg tctcattcga aagtttcagc gaagaataac    2940
ctgatcctag ctatcttgaa acattatcaa ccattgtgca agttatcttc taaagtttct    3000
gccattttct ctactcctct acaacatatt gttgaactag aatctaaggc taccgctaag    3060
gtcgctctac aagcaagaga aattttgatt caaggcgctt taccttcggt caaggaaaga    3120
actgaacaaa ttgaacatat cttaaaatcc tctgttgtga aggttgccta tggctcatcc    3180
aatccaaagc gctctgaacc agatttgaat atcttgaagg acttgatcga ttctaattac    3240
gttgtgttcg atgtttttact tcaattccta acccatcaag cccagttgt gactgctgca    3300
gctgctcaag tctatattcg tcgtgcttat cgtgcttaca ccataggaga tattagagtt    3360
cacgaaggtg tcacagttcc aattgttgaa tggaaattcc aactaccttc agctgcgttc    3420
tccaccttc caactgttaa atctaaaatg ggtatgaaca gggctgtttc tgtttcagat    3480
ttgtcatatg ttgcaaacag tcagtcatct ccgttaagag aaggtatttt gatggctgtg    3540
```

```
gatcatttag atgatgttga tgaaattttg tcacaaagtt tggaagttat tcctcgtcac   3600
caatcttctt ctaacggacc tgctcctgat cgttctggta gctccgcatc gttgagtaat   3660
gttgctaatg tttgtgttgc ttctacagaa ggtttcgaat ctgaagagga aattttggta   3720
aggttgagag aaattttgga tttgaataag caggaattaa tcaatgcttc tatccgtcgt   3780
atcacattta tgttcggttt taaagatggg tcttatccaa agtattatac ttttaacggt   3840
ccaaattata acgaaaatga aacaattcgt cacattgagc cggctttggc cttccaactg   3900
gaattaggaa gattgtccaa cttcaacatt aaaccaattt tcactgataa tagaaacatc   3960
catgtctacg aagctgttag taagacttct ccattggata agagattctt tacaagaggt   4020
attattagaa cgggtcatat ccgtgatgac atttctattc aagaatatct gacttctgaa   4080
gctaacagat tgatgagtga tatattggat aatttagaag tcaccgacac ttcaaattct   4140
gatttgaatc atatcttcat caacttcatt gcggtgtttg atatctctcc agaagatgtc   4200
gaagccgcct tcggtggttt cttagaaaga tttggtaaga gattgttgag attgcgtgtt   4260
tcttctgccg aaattagaat catcatcaaa gatcctcaaa caggtgcccc agtaccattg   4320
cgtgccttga tcaataacgt ttctggttat gttatcaaaa cagaaatgta caccgaagtc   4380
aagaacgcaa aaggtgaatg ggtatttaag tctttgggta aacctggatc catgcattta   4440
agacctattg ctactcctta ccctgttaag gaatggttgc aaccaaaacg ttataaggca   4500
cacttgatgg gtaccacata tgtctatgac ttcccagaat tattccgcca agcatcgtca   4560
tcccaatgga aaaatttctc tgcagatgtt aagttaacag atgatttctt tatttccaac   4620
gagttgattg aagatgaaaa cggcgaatta actgaggtgg aaagagaacc tggtgccaac   4680
gctattggta tggttgcctt taagattact gtaaagactc ctgaatatcc aagaggccgt   4740
caatttgttg ttgttgctaa cgatatcaca ttcaagatcg gttcctttgg tccacaagaa   4800
gacgaattct tcaataaggt tactgaatat gctagaaagc gtggtatccc aagaatttac   4860
ttggctgcaa actcaggtgc cagaattggt atggctgaag agattgttcc actatttcaa   4920
gttgcatgga atgatgctgc caatccggac aagggcttcc aatacttata cttaacaagt   4980
gaaggtatgg aaactttaaa gaaatttgac aaagaaaatt ctgttctcac tgaacgtact   5040
gttataaacg gtgaagaaag atttgtcatc aagacaatta ttggttctga agatgggtta   5100
ggtgtcgaat gtctacgtgg atctggttta attgctggtg caacgtcaag gcttaccac    5160 gatatcttca ctatcacctt agtcacttgt agatccgtcg gtatcggtgc ttatttggtt   5220
cgtttgggtc aaagagctat tcaggtcgaa ggccagccaa ttattttaac tggtgctcct   5280
gcaatcaaca aaatgctggg tagagaagtt tatacttcta acttacaatt gggtggtact   5340
caaatcatgt ataacaacgg tgtttcacat ttgactgctg ttgacgattt agctggtgta   5400
gagaagattg ttgaatggat gtcttatgtt ccagccaagc gtaatatgcc agttcctatc   5460
ttggaaacta agacacatg ggatagacca gttgatttca ctccaactaa tgatgaaact   5520
tacgatgtaa gatggatgat tgaaggtcgt gagactgaaa gtggatttga atatggtttg   5580
tttgataaag ggtctttctt tgaaactttg tcaggatggg ccaaaggtgt tgtcgttggt   5640
agagcccgtc ttggtggtat tccactgggt gttattggtt tgaaacaag aactgtcgag   5700 aacttgattc ctgctgatcc agctaatcca aatagtgctg aaacattaat tcaagaacct   5760
ggtcaagttt ggcatccaaa ctccgccttc aagactgctc aagctatcaa tgactttaac   5820
aacggtgaac aattgccaat gatgattttg gccaactgga gaggtttctc tggtggtcaa   5880
```

| | |
|---|---|
| cgtgatatgt tcaacgaagt cttgaagtat ggttcgttta ttgttgacgc attggtggat | 5940 |
| tacaaacaac caattattat ctatatccca cctaccggtg aactaagagg tggttcatgg | 6000 |
| gttgttgtcg atccaactat caacgctgac caaatggaaa tgtatgccga cgtcaacgct | 6060 |
| agagctggtg ttttggaacc acaaggtatg gttggtatca agttccgtag agaaaaattg | 6120 |
| ctggacacca tgaacagatt ggatgacaag tacagagaat tgagatctca attatccaac | 6180 |
| aagagtttgg ctccagaagt catcagcaa atatccaagc aattagctga tcgtgagaga | 6240 |
| gaactattgc caatttacgg acaaatcagt cttcaatttg ctgatttgca cgataggtct | 6300 |
| tcacgtatgg tggccaaggg tgttatttct aaggaactgg aatggaccga ggcacgtcgt | 6360 |
| ttcttcttct ggagattgag aagaagattg aacgaagaat atttgattaa aaggttgagc | 6420 |
| catcaggtag gcgaagcatc aagattagaa aagatcgcaa gaattagatc gtggtaccct | 6480 |
| gcttcagtgg accatgaaga tgataggcaa gtcgcaacat ggattgaaga aaactacaaa | 6540 |
| actttggacg ataaactaaa gggttttgaaa ttagagtcat tcgctcaaga cttagctaaa | 6600 |
| aagatcagaa gcgaccatga caatgctatt gatggattat ctgaagttat caagatgtta | 6660 |
| tctaccgatg ataaagaaaa attgttgaag actttgaaat aa | 6702 |

<210> SEQ ID NO 20
<211> LENGTH: 5664
<212> TYPE: DNA
<213> ORGANISM: Saccharomyces cerevisiae

<400> SEQUENCE: 20

| | |
|---|---|
| atgaagccgg aagttgagca agaattagct catattttgc taactgaatt gttagcttat | 60 |
| caatttgcct ctcctgtgag atggattgaa actcaagatg ttttttttgaa ggattttaac | 120 |
| actgaaaggg ttgttgaaat cggtccttct ccaactttgg ctgggatggc tcaaagaacc | 180 |
| ttgaagaata aatacgaatc ttacgatgct gctctgtctt tacatagaga atcttatgc | 240 |
| tattcgaagg atgccaaaga gatttattat accccagatc catccgaact agctgcaaag | 300 |
| gaagagcccg ctaaggaaga agctcctgct ccaactccag ctgctagtgc tcctgctcct | 360 |
| gcagcagcag ccccagctcc cgtcgcggca gcagccccag ctgcagcagc tgctgagatt | 420 |
| gccgatgaac ctgtcaaggc ttccctattg ttgcacgttt tggttgctca aagttgaag | 480 |
| aagtcgttag attccattcc aatgtccaag acaatcaaag acttggtcgg tggtaaatct | 540 |
| acagtccaaa atgaaatttt gggtgattta ggtaaagaat ttggtactac tcctgaaaaa | 600 |
| ccagaagaaa ctccattaga agaattggca gaaactttcc aagataccTT ctctggagca | 660 |
| ttgggtaagc aatcttcctc gttattatca agattaatct catctaagat gcctggtggg | 720 |
| tttactatta ctgtcgctag aaaatactta caaactcgct ggggactacc atctggtaga | 780 |
| caagatggtg tccttttggt agctttatct aacgagcctg ctgctcgtct aggttctgaa | 840 |
| gctgatgcca aggcttttctt ggactccatg gctcaaaaat acgcttccat tgttggtgtt | 900 |
| gacttatcat cagctgctag cgctagtggt gctgccggtg caggtgctgc tgccggtgca | 960 |
| gctatgatcg atgctggcgc tctggaagaa ataaccaaag accacaaggt tttggcgcgt | 1020 |
| caacaactgc aagtattggc tcgttatcta aaaatggact tggataacgg tgaaagaaag | 1080 |
| ttcttgaaag aaaaggacac tgttgctgaa cttcaagctc agttggatta cttgaatgcc | 1140 |
| gaattaggtg aattctttgt taacggtgtt gctacttctt tctctagaaa aaaggccaga | 1200 |
| accttcgatt cttcctggaa ctgggctaaa caatctttat tatcattata ctttgagata | 1260 |
| attcatggtg tcttgaaaaa cgttgataga gaggttgtta gtgaagctat caatatcatg | 1320 |

```
aacagatcta acgatgcttt gattaaattc atggaatacc atatctctaa cactgatgaa    1380
acaaaaggtg aaaactatca attggttaaa actcttggtg agcagttgat tgaaaactgt    1440
aaacaagttt tggatgttga tccagtttac aaagatgttg ctaagcctac cggtccaaaa    1500
actgctattg acaagaacgg taacattaca tactcagaag agccaagaga aaaggttagg    1560
aaattatctc aatacgtaca agaaatggcc cttggtggtc aatcaccaa agaatctcaa    1620 cctactattg aagaggattt gactcgtgtt tacaaggcaa tcagtgctca agctgataaa    1680
caagatattt ccagctccac cagggttgaa tttgaaaaac tatatagtga tttgatgaag    1740
ttcttggaaa gctccaaaga aatcgatcct tctcaaacaa cccaattggc cggtatggat    1800
gttgaggatg ctttggacaa agattccacc aaagaagttg cttctttgcc aaacaaatct    1860
accatttcta agacggtatc ttcaactatt ccaagagaaa ctattccgtt cttacatttg    1920
agaaagaaga ctcctgccgg agattggaaa tatgaccgcc aattgtcttc tctttctta    1980 gatggtttag aaaaggctgc cttcaacggt gtcaccttca aggacaaata cgtcttgatc    2040
actggtgctg gtaagggttc tattggtgct gaagtcttgc aaggtttgtt acaaggtggt    2100
gctaaggttg ttgttaccac ctctcgtttc tctaagcaag ttacagacta ctaccaatcc    2160
atttacgcca aatatggtgc taagggttct actttgattg ttgttccatt caaccaaggt    2220
tctaagcaag acgttgaagc tttgattgaa tttatctacg acactgaaaa gaatggtggt    2280
ttaggttggg atctagatgc tattattcca ttcgcggcca ttccagaaca aggtattgaa    2340
ttagaacata ttgattctaa gtctgaattt gctcatagaa tcatgttgac caatatctta    2400
agaatgatgg gttgtgtcaa gaagcaaaaa tctgcaagag gtattgaaac aagaccagct    2460
caagtcattc taccaatgtc tccaaaccat ggtactttcg gtggtgatgg tatgtattca    2520
gaatccaagt tgtctttgga aactttgttc aacagatggc actctgaatc ctgggccaat    2580
caattaaccg tttgcggtgc tattattggt tggactagag gtactggttt aatgagcgct    2640
aataacatca ttgctgaagg cattgaaaag atgggtgttc gtactttctc tcaaaaggaa    2700
atggctttca acttattggg tctattgact ccagaagtcg tagaattgtg ccaaaaatca    2760
cctgttatgg ctgacttgaa tggtggtttg caatttgttc ctgaattgaa ggaattcact    2820
gctaaattgc gtaaagagtt ggttgaaact tctgaagtta gaaaggcagt ttccatcgaa    2880
actgctttgg agcataaggt tgtcaatggc aatagcgctg atgctgcata tgctcaagtc    2940
gaaattcaac caagagctaa cattcaactg gacttcccag aattgaaacc atacaaacag    3000
gttaaacaaa ttgctcccgc tgagcttgaa ggtttgttgg atttggaaag agttattgta    3060
gttaccggtt ttgctgaagt cggcccatgg ggttcggcca aacaagatg ggaaatggaa    3120 gcttttggtg aattttcgtt ggaaggttgc gttgaaatgg cctggattat gggcttcatt    3180
tcataccata acggtaattt gaagggtcgt ccatacactg ttgggttga ttccaaaaca    3240 aaagaaccag ttgatgacaa ggacgttaag gccaagtatg aaacatcaat cctagaacac    3300
agtggtatca gattgatcga accagagtta ttcaatggtt acaacccaga aaagaaggaa    3360
atgattcaag aagtcattgt cgaagaagac ttggaaccat ttgaggcttc gaaggaaact    3420
gccgaacaat ttaaacacca acatggtgac aaagtggata tcttcgaaat cccagaaaca    3480
ggagagtact ctgttaagtt actaaagggt gccactttat acattccaaa ggctttgaga    3540
tttgaccgtt tggttgcagg tcaaattcca actggtggga atgctaagac ttatggtatc    3600
tctgatgata tcatttctca ggttgaccca atcacattat tcgttttggt ctctgttgtg    3660
```

| | |
|---|---|
| gaagcattta ttgcatctgg tatcaccgac ccatacgaaa tgtacaaata cgtacatgtt | 3720 |
| tctgaggttg gtaactgttc tggttctggt atgggtggtg tttctgcctt acgtggtatg | 3780 |
| tttaaggacc gtttcaagga tgagcctgtc caaaatgata ttttacaaga atcatttatc | 3840 |
| aacaccatgt ccgcttgggt taatatgttg ttgatttcct catctggtcc aatcaagaca | 3900 |
| cctgttggtg cctgtgccac atccgtggaa tctgttgaca ttggtgtaga aaccatcttg | 3960 |
| tctggtaagg ctagaatctg tattgtcggt ggttacgatg atttccaaga agaaggctcc | 4020 |
| tttgagttcg gtaacatgaa ggccacttcc aacactttgg aagaatttga acatggtcgt | 4080 |
| accccagcgg aaatgtccag acctgccacc actacccgta acggttttat ggaagctcaa | 4140 |
| ggtgctggta ttcaaatcat catgcaagct gatttagctt tgaagatggg tgtgccaatt | 4200 |
| tacggtattg ttgccatggc tgctaccgcc accgataaga ttggtagatc tgtgccagct | 4260 |
| ccaggtaagg gtattttaac cactgctcgt gaacaccact ccagtgttaa gtatgcttca | 4320 |
| ccaaacttga acatgaagta cagaaagcgc caattggtta ctcgtgaagc tcagattaaa | 4380 |
| gattgggtag aaaacgaatt ggaagctttg aagttggagg ccgaagaaat tccaagcgaa | 4440 |
| gaccaaaacg agttcttact gaacgtacc agagaaatcc acaacgaagc tgaaagtcaa | 4500 |
| ttgagagctg cacaacaaca atggggtaac gacttctaca agagggaccc acgtattgct | 4560 |
| ccattgagag gagcactggc tacttacggt ttaactattg atgacttggg tgtcgcttca | 4620 |
| ttccacggta catccacaaa ggctaatgac aagaacgaat ctgccacaat taatgaaatg | 4680 |
| atgaagcatt tgggtagatc tgaaggtaat cccgtcattg gtgttttcca aaagttcttg | 4740 |
| actggtcatc caaagggtgc tgctggtgca tggatgatga atggtgcttt gcaaattcta | 4800 |
| aacagtggta ttattccagg taaccgtaac gctgataacg tggataagat cttggagcaa | 4860 |
| tttgaatacg tcttgtaccc atccaagact ttaaagaccg acggtgtcag agccgtgtcc | 4920 |
| atcacttctt tcggttttgg tcaaaagggt ggtcaagcta ttgtggttca tccagactac | 4980 |
| ttatacggtg ctatcactga agacagatac aacgagtatg tcgccaaggt tagtgccaga | 5040 |
| gagaaaagtg cctacaaatt cttccataat ggtatgatct acaacaagtt gttcgtaagt | 5100 |
| aaagagcatg ctccatacac tgatgaattg gaagaggatg tttacttgga cccattagcc | 5160 |
| cgtgtatcta aggataagaa atcaggctcc ttgactttca actctaaaaa catccaaagc | 5220 |
| aaggacagtt acatcaatgc taacaccatt gaaactgcca agatgattga aaacatgacc | 5280 |
| aaggagaaag tctctaacgg tggcgtcggt gtagatgttg aattaatcac tagcatcaac | 5340 |
| gttgaaaatg atacttttat cgagcgcaat ttcaccccgc aagaaataga gtactgcagc | 5400 |
| gcgcagccta gtgtgcaaag ctctttcgct gggacatggt ccgccaaaga ggctgttttc | 5460 |
| aagtccttag gcgtcaagtc cttaggcggt ggtgctgcat tgaaagacat cgaaatcgta | 5520 |
| cgcgttaaca aaaacgctcc agccgttgaa ctgcacggta acgccaaaaa ggctgccgaa | 5580 |
| gaagctggtg ttaccgatgt gaaggtatct atttctcacg atgacctcca agctgtcgcg | 5640 |
| gtcgccgttt ctactaagaa atag | 5664 |

<210> SEQ ID NO 21
<211> LENGTH: 521
<212> TYPE: PRT
<213> ORGANISM: Candida maltosa

<400> SEQUENCE: 21

Met Ile Asp Glu Ile Leu Pro Lys Leu Val Gln Tyr Trp Tyr Ile Val
1               5                   10                  15

```
Leu Pro Thr Leu Leu Ile Ile Lys His Val Ser Tyr Ile Asn Thr
            20                  25                  30

Gln Arg Leu Met Arg Lys Phe Arg Ala Lys Pro Val Thr Asn Val Leu
        35                  40                  45

Asn Asp Gly Phe Phe Gly Ile Pro Asn Gly Ile Lys Ala Ile Lys Glu
 50                  55                  60

Lys Asn Lys Gly Arg Ala Gln Glu Tyr Asn Asp Glu Lys Phe Ala Ala
 65                  70                  75                  80

Gly Pro Lys Pro Lys Val Gly Thr Tyr Leu Phe Lys Leu Phe Thr Lys
                85                  90                  95

Asp Val Leu Val Thr Lys Asp Pro Glu Asn Ile Lys Ala Ile Leu Ala
                100                 105                 110

Thr Gln Phe Glu Asp Phe Ser Leu Gly Lys Arg Leu Asp Phe Phe Lys
            115                 120                 125

Pro Leu Leu Gly Tyr Gly Ile Phe Thr Leu Asp Gly Glu Gly Trp Lys
        130                 135                 140

His Ser Arg Ala Met Leu Arg Pro Gln Phe Ala Arg Glu Gln Val Gly
145                 150                 155                 160

His Val Lys Leu Ile Glu Pro His Phe Gln Ser Leu Lys Lys His Ile
                165                 170                 175

Ile Lys Asn Lys Gly Gln Phe Phe Asp Ile Gln Glu Leu Phe Phe Arg
            180                 185                 190

Phe Thr Val Asp Ser Ala Thr Glu Phe Leu Phe Gly Glu Ser Val Glu
        195                 200                 205

Ser Leu Lys Asp Glu Ser Ile Gly Tyr Asp Gln Asp Phe Asp Phe
    210                 215                 220

Asp Gly Arg Lys Asn Phe Ala Glu Ala Phe Asn Lys Ala Gln Glu Tyr
225                 230                 235                 240

Leu Gly Thr Arg Ala Ile Leu Gln Ser Phe Tyr Trp Leu Val Asn Gly
                245                 250                 255

Ala Asp Phe Lys Lys Ser Val Ala Glu Val His Lys Phe Thr Asp Tyr
                260                 265                 270

Tyr Val Gln Lys Ala Leu Asp Ala Thr Pro Glu Glu Leu Glu Lys His
        275                 280                 285

Ser Gly Tyr Ile Phe Leu Tyr Glu Leu Val Gln Gln Thr Arg Asp Pro
    290                 295                 300

Lys Val Leu Arg Asp Gln Ser Leu Asn Ile Leu Leu Ala Gly Arg Asp
305                 310                 315                 320

Thr Thr Ala Gly Leu Leu Ser Phe Ala Leu Phe Glu Leu Ala Arg Asn
                325                 330                 335

Pro Glu Val Trp Ser Arg Leu Arg Glu Glu Ile Gly Asp Lys Phe Gly
                340                 345                 350

Leu Asp Glu Asp Ala Thr Ile Glu Gly Ile Ser Phe Glu Ser Leu Lys
        355                 360                 365

Gln Cys Glu Tyr Leu Lys Ala Val Val Asn Glu Cys Leu Arg Met Tyr
    370                 375                 380

Pro Ser Val Pro Arg Asn Phe Arg Ile Ala Thr Lys His Thr Thr Leu
385                 390                 395                 400

Pro Arg Gly Gly Gly Pro Asp Gly Lys Asp Pro Ile Phe Ile Lys Lys
                405                 410                 415

Gly Ala Val Val Ser Tyr Gly Ile Asn Ser Thr His Leu Asp Pro Met
                420                 425                 430

Tyr Tyr Gly Pro Asp Ala Arg Leu Phe Asn Pro Asp Arg Trp Ser Lys
```

```
                435                 440                 445
Pro Glu Thr Lys Lys Leu Gly Trp Ala Phe Leu Pro Phe Asn Gly Gly
    450                 455                 460

Pro Arg Ile Cys Leu Gly Gln Gln Phe Ala Leu Thr Glu Ala Ser Tyr
465                 470                 475                 480

Val Leu Val Arg Met Ile Gln Asn Phe Lys Glu Leu Glu Leu Thr Pro
                485                 490                 495

Asn Thr Val Tyr Pro Pro Arg Arg Leu Thr Asn Leu Thr Met Ser Leu
            500                 505                 510

Tyr Asp Gly Ala Tyr Ile Lys Val Asn
            515                 520

<210> SEQ ID NO 22
<211> LENGTH: 680
<212> TYPE: PRT
<213> ORGANISM: Candida maltosa

<400> SEQUENCE: 22

Met Ala Leu Asp Lys Leu Asp Leu Tyr Val Ile Ile Val Leu Ala Val
1               5                   10                  15

Ala Val Ala Ala Tyr Phe Ala Lys Asn Gln Phe Leu Asp Gln Pro Gln
                20                  25                  30

Asp Thr Gly Phe Leu Ser Asn Asp Thr Ala Gly Gly Asn Ser Arg Asp
            35                  40                  45

Ile Leu Glu Thr Leu Lys Lys Asn Asn Lys Asn Thr Leu Leu Leu Phe
    50                  55                  60

Gly Ser Gln Thr Gly Thr Ala Glu Asp Tyr Ala Asn Lys Leu Ser Arg
65                  70                  75                  80

Glu Ile His Ser Arg Phe Gly Leu Lys Thr Met Val Ala Asp Phe Ala
                85                  90                  95

Asp Tyr Asp Trp Asp Asn Phe Gly Asp Ile Pro Asn Asp Ile Leu Val
            100                 105                 110

Phe Phe Ile Val Ala Thr Tyr Gly Glu Gly Glu Pro Thr Asp Asn Ala
    115                 120                 125

Asp Glu Phe His Thr Trp Leu Thr Asp Glu Ala Asp Thr Leu Ser Thr
130                 135                 140

Leu Arg Tyr Thr Val Phe Gly Leu Gly Asn Ser Thr Tyr Glu Phe Tyr
145                 150                 155                 160

Asn Ala Ile Gly Arg Lys Phe Asp Arg Leu Leu Glu Glu Lys Gly Gly
                165                 170                 175

Glu Arg Phe Ala Asp Tyr Gly Glu Gly Asp Asp Gly Thr Gly Thr Leu
            180                 185                 190

Asp Glu Asp Phe Leu Thr Trp Lys Asp Asn Val Phe Asp Thr Leu Lys
    195                 200                 205

Asn Asp Leu Asn Phe Glu Glu Arg Glu Leu Lys Tyr Glu Pro Asn Val
210                 215                 220

Lys Leu Thr Glu Arg Asp Asp Leu Thr Val Asp Asp Ser Glu Val Ser
225                 230                 235                 240

Leu Gly Glu Pro Asn Lys Lys Tyr Ile Gln Ser Glu Glu Ile Asp Leu
                245                 250                 255

Thr Lys Gly Pro Phe Asp His Thr His Pro Tyr Leu Ala Lys Ile Ser
            260                 265                 270

Lys Thr Arg Glu Leu Phe Ala Ser Lys Glu Arg Asn Cys Val His Val
    275                 280                 285
```

```
Glu Phe Asp Val Ser Glu Ser Asn Leu Lys Tyr Thr Thr Gly Asp His
    290                 295                 300
Leu Ala Val Trp Pro Ser Asn Ser Asp Glu Asn Ile Ala Lys Phe Ile
305                 310                 315                 320
Lys Cys Phe Gly Leu Asp Asp Lys Ile Asn Thr Val Phe Glu Leu Lys
                325                 330                 335
Ala Leu Asp Ser Thr Tyr Gln Ile Pro Phe Pro Asn Pro Ile Thr Tyr
            340                 345                 350
Gly Ala Val Val Arg His His Leu Glu Ile Ser Gly Pro Val Ser Arg
        355                 360                 365
Gln Phe Phe Leu Ala Ile Ala Gly Phe Ala Pro Asp Glu Glu Thr Lys
    370                 375                 380
Lys Thr Phe Thr Arg Ile Gly Asn Asp Lys Gln Glu Phe Ala Asn Lys
385                 390                 395                 400
Ile Thr Arg Lys Lys Leu Asn Val Ala Asp Ala Leu Leu Phe Ala Ser
                405                 410                 415
Asn Gly Arg Pro Trp Ser Asp Val Pro Phe Glu Phe Ile Ile Glu Asn
            420                 425                 430
Val Pro His Leu Gln Pro Arg Tyr Tyr Ser Ile Ser Ser Ser Ser Leu
        435                 440                 445
Ser Glu Lys Gln Thr Ile Asn Ile Thr Ala Val Val Glu Val Glu Glu
    450                 455                 460
Glu Ala Asp Gly Arg Ala Val Thr Gly Val Val Thr Asn Leu Leu Lys
465                 470                 475                 480
Asn Ile Glu Ile Glu Gln Asn Lys Thr Gly Glu Lys Pro Val Val His
                485                 490                 495
Tyr Asp Leu Ser Gly Pro Arg Asn Lys Phe Asn Lys Phe Lys Leu Pro
            500                 505                 510
Val His Val Arg Arg Ser Asn Phe Lys Leu Pro Lys Asn Thr Thr Thr
        515                 520                 525
Pro Val Ile Leu Ile Gly Pro Gly Thr Gly Val Ala Pro Leu Arg Gly
    530                 535                 540
Phe Val Arg Glu Arg Val Gln Gln Val Lys Asn Gly Val Asn Val Gly
545                 550                 555                 560
Lys Thr Val Leu Phe Tyr Gly Cys Arg Asn Glu His Asp Asp Phe Leu
                565                 570                 575
Tyr Lys Gln Glu Trp Ser Glu Tyr Ala Ser Val Leu Gly Glu Asn Phe
            580                 585                 590
Glu Met Phe Thr Ala Phe Ser Arg Gln Asp Pro Ser Lys Lys Val Tyr
        595                 600                 605
Val Gln Asp Lys Ile Ala Glu Asn Ser Lys Val Asn Asp Leu Leu
    610                 615                 620
Asn Glu Gly Ala Ile Ile Tyr Val Cys Gly Asp Ala Ser Arg Met Ala
625                 630                 635                 640
Arg Asp Val Gln Ser Thr Ile Ala Lys Ile Val Ala Lys His Arg Glu
                645                 650                 655
Ile Gln Glu Asp Lys Ala Val Glu Leu Val Lys Ser Trp Lys Val Gln
            660                 665                 670
Asn Arg Tyr Gln Glu Asp Val Trp
        675                 680

<210> SEQ ID NO 23
<211> LENGTH: 556
<212> TYPE: PRT
```

-continued

<213> ORGANISM: Humulus lupulus

<400> SEQUENCE: 23

```
Met Glu Asp Leu Lys Pro Arg Pro Ala Ser Ser Pro Leu Thr Pro
1               5                   10                  15

Leu Gly Phe Leu Glu Arg Ala Ala Thr Val Tyr Gly Asp Cys Thr Ser
            20                  25                  30

Val Val Tyr Asp Ala Val Ser Tyr Thr Trp Ser Gln Thr His Arg Arg
                35                  40                  45

Cys Leu Cys Leu Ala Ser Ser Ile Ala Ser Leu Gly Ile Glu Asn Gly
            50                  55                  60

His Val Val Ser Val Leu Ala Pro Asn Val Pro Gln Met Tyr Glu Leu
65                  70                  75                  80

His Phe Ala Val Pro Met Ala Gly Ala Ile Leu Asn Ala Val Asn Leu
                85                  90                  95

Arg Leu Asp Ala Arg Thr Ile Ser Ile Leu Leu His His Ser Glu Ser
            100                 105                 110

Lys Leu Ile Phe Val Asp His Leu Ser Arg Asp Leu Ile Leu Glu Ala
            115                 120                 125

Ile Ala Leu Phe Pro Lys Gln Ala Pro Val Pro Arg Leu Val Phe Met
130                 135                 140

Ala Asp Glu Ser Glu Ser Gly Asn Ser Ser Glu Leu Gly Lys Glu Phe
145                 150                 155                 160

Phe Cys Ser Tyr Lys Asp Leu Ile Asp Arg Gly Asp Pro Asp Phe Lys
                165                 170                 175

Trp Val Met Pro Lys Ser Glu Trp Asp Pro Met Ile Leu Asn Tyr Thr
            180                 185                 190

Ser Gly Thr Thr Ser Ser Pro Lys Gly Val Val His Cys His Arg Gly
            195                 200                 205

Ile Phe Ile Met Thr Val Asp Ser Leu Ile Asp Trp Gly Val Pro Lys
210                 215                 220

Gln Pro Val Tyr Leu Trp Thr Leu Pro Met Phe His Ala Asn Gly Trp
225                 230                 235                 240

Ser Tyr Pro Trp Gly Met Ala Ala Val Gly Gly Thr Asn Ile Cys Leu
                245                 250                 255

Arg Lys Phe Asp Ser Glu Ile Ile Tyr Asp Met Ile Lys Arg His Gly
            260                 265                 270

Val Thr His Met Cys Gly Ala Pro Val Val Leu Asn Met Leu Ser Asn
            275                 280                 285

Ala Pro Gly Ser Glu Pro Leu Lys Thr Thr Val Gln Ile Met Thr Ala
290                 295                 300

Gly Ala Pro Pro Pro Ser Ala Val Leu Phe Arg Thr Glu Ser Leu Gly
305                 310                 315                 320

Phe Ala Val Ser His Gly Tyr Gly Leu Thr Glu Thr Ala Gly Leu Val
                325                 330                 335

Val Ser Cys Ala Trp Lys Lys Glu Trp Asn His Leu Pro Ala Thr Glu
            340                 345                 350

Arg Ala Arg Leu Lys Ser Arg Gln Gly Val Gly Thr Val Met Gln Thr
            355                 360                 365

Lys Ile Asp Val Val Asp Pro Val Thr Gly Ala Ala Val Lys Arg Asp
            370                 375                 380

Gly Ser Thr Leu Gly Glu Val Val Leu Arg Gly Gly Ser Val Met Leu
385                 390                 395                 400
```

```
Gly Tyr Leu Lys Asp Pro Glu Gly Thr Ala Lys Ser Met Thr Ala Asp
            405                 410                 415
Gly Trp Phe Tyr Thr Gly Asp Val Gly Val Met His Pro Asp Gly Tyr
        420                 425                 430
Leu Glu Ile Lys Asp Arg Ser Lys Asp Val Ile Ile Ser Gly Gly Glu
            435                 440                 445
Asn Leu Ser Ser Val Glu Val Glu Ser Ile Leu Tyr Ser His Pro Asp
450                 455                 460
Ile Leu Glu Ala Ala Val Val Ala Arg Pro Asp Glu Phe Trp Gly Glu
465                 470                 475                 480
Thr Pro Cys Ala Phe Val Ser Leu Lys Lys Gly Leu Thr Lys Lys Pro
                485                 490                 495
Thr Glu Lys Glu Ile Val Glu Tyr Cys Arg Ser Lys Leu Pro Arg Tyr
            500                 505                 510
Met Val Pro Lys Thr Val Val Phe Lys Glu Glu Leu Pro Lys Thr Ser
            515                 520                 525
Thr Gly Lys Val Gln Lys Phe Ile Leu Arg Asp Met Ala Arg Gly Met
        530                 535                 540
Gly Ser Ala Thr Ala Gly Ala Ser Arg Ser Arg Met
545                 550                 555

<210> SEQ ID NO 24
<211> LENGTH: 556
<212> TYPE: PRT
<213> ORGANISM: Solanum tuberosum

<400> SEQUENCE: 24

Met Glu Asp Leu Lys Pro Arg Pro Ala Ser Ser Pro Leu Thr Pro
1               5                   10                  15
Leu Gly Phe Leu Glu Arg Ala Ala Thr Val Tyr Gly Asp Cys Thr Ser
            20                  25                  30
Val Val Tyr Asp Ala Val Ser Tyr Thr Trp Ser Gln Thr His Arg Arg
        35                  40                  45
Cys Leu Cys Leu Ala Ser Ser Ile Ala Ser Leu Gly Ile Glu Asn Gly
    50                  55                  60
His Val Val Ser Val Leu Ala Pro Asn Val Pro Gln Met Tyr Glu Leu
65                  70                  75                  80
His Phe Ala Val Pro Met Ala Gly Ala Ile Leu Asn Ala Val Asn Leu
                85                  90                  95
Arg Leu Asp Ala Arg Thr Ile Ser Ile Leu Leu His His Ser Glu Ser
            100                 105                 110
Lys Leu Ile Phe Val Asp His Leu Ser Arg Asp Leu Ile Leu Glu Ala
        115                 120                 125
Ile Ala Leu Phe Pro Lys Gln Ala Pro Val Pro Arg Leu Val Phe Met
    130                 135                 140
Ala Asp Glu Ser Glu Ser Gly Asn Ser Ser Glu Leu Gly Lys Glu Phe
145                 150                 155                 160
Phe Cys Ser Tyr Lys Asp Leu Ile Asp Arg Gly Asp Pro Asp Phe Lys
                165                 170                 175
Trp Val Met Pro Lys Ser Glu Asp Pro Met Ile Leu Asn Tyr Thr
            180                 185                 190
Ser Gly Thr Thr Ser Ser Pro Lys Gly Val Val His Cys His Arg Gly
        195                 200                 205
Ile Phe Ile Met Thr Val Asp Ser Leu Ile Asp Trp Gly Val Pro Lys
    210                 215                 220
```

Gln Pro Val Tyr Leu Trp Thr Leu Pro Met Phe His Ala Asn Gly Trp
225                 230                 235                 240

Ser Tyr Pro Trp Gly Met Ala Ala Val Gly Gly Thr Asn Ile Cys Leu
                245                 250                 255

Arg Lys Phe Asp Ser Glu Ile Ile Tyr Asp Met Ile Lys Arg His Gly
            260                 265                 270

Val Thr His Met Cys Gly Ala Pro Val Leu Asn Met Leu Ser Asn
        275                 280                 285

Ala Pro Gly Ser Glu Pro Leu Lys Thr Thr Val Gln Ile Met Thr Ala
290                 295                 300

Gly Ala Pro Pro Ser Ala Val Leu Phe Arg Thr Glu Ser Leu Gly
305                 310                 315                 320

Phe Ala Val Ser His Gly Tyr Gly Leu Thr Glu Thr Ala Gly Leu Val
                325                 330                 335

Val Ser Cys Ala Trp Lys Lys Glu Trp Asn His Leu Pro Ala Thr Glu
            340                 345                 350

Arg Ala Arg Leu Lys Ser Arg Gln Gly Val Gly Thr Val Met Gln Thr
                355                 360                 365

Lys Ile Asp Val Val Asp Pro Val Thr Gly Ala Ala Val Lys Arg Asp
370                 375                 380

Gly Ser Thr Leu Gly Glu Val Val Leu Arg Gly Gly Ser Val Met Leu
385                 390                 395                 400

Gly Tyr Leu Lys Asp Pro Glu Gly Thr Ala Lys Ser Met Thr Ala Asp
                405                 410                 415

Gly Trp Phe Tyr Thr Gly Asp Val Gly Val Met His Pro Asp Gly Tyr
                420                 425                 430

Leu Glu Ile Lys Asp Arg Ser Lys Asp Val Ile Ser Gly Gly Glu
                435                 440                 445

Asn Leu Ser Ser Val Glu Val Glu Ser Ile Leu Tyr Ser His Pro Asp
450                 455                 460

Ile Leu Glu Ala Ala Val Val Ala Arg Pro Asp Glu Phe Trp Gly Glu
465                 470                 475                 480

Thr Pro Cys Ala Phe Val Ser Leu Lys Lys Gly Leu Thr Lys Lys Pro
                485                 490                 495

Thr Glu Lys Glu Ile Val Glu Tyr Cys Arg Ser Lys Leu Pro Arg Tyr
                500                 505                 510

Met Val Pro Lys Thr Val Val Phe Lys Glu Glu Leu Pro Lys Thr Ser
                515                 520                 525

Thr Gly Lys Val Gln Lys Phe Ile Leu Arg Asp Met Ala Arg Gly Met
                530                 535                 540

Gly Ser Ala Thr Ala Gly Ala Ser Arg Ser Arg Met
545                 550                 555

<210> SEQ ID NO 25
<211> LENGTH: 2051
<212> TYPE: PRT
<213> ORGANISM: Saccharomyces cerevisiae

<400> SEQUENCE: 25

Met Asp Ala Tyr Ser Thr Arg Pro Leu Thr Leu Ser His Gly Ser Leu
1               5                   10                  15

Glu His Val Leu Leu Val Pro Thr Ala Ser Phe Phe Ile Ala Ser Gln
                20                  25                  30

Leu Gln Glu Gln Phe Asn Lys Ile Leu Pro Glu Pro Thr Glu Gly Phe

```
            35                  40                  45
Ala Ala Asp Asp Glu Pro Thr Thr Pro Ala Glu Leu Val Gly Lys Phe
    50                  55                  60
Leu Gly Tyr Val Ser Ser Leu Val Glu Pro Ser Lys Val Gly Gln Phe
 65                  70                  75                  80
Asp Gln Val Leu Asn Leu Cys Leu Thr Glu Phe Glu Asn Cys Tyr Leu
                 85                  90                  95
Glu Gly Asn Asp Ile His Ala Leu Ala Ala Lys Leu Leu Gln Glu Asn
                100                 105                 110
Asp Thr Thr Leu Val Lys Thr Lys Glu Leu Ile Lys Asn Tyr Ile Thr
                115                 120                 125
Ala Arg Ile Met Ala Lys Arg Pro Phe Asp Lys Lys Ser Asn Ser Ala
                130                 135                 140
Leu Phe Arg Ala Val Gly Glu Gly Asn Ala Gln Leu Val Ala Ile Phe
145                 150                 155                 160
Gly Gly Gln Gly Asn Thr Asp Asp Tyr Phe Glu Glu Leu Arg Asp Leu
                165                 170                 175
Tyr Gln Thr Tyr His Val Leu Val Gly Asp Leu Ile Lys Phe Ser Ala
                180                 185                 190
Glu Thr Leu Ser Glu Leu Ile Arg Thr Thr Leu Asp Ala Glu Lys Val
                195                 200                 205
Phe Thr Gln Gly Leu Asn Ile Leu Glu Trp Leu Glu Asn Pro Ser Asn
210                 215                 220
Thr Pro Asp Lys Asp Tyr Leu Leu Ser Ile Pro Ile Ser Cys Pro Leu
225                 230                 235                 240
Ile Gly Val Ile Gln Leu Ala His Tyr Val Val Thr Ala Lys Leu Leu
                245                 250                 255
Gly Phe Thr Pro Gly Glu Leu Arg Ser Tyr Leu Lys Gly Ala Thr Gly
                260                 265                 270
His Ser Gln Gly Leu Val Thr Ala Val Ala Ile Ala Glu Thr Asp Ser
                275                 280                 285
Trp Glu Ser Phe Phe Val Ser Val Arg Lys Ala Ile Thr Val Leu Phe
                290                 295                 300
Phe Ile Gly Val Arg Cys Tyr Glu Ala Tyr Pro Asn Thr Ser Leu Pro
305                 310                 315                 320
Pro Ser Ile Leu Glu Asp Ser Leu Glu Asn Asn Glu Gly Val Pro Ser
                325                 330                 335
Pro Met Leu Ser Ile Ser Asn Leu Thr Gln Glu Gln Val Gln Asp Tyr
                340                 345                 350
Val Asn Lys Thr Asn Ser His Leu Pro Ala Gly Lys Gln Val Glu Ile
                355                 360                 365
Ser Leu Val Asn Gly Ala Lys Asn Leu Val Val Ser Gly Pro Pro Gln
                370                 375                 380
Ser Leu Tyr Gly Leu Asn Leu Thr Leu Arg Lys Ala Lys Ala Pro Ser
385                 390                 395                 400
Gly Leu Asp Gln Ser Arg Ile Pro Phe Ser Glu Arg Lys Leu Lys Phe
                405                 410                 415
Ser Asn Arg Phe Leu Pro Val Ala Ser Pro Phe His Ser His Leu Leu
                420                 425                 430
Val Pro Ala Ser Asp Leu Ile Asn Lys Asp Leu Val Lys Asn Asn Val
                435                 440                 445
Ser Phe Asn Ala Lys Asp Ile Gln Ile Pro Val Tyr Asp Thr Phe Asp
                450                 455                 460
```

```
Gly Ser Asp Leu Arg Val Leu Ser Gly Ser Ile Ser Glu Arg Ile Val
465                 470                 475                 480

Asp Cys Ile Ile Arg Leu Pro Val Lys Trp Glu Thr Thr Thr Gln Phe
                    485                 490                 495

Lys Ala Thr His Ile Leu Asp Phe Gly Pro Gly Gly Ala Ser Gly Leu
                500                 505                 510

Gly Val Leu Thr His Arg Asn Lys Asp Gly Thr Gly Val Arg Val Ile
                515                 520                 525

Val Ala Gly Thr Leu Asp Ile Asn Pro Asp Asp Tyr Gly Phe Lys
530                 535                 540

Gln Glu Ile Phe Asp Val Thr Ser Asn Gly Leu Lys Lys Asn Pro Asn
545                 550                 555                 560

Trp Leu Glu Glu Tyr His Pro Lys Leu Ile Lys Asn Lys Ser Gly Lys
                565                 570                 575

Ile Phe Val Glu Thr Lys Phe Ser Lys Leu Ile Gly Arg Pro Pro Leu
                580                 585                 590

Leu Val Pro Gly Met Thr Pro Cys Thr Val Ser Pro Asp Phe Val Ala
                595                 600                 605

Ala Thr Thr Asn Ala Gly Tyr Thr Ile Glu Leu Ala Gly Gly Gly Tyr
610                 615                 620

Phe Ser Ala Ala Gly Met Thr Ala Ala Ile Asp Ser Val Val Ser Gln
625                 630                 635                 640

Ile Glu Lys Gly Ser Thr Phe Gly Ile Asn Leu Ile Tyr Val Asn Pro
                645                 650                 655

Phe Met Leu Gln Trp Gly Ile Pro Leu Ile Lys Glu Leu Arg Ser Lys
                660                 665                 670

Gly Tyr Pro Ile Gln Phe Leu Thr Ile Gly Ala Gly Val Pro Ser Leu
                675                 680                 685

Glu Val Ala Ser Glu Tyr Ile Glu Thr Leu Gly Leu Lys Tyr Leu Gly
                690                 695                 700

Leu Lys Pro Gly Ser Ile Asp Ala Ile Ser Gln Val Ile Asn Ile Ala
705                 710                 715                 720

Lys Ala His Pro Asn Phe Pro Ile Ala Leu Gln Trp Thr Gly Gly Arg
                725                 730                 735

Gly Gly Gly His His Ser Phe Glu Asp Ala His Thr Pro Met Leu Gln
                740                 745                 750

Met Tyr Ser Lys Ile Arg Arg His Pro Asn Ile Met Leu Ile Phe Gly
                755                 760                 765

Ser Gly Phe Gly Ser Ala Asp Asp Thr Tyr Pro Tyr Leu Thr Gly Glu
                770                 775                 780

Trp Ser Thr Lys Phe Asp Tyr Pro Pro Met Pro Phe Asp Gly Phe Leu
785                 790                 795                 800

Phe Gly Ser Arg Val Met Ile Ala Lys Glu Val Lys Thr Ser Pro Asp
                805                 810                 815

Ala Lys Lys Cys Ile Ala Ala Cys Thr Gly Val Pro Asp Asp Lys Trp
                820                 825                 830

Glu Gln Thr Tyr Lys Lys Pro Thr Gly Gly Ile Val Thr Val Arg Ser
                835                 840                 845

Glu Met Gly Glu Pro Ile His Lys Ile Ala Thr Arg Gly Val Met Leu
                850                 855                 860

Trp Lys Glu Phe Asp Glu Thr Ile Phe Asn Leu Pro Lys Asn Lys Leu
865                 870                 875                 880
```

-continued

```
Val Pro Thr Leu Glu Ala Lys Arg Asp Tyr Ile Ile Ser Arg Leu Asn
            885                 890                 895

Ala Asp Phe Gln Lys Pro Trp Phe Ala Thr Val Asn Gly Gln Ala Arg
            900                 905                 910

Asp Leu Ala Thr Met Thr Tyr Glu Glu Val Ala Lys Arg Leu Val Glu
            915                 920                 925

Leu Met Phe Ile Arg Ser Thr Asn Ser Trp Phe Asp Val Thr Trp Arg
930                 935                 940

Thr Phe Thr Gly Asp Phe Leu Arg Arg Val Glu Arg Phe Thr Lys
945                 950                 955                 960

Ser Lys Thr Leu Ser Leu Ile Gln Ser Tyr Ser Leu Leu Asp Lys Pro
            965                 970                 975

Asp Glu Ala Ile Glu Lys Val Phe Asn Ala Tyr Pro Ala Ala Arg Glu
            980                 985                 990

Gln Phe Leu Asn Ala Gln Asp Ile Asp His Phe Leu Ser Met Cys Gln
            995                 1000                1005

Asn Pro Met Gln Lys Pro Val Pro Phe Val Pro Val Leu Asp Arg
            1010                1015                1020

Arg Phe Glu Ile Phe Phe Lys Lys Asp Ser Leu Trp Gln Ser Glu
        1025                1030                1035

His Leu Glu Ala Val Val Asp Gln Asp Val Gln Arg Thr Cys Ile
        1040                1045                1050

Leu His Gly Pro Val Ala Ala Gln Phe Thr Lys Val Ile Asp Glu
        1055                1060                1065

Pro Ile Lys Ser Ile Met Asp Gly Ile His Asp Gly His Ile Lys
        1070                1075                1080

Lys Leu Leu His Gln Tyr Tyr Gly Asp Asp Glu Ser Lys Ile Pro
        1085                1090                1095

Ala Val Glu Tyr Phe Gly Gly Glu Ser Pro Val Asp Val Gln Ser
        1100                1105                1110

Gln Val Asp Ser Ser Ser Val Ser Glu Asp Ser Ala Val Phe Lys
        1115                1120                1125

Ala Thr Ser Ser Thr Asp Glu Glu Ser Trp Phe Lys Ala Leu Ala
        1130                1135                1140

Gly Ser Glu Ile Asn Trp Arg His Ala Ser Phe Leu Cys Ser Phe
        1145                1150                1155

Ile Thr Gln Asp Lys Met Phe Val Ser Asn Pro Ile Arg Lys Val
        1160                1165                1170

Phe Lys Pro Ser Gln Gly Met Val Val Glu Ile Ser Asn Gly Asn
        1175                1180                1185

Thr Ser Ser Lys Thr Val Val Thr Leu Ser Glu Pro Val Gln Gly
        1190                1195                1200

Glu Leu Lys Pro Thr Val Ile Leu Lys Leu Leu Lys Glu Asn Ile
        1205                1210                1215

Ile Gln Met Glu Met Ile Glu Asn Arg Thr Met Asp Gly Lys Pro
        1220                1225                1230

Val Ser Leu Pro Leu Leu Tyr Asn Phe Asn Pro Asp Asn Gly Phe
        1235                1240                1245

Ala Pro Ile Ser Glu Val Met Glu Asp Arg Asn Gln Arg Ile Lys
        1250                1255                1260

Glu Met Tyr Trp Lys Leu Trp Ile Asp Glu Pro Phe Asn Leu Asp
        1265                1270                1275

Phe Asp Pro Arg Asp Val Ile Lys Gly Lys Asp Phe Glu Ile Thr
```

-continued

```
            1280                1285                1290
Ala Lys Glu Val Tyr Asp Phe Thr His Ala Val Gly Asn Asn Cys
    1295                1300                1305
Glu Asp Phe Val Ser Arg Pro Asp Arg Thr Met Leu Ala Pro Met
    1310                1315                1320
Asp Phe Ala Ile Val Val Gly Trp Arg Ala Ile Ile Lys Ala Ile
    1325                1330                1335
Phe Pro Asn Thr Val Asp Gly Asp Leu Leu Lys Leu Val His Leu
    1340                1345                1350
Ser Asn Gly Tyr Lys Met Ile Pro Gly Ala Lys Pro Leu Gln Val
    1355                1360                1365
Gly Asp Val Val Ser Thr Thr Ala Val Ile Glu Ser Val Val Asn
    1370                1375                1380
Gln Pro Thr Gly Lys Ile Val Asp Val Val Gly Thr Leu Ser Arg
    1385                1390                1395
Asn Gly Lys Pro Val Met Glu Val Thr Ser Ser Phe Phe Tyr Arg
    1400                1405                1410
Gly Asn Tyr Thr Asp Phe Glu Asn Thr Phe Gln Lys Thr Val Glu
    1415                1420                1425
Pro Val Tyr Gln Met His Ile Lys Thr Ser Lys Asp Ile Ala Val
    1430                1435                1440
Leu Arg Ser Lys Glu Trp Phe Gln Leu Asp Asp Glu Asp Phe Asp
    1445                1450                1455
Leu Leu Asn Lys Thr Leu Thr Phe Glu Thr Glu Thr Glu Val Thr
    1460                1465                1470
Phe Lys Asn Ala Asn Ile Phe Ser Ser Val Lys Cys Phe Gly Pro
    1475                1480                1485
Ile Lys Val Glu Leu Pro Thr Lys Glu Thr Val Glu Ile Gly Ile
    1490                1495                1500
Val Asp Tyr Glu Ala Gly Ala Ser His Gly Asn Pro Val Val Asp
    1505                1510                1515
Phe Leu Lys Arg Asn Gly Ser Thr Leu Glu Gln Lys Val Asn Leu
    1520                1525                1530
Glu Asn Pro Ile Pro Ile Ala Val Leu Asp Ser Tyr Thr Pro Ser
    1535                1540                1545
Thr Asn Glu Pro Tyr Ala Arg Val Ser Gly Asp Leu Asn Pro Ile
    1550                1555                1560
His Val Ser Arg His Phe Ala Ser Tyr Ala Asn Leu Pro Gly Thr
    1565                1570                1575
Ile Thr His Gly Met Phe Ser Ser Ala Ser Val Arg Ala Leu Ile
    1580                1585                1590
Glu Asn Trp Ala Ala Asp Ser Val Ser Ser Arg Val Arg Gly Tyr
    1595                1600                1605
Thr Cys Gln Phe Val Asp Met Val Leu Pro Asn Thr Ala Leu Lys
    1610                1615                1620
Thr Ser Ile Gln His Val Gly Met Ile Asn Gly Arg Lys Leu Ile
    1625                1630                1635
Lys Phe Glu Thr Arg Asn Glu Asp Asp Val Val Val Leu Thr Gly
    1640                1645                1650
Glu Ala Glu Ile Glu Gln Pro Val Thr Thr Phe Val Phe Thr Gly
    1655                1660                1665
Gln Gly Ser Gln Glu Gln Gly Met Gly Met Asp Leu Tyr Lys Thr
    1670                1675                1680
```

```
Ser Lys Ala Ala Gln Asp Val Trp Asn Arg Ala Asp Asn His Phe
1685                1690                1695

Lys Asp Thr Tyr Gly Phe Ser Ile Leu Asp Ile Val Ile Asn Asn
    1700                1705                1710

Pro Val Asn Leu Thr Ile His Phe Gly Gly Glu Lys Gly Lys Arg
1715                1720                1725

Ile Arg Glu Asn Tyr Ser Ala Met Ile Phe Glu Thr Ile Val Asp
    1730                1735                1740

Gly Lys Leu Lys Thr Glu Lys Ile Phe Lys Glu Ile Asn Glu His
1745                1750                1755

Ser Thr Ser Tyr Thr Phe Arg Ser Glu Lys Gly Leu Leu Ser Ala
1760                1765                1770

Thr Gln Phe Thr Gln Pro Ala Leu Thr Leu Met Glu Lys Ala Ala
1775                1780                1785

Phe Glu Asp Leu Lys Ser Lys Gly Leu Ile Pro Ala Asp Ala Thr
1790                1795                1800

Phe Ala Gly His Ser Leu Gly Glu Tyr Ala Ala Leu Ala Ser Leu
1805                1810                1815

Ala Asp Val Met Ser Ile Glu Ser Leu Val Glu Val Phe Tyr
1820                1825                1830

Arg Gly Met Thr Met Gln Val Ala Val Pro Arg Asp Glu Leu Gly
1835                1840                1845

Arg Ser Asn Tyr Gly Met Ile Ala Ile Asn Pro Gly Arg Val Ala
1850                1855                1860

Ala Ser Phe Ser Gln Glu Ala Leu Gln Tyr Val Val Glu Arg Val
1865                1870                1875

Gly Lys Arg Thr Gly Trp Leu Val Glu Ile Val Asn Tyr Asn Val
1880                1885                1890

Glu Asn Gln Gln Tyr Val Ala Ala Gly Asp Leu Arg Ala Leu Asp
1895                1900                1905

Thr Val Thr Asn Val Leu Asn Phe Ile Lys Leu Gln Lys Ile Asp
1910                1915                1920

Ile Ile Glu Leu Gln Lys Ser Leu Ser Leu Glu Glu Val Glu Gly
1925                1930                1935

His Leu Phe Glu Ile Ile Asp Glu Ala Ser Lys Lys Ser Ala Val
1940                1945                1950

Lys Pro Arg Pro Leu Lys Leu Glu Arg Gly Phe Ala Cys Ile Pro
1955                1960                1965

Leu Val Gly Ile Ser Val Pro Phe His Ser Thr Tyr Leu Met Asn
1970                1975                1980

Gly Val Lys Pro Phe Lys Ser Phe Leu Lys Lys Asn Ile Ile Lys
1985                1990                1995

Glu Asn Val Lys Val Ala Arg Leu Ala Gly Lys Tyr Ile Pro Asn
2000                2005                2010

Leu Thr Ala Lys Pro Phe Gln Val Thr Lys Glu Tyr Phe Gln Asp
2015                2020                2025

Val Tyr Asp Leu Thr Gly Ser Glu Pro Ile Lys Glu Ile Ile Asp
2030                2035                2040

Asn Trp Glu Lys Tyr Glu Gln Ser
2045                2050

<210> SEQ ID NO 26
<211> LENGTH: 2051
```

```
<212> TYPE: PRT
<213> ORGANISM: Saccharomyces cerevisiae

<400> SEQUENCE: 26

Met Asp Ala Tyr Ser Thr Arg Pro Leu Thr Leu Ser His Gly Ser Leu
1               5                   10                  15

Glu His Val Leu Leu Val Pro Thr Ala Ser Phe Phe Ile Ala Ser Gln
            20                  25                  30

Leu Gln Glu Gln Phe Asn Lys Ile Leu Pro Glu Pro Thr Glu Gly Phe
        35                  40                  45

Ala Ala Asp Asp Glu Pro Thr Thr Pro Ala Glu Leu Val Gly Lys Phe
    50                  55                  60

Leu Gly Tyr Val Ser Ser Leu Val Glu Pro Ser Lys Val Gly Gln Phe
65                  70                  75                  80

Asp Gln Val Leu Asn Leu Cys Leu Thr Glu Phe Glu Asn Cys Tyr Leu
                85                  90                  95

Glu Gly Asn Asp Ile His Ala Leu Ala Ala Lys Leu Leu Gln Glu Asn
            100                 105                 110

Asp Thr Thr Leu Val Lys Thr Lys Glu Leu Ile Lys Asn Tyr Ile Thr
        115                 120                 125

Ala Arg Ile Met Ala Lys Arg Pro Phe Asp Lys Lys Ser Asn Ser Ala
    130                 135                 140

Leu Phe Arg Ala Val Gly Glu Gly Asn Ala Gln Leu Val Ala Ile Phe
145                 150                 155                 160

Gly Gly Gln Gly Asn Thr Asp Asp Tyr Phe Glu Glu Leu Arg Asp Leu
                165                 170                 175

Tyr Gln Thr Tyr His Val Leu Val Gly Asp Leu Ile Lys Phe Ser Ala
            180                 185                 190

Glu Thr Leu Ser Glu Leu Ile Arg Thr Thr Leu Asp Ala Glu Lys Val
        195                 200                 205

Phe Thr Gln Gly Leu Asn Ile Leu Glu Trp Leu Glu Asn Pro Ser Asn
    210                 215                 220

Thr Pro Asp Lys Asp Tyr Leu Leu Ser Ile Pro Ile Ser Cys Pro Leu
225                 230                 235                 240

Ile Gly Val Ile Gln Leu Ala His Tyr Val Val Thr Ala Lys Leu Leu
                245                 250                 255

Gly Phe Thr Pro Gly Glu Leu Arg Ser Tyr Leu Lys Gly Ala Thr Gly
            260                 265                 270

His Ser Gln Gly Leu Val Thr Ala Val Ala Ile Ala Glu Thr Asp Ser
        275                 280                 285

Trp Glu Ser Phe Phe Val Ser Val Arg Lys Ala Ile Thr Val Leu Phe
    290                 295                 300

Phe Ile Gly Val Arg Cys Tyr Glu Ala Tyr Pro Asn Thr Ser Leu Pro
305                 310                 315                 320

Pro Ser Ile Leu Glu Asp Ser Leu Glu Asn Asn Glu Gly Val Pro Ser
                325                 330                 335

Pro Met Leu Ser Ile Ser Asn Leu Thr Gln Glu Gln Val Gln Asp Tyr
            340                 345                 350

Val Asn Lys Thr Asn Ser His Leu Pro Ala Gly Lys Gln Val Glu Ile
        355                 360                 365

Ser Leu Val Asn Gly Ala Lys Asn Leu Val Val Ser Gly Pro Pro Gln
    370                 375                 380

Ser Leu Tyr Gly Leu Asn Leu Thr Leu Arg Lys Ala Lys Ala Pro Ser
385                 390                 395                 400
```

```
Gly Leu Asp Gln Ser Arg Ile Pro Phe Ser Glu Arg Lys Leu Lys Phe
            405                 410                 415

Ser Asn Arg Phe Leu Pro Val Ala Ser Pro Phe His Ser His Leu Leu
            420                 425                 430

Val Pro Ala Ser Asp Leu Ile Asn Lys Asp Leu Val Lys Asn Asn Val
            435                 440                 445

Ser Phe Asn Ala Lys Asp Ile Gln Ile Pro Val Tyr Asp Thr Phe Asp
450                 455                 460

Gly Ser Asp Leu Arg Val Leu Ser Gly Ser Ile Ser Glu Arg Ile Val
465                 470                 475                 480

Asp Cys Ala Ile Arg Leu Pro Val Lys Trp Glu Thr Thr Thr Gln Phe
                485                 490                 495

Lys Ala Thr His Ile Leu Asp Phe Gly Pro Gly Gly Ala Ser Gly Leu
                500                 505                 510

Gly Val Leu Thr His Arg Asn Lys Asp Gly Thr Gly Val Arg Val Ile
                515                 520                 525

Val Ala Gly Thr Leu Asp Ile Asn Pro Asp Asp Asp Tyr Gly Phe Lys
            530                 535                 540

Gln Glu Ile Phe Asp Val Thr Ser Asn Gly Leu Lys Lys Asn Pro Asn
545                 550                 555                 560

Trp Leu Glu Glu Tyr His Pro Lys Leu Ile Lys Asn Lys Ser Gly Lys
                565                 570                 575

Ile Phe Val Glu Thr Lys Phe Ser Lys Leu Ile Gly Arg Pro Pro Leu
                580                 585                 590

Leu Val Pro Gly Met Thr Pro Cys Thr Val Ser Pro Asp Phe Val Ala
                595                 600                 605

Ala Thr Thr Asn Ala Gly Tyr Thr Ile Glu Leu Ala Gly Gly Gly Tyr
            610                 615                 620

Phe Ser Ala Ala Gly Met Thr Ala Ala Ile Asp Ser Val Val Ser Gln
625                 630                 635                 640

Ile Glu Lys Gly Ser Thr Phe Gly Ile Asn Leu Ile Tyr Val Asn Pro
                645                 650                 655

Phe Met Leu Gln Trp Gly Ile Pro Leu Ile Lys Glu Leu Arg Ser Lys
                660                 665                 670

Gly Tyr Pro Ile Gln Phe Leu Thr Ile Gly Ala Gly Val Pro Ser Leu
                675                 680                 685

Glu Val Ala Ser Glu Tyr Ile Glu Thr Leu Gly Leu Lys Tyr Leu Gly
            690                 695                 700

Leu Lys Pro Gly Ser Ile Asp Ala Ile Ser Gln Val Ile Asn Ile Ala
705                 710                 715                 720

Lys Ala His Pro Asn Phe Pro Ile Ala Leu Gln Trp Thr Gly Gly Arg
                725                 730                 735

Gly Gly Gly His His Ser Phe Glu Asp Ala His Thr Pro Met Leu Gln
                740                 745                 750

Met Tyr Ser Lys Ile Arg Arg His Pro Asn Ile Met Leu Ile Phe Gly
                755                 760                 765

Ser Gly Phe Gly Ser Ala Asp Asp Thr Tyr Pro Tyr Leu Thr Gly Glu
                770                 775                 780

Trp Ser Thr Lys Phe Asp Tyr Pro Pro Met Pro Phe Asp Gly Phe Leu
785                 790                 795                 800

Phe Gly Ser Arg Val Met Ile Ala Lys Glu Val Lys Thr Ser Pro Asp
                805                 810                 815
```

```
Ala Lys Lys Cys Ile Ala Ala Cys Thr Gly Val Pro Asp Lys Trp
                820             825             830

Glu Gln Thr Tyr Lys Lys Pro Thr Gly Gly Ile Val Thr Val Arg Ser
            835             840             845

Glu Met Gly Glu Pro Ile His Lys Ile Ala Thr Arg Gly Val Met Leu
        850             855             860

Trp Lys Glu Phe Asp Glu Thr Ile Phe Asn Leu Pro Lys Asn Lys Leu
865             870             875             880

Val Pro Thr Leu Glu Ala Lys Arg Asp Tyr Ile Ile Ser Arg Leu Asn
                885             890             895

Ala Asp Phe Gln Lys Pro Trp Phe Ala Thr Val Asn Gly Gln Ala Arg
            900             905             910

Asp Leu Ala Thr Met Thr Tyr Glu Glu Val Ala Lys Arg Leu Val Glu
        915             920             925

Leu Met Phe Ile Arg Ser Thr Asn Ser Trp Phe Asp Val Thr Trp Arg
930             935             940

Thr Phe Thr Gly Asp Phe Leu Arg Arg Val Glu Glu Arg Phe Thr Lys
945             950             955             960

Ser Lys Thr Leu Ser Leu Ile Gln Ser Tyr Ser Leu Leu Asp Lys Pro
            965             970             975

Asp Glu Ala Ile Glu Lys Val Phe Asn Ala Tyr Pro Ala Ala Arg Glu
        980             985             990

Gln Phe Leu Asn Ala Gln Asp Ile Asp His Phe Leu Ser Met Cys Gln
            995             1000            1005

Asn Pro Met Gln Lys Pro Val Pro Phe Val Pro Val Leu Asp Arg
        1010            1015            1020

Arg Phe Glu Ile Phe Phe Lys Lys Asp Ser Leu Trp Gln Ser Glu
        1025            1030            1035

His Leu Glu Ala Val Val Asp Gln Asp Val Gln Arg Thr Cys Ile
        1040            1045            1050

Leu His Gly Pro Val Ala Ala Gln Phe Thr Lys Val Ile Asp Glu
        1055            1060            1065

Pro Ile Lys Ser Ile Met Asp Gly Ile His Asp Gly His Ile Lys
        1070            1075            1080

Lys Leu Leu His Gln Tyr Tyr Gly Asp Asp Glu Ser Lys Ile Pro
        1085            1090            1095

Ala Val Glu Tyr Phe Gly Gly Glu Ser Pro Val Asp Val Gln Ser
        1100            1105            1110

Gln Val Asp Ser Ser Ser Val Ser Glu Asp Ser Ala Val Phe Lys
        1115            1120            1125

Ala Thr Ser Ser Thr Asp Glu Glu Ser Trp Phe Lys Ala Leu Ala
        1130            1135            1140

Gly Ser Glu Ile Asn Trp Arg His Ala Ser Phe Leu Cys Ser Phe
        1145            1150            1155

Ile Thr Gln Asp Lys Met Phe Val Ser Asn Pro Ile Arg Lys Val
        1160            1165            1170

Phe Lys Pro Ser Gln Gly Met Val Val Glu Ile Ser Asn Gly Asn
        1175            1180            1185

Thr Ser Ser Lys Thr Val Val Thr Leu Ser Glu Pro Val Gln Gly
        1190            1195            1200

Glu Leu Lys Pro Thr Val Ile Leu Lys Leu Leu Lys Glu Asn Ile
        1205            1210            1215

Ile Gln Met Glu Met Ile Glu Asn Arg Thr Met Asp Gly Lys Pro
```

```
                1220                1225                1230
Val Ser Leu Pro Leu Leu Tyr Asn Phe Asn Pro Asp Asn Gly Phe
    1235                1240                1245

Ala Pro Ile Ser Glu Val Met Glu Asp Arg Asn Gln Arg Ile Lys
    1250                1255                1260

Glu Met Tyr Trp Lys Leu Trp Ile Asp Glu Pro Phe Asn Leu Asp
    1265                1270                1275

Phe Asp Pro Arg Asp Val Ile Lys Gly Lys Asp Phe Glu Ile Thr
    1280                1285                1290

Ala Lys Glu Val Tyr Asp Phe Thr His Ala Val Gly Asn Asn Cys
    1295                1300                1305

Glu Asp Phe Val Ser Arg Pro Asp Arg Thr Met Leu Ala Pro Met
    1310                1315                1320

Asp Phe Ala Ile Val Val Gly Trp Arg Ala Ile Ile Lys Ala Ile
    1325                1330                1335

Phe Pro Asn Thr Val Asp Gly Asp Leu Leu Lys Leu Val His Leu
    1340                1345                1350

Ser Asn Gly Tyr Lys Met Ile Pro Gly Ala Lys Pro Leu Gln Val
    1355                1360                1365

Gly Asp Val Val Ser Thr Thr Ala Val Ile Glu Ser Val Val Asn
    1370                1375                1380

Gln Pro Thr Gly Lys Ile Val Asp Val Val Gly Thr Leu Ser Arg
    1385                1390                1395

Asn Gly Lys Pro Val Met Glu Val Thr Ser Ser Phe Phe Tyr Arg
    1400                1405                1410

Gly Asn Tyr Thr Asp Phe Glu Asn Thr Phe Gln Lys Thr Val Glu
    1415                1420                1425

Pro Val Tyr Gln Met His Ile Lys Thr Ser Lys Asp Ile Ala Val
    1430                1435                1440

Leu Arg Ser Lys Glu Trp Phe Gln Leu Asp Asp Glu Asp Phe Asp
    1445                1450                1455

Leu Leu Asn Lys Thr Leu Thr Phe Glu Thr Glu Thr Glu Val Thr
    1460                1465                1470

Phe Lys Asn Ala Asn Ile Phe Ser Ser Val Lys Cys Phe Gly Pro
    1475                1480                1485

Ile Lys Val Glu Leu Pro Thr Lys Glu Thr Val Glu Ile Gly Ile
    1490                1495                1500

Val Asp Tyr Glu Ala Gly Ala Ser His Gly Asn Pro Val Val Asp
    1505                1510                1515

Phe Leu Lys Arg Asn Gly Ser Thr Leu Glu Gln Lys Val Asn Leu
    1520                1525                1530

Glu Asn Pro Ile Pro Ile Ala Val Leu Asp Ser Tyr Thr Pro Ser
    1535                1540                1545

Thr Asn Glu Pro Tyr Ala Arg Val Ser Gly Asp Leu Asn Pro Ile
    1550                1555                1560

His Val Ser Arg His Phe Ala Ser Tyr Ala Asn Leu Pro Gly Thr
    1565                1570                1575

Ile Thr His Gly Met Phe Ser Ser Ala Ser Val Arg Ala Leu Ile
    1580                1585                1590

Glu Asn Trp Ala Ala Asp Ser Val Ser Ser Arg Val Arg Gly Tyr
    1595                1600                1605

Thr Cys Gln Phe Val Asp Met Val Leu Pro Asn Thr Ala Leu Lys
    1610                1615                1620
```

```
Thr Ser Ile Gln His Val Gly Met Ile Asn Gly Arg Lys Leu Ile
    1625            1630            1635

Lys Phe Glu Thr Arg Asn Glu Asp Val Val Leu Thr Gly
    1640            1645            1650

Glu Ala Glu Ile Glu Gln Pro Val Thr Thr Phe Val Phe Thr Gly
    1655            1660            1665

Gln Gly Ser Gln Glu Gln Gly Met Gly Met Asp Leu Tyr Lys Thr
    1670            1675            1680

Ser Lys Ala Ala Gln Asp Val Trp Asn Arg Ala Asp Asn His Phe
    1685            1690            1695

Lys Asp Thr Tyr Gly Phe Ser Ile Leu Asp Ile Val Ile Asn Asn
    1700            1705            1710

Pro Val Asn Leu Thr Ile His Phe Gly Gly Glu Lys Gly Lys Arg
    1715            1720            1725

Ile Arg Glu Asn Tyr Ser Ala Met Ile Phe Glu Thr Ile Val Asp
    1730            1735            1740

Gly Lys Leu Lys Thr Glu Lys Ile Phe Lys Glu Ile Asn Glu His
    1745            1750            1755

Ser Thr Ser Tyr Thr Phe Arg Ser Glu Lys Gly Leu Leu Ser Ala
    1760            1765            1770

Thr Gln Phe Thr Gln Pro Ala Leu Thr Leu Met Glu Lys Ala Ala
    1775            1780            1785

Phe Glu Asp Leu Lys Ser Lys Gly Leu Ile Pro Ala Asp Ala Thr
    1790            1795            1800

Phe Ala Gly His Ser Leu Gly Glu Tyr Ala Ala Leu Ala Ser Leu
    1805            1810            1815

Ala Asp Val Met Ser Ile Glu Ser Leu Val Glu Val Val Phe Tyr
    1820            1825            1830

Arg Gly Met Thr Met Gln Val Ala Val Pro Arg Asp Glu Leu Gly
    1835            1840            1845

Arg Ser Asn Tyr Gly Met Ile Ala Ile Asn Pro Gly Arg Val Ala
    1850            1855            1860

Ala Ser Phe Ser Gln Glu Ala Leu Gln Tyr Val Val Glu Arg Val
    1865            1870            1875

Gly Lys Arg Thr Gly Trp Leu Val Glu Ile Val Asn Tyr Asn Val
    1880            1885            1890

Glu Asn Gln Gln Tyr Val Ala Ala Gly Asp Leu Arg Ala Leu Asp
    1895            1900            1905

Thr Val Thr Asn Val Leu Asn Phe Ile Lys Leu Gln Lys Ile Asp
    1910            1915            1920

Ile Ile Glu Leu Gln Lys Ser Leu Ser Leu Glu Glu Val Glu Gly
    1925            1930            1935

His Leu Phe Glu Ile Ile Asp Glu Ala Ser Lys Lys Ser Ala Val
    1940            1945            1950

Lys Pro Arg Pro Leu Lys Leu Glu Arg Gly Phe Ala Cys Ile Pro
    1955            1960            1965

Leu Val Gly Ile Ser Val Pro Phe His Ser Thr Tyr Leu Met Asn
    1970            1975            1980

Gly Val Lys Pro Phe Lys Ser Phe Leu Lys Lys Asn Ile Ile Lys
    1985            1990            1995

Glu Asn Val Lys Val Ala Arg Leu Ala Gly Lys Tyr Ile Pro Asn
    2000            2005            2010
```

```
Leu Thr Ala Lys Pro Phe Gln Val Thr Lys Glu Tyr Phe Gln Asp
    2015                2020                2025

Val Tyr Asp Leu Thr Gly Ser Glu Pro Ile Lys Glu Ile Ile Asp
    2030                2035                2040

Asn Trp Glu Lys Tyr Glu Gln Ser
    2045                2050

<210> SEQ ID NO 27
<211> LENGTH: 2051
<212> TYPE: PRT
<213> ORGANISM: Saccharomyces cerevisiae

<400> SEQUENCE: 27

Met Asp Ala Tyr Ser Thr Arg Pro Leu Thr Leu Ser His Gly Ser Leu
1               5                   10                  15

Glu His Val Leu Leu Val Pro Thr Ala Ser Phe Phe Ile Ala Ser Gln
                20                  25                  30

Leu Gln Glu Gln Phe Asn Lys Ile Leu Pro Glu Pro Thr Glu Gly Phe
            35                  40                  45

Ala Ala Asp Asp Glu Pro Thr Thr Pro Ala Glu Leu Val Gly Lys Phe
        50                  55                  60

Leu Gly Tyr Val Ser Ser Leu Val Glu Pro Ser Lys Val Gly Gln Phe
65                  70                  75                  80

Asp Gln Val Leu Asn Leu Cys Leu Thr Glu Phe Glu Asn Cys Tyr Leu
                85                  90                  95

Glu Gly Asn Asp Ile His Ala Leu Ala Ala Lys Leu Leu Gln Glu Asn
            100                 105                 110

Asp Thr Thr Leu Val Lys Thr Lys Glu Leu Ile Lys Asn Tyr Ile Thr
        115                 120                 125

Ala Arg Ile Met Ala Lys Arg Pro Phe Asp Lys Ser Asn Ser Ala
    130                 135                 140

Leu Phe Arg Ala Val Gly Glu Gly Asn Ala Gln Leu Val Ala Ile Phe
145                 150                 155                 160

Gly Gly Gln Gly Asn Thr Asp Asp Tyr Phe Glu Glu Leu Arg Asp Leu
                165                 170                 175

Tyr Gln Thr Tyr His Val Leu Val Gly Asp Leu Ile Lys Phe Ser Ala
            180                 185                 190

Glu Thr Leu Ser Glu Leu Ile Arg Thr Thr Leu Asp Ala Glu Lys Val
        195                 200                 205

Phe Thr Gln Gly Leu Asn Ile Leu Glu Trp Leu Glu Asn Pro Ser Asn
    210                 215                 220

Thr Pro Asp Lys Asp Tyr Leu Leu Ser Ile Pro Ile Ser Cys Pro Leu
225                 230                 235                 240

Ile Gly Val Ile Gln Leu Ala His Tyr Val Val Thr Ala Lys Leu Leu
                245                 250                 255

Gly Phe Thr Pro Gly Glu Leu Arg Ser Tyr Leu Lys Gly Ala Thr Gly
            260                 265                 270

His Ser Gln Gly Leu Val Thr Ala Val Ala Ile Ala Glu Thr Asp Ser
        275                 280                 285

Trp Glu Ser Phe Phe Val Ser Val Arg Lys Ala Ile Thr Val Leu Phe
    290                 295                 300

Phe Ile Gly Val Arg Cys Tyr Glu Ala Tyr Pro Asn Thr Ser Leu Pro
305                 310                 315                 320

Pro Ser Ile Leu Glu Asp Ser Leu Glu Asn Asn Glu Gly Val Pro Ser
                325                 330                 335
```

```
Pro Met Leu Ser Ile Ser Asn Leu Thr Gln Glu Gln Val Gln Asp Tyr
            340                 345                 350

Val Asn Lys Thr Asn Ser His Leu Pro Ala Gly Lys Gln Val Glu Ile
            355                 360                 365

Ser Leu Val Asn Gly Ala Lys Asn Leu Val Val Ser Gly Pro Pro Gln
370                 375                 380

Ser Leu Tyr Gly Leu Asn Leu Thr Leu Arg Lys Ala Lys Ala Pro Ser
385                 390                 395                 400

Gly Leu Asp Gln Ser Arg Ile Pro Phe Ser Glu Arg Lys Leu Lys Phe
            405                 410                 415

Ser Asn Arg Phe Leu Pro Val Ala Ser Pro Ala His Ser His Leu Leu
            420                 425                 430

Val Pro Ala Ser Asp Leu Ile Asn Lys Asp Leu Val Lys Asn Asn Val
            435                 440                 445

Ser Phe Asn Ala Lys Asp Ile Gln Ile Pro Val Tyr Asp Thr Phe Asp
            450                 455                 460

Gly Ser Asp Leu Arg Val Leu Ser Gly Ser Ile Ser Glu Arg Ile Val
465                 470                 475                 480

Asp Cys Ile Ile Arg Leu Pro Val Lys Trp Glu Thr Thr Thr Gln Phe
                485                 490                 495

Lys Ala Thr His Ile Leu Asp Phe Gly Pro Gly Gly Ala Ser Gly Leu
            500                 505                 510

Gly Val Leu Thr His Arg Asn Lys Asp Gly Thr Gly Val Arg Val Ile
            515                 520                 525

Val Ala Gly Thr Leu Asp Ile Asn Pro Asp Asp Tyr Gly Phe Lys
530                 535                 540

Gln Glu Ile Phe Asp Val Thr Ser Asn Gly Leu Lys Lys Asn Pro Asn
545                 550                 555                 560

Trp Leu Glu Glu Tyr His Pro Lys Leu Ile Lys Asn Lys Ser Gly Lys
                565                 570                 575

Ile Phe Val Glu Thr Lys Phe Ser Lys Leu Ile Gly Arg Pro Pro Leu
            580                 585                 590

Leu Val Pro Gly Met Thr Pro Cys Thr Val Ser Pro Asp Phe Val Ala
            595                 600                 605

Ala Thr Thr Asn Ala Gly Tyr Thr Ile Glu Leu Ala Gly Gly Gly Tyr
610                 615                 620

Phe Ser Ala Ala Gly Met Thr Ala Ala Ile Asp Ser Val Val Ser Gln
625                 630                 635                 640

Ile Glu Lys Gly Ser Thr Phe Gly Ile Asn Leu Ile Tyr Val Asn Pro
                645                 650                 655

Phe Met Leu Gln Trp Gly Ile Pro Leu Ile Lys Glu Leu Arg Ser Lys
            660                 665                 670

Gly Tyr Pro Ile Gln Phe Leu Thr Ile Gly Ala Gly Val Pro Ser Leu
            675                 680                 685

Glu Val Ala Ser Glu Tyr Ile Glu Thr Leu Gly Leu Lys Tyr Leu Gly
            690                 695                 700

Leu Lys Pro Gly Ser Ile Asp Ala Ile Ser Gln Val Ile Asn Ile Ala
705                 710                 715                 720

Lys Ala His Pro Asn Phe Pro Ile Ala Leu Gln Trp Thr Gly Gly Arg
                725                 730                 735

Gly Gly Gly His His Ser Phe Glu Asp Ala His Thr Pro Met Leu Gln
            740                 745                 750
```

```
Met Tyr Ser Lys Ile Arg Arg His Pro Asn Ile Met Leu Ile Phe Gly
            755                 760                 765
Ser Gly Phe Gly Ser Ala Asp Asp Thr Tyr Pro Tyr Leu Thr Gly Glu
    770                 775                 780
Trp Ser Thr Lys Phe Asp Tyr Pro Pro Met Pro Phe Asp Gly Phe Leu
785                 790                 795                 800
Phe Gly Ser Arg Val Met Ile Ala Lys Glu Val Lys Thr Ser Pro Asp
                805                 810                 815
Ala Lys Lys Cys Ile Ala Ala Cys Thr Gly Val Pro Asp Lys Trp
                820                 825                 830
Glu Gln Thr Tyr Lys Lys Pro Thr Gly Gly Ile Val Thr Val Arg Ser
            835                 840                 845
Glu Met Gly Glu Pro Ile His Lys Ile Ala Thr Arg Gly Val Met Leu
    850                 855                 860
Trp Lys Glu Phe Asp Glu Thr Ile Phe Asn Leu Pro Lys Asn Lys Leu
865                 870                 875                 880
Val Pro Thr Leu Glu Ala Lys Arg Asp Tyr Ile Ile Ser Arg Leu Asn
                885                 890                 895
Ala Asp Phe Gln Lys Pro Trp Phe Ala Thr Val Asn Gly Gln Ala Arg
            900                 905                 910
Asp Leu Ala Thr Met Thr Tyr Glu Glu Val Ala Lys Arg Leu Val Glu
    915                 920                 925
Leu Met Phe Ile Arg Ser Thr Asn Ser Trp Phe Asp Val Thr Trp Arg
930                 935                 940
Thr Phe Thr Gly Asp Phe Leu Arg Arg Val Glu Glu Arg Phe Thr Lys
945                 950                 955                 960
Ser Lys Thr Leu Ser Leu Ile Gln Ser Tyr Ser Leu Leu Asp Lys Pro
                965                 970                 975
Asp Glu Ala Ile Glu Lys Val Phe Asn Ala Tyr Pro Ala Ala Arg Glu
            980                 985                 990
Gln Phe Leu Asn Ala Gln Asp Ile Asp His Phe Leu Ser Met Cys Gln
    995                 1000                1005
Asn Pro Met Gln Lys Pro Val Pro Phe Val Pro Val Leu Asp Arg
    1010                1015                1020
Arg Phe Glu Ile Phe Phe Lys Lys Asp Ser Leu Trp Gln Ser Glu
    1025                1030                1035
His Leu Glu Ala Val Val Asp Gln Asp Val Gln Arg Thr Cys Ile
    1040                1045                1050
Leu His Gly Pro Val Ala Ala Gln Phe Thr Lys Val Ile Asp Glu
    1055                1060                1065
Pro Ile Lys Ser Ile Met Asp Gly Ile His Asp Gly His Ile Lys
    1070                1075                1080
Lys Leu Leu His Gln Tyr Tyr Gly Asp Asp Glu Ser Lys Ile Pro
    1085                1090                1095
Ala Val Glu Tyr Phe Gly Gly Glu Ser Pro Val Asp Val Gln Ser
    1100                1105                1110
Gln Val Asp Ser Ser Val Ser Glu Asp Ser Ala Val Phe Lys
    1115                1120                1125
Ala Thr Ser Ser Thr Asp Glu Glu Ser Trp Phe Lys Ala Leu Ala
    1130                1135                1140
Gly Ser Glu Ile Asn Trp Arg His Ala Ser Phe Leu Cys Ser Phe
    1145                1150                1155
Ile Thr Gln Asp Lys Met Phe Val Ser Asn Pro Ile Arg Lys Val
```

|       |       |       |       | 1160  |       |       |       | 1165  |       |       |       | 1170  |       |       |

Phe Lys Pro Ser Gln Gly Met Val Val Glu Ile Ser Asn Gly Asn
            1175                1180                1185

Thr Ser Ser Lys Thr Val Val Thr Leu Ser Glu Pro Val Gln Gly
            1190                1195                1200

Glu Leu Lys Pro Thr Val Ile Leu Lys Leu Leu Lys Glu Asn Ile
            1205                1210                1215

Ile Gln Met Glu Met Ile Glu Asn Arg Thr Met Asp Gly Lys Pro
            1220                1225                1230

Val Ser Leu Pro Leu Leu Tyr Asn Phe Asn Pro Asp Asn Gly Phe
            1235                1240                1245

Ala Pro Ile Ser Glu Val Met Glu Asp Arg Asn Gln Arg Ile Lys
            1250                1255                1260

Glu Met Tyr Trp Lys Leu Trp Ile Asp Glu Pro Phe Asn Leu Asp
            1265                1270                1275

Phe Asp Pro Arg Asp Val Ile Lys Gly Lys Asp Phe Glu Ile Thr
            1280                1285                1290

Ala Lys Glu Val Tyr Asp Phe Thr His Ala Val Gly Asn Asn Cys
            1295                1300                1305

Glu Asp Phe Val Ser Arg Pro Asp Arg Thr Met Leu Ala Pro Met
            1310                1315                1320

Asp Phe Ala Ile Val Val Gly Trp Arg Ala Ile Ile Lys Ala Ile
            1325                1330                1335

Phe Pro Asn Thr Val Asp Gly Asp Leu Leu Lys Leu Val His Leu
            1340                1345                1350

Ser Asn Gly Tyr Lys Met Ile Pro Gly Ala Lys Pro Leu Gln Val
            1355                1360                1365

Gly Asp Val Val Ser Thr Thr Ala Val Ile Glu Ser Val Val Asn
            1370                1375                1380

Gln Pro Thr Gly Lys Ile Val Asp Val Val Gly Thr Leu Ser Arg
            1385                1390                1395

Asn Gly Lys Pro Val Met Glu Val Thr Ser Ser Phe Phe Tyr Arg
            1400                1405                1410

Gly Asn Tyr Thr Asp Phe Glu Asn Thr Phe Gln Lys Thr Val Glu
            1415                1420                1425

Pro Val Tyr Gln Met His Ile Lys Thr Ser Lys Asp Ile Ala Val
            1430                1435                1440

Leu Arg Ser Lys Glu Trp Phe Gln Leu Asp Asp Glu Asp Phe Asp
            1445                1450                1455

Leu Leu Asn Lys Thr Leu Thr Phe Glu Thr Glu Thr Glu Val Thr
            1460                1465                1470

Phe Lys Asn Ala Asn Ile Phe Ser Ser Val Lys Cys Phe Gly Pro
            1475                1480                1485

Ile Lys Val Glu Leu Pro Thr Lys Glu Thr Val Glu Ile Gly Ile
            1490                1495                1500

Val Asp Tyr Glu Ala Gly Ala Ser His Gly Asn Pro Val Val Asp
            1505                1510                1515

Phe Leu Lys Arg Asn Gly Ser Thr Leu Glu Gln Lys Val Asn Leu
            1520                1525                1530

Glu Asn Pro Ile Pro Ile Ala Val Leu Asp Ser Tyr Thr Pro Ser
            1535                1540                1545

Thr Asn Glu Pro Tyr Ala Arg Val Ser Gly Asp Leu Asn Pro Ile
            1550                1555                1560

```
His Val Ser Arg His Phe Ala Ser Tyr Ala Asn Leu Pro Gly Thr
    1565            1570            1575

Ile Thr His Gly Met Phe Ser Ser Ala Ser Val Arg Ala Leu Ile
    1580            1585            1590

Glu Asn Trp Ala Ala Asp Ser Val Ser Ser Arg Val Arg Gly Tyr
    1595            1600            1605

Thr Cys Gln Phe Val Asp Met Val Leu Pro Asn Thr Ala Leu Lys
    1610            1615            1620

Thr Ser Ile Gln His Val Gly Met Ile Asn Gly Arg Lys Leu Ile
    1625            1630            1635

Lys Phe Glu Thr Arg Asn Glu Asp Asp Val Val Leu Thr Gly
    1640            1645            1650

Glu Ala Glu Ile Glu Gln Pro Val Thr Thr Phe Val Phe Thr Gly
    1655            1660            1665

Gln Gly Ser Gln Glu Gln Gly Met Gly Met Asp Leu Tyr Lys Thr
    1670            1675            1680

Ser Lys Ala Ala Gln Asp Val Trp Asn Arg Ala Asp Asn His Phe
    1685            1690            1695

Lys Asp Thr Tyr Gly Phe Ser Ile Leu Asp Ile Val Ile Asn Asn
    1700            1705            1710

Pro Val Asn Leu Thr Ile His Phe Gly Gly Glu Lys Gly Lys Arg
    1715            1720            1725

Ile Arg Glu Asn Tyr Ser Ala Met Ile Phe Glu Thr Ile Val Asp
    1730            1735            1740

Gly Lys Leu Lys Thr Glu Lys Ile Phe Lys Glu Ile Asn Glu His
    1745            1750            1755

Ser Thr Ser Tyr Thr Phe Arg Ser Glu Lys Gly Leu Leu Ser Ala
    1760            1765            1770

Thr Gln Phe Thr Gln Pro Ala Leu Thr Leu Met Glu Lys Ala Ala
    1775            1780            1785

Phe Glu Asp Leu Lys Ser Lys Gly Leu Ile Pro Ala Asp Ala Thr
    1790            1795            1800

Phe Ala Gly His Ser Leu Gly Glu Tyr Ala Ala Leu Ala Ser Leu
    1805            1810            1815

Ala Asp Val Met Ser Ile Glu Ser Leu Val Glu Val Val Phe Tyr
    1820            1825            1830

Arg Gly Met Thr Met Gln Val Ala Val Pro Arg Asp Glu Leu Gly
    1835            1840            1845

Arg Ser Asn Tyr Gly Met Ile Ala Ile Asn Pro Gly Arg Val Ala
    1850            1855            1860

Ala Ser Phe Ser Gln Glu Ala Leu Gln Tyr Val Val Glu Arg Val
    1865            1870            1875

Gly Lys Arg Thr Gly Trp Leu Val Glu Ile Val Asn Tyr Asn Val
    1880            1885            1890

Glu Asn Gln Gln Tyr Val Ala Ala Gly Asp Leu Arg Ala Leu Asp
    1895            1900            1905

Thr Val Thr Asn Val Leu Asn Phe Ile Lys Leu Gln Lys Ile Asp
    1910            1915            1920

Ile Ile Glu Leu Gln Lys Ser Leu Ser Leu Glu Glu Val Glu Gly
    1925            1930            1935

His Leu Phe Glu Ile Ile Asp Glu Ala Ser Lys Lys Ser Ala Val
    1940            1945            1950
```

-continued

```
Lys Pro Arg Pro Leu Lys Leu Glu Arg Gly Phe Ala Cys Ile Pro
    1955                1960                1965

Leu Val Gly Ile Ser Val Pro Phe His Ser Thr Tyr Leu Met Asn
    1970                1975                1980

Gly Val Lys Pro Phe Lys Ser Phe Leu Lys Lys Asn Ile Ile Lys
    1985                1990                1995

Glu Asn Val Lys Val Ala Arg Leu Ala Gly Lys Tyr Ile Pro Asn
    2000                2005                2010

Leu Thr Ala Lys Pro Phe Gln Val Thr Lys Glu Tyr Phe Gln Asp
    2015                2020                2025

Val Tyr Asp Leu Thr Gly Ser Glu Pro Ile Lys Glu Ile Ile Asp
    2030                2035                2040

Asn Trp Glu Lys Tyr Glu Gln Ser
    2045                2050

<210> SEQ ID NO 28
<211> LENGTH: 2051
<212> TYPE: PRT
<213> ORGANISM: Saccharomyces cerevisiae

<400> SEQUENCE: 28

Met Asp Ala Tyr Ser Thr Arg Pro Leu Thr Leu Ser His Gly Ser Leu
1               5                   10                  15

Glu His Val Leu Leu Val Pro Thr Ala Ser Phe Phe Ile Ala Ser Gln
                20                  25                  30

Leu Gln Glu Gln Phe Asn Lys Ile Leu Pro Glu Pro Thr Glu Gly Phe
            35                  40                  45

Ala Ala Asp Asp Glu Pro Thr Thr Pro Ala Glu Leu Val Gly Lys Phe
        50                  55                  60

Leu Gly Tyr Val Ser Ser Leu Val Glu Pro Ser Lys Val Gly Gln Phe
65                  70                  75                  80

Asp Gln Val Leu Asn Leu Cys Leu Thr Glu Phe Glu Asn Cys Tyr Leu
                85                  90                  95

Glu Gly Asn Asp Ile His Ala Leu Ala Ala Lys Leu Leu Gln Glu Asn
                100                 105                 110

Asp Thr Thr Leu Val Lys Thr Lys Glu Leu Ile Lys Asn Tyr Ile Thr
            115                 120                 125

Ala Arg Ile Met Ala Lys Arg Pro Phe Asp Lys Lys Ser Asn Ser Ala
        130                 135                 140

Leu Phe Arg Ala Val Gly Glu Gly Asn Ala Gln Leu Val Ala Ile Phe
145                 150                 155                 160

Gly Gly Gln Gly Asn Thr Asp Asp Tyr Phe Glu Glu Leu Arg Asp Leu
                165                 170                 175

Tyr Gln Thr Tyr His Val Leu Val Gly Asp Leu Ile Lys Phe Ser Ala
                180                 185                 190

Glu Thr Leu Ser Glu Leu Ile Arg Thr Thr Leu Asp Ala Glu Lys Val
            195                 200                 205

Phe Thr Gln Gly Leu Asn Ile Leu Glu Trp Leu Glu Asn Pro Ser Asn
        210                 215                 220

Thr Pro Asp Lys Asp Tyr Leu Leu Ser Ile Pro Ile Ser Cys Pro Leu
225                 230                 235                 240

Ile Gly Val Ile Gln Leu Ala His Tyr Val Val Thr Ala Lys Leu Leu
                245                 250                 255

Gly Phe Thr Pro Gly Glu Leu Arg Ser Tyr Leu Lys Gly Ala Thr Gly
                260                 265                 270
```

-continued

His Ser Gln Gly Leu Val Thr Ala Val Ala Ile Ala Glu Thr Asp Ser
        275                 280                 285

Trp Glu Ser Phe Phe Val Ser Val Arg Lys Ala Ile Thr Val Leu Phe
        290                 295                 300

Phe Ile Gly Val Arg Cys Tyr Glu Ala Tyr Pro Asn Thr Ser Leu Pro
305                 310                 315                 320

Pro Ser Ile Leu Glu Asp Ser Leu Glu Asn Asn Glu Gly Val Pro Ser
                325                 330                 335

Pro Met Leu Ser Ile Ser Asn Leu Thr Gln Glu Gln Val Gln Asp Tyr
                340                 345                 350

Val Asn Lys Thr Asn Ser His Leu Pro Ala Gly Lys Gln Val Glu Ile
                355                 360                 365

Ser Leu Val Asn Gly Ala Lys Asn Leu Val Val Ser Gly Pro Pro Gln
        370                 375                 380

Ser Leu Tyr Gly Leu Asn Leu Thr Leu Arg Lys Ala Lys Ala Pro Ser
385                 390                 395                 400

Gly Leu Asp Gln Ser Arg Ile Pro Phe Ser Glu Arg Lys Leu Lys Phe
                405                 410                 415

Ser Asn Arg Phe Leu Pro Val Ala Ser Pro Ala His Ser His Leu Leu
                420                 425                 430

Val Pro Ala Ser Asp Leu Ile Asn Lys Asp Leu Val Lys Asn Asn Val
        435                 440                 445

Ser Phe Asn Ala Lys Asp Ile Gln Ile Pro Val Tyr Asp Thr Phe Asp
        450                 455                 460

Gly Ser Asp Leu Arg Val Leu Ser Gly Ser Ile Ser Glu Arg Ile Val
465                 470                 475                 480

Asp Cys Ala Ile Arg Leu Pro Val Lys Trp Glu Thr Thr Thr Gln Phe
                485                 490                 495

Lys Ala Thr His Ile Leu Asp Phe Gly Pro Gly Gly Ala Ser Gly Leu
                500                 505                 510

Gly Val Leu Thr His Arg Asn Lys Asp Gly Thr Gly Val Arg Val Ile
        515                 520                 525

Val Ala Gly Thr Leu Asp Ile Asn Pro Asp Asp Tyr Gly Phe Lys
        530                 535                 540

Gln Glu Ile Phe Asp Val Thr Ser Asn Gly Leu Lys Lys Asn Pro Asn
545                 550                 555                 560

Trp Leu Glu Glu Tyr His Pro Lys Leu Ile Lys Asn Lys Ser Gly Lys
                565                 570                 575

Ile Phe Val Glu Thr Lys Phe Ser Lys Leu Ile Gly Arg Pro Pro Leu
                580                 585                 590

Leu Val Pro Gly Met Thr Pro Cys Thr Val Ser Pro Asp Phe Val Ala
        595                 600                 605

Ala Thr Thr Asn Ala Gly Tyr Thr Ile Glu Leu Ala Gly Gly Gly Tyr
        610                 615                 620

Phe Ser Ala Ala Gly Met Thr Ala Ala Ile Asp Ser Val Val Ser Gln
625                 630                 635                 640

Ile Glu Lys Gly Ser Thr Phe Gly Ile Asn Leu Ile Tyr Val Asn Pro
                645                 650                 655

Phe Met Leu Gln Trp Gly Ile Pro Leu Ile Lys Glu Leu Arg Ser Lys
                660                 665                 670

Gly Tyr Pro Ile Gln Phe Leu Thr Ile Gly Ala Gly Val Pro Ser Leu
                675                 680                 685

```
Glu Val Ala Ser Glu Tyr Ile Glu Thr Leu Gly Leu Lys Tyr Leu Gly
    690                 695                 700

Leu Lys Pro Gly Ser Ile Asp Ala Ile Ser Gln Val Ile Asn Ile Ala
705                 710                 715                 720

Lys Ala His Pro Asn Phe Pro Ile Ala Leu Gln Trp Thr Gly Gly Arg
                    725                 730                 735

Gly Gly Gly His His Ser Phe Glu Asp Ala His Thr Pro Met Leu Gln
                740                 745                 750

Met Tyr Ser Lys Ile Arg Arg His Pro Asn Ile Met Leu Ile Phe Gly
            755                 760                 765

Ser Gly Phe Gly Ser Ala Asp Asp Thr Tyr Pro Tyr Leu Thr Gly Glu
770                 775                 780

Trp Ser Thr Lys Phe Asp Tyr Pro Pro Met Pro Phe Asp Gly Phe Leu
785                 790                 795                 800

Phe Gly Ser Arg Val Met Ile Ala Lys Glu Val Lys Thr Ser Pro Asp
                805                 810                 815

Ala Lys Lys Cys Ile Ala Ala Cys Thr Gly Val Pro Asp Asp Lys Trp
            820                 825                 830

Glu Gln Thr Tyr Lys Lys Pro Thr Gly Gly Ile Val Thr Val Arg Ser
                835                 840                 845

Glu Met Gly Glu Pro Ile His Lys Ile Ala Thr Arg Gly Val Met Leu
850                 855                 860

Trp Lys Glu Phe Asp Glu Thr Ile Phe Asn Leu Pro Lys Asn Lys Leu
865                 870                 875                 880

Val Pro Thr Leu Glu Ala Lys Arg Asp Tyr Ile Ile Ser Arg Leu Asn
                885                 890                 895

Ala Asp Phe Gln Lys Pro Trp Phe Ala Thr Val Asn Gly Gln Ala Arg
            900                 905                 910

Asp Leu Ala Thr Met Thr Tyr Glu Glu Val Ala Lys Arg Leu Val Glu
                915                 920                 925

Leu Met Phe Ile Arg Ser Thr Asn Ser Trp Phe Asp Val Thr Trp Arg
930                 935                 940

Thr Phe Thr Gly Asp Phe Leu Arg Arg Val Glu Glu Arg Phe Thr Lys
945                 950                 955                 960

Ser Lys Thr Leu Ser Leu Ile Gln Ser Tyr Ser Leu Leu Asp Lys Pro
                965                 970                 975

Asp Glu Ala Ile Glu Lys Val Phe Asn Ala Tyr Pro Ala Ala Arg Glu
            980                 985                 990

Gln Phe Leu Asn Ala Gln Asp Ile Asp His Phe Leu Ser Met Cys Gln
                995                 1000                1005

Asn Pro Met Gln Lys Pro Val Pro Phe Val Pro Val Leu Asp Arg
    1010                1015                1020

Arg Phe Glu Ile Phe Phe Lys Lys Asp Ser Leu Trp Gln Ser Glu
    1025                1030                1035

His Leu Glu Ala Val Val Asp Gln Asp Val Gln Arg Thr Cys Ile
    1040                1045                1050

Leu His Gly Pro Val Ala Ala Gln Phe Thr Lys Val Ile Asp Glu
    1055                1060                1065

Pro Ile Lys Ser Ile Met Asp Gly Ile His Asp Gly His Ile Lys
    1070                1075                1080

Lys Leu Leu His Gln Tyr Tyr Gly Asp Asp Glu Ser Lys Ile Pro
    1085                1090                1095

Ala Val Glu Tyr Phe Gly Gly Glu Ser Pro Val Asp Val Gln Ser
```

-continued

```
             1100                1105                1110
Gln Val Asp Ser Ser Val Ser Glu Asp Ser Ala Val Phe Lys
             1115                1120                1125
Ala Thr Ser Ser Thr Asp Glu Glu Ser Trp Phe Lys Ala Leu Ala
             1130                1135                1140
Gly Ser Glu Ile Asn Trp Arg His Ala Ser Phe Leu Cys Ser Phe
             1145                1150                1155
Ile Thr Gln Asp Lys Met Phe Val Ser Asn Pro Ile Arg Lys Val
             1160                1165                1170
Phe Lys Pro Ser Gln Gly Met Val Val Glu Ile Ser Asn Gly Asn
             1175                1180                1185
Thr Ser Ser Lys Thr Val Val Thr Leu Ser Glu Pro Val Gln Gly
             1190                1195                1200
Glu Leu Lys Pro Thr Val Ile Leu Lys Leu Leu Lys Glu Asn Ile
             1205                1210                1215
Ile Gln Met Glu Met Ile Glu Asn Arg Thr Met Asp Gly Lys Pro
             1220                1225                1230
Val Ser Leu Pro Leu Leu Tyr Asn Phe Asn Pro Asp Asn Gly Phe
             1235                1240                1245
Ala Pro Ile Ser Glu Val Met Glu Asp Arg Asn Gln Arg Ile Lys
             1250                1255                1260
Glu Met Tyr Trp Lys Leu Trp Ile Asp Glu Pro Phe Asn Leu Asp
             1265                1270                1275
Phe Asp Pro Arg Asp Val Ile Lys Gly Lys Asp Phe Glu Ile Thr
             1280                1285                1290
Ala Lys Glu Val Tyr Asp Phe Thr His Ala Val Gly Asn Asn Cys
             1295                1300                1305
Glu Asp Phe Val Ser Arg Pro Asp Arg Thr Met Leu Ala Pro Met
             1310                1315                1320
Asp Phe Ala Ile Val Val Gly Trp Arg Ala Ile Ile Lys Ala Ile
             1325                1330                1335
Phe Pro Asn Thr Val Asp Gly Asp Leu Leu Lys Leu Val His Leu
             1340                1345                1350
Ser Asn Gly Tyr Lys Met Ile Pro Gly Ala Lys Pro Leu Gln Val
             1355                1360                1365
Gly Asp Val Val Ser Thr Thr Ala Val Ile Glu Ser Val Val Asn
             1370                1375                1380
Gln Pro Thr Gly Lys Ile Val Asp Val Val Gly Thr Leu Ser Arg
             1385                1390                1395
Asn Gly Lys Pro Val Met Glu Val Thr Ser Ser Phe Phe Tyr Arg
             1400                1405                1410
Gly Asn Tyr Thr Asp Phe Glu Asn Thr Phe Gln Lys Thr Val Glu
             1415                1420                1425
Pro Val Tyr Gln Met His Ile Lys Thr Ser Lys Asp Ile Ala Val
             1430                1435                1440
Leu Arg Ser Lys Glu Trp Phe Gln Leu Asp Asp Glu Asp Phe Asp
             1445                1450                1455
Leu Leu Asn Lys Thr Leu Thr Phe Glu Thr Glu Thr Glu Val Thr
             1460                1465                1470
Phe Lys Asn Ala Asn Ile Phe Ser Ser Val Lys Cys Phe Gly Pro
             1475                1480                1485
Ile Lys Val Glu Leu Pro Thr Lys Glu Thr Val Glu Ile Gly Ile
             1490                1495                1500
```

-continued

```
Val Asp Tyr Glu Ala Gly Ala Ser His Gly Asn Pro Val Val Asp
1505                1510                1515

Phe Leu Lys Arg Asn Gly Ser Thr Leu Glu Gln Lys Val Asn Leu
1520                1525                1530

Glu Asn Pro Ile Pro Ile Ala Val Leu Asp Ser Tyr Thr Pro Ser
1535                1540                1545

Thr Asn Glu Pro Tyr Ala Arg Val Ser Gly Asp Leu Asn Pro Ile
1550                1555                1560

His Val Ser Arg His Phe Ala Ser Tyr Ala Asn Leu Pro Gly Thr
1565                1570                1575

Ile Thr His Gly Met Phe Ser Ser Ala Ser Val Arg Ala Leu Ile
1580                1585                1590

Glu Asn Trp Ala Ala Asp Ser Val Ser Ser Arg Val Arg Gly Tyr
1595                1600                1605

Thr Cys Gln Phe Val Asp Met Val Leu Pro Asn Thr Ala Leu Lys
1610                1615                1620

Thr Ser Ile Gln His Val Gly Met Ile Asn Gly Arg Lys Leu Ile
1625                1630                1635

Lys Phe Glu Thr Arg Asn Glu Asp Asp Val Val Val Leu Thr Gly
1640                1645                1650

Glu Ala Glu Ile Glu Gln Pro Val Thr Thr Phe Val Phe Thr Gly
1655                1660                1665

Gln Gly Ser Gln Glu Gln Gly Met Gly Met Asp Leu Tyr Lys Thr
1670                1675                1680

Ser Lys Ala Ala Gln Asp Val Trp Asn Arg Ala Asp Asn His Phe
1685                1690                1695

Lys Asp Thr Tyr Gly Phe Ser Ile Leu Asp Ile Val Ile Asn Asn
1700                1705                1710

Pro Val Asn Leu Thr Ile His Phe Gly Gly Glu Lys Gly Lys Arg
1715                1720                1725

Ile Arg Glu Asn Tyr Ser Ala Met Ile Phe Glu Thr Ile Val Asp
1730                1735                1740

Gly Lys Leu Lys Thr Glu Lys Ile Phe Lys Glu Ile Asn Glu His
1745                1750                1755

Ser Thr Ser Tyr Thr Phe Arg Ser Glu Lys Gly Leu Leu Ser Ala
1760                1765                1770

Thr Gln Phe Thr Gln Pro Ala Leu Thr Leu Met Glu Lys Ala Ala
1775                1780                1785

Phe Glu Asp Leu Lys Ser Lys Gly Leu Ile Pro Ala Asp Ala Thr
1790                1795                1800

Phe Ala Gly His Ser Leu Gly Glu Tyr Ala Ala Leu Ala Ser Leu
1805                1810                1815

Ala Asp Val Met Ser Ile Glu Ser Leu Val Glu Val Val Phe Tyr
1820                1825                1830

Arg Gly Met Thr Met Gln Val Ala Val Pro Arg Asp Glu Leu Gly
1835                1840                1845

Arg Ser Asn Tyr Gly Met Ile Ala Ile Asn Pro Gly Arg Val Ala
1850                1855                1860

Ala Ser Phe Ser Gln Glu Ala Leu Gln Tyr Val Val Glu Arg Val
1865                1870                1875

Gly Lys Arg Thr Gly Trp Leu Val Glu Ile Val Asn Tyr Asn Val
1880                1885                1890
```

Glu Asn Gln Gln Tyr Val Ala Ala Gly Asp Leu Arg Ala Leu Asp
    1895                1900                1905

Thr Val Thr Asn Val Leu Asn Phe Ile Lys Leu Gln Lys Ile Asp
    1910                1915                1920

Ile Ile Glu Leu Gln Lys Ser Leu Ser Leu Glu Val Glu Gly
    1925                1930                1935

His Leu Phe Glu Ile Ile Asp Glu Ala Ser Lys Ser Ala Val
    1940                1945                1950

Lys Pro Arg Pro Leu Lys Leu Glu Arg Gly Phe Ala Cys Ile Pro
    1955                1960                1965

Leu Val Gly Ile Ser Val Pro Phe His Ser Thr Tyr Leu Met Asn
    1970                1975                1980

Gly Val Lys Pro Phe Lys Ser Phe Leu Lys Lys Asn Ile Ile Lys
    1985                1990                1995

Glu Asn Val Lys Val Ala Arg Leu Ala Gly Lys Tyr Ile Pro Asn
    2000                2005                2010

Leu Thr Ala Lys Pro Phe Gln Val Thr Lys Glu Tyr Phe Gln Asp
    2015                2020                2025

Val Tyr Asp Leu Thr Gly Ser Glu Pro Ile Lys Glu Ile Ile Asp
    2030                2035                2040

Asn Trp Glu Lys Tyr Glu Gln Ser
    2045            2050

<210> SEQ ID NO 29
<211> LENGTH: 2051
<212> TYPE: PRT
<213> ORGANISM: Saccharomyces cerevisiae

<400> SEQUENCE: 29

Met Asp Ala Tyr Ser Thr Arg Pro Leu Thr Leu Ser His Gly Ser Leu
1               5                   10                  15

Glu His Val Leu Leu Val Pro Thr Ala Ser Phe Phe Ile Ala Ser Gln
            20                  25                  30

Leu Gln Glu Gln Phe Asn Lys Ile Leu Pro Glu Pro Thr Glu Gly Phe
        35                  40                  45

Ala Ala Asp Asp Glu Pro Thr Thr Pro Ala Glu Leu Val Gly Lys Phe
    50                  55                  60

Leu Gly Tyr Val Ser Ser Leu Val Glu Pro Ser Lys Val Gly Gln Phe
65                  70                  75                  80

Asp Gln Val Leu Asn Leu Cys Leu Thr Glu Phe Glu Asn Cys Tyr Leu
                85                  90                  95

Glu Gly Asn Asp Ile His Ala Leu Ala Ala Lys Leu Leu Gln Glu Asn
            100                 105                 110

Asp Thr Thr Leu Val Lys Thr Lys Glu Leu Ile Lys Asn Tyr Ile Thr
        115                 120                 125

Ala Arg Ile Met Ala Lys Arg Pro Phe Asp Lys Lys Ser Asn Ser Ala
    130                 135                 140

Leu Phe Arg Ala Val Gly Glu Gly Asn Ala Gln Leu Val Ala Ile Phe
145                 150                 155                 160

Gly Gly Gln Gly Asn Thr Asp Asp Tyr Phe Glu Glu Leu Arg Asp Leu
                165                 170                 175

Tyr Gln Thr Tyr His Val Leu Val Gly Asp Leu Ile Lys Phe Ser Ala
            180                 185                 190

Glu Thr Leu Ser Glu Leu Ile Arg Thr Thr Leu Asp Ala Glu Lys Val
        195                 200                 205

```
Phe Thr Gln Gly Leu Asn Ile Leu Glu Trp Leu Glu Asn Pro Ser Asn
    210                 215                 220
Thr Pro Asp Lys Asp Tyr Leu Leu Ser Ala Pro Ile Ser Cys Pro Leu
225                 230                 235                 240
Ile Gly Val Ile Gln Leu Ala His Tyr Val Thr Ala Lys Leu Leu
            245                 250                 255
Gly Phe Thr Pro Gly Glu Leu Arg Ser Tyr Leu Lys Gly Ala Thr Gly
        260                 265                 270
His Ser Gln Gly Leu Val Thr Ala Val Ala Ile Ala Glu Thr Asp Ser
    275                 280                 285
Trp Glu Ser Phe Phe Val Ser Val Arg Lys Ala Ile Thr Val Leu Phe
    290                 295                 300
Phe Ile Gly Val Arg Cys Tyr Glu Ala Tyr Pro Asn Thr Ser Leu Pro
305                 310                 315                 320
Pro Ser Ile Leu Glu Asp Ser Leu Glu Asn Asn Glu Gly Val Pro Ser
            325                 330                 335
Pro Met Leu Ser Ile Ser Asn Leu Thr Gln Glu Gln Val Gln Asp Tyr
        340                 345                 350
Val Asn Lys Thr Asn Ser His Leu Pro Ala Gly Lys Gln Val Glu Ile
    355                 360                 365
Ser Leu Val Asn Gly Ala Lys Asn Leu Val Val Ser Gly Pro Pro Gln
    370                 375                 380
Ser Leu Tyr Gly Leu Asn Leu Thr Leu Arg Lys Ala Lys Ala Pro Ser
385                 390                 395                 400
Gly Leu Asp Gln Ser Arg Ile Pro Phe Ser Glu Arg Lys Leu Lys Phe
            405                 410                 415
Ser Asn Arg Phe Leu Pro Val Ala Ser Pro Ser His Ser His Leu Leu
        420                 425                 430
Val Pro Ala Ser Asp Leu Ile Asn Lys Asp Leu Val Lys Asn Asn Val
    435                 440                 445
Ser Phe Asn Ala Lys Asp Ile Gln Ile Pro Val Tyr Asp Thr Phe Asp
    450                 455                 460
Gly Ser Asp Leu Arg Val Leu Ser Gly Ser Ile Ser Glu Arg Ile Val
465                 470                 475                 480
Asp Cys Ile Ile Arg Leu Pro Val Lys Trp Glu Thr Thr Thr Gln Phe
            485                 490                 495
Lys Ala Thr His Ile Leu Asp Phe Gly Pro Gly Gly Ala Ser Gly Leu
        500                 505                 510
Gly Val Leu Thr His Arg Asn Lys Asp Gly Thr Gly Val Arg Val Ile
    515                 520                 525
Val Ala Gly Thr Leu Asp Ile Asn Pro Asp Asp Tyr Gly Phe Lys
    530                 535                 540
Gln Glu Ile Phe Asp Val Thr Ser Asn Gly Leu Lys Lys Asn Pro Asn
545                 550                 555                 560
Trp Leu Glu Glu Tyr His Pro Lys Leu Ile Lys Asn Lys Ser Gly Lys
            565                 570                 575
Ile Phe Val Glu Thr Lys Phe Ser Lys Leu Ile Gly Arg Pro Pro Leu
        580                 585                 590
Leu Val Pro Gly Met Thr Pro Cys Thr Val Ser Pro Asp Phe Val Ala
    595                 600                 605
Ala Thr Thr Asn Ala Gly Tyr Thr Ile Glu Leu Ala Gly Gly Gly Tyr
    610                 615                 620
```

-continued

```
Phe Ser Ala Ala Gly Met Thr Ala Ala Ile Asp Ser Val Val Ser Gln
625                 630                 635                 640

Ile Glu Lys Gly Ser Thr Phe Gly Ile Asn Leu Ile Tyr Val Asn Pro
            645                 650                 655

Phe Met Leu Gln Trp Gly Ile Pro Leu Ile Lys Glu Leu Arg Ser Lys
        660                 665                 670

Gly Tyr Pro Ile Gln Phe Leu Thr Ile Gly Ala Gly Val Pro Ser Leu
    675                 680                 685

Glu Val Ala Ser Glu Tyr Ile Glu Thr Leu Gly Leu Lys Tyr Leu Gly
690                 695                 700

Leu Lys Pro Gly Ser Ile Asp Ala Ile Ser Gln Val Ile Asn Ile Ala
705                 710                 715                 720

Lys Ala His Pro Asn Phe Pro Ile Ala Leu Gln Trp Thr Gly Gly Arg
                725                 730                 735

Gly Gly Gly His His Ser Phe Glu Asp Ala His Thr Pro Met Leu Gln
            740                 745                 750

Met Tyr Ser Lys Ile Arg Arg His Pro Asn Ile Met Leu Ile Phe Gly
        755                 760                 765

Ser Gly Phe Gly Ser Ala Asp Asp Thr Tyr Pro Tyr Leu Thr Gly Glu
    770                 775                 780

Trp Ser Thr Lys Phe Asp Tyr Pro Pro Met Pro Phe Asp Gly Phe Leu
785                 790                 795                 800

Phe Gly Ser Arg Val Met Ile Ala Lys Glu Val Lys Thr Ser Pro Asp
                805                 810                 815

Ala Lys Lys Cys Ile Ala Ala Cys Thr Gly Val Pro Asp Asp Lys Trp
            820                 825                 830

Glu Gln Thr Tyr Lys Lys Pro Thr Gly Gly Ile Val Thr Val Arg Ser
        835                 840                 845

Glu Met Gly Glu Pro Ile His Lys Ile Ala Thr Arg Gly Val Met Leu
    850                 855                 860

Trp Lys Glu Phe Asp Glu Thr Ile Phe Asn Leu Pro Lys Asn Lys Leu
865                 870                 875                 880

Val Pro Thr Leu Glu Ala Lys Arg Asp Tyr Ile Ile Ser Arg Leu Asn
                885                 890                 895

Ala Asp Phe Gln Lys Pro Trp Phe Ala Thr Val Asn Gly Gln Ala Arg
            900                 905                 910

Asp Leu Ala Thr Met Thr Tyr Glu Glu Val Ala Lys Arg Leu Val Glu
        915                 920                 925

Leu Met Phe Ile Arg Ser Thr Asn Ser Trp Phe Asp Val Thr Trp Arg
    930                 935                 940

Thr Phe Thr Gly Asp Phe Leu Arg Arg Val Glu Glu Arg Phe Thr Lys
945                 950                 955                 960

Ser Lys Thr Leu Ser Leu Ile Gln Ser Tyr Ser Leu Leu Asp Lys Pro
                965                 970                 975

Asp Glu Ala Ile Glu Lys Val Phe Asn Ala Tyr Pro Ala Ala Arg Glu
            980                 985                 990

Gln Phe Leu Asn Ala Gln Asp Ile Asp His Phe Leu Ser Met Cys Gln
        995                 1000                1005

Asn Pro Met Gln Lys Pro Val Pro Phe Val Pro Val Leu Asp Arg
            1010                1015                1020

Arg Phe Glu Ile Phe Phe Lys Lys Asp Ser Leu Trp Gln Ser Glu
            1025                1030                1035

His Leu Glu Ala Val Val Asp Gln Asp Val Gln Arg Thr Cys Ile
```

```
            1040              1045              1050
Leu His Gly Pro Val Ala Ala Gln Phe Thr Lys Val Ile Asp Glu
    1055              1060              1065

Pro Ile Lys Ser Ile Met Asp Gly Ile His Asp Gly His Ile Lys
    1070              1075              1080

Lys Leu Leu His Gln Tyr Tyr Gly Asp Asp Glu Ser Lys Ile Pro
    1085              1090              1095

Ala Val Glu Tyr Phe Gly Gly Glu Ser Pro Val Asp Val Gln Ser
    1100              1105              1110

Gln Val Asp Ser Ser Val Ser Glu Asp Ser Ala Val Phe Lys
    1115              1120              1125

Ala Thr Ser Ser Thr Asp Glu Glu Ser Trp Phe Lys Ala Leu Ala
    1130              1135              1140

Gly Ser Glu Ile Asn Trp Arg His Ala Ser Phe Leu Cys Ser Phe
    1145              1150              1155

Ile Thr Gln Asp Lys Met Phe Val Ser Asn Pro Ile Arg Lys Val
    1160              1165              1170

Phe Lys Pro Ser Gln Gly Met Val Val Glu Ile Ser Asn Gly Asn
    1175              1180              1185

Thr Ser Ser Lys Thr Val Val Thr Leu Ser Glu Pro Val Gln Gly
    1190              1195              1200

Glu Leu Lys Pro Thr Val Ile Leu Lys Leu Leu Lys Glu Asn Ile
    1205              1210              1215

Ile Gln Met Glu Met Ile Glu Asn Arg Thr Met Asp Gly Lys Pro
    1220              1225              1230

Val Ser Leu Pro Leu Leu Tyr Asn Phe Asn Pro Asp Asn Gly Phe
    1235              1240              1245

Ala Pro Ile Ser Glu Val Met Glu Asp Arg Asn Gln Arg Ile Lys
    1250              1255              1260

Glu Met Tyr Trp Lys Leu Trp Ile Asp Glu Pro Phe Asn Leu Asp
    1265              1270              1275

Phe Asp Pro Arg Asp Val Ile Lys Gly Lys Asp Phe Glu Ile Thr
    1280              1285              1290

Ala Lys Glu Val Tyr Asp Phe Thr His Ala Val Gly Asn Asn Cys
    1295              1300              1305

Glu Asp Phe Val Ser Arg Pro Asp Arg Thr Met Leu Ala Pro Met
    1310              1315              1320

Asp Phe Ala Ile Val Val Gly Trp Arg Ala Ile Ile Lys Ala Ile
    1325              1330              1335

Phe Pro Asn Thr Val Asp Gly Asp Leu Leu Lys Leu Val His Leu
    1340              1345              1350

Ser Asn Gly Tyr Lys Met Ile Pro Gly Ala Lys Pro Leu Gln Val
    1355              1360              1365

Gly Asp Val Val Ser Thr Thr Ala Val Ile Glu Ser Val Val Asn
    1370              1375              1380

Gln Pro Thr Gly Lys Ile Val Asp Val Val Gly Thr Leu Ser Arg
    1385              1390              1395

Asn Gly Lys Pro Val Met Glu Val Thr Ser Ser Phe Phe Tyr Arg
    1400              1405              1410

Gly Asn Tyr Thr Asp Phe Glu Asn Thr Phe Gln Lys Thr Val Glu
    1415              1420              1425

Pro Val Tyr Gln Met His Ile Lys Thr Ser Lys Asp Ile Ala Val
    1430              1435              1440
```

```
Leu Arg Ser Lys Glu Trp Phe Gln Leu Asp Asp Glu Asp Phe Asp
1445                1450                1455

Leu Leu Asn Lys Thr Leu Thr Phe Glu Thr Glu Thr Glu Val Thr
1460                1465                1470

Phe Lys Asn Ala Asn Ile Phe Ser Ser Val Lys Cys Phe Gly Pro
1475                1480                1485

Ile Lys Val Glu Leu Pro Thr Lys Glu Thr Val Glu Ile Gly Ile
1490                1495                1500

Val Asp Tyr Glu Ala Gly Ala Ser His Gly Asn Pro Val Val Asp
1505                1510                1515

Phe Leu Lys Arg Asn Gly Ser Thr Leu Glu Gln Lys Val Asn Leu
1520                1525                1530

Glu Asn Pro Ile Pro Ile Ala Val Leu Asp Ser Tyr Thr Pro Ser
1535                1540                1545

Thr Asn Glu Pro Tyr Ala Arg Val Ser Gly Asp Leu Asn Pro Ile
1550                1555                1560

His Val Ser Arg His Phe Ala Ser Tyr Ala Asn Leu Pro Gly Thr
1565                1570                1575

Ile Thr His Gly Met Phe Ser Ser Ala Ser Val Arg Ala Leu Ile
1580                1585                1590

Glu Asn Trp Ala Ala Asp Ser Val Ser Ser Arg Val Arg Gly Tyr
1595                1600                1605

Thr Cys Gln Phe Val Asp Met Val Leu Pro Asn Thr Ala Leu Lys
1610                1615                1620

Thr Ser Ile Gln His Val Gly Met Ile Asn Gly Arg Lys Leu Ile
1625                1630                1635

Lys Phe Glu Thr Arg Asn Glu Asp Asp Val Val Val Leu Thr Gly
1640                1645                1650

Glu Ala Glu Ile Glu Gln Pro Val Thr Thr Phe Val Phe Thr Gly
1655                1660                1665

Gln Gly Ser Gln Glu Gln Gly Met Gly Met Asp Leu Tyr Lys Thr
1670                1675                1680

Ser Lys Ala Ala Gln Asp Val Trp Asn Arg Ala Asp Asn His Phe
1685                1690                1695

Lys Asp Thr Tyr Gly Phe Ser Ile Leu Asp Ile Val Ile Asn Asn
1700                1705                1710

Pro Val Asn Leu Thr Ile His Phe Gly Gly Glu Lys Gly Lys Arg
1715                1720                1725

Ile Arg Glu Asn Tyr Ser Ala Met Ile Phe Glu Thr Ile Val Asp
1730                1735                1740

Gly Lys Leu Lys Thr Glu Lys Ile Phe Lys Glu Ile Asn Glu His
1745                1750                1755

Ser Thr Ser Tyr Thr Phe Arg Ser Glu Lys Gly Leu Leu Ser Ala
1760                1765                1770

Thr Gln Phe Thr Gln Pro Ala Leu Thr Leu Met Glu Lys Ala Ala
1775                1780                1785

Phe Glu Asp Leu Lys Ser Lys Gly Leu Ile Pro Ala Asp Ala Thr
1790                1795                1800

Phe Ala Gly His Ser Leu Gly Glu Tyr Ala Ala Leu Ala Ser Leu
1805                1810                1815

Ala Asp Val Met Ser Ile Glu Ser Leu Val Glu Val Val Phe Tyr
1820                1825                1830
```

```
Arg Gly Met Thr Met Gln Val Ala Val Pro Arg Asp Glu Leu Gly
    1835                1840                1845

Arg Ser Asn Tyr Gly Met Ile Ala Ile Asn Pro Gly Arg Val Ala
    1850                1855                1860

Ala Ser Phe Ser Gln Glu Ala Leu Gln Tyr Val Val Glu Arg Val
    1865                1870                1875

Gly Lys Arg Thr Gly Trp Leu Val Glu Ile Val Asn Tyr Asn Val
    1880                1885                1890

Glu Asn Gln Gln Tyr Val Ala Ala Gly Asp Leu Arg Ala Leu Asp
    1895                1900                1905

Thr Val Thr Asn Val Leu Asn Phe Ile Lys Leu Gln Lys Ile Asp
    1910                1915                1920

Ile Ile Glu Leu Gln Lys Ser Leu Ser Leu Glu Glu Val Glu Gly
    1925                1930                1935

His Leu Phe Glu Ile Ile Asp Glu Ala Ser Lys Lys Ser Ala Val
    1940                1945                1950

Lys Pro Arg Pro Leu Lys Leu Glu Arg Gly Phe Ala Cys Ile Pro
    1955                1960                1965

Leu Val Gly Ile Ser Val Pro Phe His Ser Thr Tyr Leu Met Asn
    1970                1975                1980

Gly Val Lys Pro Phe Lys Ser Phe Leu Lys Lys Asn Ile Ile Lys
    1985                1990                1995

Glu Asn Val Lys Val Ala Arg Leu Ala Gly Lys Tyr Ile Pro Asn
    2000                2005                2010

Leu Thr Ala Lys Pro Phe Gln Val Thr Lys Glu Tyr Phe Gln Asp
    2015                2020                2025

Val Tyr Asp Leu Thr Gly Ser Glu Pro Ile Lys Glu Ile Ile Asp
    2030                2035                2040

Asn Trp Glu Lys Tyr Glu Gln Ser
    2045                2050

<210> SEQ ID NO 30
<211> LENGTH: 2051
<212> TYPE: PRT
<213> ORGANISM: Saccharomyces cerevisiae

<400> SEQUENCE: 30

Met Asp Ala Tyr Ser Thr Arg Pro Leu Thr Leu Ser His Gly Ser Leu
1               5                   10                  15

Glu His Val Leu Leu Val Pro Thr Ala Ser Phe Phe Ile Ala Ser Gln
                20                  25                  30

Leu Gln Glu Gln Phe Asn Lys Ile Leu Pro Glu Pro Thr Glu Gly Phe
            35                  40                  45

Ala Ala Asp Asp Glu Pro Thr Thr Pro Ala Glu Leu Val Gly Lys Phe
        50                  55                  60

Leu Gly Tyr Val Ser Ser Leu Val Glu Pro Ser Lys Val Gly Gln Phe
65                  70                  75                  80

Asp Gln Val Leu Asn Leu Cys Leu Thr Glu Phe Glu Asn Cys Tyr Leu
                85                  90                  95

Glu Gly Asn Asp Ile His Ala Leu Ala Ala Lys Leu Leu Gln Glu Asn
            100                 105                 110

Asp Thr Thr Leu Val Lys Thr Lys Glu Leu Ile Lys Asn Tyr Ile Thr
        115                 120                 125

Ala Arg Ile Met Ala Lys Arg Pro Phe Asp Lys Lys Ser Asn Ser Ala
    130                 135                 140
```

-continued

```
Leu Phe Arg Ala Val Gly Glu Gly Asn Ala Gln Leu Val Ala Ile Phe
145                 150                 155                 160

Gly Gly Ala Gly Asn Thr Asp Asp Tyr Phe Glu Leu Arg Asp Leu
            165                 170                 175

Tyr Gln Thr Tyr His Val Leu Val Gly Asp Leu Ile Lys Phe Ser Ala
            180                 185                 190

Glu Thr Leu Ser Glu Leu Ile Arg Thr Thr Leu Asp Ala Glu Lys Val
            195                 200                 205

Phe Thr Gln Gly Leu Asn Ile Leu Glu Trp Leu Glu Asn Pro Ser Asn
210                 215                 220

Thr Pro Asp Lys Asp Tyr Leu Leu Ser Ile Pro Ile Ser Cys Pro Leu
225                 230                 235                 240

Ile Gly Val Ile Gln Leu Ala His Tyr Val Val Thr Ala Lys Leu Leu
                245                 250                 255

Gly Phe Thr Pro Gly Glu Leu Arg Ser Tyr Leu Lys Gly Ala Thr Gly
            260                 265                 270

His Ser Gln Gly Leu Val Thr Ala Val Ala Ile Ala Glu Thr Asp Ser
        275                 280                 285

Trp Glu Ser Phe Phe Val Ser Val Arg Lys Ala Ile Thr Val Leu Phe
290                 295                 300

Phe Ile Gly Val Arg Cys Tyr Glu Ala Tyr Pro Asn Thr Ser Leu Pro
305                 310                 315                 320

Pro Ser Ile Leu Glu Asp Ser Leu Glu Asn Asn Glu Gly Val Pro Ser
                325                 330                 335

Pro Met Leu Ser Ile Ser Asn Leu Thr Gln Gln Val Gln Asp Tyr
            340                 345                 350

Val Asn Lys Thr Asn Ser His Leu Pro Ala Gly Lys Gln Val Glu Ile
            355                 360                 365

Ser Leu Val Asn Gly Ala Lys Asn Leu Val Val Ser Gly Pro Pro Gln
370                 375                 380

Ser Leu Tyr Gly Leu Asn Leu Thr Leu Arg Lys Ala Lys Ala Pro Ser
385                 390                 395                 400

Gly Leu Asp Gln Ser Arg Ile Pro Phe Ser Glu Arg Lys Leu Lys Phe
                405                 410                 415

Ser Asn Arg Phe Leu Pro Val Ala Ser Pro Ala His Ser His Leu Leu
                420                 425                 430

Val Pro Ala Ser Asp Leu Ile Asn Lys Asp Leu Val Lys Asn Asn Val
            435                 440                 445

Ser Phe Asn Ala Lys Asp Ile Gln Ile Pro Val Tyr Asp Thr Phe Asp
            450                 455                 460

Gly Ser Asp Leu Arg Val Leu Ser Gly Ser Ile Ser Glu Arg Ile Val
465                 470                 475                 480

Asp Cys Ile Ile Arg Leu Pro Val Lys Trp Glu Thr Thr Gln Phe
                485                 490                 495

Lys Ala Thr His Ile Leu Asp Phe Gly Pro Gly Gly Ala Ser Gly Leu
            500                 505                 510

Gly Val Leu Thr His Arg Asn Lys Asp Gly Thr Gly Val Arg Val Ile
            515                 520                 525

Val Ala Gly Thr Leu Asp Ile Asn Pro Asp Asp Tyr Gly Phe Lys
        530                 535                 540

Gln Glu Ile Phe Asp Val Thr Ser Asn Gly Leu Lys Lys Asn Pro Asn
545                 550                 555                 560
```

Trp Leu Glu Glu Tyr His Pro Lys Leu Ile Lys Asn Lys Ser Gly Lys
            565                 570                 575

Ile Phe Val Glu Thr Lys Phe Ser Lys Leu Ile Gly Arg Pro Pro Leu
            580                 585                 590

Leu Val Pro Gly Met Thr Pro Cys Thr Val Ser Pro Asp Phe Val Ala
            595                 600                 605

Ala Thr Thr Asn Ala Gly Tyr Thr Ile Glu Leu Ala Gly Gly Gly Tyr
            610                 615                 620

Phe Ser Ala Ala Gly Met Thr Ala Ala Ile Asp Ser Val Val Ser Gln
625                 630                 635                 640

Ile Glu Lys Gly Ser Thr Phe Gly Ile Asn Leu Ile Tyr Val Asn Pro
                645                 650                 655

Phe Met Leu Gln Trp Gly Ile Pro Leu Ile Lys Glu Leu Arg Ser Lys
            660                 665                 670

Gly Tyr Pro Ile Gln Phe Leu Thr Ile Gly Ala Gly Val Pro Ser Leu
            675                 680                 685

Glu Val Ala Ser Glu Tyr Ile Glu Thr Leu Gly Leu Lys Tyr Leu Gly
            690                 695                 700

Leu Lys Pro Gly Ser Ile Asp Ala Ile Ser Gln Val Ile Asn Ile Ala
705                 710                 715                 720

Lys Ala His Pro Asn Phe Pro Ile Ala Leu Gln Trp Thr Gly Gly Arg
                725                 730                 735

Gly Gly Gly His His Ser Phe Glu Asp Ala His Thr Pro Met Leu Gln
                740                 745                 750

Met Tyr Ser Lys Ile Arg Arg His Pro Asn Ile Met Leu Ile Phe Gly
            755                 760                 765

Ser Gly Phe Gly Ser Ala Asp Asp Thr Tyr Pro Tyr Leu Thr Gly Glu
            770                 775                 780

Trp Ser Thr Lys Phe Asp Tyr Pro Pro Met Pro Phe Asp Gly Phe Leu
785                 790                 795                 800

Phe Gly Ser Arg Val Met Ile Ala Lys Glu Val Lys Thr Ser Pro Asp
                805                 810                 815

Ala Lys Lys Cys Ile Ala Ala Cys Thr Gly Val Pro Asp Asp Lys Trp
            820                 825                 830

Glu Gln Thr Tyr Lys Lys Pro Thr Gly Gly Ile Val Thr Val Arg Ser
            835                 840                 845

Glu Met Gly Glu Pro Ile His Lys Ile Ala Thr Arg Gly Val Met Leu
            850                 855                 860

Trp Lys Glu Phe Asp Glu Thr Ile Phe Asn Leu Pro Lys Asn Lys Leu
865                 870                 875                 880

Val Pro Thr Leu Glu Ala Lys Arg Asp Tyr Ile Ile Ser Arg Leu Asn
                885                 890                 895

Ala Asp Phe Gln Lys Pro Trp Phe Ala Thr Val Asn Gly Gln Ala Arg
            900                 905                 910

Asp Leu Ala Thr Met Thr Tyr Glu Glu Val Ala Lys Arg Leu Val Glu
            915                 920                 925

Leu Met Phe Ile Arg Ser Thr Asn Ser Trp Phe Asp Val Thr Trp Arg
            930                 935                 940

Thr Phe Thr Gly Asp Phe Leu Arg Arg Val Glu Arg Phe Thr Lys
945                 950                 955                 960

Ser Lys Thr Leu Ser Leu Ile Gln Ser Tyr Ser Leu Leu Asp Lys Pro
                965                 970                 975

Asp Glu Ala Ile Glu Lys Val Phe Asn Ala Tyr Pro Ala Ala Arg Glu

```
                980             985              990
        Gln Phe Leu Asn Ala Gln Asp Ile Asp His Phe Leu Ser Met Cys Gln
                    995              1000             1005

Asn Pro Met Gln Lys Pro Val Pro Phe Val Pro Val Leu Asp Arg
            1010             1015             1020

Arg Phe Glu Ile Phe Phe Lys Lys Asp Ser Leu Trp Gln Ser Glu
            1025             1030             1035

His Leu Glu Ala Val Val Asp Gln Asp Val Gln Arg Thr Cys Ile
            1040             1045             1050

Leu His Gly Pro Val Ala Ala Gln Phe Thr Lys Val Ile Asp Glu
            1055             1060             1065

Pro Ile Lys Ser Ile Met Asp Gly Ile His Asp Gly His Ile Lys
            1070             1075             1080

Lys Leu Leu His Gln Tyr Tyr Gly Asp Asp Glu Ser Lys Ile Pro
            1085             1090             1095

Ala Val Glu Tyr Phe Gly Gly Glu Ser Pro Val Asp Val Gln Ser
            1100             1105             1110

Gln Val Asp Ser Ser Ser Val Ser Glu Asp Ser Ala Val Phe Lys
            1115             1120             1125

Ala Thr Ser Ser Thr Asp Glu Glu Ser Trp Phe Lys Ala Leu Ala
            1130             1135             1140

Gly Ser Glu Ile Asn Trp Arg His Ala Ser Phe Leu Cys Ser Phe
            1145             1150             1155

Ile Thr Gln Asp Lys Met Phe Val Ser Asn Pro Ile Arg Lys Val
            1160             1165             1170

Phe Lys Pro Ser Gln Gly Met Val Val Glu Ile Ser Asn Gly Asn
            1175             1180             1185

Thr Ser Ser Lys Thr Val Val Thr Leu Ser Glu Pro Val Gln Gly
            1190             1195             1200

Glu Leu Lys Pro Thr Val Ile Leu Lys Leu Leu Lys Glu Asn Ile
            1205             1210             1215

Ile Gln Met Glu Met Ile Glu Asn Arg Thr Met Asp Gly Lys Pro
            1220             1225             1230

Val Ser Leu Pro Leu Leu Tyr Asn Phe Asn Pro Asp Asn Gly Phe
            1235             1240             1245

Ala Pro Ile Ser Glu Val Met Glu Asp Arg Asn Gln Arg Ile Lys
            1250             1255             1260

Glu Met Tyr Trp Lys Leu Trp Ile Asp Glu Pro Phe Asn Leu Asp
            1265             1270             1275

Phe Asp Pro Arg Asp Val Ile Lys Gly Lys Asp Phe Glu Ile Thr
            1280             1285             1290

Ala Lys Glu Val Tyr Asp Phe Thr His Ala Val Gly Asn Asn Cys
            1295             1300             1305

Glu Asp Phe Val Ser Arg Pro Asp Arg Thr Met Leu Ala Pro Met
            1310             1315             1320

Asp Phe Ala Ile Val Val Gly Trp Arg Ala Ile Lys Ala Ile
            1325             1330             1335

Phe Pro Asn Thr Val Asp Gly Asp Leu Leu Lys Leu Val His Leu
            1340             1345             1350

Ser Asn Gly Tyr Lys Met Ile Pro Gly Ala Lys Pro Leu Gln Val
            1355             1360             1365

Gly Asp Val Val Ser Thr Thr Ala Val Ile Glu Ser Val Val Asn
            1370             1375             1380
```

```
Gln Pro Thr Gly Lys Ile Val Asp Val Val Gly Thr Leu Ser Arg
1385                1390                1395

Asn Gly Lys Pro Val Met Glu Val Thr Ser Ser Phe Phe Tyr Arg
1400                1405                1410

Gly Asn Tyr Thr Asp Phe Glu Asn Thr Phe Gln Lys Thr Val Glu
1415                1420                1425

Pro Val Tyr Gln Met His Ile Lys Thr Ser Lys Asp Ile Ala Val
1430                1435                1440

Leu Arg Ser Lys Glu Trp Phe Gln Leu Asp Asp Glu Asp Phe Asp
1445                1450                1455

Leu Leu Asn Lys Thr Leu Thr Phe Glu Thr Glu Thr Glu Val Thr
1460                1465                1470

Phe Lys Asn Ala Asn Ile Phe Ser Ser Val Lys Cys Phe Gly Pro
1475                1480                1485

Ile Lys Val Glu Leu Pro Thr Lys Glu Thr Val Glu Ile Gly Ile
1490                1495                1500

Val Asp Tyr Glu Ala Gly Ala Ser His Gly Asn Pro Val Val Asp
1505                1510                1515

Phe Leu Lys Arg Asn Gly Ser Thr Leu Glu Gln Lys Val Asn Leu
1520                1525                1530

Glu Asn Pro Ile Pro Ile Ala Val Leu Asp Ser Tyr Thr Pro Ser
1535                1540                1545

Thr Asn Glu Pro Tyr Ala Arg Val Ser Gly Asp Leu Asn Pro Ile
1550                1555                1560

His Val Ser Arg His Phe Ala Ser Tyr Ala Asn Leu Pro Gly Thr
1565                1570                1575

Ile Thr His Gly Met Phe Ser Ser Ala Ser Val Arg Ala Leu Ile
1580                1585                1590

Glu Asn Trp Ala Ala Asp Ser Val Ser Ser Arg Val Arg Gly Tyr
1595                1600                1605

Thr Cys Gln Phe Val Asp Met Val Leu Pro Asn Thr Ala Leu Lys
1610                1615                1620

Thr Ser Ile Gln His Val Gly Met Ile Asn Gly Arg Lys Leu Ile
1625                1630                1635

Lys Phe Glu Thr Arg Asn Glu Asp Asp Val Val Val Leu Thr Gly
1640                1645                1650

Glu Ala Glu Ile Glu Gln Pro Val Thr Thr Phe Val Phe Thr Gly
1655                1660                1665

Gln Gly Ser Gln Glu Gln Gly Met Gly Met Asp Leu Tyr Lys Thr
1670                1675                1680

Ser Lys Ala Ala Gln Asp Val Trp Asn Arg Ala Asp Asn His Phe
1685                1690                1695

Lys Asp Thr Tyr Gly Phe Ser Ile Leu Asp Ile Val Ile Asn Asn
1700                1705                1710

Pro Val Asn Leu Thr Ile His Phe Gly Gly Glu Lys Gly Lys Arg
1715                1720                1725

Ile Arg Glu Asn Tyr Ser Ala Met Ile Phe Glu Thr Ile Val Asp
1730                1735                1740

Gly Lys Leu Lys Thr Glu Lys Ile Phe Lys Glu Ile Asn Glu His
1745                1750                1755

Ser Thr Ser Tyr Thr Phe Arg Ser Glu Lys Gly Leu Leu Ser Ala
1760                1765                1770
```

```
Thr Gln Phe Thr Gln Pro Ala Leu Thr Leu Met Glu Lys Ala Ala
    1775                1780                1785

Phe Glu Asp Leu Lys Ser Lys Gly Leu Ile Pro Ala Asp Ala Thr
    1790                1795                1800

Phe Ala Gly His Ser Leu Gly Glu Tyr Ala Ala Leu Ala Ser Leu
    1805                1810                1815

Ala Asp Val Met Ser Ile Glu Ser Leu Val Glu Val Val Phe Tyr
    1820                1825                1830

Arg Gly Met Thr Met Gln Val Ala Val Pro Arg Asp Glu Leu Gly
    1835                1840                1845

Arg Ser Asn Tyr Gly Met Ile Ala Ile Asn Pro Gly Arg Val Ala
    1850                1855                1860

Ala Ser Phe Ser Gln Glu Ala Leu Gln Tyr Val Val Glu Arg Val
    1865                1870                1875

Gly Lys Arg Thr Gly Trp Leu Val Glu Ile Val Asn Tyr Asn Val
    1880                1885                1890

Glu Asn Gln Gln Tyr Val Ala Ala Gly Asp Leu Arg Ala Leu Asp
    1895                1900                1905

Thr Val Thr Asn Val Leu Asn Phe Ile Lys Leu Gln Lys Ile Asp
    1910                1915                1920

Ile Ile Glu Leu Gln Lys Ser Leu Ser Leu Glu Glu Val Glu Gly
    1925                1930                1935

His Leu Phe Glu Ile Ile Asp Glu Ala Ser Lys Lys Ser Ala Val
    1940                1945                1950

Lys Pro Arg Pro Leu Lys Leu Glu Arg Gly Phe Ala Cys Ile Pro
    1955                1960                1965

Leu Val Gly Ile Ser Val Pro Phe His Ser Thr Tyr Leu Met Asn
    1970                1975                1980

Gly Val Lys Pro Phe Lys Ser Phe Leu Lys Lys Asn Ile Ile Lys
    1985                1990                1995

Glu Asn Val Lys Val Ala Arg Leu Ala Gly Lys Tyr Ile Pro Asn
    2000                2005                2010

Leu Thr Ala Lys Pro Phe Gln Val Thr Lys Glu Tyr Phe Gln Asp
    2015                2020                2025

Val Tyr Asp Leu Thr Gly Ser Glu Pro Ile Lys Glu Ile Ile Asp
    2030                2035                2040

Asn Trp Glu Lys Tyr Glu Gln Ser
    2045                2050
```

<210> SEQ ID NO 31
<211> LENGTH: 2051
<212> TYPE: PRT
<213> ORGANISM: Saccharomyces cerevisiae

<400> SEQUENCE: 31

```
Met Asp Ala Tyr Ser Thr Arg Pro Leu Thr Leu Ser His Gly Ser Leu
1               5                   10                  15

Glu His Val Leu Leu Val Pro Thr Ala Ser Phe Phe Ile Ala Ser Gln
                20                  25                  30

Leu Gln Glu Gln Phe Asn Lys Ile Leu Pro Glu Pro Thr Glu Gly Phe
            35                  40                  45

Ala Ala Asp Asp Glu Pro Thr Thr Pro Ala Glu Leu Val Gly Lys Phe
        50                  55                  60

Leu Gly Tyr Val Ser Ser Leu Val Glu Pro Ser Lys Val Gly Gln Phe
65                  70                  75                  80
```

-continued

```
Asp Gln Val Leu Asn Leu Cys Leu Thr Glu Phe Glu Asn Cys Tyr Leu
                 85                  90                  95
Glu Gly Asn Asp Ile His Ala Leu Ala Ala Lys Leu Leu Gln Glu Asn
            100                 105                 110
Asp Thr Thr Leu Val Lys Thr Lys Glu Leu Ile Lys Asn Tyr Ile Thr
        115                 120                 125
Ala Arg Ile Met Ala Lys Arg Pro Phe Asp Lys Lys Ser Asn Ser Ala
    130                 135                 140
Leu Phe Arg Ala Val Gly Glu Gly Asn Ala Gln Leu Val Ala Ile Phe
145                 150                 155                 160
Gly Gly Gln Gly Asn Thr Asp Asp Tyr Phe Glu Glu Leu Arg Asp Leu
                165                 170                 175
Tyr Gln Thr Tyr His Val Leu Val Gly Asp Leu Ile Lys Phe Ser Ala
            180                 185                 190
Glu Thr Leu Ser Glu Leu Ile Arg Thr Thr Leu Asp Ala Glu Lys Val
        195                 200                 205
Phe Thr Gln Gly Leu Asn Ile Leu Glu Trp Leu Glu Asn Pro Ser Asn
    210                 215                 220
Thr Pro Asp Lys Asp Tyr Leu Leu Ser Ile Pro Ile Ser Cys Pro Leu
225                 230                 235                 240
Ile Gly Val Ile Gln Leu Ala His Tyr Val Val Thr Ala Lys Leu Leu
                245                 250                 255
Gly Phe Thr Pro Gly Glu Leu Arg Ser Tyr Leu Lys Gly Ala Thr Gly
            260                 265                 270
His Ser Gln Gly Leu Val Thr Ala Val Ala Ile Ala Glu Thr Asp Ser
        275                 280                 285
Trp Glu Ser Phe Phe Val Ser Val Arg Lys Ala Ile Thr Val Leu Phe
    290                 295                 300
Phe Ala Gly Val Arg Cys Tyr Glu Ala Tyr Pro Asn Thr Ser Leu Pro
305                 310                 315                 320
Pro Ser Ile Leu Glu Asp Ser Leu Glu Asn Asn Glu Gly Val Pro Ser
                325                 330                 335
Pro Met Leu Ser Ile Ser Asn Leu Thr Gln Gln Val Gln Asp Tyr
            340                 345                 350
Val Asn Lys Thr Asn Ser His Leu Pro Ala Gly Lys Gln Val Glu Ile
        355                 360                 365
Ser Leu Val Asn Gly Ala Lys Asn Leu Val Val Ser Gly Pro Pro Gln
    370                 375                 380
Ser Leu Tyr Gly Leu Asn Leu Thr Leu Arg Lys Ala Lys Ala Pro Ser
385                 390                 395                 400
Gly Leu Asp Gln Ser Arg Ile Pro Phe Ser Glu Arg Lys Leu Lys Phe
                405                 410                 415
Ser Asn Arg Phe Leu Pro Val Ala Ser Pro Phe His Ser His Leu Leu
            420                 425                 430
Val Pro Ala Ser Asp Leu Ile Asn Lys Asp Leu Val Lys Asn Asn Val
        435                 440                 445
Ser Phe Asn Ala Lys Asp Ile Gln Ile Pro Val Tyr Asp Thr Phe Asp
    450                 455                 460
Gly Ser Asp Leu Arg Val Leu Ser Gly Ser Ile Ser Glu Arg Ile Val
465                 470                 475                 480
Asp Cys Ile Ile Arg Leu Pro Val Lys Trp Glu Thr Thr Thr Gln Phe
                485                 490                 495
```

```
Lys Ala Thr His Ile Leu Asp Phe Gly Pro Gly Ala Ser Gly Leu
            500                 505                 510

Gly Val Leu Thr His Arg Asn Lys Asp Gly Thr Gly Val Arg Val Ile
        515                 520                 525

Val Ala Gly Thr Leu Asp Ile Asn Pro Asp Asp Tyr Gly Phe Lys
        530                 535                 540

Gln Glu Ile Phe Asp Val Thr Ser Asn Gly Leu Lys Lys Asn Pro Asn
545                 550                 555                 560

Trp Leu Glu Glu Tyr His Pro Lys Leu Ile Lys Asn Lys Ser Gly Lys
                565                 570                 575

Ile Phe Val Glu Thr Lys Phe Ser Lys Leu Ile Gly Arg Pro Pro Leu
            580                 585                 590

Leu Val Pro Gly Met Thr Pro Cys Thr Val Ser Pro Asp Phe Val Ala
            595                 600                 605

Ala Thr Thr Asn Ala Gly Tyr Thr Ile Glu Leu Ala Gly Gly Gly Tyr
            610                 615                 620

Phe Ser Ala Ala Gly Met Thr Ala Ala Ile Asp Ser Val Val Ser Gln
625                 630                 635                 640

Ile Glu Lys Gly Ser Thr Phe Gly Ile Asn Leu Ile Tyr Val Asn Pro
            645                 650                 655

Phe Met Leu Gln Trp Gly Ile Pro Leu Ile Lys Glu Leu Arg Ser Lys
            660                 665                 670

Gly Tyr Pro Ile Gln Phe Leu Thr Ile Gly Ala Gly Val Pro Ser Leu
            675                 680                 685

Glu Val Ala Ser Glu Tyr Ile Glu Thr Leu Gly Leu Lys Tyr Leu Gly
            690                 695                 700

Leu Lys Pro Gly Ser Ile Asp Ala Ile Ser Gln Val Ile Asn Ile Ala
705                 710                 715                 720

Lys Ala His Pro Asn Phe Pro Ile Ala Leu Gln Trp Thr Gly Gly Arg
                725                 730                 735

Gly Gly Gly His His Ser Phe Glu Asp Ala His Thr Pro Met Leu Gln
            740                 745                 750

Met Tyr Ser Lys Ile Arg Arg His Pro Asn Ile Met Leu Ile Phe Gly
            755                 760                 765

Ser Gly Phe Gly Ser Ala Asp Asp Thr Tyr Pro Tyr Leu Thr Gly Glu
            770                 775                 780

Trp Ser Thr Lys Phe Asp Tyr Pro Pro Met Pro Phe Asp Gly Phe Leu
785                 790                 795                 800

Phe Gly Ser Arg Val Met Ile Ala Lys Glu Val Lys Thr Ser Pro Asp
                805                 810                 815

Ala Lys Lys Cys Ile Ala Ala Cys Thr Gly Val Pro Asp Asp Lys Trp
            820                 825                 830

Glu Gln Thr Tyr Lys Lys Pro Thr Gly Gly Ile Val Thr Val Arg Ser
            835                 840                 845

Glu Met Gly Glu Pro Ile His Lys Ile Ala Thr Arg Gly Val Met Leu
            850                 855                 860

Trp Lys Glu Phe Asp Glu Thr Ile Phe Asn Leu Pro Lys Asn Lys Leu
865                 870                 875                 880

Val Pro Thr Leu Glu Ala Lys Arg Asp Tyr Ile Ile Ser Arg Leu Asn
                885                 890                 895

Ala Asp Phe Gln Lys Pro Trp Phe Ala Thr Val Asn Gly Gln Ala Arg
                900                 905                 910

Asp Leu Ala Thr Met Thr Tyr Glu Glu Val Ala Lys Arg Leu Val Glu
```

```
                915                 920                 925
Leu Met Phe Ile Arg Ser Thr Asn Ser Trp Phe Asp Val Thr Trp Arg
                930                 935                 940

Thr Phe Thr Gly Asp Phe Leu Arg Arg Val Glu Glu Arg Phe Thr Lys
945                 950                 955                 960

Ser Lys Thr Leu Ser Leu Ile Gln Ser Tyr Ser Leu Leu Asp Lys Pro
                965                 970                 975

Asp Glu Ala Ile Glu Lys Val Phe Asn Ala Tyr Pro Ala Ala Arg Glu
                980                 985                 990

Gln Phe Leu Asn Ala Gln Asp Ile Asp His Phe Leu Ser Met Cys Gln
                995                 1000                1005

Asn Pro Met Gln Lys Pro Val Pro Phe Val Pro Val Leu Asp Arg
    1010                1015                1020

Arg Phe Glu Ile Phe Lys Lys Asp Ser Leu Trp Gln Ser Glu
    1025                1030                1035

His Leu Glu Ala Val Val Asp Gln Asp Val Gln Arg Thr Cys Ile
    1040                1045                1050

Leu His Gly Pro Val Ala Ala Gln Phe Thr Lys Val Ile Asp Glu
    1055                1060                1065

Pro Ile Lys Ser Ile Met Asp Gly Ile His Asp Gly His Ile Lys
    1070                1075                1080

Lys Leu Leu His Gln Tyr Tyr Gly Asp Asp Glu Ser Lys Ile Pro
    1085                1090                1095

Ala Val Glu Tyr Phe Gly Gly Glu Ser Pro Val Asp Val Gln Ser
    1100                1105                1110

Gln Val Asp Ser Ser Ser Val Ser Glu Asp Ser Ala Val Phe Lys
    1115                1120                1125

Ala Thr Ser Ser Thr Asp Glu Glu Ser Trp Phe Lys Ala Leu Ala
    1130                1135                1140

Gly Ser Glu Ile Asn Trp Arg His Ala Ser Phe Leu Cys Ser Phe
    1145                1150                1155

Ile Thr Gln Asp Lys Met Phe Val Ser Asn Pro Ile Arg Lys Val
    1160                1165                1170

Phe Lys Pro Ser Gln Gly Met Val Val Glu Ile Ser Asn Gly Asn
    1175                1180                1185

Thr Ser Ser Lys Thr Val Val Thr Leu Ser Glu Pro Val Gln Gly
    1190                1195                1200

Glu Leu Lys Pro Thr Val Ile Leu Lys Leu Leu Lys Glu Asn Ile
    1205                1210                1215

Ile Gln Met Glu Met Ile Glu Asn Arg Thr Met Asp Gly Lys Pro
    1220                1225                1230

Val Ser Leu Pro Leu Leu Tyr Asn Phe Asn Pro Asp Asn Gly Phe
    1235                1240                1245

Ala Pro Ile Ser Glu Val Met Glu Asp Arg Asn Gln Arg Ile Lys
    1250                1255                1260

Glu Met Tyr Trp Lys Leu Trp Ile Asp Glu Pro Phe Asn Leu Asp
    1265                1270                1275

Phe Asp Pro Arg Asp Val Ile Lys Gly Lys Asp Phe Glu Ile Thr
    1280                1285                1290

Ala Lys Glu Val Tyr Asp Phe Thr His Ala Val Gly Asn Asn Cys
    1295                1300                1305

Glu Asp Phe Val Ser Arg Pro Asp Arg Thr Met Leu Ala Pro Met
    1310                1315                1320
```

```
Asp Phe Ala Ile Val Val Gly Trp Arg Ala Ile Ile Lys Ala Ile
1325                1330                1335

Phe Pro Asn Thr Val Asp Gly Asp Leu Leu Lys Leu Val His Leu
1340                1345                1350

Ser Asn Gly Tyr Lys Met Ile Pro Gly Ala Lys Pro Leu Gln Val
1355                1360                1365

Gly Asp Val Val Ser Thr Thr Ala Val Ile Glu Ser Val Val Asn
1370                1375                1380

Gln Pro Thr Gly Lys Ile Val Asp Val Val Gly Thr Leu Ser Arg
1385                1390                1395

Asn Gly Lys Pro Val Met Glu Val Thr Ser Ser Phe Phe Tyr Arg
1400                1405                1410

Gly Asn Tyr Thr Asp Phe Glu Asn Thr Phe Gln Lys Thr Val Glu
1415                1420                1425

Pro Val Tyr Gln Met His Ile Lys Thr Ser Lys Asp Ile Ala Val
1430                1435                1440

Leu Arg Ser Lys Glu Trp Phe Gln Leu Asp Asp Glu Asp Phe Asp
1445                1450                1455

Leu Leu Asn Lys Thr Leu Thr Phe Glu Thr Glu Thr Glu Val Thr
1460                1465                1470

Phe Lys Asn Ala Asn Ile Phe Ser Ser Val Lys Cys Phe Gly Pro
1475                1480                1485

Ile Lys Val Glu Leu Pro Thr Lys Glu Thr Val Glu Ile Gly Ile
1490                1495                1500

Val Asp Tyr Glu Ala Gly Ala Ser His Gly Asn Pro Val Val Asp
1505                1510                1515

Phe Leu Lys Arg Asn Gly Ser Thr Leu Glu Gln Lys Val Asn Leu
1520                1525                1530

Glu Asn Pro Ile Pro Ile Ala Val Leu Asp Ser Tyr Thr Pro Ser
1535                1540                1545

Thr Asn Glu Pro Tyr Ala Arg Val Ser Gly Asp Leu Asn Pro Ile
1550                1555                1560

His Val Ser Arg His Phe Ala Ser Tyr Ala Asn Leu Pro Gly Thr
1565                1570                1575

Ile Thr His Gly Met Phe Ser Ser Ala Ser Val Arg Ala Leu Ile
1580                1585                1590

Glu Asn Trp Ala Ala Asp Ser Val Ser Ser Arg Val Arg Gly Tyr
1595                1600                1605

Thr Cys Gln Phe Val Asp Met Val Leu Pro Asn Thr Ala Leu Lys
1610                1615                1620

Thr Ser Ile Gln His Val Gly Met Ile Asn Gly Arg Lys Leu Ile
1625                1630                1635

Lys Phe Glu Thr Arg Asn Glu Asp Asp Val Val Val Leu Thr Gly
1640                1645                1650

Glu Ala Glu Ile Glu Gln Pro Val Thr Thr Phe Val Phe Thr Gly
1655                1660                1665

Gln Gly Ser Gln Glu Gln Gly Met Gly Met Asp Leu Tyr Lys Thr
1670                1675                1680

Ser Lys Ala Ala Gln Asp Val Trp Asn Arg Ala Asp Asn His Phe
1685                1690                1695

Lys Asp Thr Tyr Gly Phe Ser Ile Leu Asp Ile Val Ile Asn Asn
1700                1705                1710
```

Pro Val Asn Leu Thr Ile His Phe Gly Gly Glu Lys Gly Lys Arg
    1715                1720                1725

Ile Arg Glu Asn Tyr Ser Ala Met Ile Phe Glu Thr Ile Val Asp
    1730                1735                1740

Gly Lys Leu Lys Thr Glu Lys Ile Phe Lys Glu Ile Asn Glu His
    1745                1750                1755

Ser Thr Ser Tyr Thr Phe Arg Ser Glu Lys Gly Leu Leu Ser Ala
    1760                1765                1770

Thr Gln Phe Thr Gln Pro Ala Leu Thr Leu Met Glu Lys Ala Ala
    1775                1780                1785

Phe Glu Asp Leu Lys Ser Lys Gly Leu Ile Pro Ala Asp Ala Thr
    1790                1795                1800

Phe Ala Gly His Ser Leu Gly Glu Tyr Ala Ala Leu Ala Ser Leu
    1805                1810                1815

Ala Asp Val Met Ser Ile Glu Ser Leu Val Glu Val Val Phe Tyr
    1820                1825                1830

Arg Gly Met Thr Met Gln Val Ala Val Pro Arg Asp Glu Leu Gly
    1835                1840                1845

Arg Ser Asn Tyr Gly Met Ile Ala Ile Asn Pro Gly Arg Val Ala
    1850                1855                1860

Ala Ser Phe Ser Gln Glu Ala Leu Gln Tyr Val Val Glu Arg Val
    1865                1870                1875

Gly Lys Arg Thr Gly Trp Leu Val Glu Ile Val Asn Tyr Asn Val
    1880                1885                1890

Glu Asn Gln Gln Tyr Val Ala Ala Gly Asp Leu Arg Ala Leu Asp
    1895                1900                1905

Thr Val Thr Asn Val Leu Asn Phe Ile Lys Leu Gln Lys Ile Asp
    1910                1915                1920

Ile Ile Glu Leu Gln Lys Ser Leu Ser Leu Glu Glu Val Glu Gly
    1925                1930                1935

His Leu Phe Glu Ile Ile Asp Glu Ala Ser Lys Lys Ser Ala Val
    1940                1945                1950

Lys Pro Arg Pro Leu Lys Leu Glu Arg Gly Phe Ala Cys Ile Pro
    1955                1960                1965

Leu Val Gly Ile Ser Val Pro Phe His Ser Thr Tyr Leu Met Asn
    1970                1975                1980

Gly Val Lys Pro Phe Lys Ser Phe Leu Lys Lys Asn Ile Ile Lys
    1985                1990                1995

Glu Asn Val Lys Val Ala Arg Leu Ala Gly Lys Tyr Ile Pro Asn
    2000                2005                2010

Leu Thr Ala Lys Pro Phe Gln Val Thr Lys Glu Tyr Phe Gln Asp
    2015                2020                2025

Val Tyr Asp Leu Thr Gly Ser Glu Pro Ile Lys Glu Ile Ile Asp
    2030                2035                2040

Asn Trp Glu Lys Tyr Glu Gln Ser
    2045                2050

<210> SEQ ID NO 32
<211> LENGTH: 2051
<212> TYPE: PRT
<213> ORGANISM: Saccharomyces cerevisiae

<400> SEQUENCE: 32

Met Asp Ala Tyr Ser Thr Arg Pro Leu Thr Leu Ser His Gly Ser Leu
1               5                   10                  15

-continued

```
Glu His Val Leu Leu Val Pro Thr Ala Ser Phe Phe Ile Ala Ser Gln
             20                  25                  30

Leu Gln Glu Gln Phe Asn Lys Ile Leu Pro Glu Pro Thr Glu Gly Phe
         35                  40                  45

Ala Ala Asp Asp Glu Pro Thr Thr Pro Ala Glu Leu Val Gly Lys Phe
 50                  55                  60

Leu Gly Tyr Val Ser Ser Leu Val Glu Pro Ser Lys Val Gly Gln Phe
 65                  70                  75                  80

Asp Gln Val Leu Asn Leu Cys Leu Thr Glu Phe Glu Asn Cys Tyr Leu
                 85                  90                  95

Glu Gly Asn Asp Ile His Ala Leu Ala Ala Lys Leu Leu Gln Glu Asn
                 100                 105                 110

Asp Thr Thr Leu Val Lys Thr Lys Glu Leu Ile Lys Asn Tyr Ile Thr
             115                 120                 125

Ala Arg Ile Met Ala Lys Arg Pro Phe Asp Lys Lys Ser Asn Ser Ala
 130                 135                 140

Leu Phe Arg Ala Val Gly Glu Gly Asn Ala Gln Leu Val Ala Ile Phe
145                 150                 155                 160

Gly Gly Gln Gly Asn Thr Asp Asp Tyr Phe Glu Glu Leu Arg Asp Leu
                 165                 170                 175

Tyr Gln Thr Tyr His Val Leu Val Gly Asp Leu Ile Lys Phe Ser Ala
             180                 185                 190

Glu Thr Leu Ser Glu Leu Ile Arg Thr Thr Leu Asp Ala Glu Lys Val
             195                 200                 205

Phe Thr Gln Gly Leu Asn Ile Leu Glu Trp Leu Glu Asn Pro Ser Asn
 210                 215                 220

Thr Pro Asp Lys Asp Tyr Leu Leu Ser Ile Pro Ile Ser Cys Pro Leu
225                 230                 235                 240

Ile Gly Val Ile Gln Leu Ala His Tyr Val Thr Ala Lys Leu Leu
                 245                 250                 255

Gly Phe Thr Pro Gly Glu Leu Arg Ser Tyr Leu Lys Gly Ala Thr Gly
                 260                 265                 270

His Ser Gln Gly Leu Val Thr Ala Val Ala Ile Ala Glu Thr Asp Ser
             275                 280                 285

Trp Glu Ser Phe Phe Val Ser Val Arg Lys Ala Ile Thr Val Leu Phe
 290                 295                 300

Phe Ala Gly Val Arg Cys Tyr Glu Ala Tyr Pro Asn Thr Ser Leu Pro
305                 310                 315                 320

Pro Ser Ile Leu Glu Asp Ser Leu Glu Asn Asn Glu Gly Val Pro Ser
                 325                 330                 335

Pro Met Leu Ser Ile Ser Asn Leu Thr Gln Glu Gln Val Gln Asp Tyr
             340                 345                 350

Val Asn Lys Thr Asn Ser His Leu Pro Ala Gly Lys Gln Val Glu Ile
             355                 360                 365

Ser Leu Val Asn Gly Ala Lys Asn Leu Val Val Ser Gly Pro Pro Gln
         370                 375                 380

Ser Leu Tyr Gly Leu Asn Leu Thr Leu Arg Lys Ala Lys Ala Pro Ser
385                 390                 395                 400

Gly Leu Asp Gln Ser Arg Ile Pro Phe Ser Glu Arg Lys Leu Lys Phe
                 405                 410                 415

Ser Asn Arg Phe Leu Pro Val Ala Ser Pro Phe His Ser His Leu Leu
             420                 425                 430
```

-continued

Val Pro Ala Ser Asp Leu Ile Asn Lys Asp Leu Val Lys Asn Asn Val
            435                 440                 445

Ser Phe Asn Ala Lys Asp Ile Gln Ile Pro Val Tyr Asp Thr Phe Asp
        450                 455                 460

Gly Ser Asp Leu Arg Val Leu Ser Gly Ser Ile Ser Glu Arg Ile Val
465                 470                 475                 480

Asp Cys Ala Ile Arg Leu Pro Val Lys Trp Glu Thr Thr Thr Gln Phe
                485                 490                 495

Lys Ala Thr His Ile Leu Asp Phe Gly Pro Gly Ala Ser Gly Leu
            500                 505                 510

Gly Val Leu Thr His Arg Asn Lys Asp Gly Thr Gly Val Arg Val Ile
            515                 520                 525

Val Ala Gly Thr Leu Asp Ile Asn Pro Asp Asp Tyr Gly Phe Lys
530                 535                 540

Gln Glu Ile Phe Asp Val Thr Ser Asn Gly Leu Lys Lys Asn Pro Asn
545                 550                 555                 560

Trp Leu Glu Glu Tyr His Pro Lys Leu Ile Lys Asn Lys Ser Gly Lys
                565                 570                 575

Ile Phe Val Glu Thr Lys Phe Ser Lys Leu Ile Gly Arg Pro Pro Leu
                580                 585                 590

Leu Val Pro Gly Met Thr Pro Cys Thr Val Ser Pro Asp Phe Val Ala
            595                 600                 605

Ala Thr Thr Asn Ala Gly Tyr Thr Ile Glu Leu Ala Gly Gly Gly Tyr
            610                 615                 620

Phe Ser Ala Ala Gly Met Thr Ala Ala Ile Asp Ser Val Val Ser Gln
625                 630                 635                 640

Ile Glu Lys Gly Ser Thr Phe Gly Ile Asn Leu Ile Tyr Val Asn Pro
                645                 650                 655

Phe Met Leu Gln Trp Gly Ile Pro Leu Ile Lys Glu Leu Arg Ser Lys
                660                 665                 670

Gly Tyr Pro Ile Gln Phe Leu Thr Ile Gly Ala Gly Val Pro Ser Leu
            675                 680                 685

Glu Val Ala Ser Glu Tyr Ile Glu Thr Leu Gly Leu Lys Tyr Leu Gly
            690                 695                 700

Leu Lys Pro Gly Ser Ile Asp Ala Ile Ser Gln Val Ile Asn Ile Ala
705                 710                 715                 720

Lys Ala His Pro Asn Phe Pro Ile Ala Leu Gln Trp Thr Gly Gly Arg
                725                 730                 735

Gly Gly Gly His His Ser Phe Glu Asp Ala His Thr Pro Met Leu Gln
            740                 745                 750

Met Tyr Ser Lys Ile Arg Arg His Pro Asn Ile Met Leu Ile Phe Gly
            755                 760                 765

Ser Gly Phe Gly Ser Ala Asp Asp Thr Tyr Pro Tyr Leu Thr Gly Glu
            770                 775                 780

Trp Ser Thr Lys Phe Asp Tyr Pro Pro Met Pro Phe Asp Gly Phe Leu
785                 790                 795                 800

Phe Gly Ser Arg Val Met Ile Ala Lys Glu Val Lys Thr Ser Pro Asp
                805                 810                 815

Ala Lys Lys Cys Ile Ala Ala Cys Thr Gly Val Pro Asp Asp Lys Trp
            820                 825                 830

Glu Gln Thr Tyr Lys Lys Pro Thr Gly Gly Ile Val Thr Val Arg Ser
            835                 840                 845

Glu Met Gly Glu Pro Ile His Lys Ile Ala Thr Arg Gly Val Met Leu

```
            850                 855                 860
Trp Lys Glu Phe Asp Glu Thr Ile Phe Asn Leu Pro Lys Asn Lys Leu
865                 870                 875                 880

Val Pro Thr Leu Glu Ala Lys Arg Asp Tyr Ile Ile Ser Arg Leu Asn
                885                 890                 895

Ala Asp Phe Gln Lys Pro Trp Phe Ala Thr Val Asn Gly Gln Ala Arg
            900                 905                 910

Asp Leu Ala Thr Met Thr Tyr Glu Glu Val Ala Lys Arg Leu Val Glu
            915                 920                 925

Leu Met Phe Ile Arg Ser Thr Asn Ser Trp Phe Asp Val Thr Trp Arg
930                 935                 940

Thr Phe Thr Gly Asp Phe Leu Arg Arg Val Glu Glu Arg Phe Thr Lys
945                 950                 955                 960

Ser Lys Thr Leu Ser Leu Ile Gln Ser Tyr Ser Leu Leu Asp Lys Pro
                965                 970                 975

Asp Glu Ala Ile Glu Lys Val Phe Asn Ala Tyr Pro Ala Ala Arg Glu
            980                 985                 990

Gln Phe Leu Asn Ala Gln Asp Ile Asp His Phe Leu Ser Met Cys Gln
            995                 1000                1005

Asn Pro Met Gln Lys Pro Val Pro Phe Val Pro Val Leu Asp Arg
    1010                1015                1020

Arg Phe Glu Ile Phe Phe Lys Lys Asp Ser Leu Trp Gln Ser Glu
    1025                1030                1035

His Leu Glu Ala Val Val Asp Gln Asp Val Gln Arg Thr Cys Ile
    1040                1045                1050

Leu His Gly Pro Val Ala Ala Gln Phe Thr Lys Val Ile Asp Glu
    1055                1060                1065

Pro Ile Lys Ser Ile Met Asp Gly Ile His Asp Gly His Ile Lys
    1070                1075                1080

Lys Leu Leu His Gln Tyr Tyr Gly Asp Asp Glu Ser Lys Ile Pro
    1085                1090                1095

Ala Val Glu Tyr Phe Gly Gly Glu Ser Pro Val Asp Val Gln Ser
    1100                1105                1110

Gln Val Asp Ser Ser Ser Val Ser Glu Asp Ser Ala Val Phe Lys
    1115                1120                1125

Ala Thr Ser Ser Thr Asp Glu Glu Ser Trp Phe Lys Ala Leu Ala
    1130                1135                1140

Gly Ser Glu Ile Asn Trp Arg His Ala Ser Phe Leu Cys Ser Phe
    1145                1150                1155

Ile Thr Gln Asp Lys Met Phe Val Ser Asn Pro Ile Arg Lys Val
    1160                1165                1170

Phe Lys Pro Ser Gln Gly Met Val Val Glu Ile Ser Asn Gly Asn
    1175                1180                1185

Thr Ser Ser Lys Thr Val Val Thr Leu Ser Glu Pro Val Gln Gly
    1190                1195                1200

Glu Leu Lys Pro Thr Val Ile Leu Lys Leu Leu Lys Glu Asn Ile
    1205                1210                1215

Ile Gln Met Glu Met Ile Glu Asn Arg Thr Met Asp Gly Lys Pro
    1220                1225                1230

Val Ser Leu Pro Leu Leu Tyr Asn Phe Asn Pro Asp Asn Gly Phe
    1235                1240                1245

Ala Pro Ile Ser Glu Val Met Glu Asp Arg Asn Gln Arg Ile Lys
    1250                1255                1260
```

-continued

```
Glu Met Tyr Trp Lys Leu Trp Ile Asp Glu Pro Phe Asn Leu Asp
    1265                1270            1275

Phe Asp Pro Arg Asp Val Ile Lys Gly Lys Asp Phe Glu Ile Thr
    1280                1285            1290

Ala Lys Glu Val Tyr Asp Phe Thr His Ala Val Gly Asn Asn Cys
    1295                1300            1305

Glu Asp Phe Val Ser Arg Pro Asp Arg Thr Met Leu Ala Pro Met
    1310                1315            1320

Asp Phe Ala Ile Val Val Gly Trp Arg Ala Ile Ile Lys Ala Ile
    1325                1330            1335

Phe Pro Asn Thr Val Asp Gly Asp Leu Leu Lys Leu Val His Leu
    1340                1345            1350

Ser Asn Gly Tyr Lys Met Ile Pro Gly Ala Lys Pro Leu Gln Val
    1355                1360            1365

Gly Asp Val Val Ser Thr Thr Ala Val Ile Glu Ser Val Val Asn
    1370                1375            1380

Gln Pro Thr Gly Lys Ile Val Asp Val Val Gly Thr Leu Ser Arg
    1385                1390            1395

Asn Gly Lys Pro Val Met Glu Val Thr Ser Ser Phe Phe Tyr Arg
    1400                1405            1410

Gly Asn Tyr Thr Asp Phe Glu Asn Thr Phe Gln Lys Thr Val Glu
    1415                1420            1425

Pro Val Tyr Gln Met His Ile Lys Thr Ser Lys Asp Ile Ala Val
    1430                1435            1440

Leu Arg Ser Lys Glu Trp Phe Gln Leu Asp Glu Asp Phe Asp
    1445                1450            1455

Leu Leu Asn Lys Thr Leu Thr Phe Glu Thr Glu Thr Glu Val Thr
    1460                1465            1470

Phe Lys Asn Ala Asn Ile Phe Ser Ser Val Lys Cys Phe Gly Pro
    1475                1480            1485

Ile Lys Val Glu Leu Pro Thr Lys Glu Thr Val Glu Ile Gly Ile
    1490                1495            1500

Val Asp Tyr Glu Ala Gly Ala Ser His Gly Asn Pro Val Val Asp
    1505                1510            1515

Phe Leu Lys Arg Asn Gly Ser Thr Leu Glu Gln Lys Val Asn Leu
    1520                1525            1530

Glu Asn Pro Ile Pro Ile Ala Val Leu Asp Ser Tyr Thr Pro Ser
    1535                1540            1545

Thr Asn Glu Pro Tyr Ala Arg Val Ser Gly Asp Leu Asn Pro Ile
    1550                1555            1560

His Val Ser Arg His Phe Ala Ser Tyr Ala Asn Leu Pro Gly Thr
    1565                1570            1575

Ile Thr His Gly Met Phe Ser Ser Ala Ser Val Arg Ala Leu Ile
    1580                1585            1590

Glu Asn Trp Ala Ala Asp Ser Val Ser Ser Arg Val Arg Gly Tyr
    1595                1600            1605

Thr Cys Gln Phe Val Asp Met Val Leu Pro Asn Thr Ala Leu Lys
    1610                1615            1620

Thr Ser Ile Gln His Val Gly Met Ile Asn Gly Arg Lys Leu Ile
    1625                1630            1635

Lys Phe Glu Thr Arg Asn Glu Asp Asp Val Val Val Leu Thr Gly
    1640                1645            1650
```

```
Glu Ala Glu Ile Glu Gln Pro Val Thr Thr Phe Val Phe Thr Gly
1655                 1660                1665

Gln Gly Ser Gln Glu Gln Gly Met Gly Met Asp Leu Tyr Lys Thr
1670                 1675                1680

Ser Lys Ala Ala Gln Asp Val Trp Asn Arg Ala Asp Asn His Phe
1685                 1690                1695

Lys Asp Thr Tyr Gly Phe Ser Ile Leu Asp Ile Val Ile Asn Asn
1700                 1705                1710

Pro Val Asn Leu Thr Ile His Phe Gly Gly Glu Lys Gly Lys Arg
1715                 1720                1725

Ile Arg Glu Asn Tyr Ser Ala Met Ile Phe Glu Thr Ile Val Asp
1730                 1735                1740

Gly Lys Leu Lys Thr Glu Lys Ile Phe Lys Glu Ile Asn Glu His
1745                 1750                1755

Ser Thr Ser Tyr Thr Phe Arg Ser Glu Lys Gly Leu Leu Ser Ala
1760                 1765                1770

Thr Gln Phe Thr Gln Pro Ala Leu Thr Leu Met Glu Lys Ala Ala
1775                 1780                1785

Phe Glu Asp Leu Lys Ser Lys Gly Leu Ile Pro Ala Asp Ala Thr
1790                 1795                1800

Phe Ala Gly His Ser Leu Gly Glu Tyr Ala Ala Leu Ala Ser Leu
1805                 1810                1815

Ala Asp Val Met Ser Ile Glu Ser Leu Val Glu Val Val Phe Tyr
1820                 1825                1830

Arg Gly Met Thr Met Gln Val Ala Val Pro Arg Asp Glu Leu Gly
1835                 1840                1845

Arg Ser Asn Tyr Gly Met Ile Ala Ile Asn Pro Gly Arg Val Ala
1850                 1855                1860

Ala Ser Phe Ser Gln Glu Ala Leu Gln Tyr Val Val Glu Arg Val
1865                 1870                1875

Gly Lys Arg Thr Gly Trp Leu Val Glu Ile Val Asn Tyr Asn Val
1880                 1885                1890

Glu Asn Gln Gln Tyr Val Ala Ala Gly Asp Leu Arg Ala Leu Asp
1895                 1900                1905

Thr Val Thr Asn Val Leu Asn Phe Ile Lys Leu Gln Lys Ile Asp
1910                 1915                1920

Ile Ile Glu Leu Gln Lys Ser Leu Ser Leu Glu Glu Val Glu Gly
1925                 1930                1935

His Leu Phe Glu Ile Ile Asp Glu Ala Ser Lys Lys Ser Ala Val
1940                 1945                1950

Lys Pro Arg Pro Leu Lys Leu Glu Arg Gly Phe Ala Cys Ile Pro
1955                 1960                1965

Leu Val Gly Ile Ser Val Pro Phe His Ser Thr Tyr Leu Met Asn
1970                 1975                1980

Gly Val Lys Pro Phe Lys Ser Phe Leu Lys Lys Asn Ile Ile Lys
1985                 1990                1995

Glu Asn Val Lys Val Ala Arg Leu Ala Gly Lys Tyr Ile Pro Asn
2000                 2005                2010

Leu Thr Ala Lys Pro Phe Gln Val Thr Lys Glu Tyr Phe Gln Asp
2015                 2020                2025

Val Tyr Asp Leu Thr Gly Ser Glu Pro Ile Lys Glu Ile Ile Asp
2030                 2035                2040

Asn Trp Glu Lys Tyr Glu Gln Ser
```

-continued

```
       2045              2050

<210> SEQ ID NO 33
<211> LENGTH: 728
<212> TYPE: PRT
<213> ORGANISM: Ondatra zibethicus

<400> SEQUENCE: 33

Met Pro Glu Ala Leu Leu Arg Ser Ala Ser Ile Leu Arg Thr
1               5                   10                  15

Val Phe Leu Ser Arg Leu Leu Pro Gly Gly Pro Gly Cys Val Arg Lys
                20                  25                  30

Leu Ser Leu Asn Leu Gln Tyr Gln Gln Gly Ile Arg Pro Asn Val Gln
            35                  40                  45

Ser Ser Ser Leu Thr Asp Gly Arg Thr Leu Ser Lys Glu Ser Ser Thr
        50                  55                  60

His Gly Leu Glu Phe Ser Ala Pro Glu Lys Ala Ser Pro Pro Asp Thr
65                  70                  75                  80

Ala Glu Glu Ala Leu Trp Thr Ala Arg Ala Asp Gly Arg Val Arg Leu
                85                  90                  95

Arg Arg Glu Pro Phe Cys Thr Gln Pro Pro Tyr Thr Val His Arg Met
            100                 105                 110

Phe Tyr Glu Ala Leu Asp Lys Tyr Gly Ser Leu Ser Ala Leu Gly Val
        115                 120                 125

Lys Arg Arg Asn Lys Trp Glu Arg Ile Ser Tyr Tyr Gln Tyr Tyr Glu
    130                 135                 140

Ile Ala Arg Lys Val Ala Arg Gly Phe Leu Lys Leu Gly Leu Glu Arg
145                 150                 155                 160

Ala His Ser Val Gly Ile Leu Gly Phe Asn Ser Pro Glu Trp Phe Phe
                165                 170                 175

Ser Ala Val Gly Thr Val Phe Ala Gly Gly Ile Val Thr Gly Ile Tyr
            180                 185                 190

Thr Thr Ser Ser Leu Glu Ala Cys Gln Tyr Ile Ala His Asp Cys Arg
        195                 200                 205

Ala Asn Val Ile Val Val Asp Thr Gln Lys Gln Leu Glu Lys Ile Leu
    210                 215                 220

Lys Ile Trp Lys Asp Leu Pro His Leu Lys Ala Val Val Ile Tyr Gln
225                 230                 235                 240

Glu Pro Leu Pro Lys Lys Met Val Asn Val Tyr Thr Met Glu Glu Leu
                245                 250                 255

Ile Glu Leu Gly Gln Glu Val Pro Glu Glu Ala Leu Asp Thr Ile Ile
            260                 265                 270

Asp Thr Gln Gln Pro Asn Gln Cys Cys Val Leu Val Tyr Thr Ser Gly
        275                 280                 285

Thr Thr Gly Asn Pro Lys Gly Val Met Leu Ser Gln Asp Asn Ile Thr
    290                 295                 300

Trp Thr Ala Arg Tyr Gly Ser Gln Ala Gly Asp Ile Gln Pro Ala Glu
305                 310                 315                 320

Val Gln Gln Glu Val Val Ser Tyr Leu Pro Leu Ser His Ile Ala
                325                 330                 335

Ala Gln Ile Tyr Asp Leu Trp Thr Gly Ile Gln Trp Gly Ala Gln Val
            340                 345                 350

Cys Phe Ala Asp Pro Asp Ala Leu Lys Gly Ser Leu Val Asn Thr Leu
        355                 360                 365
```

Arg Glu Val Glu Pro Thr Ser His Met Gly Val Pro Arg Val Trp Glu
370                 375                 380

Lys Ile Met Glu Gly Ile Gln Glu Val Ala Ala Gln Ser Gly Phe Ile
385                 390                 395                 400

Arg Arg Lys Met Leu Leu Trp Ala Met Ser Val Thr Leu Glu Gln Asn
            405                 410                 415

Leu Thr Cys Pro Ser Asn Asp Leu Lys Pro Phe Thr Ser Arg Leu Ala
            420                 425                 430

Asp Tyr Leu Val Leu Ala Lys Val Arg Gln Ala Leu Gly Phe Ala Lys
            435                 440                 445

Cys Gln Lys Asn Phe Tyr Gly Ala Ala Pro Met Thr Ala Glu Thr Gln
450                 455                 460

Arg Phe Phe Leu Gly Leu Asn Ile Arg Leu Tyr Ala Gly Tyr Gly Leu
465                 470                 475                 480

Ser Glu Ser Thr Gly Pro His Phe Met Ser Ser Pro Tyr Asn Tyr Arg
                485                 490                 495

Leu Tyr Ser Ser Gly Lys Leu Ile Pro Gly Cys Arg Val Lys Leu Val
            500                 505                 510

Asn Gln Asp Ala Asn Gly Ile Gly Glu Ile Cys Leu Trp Gly Arg Thr
            515                 520                 525

Ile Phe Met Gly Tyr Leu Asn Met Glu Asp Lys Thr Cys Glu Ala Ile
530                 535                 540

Asp Ser Glu Gly Trp Leu His Thr Gly Asp Met Gly Arg Leu Asp Ser
545                 550                 555                 560

Asp Gly Phe Leu Tyr Ile Thr Gly Arg Leu Lys Glu Leu Ile Ile Thr
                565                 570                 575

Ala Gly Gly Glu Asn Val Pro Pro Val Pro Ile Glu Glu Ala Val Lys
            580                 585                 590

Thr Glu Leu Pro Ile Ile Ser Ser Ala Met Leu Ile Gly Asp Gln Arg
            595                 600                 605

Lys Phe Leu Ser Met Leu Leu Thr Leu Lys Cys Thr Leu Asp Pro Glu
610                 615                 620

Thr Ser Glu Pro Thr Asp Asn Leu Thr Glu Gln Ala Val Glu Phe Cys
625                 630                 635                 640

Gln Arg Val Gly Ser Gly Ala Ser Thr Val Ser Glu Ile Val Gly Gln
                645                 650                 655

Arg Asp Glu Ala Val Tyr Gln Ala Ile Gln Gly Ile Gln Arg Val
            660                 665                 670

Asn Ala Asn Ala Ala Arg Pro Tyr His Ile Gln Lys Trp Ala Ile
            675                 680                 685

Leu Lys Arg Asp Phe Ser Ile Ser Gly Gly Glu Leu Gly Pro Thr Met
            690                 695                 700

Lys Leu Lys Arg Leu Thr Val Leu Glu Lys Tyr Lys Asp Ile Ile Asp
705                 710                 715                 720

Ser Phe Tyr Gln Glu Gln Lys Gln
                725

<210> SEQ ID NO 34
<211> LENGTH: 393
<212> TYPE: PRT
<213> ORGANISM: Saccharomyces cerevisiae

<400> SEQUENCE: 34

Met Leu Gln Arg His Ser Leu Lys Leu Gly Lys Phe Ser Ile Arg Thr
1               5                   10                  15

Leu Ala Thr Gly Ala Pro Leu Asp Ala Ser Lys Leu Lys Ile Thr Arg
            20                  25                  30

Asn Pro Asn Pro Ser Lys Pro Arg Pro Asn Glu Glu Leu Val Phe Gly
            35                  40                  45

Gln Thr Phe Thr Asp His Met Leu Thr Ile Pro Trp Ser Ala Lys Glu
 50                  55                  60

Gly Trp Gly Thr Pro His Ile Lys Pro Tyr Gly Asn Leu Ser Leu Asp
 65                  70                  75                  80

Pro Ser Ala Cys Val Phe His Tyr Ala Phe Glu Leu Phe Glu Gly Leu
                85                  90                  95

Lys Ala Tyr Arg Thr Pro Gln Asn Thr Ile Thr Met Phe Arg Pro Asp
            100                 105                 110

Lys Asn Met Ala Arg Met Asn Lys Ser Ala Ala Arg Ile Cys Leu Pro
            115                 120                 125

Thr Phe Glu Ser Glu Glu Leu Ile Lys Leu Thr Gly Lys Leu Ile Glu
130                 135                 140

Gln Asp Lys His Leu Val Pro Gln Gly Asn Gly Tyr Ser Leu Tyr Ile
145                 150                 155                 160

Arg Pro Thr Met Ile Gly Thr Ser Lys Gly Leu Gly Val Gly Thr Pro
                165                 170                 175

Ser Glu Ala Leu Leu Tyr Val Ile Thr Ser Pro Val Gly Pro Tyr Tyr
            180                 185                 190

Lys Thr Gly Phe Lys Ala Val Arg Leu Glu Ala Thr Asp Tyr Ala Thr
            195                 200                 205

Arg Ala Trp Pro Gly Gly Val Gly Asp Lys Lys Leu Gly Ala Asn Tyr
            210                 215                 220

Ala Pro Cys Ile Leu Pro Gln Leu Gln Ala Ala Lys Arg Gly Tyr Gln
225                 230                 235                 240

Gln Asn Leu Trp Leu Phe Gly Pro Glu Lys Asn Ile Thr Glu Val Gly
                245                 250                 255

Thr Met Asn Val Phe Phe Val Phe Leu Asn Lys Val Thr Gly Lys Lys
            260                 265                 270

Glu Leu Val Thr Ala Pro Leu Asp Gly Thr Ile Leu Glu Gly Val Thr
            275                 280                 285

Arg Asp Ser Val Leu Thr Leu Ala Arg Asp Lys Leu Asp Pro Gln Glu
290                 295                 300

Trp Asp Ile Asn Glu Arg Tyr Tyr Thr Ile Thr Glu Val Ala Thr Arg
305                 310                 315                 320

Ala Lys Gln Gly Glu Leu Leu Glu Ala Phe Gly Ser Gly Thr Ala Ala
                325                 330                 335

Val Val Ser Pro Ile Lys Glu Ile Gly Trp Asn Asn Glu Asp Ile His
            340                 345                 350

Val Pro Leu Leu Pro Gly Glu Gln Cys Gly Ala Leu Thr Lys Gln Val
            355                 360                 365

Ala Gln Trp Ile Ala Asp Ile Gln Tyr Gly Arg Val Asn Tyr Gly Asn
            370                 375                 380

Trp Ser Lys Thr Val Ala Asp Leu Asn
385                 390

<210> SEQ ID NO 35
<211> LENGTH: 376
<212> TYPE: PRT
<213> ORGANISM: Saccharomyces cerevisiae

<400> SEQUENCE: 35

```
Met Thr Leu Ala Pro Leu Asp Ala Ser Lys Val Lys Ile Thr Thr Thr
1               5                   10                  15

Gln His Ala Ser Lys Pro Lys Pro Asn Ser Glu Leu Val Phe Gly Lys
            20                  25                  30

Ser Phe Thr Asp His Met Leu Thr Ala Glu Trp Thr Ala Glu Lys Gly
        35                  40                  45

Trp Gly Thr Pro Glu Ile Lys Pro Tyr Gln Asn Leu Ser Leu Asp Pro
    50                  55                  60

Ser Ala Val Val Phe His Tyr Ala Phe Glu Leu Phe Glu Gly Met Lys
65                  70                  75                  80

Ala Tyr Arg Thr Val Asp Asn Lys Ile Thr Met Phe Arg Pro Asp Met
                85                  90                  95

Asn Met Lys Arg Met Asn Lys Ser Ala Gln Arg Ile Cys Leu Pro Thr
            100                 105                 110

Phe Asp Pro Glu Glu Leu Ile Thr Leu Ile Gly Lys Leu Ile Gln Gln
        115                 120                 125

Asp Lys Cys Leu Val Pro Glu Gly Lys Gly Tyr Ser Leu Tyr Ile Arg
    130                 135                 140

Pro Thr Leu Ile Gly Thr Thr Ala Gly Leu Gly Val Ser Thr Pro Asp
145                 150                 155                 160

Arg Ala Leu Leu Tyr Val Ile Cys Cys Pro Val Gly Pro Tyr Tyr Lys
                165                 170                 175

Thr Gly Phe Lys Ala Val Arg Leu Glu Ala Thr Asp Tyr Ala Thr Arg
            180                 185                 190

Ala Trp Pro Gly Gly Cys Gly Asp Lys Lys Leu Gly Ala Asn Tyr Ala
        195                 200                 205

Pro Cys Val Leu Pro Gln Leu Gln Ala Ala Ser Arg Gly Tyr Gln Gln
    210                 215                 220

Asn Leu Trp Leu Phe Gly Pro Asn Asn Ile Thr Glu Val Gly Thr
225                 230                 235                 240

Met Asn Ala Phe Phe Val Phe Lys Asp Ser Lys Thr Gly Lys Lys Glu
                245                 250                 255

Leu Val Thr Ala Pro Leu Asp Gly Thr Ile Leu Glu Gly Val Thr Arg
            260                 265                 270

Asp Ser Ile Leu Asn Leu Ala Lys Glu Arg Leu Glu Pro Ser Glu Trp
        275                 280                 285

Thr Ile Ser Glu Arg Tyr Phe Thr Ile Gly Glu Val Thr Glu Arg Ser
    290                 295                 300

Lys Asn Gly Glu Leu Leu Glu Ala Phe Gly Ser Gly Thr Ala Ala Ile
305                 310                 315                 320

Val Ser Pro Ile Lys Glu Ile Gly Trp Lys Gly Glu Gln Ile Asn Ile
                325                 330                 335

Pro Leu Leu Pro Gly Glu Gln Thr Gly Pro Leu Ala Lys Glu Val Ala
            340                 345                 350

Gln Trp Ile Asn Gly Ile Gln Tyr Gly Glu Thr Glu His Gly Asn Trp
        355                 360                 365

Ser Arg Val Val Thr Asp Leu Asn
    370                 375
```

<210> SEQ ID NO 36
<211> LENGTH: 635
<212> TYPE: PRT
<213> ORGANISM: Saccharomyces cerevisiae

<400> SEQUENCE: 36

Met Ala Pro Val Thr Ile Glu Lys Phe Val Asn Gln Glu Arg His
1               5                   10                  15

Leu Val Ser Asn Arg Ser Ala Thr Ile Pro Phe Gly Glu Tyr Ile Phe
            20                  25                  30

Lys Arg Leu Leu Ser Ile Asp Thr Lys Ser Val Phe Gly Val Pro Gly
                35                  40                  45

Asp Phe Asn Leu Ser Leu Leu Glu Tyr Leu Tyr Ser Pro Ser Val Glu
    50                  55                  60

Ser Ala Gly Leu Arg Trp Val Gly Thr Cys Asn Glu Leu Asn Ala Ala
65              70                  75                  80

Tyr Ala Ala Asp Gly Tyr Ser Arg Tyr Ser Asn Lys Ile Gly Cys Leu
                85                  90                  95

Ile Thr Thr Tyr Gly Val Gly Glu Leu Ser Ala Leu Asn Gly Ile Ala
            100                 105                 110

Gly Ser Phe Ala Glu Asn Val Lys Val Leu His Ile Val Gly Val Ala
        115                 120                 125

Lys Ser Ile Asp Ser Arg Ser Ser Asn Phe Ser Asp Arg Asn Leu His
    130                 135                 140

His Leu Val Pro Gln Leu His Asp Ser Asn Phe Lys Gly Pro Asn His
145                 150                 155                 160

Lys Val Tyr His Asp Met Val Lys Asp Arg Val Ala Cys Ser Val Ala
                165                 170                 175

Tyr Leu Glu Asp Ile Glu Thr Ala Cys Asp Gln Val Asp Asn Val Ile
            180                 185                 190

Arg Asp Ile Tyr Lys Tyr Ser Lys Pro Gly Tyr Ile Phe Val Pro Ala
        195                 200                 205

Asp Phe Ala Asp Met Ser Val Thr Cys Asp Asn Leu Val Asn Val Pro
    210                 215                 220

Arg Ile Ser Gln Gln Asp Cys Ile Val Tyr Pro Ser Glu Asn Gln Leu
225                 230                 235                 240

Ser Asp Ile Ile Asn Lys Ile Thr Ser Trp Ile Tyr Ser Ser Lys Thr
                245                 250                 255

Pro Ala Ile Leu Gly Asp Val Leu Thr Asp Arg Tyr Gly Val Ser Asn
            260                 265                 270

Phe Leu Asn Lys Leu Ile Cys Lys Thr Gly Ile Trp Asn Phe Ser Thr
        275                 280                 285

Val Met Gly Lys Ser Val Ile Asp Glu Ser Asn Pro Thr Tyr Met Gly
    290                 295                 300

Gln Tyr Asn Gly Lys Glu Gly Leu Lys Gln Val Tyr Glu His Phe Glu
305                 310                 315                 320

Leu Cys Asp Leu Val Leu His Phe Gly Val Asp Ile Asn Glu Ile Asn
                325                 330                 335

Asn Gly His Tyr Thr Phe Thr Tyr Lys Pro Asn Ala Lys Ile Ile Gln
            340                 345                 350

Phe His Pro Asn Tyr Ile Arg Leu Val Asp Thr Arg Gln Gly Asn Glu
        355                 360                 365

Gln Met Phe Lys Gly Ile Asn Phe Ala Pro Ile Leu Lys Glu Leu Tyr
    370                 375                 380

Lys Arg Ile Asp Val Ser Lys Leu Ser Leu Gln Tyr Asp Ser Asn Val
385                 390                 395                 400

Thr Gln Tyr Thr Asn Glu Thr Met Arg Leu Glu Asp Pro Thr Asn Gly 405                 410                 415
Gln Ser Ser Ile Ile Thr Gln Val His Leu Gln Lys Thr Met Pro Lys
            420                 425                 430

Phe Leu Asn Pro Gly Asp Val Val Cys Glu Thr Gly Ser Phe Gln
            435                 440                 445

Phe Ser Val Arg Asp Phe Ala Phe Pro Ser Gln Leu Lys Tyr Ile Ser
            450                 455                 460

Gln Gly Phe Phe Leu Ser Ile Gly Met Ala Leu Pro Ala Ala Leu Gly
465                 470                 475                 480

Val Gly Ile Ala Met Gln Asp His Ser Asn Ala His Ile Asn Gly Gly
                485                 490                 495

Asn Val Lys Glu Asp Tyr Lys Pro Arg Leu Ile Leu Phe Glu Gly Asp
                500                 505                 510

Gly Ala Ala Gln Met Thr Ile Gln Glu Leu Ser Thr Ile Leu Lys Cys
                515                 520                 525

Asn Ile Pro Leu Glu Val Ile Ile Trp Asn Asn Asn Gly Tyr Thr Ile
            530                 535                 540

Glu Arg Ala Ile Met Gly Pro Thr Arg Ser Tyr Asn Asp Val Met Ser
545                 550                 555                 560

Trp Lys Trp Thr Lys Leu Phe Glu Ala Phe Gly Asp Phe Asp Gly Lys
                565                 570                 575

Tyr Thr Asn Ser Thr Leu Ile Gln Cys Pro Ser Lys Leu Ala Leu Lys
                580                 585                 590

Leu Glu Glu Leu Lys Asn Ser Asn Lys Arg Ser Gly Ile Glu Leu Leu
            595                 600                 605

Glu Val Lys Leu Gly Glu Leu Asp Phe Pro Glu Gln Leu Lys Cys Met
610                 615                 620

Val Glu Ala Ala Ala Leu Lys Arg Asn Lys Lys
625                 630                 635

<210> SEQ ID NO 37
<211> LENGTH: 506
<212> TYPE: PRT
<213> ORGANISM: Saccharomyces cerevisiae

<400> SEQUENCE: 37

Met Pro Thr Leu Tyr Thr Asp Ile Glu Ile Pro Gln Leu Lys Ile Ser
1               5                   10                  15

Leu Lys Gln Pro Leu Gly Leu Phe Ile Asn Asn Glu Phe Cys Pro Ser
            20                  25                  30

Ser Asp Gly Lys Thr Ile Glu Thr Val Asn Pro Ala Thr Gly Glu Pro
        35                  40                  45

Ile Thr Ser Phe Gln Ala Ala Asn Glu Lys Asp Val Asp Lys Ala Val
    50                  55                  60

Lys Ala Ala Arg Ala Ala Phe Asp Asn Val Trp Ser Lys Thr Ser Ser
65                  70                  75                  80

Glu Gln Arg Gly Ile Tyr Leu Ser Asn Leu Lys Leu Ile Glu Glu
                85                  90                  95

Glu Gln Asp Thr Leu Ala Ala Leu Glu Thr Leu Asp Ala Gly Lys Pro
            100                 105                 110

Tyr His Ser Asn Ala Lys Gly Asp Leu Ala Gln Ile Leu Gln Leu Thr
            115                 120                 125

Arg Tyr Phe Ala Gly Ser Ala Asp Lys Phe Asp Lys Gly Ala Thr Ile
        130                 135                 140

```
Pro Leu Thr Phe Asn Lys Phe Ala Tyr Thr Leu Lys Val Pro Phe Gly
145                 150                 155                 160

Val Val Ala Gln Ile Val Pro Trp Asn Tyr Pro Leu Ala Met Ala Cys
            165                 170                 175

Trp Lys Leu Gln Gly Ala Leu Ala Ala Gly Asn Thr Val Ile Ile Lys
        180                 185                 190

Pro Ala Glu Asn Thr Ser Leu Ser Leu Leu Tyr Phe Ala Thr Leu Ile
    195                 200                 205

Lys Lys Ala Gly Phe Pro Pro Gly Val Val Asn Ile Val Pro Gly Tyr
210                 215                 220

Gly Ser Leu Val Gly Gln Ala Leu Ala Ser His Met Asp Ile Asp Lys
225                 230                 235                 240

Ile Ser Phe Thr Gly Ser Thr Lys Val Gly Gly Phe Val Leu Glu Ala
            245                 250                 255

Ser Gly Gln Ser Asn Leu Lys Asp Val Thr Leu Glu Cys Gly Gly Lys
        260                 265                 270

Ser Pro Ala Leu Val Phe Glu Asp Ala Asp Leu Asp Lys Ala Ile Asp
    275                 280                 285

Trp Ile Ala Ala Gly Ile Phe Tyr Asn Ser Gly Gln Asn Cys Thr Ala
290                 295                 300

Asn Ser Arg Val Tyr Val Gln Ser Ser Ile Tyr Asp Lys Phe Val Glu
305                 310                 315                 320

Lys Phe Lys Glu Thr Ala Lys Lys Glu Trp Asp Val Ala Gly Lys Phe
            325                 330                 335

Asp Pro Phe Asp Glu Lys Cys Ile Val Gly Pro Val Ile Ser Ser Thr
        340                 345                 350

Gln Tyr Asp Arg Ile Lys Ser Tyr Ile Glu Arg Gly Lys Arg Glu Glu
    355                 360                 365

Lys Leu Asp Met Phe Gln Thr Ser Glu Phe Pro Ile Gly Gly Ala Lys
370                 375                 380

Gly Tyr Phe Ile Pro Pro Thr Ile Phe Thr Asp Val Pro Gln Thr Ser
385                 390                 395                 400

Lys Leu Leu Gln Asp Glu Ile Phe Gly Pro Val Val Val Ser Lys
            405                 410                 415

Phe Thr Asn Tyr Asp Asp Ala Leu Lys Leu Ala Asn Asp Thr Cys Tyr
        420                 425                 430

Gly Leu Ala Ser Ala Val Phe Thr Lys Asp Val Lys Lys Ala His Met
    435                 440                 445

Phe Ala Arg Asp Ile Lys Ala Gly Thr Val Trp Ile Asn Ser Ser Asn
450                 455                 460

Asp Glu Asp Val Thr Val Pro Phe Gly Gly Phe Lys Met Ser Gly Ile
465                 470                 475                 480

Gly Arg Glu Leu Gly Gln Ser Gly Val Asp Thr Tyr Leu Gln Thr Lys
            485                 490                 495

Ala Val His Ile Asn Leu Ser Leu Asp Asn
        500                 505

<210> SEQ ID NO 38
<211> LENGTH: 506
<212> TYPE: PRT
<213> ORGANISM: Saccharomyces cerevisiae

<400> SEQUENCE: 38

Met Pro Thr Leu Tyr Thr Asp Ile Glu Ile Pro Gln Leu Lys Ile Ser
1               5                   10                  15
```

```
Leu Lys Gln Pro Leu Gly Leu Phe Ile Asn Asn Glu Phe Cys Pro Ser
         20                  25                  30

Ser Asp Gly Lys Thr Ile Glu Thr Val Asn Pro Ala Thr Gly Glu Pro
         35                  40                  45

Ile Thr Ser Phe Gln Ala Ala Asn Glu Lys Asp Val Asp Lys Ala Val
 50                  55                  60

Lys Ala Ala Arg Ala Ala Phe Asp Asn Val Trp Ser Lys Thr Ser Ser
 65                  70                  75                  80

Glu Gln Arg Gly Ile Tyr Leu Ser Asn Leu Leu Lys Leu Ile Glu Glu
                 85                  90                  95

Glu Gln Asp Thr Leu Ala Ala Leu Glu Thr Leu Asp Ala Gly Lys Pro
            100                 105                 110

Tyr His Ser Asn Ala Lys Gly Asp Leu Ala Gln Ile Leu Gln Leu Thr
            115                 120                 125

Arg Tyr Phe Ala Gly Ser Ala Asp Lys Phe Asp Lys Gly Ala Thr Ile
130                 135                 140

Pro Leu Thr Phe Asn Lys Phe Ala Tyr Thr Leu Lys Val Pro Phe Gly
145                 150                 155                 160

Val Val Ala Gln Ile Val Pro Trp Asn Tyr Pro Leu Ala Met Ala Cys
                165                 170                 175

Trp Lys Leu Gln Gly Ala Leu Ala Ala Gly Asn Thr Val Ile Ile Lys
            180                 185                 190

Pro Ala Glu Asn Thr Ser Leu Ser Leu Leu Tyr Phe Ala Thr Leu Ile
            195                 200                 205

Lys Lys Ala Gly Phe Pro Pro Gly Val Val Asn Ile Val Pro Gly Tyr
210                 215                 220

Gly Ser Leu Val Gly Gln Ala Leu Ala Ser His Met Asp Ile Asp Lys
225                 230                 235                 240

Ile Ser Phe Thr Gly Ser Thr Lys Val Gly Gly Phe Val Leu Glu Ala
                245                 250                 255

Ser Gly Gln Ser Asn Leu Lys Asp Val Thr Leu Glu Cys Gly Gly Lys
            260                 265                 270

Ser Pro Ala Leu Val Phe Glu Asp Ala Asp Leu Asp Lys Ala Ile Asp
            275                 280                 285

Trp Ile Ala Ala Gly Ile Phe Tyr Asn Ser Gly Gln Asn Cys Thr Ala
290                 295                 300

Asn Ser Arg Val Tyr Val Gln Ser Ser Ile Tyr Asp Lys Phe Val Glu
305                 310                 315                 320

Lys Phe Lys Glu Thr Ala Lys Lys Glu Trp Asp Val Ala Gly Lys Phe
                325                 330                 335

Asp Pro Phe Asp Glu Lys Cys Ile Val Gly Pro Val Ile Ser Ser Thr
            340                 345                 350

Gln Tyr Asp Arg Ile Lys Ser Tyr Ile Glu Arg Gly Lys Arg Glu Glu
            355                 360                 365

Lys Leu Asp Met Phe Gln Thr Ser Glu Phe Pro Ile Gly Gly Ala Lys
            370                 375                 380

Gly Tyr Phe Ile Pro Pro Thr Ile Phe Thr Asp Val Pro Gln Thr Ser
385                 390                 395                 400

Lys Leu Leu Gln Asp Glu Ile Phe Gly Pro Val Val Val Ser Lys
                405                 410                 415

Phe Thr Asn Tyr Asp Asp Ala Leu Lys Leu Ala Asn Asp Thr Cys Tyr
            420                 425                 430
```

```
Gly Leu Ala Ser Ala Val Phe Thr Lys Asp Val Lys Ala His Met
            435                 440                 445

Phe Ala Arg Asp Ile Lys Ala Gly Thr Val Trp Ile Asn Ser Ser Asn
450                 455                 460

Asp Glu Asp Val Thr Val Pro Phe Gly Phe Lys Met Ser Gly Ile
465                 470                 475                 480

Gly Arg Glu Leu Gly Gln Ser Gly Val Asp Thr Tyr Leu Gln Thr Lys
                    485                 490                 495

Ala Val His Ile Asn Leu Ser Leu Asp Asn
                500                 505

<210> SEQ ID NO 39
<211> LENGTH: 2233
<212> TYPE: PRT
<213> ORGANISM: Saccharomyces cerevisiae

<400> SEQUENCE: 39

Met Ser Glu Glu Ser Leu Phe Glu Ser Pro Gln Lys Met Glu Tyr
1               5                   10                  15

Glu Ile Thr Asn Tyr Ser Glu Arg His Thr Glu Leu Pro Gly His Phe
                20                  25                  30

Ile Gly Leu Asn Thr Val Asp Lys Leu Glu Glu Ser Pro Leu Arg Asp
            35                  40                  45

Phe Val Lys Ser His Gly Gly His Thr Val Ile Ser Lys Ile Leu Ile
    50                  55                  60

Ala Asn Asn Gly Ile Ala Ala Val Lys Glu Ile Arg Ser Val Arg Lys
65                  70                  75                  80

Trp Ala Tyr Glu Thr Phe Gly Asp Asp Arg Thr Val Gln Phe Val Ala
                85                  90                  95

Met Ala Thr Pro Glu Asp Leu Glu Ala Asn Ala Glu Tyr Ile Arg Met
            100                 105                 110

Ala Asp Gln Tyr Ile Glu Val Pro Gly Gly Thr Asn Asn Asn Asn Tyr
        115                 120                 125

Ala Asn Val Asp Leu Ile Val Asp Ile Ala Glu Arg Ala Asp Val Asp
    130                 135                 140

Ala Val Trp Ala Gly Trp Gly His Ala Ser Glu Asn Pro Leu Leu Pro
145                 150                 155                 160

Glu Lys Leu Ser Gln Ser Lys Arg Lys Val Ile Phe Ile Gly Pro Pro
                165                 170                 175

Gly Asn Ala Met Arg Ser Leu Gly Asp Lys Ile Ser Ser Thr Ile Val
            180                 185                 190

Ala Gln Ser Ala Lys Val Pro Cys Ile Pro Trp Ser Gly Thr Gly Val
        195                 200                 205

Asp Thr Val His Val Asp Glu Lys Thr Gly Leu Val Ser Val Asp Asp
    210                 215                 220

Asp Ile Tyr Gln Lys Gly Cys Cys Thr Ser Pro Glu Asp Gly Leu Gln
225                 230                 235                 240

Lys Ala Lys Arg Ile Gly Phe Pro Val Met Ile Lys Ala Ser Glu Gly
                245                 250                 255

Gly Gly Gly Lys Gly Ile Arg Gln Val Glu Arg Glu Glu Asp Phe Ile
            260                 265                 270

Ala Leu Tyr His Gln Ala Ala Asn Glu Ile Pro Gly Ser Pro Ile Phe
        275                 280                 285

Ile Met Lys Leu Ala Gly Arg Ala Arg His Leu Glu Val Gln Leu Leu
    290                 295                 300
```

```
Ala Asp Gln Tyr Gly Thr Asn Ile Ser Leu Phe Gly Arg Asp Cys Ser
305                 310                 315                 320

Val Gln Arg Arg His Gln Lys Ile Ile Glu Glu Ala Pro Val Thr Ile
            325                 330                 335

Ala Lys Ala Glu Thr Phe His Glu Met Glu Lys Ala Ala Val Arg Leu
            340                 345                 350

Gly Lys Leu Val Gly Tyr Val Ser Ala Gly Thr Val Glu Tyr Leu Tyr
            355                 360                 365

Ser His Asp Asp Gly Lys Phe Tyr Phe Leu Glu Leu Asn Pro Arg Leu
370                 375                 380

Gln Val Glu His Pro Thr Thr Glu Met Val Ser Gly Val Asn Leu Pro
385                 390                 395                 400

Ala Ala Gln Leu Gln Ile Ala Met Gly Ile Pro Met His Arg Ile Ser
            405                 410                 415

Asp Ile Arg Thr Leu Tyr Gly Met Asn Pro His Ser Ala Ser Glu Ile
            420                 425                 430

Asp Phe Glu Phe Lys Thr Gln Asp Ala Thr Lys Lys Gln Arg Arg Pro
            435                 440                 445

Ile Pro Lys Gly His Cys Thr Ala Cys Arg Ile Thr Ser Glu Asp Pro
450                 455                 460

Asn Asp Gly Phe Lys Pro Ser Gly Gly Thr Leu His Glu Leu Asn Phe
465                 470                 475                 480

Arg Ser Ser Asn Val Trp Gly Tyr Phe Ser Val Gly Asn Asn Gly
            485                 490                 495

Asn Ile His Ser Phe Ser Asp Ser Gln Phe Gly His Ile Phe Ala Phe
            500                 505                 510

Gly Glu Asn Arg Gln Ala Ser Arg Lys His Met Val Val Ala Leu Lys
            515                 520                 525

Glu Leu Ser Ile Arg Gly Asp Phe Arg Thr Thr Val Glu Tyr Leu Ile
            530                 535                 540

Lys Leu Leu Glu Thr Glu Asp Phe Glu Asp Asn Thr Ile Thr Thr Gly
545                 550                 555                 560

Trp Leu Asp Asp Leu Ile Thr His Lys Met Thr Ala Glu Lys Pro Asp
                565                 570                 575

Pro Thr Leu Ala Val Ile Cys Gly Ala Ala Thr Lys Ala Phe Leu Ala
            580                 585                 590

Ser Glu Glu Ala Arg His Lys Tyr Ile Glu Ser Leu Gln Lys Gly Gln
            595                 600                 605

Val Leu Ser Lys Asp Leu Leu Gln Thr Met Phe Pro Val Asp Phe Ile
            610                 615                 620

His Glu Gly Lys Arg Tyr Lys Phe Thr Val Ala Lys Ser Gly Asn Asp
625                 630                 635                 640

Arg Tyr Thr Leu Phe Ile Asn Gly Ser Lys Cys Asp Ile Ile Leu Arg
                645                 650                 655

Gln Leu Ser Asp Gly Gly Leu Leu Ile Ala Ile Gly Gly Lys Ser His
                660                 665                 670

Thr Ile Tyr Trp Lys Glu Glu Val Ala Ala Thr Arg Leu Ser Val Asp
            675                 680                 685

Ser Met Thr Thr Leu Leu Glu Val Glu Asn Asp Pro Thr Gln Leu Arg
            690                 695                 700

Thr Pro Ser Pro Gly Lys Leu Val Lys Phe Leu Val Glu Asn Gly Glu
705                 710                 715                 720
```

-continued

His Ile Ile Lys Gly Gln Pro Tyr Ala Glu Ile Glu Val Met Lys Met
            725                 730                 735

Gln Met Pro Leu Val Ser Gln Glu Asn Gly Ile Val Gln Leu Leu Lys
            740                 745                 750

Gln Pro Gly Ser Thr Ile Val Ala Gly Asp Ile Met Ala Ile Met Thr
            755                 760                 765

Leu Asp Asp Pro Ser Lys Val Lys His Ala Leu Pro Phe Glu Gly Met
        770                 775                 780

Leu Pro Asp Phe Gly Ser Pro Val Ile Glu Gly Thr Lys Pro Ala Tyr
785                 790                 795                 800

Lys Phe Lys Ser Leu Val Ser Thr Leu Glu Asn Ile Leu Lys Gly Tyr
                805                 810                 815

Asp Asn Gln Val Ile Met Asn Ala Ser Leu Gln Gln Leu Ile Glu Val
            820                 825                 830

Leu Arg Asn Pro Lys Leu Pro Tyr Ser Glu Trp Lys Leu His Ile Ser
        835                 840                 845

Ala Leu His Ser Arg Leu Pro Ala Lys Leu Asp Glu Gln Met Glu Glu
    850                 855                 860

Leu Val Ala Arg Ser Leu Arg Arg Gly Ala Val Phe Pro Ala Arg Gln
865                 870                 875                 880

Leu Ser Lys Leu Ile Asp Met Ala Val Lys Asn Pro Glu Tyr Asn Pro
                885                 890                 895

Asp Lys Leu Leu Gly Ala Val Val Glu Pro Leu Ala Asp Ile Ala His
            900                 905                 910

Lys Tyr Ser Asn Gly Leu Glu Ala His Glu His Ser Ile Phe Val His
        915                 920                 925

Phe Leu Glu Glu Tyr Tyr Glu Val Lys Leu Phe Asn Gly Pro Asn
    930                 935                 940

Val Arg Glu Glu Asn Ile Ile Leu Lys Leu Arg Asp Glu Asn Pro Lys
945                 950                 955                 960

Asp Leu Asp Lys Val Ala Leu Thr Val Leu Ser His Ser Lys Val Ser
                965                 970                 975

Ala Lys Asn Asn Leu Ile Leu Ala Ile Leu Lys His Tyr Gln Pro Leu
            980                 985                 990

Cys Lys Leu Ser Ser Lys Val Ser Ala Ile Phe Ser Thr Pro Leu Gln
        995                 1000                1005

His Ile Val Glu Leu Glu Ser Lys Ala Thr Ala Lys Val Ala Leu
    1010                1015                1020

Gln Ala Arg Glu Ile Leu Ile Gln Gly Ala Leu Pro Ser Val Lys
    1025                1030                1035

Glu Arg Thr Glu Gln Ile Glu His Ile Leu Lys Ser Ser Val Val
    1040                1045                1050

Lys Val Ala Tyr Gly Ser Ser Asn Pro Lys Arg Ser Glu Pro Asp
    1055                1060                1065

Leu Asn Ile Leu Lys Asp Leu Ile Asp Ser Asn Tyr Val Val Phe
    1070                1075                1080

Asp Val Leu Leu Gln Phe Leu Thr His Gln Asp Pro Val Val Thr
    1085                1090                1095

Ala Ala Ala Ala Gln Val Tyr Ile Arg Arg Ala Tyr Arg Ala Tyr
    1100                1105                1110

Thr Ile Gly Asp Ile Arg Val His Glu Gly Val Thr Val Pro Ile
    1115                1120                1125

Val Glu Trp Lys Phe Gln Leu Pro Ser Ala Ala Phe Ser Thr Phe

|   |   |   | 1130 |   |   |   | 1135 |   |   |   | 1140 |
|---|---|---|---|---|---|---|---|---|---|---|---|

Pro Thr Val Lys Ser Lys Met Gly Met Asn Arg Ala Val Ser Val
        1145            1150            1155

Ser Asp Leu Ser Tyr Val Ala Asn Ser Gln Ser Ser Pro Leu Arg
        1160            1165            1170

Glu Gly Ile Leu Met Ala Val Asp His Leu Asp Asp Val Asp Glu
        1175            1180            1185

Ile Leu Ser Gln Ser Leu Glu Val Ile Pro Arg His Gln Ser Ser
        1190            1195            1200

Ser Asn Gly Pro Ala Pro Asp Arg Ser Gly Ser Ser Ala Ser Leu
        1205            1210            1215

Ser Asn Val Ala Asn Val Cys Val Ala Ser Thr Glu Gly Phe Glu
        1220            1225            1230

Ser Glu Glu Glu Ile Leu Val Arg Leu Arg Glu Ile Leu Asp Leu
        1235            1240            1245

Asn Lys Gln Glu Leu Ile Asn Ala Ser Ile Arg Arg Ile Thr Phe
        1250            1255            1260

Met Phe Gly Phe Lys Asp Gly Ser Tyr Pro Lys Tyr Tyr Thr Phe
        1265            1270            1275

Asn Gly Pro Asn Tyr Asn Glu Asn Glu Thr Ile Arg His Ile Glu
        1280            1285            1290

Pro Ala Leu Ala Phe Gln Leu Glu Leu Gly Arg Leu Ser Asn Phe
        1295            1300            1305

Asn Ile Lys Pro Ile Phe Thr Asp Asn Arg Asn Ile His Val Tyr
        1310            1315            1320

Glu Ala Val Ser Lys Thr Ser Pro Leu Asp Lys Arg Phe Phe Thr
        1325            1330            1335

Arg Gly Ile Ile Arg Thr Gly His Ile Arg Asp Asp Ile Ser Ile
        1340            1345            1350

Gln Glu Tyr Leu Thr Ser Glu Ala Asn Arg Leu Met Ser Asp Ile
        1355            1360            1365

Leu Asp Asn Leu Glu Val Thr Asp Thr Ser Asn Ser Asp Leu Asn
        1370            1375            1380

His Ile Phe Ile Asn Phe Ile Ala Val Phe Asp Ile Ser Pro Glu
        1385            1390            1395

Asp Val Glu Ala Ala Phe Gly Gly Phe Leu Glu Arg Phe Gly Lys
        1400            1405            1410

Arg Leu Leu Arg Leu Arg Val Ser Ser Ala Glu Ile Arg Ile Ile
        1415            1420            1425

Ile Lys Asp Pro Gln Thr Gly Ala Pro Val Pro Leu Arg Ala Leu
        1430            1435            1440

Ile Asn Asn Val Ser Gly Tyr Val Ile Lys Thr Glu Met Tyr Thr
        1445            1450            1455

Glu Val Lys Asn Ala Lys Gly Glu Trp Val Phe Lys Ser Leu Gly
        1460            1465            1470

Lys Pro Gly Ser Met His Leu Arg Pro Ile Ala Thr Pro Tyr Pro
        1475            1480            1485

Val Lys Glu Trp Leu Gln Pro Lys Arg Tyr Lys Ala His Leu Met
        1490            1495            1500

Gly Thr Thr Tyr Val Tyr Asp Phe Pro Glu Leu Phe Arg Gln Ala
        1505            1510            1515

Ser Ser Ser Gln Trp Lys Asn Phe Ser Ala Asp Val Lys Leu Thr
        1520            1525            1530

```
Asp Asp Phe Phe Ile Ser Asn Glu Leu Ile Glu Asp Glu Asn Gly
1535                1540                1545

Glu Leu Thr Glu Val Glu Arg Glu Pro Gly Ala Asn Ala Ile Gly
1550                1555                1560

Met Val Ala Phe Lys Ile Thr Val Lys Thr Pro Glu Tyr Pro Arg
1565                1570                1575

Gly Arg Gln Phe Val Val Ala Asn Asp Ile Thr Phe Lys Ile
1580                1585                1590

Gly Ser Phe Gly Pro Gln Glu Asp Glu Phe Phe Asn Lys Val Thr
1595                1600                1605

Glu Tyr Ala Arg Lys Arg Gly Ile Pro Arg Ile Tyr Leu Ala Ala
1610                1615                1620

Asn Ser Gly Ala Arg Ile Gly Met Ala Glu Glu Ile Val Pro Leu
1625                1630                1635

Phe Gln Val Ala Trp Asn Asp Ala Ala Asn Pro Asp Lys Gly Phe
1640                1645                1650

Gln Tyr Leu Tyr Leu Thr Ser Glu Gly Met Glu Thr Leu Lys Lys
1655                1660                1665

Phe Asp Lys Glu Asn Ser Val Leu Thr Glu Arg Thr Val Ile Asn
1670                1675                1680

Gly Glu Glu Arg Phe Val Ile Lys Thr Ile Ile Gly Ser Glu Asp
1685                1690                1695

Gly Leu Gly Val Glu Cys Leu Arg Gly Ser Gly Leu Ile Ala Gly
1700                1705                1710

Ala Thr Ser Arg Ala Tyr His Asp Ile Phe Thr Ile Thr Leu Val
1715                1720                1725

Thr Cys Arg Ser Val Gly Ile Gly Ala Tyr Leu Val Arg Leu Gly
1730                1735                1740

Gln Arg Ala Ile Gln Val Glu Gly Gln Pro Ile Ile Leu Thr Gly
1745                1750                1755

Ala Pro Ala Ile Asn Lys Met Leu Gly Arg Glu Val Tyr Thr Ser
1760                1765                1770

Asn Leu Gln Leu Gly Gly Thr Gln Ile Met Tyr Asn Asn Gly Val
1775                1780                1785

Ser His Leu Thr Ala Val Asp Asp Leu Ala Gly Val Glu Lys Ile
1790                1795                1800

Val Glu Trp Met Ser Tyr Val Pro Ala Lys Arg Asn Met Pro Val
1805                1810                1815

Pro Ile Leu Glu Thr Lys Asp Thr Trp Asp Arg Pro Val Asp Phe
1820                1825                1830

Thr Pro Thr Asn Asp Glu Thr Tyr Asp Val Arg Trp Met Ile Glu
1835                1840                1845

Gly Arg Glu Thr Glu Ser Gly Phe Glu Tyr Gly Leu Phe Asp Lys
1850                1855                1860

Gly Ser Phe Phe Glu Thr Leu Ser Gly Trp Ala Lys Gly Val Val
1865                1870                1875

Val Gly Arg Ala Arg Leu Gly Gly Ile Pro Leu Gly Val Ile Gly
1880                1885                1890

Val Glu Thr Arg Thr Val Glu Asn Leu Ile Pro Ala Asp Pro Ala
1895                1900                1905

Asn Pro Asn Ser Ala Glu Thr Leu Ile Gln Glu Pro Gly Gln Val
1910                1915                1920
```

```
Trp His Pro Asn Ser Ala Phe Lys Thr Ala Gln Ala Ile Asn Asp
    1925                1930                1935

Phe Asn Asn Gly Glu Gln Leu Pro Met Met Ile Leu Ala Asn Trp
    1940                1945                1950

Arg Gly Phe Ser Gly Gly Gln Arg Asp Met Phe Asn Glu Val Leu
    1955                1960                1965

Lys Tyr Gly Ser Phe Ile Val Asp Ala Leu Val Asp Tyr Lys Gln
    1970                1975                1980

Pro Ile Ile Ile Tyr Ile Pro Pro Thr Gly Glu Leu Arg Gly Gly
    1985                1990                1995

Ser Trp Val Val Asp Pro Thr Ile Asn Ala Asp Gln Met Glu
    2000                2005                2010

Met Tyr Ala Asp Val Asn Ala Arg Ala Gly Val Leu Glu Pro Gln
    2015                2020                2025

Gly Met Val Gly Ile Lys Phe Arg Arg Glu Lys Leu Leu Asp Thr
    2030                2035                2040

Met Asn Arg Leu Asp Asp Lys Tyr Arg Glu Leu Arg Ser Gln Leu
    2045                2050                2055

Ser Asn Lys Ser Leu Ala Pro Glu Val His Gln Gln Ile Ser Lys
    2060                2065                2070

Gln Leu Ala Asp Arg Glu Arg Glu Leu Leu Pro Ile Tyr Gly Gln
    2075                2080                2085

Ile Ser Leu Gln Phe Ala Asp Leu His Asp Arg Ser Ser Arg Met
    2090                2095                2100

Val Ala Lys Gly Val Ile Ser Lys Glu Leu Glu Trp Thr Glu Ala
    2105                2110                2115

Arg Arg Phe Phe Phe Trp Arg Leu Arg Arg Leu Asn Glu Glu
    2120                2125                2130

Tyr Leu Ile Lys Arg Leu Ser His Gln Val Gly Glu Ala Ser Arg
    2135                2140                2145

Leu Glu Lys Ile Ala Arg Ile Arg Ser Trp Tyr Pro Ala Ser Val
    2150                2155                2160

Asp His Glu Asp Asp Arg Gln Val Ala Thr Trp Ile Glu Glu Asn
    2165                2170                2175

Tyr Lys Thr Leu Asp Asp Lys Leu Lys Gly Leu Lys Leu Glu Ser
    2180                2185                2190

Phe Ala Gln Asp Leu Ala Lys Lys Ile Arg Ser Asp His Asp Asn
    2195                2200                2205

Ala Ile Asp Gly Leu Ser Glu Val Ile Lys Met Leu Ser Thr Asp
    2210                2215                2220

Asp Lys Glu Lys Leu Leu Lys Thr Leu Lys
    2225                2230

<210> SEQ ID NO 40
<211> LENGTH: 1887
<212> TYPE: PRT
<213> ORGANISM: Saccharomyces cerevisiae

<400> SEQUENCE: 40

Met Lys Pro Glu Val Glu Gln Glu Leu Ala His Ile Leu Leu Thr Glu
1               5                   10                  15

Leu Leu Ala Tyr Gln Phe Ala Ser Pro Val Arg Trp Ile Glu Thr Gln
                20                  25                  30

Asp Val Phe Leu Lys Asp Phe Asn Thr Glu Arg Val Val Glu Ile Gly
            35                  40                  45
```

```
Pro Ser Pro Thr Leu Ala Gly Met Ala Gln Arg Thr Leu Lys Asn Lys
    50                  55                  60

Tyr Glu Ser Tyr Asp Ala Ala Leu Ser Leu His Arg Glu Ile Leu Cys
65                  70                  75                  80

Tyr Ser Lys Asp Ala Lys Glu Ile Tyr Tyr Thr Pro Asp Pro Ser Glu
                85                  90                  95

Leu Ala Ala Lys Glu Glu Pro Ala Lys Glu Ala Pro Ala Pro Thr
                100                 105                 110

Pro Ala Ala Ser Ala Pro Ala Pro Ala Ala Ala Pro Ala Pro Val
                115                 120                 125

Ala Ala Ala Ala Pro Ala Ala Ala Ala Glu Ile Ala Asp Glu Pro
            130                 135                 140

Val Lys Ala Ser Leu Leu Leu His Val Leu Ala His Lys Leu Lys
145                 150                 155                 160

Lys Ser Leu Asp Ser Ile Pro Met Ser Lys Thr Ile Lys Asp Leu Val
                165                 170                 175

Gly Gly Lys Ser Thr Val Gln Asn Glu Ile Leu Gly Asp Leu Gly Lys
                180                 185                 190

Glu Phe Gly Thr Thr Pro Glu Lys Pro Glu Glu Thr Pro Leu Glu Glu
        195                 200                 205

Leu Ala Glu Thr Phe Gln Asp Thr Phe Ser Gly Ala Leu Gly Lys Gln
    210                 215                 220

Ser Ser Ser Leu Leu Ser Arg Leu Ile Ser Ser Lys Met Pro Gly Gly
225                 230                 235                 240

Phe Thr Ile Thr Val Ala Arg Lys Tyr Leu Gln Thr Arg Trp Gly Leu
                245                 250                 255

Pro Ser Gly Arg Gln Asp Gly Val Leu Leu Val Ala Leu Ser Asn Glu
            260                 265                 270

Pro Ala Ala Arg Leu Gly Ser Glu Ala Asp Ala Lys Ala Phe Leu Asp
            275                 280                 285

Ser Met Ala Gln Lys Tyr Ala Ser Ile Val Gly Val Asp Leu Ser Ser
    290                 295                 300

Ala Ala Ser Ala Ser Gly Ala Ala Gly Ala Gly Ala Ala Ala Gly Ala
305                 310                 315                 320

Ala Met Ile Asp Ala Gly Ala Leu Glu Glu Ile Thr Lys Asp His Lys
                325                 330                 335

Val Leu Ala Arg Gln Gln Leu Gln Val Leu Ala Arg Tyr Leu Lys Met
                340                 345                 350

Asp Leu Asp Asn Gly Glu Arg Lys Phe Leu Lys Glu Lys Asp Thr Val
            355                 360                 365

Ala Glu Leu Gln Ala Gln Leu Asp Tyr Leu Asn Ala Glu Leu Gly Glu
    370                 375                 380

Phe Phe Val Asn Gly Val Ala Thr Ser Phe Ser Arg Lys Lys Ala Arg
385                 390                 395                 400

Thr Phe Asp Ser Ser Trp Asn Trp Ala Lys Gln Ser Leu Leu Ser Leu
                405                 410                 415

Tyr Phe Glu Ile Ile His Gly Val Leu Lys Asn Val Asp Arg Glu Val
                420                 425                 430

Val Ser Glu Ala Ile Asn Ile Met Asn Arg Ser Asn Asp Ala Leu Ile
            435                 440                 445

Lys Phe Met Glu Tyr His Ile Ser Asn Thr Asp Glu Thr Lys Gly Glu
    450                 455                 460
```

-continued

```
Asn Tyr Gln Leu Val Lys Thr Leu Gly Glu Gln Leu Ile Glu Asn Cys
465                 470                 475                 480

Lys Gln Val Leu Asp Val Asp Pro Val Tyr Lys Asp Val Ala Lys Pro
            485                 490                 495

Thr Gly Pro Lys Thr Ala Ile Asp Lys Asn Gly Asn Ile Thr Tyr Ser
        500                 505                 510

Glu Glu Pro Arg Glu Lys Val Arg Lys Leu Ser Gln Tyr Val Gln Glu
    515                 520                 525

Met Ala Leu Gly Gly Pro Ile Thr Lys Glu Ser Gln Pro Thr Ile Glu
530                 535                 540

Glu Asp Leu Thr Arg Val Tyr Lys Ala Ile Ser Ala Gln Ala Asp Lys
545                 550                 555                 560

Gln Asp Ile Ser Ser Ser Thr Arg Val Glu Phe Glu Lys Leu Tyr Ser
            565                 570                 575

Asp Leu Met Lys Phe Leu Glu Ser Ser Lys Glu Ile Asp Pro Ser Gln
        580                 585                 590

Thr Thr Gln Leu Ala Gly Met Asp Val Glu Asp Ala Leu Asp Lys Asp
    595                 600                 605

Ser Thr Lys Glu Val Ala Ser Leu Pro Asn Lys Ser Thr Ile Ser Lys
610                 615                 620

Thr Val Ser Ser Thr Ile Pro Arg Glu Thr Ile Pro Phe Leu His Leu
625                 630                 635                 640

Arg Lys Lys Thr Pro Ala Gly Asp Trp Lys Tyr Asp Arg Gln Leu Ser
            645                 650                 655

Ser Leu Phe Leu Asp Gly Leu Glu Lys Ala Ala Phe Asn Gly Val Thr
        660                 665                 670

Phe Lys Asp Lys Tyr Val Leu Ile Thr Gly Ala Gly Lys Gly Ser Ile
    675                 680                 685

Gly Ala Glu Val Leu Gln Gly Leu Leu Gln Gly Gly Ala Lys Val Val
690                 695                 700

Val Thr Thr Ser Arg Phe Ser Lys Gln Val Thr Asp Tyr Tyr Gln Ser
705                 710                 715                 720

Ile Tyr Ala Lys Tyr Gly Ala Lys Gly Ser Thr Leu Ile Val Val Pro
            725                 730                 735

Phe Asn Gln Gly Ser Lys Gln Asp Val Glu Ala Leu Ile Glu Phe Ile
        740                 745                 750

Tyr Asp Thr Glu Lys Asn Gly Gly Leu Gly Trp Asp Leu Asp Ala Ile
    755                 760                 765

Ile Pro Phe Ala Ala Ile Pro Glu Gln Gly Ile Glu Leu Glu His Ile
770                 775                 780

Asp Ser Lys Ser Glu Phe Ala His Arg Ile Met Leu Thr Asn Ile Leu
785                 790                 795                 800

Arg Met Met Gly Cys Val Lys Lys Gln Lys Ser Ala Arg Gly Ile Glu
            805                 810                 815

Thr Arg Pro Ala Gln Val Ile Leu Pro Met Ser Pro Asn His Gly Thr
        820                 825                 830

Phe Gly Gly Asp Gly Met Tyr Ser Glu Ser Lys Leu Ser Leu Glu Thr
    835                 840                 845

Leu Phe Asn Arg Trp His Ser Glu Ser Trp Ala Asn Gln Leu Thr Val
850                 855                 860

Cys Gly Ala Ile Ile Gly Trp Thr Arg Gly Thr Gly Leu Met Ser Ala
865                 870                 875                 880

Asn Asn Ile Ile Ala Glu Gly Ile Glu Lys Met Gly Val Arg Thr Phe
```

```
                885                 890                 895
Ser Gln Lys Glu Met Ala Phe Asn Leu Leu Gly Leu Leu Thr Pro Glu
                900                 905                 910

Val Val Glu Leu Cys Gln Lys Ser Pro Val Met Ala Asp Leu Asn Gly
                915                 920                 925

Gly Leu Gln Phe Val Pro Glu Leu Lys Glu Phe Thr Ala Lys Leu Arg
            930                 935                 940

Lys Glu Leu Val Glu Thr Ser Glu Val Arg Lys Ala Val Ser Ile Glu
945                 950                 955                 960

Thr Ala Leu Glu His Lys Val Val Asn Gly Asn Ser Ala Asp Ala Ala
                965                 970                 975

Tyr Ala Gln Val Glu Ile Gln Pro Arg Ala Asn Ile Gln Leu Asp Phe
            980                 985                 990

Pro Glu Leu Lys Pro Tyr Lys Gln Val Lys Gln Ile Ala Pro Ala Glu
                995                 1000                1005

Leu Glu Gly Leu Leu Asp Leu Glu Arg Val Ile Val Val Thr Gly
        1010                1015                1020

Phe Ala Glu Val Gly Pro Trp Gly Ser Ala Arg Thr Arg Trp Glu
        1025                1030                1035

Met Glu Ala Phe Gly Glu Phe Ser Leu Glu Gly Cys Val Glu Met
        1040                1045                1050

Ala Trp Ile Met Gly Phe Ile Ser Tyr His Asn Gly Asn Leu Lys
        1055                1060                1065

Gly Arg Pro Tyr Thr Gly Trp Val Asp Ser Lys Thr Lys Glu Pro
        1070                1075                1080

Val Asp Asp Lys Asp Val Lys Ala Lys Tyr Glu Thr Ser Ile Leu
        1085                1090                1095

Glu His Ser Gly Ile Arg Leu Ile Glu Pro Glu Leu Phe Asn Gly
        1100                1105                1110

Tyr Asn Pro Glu Lys Lys Glu Met Ile Gln Glu Val Ile Val Glu
        1115                1120                1125

Glu Asp Leu Glu Pro Phe Glu Ala Ser Lys Glu Thr Ala Glu Gln
        1130                1135                1140

Phe Lys His Gln His Gly Asp Lys Val Asp Ile Phe Glu Ile Pro
        1145                1150                1155

Glu Thr Gly Glu Tyr Ser Val Lys Leu Leu Lys Gly Ala Thr Leu
        1160                1165                1170

Tyr Ile Pro Lys Ala Leu Arg Phe Asp Arg Leu Val Ala Gly Gln
        1175                1180                1185

Ile Pro Thr Gly Trp Asn Ala Lys Thr Tyr Gly Ile Ser Asp Asp
        1190                1195                1200

Ile Ile Ser Gln Val Asp Pro Ile Thr Leu Phe Val Leu Val Ser
        1205                1210                1215

Val Val Glu Ala Phe Ile Ala Ser Gly Ile Thr Asp Pro Tyr Glu
        1220                1225                1230

Met Tyr Lys Tyr Val His Val Ser Glu Val Gly Asn Cys Ser Gly
        1235                1240                1245

Ser Gly Met Gly Gly Val Ser Ala Leu Arg Gly Met Phe Lys Asp
        1250                1255                1260

Arg Phe Lys Asp Glu Pro Val Gln Asn Asp Ile Leu Gln Glu Ser
        1265                1270                1275

Phe Ile Asn Thr Met Ser Ala Trp Val Asn Met Leu Leu Ile Ser
        1280                1285                1290
```

-continued

Ser Ser Gly Pro Ile Lys Thr Pro Val Gly Ala Cys Ala Thr Ser
1295              1300              1305

Val Glu Ser Val Asp Ile Gly Val Glu Thr Ile Leu Ser Gly Lys
1310              1315              1320

Ala Arg Ile Cys Ile Val Gly Gly Tyr Asp Asp Phe Gln Glu Glu
1325              1330              1335

Gly Ser Phe Glu Phe Gly Asn Met Lys Ala Thr Ser Asn Thr Leu
1340              1345              1350

Glu Glu Phe Glu His Gly Arg Thr Pro Ala Glu Met Ser Arg Pro
1355              1360              1365

Ala Thr Thr Thr Arg Asn Gly Phe Met Glu Ala Gln Gly Ala Gly
1370              1375              1380

Ile Gln Ile Ile Met Gln Ala Asp Leu Ala Leu Lys Met Gly Val
1385              1390              1395

Pro Ile Tyr Gly Ile Val Ala Met Ala Ala Thr Ala Thr Asp Lys
1400              1405              1410

Ile Gly Arg Ser Val Pro Ala Pro Gly Lys Gly Ile Leu Thr Thr
1415              1420              1425

Ala Arg Glu His His Ser Ser Val Lys Tyr Ala Ser Pro Asn Leu
1430              1435              1440

Asn Met Lys Tyr Arg Lys Arg Gln Leu Val Thr Arg Glu Ala Gln
1445              1450              1455

Ile Lys Asp Trp Val Glu Asn Glu Leu Glu Ala Leu Lys Leu Glu
1460              1465              1470

Ala Glu Glu Ile Pro Ser Glu Asp Gln Asn Glu Phe Leu Leu Glu
1475              1480              1485

Arg Thr Arg Glu Ile His Asn Glu Ala Glu Ser Gln Leu Arg Ala
1490              1495              1500

Ala Gln Gln Gln Trp Gly Asn Asp Phe Tyr Lys Arg Asp Pro Arg
1505              1510              1515

Ile Ala Pro Leu Arg Gly Ala Leu Ala Thr Tyr Gly Leu Thr Ile
1520              1525              1530

Asp Asp Leu Gly Val Ala Ser Phe His Gly Thr Ser Thr Lys Ala
1535              1540              1545

Asn Asp Lys Asn Glu Ser Ala Thr Ile Asn Glu Met Met Lys His
1550              1555              1560

Leu Gly Arg Ser Glu Gly Asn Pro Val Ile Gly Val Phe Gln Lys
1565              1570              1575

Phe Leu Thr Gly His Pro Lys Gly Ala Ala Gly Ala Trp Met Met
1580              1585              1590

Asn Gly Ala Leu Gln Ile Leu Asn Ser Gly Ile Ile Pro Gly Asn
1595              1600              1605

Arg Asn Ala Asp Asn Val Asp Lys Ile Leu Glu Gln Phe Glu Tyr
1610              1615              1620

Val Leu Tyr Pro Ser Lys Thr Leu Lys Thr Asp Gly Val Arg Ala
1625              1630              1635

Val Ser Ile Thr Ser Phe Gly Phe Gly Gln Lys Gly Gly Gln Ala
1640              1645              1650

Ile Val Val His Pro Asp Tyr Leu Tyr Gly Ala Ile Thr Glu Asp
1655              1660              1665

Arg Tyr Asn Glu Tyr Val Ala Lys Val Ser Ala Arg Glu Lys Ser
1670              1675              1680

-continued

Ala Tyr Lys Phe Phe His Asn Gly Met Ile Tyr Asn Lys Leu Phe
1685                1690                1695

Val Ser Lys Glu His Ala Pro Tyr Thr Asp Glu Leu Glu Glu Asp
1700                1705                1710

Val Tyr Leu Asp Pro Leu Ala Arg Val Ser Lys Asp Lys Lys Ser
1715                1720                1725

Gly Ser Leu Thr Phe Asn Ser Lys Asn Ile Gln Ser Lys Asp Ser
1730                1735                1740

Tyr Ile Asn Ala Asn Thr Ile Glu Thr Ala Lys Met Ile Glu Asn
1745                1750                1755

Met Thr Lys Glu Lys Val Ser Asn Gly Gly Val Gly Val Asp Val
1760                1765                1770

Glu Leu Ile Thr Ser Ile Asn Val Glu Asn Asp Thr Phe Ile Glu
1775                1780                1785

Arg Asn Phe Thr Pro Gln Glu Ile Glu Tyr Cys Ser Ala Gln Pro
1790                1795                1800

Ser Val Gln Ser Ser Phe Ala Gly Thr Trp Ser Ala Lys Glu Ala
1805                1810                1815

Val Phe Lys Ser Leu Gly Val Lys Ser Leu Gly Gly Ala Ala
1820                1825                1830

Leu Lys Asp Ile Glu Ile Val Arg Val Asn Lys Asn Ala Pro Ala
1835                1840                1845

Val Glu Leu His Gly Asn Ala Lys Lys Ala Ala Glu Ala Gly
1850                1855                1860

Val Thr Asp Val Lys Val Ser Ile Ser His Asp Asp Leu Gln Ala
1865                1870                1875

Val Ala Val Ala Val Ser Thr Lys Lys
1880                1885

<210> SEQ ID NO 41
<211> LENGTH: 522
<212> TYPE: PRT
<213> ORGANISM: Candida maltosa

<400> SEQUENCE: 41

Met Met Ala Ile Glu Gln Ile Ile Glu Glu Val Leu Pro Tyr Leu Thr
1               5                   10                  15

Lys Trp Tyr Thr Ile Ile Phe Gly Ala Ala Val Thr Tyr Phe Leu Ser
                20                  25                  30

Ile Ala Leu Arg Asn Lys Phe Tyr Glu Tyr Lys Leu Lys Cys Glu Asn
            35                  40                  45

Pro Val Tyr Phe Gln Asp Ala Gly Leu Phe Gly Ile Pro Ala Leu Ile
        50                  55                  60

Asp Ile Ile Lys Val Arg Lys Ala Gly Gln Leu Ala Asp Tyr Thr Asp
65                  70                  75                  80

Thr Thr Phe Asp Lys Tyr Pro Asn Leu Ser Ser Tyr Met Thr Val Ala
                85                  90                  95

Gly Val Leu Lys Ile Val Phe Thr Val Asp Pro Glu Asn Ile Lys Ala
            100                 105                 110

Val Leu Ala Thr Gln Phe Asn Asp Phe Ala Leu Gly Ala Arg His Ala
        115                 120                 125

His Phe Asp Pro Leu Leu Gly Asp Gly Ile Phe Thr Leu Asp Gly Glu
    130                 135                 140

Gly Trp Lys His Ser Arg Ala Met Leu Arg Pro Gln Phe Ala Arg Glu
145                 150                 155                 160

Gln Ile Ala His Val Lys Ala Leu Glu Pro His Val Gln Ile Leu Ala
                165                 170                 175

Lys Gln Ile Lys Leu Asn Lys Gly Lys Thr Phe Asp Leu Gln Glu Leu
            180                 185                 190

Phe Phe Arg Phe Thr Val Asp Thr Ala Thr Glu Phe Leu Phe Gly Glu
        195                 200                 205

Ser Val His Ser Leu Tyr Asp Glu Lys Ser Gly Ile Pro Asn Asp Ile
    210                 215                 220

Pro Gly Arg Glu Asn Val Arg Glu Ala Phe Asn Thr Ser Gln His Tyr
225                 230                 235                 240

Leu Ala Thr Arg Thr Tyr Ser Gln Ile Phe Tyr Trp Leu Thr Asn Pro
                245                 250                 255

Lys Glu Phe Arg Asp Cys Asn Ala Lys Val His Lys Leu Ala Gln Tyr
            260                 265                 270

Phe Val Asn Thr Ala Leu Asn Ala Thr Glu Lys Glu Val Glu Glu Lys
        275                 280                 285

Ser Lys Gly Gly Tyr Val Phe Leu Tyr Glu Leu Val Lys Gln Thr Arg
    290                 295                 300

Asp Pro Lys Val Leu Gln Asp Gln Leu Leu Asn Ile Met Val Ala Gly
305                 310                 315                 320

Arg Asp Thr Thr Ala Gly Leu Leu Ser Phe Ala Met Phe Glu Leu Ala
                325                 330                 335

Arg Asn Pro Lys Ile Trp Asn Lys Leu Arg Glu Val Glu Val Asn
            340                 345                 350

Phe Gly Leu Gly Asp Glu Ala Arg Val Asp Glu Ile Ser Phe Glu Thr
        355                 360                 365

Leu Lys Lys Cys Glu Tyr Leu Lys Ala Val Leu Asn Glu Thr Leu Arg
    370                 375                 380

Met Tyr Pro Ser Val Pro Ile Asn Phe Arg Thr Ala Thr Arg Asp Thr
385                 390                 395                 400

Thr Leu Pro Arg Gly Gly Lys Asp Gly Asn Ser Pro Ile Phe Val
                405                 410                 415

Pro Lys Gly Ser Ser Val Val Tyr Ser Val Tyr Lys Thr His Arg Leu
            420                 425                 430

Lys Gln Phe Tyr Gly Glu Asp Ala Tyr Glu Phe Arg Pro Glu Arg Trp
        435                 440                 445

Phe Glu Pro Ser Thr Arg Lys Leu Gly Trp Ala Tyr Leu Pro Phe Asn
    450                 455                 460

Gly Gly Pro Arg Ile Cys Leu Gly Gln Gln Phe Ala Leu Thr Glu Ala
465                 470                 475                 480

Ser Tyr Val Ile Ala Arg Leu Ala Gln Met Phe Glu His Leu Glu Ser
                485                 490                 495

Lys Asp Glu Thr Tyr Pro Pro Asn Lys Cys Ile His Leu Thr Met Asn
            500                 505                 510

His Asn Glu Gly Val Phe Ile Ser Ala Lys
        515                 520

<210> SEQ ID NO 42
<211> LENGTH: 523
<212> TYPE: PRT
<213> ORGANISM: Starmerella bombicola

<400> SEQUENCE: 42

Met Ile Leu Tyr Ala Val Leu Gly Ala Phe Ala Ala Phe Leu Leu Tyr

```
  1               5                   10                  15
Met Asp Val Leu Tyr Pro Phe Val Ile Tyr Pro Leu Arg Ala Arg Trp
                 20                  25                  30
His Lys Cys Gly Tyr Ile Pro Arg Asp Leu Ser Trp Pro Leu Gly Ile
                 35                  40                  45
Pro Leu Thr Leu Val Val Leu Ser Lys Leu Arg Lys Asp Met Leu Leu
        50                  55                  60
Gln Phe Met Ala Ala Gln Asp Leu Ser Arg Pro Tyr Lys Thr Ser Leu
65                  70                  75                  80
Arg Gln Phe Leu Gly Lys Trp Val Ile Ala Thr Arg Asp Pro Glu Asn
                     85                  90                  95
Ile Lys Ala Val Leu Ser Thr Lys Phe Asn Asp Phe Ser Leu Lys Glu
                 100                 105                 110
Arg Gly Asn Arg Met Arg His Val Ile Gly Asp Gly Ile Phe Thr Gln
                 115                 120                 125
Asp Gly Ala Pro Trp Lys His Ser Arg Asp Met Leu Arg Pro Gln Phe
        130                 135                 140
Thr Lys Asp Gln Ile Ser Arg Val Glu Leu Leu Ser His His Ile Asp
145                 150                 155                 160
Val Leu Ile Arg Glu Ile Arg Lys Ser Gly Asn Val Glu Leu Gln
                     165                 170                 175
Arg Leu Phe His Leu Met Thr Met Asp Thr Ala Thr His Phe Leu Phe
                 180                 185                 190
Gly Glu Ser Val Gly Ser Leu Glu Val Ser Gly Glu Ser Lys Gly Ile
                 195                 200                 205
Glu Ile Thr Asp Pro Lys Thr Gly Glu Ile Val Asn Thr Val Asp Phe
        210                 215                 220
Val Glu Ser Tyr Thr Phe Ala Asn Lys Phe Ala Leu Lys Lys Ile Ile
225                 230                 235                 240
Leu Asn Asp Leu Glu Phe Leu Ala Asp Leu Thr Glu Pro Ser Tyr Lys
                     245                 250                 255
Trp His Leu Arg Arg Val His Thr Val Met Asp His Tyr Val Gln Leu
                 260                 265                 270
Ala Leu Lys Ala Thr Glu Lys Tyr Asp Pro Asp Asp Ser Glu Lys
                 275                 280                 285
Gly Glu Tyr Tyr Phe Ser His Glu Leu Ala Lys Leu Thr Arg Asp Pro
        290                 295                 300
Leu Ser Leu Arg Asp Gln Leu Phe Asn Ile Leu Ile Ala Gly Arg Asp
305                 310                 315                 320
Thr Thr Ala Ala Thr Leu Ser Tyr Ala Phe His Tyr Leu Thr Lys Asn
                     325                 330                 335
Pro Ala Ile Tyr Ala Lys Val Arg Glu Asp Val Leu Thr Val Phe Pro
                 340                 345                 350
Asn Gly Asp Ala Ser Leu Ala Thr Tyr Glu Asp Leu Arg Lys Ala Lys
                 355                 360                 365
Tyr Leu Gln Met Val Ile Lys Glu Val Leu Arg Leu Ala Pro Ala Val
        370                 375                 380
Pro Leu Asn Thr Arg Ala Ala Val Arg Asp Thr Tyr Leu Pro Arg Gly
385                 390                 395                 400
Gly Gly Pro Ala Gly Asn Leu Pro Val Phe Val Pro Lys Gly Thr Ala
                     405                 410                 415
Val Asn Tyr Pro Thr Tyr Ile Leu His Arg Asp Pro Asp Ile Tyr Gly
                 420                 425                 430
```

```
Ala Asp Ala Tyr Glu Phe Asn Pro Glu Arg Trp Arg Pro Glu Asn Lys
        435                 440                 445

Leu Pro Asn Ser Pro Met Tyr Ser Trp Gly Tyr Ile Pro Phe Asn Gly
    450                 455                 460

Gly Pro Arg Ile Cys Ile Gly Gln Gln Phe Ala Leu Thr Glu Ile Ala
465                 470                 475                 480

Leu Thr Met Ile Lys Leu Val Leu Glu Phe Glu Arg Leu Glu Pro Ala
                485                 490                 495

Asp Asp Phe Glu Pro Asn Leu Gln Asp Lys Ser Ser Leu Thr Val Met
                500                 505                 510

Val Gly Gly Ser Gly Val Arg Val Lys Leu Ser
                515                 520

<210> SEQ ID NO 43
<211> LENGTH: 687
<212> TYPE: PRT
<213> ORGANISM: Starmerella bombicola

<400> SEQUENCE: 43

Met Ala Asp Ile Asn Phe Ile Ala Ser Val Val Ala Leu Ala Val
1               5                   10                  15

Val Phe Val Ala Tyr Lys Tyr Phe Asn Gly Gly Pro Asp Val Gln Ser
            20                  25                  30

Ser Lys Ala Gly Asn Ser Thr Pro Phe Gly Asn Ser Lys Ala Asp Glu
        35                  40                  45

Asp Gly Asp Ser Arg Asp Phe Val Ala Leu Met Glu Lys Asn Asn Lys
50                  55                  60

Asn Val Ile Val Phe Tyr Gly Ser Gln Thr Gly Thr Ala Glu Asp Leu
65                  70                  75                  80

Ala Ser Lys Leu Ala Lys Glu Leu Ser Ser Lys Tyr Gly Leu Arg Thr
                85                  90                  95

Met Thr Ala Asp Pro Glu Asn Phe Asp Phe Glu Lys Leu Asp Thr Phe
            100                 105                 110

Pro Glu Ser His Leu Ala Val Phe Leu Met Ala Ser Tyr Gly Asp Gly
        115                 120                 125

Glu Pro Thr Asp Asn Ala Gln Asp Leu Tyr Ser Phe Leu Gly Asn Ser
130                 135                 140

Pro Ser Phe Ser Gln Asp Gly Glu Thr Leu Glu Asn Leu Asn Phe Ala
145                 150                 155                 160

Val Phe Gly Leu Gly Asn Val Leu Tyr Glu Phe Tyr Asn Lys Ala Gly
                165                 170                 175

Lys Asp Met His Lys Tyr Leu Thr Asp Leu Gly Gly His Ser Ile Gly
            180                 185                 190

Pro Tyr Gly Glu Gly Asp Asp Ser Lys Gly Met Leu Glu Glu Asp Tyr
        195                 200                 205

Met Ala Trp Lys Asp Glu Phe Leu Ala Ala Leu Val Ala Lys Trp Gly
210                 215                 220

Leu Thr Glu Arg Glu Ala Val Tyr Glu Pro Ser Ile Ser Val Lys Glu
225                 230                 235                 240

Ile Glu Glu Asp Ala His Ser His Asp Val Tyr Leu Gly Glu Pro Asn
                245                 250                 255

Leu Lys His Leu Gln Ala Ser Lys Ala Gln Glu Ile Pro Lys Gly Pro
            260                 265                 270

Tyr Asn Ala Ser Asn Pro Met Leu Ala Lys Ile Thr Ala Ala Arg Glu
```

-continued

```
                275                 280                 285

Leu Phe Thr Asn Thr Asp Arg His Cys Ile His Met Glu Phe Asp Thr
    290                 295                 300

Thr Gly Ala Arg Tyr Thr Thr Gly Asp His Leu Ala Phe Trp Phe Gln
305                 310                 315                 320

Asn Asn Glu Glu Val Gln Arg Phe Val Lys Ala Leu Gly Ile Ala
                325                 330                 335

Asn Pro Gln Gln Pro Ile Ala Ile Ser Val Leu Asp Lys Thr Ser Thr
                340                 345                 350

Val Arg Ile Pro Ser Pro Thr Thr Tyr Glu Thr Ile Ile Arg His Phe
                355                 360                 365

Leu Glu Ile Asn Gly Pro Val Ser Arg Gln Val Leu Ser Ser Ile Ala
    370                 375                 380

Pro Phe Ala Pro Ser Glu Val Lys Lys Ala Thr Gln Gln Leu Gly
385                 390                 395                 400

Ser Asn Lys Glu Leu Phe Ala Ser His Val Ala Ala Lys Lys Phe Asn
                405                 410                 415

Ile Ala Arg Leu Leu Leu His Leu Ser Gly Gln Pro Trp Lys Asn
                420                 425                 430

Val Pro Phe Ser Phe Val Ile Glu Thr Ile Pro His Leu Gln Pro Arg
            435                 440                 445

Tyr Tyr Ser Ile Ser Ser Ser Val Gln Ser Pro Asn Thr Val Ser
450                 455                 460

Ile Thr Ala Val Val Glu Arg Gln Thr Leu Thr Gly Val Asp His Glu
465                 470                 475                 480

Leu Arg Gly Val Ala Thr Asn Gln Ile Leu Ala Leu Ser Glu Ala Leu
                485                 490                 495

Val Gly His Pro Ser Met Thr Tyr Arg Leu Gln Gln Pro His Asp Phe
                500                 505                 510

Thr Asn Ser Leu Ser Ser Gln Asp Ile Arg Val Pro Val His Ile Arg
            515                 520                 525

His Ser Leu Phe Lys Leu Pro Gly Lys Pro Thr Val Pro Ile Ile Met
    530                 535                 540

Val Gly Pro Gly Thr Gly Val Ala Pro Phe Arg Gly Phe Val His Glu
545                 550                 555                 560

Arg Ala Ser Gln Lys Ala Ala Gly Lys Glu Val Gly Lys Ala Met Leu
                565                 570                 575

Phe Thr Gly Ser Arg His Ala Asn Glu Asp Phe Leu Tyr Arg Asp Glu
                580                 585                 590

Trp Lys Gln Phe Ser Asp Phe Leu Asp Leu Glu Thr Ala Phe Ser Arg
            595                 600                 605

Asp Ser Ser Lys Lys Val Tyr Val Gln His Lys Leu Lys Glu Arg Ala
    610                 615                 620

Lys Asp Val Phe Ala Leu Leu Asn Glu Gly Ala Val Phe Tyr Val Cys
625                 630                 635                 640

Gly Asp Ala Gly Gly Met Ser His Asp Val His Ser Ala Leu Leu Glu
                645                 650                 655

Ile Val Ala Gln Glu Gly Asn Leu Ser Ser Asp Ala Asp Lys Phe
                660                 665                 670

Val Arg Lys Met Arg Ser Arg Asn Lys Tyr Gln Glu Asp Val Trp
            675                 680                 685
```

<210> SEQ ID NO 44

<211> LENGTH: 543
<212> TYPE: PRT
<213> ORGANISM: Candida tropicalis

<400> SEQUENCE: 44

```
Met Ser Ser Ser Pro Ser Ile Ala Gln Glu Phe Leu Ala Thr Ile Thr
1               5                   10                  15

Pro Tyr Val Glu Tyr Cys Gln Glu Asn Tyr Thr Lys Trp Tyr Tyr Phe
            20                  25                  30

Ile Pro Leu Val Ile Leu Ser Leu Asn Leu Ile Ser Met Leu His Thr
        35                  40                  45

Lys Tyr Leu Glu Arg Lys Phe Lys Ala Lys Pro Leu Ala Val Tyr Val
    50                  55                  60

Gln Asp Tyr Thr Phe Cys Leu Ile Thr Pro Leu Val Leu Ile Tyr Tyr
65                  70                  75                  80

Lys Ser Lys Gly Thr Val Met Gln Phe Ala Cys Asp Leu Trp Asp Lys
                85                  90                  95

Asn Leu Ile Val Ser Asp Pro Lys Ala Lys Thr Ile Gly Leu Lys Ile
            100                 105                 110

Leu Gly Ile Pro Leu Ile Glu Thr Lys Asp Pro Glu Asn Val Lys Ala
        115                 120                 125

Ile Leu Ala Thr Gln Phe Asn Asp Phe Ser Leu Gly Thr Arg His Asp
    130                 135                 140

Phe Leu Tyr Ser Leu Leu Gly Asp Gly Ile Phe Thr Leu Asp Gly Ala
145                 150                 155                 160

Gly Trp Lys His Ser Arg Thr Met Leu Arg Pro Gln Phe Ala Arg Glu
                165                 170                 175

Gln Val Ser His Val Lys Leu Leu Glu Pro His Met Gln Val Leu Phe
            180                 185                 190

Lys His Ile Arg Lys His His Gly Gln Thr Phe Asp Ile Gln Glu Leu
        195                 200                 205

Phe Phe Arg Leu Thr Val Asp Ser Ala Thr Glu Phe Leu Leu Gly Glu
    210                 215                 220

Ser Ala Glu Ser Leu Arg Asp Glu Ser Val Gly Leu Thr Pro Thr Thr
225                 230                 235                 240

Lys Asp Phe Asp Gly Arg Asn Glu Phe Ala Asp Ala Phe Asn Tyr Ser
                245                 250                 255

Gln Thr Asn Gln Ala Tyr Arg Phe Leu Leu Gln Met Tyr Trp Ile
            260                 265                 270

Leu Asn Gly Ser Glu Phe Arg Lys Ser Ile Ala Ile Val His Lys Phe
        275                 280                 285

Ala Asp His Tyr Val Gln Lys Ala Leu Glu Leu Thr Asp Glu Asp Leu
    290                 295                 300

Glu Lys Lys Glu Gly Tyr Val Phe Leu Phe Glu Leu Ala Lys Gln Thr
305                 310                 315                 320

Arg Asp Pro Lys Val Leu Arg Asp Gln Leu Asn Ile Leu Val Ala
                325                 330                 335

Gly Arg Asp Thr Thr Ala Gly Leu Leu Ser Phe Leu Phe Phe Glu Leu
            340                 345                 350

Ser Arg Asn Pro Glu Ile Phe Ala Lys Leu Arg Glu Ile Glu Asn
        355                 360                 365

Lys Phe Gly Leu Gly Gln Asp Ala Arg Val Glu Glu Ile Ser Phe Glu
    370                 375                 380

Thr Leu Lys Ser Cys Glu Tyr Leu Lys Ala Val Ile Asn Glu Thr Leu
```

```
                385                 390                 395                 400
Arg Ile Tyr Pro Ser Val Pro His Asn Phe Arg Val Ala Thr Arg Asn
            405                 410                 415

Thr Thr Leu Pro Arg Gly Gly Glu Gly Gly Leu Ser Pro Ile Ala
        420                 425                 430

Ile Lys Lys Gly Gln Val Val Met Tyr Thr Ile Leu Ala Thr His Arg
            435                 440                 445

Asp Lys Asp Ile Tyr Gly Glu Asp Ala Tyr Val Phe Arg Pro Glu Arg
450                 455                 460

Trp Phe Glu Pro Glu Thr Arg Lys Leu Gly Trp Ala Tyr Val Pro Phe
465                 470                 475                 480

Asn Gly Gly Pro Arg Ile Cys Leu Gly Gln Gln Phe Ala Leu Thr Glu
            485                 490                 495

Ala Ser Tyr Val Thr Val Arg Leu Leu Gln Glu Phe Gly Asn Leu Lys
            500                 505                 510

Gln Asp Pro Asn Thr Glu Tyr Pro Pro Lys Leu Gln Asn Thr Leu Thr
        515                 520                 525

Leu Ser Leu Phe Glu Gly Ala Glu Val Gln Met Tyr Leu Ile Leu
    530                 535                 540

<210> SEQ ID NO 45
<211> LENGTH: 517
<212> TYPE: PRT
<213> ORGANISM: Candida tropicalis

<400> SEQUENCE: 45

Met Ile Glu Gln Leu Leu Glu Tyr Trp Tyr Val Val Pro Val Leu
1               5                   10                  15

Tyr Ile Ile Lys Gln Leu Leu Ala Tyr Thr Lys Thr Arg Val Leu Met
            20                  25                  30

Lys Lys Leu Gly Ala Ala Pro Val Thr Asn Lys Leu Tyr Asp Asn Ala
        35                  40                  45

Phe Gly Ile Val Asn Gly Trp Lys Ala Leu Gln Phe Lys Lys Glu Gly
    50                  55                  60

Arg Ala Gln Glu Tyr Asn Asp Tyr Lys Phe Asp His Ser Lys Asn Pro
65                  70                  75                  80

Ser Val Gly Thr Tyr Val Ser Ile Leu Phe Gly Thr Arg Ile Val Val
            85                  90                  95

Thr Lys Asp Pro Glu Asn Ile Lys Ala Ile Leu Ala Thr Gln Phe Gly
        100                 105                 110

Asp Phe Ser Leu Gly Lys Arg His Thr Leu Phe Lys Pro Leu Leu Gly
    115                 120                 125

Asp Gly Ile Phe Thr Leu Asp Gly Glu Gly Trp Lys His Ser Arg Ala
    130                 135                 140

Met Leu Arg Pro Gln Phe Ala Arg Glu Gln Val Ala His Val Thr Ser
145                 150                 155                 160

Leu Glu Pro His Phe Gln Leu Leu Lys Lys His Ile Leu Lys His Lys
            165                 170                 175

Gly Glu Tyr Phe Asp Ile Gln Glu Leu Phe Phe Arg Phe Thr Val Asp
        180                 185                 190

Ser Ala Thr Glu Phe Leu Phe Gly Glu Ser Val His Ser Leu Lys Asp
    195                 200                 205

Glu Ser Ile Gly Ile Asn Gln Asp Asp Ile Asp Phe Ala Gly Arg Lys
    210                 215                 220
```

```
Asp Phe Ala Glu Ser Phe Asn Lys Ala Gln Glu Tyr Leu Ala Ile Arg
225                 230                 235                 240

Thr Leu Val Gln Thr Phe Tyr Trp Leu Val Asn Asn Lys Glu Phe Arg
            245                 250                 255

Asp Cys Thr Lys Ser Val His Lys Phe Thr Asn Tyr Tyr Val Gln Lys
        260                 265                 270

Ala Leu Asp Ala Ser Pro Glu Glu Leu Glu Lys Gln Ser Gly Tyr Val
    275                 280                 285

Phe Leu Tyr Glu Leu Val Lys Gln Thr Arg Asp Pro Asn Val Leu Arg
290                 295                 300

Asp Gln Ser Leu Asn Ile Leu Leu Ala Gly Arg Asp Thr Thr Ala Gly
305                 310                 315                 320

Leu Leu Ser Phe Ala Val Phe Glu Leu Ala Arg His Pro Glu Ile Trp
                325                 330                 335

Ala Lys Leu Arg Glu Glu Ile Glu Gln Gln Phe Gly Leu Gly Glu Asp
            340                 345                 350

Ser Arg Val Glu Glu Ile Thr Phe Glu Ser Leu Lys Arg Cys Glu Tyr
        355                 360                 365

Leu Lys Ala Phe Leu Asn Glu Thr Leu Arg Ile Tyr Pro Ser Val Pro
    370                 375                 380

Arg Asn Phe Arg Ile Ala Thr Lys Asn Thr Thr Leu Pro Arg Gly Gly
385                 390                 395                 400

Gly Ser Asp Gly Thr Ser Pro Ile Leu Ile Gln Lys Gly Glu Ala Val
                405                 410                 415

Ser Tyr Gly Ile Asn Ser Thr His Leu Asp Pro Val Tyr Tyr Gly Pro
            420                 425                 430

Asp Ala Ala Glu Phe Arg Pro Glu Arg Trp Phe Glu Pro Ser Thr Lys
        435                 440                 445

Lys Leu Gly Trp Ala Tyr Leu Pro Phe Asn Gly Gly Pro Arg Ile Cys
    450                 455                 460

Leu Gly Gln Gln Phe Ala Leu Thr Glu Ala Gly Tyr Val Leu Val Arg
465                 470                 475                 480

Leu Val Gln Glu Phe Ser His Val Arg Ser Asp Pro Asp Glu Val Tyr
                485                 490                 495

Pro Pro Lys Arg Leu Thr Asn Leu Thr Met Cys Leu Gln Asp Gly Ala
            500                 505                 510

Ile Val Lys Phe Asp
            515

<210> SEQ ID NO 46
<211> LENGTH: 680
<212> TYPE: PRT
<213> ORGANISM: Candida tropicalis

<400> SEQUENCE: 46

Met Ala Leu Asp Lys Leu Asp Leu Tyr Val Ile Ile Thr Leu Val Val
1               5                   10                  15

Ala Ile Ala Ala Tyr Phe Ala Lys Asn Gln Phe Leu Asp Gln Gln Gln
            20                  25                  30

Asp Thr Gly Phe Leu Asn Thr Asp Ser Gly Asp Gly Asn Ser Arg Asp
        35                  40                  45

Ile Ser Gln Ala Leu Lys Lys Asn Asn Lys Asn Thr Leu Leu Leu Phe
    50                  55                  60

Gly Ser Gln Thr Gly Thr Ala Glu Asp Tyr Ala Asn Lys Leu Ser Arg
65                  70                  75                  80
```

```
Glu Leu His Ser Arg Phe Gly Leu Lys Thr Met Val Ala Asp Phe Ala
                85                  90                  95
Asp Tyr Asp Phe Glu Asn Phe Gly Asp Ile Thr Glu Asp Ile Leu Val
            100                 105                 110
Phe Phe Ile Val Ala Thr Tyr Gly Gly Glu Pro Thr Asp Asn Ala
        115                 120                 125
Asp Glu Phe His Thr Trp Leu Thr Glu Glu Ala Asp Thr Leu Ser Thr
    130                 135                 140
Leu Lys Tyr Thr Val Phe Gly Leu Gly Asn Ser Thr Tyr Glu Phe Phe
145                 150                 155                 160
Asn Ala Ile Gly Arg Lys Phe Asp Arg Leu Leu Gly Glu Lys Gly Gly
                165                 170                 175
Asp Arg Phe Ala Glu Tyr Gly Glu Gly Asp Asp Gly Thr Gly Thr Leu
            180                 185                 190
Asp Glu Asp Phe Leu Ala Trp Lys Asp Asn Val Phe Asp Ser Leu Lys
    195                 200                 205
Asn Asp Leu Asn Phe Glu Glu Lys Glu Leu Lys Tyr Glu Pro Asn Val
    210                 215                 220
Lys Leu Thr Glu Arg Asp Asp Leu Ser Gly Asn Asp Pro Asp Val Ser
225                 230                 235                 240
Leu Gly Glu Pro Asn Val Lys Tyr Ile Lys Ser Glu Gly Val Asp Leu
                245                 250                 255
Thr Lys Gly Pro Phe Asp His Thr His Pro Phe Leu Ala Arg Ile Val
            260                 265                 270
Lys Thr Lys Glu Leu Phe Thr Ser Glu Asp Arg His Cys Val His Val
    275                 280                 285
Glu Phe Asp Ile Ser Glu Ser Asn Leu Lys Tyr Thr Thr Gly Asp His
    290                 295                 300
Leu Ala Ile Trp Pro Ser Asn Ser Asp Glu Asn Ile Lys Gln Phe Ala
305                 310                 315                 320
Lys Cys Phe Gly Leu Glu Asp Lys Leu Asp Thr Val Ile Glu Leu Lys
                325                 330                 335
Ala Leu Asp Ser Thr Tyr Ser Ile Pro Phe Pro Asn Pro Ile Thr Tyr
            340                 345                 350
Gly Ala Val Ile Arg His His Leu Glu Ile Ser Gly Pro Val Ser Arg
        355                 360                 365
Gln Phe Phe Leu Ser Ile Ala Gly Phe Ala Pro Asp Glu Glu Thr Lys
    370                 375                 380
Lys Ser Phe Thr Arg Ile Gly Gly Asp Lys Gln Glu Phe Ala Ser Lys
385                 390                 395                 400
Val Thr Arg Arg Lys Phe Asn Ile Ala Asp Ala Leu Leu Phe Ala Ser
                405                 410                 415
Asn Asn Arg Pro Trp Ser Asp Val Pro Phe Glu Phe Leu Ile Glu Asn
            420                 425                 430
Val Gln His Leu Thr Pro Arg Tyr Tyr Ser Ile Ser Ser Ser Ser Leu
        435                 440                 445
Ser Glu Lys Gln Thr Ile Asn Val Thr Ala Val Glu Ala Glu Glu
    450                 455                 460
Glu Ala Asp Gly Arg Pro Val Thr Gly Val Val Thr Asn Leu Leu Lys
465                 470                 475                 480
Asn Ile Glu Ile Glu Gln Asn Lys Thr Gly Glu Thr Pro Met Val His
                485                 490                 495
```

```
Tyr Asp Leu Asn Gly Pro Arg Gly Lys Phe Ser Lys Phe Arg Leu Pro
            500                 505                 510

Val His Val Arg Arg Ser Asn Phe Lys Leu Pro Lys Asn Ser Thr Thr
        515                 520                 525

Pro Val Ile Leu Ile Gly Pro Gly Thr Gly Val Ala Pro Leu Arg Gly
    530                 535                 540

Phe Val Arg Glu Arg Val Gln Gln Val Lys Asn Gly Val Asn Val Gly
545                 550                 555                 560

Lys Thr Val Leu Phe Tyr Gly Cys Arg Asn Ser Glu Gln Asp Phe Leu
                565                 570                 575

Tyr Lys Gln Glu Trp Ser Glu Tyr Ala Ser Val Leu Gly Glu Asn Phe
            580                 585                 590

Glu Met Phe Asn Ala Phe Ser Arg Gln Asp Pro Thr Lys Lys Val Tyr
        595                 600                 605

Val Gln Asp Lys Ile Leu Glu Asn Ser Ala Leu Val Asp Glu Leu Leu
    610                 615                 620

Ser Ser Gly Ala Ile Ile Tyr Val Cys Gly Asp Ala Ser Arg Met Ala
625                 630                 635                 640

Arg Asp Val Gln Ala Ala Ile Ala Lys Ile Val Ala Lys Ser Arg Asp
                645                 650                 655

Ile His Glu Asp Lys Ala Ala Glu Leu Val Lys Ser Trp Lys Val Gln
            660                 665                 670

Asn Arg Tyr Gln Glu Asp Val Trp
            675                 680

<210> SEQ ID NO 47
<211> LENGTH: 1569
<212> TYPE: DNA
<213> ORGANISM: Candida maltosa

<400> SEQUENCE: 47
atgatggcca tcgaacaaat catcgaagaa gtcttgccat acttgactaa gtggtacacc      60
attattttcg gtgctgctgt tacttacttc ttgtccattg ctttgagaaa caagttctac     120
gaatacaagt tgaagtgcga aaacccagtt tactttcaag atgctggttt gtttggtatt     180
ccagccttga tcgatattat caaggttaga aaagctggtc aattggctga ttacactgat     240 accactttg acaagtaccc aaacttgtcc tcttacatga ctgttgctgg tgttttgaag      300
atcgttttca ctgttgatcc agaaaacatc aaagctgttt ggctacccca attcaacgat     360
tttgctttgg gtgctagaca tgctcatttt gatccattat gggtgatgg tatcttcacc      420 ttggatggtg aaggttggaa acattctaga gctatgttaa gaccacaatt cgccagagaa     480
caaattgctc atgttaaggc tttggaacca cacgttcaaa ttttggctaa gcaaatcaag     540
ttgaacaagg gtaagacttt cgacttgcaa gaattattct tcagattcac cgttgatacc     600
gccaccgaat ttttgttcgg tgaatcagtt cattccttgt acgacgaaaa atccggtatt     660
ccaaatgata tcccaggtag agaaaatgtc agagaagcct taacacctc ccaacattat      720 ttggctacta gaacctactc ccaaatcttc tactggttga ctaacccaaa agaatttaga     780
gattgcaacg ccaaggttca taagttggct caatactttg ttaacaccgc tttgaacgct     840
accgaaaaag aagttgaaga aagtctaag ggtggttacg ttttcttgta cgaattggtt      900
aagcaaacca gagatccaaa ggtattgcaa gaccaattat tgaacattat ggttgccggt     960
agagatacaa ctgctggttt attgtctttc gccatgtttg aattggctag aaacccaaag    1020
atttggaaca agttgagaga agaagtagaa gtcaatttcg gtttaggtga tgaagctaga    1080
```

```
gttgacgaaa tttccttcga aaccttgaag aagtgtgaat acttgaaggc cgttttgaac      1140
gaaactttga gaatgtatcc atccgtccca atcaatttca gaactgctac tagagatacc      1200
acattgccaa gaggtggtgg taaagatggt aattctccaa tttttgtccc aaagggttcc      1260
tccgttgttt actctgttta caagactcac agattgaagc aattctacgg tgaagatgcc      1320
tacgaattta gaccagaaag atggtttgaa ccatccacta gaaaattggg ttgggcttat      1380
ttgcctttta atggtggtcc aagaatttgc ttgggtcaac aatttgcttt gactgaagcc      1440
tcttacgtta ttgctagatt ggctcaaatg tttgaacact tggaatctaa ggacgaaact      1500
tacccaccaa acaagtgtat tcatttgacc atgaaccata cgaaggtgt  tttcatttcc      1560 gccaagtaa                                                               1569
```

<210> SEQ ID NO 48
<211> LENGTH: 1572
<212> TYPE: DNA
<213> ORGANISM: Starmerella bombicola

<400> SEQUENCE: 48

```
atgatcttgt acgctgtttt gggtgctttt gctgcttttt tgttgtacat ggatgtcttg        60
tacccattcg ttatctatcc attgagagct agatggcata agtgtggtta tcccaagaa        120 gatttgtctt ggccattggg tattccattg actttggttg ttttgtccaa gttgagaaag       180
gatatgttgt tgcaattcat ggctgctcaa gatttgtcca gaccatacaa acatccttg        240 agacaattct tgggtaaatg ggttattgct accagagatc cagaaaacat taaggctgtt       300
ttgtctacca agttcaacga cttctcattg aaagaaagag gtaacagaat gagacacgtt       360
atcggtgatg gtatttttcac tcaagatggt gcaccttgga acactctag agatatgtta       420 agaccacaat tcaccaagga ccaaatctcc agagttgaat tattgtccca ccatatcgat       480
gtcttgatca gagaaattag aaagtccggt ggtaacgtcg aattgcaaag attattccac       540
ttgatgacta tggataccgc tacccattt  ttgttcggtg aatctgttgg ttccttggaa       600
gtttctggtg aatctaaggg tattgaaatc actgatccaa agaccggtga atcgttaac        660 actgttgatt tcgttgaatc ctacaccttc gctaacaagt ttgccttgaa aaagatcatc       720
ttgaacgatt tggaatttt  tggccgatttg accgaaccat cttacaaatg gcatttgaga       780
agagttcaca ccgttatgga tcactatgtt caattggctt tgaaggctac cgaaaagtat       840
gatccagatg atgattctga aaagggtgaa tattacttct cccacgaatt ggctaagttg       900
actagagatc cattgtcctt gagagatcaa ttattcaaca ttttgatcgc cggtagagat       960
acaactgctg ctactttgtc ttacgctttt cattacttga ctaagaaccc agctatctac      1020
gctaaggtta gagaagatgt tttgaccgtt tttccaaacg tgatgcttc tttggctact      1080 tacgaagatt tgagaaaagc taagtacttg caaatggtca tcaaagaagt tttgagattg       1140
gctccagctg ttccattgaa cactagagct gctgttagag atacttattt gccaagaggt      1200
ggtggtccag ctggtaattt gccagttttt gttccaaaag gtactgccgt taattaccca      1260
acttacatct tgcatagaga tcctgatatc tatggtgctg atgcctacga atttaatcca      1320
gaaagatgga gacctgaaaa caagttgcca aattctccaa tgtattcctg gggttacatt      1380
ccattcaatg gtggtcctag aatctgcatt ggtcaacaat ttgctttgac tgaaattgcc      1440
ttgaccatga tcaagttggt cttggaattt gaaagattgg aaccagccga tgatttcgaa      1500
cctaacttgc aagataagtc ctccttgact gttatggttg gtggttctgg tgttagagtt      1560
```

```
aagttgtctt aa                                                        1572

<210> SEQ ID NO 49
<211> LENGTH: 2064
<212> TYPE: DNA
<213> ORGANISM: Starmerella bombicola

<400> SEQUENCE: 49
atggccgata tcaacttcat tgcctccgtt gttgttgctt tggctgttgt ttttgttgcc      60
tacaagtact ttaatggtgg tccagatgtt caatcttcta aggctggtaa ttctactcca     120
ttcggtaact ctaaagctga tgaagatggt gattccagag atttcgttgc tttgatggaa     180
aagaacaaca agaacgtcat cgttttctac ggttctcaaa ctggtactgc tgaagatttg     240
gcttctaagt tggctaaaga attgtcctct aagtacggtt taagaaccat gactgctgat     300
ccagaaaact tcgatttcga aaagttggat accttcccag aatctcattt ggccgttttt     360
ttgatggctt cttatggtga tggtgaacct actgataatg ctcaagactt gtactctttc     420
ttgggtaact ctccatcttt ctcacaagac ggtgaaactt tggaaaactt gaactttgct     480
gttttcggtt tgggtaacgt cttgtacgaa ttttacaaca agccggtaa ggacatgcat     540
aagtacttga ctgatttggg tggtcattct attggtccat acggtgaagg tgatgattct     600
aaaggtatgt tggaagaaga ttacatggcc tggaaggatg aatttttggc tgctttggtt     660
gctaaatggg gtttgactga agagaagct gtttacgaac catccatctc cgtcaaagaa     720
attgaagaag atgctcactc tcacgatgtt tatttgggtg aacctaattt gaaacacttg     780
caagcctcaa aggctcaaga aattccaaaa ggtccataca atgcttccaa tccaatgttg     840
gcaaaaatta ccgctgccag agaattattc actaacactg atagacattg catccacatg     900
gaatttgata caactggtgc tagatacact accggtgatc atttggcttt ttggttccaa     960
aacaacgaag aagaagtcca agattcgtt aaggctttgg gtattgctaa tccacaacaa    1020
cctattgcca tttccgtttt ggataagact tctaccgtta gaataccatc tccaactacc    1080
tacgaaacca tcatcagaca tttcttggaa atcaacggtc cagtttccag acaagttttg    1140
tcatctattg caccatttgc cccatctgaa gaagttaaga agctactca acaattgggt    1200
tccaacaaag aattatttgc ctctcatgtt gctgccaaga agttcaatat tgccagattg    1260
ttgttacatt tgtccggtgg tcaaccttgg aagaatgttc catttccctt cgtcattgaa    1320
accatcccac acttacaacc tagatattac tccatctcct cctcatctgt tcaatcccca    1380
aatactgttt ccattactgc cgttgttgaa agacaaactt tgaccggtgt tgatcatgaa    1440
tgagaggtg ttgctaccaa tcaaattttg gctttgtctg aagccttggt tggtcatcca    1500
tctatgactt atagattgca acaaccacac gacttcacca actcattatc ctctcaagat    1560
atcagagttc cagtccatat tagacacagt tgtttaagt tgccaggtaa gccaactgtt    1620
ccaattatca tggttggtcc aggtactggt gttgctcctt ttagaggttt tgttcacgaa    1680
agagcttctc aaaaagctgc cggtaaagaa gttggtaagg ctatgttgtt taccggttct    1740
agacatgcta acgaagattt cttgtacaga gatgaatgga agcaattctc cgacttcttg    1800
gatttggaaa ctgcctttc tagagactcc tccaaaaagg tttacgtcca acacaagttg    1860
aaagaaagag ctaaggacgt tttcgccttg ttgaatgaag gtgctgtttt ttacgtttgt    1920
ggtgatgctg gtgtatgtc tcatgatgtt cattctgctt tgttagaaat cgttgcccaa    1980
gaaggtaact tgagttctga agatgctgat aagttcgtca gaaagatgag atcaagaaac    2040
aagtaccaag aagatgtttg gtaa                                          2064
```

<210> SEQ ID NO 50
<211> LENGTH: 1632
<212> TYPE: DNA
<213> ORGANISM: Candida tropicalis

<400> SEQUENCE: 50

```
atgtcctcct ccccatctat tgcccaagaa ttttggcta ctattacccc atacgtcgaa      60
tactgtcaag aaaactacac taagtggtac tacttcatcc cattggtcat cttgtccttg     120
aacttgattt ctatgttgca cactaagtac ttggaaagaa agtttaaggc taagccattg     180
gccgtttacg ttcaagatta caccttctgt ttgatcaccc cattggtttt gatctactac     240
aagtctaagg gtactgttat gcaattcgct tgtgatttgt gggacaagaa cttgatagtt     300
tctgatccaa aggccaagac tatcggtttg aagattttgg gtattccatt gatcgaaact     360
aaggacccag aaaacgttaa ggctattttg gccactcaat tcaacgattt ctcattgggt     420
actagacacg acttcttgta ttctttgttg ggtgatggta tcttcacttt ggatggtgct     480
ggttggaaac attctagaac tatgttaaga ccacaattcg ccagagaaca agtttcccat     540
gttaagttgt tggaaccaca catgcaagtt ttgttcaagc acatcagaaa acatcacggt     600
caaaccttcg atatccaaga attattcttc agattgaccg ttgattccgc caccgaattt     660
ttgttaggtg aatctgctga atccttgaga gatgaatctg ttggttttgac tccaactacc     720
aaggattttg atggtagaaa cgaatttgct gacgccttca attactccca aactaatcaa     780
gcctacagat tcttgttaca acaaatgtac tggattttga acggttccga atttagaaag     840
tccattgcca tcgttcataa gttcgctgat cactatgttc aaaaggcttt ggaattgacc     900
gacgaagatt tggaaaagaa agaaggttac gttttcttgt tcgaattggc caagcaaact     960
agagatccta aggttttgag atcaattta ttgaacatct tggttgccgg tagagataca    1020
actgctggtt tgttgtcttt tttgttcttc gaattgtcca gaaaccctga aattttcgcc    1080
aagttgagag aagaaatcga aaacaagttt ggtttgggtc aagatgccag agttgaagaa    1140
atctctttcg aaaccttgaa gtcctgcgaa tacttgaagg ctgttatcaa cgaaactttg    1200
agaatctacc catccgttcc acataatttc agagttgcta ctagaaacac taccttgcca    1260
agaggtggtg gtgaaggtgg tttatctcca attgctatta agaaaggtca agtcgtcatg    1320
tacactatct tggctactca tagagataag gacatctatg tgaagatgc ctacgttttt    1380
agaccagaaa gatggtttga accagaaacc agaaaattgg gttgggctta tgttcctttt    1440
aatggtggtc ctagaatttg cttgggtcaa caatttgctt tgactgaagc ctcttacgtt    1500
accgtcagat tattgcaaga atttggtaac ttgaagcaag acccaaacac tgaatatcca    1560
ccaaagttgc aaaacacctt gaccttgtca ttattcgaag gtgctgaagt tcaaatgtat    1620
ttgatcttgt aa                                                        1632
```

<210> SEQ ID NO 51
<211> LENGTH: 1554
<212> TYPE: DNA
<213> ORGANISM: Candida tropicalis

<400> SEQUENCE: 51

```
atgatcgaac aattattgga atactggtac gttgttgtcc cagtcttgta catcatcaag      60
caattattag cttacaccaa gaccagagtc ttgatgaaga aattgggtgc tgctccagtt     120
acaaacaagt tgtacgataa tgctttcggt atcgttaatg gttggaaagc cttgcaattc     180
```

```
aagaaagaag gtagagccca agaatacaac gattacaagt ttgaccattc caagaaccca    240
tctgttggta cttacgtttc tatcttgttc ggtactagaa tcgttgttac taaggaccca    300
gaaaacatta aggctatttt ggctactcaa ttcggtgact tttcattggg taagagacat    360
actttgttca agcctttgtt gggtgatggt attttcactt ggatggtga aggttggaaa     420 cattccagag ctatgttaag accacaattc gctagagaac aagttgccca tgttacatct    480
ttggaaccac acttccaatt attgaagaag cacatcttga agcacaaggg tgaatacttc    540
gatatccaag aattattctt cagattcacc gttgattccg ccaccgaatt tttgtttggt    600
gaatcagttc actccttgaa ggatgaatcc atcggtatca atcaagatga tattgatttc    660
gccggtagaa aggatttcgc tgaatctttt aacaaggctc aagaatactt ggccattaga    720
actttggttc aaaccttcta ctggttggtc aacaacaaag aatttagaga ctgcaccaag    780
tccgttcata agttcactaa ttactacgtc caaaaggctt ggatgcttc tccagaagaa     840 ttggaaaaac aatccggtta cgttttcttg tacgaattgg ttaagcaaac cagagatcca    900
aacgtcttga gagatcaatc cttgaacatt ttgttggctg gtagagatac aactgctggt    960
ttgttgtctt ttgccgtttt tgaattggct agacatccag aaatttgggc caagttgaga    1020
gaagaaatcg aacaacaatt tggttttggg gaagattcca gagttgaaga aatcaccttc    1080
gaatctttga gagatgcga atacttgaag gccttttga acgaaacctt gagaatctat     1140
ccatccgttc caagaaactt cagaattgct actaagaaca ctaccttgcc aagaggtggt    1200
ggttctgatg gtacttctcc aattttgatt caaaagggtg aagccgtttc ctacggtatt    1260
aactctactc acttagatcc agtttactac ggtccagatg ctgctgaatt tagaccagaa    1320
agatggtttg aaccttccac taagaaatta ggttgggctt acttgccttt taatggtggt    1380
cctagaattt gcttgggtca acaattcgca ttgactgaag ctggttatgt tttggttaga    1440
ttggttcaag aattttccca cgttagatcc gatccagatg aagtttatcc accaaagaga    1500
ttgactaact tgaccatgtg tttacaagat ggtgccatcg ttaagttcga ctaa           1554
```

<210> SEQ ID NO 52
<211> LENGTH: 2043
<212> TYPE: DNA
<213> ORGANISM: Candida tropicalis

<400> SEQUENCE: 52

```
atggccttgg acaagttgga cttgtacgtt attatcacct tggttgttgc tattgctgct     60
tacttcgcta agaatcaatt cttggatcaa caacaagaca ctggtttctt gaacactgat    120
tctggtgatg gtaactccag agatatttct caagccttga agaagaacaa caaaaacact    180
ttgttgttgt tcggttccca aactggtact gctgaagatt atgctaacaa gttgtccaga    240
gaattgcact ctagattcgg tttgaaaact atggttgctg atttcgccga ttacgacttt    300
gaaaatttcg gtgacattac cgaagatatt tggttttct tcatcgttgc tacctacggt    360
gaaggtgaac ctactgataa tgctgatgaa tttcatacct ggttgaccga agaagctgat    420
actttgtcta ctttgaagta caccgttttc ggtttgggta actctaccta cgaattttc     480 aacgccattg gtgaaaagtt cgatagatta ttgggtgaaa agggtggtga tagattgct     540 gaatatggtg aaggtgatga tggtactggt actttggatg aagatttttt ggcttggaag    600
gacaacgttt tcgactcttt gaagaacgac ttgaacttcg aagaaaaaga attgaagtac    660
gaacctaacg tcaagttgac tgaaagagat gatttgtctg gtaacgatcc agatgttttct    720 ttgggtgaac ctaatgttaa gtacatcaag tccgaaggtg ttgatttgac taaggtccca    780
```

-continued

```
tttgatcata cccatccatt tttggctaga atcgtcaaga ccaaagaatt attcacctcc    840
gaagatagac attgcgttca cgttgaattt gacatctccg aatctaactt gaagtatacc    900
actggtgatc atttggctat ttggccatct aattctgacg aaaacattaa gcaattcgcc    960
aagtgctttg gtttggaaga taagttggat accgtcattg aattgaaggc tttggattcc   1020
acttactcca ttccatttcc aaacccaatt acttacggtg ccgttatcag acatcatttg   1080
gaaatttctg gtccagtctc cagacaattc ttcttgtcta ttgctggttt tgccccagac   1140
gaagaaacta agaaatcctt cactagaatt ggtggtgaca aacaagaatt tgcctctaag   1200
gttaccagaa gaaagttcaa cattgctgat gccttgttgt ttgcctcaaa caatagacct   1260
tggtctgatg tcccattcga atttttgatt gaaaacgtcc aacacttgac cccaagatat   1320
tactctatct cctcttcctc attgtccgaa aagcaaacta ttaacgttac cgctgttgtt   1380
gaagccgaag aagaagcaga cggtagacca gttactggtg ttgttactaa tttgttgaag   1440
aacatcgaaa tcgaacaaaa caagactggt gaaacccaa tggttcacta tgatttgaat    1500
ggtccaagag gtaagttctc caagtttaga ttgccagttc acgtcagaag atccaatttc   1560
aaattgccaa agaactctac caccccagtt attttgattg gtccaggtac aggtgttgct   1620
ccattgagag gttttgttag agaaagagtt caacaagtca agaacggtgt taacgttggt   1680
aagaccgttt tgttttacgg ttgcagaaac tccgaacaag acttcttgta taagcaagaa   1740
tggtccgaat acgcttccgt tttaggtgaa aacttcgaaa tgttcaacgc cttctctaga   1800
caagatccta ctaagaaggt ttacgtccaa gacaagattt tggaaaactc cgctttggtt   1860
gacgaattat tgtcatctgg tgccattatc tacgtttgtg gtgatgcttc tagaatggct   1920
agagatgttc aagctgctat tgcaaaaatt gtcgccaagt ctagagatat ccatgaagat   1980
aaggctgccg aattggttaa gtcttggaag gttcaaaaca gataccaaga agatgtctgg   2040
taa                                                                  2043
```

PRODUCTION OF MACROCYCLIC KETONES IN RECOMBINANT HOSTS

BACKGROUND OF THE INVENTION

Field of the Invention

This disclosure relates to recombinant production of macrocylic ketones and macrocyclic ketone precursors, such as muscone, civetone and precursors thereof, in recombinant hosts. In particular, this disclosure relates to production of muscone molecules such as I- and/or nor-muscone, and muscone precursors comprising hexadecanedioic acid, (S)-2-methylbutyryl acid-CoA, 14-methylhexadecanoic acid, and 3-methylhexadecanedioic acid in recombinant hosts and/or excretion of such muscone, civetone and/or precursors thereof into the culture medium of the recombinant host cell. The disclosure further relates to producing muscone, civetone and precursors thereof by bioconversion or in vitro reactions.

Description of Related Art

Macrocyclic ketones have applications in the fragrance industry, specifically perfume. Macrocyclic ketones include, but are not limited to, muscone and civetone. Both muscone and civetone are characterized as having a musky odor. Civetone is a commercially useful pheromone obtained from the African civet. Muscone is naturally obtained from a glandular secretion of the musk deer, extraction of which often results in the death of the animal. Because musk deer are endangered species, muscone must be made synthetically. Because muscone and civetone are large molecules, they are involatile and act as fixatives which reduce the evaporation rate of lighter molecules found in fragrances.

As recovery and purification of muscone has proven to be labor-intensive and inefficient, there remains a need for a recombinant production system that can produce high yields of desired muscone and muscone precursors, such as I-muscone, nor-muscone, (R)-2-methylbutyryl-CoA and/or (S)-2-methylbutyryl-CoA (FIGS. 1A-1K). There also remains a need for improved production of muscone in recombinant hosts for commercial uses.

SUMMARY OF THE INVENTION

It is against the above background that the present invention provides certain advantages and advancements over the prior art.

Although this invention disclosed herein is not limited to specific advantages or functionalities the invention provides a recombinant host cell producing one or more macrocyclic ketone precursors and/or one or more macrocyclic ketones, comprising:
(a) a gene encoding a polypeptide capable of synthesizing 3-methyl-2-oxopentanoate from L-isoleucine;
(b) a gene encoding a polypeptide capable of synthesizing (S)-2-methylbutanal from 3-methyl-2-oxopentanoate;
(c) a gene encoding a polypeptide capable of synthesizing (S)-2-methylbutyric acid from (S)-2-methylbutanal;
(d) a gene encoding a polypeptide capable of synthesizing (S)-2-methylbutyryl-CoA from (S)-2-methylbutyric acid;
(e) a gene encoding a polypeptide capable of synthesizing an anteiso fatty acid from (S)-2-methylbutyryl-CoA;
(f) a gene encoding a polypeptide capable of synthesizing a dicarboxylic acid (DCA) from the anteiso fatty acid or from an iso fatty acid;
(g) a gene encoding a polypeptide capable of synthesizing a CoA activated DCA (DCA-CoA) from the DCA;
(h) a gene encoding a polypeptide having cyclisation activity capable of synthesizing a muscone from the DCA; and/or
(i) a gene encoding a polypeptide having cyclisation activity capable of synthesizing the muscone from the DCA-CoA;
wherein at least one of the genes is a recombinant gene.

In one aspect, the recombinant host cell disclosed herein comprises:
(a) the gene encoding the polypeptide capable of synthesizing 3-methyl-2-oxopentanoate from L-isoleucine;
(b) the gene encoding the polypeptide capable of synthesizing (S)-2-methylbutanal from 3-methyl-2-oxopentanoate;
(c) the gene encoding the polypeptide capable of synthesizing (S)-2-methylbutyric acid from (S)-2-methylbutanal;
(d) the gene encoding the polypeptide capable of synthesizing (S)-2-methylbutyryl-CoA from (S)-2-methylbutyric acid;
(e) the gene encoding the polypeptide capable of synthesizing the anteiso fatty acid from (S)-2-methylbutyryl-CoA;
(f) the gene encoding the polypeptide capable of synthesizing the DCA from the anteiso fatty acid or from an iso fatty acid; and
(g) the gene encoding the polypeptide capable of synthesizing the DCA-CoA from the DCA;
wherein the recombinant host cell produces the one or more macrocyclic ketone precursors.

In one aspect, the recombinant host cell disclosed herein comprises:
(a) the gene encoding the polypeptide capable of synthesizing 3-methyl-2-oxopentanoate from L-isoleucine;
(b) the gene encoding the polypeptide capable of synthesizing (S)-2-methylbutanal from 3-methyl-2-oxopentanoate;
(c) the gene encoding the polypeptide capable of synthesizing (S)-2-methylbutyric acid from (S)-2-methylbutanal;
(d) the gene encoding the polypeptide capable of synthesizing (S)-2-methylbutyryl-CoA from (S)-2-methylbutyric acid;
(e) the gene encoding the polypeptide capable of synthesizing the anteiso fatty acid from (S)-2-methylbutyryl-CoA;
(f) the gene encoding the polypeptide capable of synthesizing the DCA from the anteiso fatty acid or from an iso fatty acid;
(g) the gene encoding the polypeptide capable of synthesizing the DCA-CoA from the DCA; and
(h) the gene encoding the polypeptide capable of synthesizing the muscone from the DCA;
wherein the recombinant host cell produces the one or more macrocyclic ketones.

In one aspect, the recombinant host cell disclosed herein comprises:
(a) the gene encoding the polypeptide capable of synthesizing 3-methyl-2-oxopentanoate from L-isoleucine;
(b) the gene encoding the polypeptide capable of synthesizing (S)-2-methylbutanal from 3-methyl-2-oxopentanoate;

(c) the gene encoding the polypeptide capable of synthesizing (S)-2-methylbutyric acid from (S)-2-methylbutanal;
(d) the gene encoding the polypeptide capable of synthesizing (S)-2-methylbutyryl-CoA from (S)-2-methylbutyric acid;
(e) the gene encoding the polypeptide capable of synthesizing the anteiso fatty acid from (S)-2-methylbutyryl-CoA;
(f) the gene encoding the polypeptide capable of synthesizing the DCA from the anteiso fatty acid or from an iso fatty acid;
(g) the gene encoding the polypeptide capable of synthesizing the DCA-CoA from the DCA; and
(i) the gene encoding the polypeptide capable of synthesizing the muscone from the DCA-CoA;
wherein the recombinant host cell produces the one or more macrocyclic ketones.

In one aspect, the recombinant host cell disclosed herein has a deletion in a genetic locus encoding a polypeptide capable of oxidizing one or more muscone precursors.

In one aspect of the recombinant host cell disclosed herein, the genetic locus encoding a polypeptide capable of oxidizing one or more muscone precursors comprises a peroxisomal acyl-CoA oxidase (POX1) gene.

In one aspect of the recombinant host cell disclosed herein:
(a) the anteiso fatty acid is 12-methyltetradecanoic acid, 14-methylhexadecanoic acid or 16-methyloctadecanoic acid;
(b) the iso fatty acid is palmitic acid;
(c) the DCA is dodecanedioic acid, n-dodecandioic acid, tetradecanedioic acid, n-tetradecanedioic acid, hexadecanedioic acid, n-hexadecanedioic acid, n-methylhexadecanedioic acid octadecanedioic acid, n-octadecanedioic acid, n-methylhexadecanoic acid or eicosanoic acid; and
(d) the CoA activated DCA is hexadecanedioic acid-CoA, n-hexadecanedioic acid-CoA, n-methylhexadecanedioic acid-CoA octadecanedioic acid-CoA, or n-octadecanedioic acid-CoA.

In one aspect of the recombinant host cell disclosed herein:
(a) the anteiso fatty acid is 12-methyltetradecanoic acid, 14-methylhexadecanoic acid or 16-methyloctadecanoic acid;
(b) the iso fatty acid is palmitic acid;
(c) the DCA is n-methylhexadecanoic acid or n-hexadecanedioic acid; and
(d) the DCA-CoA is n-hexadecanedioic acid-CoA or n-methylhexadecanedioic acid-CoA.

In one aspect of the recombinant host cell disclosed herein, the (S)-2-methylbutyric acid has an optical purity of at least 80% ee.

In one aspect of the recombinant host cell disclosed herein:
(a) the polypeptide capable of synthesizing 3-methyl-2-oxopentanoate from L-isoleucine comprises a polypeptide having at least 90% sequence identity to any one of the amino acid sequences of SEQ ID NOs:34 or 35;
(b) the polypeptide capable of synthesizing (S)-2-methylbutanal from 3-methyl-2-oxopentanoate comprises a polypeptide having at least 90% sequence identity to any one of the amino acid sequences of SEQ ID NO:36;
(c) the polypeptide capable of synthesizing (S)-2-methylbutyric acid from (S)-2-methylbutanal comprises a polypeptide having at least 90% sequence identity to any one of the amino acid sequences of SEQ ID NOs:37 or 38;
(d) the polypeptide capable of synthesizing (S)-2-methylbutyryl-CoA from (S)-2-methylbutyric acid comprises a polypeptide having at least 65% sequence identity to any one of the amino acid sequences of SEQ ID NOs:23 or 24;
(e) the polypeptide capable of synthesizing the anteiso fatty acid from (S)-2-methylbutyryl-CoA comprises a polypeptide having at least 60% sequence identity to any one of the amino acid sequences of SEQ ID NOs:25, 26, 27, 28, 29, 30, 31, or 32;
(f) the polypeptide capable of synthesizing the DCA from the anteiso fatty acid or from the iso fatty acid comprises a polypeptide having at least 60% sequence identity to any one of the amino acid sequences of SEQ ID NOs: 21, 22, 41, 42, 43, 44, 45, or 46;
(g) the polypeptide capable of synthesizing the DCA-CoA from the DCA comprises a polypeptide having at least 85% sequence identity to the amino acid sequence of SEQ ID NO:33;
(h) the polypeptide capable of synthesizing muscone from the DCA-CoA; and
(i) the polypeptide capable of synthesizing the muscone from the DCA.

In one aspect of the recombinant host cell disclosed herein, the one or more macrocyclic ketone precursor is 12-methyltetradecanoic acid, (S)-12-methyltetradecanoic acid, 14-methylhexadecanoic acid, (S)-14-methylhexadecanoate, 16-methyloctadecanoic acid, (S)-16-methyloctadecanoic acid, dodecanedioic acid (dodecane-1,12-dioic acid), (E)-2-dodecenedioic acid, n-dodecenedioic acid, 3-dodecenedioic acid (double bond undefined), tetradecanedioic acid (tetradecane-1,14-dioic acid), 5-tetradecenedioic acid, (5Z)-, n-tetradecanedioic acid, hexadecanedioic acid (hexadecane-1,16-dioic acid), 7-hexadecenedioic acid, (7Z)-n-hexadecenedioic acid, octadecanedioic acid (octadecane-1,18-dioic acid), 9-octadecenedioic acid, (9Z)-, n-octadecenedioic acid, eicosanedioic acid, eicosanoic acid, 9-eicosenedioic acid, (9Z)-, hexadecanedioyl-coenzyme A, cis-9-hexadecenedioyl-CoA, ocadecanedioyl-coenzyme A, cis-9-octadecenedioyl-CoA, hexadecenedioic acid-CoA, n-hexadecenedioic acid-CoA, octadecanedioic acid-CoA, (S)-2-methylbutanoyl-CoA, (R)-3-methyldodecane-1,12-dioic acid, (R)-3-methyldodecane-1,12-dioyl-CoA, (R)-10-methyldodecane-1,12-dioyl-CoA, (R)-3-methyltetradecane-1,14-dioic acid, (R)-(+)-3-methylhexadecanoic acid, (R)-3-methyltetradecane-1,14-dioyl-CoA, (R)-12-methyltetradecane-1,14-dioyl-CoA, (R)-3-methylhexadecane-1,16-dioic acid, (R)-3-methylhexadecane-1,16-dioyl-CoA, (R)-14-methyldexadecane-1,16-dioyl-CoA, (R)-3-methyloctadecane-1,18-dioyl-CoA, (R)-16-methyloctadecane-1,18-dioyl-CoA, (S)-2-methylbutyryl CoA, 3-methylhexadecandioic acid, 3-methylhexadecanedioic acid-CoA, or n-octadecenedioic acid-CoA.

In one aspect of the recombinant host cell disclosed herein, the one or more macrocyclic ketone is l-muscone, nor-muscone, or civetone.

In one aspect of the recombinant host cell disclosed herein, the recombinant host cell is a plant cell, a mammalian cell, an insect cell, a fungal cell, an algal cell, an archaeal cell, or a bacterial cell.

The invention also provides a method of producing a one or more macrocyclic ketone precursors and/or a one or more macrocyclic ketones a dicarboxylic acid (DCA), a CoA activated DCA (DCA-CoA), an anteiso fatty acid, or a combination thereof in a cell culture, comprising culturing the recombinant host cell disclosed herein in the cell culture, under conditions in which the genes are expressed; wherein the one or more macrocyclic ketone precursors and/or the one or more macrocyclic ketones, the DCA, the DCA-CoA, the anteiso fatty acid, or the combination thereof is produced by the recombinant host cell.

In one aspect of the methods disclosed herein, the genes are constitutively expressed and/or expression of the genes is induced.

In one aspect of the methods disclosed herein, the recombinant host cell is grown in a fermentor at a temperature for a period of time, wherein the temperature and period of time facilitate the production of the one or more macrocyclic ketone precursors and/or the one or more macrocyclic ketones thereof, the DCA, the DCA-CoA, the anteiso fatty acid, or the combination thereof.

The invention also provides a method of producing a one or more macrocyclic ketone precursors and/or a one or more macrocyclic ketones, a dicarboxylic acid (DCA), a CoA activated DCA (DCA-CoA), an anteiso fatty acid, or a combination thereof, comprising whole cell bioconversion of a plant-derived or synthetic L-isoleucine, (S)-2-methylbutyric acid, 3-methyl-2-oxopentanoate, (S)-2-methylbutanal, (S)-2-methylbutyric acid, (S)-2-methylbutyryl-CoA, an anteiso fatty acid, an iso fatty acid, a DCA, or a DCA-CoA in a cell culture of a recombinant host cell disclosed herein using:
  (a) a polypeptide capable of synthesizing 3-methyl-2-oxopentanoate from L-isoleucine, comprising a polypeptide having at least 90% sequence identity to any one of the amino acid sequences of SEQ ID NOs:34 or 35;
  (b) a polypeptide capable of synthesizing (S)-2-methylbutanal from 3-methyl-2-oxopentanoate, comprising a polypeptide having at least 90% sequence identity to any one of the amino acid sequences of SEQ ID NO:36;
  (c) a polypeptide capable of synthesizing (S)-2-methylbutyric acid from (S)-2-methylbutanal, comprising a polypeptide having at least 95% sequence identity to any one of the amino acid sequences of SEQ ID NO:37 or 38;
  (d) a polypeptide capable of synthesizing (S)-2-methylbutyryl-CoA from (S)-2-methylbutyric acid, comprising a polypeptide having at least 65% sequence identity to any one of the amino acid sequences of SEQ ID NOs:23 or 24;
  (e) a polypeptide capable of synthesizing the anteiso fatty acid from (S)-2-methylbutyryl-CoA, comprising a polypeptide having at least 60% sequence identity to any one of the amino acid sequence of SEQ ID NOs:25, 26, 27, 28, 29, 30, 31, or 32;
  (f) a polypeptide capable of synthesizing the DCA from the anteiso fatty acid or from the iso fatty acid, comprising a polypeptide having at least 60% sequence identity to any one of the amino acid sequences of SEQ ID NOs: 21, 22, 41, 42, 43, 44, 45, or 46;
  (g) a polypeptide capable of synthesizing the DCA-CoA from the DCA, comprising a polypeptide having at least 85% sequence identity to the amino acid sequence of SEQ ID NO:33; and
  (h) the polypeptide capable of synthesizing the muscone from the DCA; wherein at least one of the polypeptides is a recombinant polypeptide.

In one aspect of the methods disclosed herein, the one or more macrocyclic ketone precursors and/or the one or more macrocyclic ketones, the DCA, the DCA-CoA, the anteiso fatty acid, or the combination thereof is produced in a permeabilized recombinant host cell that has been transformed with:
  (a) a gene encoding the polypeptide capable of synthesizing 3-methyl-2-oxopentanoate from L-isoleucine;
    wherein the polypeptide comprises a polypeptide having at least 90% sequence identity to any one of the amino acid sequences of SEQ ID NOs:34 or 35;
  (b) a gene encoding the polypeptide capable of synthesizing (S)-2-methylbutanal from 3-methyl-2-oxopentanoate;
    wherein the polypeptide comprises a polypeptide having at least 90% sequence identity to the amino acid sequence of SEQ ID NO:36;
  (c) a gene encoding the polypeptide capable of synthesizing 2-methylbutyric acid from (S)-2-methylbutanal;
    wherein the polypeptide comprises a polypeptide having at least 95% sequence identity to any one of the amino acid sequences of SEQ ID NOs:37 or 38;
  (d) a gene encoding the polypeptide capable of synthesizing (S)-2-methylbutyryl-CoA from (S)-2-methylbutyric acid;
    wherein the polypeptide comprises a polypeptide having at least 65% sequence identity to any one of the amino acid sequences of SEQ ID NOs:23 or 24;
  (e) a gene encoding the polypeptide capable of synthesizing the anteiso fatty acid from (S)-2-methylbutyryl-CoA;
    wherein the polypeptide comprises a polypeptide having at least 60% sequence identity to any one of the amino acid sequences of SEQ ID NOs:25, 26, 27, 28, 29, 30, 31, or 32;
  (f) a gene encoding the polypeptide capable of synthesizing the DCA from the anteiso fatty acid or from the iso fatty acid;
    wherein the polypeptide comprises a polypeptide having at least 60% sequence identity to any one of the amino acid sequences of SEQ ID NOs: 21, 22, 41, 42, 43, 44, 45, or 46;
  (g) a gene encoding the polypeptide capable of synthesizing the DCA-CoA from the DCA;
    wherein the polypeptide comprises a polypeptide having at least 85% sequence identity to the amino acid sequence of SEQ ID NO:33;
  (h) a gene encoding the polypeptide capable of synthesizing the muscone from the DCA-CoA; and/or
  (i) a gene encoding the polypeptide capable of synthesizing the muscone from the DCA.

In one aspect of the methods disclosed herein, the cell culture comprises:
  (a) the macrocyclic ketone, the one or more macrocyclic ketone precursors thereof, the DCA, the DCA-CoA, the anteiso fatty acid, or the combination thereof produced by the recombinant host cell disclosed herein or whole cell bioconversion of the plant-derived or synthetic L-isoleucine, (S)-2-methylbutyric acid, 3-methyl-2-oxopentanoate, (S)-2-methylbutanal, (S)-2-methylbutyric acid, (S)-2-methylbutyryl-CoA, an anteiso fatty acid, an iso fatty acid, a DCA, or a DCA-CoA; and
  (b) supplemental nutrients comprising trace metals, vitamins, salts, yeast nitrogen base (YNB), and/or amino acids.

In one aspect of the methods disclosed herein, the (S)-2-methylbutyric acid has an optical purity of at least 80% ee.

In one aspect, the methods disclosed herein further comprise isolating the one or more macrocyclic ketone precursors and/or the one or more macrocyclic ketones thereof, the DCA, the DCA-CoA, the anteiso fatty acid, or a combination thereof.

In one aspect of the methods disclosed herein, the isolating step comprises separating a liquid phase of the cell culture from a solid phase of the cell culture to obtain a supernatant comprising the produced macrocyclic ketone, the one or more macrocyclic ketone precursors, the DCA, the DCA-CoA, or the anteiso fatty acid, and:
 (a) contacting the supernatant with one or more adsorbent resins in order to obtain at least a portion of the produced macrocyclic ketone, the one or more macrocyclic ketone precursors, the DCA, the DCA-CoA, or the anteiso fatty acid; or
 (b) contacting the supernatant with one or more ion exchange or reverse-phase chromatography columns in order to obtain at least a portion of the produced macrocyclic ketone, the one or more macrocyclic ketone precursors, the DCA, the DCA-CoA, or the anteiso fatty acid; or
 (c) crystallizing or extracting the produced macrocyclic ketone, the one or more macrocyclic ketone precursors, the DCA, the DCA-CoA, or the anteiso fatty acid;
thereby isolating the produced macrocyclic ketone, the one or more macrocyclic ketone precursors, the DCA, the DCA-CoA, or the anteiso fatty acid.

In one aspect, the methods disclosed herein further comprise recovering the macrocyclic ketone, the one or more macrocyclic precursors thereof, the DCA, the DCA-CoA, the anteiso fatty acid alone, or a composition thereof from the cell culture.

The invention further provides an in vitro method for producing a one or more macrocyclic ketone precursors and/or a one or more macrocyclic ketones a dicarboxylic acid (DCA), a CoA activated DCA (DCA-CoA), an anteiso fatty acid, or a combination thereof, comprising adding:
 (a) a polypeptide capable of synthesizing 3-methyl-2-oxopentanoate from L-isoleucine and having at least 90% sequence identity to any one of the amino acid sequences of SEQ ID NOs:34 or 35;
 (b) a polypeptide capable of synthesizing (S)-2-methylbutanal from 3-methyl oxopentanoate and having at least 90% sequence identity to the amino acid sequence of SEQ ID NO:36;
 (c) a polypeptide capable of synthesizing 2-methylbutyric acid from (S)-2-methylbutanal and having at least 95% sequence identity to any one of the amino acid sequences of SEQ ID NOs:37 or 38;
 (d) a polypeptide capable of synthesizing (S)-2-methylbutyryl-CoA from (S)-2-methylbutyric acid and having at least 65% sequence identity to any one of the amino acid sequences of SEQ ID NOs:23 or 24;
 (e) a polypeptide capable of synthesizing the anteiso fatty acid from (S)-2-methylbutyryl-CoA and having at least 60% sequence identity to any one of the amino acid sequences of SEQ ID NOs:25, 26, 27, 28, 29, 30, 31, or 32;
 (f) a polypeptide capable of synthesizing the DCA from the anteiso fatty acid or from the iso fatty acid and having at least 60% sequence identity to any one of the amino acid sequences of SEQ ID NOs: 21, 22, 41, 42, 43, 44, 45, or 46;
 (g) a polypeptide capable of synthesizing the DCA-CoA from the DCA and having at least 85% sequence identity to the amino acid sequence of SEQ ID NO:33;
 (h) a polypeptide capable of synthesizing the muscone from the CoA activated DCA; and/or
 (i) a polypeptide capable of synthesizing the muscone from DCA;
and a plant-derived or synthetic L-isoleucine, (S)-2-methylbutyric acid, 3-methyl-2-oxopentanoate, (S)-2-methylbutanal, (S)-2-methylbutyric acid, (S)-2-methylbutyryl-CoA, an anteiso fatty acid, an iso fatty acid, a DCA or a DCA-CoA to a reaction mixture;
wherein at least one of the polypeptides is a recombinant polypeptide; and synthesizing the one or more macrocyclic ketone precursors and/or the one or more macrocyclic ketones, the DCA, the DCA-CoA, the anteiso fatty acid, or the combination thereof.

In one aspect of the methods disclosed herein, the reaction mixture comprises:
 (a) the polypeptide capable of synthesizing the DCA from the anteiso fatty acid or from the iso fatty acid and having at least 60% sequence identity to any one of the amino acid sequences of SEQ ID NOs: 21, 22, 41, 42, 43, 44, 45, and 46; and
 (b) the polypeptide capable of synthesizing the DCA-CoA from the DCA and having at least 85% sequence identity to the amino acid sequence of SEQ ID NO:33; and
wherein at least one of the polypeptides is a recombinant polypeptide; and synthesizing the one or more macrocyclic ketone precursors and/or the one or more macrocyclic ketones, the DCA, the DCA-CoA, the anteiso fatty acid, or the combination thereof.

In one aspect of the methods disclosed herein, the one or more macrocyclic ketone is I-muscone, nor-muscone, or civetone.

In one aspect of the methods disclosed herein:
 (a) the one or more precursors include 12-methyltetradecanoic acid, (S)-12-methyltetradecanoic acid, 14-methylhexadecanoic acid, (S)-14-methylhexadecanoate, 16-methyloctadecanoic acid, (S)-16-methyloctadecanoic acid, dodecanedioic acid (dodecane-1,12-dioic acid), (E)-2-dodecenedioic acid, n-dodecenedioic acid, 3-dodecenedioic acid (double bond undefined), tetradecanedioic acid (tetradecane-1,14-dioic acid), 5-tetradecenedioic acid, (5Z)- , n-tetradecanedioic acid, hexadecanedioic acid (hexadecane-1,16-dioic acid), 7-hexadecenedioic acid, (7Z)-n-hexadecenedioic acid, octadecanedioic acid (octadecane-1,18-dioic acid), 9-octadecenedioic acid, (9Z)-, n-octadecenedioic acid, eicosanedioic acid, eicosanoic acid, 9-eicosenedioic acid, (9Z)-, hexadecanedioyl-coenzyme A, cis-9-hexadecenedioyl-CoA, ocadecanedioyl-coenzyme A, cis-9-octadecenedioyl-CoA, hexadecanedioic acid-CoA, n-hexadecenedioic acid-CoA, octadecanedioic acid-CoA, n-methylhexadecanoic acid, n-methylhexadecanoic acid-CoA, (S)-2-methylbutanoyl-CoA, (R)-3-methyldodecane-1,12-dioic acid, (R)-3-methyldodecane-1,12-dioyl-CoA, (R)-10-methyldodecane-1,12-dioyl-CoA, (R)-+-3-methylhexadecanoic acid, (R)-3-methyltetradecane-1,14-dioic acid, (R)-3-methyltetradecane-1,14-dioyl-CoA, (R)-12-methyltetradecane-1,14-dioyl-CoA, (R)-3-methylhexadecane-1,16-dioic acid, (R)-3-methylhexadecane-1,16-dioyl-CoA, (R)-14-methyldexadecane-1,16-dioyl-CoA, (R)-3-methyloctadecane-1,18-dioyl-CoA, (R)-16-methyloctadecane-1,18-dioyl-CoA, (S)-2-methylbutyryl CoA, 3-methylhexadecandioic acid, 3-methylhexadecanedioic acid-CoA, or n-octadecenedioic acid-CoA;

(b) the anteiso fatty acid is 12-methyltetradecanoic acid, 14-methylhexadecanoic acid, or 16-methyloctadecanoic acid;
(c) the iso fatty acid is palmitic acid;
(d) the DCA is dodecandioic acid, n-dodecandioic acid, tetradecanedioic acid, n-tetradecanedioic acid, hexadecanedioic acid, n-methylhexadecanoic acid, n-hexadecanedioic acid, octadecanedioic acid, n-octadecanedioic acid, or eicosanoic acid; and
(e) the DCA-CoA is hexadecanedioic acid-CoA, n-methylhexadecanedioic acid-CoA n-hexadecanedioic acid-CoA, octadecanedioic acid-CoA, or n-octadecanedioic acid-CoA.

In one aspect of the methods disclosed herein:
(a) the anteiso fatty acid is 12-methyltetradecanoic acid, 14-methylhexadecanoic acid, or 16-methyloctadecanoic acid;
(b) the iso fatty acid is palmitic acid;
(c) the DCA is n-methylhexadecanoic acid or n-hexadecanedioic acid; and
(d) the DCA-CoA is n-methylhexadecanoic acid-CoA or n-hexadecanedioic acid-CoA.

In one aspect of the methods disclosed herein, the recombinant host cell or the whole cell comprises a plant cell, a mammalian cell, an insect cell, a fungal cell, an algal cell, an archaeal cell, or a bacterial cell.

The invention also provides a cell culture, comprising the recombinant host cell disclosed herein, the cell culture further comprising:
(a) the one or more macrocyclic ketone precursors and/or the one or more macrocyclic ketones, the DCA, the DCA-CoA, the anteiso fatty acid, or the combination thereof produced by the recombinant host cell; and
(b) supplemental nutrients comprising trace metals, vitamins, salts, yeast nitrogen base (YNB), and/or amino acids;
wherein the one or more macrocyclic ketone precursors and/or one or more macrocyclic ketones, the DCA, the DCA-CoA, the anteiso fatty acid, or the combination thereof are present at a concentration of at least 1 mg/liter of the cell culture.

The invention also provides a cell culture lysate from the recombinant host cell disclosed herein, grown in the cell culture, comprising:
(a) the one or more macrocyclic ketone precursors and/or the one or more macrocyclic ketones, the DCA, the DCA-CoA, the anteiso fatty acid, or the combination thereof produced by the recombinant host cell; and
(b) supplemental nutrients comprising trace metals, vitamins, salts, yeast nitrogen base (YNB), and/or amino acids;
wherein the one or more macrocyclic ketone precursors and/or the one or more macrocyclic ketones, the DCA, the DCA-CoA, the anteiso fatty acid, or the combination thereof are present at a concentration of at least 1 mg/liter of the cell culture.

The invention also provides a nucleic acid molecule encoding:
(a) a polypeptide capable of synthesizing 3-methyl-2-oxopentanoate from L-isoleucine and having at least 90% sequence identity to any one of the amino acid sequences of SEQ ID NOs:34 or 35;
(b) a polypeptide capable of synthesizing (S)-2-methylbutanal from 3-methyl-2-oxopentanoate and having at least 90% sequence identity to the amino acid sequence of SEQ ID NO:36;
(c) a polypeptide capable of synthesizing (S)-2-methylbutyric acid from (S)-2-methylbutanal and having at least 95% sequence identity to any one of the amino acid sequences of SEQ ID NOs:37 or 38;
(d) a polypeptide capable of synthesizing (S)-2-methylbutyryl-CoA from (S)-2-methylbutyric acid and having at least 65% sequence identity to the amino acid sequence of SEQ ID NOs:23 or 24;
(e) a polypeptide capable of synthesizing an anteiso fatty acid from (S)-2-methylbutyryl-CoA and having at least 60% sequence identity to any one of the amino acid sequences of SEQ ID NOs:25, 26, 27, 28, 29, 30, 31, or 32;
(f) a polypeptide capable of synthesizing a DCA from the anteiso fatty acid or from an iso fatty acid and having at least 60% sequence identity to any one of the amino acid sequences of SEQ ID NOs: 21, 22, 41, 42, 43, 44, 45, or 46;
(g) a polypeptide capable of synthesizing a DCA-CoA from the DCA and having at least 85% sequence identity to the amino acid sequence of SEQ ID NO:33;
(h) a polypeptide capable of synthesizing a muscone from the DCA; and/or
(i) a polypeptide capable of synthesizing a muscone from the DCA-CoA.

In one aspect of the nucleic acid molecules disclosed herein, the nucleic acid molecule is cDNA.

The invention also provides a purified polypeptide or a catalytically active portion thereof capable of producing:
(a) 3-methyl-2-oxopentanoate from L-isoleucine and having at least 90% sequence identity to any one of the amino acid sequences of SEQ ID NOs:34 or 35;
(b) (S)-2-methylbutanal from 3-methyl-2-oxopentanoate and having at least 90% sequence identity to the amino acid sequence of SEQ ID NO:36;
(c) 2-methylbutyric acid from (S)-2-methylbutanal and having at least 95% sequence identity to any one of the amino acid sequences of SEQ ID NOs:37 or 38;
(d) (S)-2-methylbutyryl-CoA from (S)-2-methylbutyric acid and having at least 65% sequence identity to any one of the amino acid sequences of SEQ ID NOs:23 or 24;
(e) an anteiso fatty acid from (S)-2-methylbutyryl-CoA and having at least 60% sequence identity to any one of the amino acid sequences of SEQ ID NOs:25, 26, 27, 28, 29, 30, 31, or 32;
(f) a DCA from the anteiso fatty acid or from the iso fatty acid and having at least 60% sequence identity to any one of the amino acid sequences of SEQ ID NOs:21, 22, 41, 42, 43, 44, 45, and 46;
(g) a DCA-CoA from the DCA and having at least 85% sequence identity to the amino acid sequence of SEQ ID NO:33;
(h) a muscone from the DCA-CoAA; and/or
(i) the muscone from the DCA.

The invention also provides a composition comprising the macrocyclic ketone, the one or more macrocyclic ketone precursors, the DCA, the DCA-CoA, the anteiso fatty acid, or the combination thereof produced by the recombinant host cell or the method disclosed herein.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which:

FIGS. 1A-1K shows biosynthetic pathways for production of I-muscone (FIG. 1A), production of nor-muscone (FIG. 1B), and molecular structure of muscone intermediates (FIGS. 1C-1K).

Figure 1A:
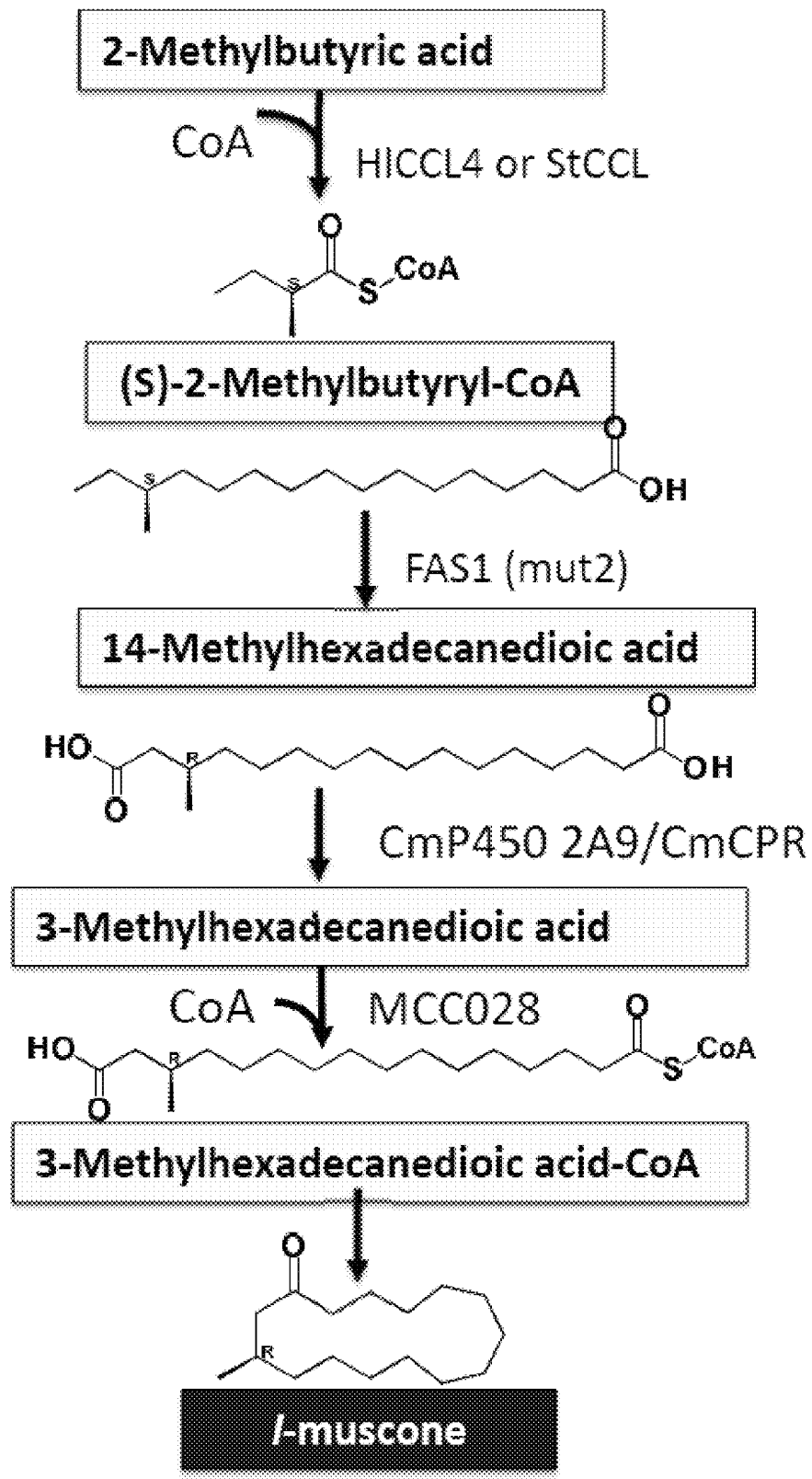

Skilled artisans will appreciate that elements in the Figures are illustrated for simplicity and clarity and have not necessarily been drawn to scale. For example, the dimensions of some of the elements in the Figures can be exaggerated relative to other elements to help improve understanding of the embodiment(s) of the present invention.

DETAILED DESCRIPTION OF THE INVENTION

All publications, patents and patent applications cited herein are hereby expressly incorporated by reference for all purposes.

Before describing the present invention in detail, a number of terms will be defined. As used herein, the singular forms "a," "an," and "the" include plural referents unless the context clearly dictates otherwise. For example, reference to a "nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Green & Sambrook, 2012, MOLECULAR CLONING: A LABORATORY MANUAL, Fourth Edition, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

As used herein, the terms "polynucleotide", "nucleotide", "oligonucleotide", and "nucleic acid" can be used interchangeably to refer to nucleic acid comprising DNA, RNA, derivatives thereof, or combinations thereof, in either single-stranded or double-stranded embodiments depending on context as understood by the skilled worker.

As used herein, the terms "microorganism," "microorganism host," "microorganism host cell," "recombinant host," and "recombinant host cell" can be used interchangeably. As used herein, the term "recombinant host" is intended to refer to a host, the genome of which has been augmented by at least one DNA sequence. Such DNA sequences include but are not limited to genes that are not naturally present, DNA sequences that are not normally transcribed into RNA or translated into a protein ("expressed"), and other genes or DNA sequences which one desires to introduce into a host. It will be appreciated that typically the genome of a recombinant host described herein is augmented through stable introduction of one or more recombinant genes. Generally, introduced DNA is not originally resident in the host that is the recipient of the DNA, but it is within the scope of this disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms.

As used herein, the term "cell culture" refers to a culture medium comprising one or more recombinant hosts. A cell culture can comprise a single strain of recombinant host, or can comprise two or more distinct host strains. The culture medium can be any medium that can comprise a recombinant host, e.g., a liquid medium (i.e., a culture broth) or a semi-solid medium, and can comprise additional components, e.g., N-acetyl-glucosamine, glucose, fructose, sucrose, trace metals, vitamins, salts, yeast nitrogen base (YNB), etc.

As used herein, the term "recombinant gene" refers to a gene or DNA sequence that is introduced into a recipient host, regardless of whether the same or a similar gene or DNA sequence can already be present in such a host. "Introduced," or "augmented" in this context, is known in the art to mean introduced or augmented by the hand of man. Thus, a recombinant gene can be a DNA sequence from another species or can be a DNA sequence that originated from or is present in the same species but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA. In some aspects, said recombinant genes are encoded by cDNA. In other embodiments, recombinant genes are synthetic and/or codon-optimized for expression in *S. cerevisiae*.

As used herein, the term "engineered biosynthetic pathway" refers to a biosynthetic pathway that occurs in a recombinant host, as described herein. In some aspects, one or more steps of the biosynthetic pathway do not naturally occur in an unmodified host. In some embodiments, a heterologous version of a gene is introduced into a host that comprises an endogenous version of the gene.

As used herein, the term "endogenous" gene refers to a gene that originates from and is produced or synthesized within a particular organism, tissue, or cell. In some embodiments, the endogenous gene is a yeast gene. In some embodiments, the gene is endogenous to *S. cerevisiae*, including, but not limited to *S. cerevisiae* strain S288C. In some embodiments, an endogenous yeast gene is overexpressed. As used herein, the term "overexpress" is used to refer to the expression of a gene in an organism at levels higher than the level of gene expression in a wild type organism. See, e.g., Prelich, 2012, Genetics 190:841-54. In some embodiments, an endogenous yeast gene is deleted. See, e.g., Giaever & Nislow, 2014, Genetics 197(2):451-65. As used herein, the terms "deletion," "deleted," "knockout," and "knocked out" can be used interchangeably to refer to an endogenous gene that has been manipulated to no longer be expressed in an organism, including, but not limited to, *S. cerevisiae*.

As used herein, the terms "heterologous sequence" and "heterologous coding sequence" are used to describe a sequence derived from a species other than the recombinant host cell. In some embodiments, the recombinant host cell is an *S. cerevisiae* cell, and a heterologous sequence is derived from an organism other than *S. cerevisiae*. A heterologous coding sequence, for example, can be from a prokaryotic microorganism, a eukaryotic microorganism, a plant, an animal, an insect, or a fungus different than the recombinant host cell expressing the heterologous sequence. In some embodiments, a coding sequence is a sequence that is native to the host.

A "selectable marker" can be one of any number of genes that, inter alia, complement host cell auxotrophy, provide antibiotic resistance, or result in a color change. Linearized DNA fragments of the gene replacement vector are introduced into the cells using methods well known in the art (see below). Integration of linear fragments into the genome and disruption of the gene can be determined based on the selection marker and can be verified by, for example, PCR or Southern blot analysis. Subsequent to its use in selection, a selectable marker can be removed from the genome of the host cell by, e.g., Cre-LoxP systems (see, e.g., Gossen et al., 2002, Ann. Rev. Genetics 36:153-173 and U.S. 2006/0014264). Alternatively, a gene replacement vector can be constructed in such a way as to include a portion of the gene to be disrupted, where the portion is devoid of any endogenous gene promoter sequence and encodes none, or an inactive fragment of, the coding sequence of the gene.

As used herein, the terms "variant" and "mutant" are used to describe a protein sequence that has been modified at one or more amino acids, compared to the wild-type sequence of a particular protein. For example, fatty acid synthase (FAS) mutants, fas1 mut1, fas1 mut 2, fas1 mut 3, etc. are all variants of wildtype fas1.

As used herein, the term "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of a gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene with inactivation thereof.

As used herein, the term "macrocyclic ketone" refers to a ketone containing rings of 8 or more atoms synthesized from linear molecules. Non-limiting examples of macrocyclic ketones considered herein include nor-muscone(cyclopentadecanone or exaltone), L-muscone(cyclopentadecanone, 3-methyl-, (3R)-, or (R)-muscone), and civetone (also known as (Z)-9-Cycloheptadecen-1-one; cis-civetone; 9-Cycloheptadecen-1-one; Cycloheptadeca-9-en-1-one; (Z)-9-Cyclohepta-decen-1-one).

Also as used herein, the terms "macrocyclic ketone precursors" is used to refer to the production and/or presence of intermediate compounds in the macrocyclic ketone biosynthetic pathway for production of macrocylic ketones. In some embodiments the macrocyclic ketone precursors can be L-muscone precursors, nor-muscone precursors, civetone precursors, or a combination of these. Macrocyclic ketone precursors include, but are not limited to, 12-methyltetradecanoic acid, (S)-12-methyltetradecanoic acid, 14-methylhexadecanoic acid, (S)-14-methylhexadecanoate, 16-methyloctadecanoic acid, (S)-16-methyloctadecanoic acid, dodecanedioic acid (dodecane-1,12-dioic acid), (E)-2-dodecenedioic acid, n-dodecenedioic acid, 3-dodecenedioic acid (double bond undefined), tetradecanedioic acid (tetradecane-1,14-dioic acid), 5-tetradecenedioic acid, (5Z)-, n-tetradecanedioic acid, hexadecanedioic acid (hexadecane-1,16-dioic acid), 7-hexadecenedioic acid, (7Z)-n-hexadecenedioic acid, octadecanedioic acid (octadecane-1,18-dioic acid), 9-octadecenedioic acid, (9Z)-, n-octadecenedioic acid, eicosanedioic acid, eicosanoic acid, 9-eicosenedioic acid, (9Z)-, hexadecanedioyl-coenzyme A, cis-9-hexadecenedioyl-CoA, ocadecanedioyl-coenzyme A, cis-9-octadecenedioyl-CoA, hexadecanedioic acid-CoA, n-hexadecenedioic acid-CoA, octadecanedioic acid-CoA, (S)-2-methylbutanoyl-CoA, (R)-3-methyldodecane-1,12-dioic acid, (R)-3-methyldodecane-1,12-dioyl-CoA, (R)-10-methyldodecane-1,12-dioyl-CoA, (R)-3-methyltetradecane-1,14-dioic acid, (R)-3-methyltetradecane-1,14-dioyl-CoA, (R)-12-methyltetradecane-1,14-dioyl-CoA, (R)-3-methylhexadecane-1,16-dioic acid, (R)-3-methylhexadecane-1,16-dioyl-CoA, (R)-14-methyldexadecane-1,16-dioyl-CoA, (R)-3-methyloctadecane-1,18-dioyl-CoA, (R)-16-methyloctadecane-1,18-dioyl-CoA, (S)-2-methylbutyryl CoA, 3-methylhexdecandioic acid, 3-methylhexadecane-dioic acid-CoA, and n-octadecenedioic acid-CoA (FIGS. 1C-1K).

As used herein, the term "I-muscone precursor" refers to intermediates produced during the synthesis of I-muscone. For example, I-muscone precursors include, but are not limited to, (S)-2-methylbutyryl-CoA, 14-methylhexadecanoic acid, 3-methylhexadecanedioic acid, and 3-methylhexadecanedioic acid-CoA.

As used herein the term "nor-muscone precursor" refers to intermediates produced during the synthesis of nor-muscone. For example, nor-muscone precursors include, but are not limited to, hexadecanedioic acid and hexadecanedioic acid-CoA.

Macrocyclic ketone precursors can be produced in vivo (i.e., in a recombinant host), in vitro (i.e., enzymatically), or by whole cell bioconversion. As used herein, the terms "produce" and "accumulate" can be used interchangeably to describe synthesis of muscone and muscone precursors in vivo, in vitro, or by whole cell bioconversion.

As used herein, the term "long chain branched fatty acid" is used to refer to a fatty acid which has 12 or more carbon atoms in its tail. Monomethyl long chain branched fatty acids typically comprise a single methyl group on a backbone of 12 to 20 carbon atoms. Long chain branched fatty acids for example, include, but are not limited to, 14-methylhexadecanedioic acid and 3-methylhexadecanedioic acid-CoA.

As used herein, the term "short chain branched fatty acid" is used to refer to a fatty acid that has 5 or fewer carbon atoms. Short chain branched fatty acids for example, include, but are not limited to, (S)-2-methylbutyric acid and (S)-2-methylbutyric acid-CoA.

As used herein the term "monomethyl branched chain fatty acid" and "MMBCFA" are used to refer to fatty acid molecules with a single methyl group "branching" off one of the carbon atoms. MMBCFAs for example, include, but are not limited to, 12-methyltetradecanoic acid (C15 anteiso fatty acid), 14-methylhexadecanoic acid (C17 anteiso fatty acid), or 16-methyloctadecanoic acid (C19 anteiso fatty acid) (FIGS. 1B-1K).

Figure 1B:
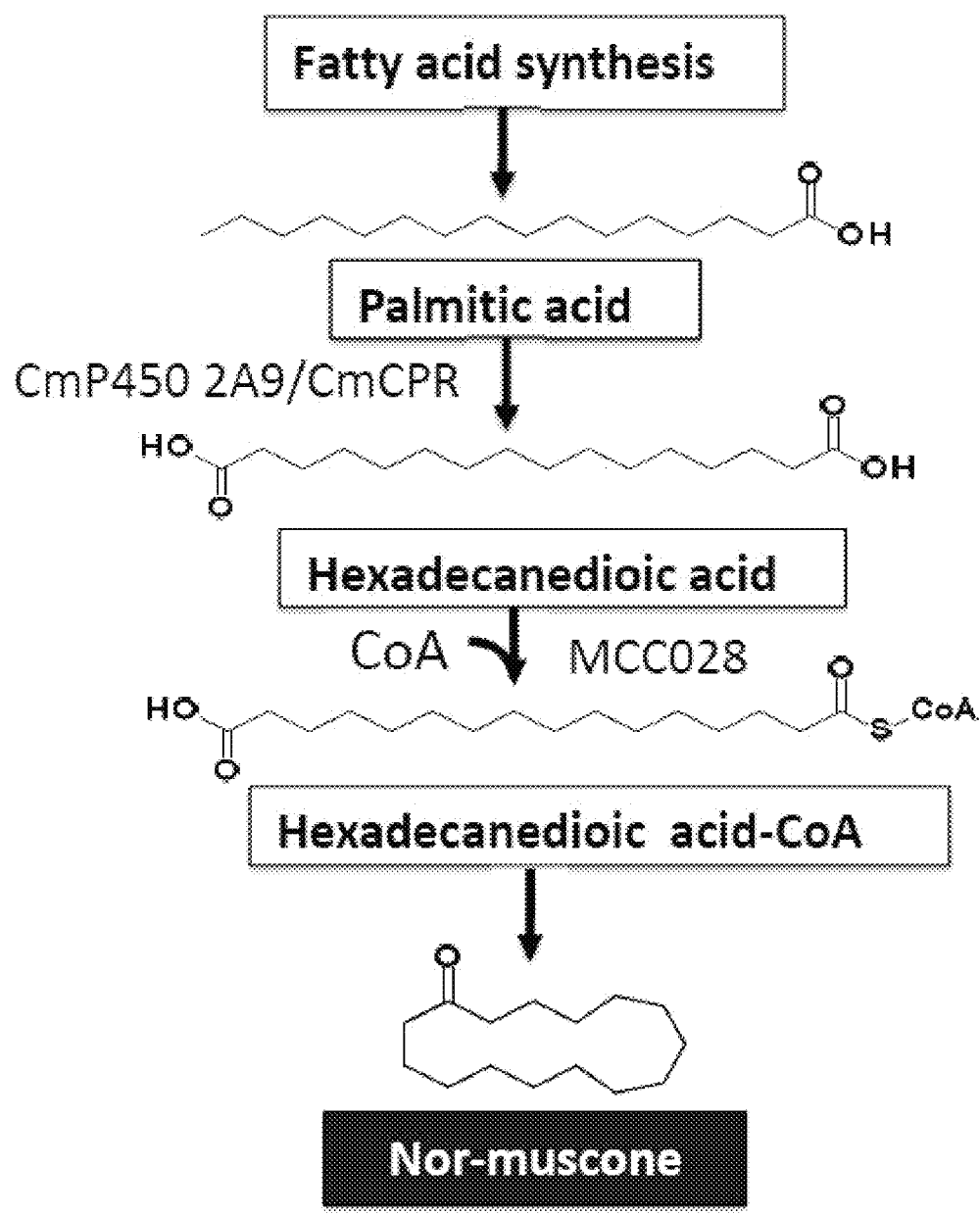
Figure 1F:
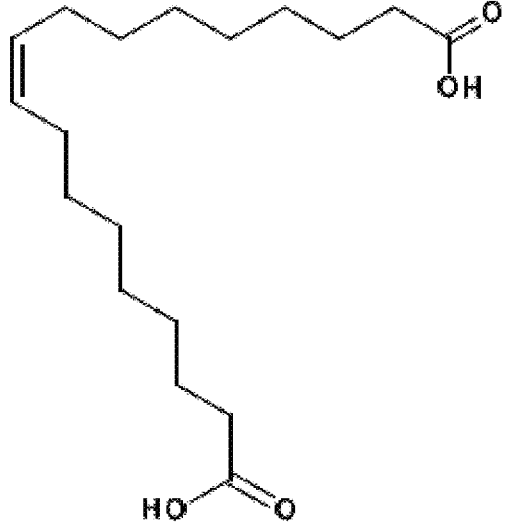
Figure 1F:
Figure 1F:
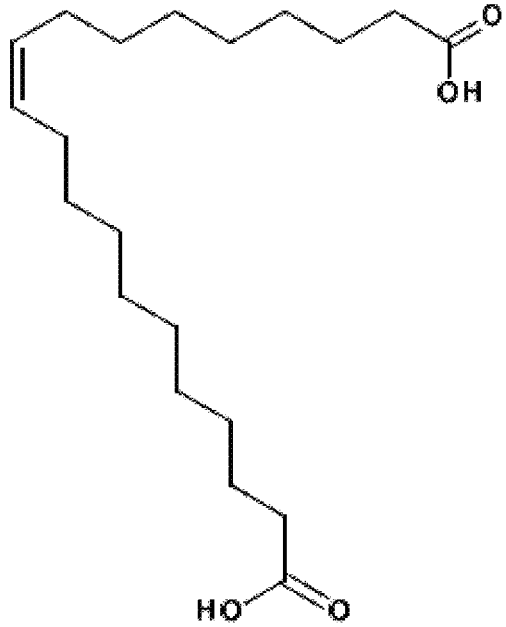
Figure 1G:
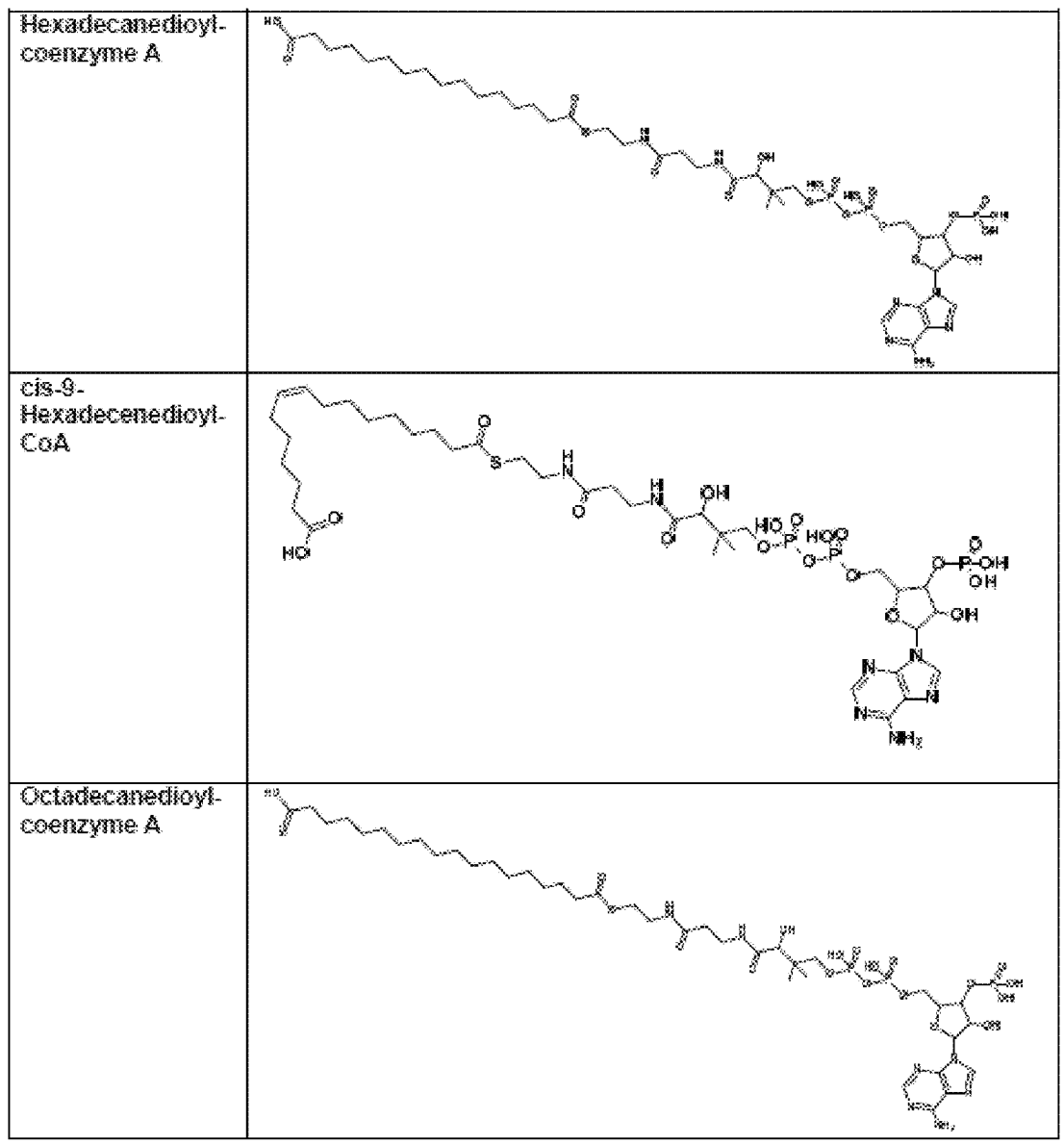
Figure 1H:
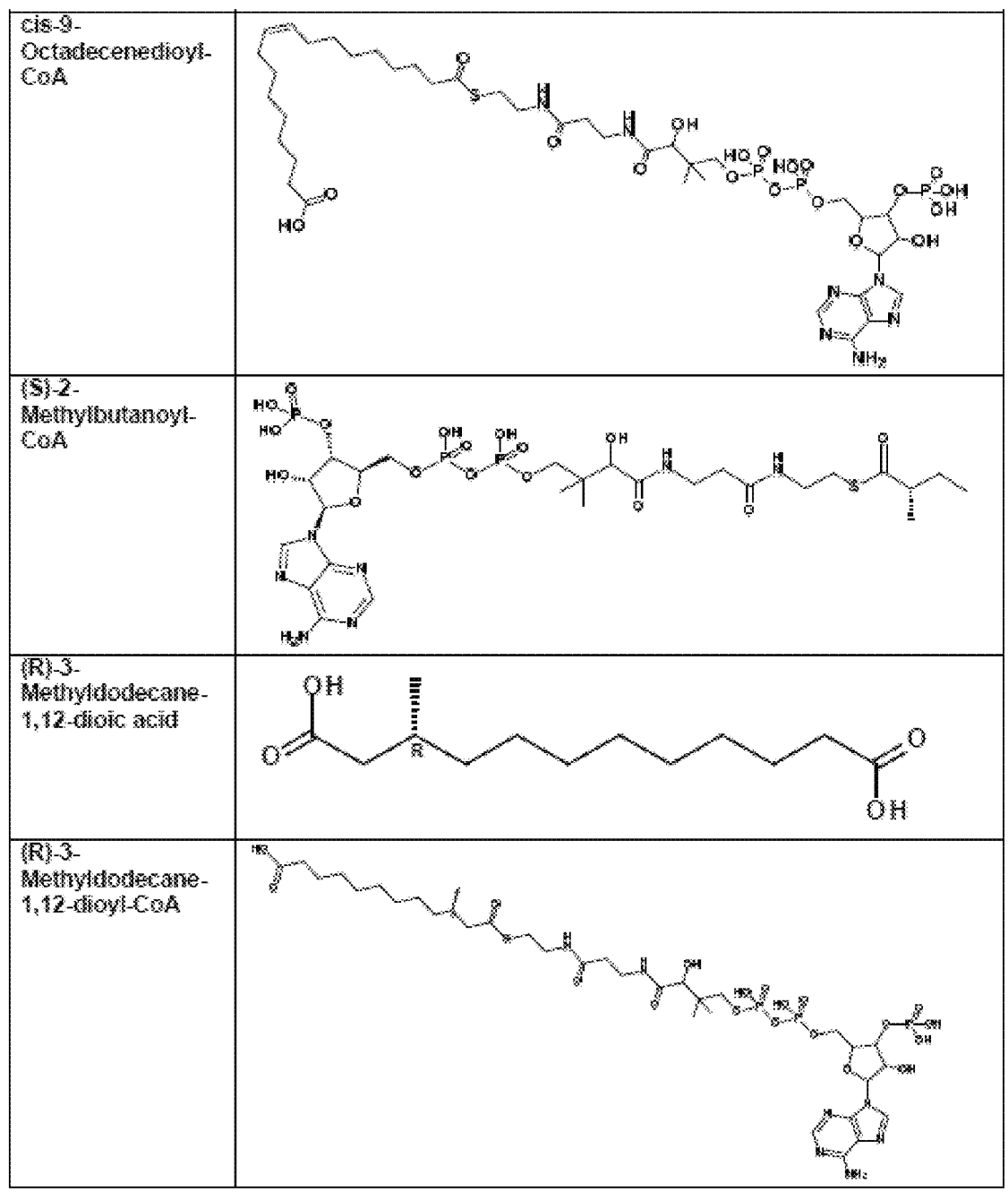
Figure 1I:
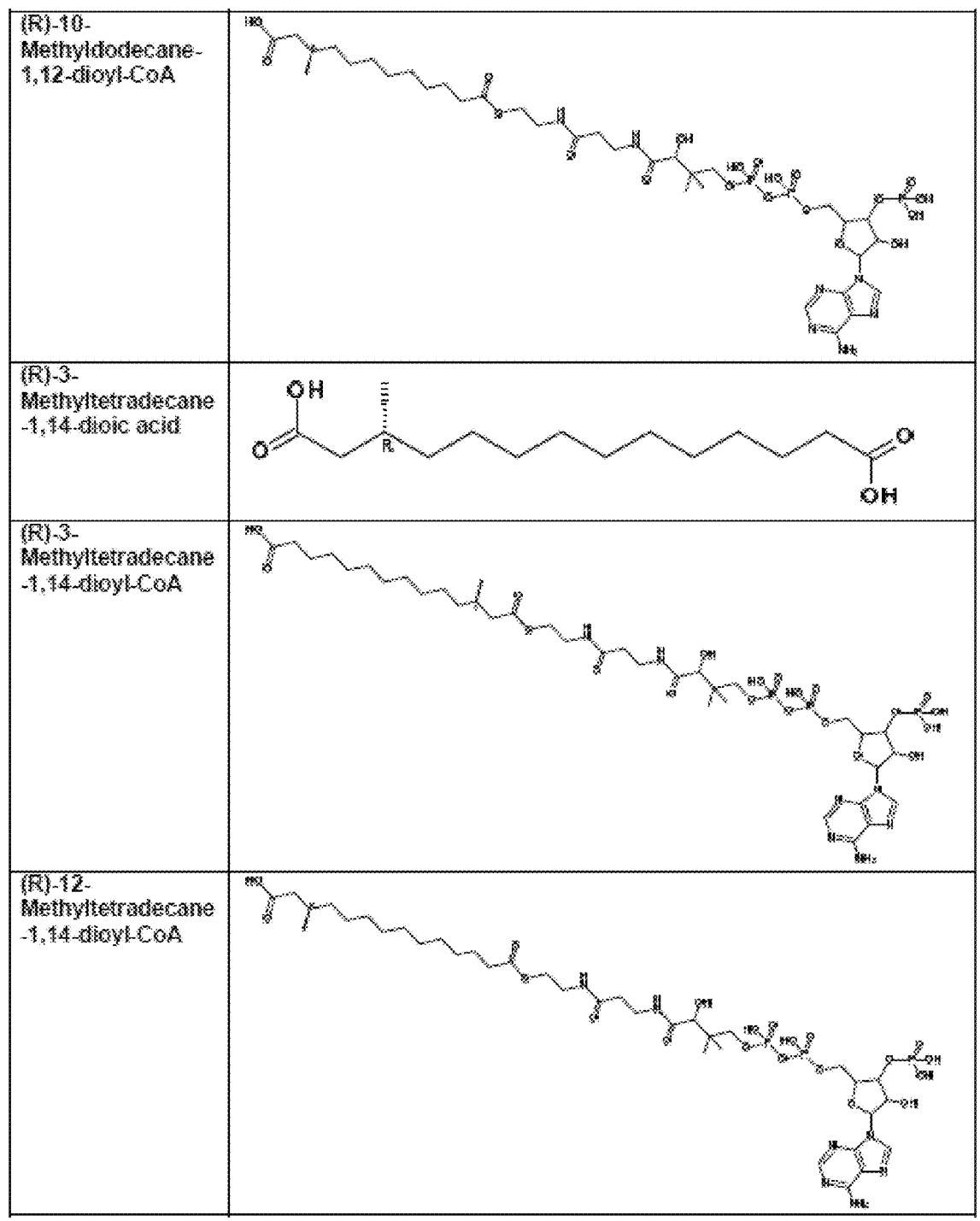
Figure 1K:
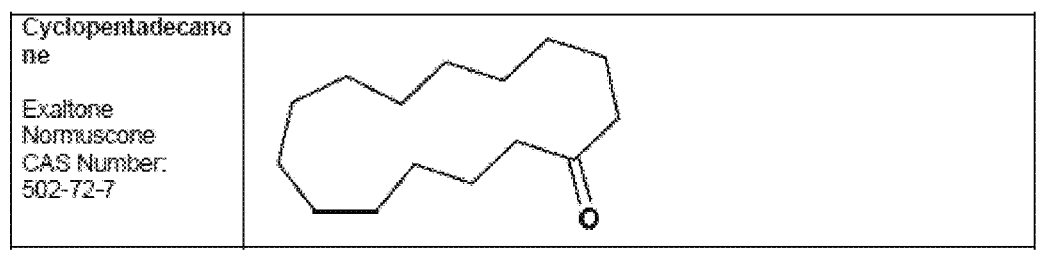

As used herein the term, "iso fatty acid" is used to refer to intermediate fatty acid compounds in the macrocyclic ketone biosynthesis pathway with a single methyl group "branching" off one of the carbon atom in the iso position. Iso fatty acids for example include, but is not limited to, palmitic acid (FIG. 1B).

As used herein, the term "anteiso fatty acid" is used to refer to intermediate fatty acid compounds in the macrocyclic ketone biosynthetic pathway. Anteiso fatty acids, for example include, but are not limited to, 12-methyltetradecanoic acid (C15 anteiso fatty acid), 14-methylhexadecanoic acid (C17 anteiso fatty acid), or 16-methyloctadecanoic acid (C19 anteiso fatty acid) (FIGS. 1C-1K).

As used herein the terms "enantiomer" or "enantiomers", refer to a chiral molecule or chiral molecules that are mirror images of one another. These molecules are non-superimposable on one another.

As used herein, the term "derivative" refers to a molecule or compound that is derived from a similar compound by some chemical or physical process.

As used herein, S- (or S-configuration) refers to a configuration of a molecule in which a curved arrow from the one position to the two position turns counterclockwise. Examples include, but are not limited to, (S)-2-methylbutyric acid and (S)-2-methylbutyric acid-CoA.

As used herein, R- (or R-configuration) refers to a configuration of a molecule in which a curved arrow from the one position to the two position turns clockwise. Examples include, but are not limited to, (R)-2-methylbutyric acid and (R)-2-methylbutyric acid-CoA.

As used herein, the term "enantiomeric excess (ee)" and "optical purity" can be used interchangeably and refer to a measure of purity used for chiral substances. For example, if the enantiomeric excess is 100% then only one enantiomer (either S- or R-) was produced. Additionally, if the pathway produces 90% S-2-methylbutyric acid and 10% (R)-2-methylbutyric acid then the enantiomeric excess of S-2-methylbutyric acid is 90%−10%=80% enantiomeric excess (ee), or has an optical purity of 80% ee.

As used herein, the term "Dieckmann condensation reaction" refers to the intracellular chemical reaction of diesters with base to give β-keto esters.

As used herein the term "straight chain fatty acid" is used to refer to intermediate fatty acid compounds, with no branches, in the macrocyclic ketone biosynthetic pathway. Straight chain fatty acids include, but are not limited to, palmitic acid (FIG. 1A).

As used herein, the term "Co-enzyme A (CoA) activation" is used to refer to the addition of a CoA to the end of a fatty acid. For example, when a dicarboxylic acid undergoes CoA activation it forms a dicarboxylic acid-CoA (DCA-CoA) molecule. CoA activated DCAs, for example include, but are not limited to, n-methylhexadecanedioic acid-CoA and n-hexadecanedioic acid-CoA.

As used herein, the term "acyl CoA ligase" or "CoA ligase" is used to refer to an enzyme of the ligase family that activates fatty acids with CoA. CoA ligases can be derived from, for example, hops (*Humulus lupulus*) (SEQ ID NOs:3; 23) or potatoes (*Solanum tuberosom*) (SEQ ID NOs:4; 24).

As used herein, the term "fatty acid synthase (FAS)" is used to refer to an enzyme that catalyzes fatty acid synthesis. Fatty acid synthases for example, include, but are not limited to, FAS1, FAS1 mut2, FAS1 mut3, FAS1 mut4, FAS1 mut5, FAS1 mut6, and FAS1 mut7.

As used herein, the terms "detectable amount," "detectable concentration," "measurable amount," and "measurable concentration" refer to a level of muscone and/or muscone precursors measured in AUC, $\mu M/OD_{600}$, mg/L, $\mu M$, or mM. Muscone and muscone precursor production (i.e., total, supernatant, and/or intracellular muscone and muscone precursor levels) can be detected and/or analyzed by techniques generally available to one skilled in the art, for example, but not limited to, liquid chromatography-mass spectrometry (LC-MS), gas chromatography-mass spectrometry (GC-MS), thin layer chromatography (TLC), high-performance liquid chromatography (HPLC), ultraviolet-visible spectroscopy/spectrophotometry (UV-Vis), mass spectrometry (MS), and nuclear magnetic resonance spectroscopy (NMR).

As used herein, the term "undetectable concentration" refers to a level of a compound that is too low to be measured and/or analyzed by techniques such as TLC, HPLC, UV-Vis, MS, or NMR. In some embodiments, a compound of an "undetectable concentration" is not present in muscone or muscone precursor composition.

As used herein, the terms "or" and "and/or" is utilized to describe multiple components in combination or exclusive of one another. For example, "x, y, and/or z" can refer to "x" alone, "y" alone, "z" alone, "x, y, and z," "(x and y) or z,"

"x or (y and z)," or "x or y or z." In some embodiments, "and/or" is used to refer to the exogenous nucleic acids that a recombinant cell comprises, wherein a recombinant cell comprises one or more exogenous nucleic acids selected from a group. In some embodiments, "and/or" is used to refer to production of macrocyclic ketones and/or macrocyclic ketone precursors, such as muscone and/or muscone precursors). In some embodiments, "and/or" is used to refer to production of macrocyclic ketones or macrocyclic ketone precursors (such as muscone or muscone precursors), wherein one or more macrocyclic ketones and/or macrocyclic ketone precursors are produced. In some embodiments, "and/or" is used to refer to production of macrocyclic ketones and/or macrocyclic ketone precursors (such as muscone and/or muscone precursors), wherein one or more macrocyclic ketones and/or macrocyclic ketone precursors are produced through the following steps: culturing a recombinant microorganism, synthesizing macrocyclic ketones and/or macrocyclic ketone precursors (such as muscone and/or muscone precursors) in a recombinant microorganism, and/or isolating one or more macrocyclic ketones and/or macrocyclic ketone precursors (such as muscone and/or muscone precursors).

In one embodiment, the recombinant host cell can include genes encoding several polypeptides that are capable of producing macrocyclic ketones and/or macrocyclic ketone precursors (such as muscone and muscone precursors). Muscone, as described herein, includes but is not limited to nor- and/or I-muscone.

In some embodiments, a recombinant host expressing a gene encoding a polypeptide capable of synthesizing (S)-2-methylbutyryl-CoA from (S)-2-methylbutyric acid; a gene encoding a polypeptide capable of synthesizing 14-methylhexadecanoic acid, or another anteiso fatty acid (see FIGS. 1C-1K), from (S)-2-methylbutyryl-CoA; genes encoding polypeptides capable of synthesizing 3-methylhexadecanedioic acid from 14-methylhexadecanoic acid; a gene encoding a polypeptide capable of synthesizing 3-methylhexadecanedioic acid-CoA from 3-methylhexadecanedioic acid; and a set of genes encoding polypeptides capable of synthesizing I-muscone from 3-methylhexadecanedioic acid-CoA can produce (S)-2-methylbutyryl-CoA, 14-methylhexadecanoic acid, or another monomethyl branched chain fatty acid (see FIGS. 1C-1K), 3-methylhexadecanedioic acid, 3-methylhexadecanedioic acid-CoA, and I-muscone in vivo.

In some aspects, the polypeptide capable of synthesizing (S)-2-methylbutyryl-CoA from (S)-2-methylbutyric acid comprises a polypeptide having an amino acid sequence set forth in SEQ ID NO:23 and SEQ ID NO:24; the polypeptide capable of synthesizing 14-methylhexadecanoic acid, or another anteiso fatty acid, from (S)-2-methylbutyryl-CoA comprises a polypeptide having an amino acid sequences sets forth in SEQ ID NO:25; SEQ ID NO:26; SEQ ID NO:27; SEQ ID NO:28; SEQ ID NO:29; SEQ ID NO:30; SEQ ID NO:31; SEQ ID NO:32; the polypeptides capable of synthesizing 3-methylhexadecanedioic acid from 14-methylhexadecanoic acid comprise polypeptides having an amino acid sequence set forth in SEQ ID NO:21 SEQ ID NO:22, SEQ ID NO:41, SEQ ID NO:42, SEQ ID NO:43, SEQ ID NO:44, SEQ ID NO:45, and SEQ ID NO:46; the polypeptide capable of synthesizing 3-methylhexadecanedioic acid-CoA from 3-methylhexadecanedioic acid comprises a polypeptide having an amino acid sequence set forth in SEQ ID NO:33; a gene encoding a polypeptide capable of synthesizing I-muscone from a DCA, for example, (R)-(+)-3-methylhexadecanoic acid. The skilled worker will appreciate that these genes can be endogenous to the host provided that at least one (and in some embodiments, all) of these genes is a recombinant gene introduced into the recombinant host cell.

In some embodiments, a recombinant host expressing a gene encoding a polypeptide capable of synthesizing hexadecanedioic acid, or another dicarboxylic acid (see FIGS. 1C-1K) from palmitic acid; a gene encoding a polypeptide capable of synthesizing hexadecanedioic acid-CoA, or another CoA activated dicarboxylic acid, from hexadecanedioic acid; and genes encoding polypeptides capable of synthesizing nor-muscone from hexadecanedioic acid-CoA. can produce hexadecanedioic acid, or another dicarboxylic acid (see FIGS. 1C-1K), hexadecanedioic acid-CoA, or another CoA activated dicarboxylic acid (see FIGS. 1C-1K), and nor-muscone in vivo.

In some aspects, the polypeptides capable of synthesizing hexadecanedioic acid, or another dicarboxylic acid (see FIGS. 1C-1K) from palmitic acid comprise polypeptide having the amino acid sequence set forth in SEQ ID NO:21 SEQ ID NO:22, SEQ ID NO:41, SEQ ID NO:42, SEQ ID NO:43, SEQ ID NO:44, SEQ ID NO:45, and SEQ ID NO:46; the polypeptide capable of synthesizing hexadecanedioic acid-CoA, or another CoA activated dicarboxylic acid, from hexadecanedioic acid comprises a polypeptide having the amino acid sequence set forth in SEQ ID NO:33; and a gene encoding a polypeptide capable of synthesizing nor-muscone from a dicarboxylic acid. The skilled worker will appreciate that these genes can be endogenous to the host provided that at least one (and in some embodiments, all) of these genes is a recombinant gene introduced into the recombinant host cell.

In some embodiments, the recombinant host cell that can produce macrocyclic ketones and/or macrocyclic ketone precursors (such as I- and/or nor-muscone) in vivo can express a peroxisomal acyl-CoA oxidase (POX1) gene, which encodes a polypeptide capable of producing acyl-coenzyme A oxidase. Acyl-coenzyme A oxidase is involved in fatty acid-beta oxidation, and can result in the oxidation of one or more muscone precursors. In one embodiment, the muscone-producing recombinant host can comprise a pox1Δ0 gene deletion. Reduction of the expression of acyl-coenzyme A oxidase in the muscone-producing recombinant host can act to reduce oxidation of muscone precursors in the I- and nor-muscone biosynthetic pathways.

Macrocyclic Ketone Biosynthetic Pathways

L-muscone Biosynthetic Pathway

In one embodiment, l-muscone and l-muscone precursor production can be achieved via the l-muscone biosynthetic pathway which includes the production of (S)-2-methylbutyryl acid-CoA which can then be used as a priming unit, or substrate for acyl-CoA ligase, to form a monomethyl branched chain fatty acid (MMBCFA) or an anteiso fatty acid molecule (see FIGS. 1A and 1C-1K). Oxidation of a MMBCFA, followed by CoA activation of a dicarboxylic acid, such as 3-methylhexadecanedioic acid, results in the production of a CoA activated dicarboxylic acid. l-muscone is subsequently produced via cyclisation and decarboxylation of a CoA activated dicarboxylic acid (see FIGS. 1A and 1C-1K).

In another embodiment, l-muscone and l-muscone precursor production can be achieved via the l-muscone biosynthetic pathway which includes the production of (S)-2-methylbutyryl acid-CoA which can then be used as a priming unit, or substrate for acyl-CoA ligase, to form a monomethyl branched chain fatty acid (MMBCFA) or an anteiso fatty acid molecule (see FIGS. 1A and 1C-1K). L-muscone is subsequently produced via a Dieckmann condensation reaction with a dicarboxylic acid acting as a substrate.

In one embodiment, the I-muscone-producing recombinant host produces a (S)-2-methylbutyryl-CoA for the downstream production of muscone intermediates. The recombinant host cell comprising the I-muscone biosynthetic pathway can comprise a gene encoding a polypeptide capable of synthesizing 3-methyl-2-oxopentanoate from L-isoleucine (e.g., transaminase (e.g., BAT1/BAT2)) (SEQ ID NOs:14 and 15; 34 and 35), a gene encoding a polypeptide capable of synthesizing (S)-2-methylbutanal from (S)-3-methyl-2-oxopentanaoate (e.g., transaminated amino acid decarboxylase (ARO10)) (SEQ ID NOs:16; 36); a gene encoding a polypeptide capable of synthesizing (S)-2-methylbutyric acid from (S)-2-methylbutanal (e.g., aldehyde dehydrogenase (ALD2/ALD5)) (SEQ ID NOs:17 and 18; 37 and 38); a gene encoding a polypeptide capable of synthesizing (S)-2-methylbutyryl-CoA from (S)-2-methylbutyric acid (e.g., CoA ligase) (SEQ ID NOs:3 and 4; 23 and 24). Production of (S)-2-methylbutyryl-CoA by the I-muscone-producing recombinant host can then act as a priming unit for the in vitro formation of mono-methyl branched chain fatty acids such as 14-methylhexadecanoic acid.

In one embodiment, the I-muscone-producing recombinant host can further comprise a gene encoding a polypeptide that can synthesize a monomethyl branched chain fatty acid (MMBCFA), such as 14-methylhexadecanoic acid, from 2-methylbutyryl-CoA (e.g., fatty acid synthase (FAS)) (SEQ ID NOs: 5, 6, 7, 8, 9, 10, 11, and 12; 25, 26, 27, 28, 29, 30, 31, and 32). Monomethyl branched chain fatty acids, or anteiso fatty acids, formed from this reaction can include, but are not limited to, 12-methyltetradecanoic acid, 14-methylhexadecanoic acid, and 16-methyloctadecanoic acid (see FIGS. 1C-1K). These anteiso fatty acids produced in vitro by the I-muscone-producing recombinant host can then be used to produce additional downstream I-muscone pathway intermediates (see FIG. 9 and Table 2).

Figure 9:
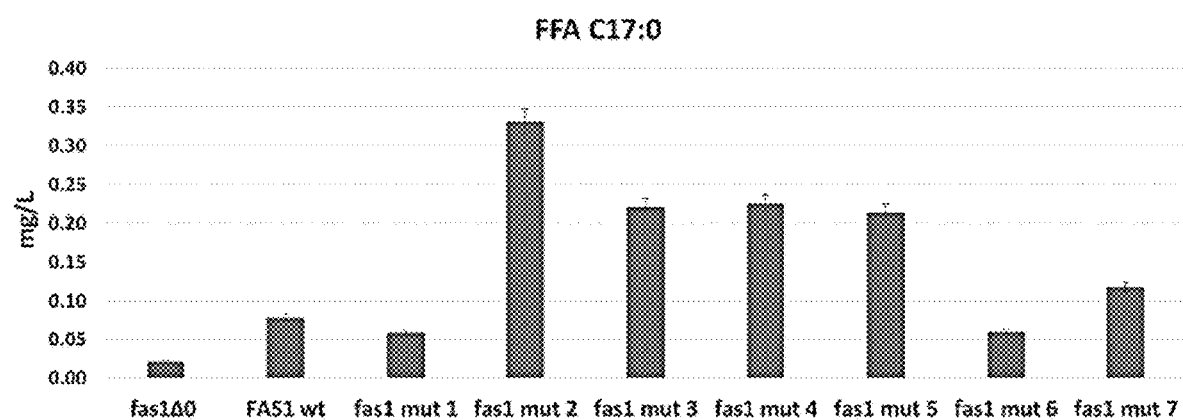
FIG. 9 shows restoration of fatty acid synthase (FAS) activity in a *S. cerevisiae* strain with fas1 deleted background and expressing HICCL4 CoA ligase.
Figure 10:
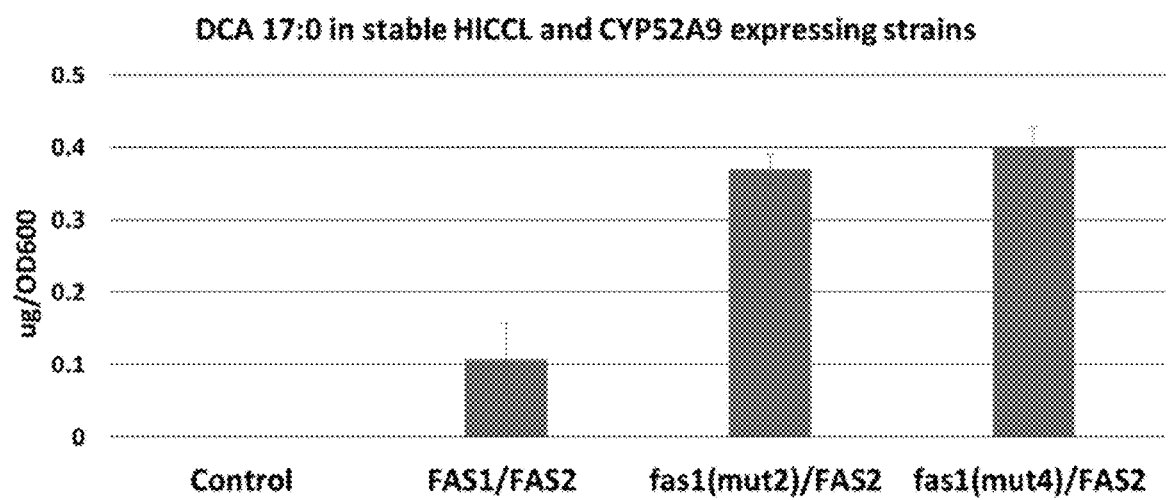
FIG. 10 shows C17 anteiso fatty acid production in *S. cerevisiae* strain expressing HICCL4 and CYP52A CYP52A9 genes.

In one embodiment, I-muscone-producing recombinant host can further comprise a fatty acid synthase 1 (fas1) gene deletion with an exogenously expressed FAS1 mutant to increase production of odd chain fatty acids, for example, C17:0 anteiso fatty acids (see FIGS. 9 and 10). The FAS1 mutants include, but are not limited to, fas1 mut 1 (I483A) (SEQ ID NO:6; 26), fas1 mut 2 (F427A) (SEQ ID NO:7; 27), fas1 mut 3 (F427A, I483A) (SEQ ID NO:8; 28), fas1 mut 4 (I234A, F427S) (SEQ ID NO:9; 29), fas1 mut 5 (Q163A, F427A) (SEQ ID NO:10; 30), fas1 mut6 (I306A) (SEQ ID NO:11;31), and fas1 mut 7 (I306A, I483A) (SEQ ID NO:12; 32). The odd chain fatty acids produced by the I-muscone-producing recombinant host following FAS activity can then be used as substrate by cytochrome P450 monoxoygenase and cytochrome P450 reductase enzymes to produce additional downstream intermediates in the I-muscone biosynthetic pathway such as dicarboxylic acids (see FIG. 9, Table 2, and FIG. 10).

In one embodiment, I-muscone-producing recombinant host can further comprise genes encoding polypeptides for the oxidation of monomethyl branched chain fatty acids resulting in the formation of a dicarboxylic acid (e.g., cytochrome P450 monooxygenase (SEQ ID NO:1, 47, 48, 50, and 51; 21, 41, 42, 44, and 45) cytochrome P450 reductase (SEQ ID NOs:2, 49, and 52; 22, 43, and 46)). The dicarboxylic acid can include but is not limited to 3-methylhexadecanedioic acid.

In one embodiment, I-muscone-producing recombinant host can further comprise a gene encoding a polypeptide capable of activating a dicarboxylic acid to produce a dicarboxylic acid-CoA molecule (e.g., Acyl-CoA synthase) (SEQ ID NOs:13; 33). For example, the recombinant host cell can comprise a constitutively expressed cloned gene MCC028 of Ondatra zibethicus which was annotated to the murine Acyl CoA synthase (ACBG1). For example, MCC028 uses 3-methylhexadecanedioic acid as a substrate for the formation of 3-methyldecadecanedioic acid-CoA (see FIG. 11).

In another embodiment, the I-muscone-producing recombinant host can comprise a gene encoding a polypeptide capable of synthesiznig I-muscone from a dicarboxylic acid.

In one embodiment, I-muscone-producing recombinant host comprises a gene encoding a polypeptide capable of synthesizing 3-methyl-2-oxopentanoate from L-isoleucine (e.g., transaminase (e.g., branched-chain amino-acid transaminase (BAT1/BAT2)) (SEQ ID NOs:14 or 15; 34 or 35), a gene encoding a polypeptide capable of synthesizing (S)-2-methylbutanal from (S)-3-methyl-2-oxopentanaoate (e.g., transaminated amino acid decarboxylase (ARO10)) (SEQ ID NOs:16, 36); a gene encoding a polypeptide capable of synthesizing (S)-2-methylbutyric acid from (S)-2-methylbutanal (e.g., aldehyde dehydrogenase (ALD2/ALD5)) (SEQ ID NOs:17 and 18; 37, or 38); a gene encoding a polypeptide capable of synthesizing (S)-2-methylbutyryl-CoA from (S)-2-methylbutyric acid (e.g., CoA ligase) (SEQ ID NO:3 or 4; 23 or 24); a gene encoding a polypeptide that can synthesize a mono-methyl branched chain fatty acid from 2-methylbutyryl-CoA (e.g., fatty acid synthase (FAS) (SEQ ID NOs:5, 6, 7, 8, 9, 10, 11, or 12; 25, 26, 27, 28, 29, 30, 31, or 32); genes encoding polypeptides for the oxidation of mono-methyl branched chain fatty acids to a dicarboxylic acid (e.g., cytochrome P450 monooxygenase (SEQ ID NO:1, 47, 48, 50, and 51; 21, 41, 42, 44, and 45) cytochrome P450 reductase (SEQ ID NOs:2, 49, and 52; 22, 43, and 46)); a gene encoding a polypeptide capable of activating a dicarboxylic acid to produce a dicarboxylic acid-CoA molecule (e.g., Acyl-CoA synthase) (SEQ ID NOs:13; 33); and a gene encoding a polypeptide capable of synthesizing I-muscone from a dicarboxylic acid.

In some embodiments, I-muscone and/or I-muscone precursors are produced in vivo through expression in a recombinant host of one or more enzymes capable of reactions found in the I-muscone biosynthetic pathway. For example, a I-muscone-producing recombinant host expressing a gene encoding a polypeptide capable of synthesizing 3-methyl-2-oxopentanoate from L-isoleucine (e.g., transaminase (e.g., branched-chain amino-acid transaminase (BAT1/BAT2)) (SEQ ID NOs:14 or 15; 34 or 35), a gene encoding a polypeptide capable of synthesizing (S)-2-methylbutanal from (S)-3-methyl-2oxopentanaoate (e.g., transaminated amino acid decarboxylase (ARO10)) (SEQ ID NOs:16;36); a gene encoding a polypeptide capable of synthesizing (S)-2-methylbutyric acid from (S)-2-methylbutanal (e.g., aldehyde dehydrogenase (ALD2/ALD5)) (SEQ ID NOs:17 and 18; 37, or 38); a gene encoding a polypeptide capable of synthesizing (S)-2-methylbutyryl-CoA from (S)-2-methylbutyric acid (e.g., CoA ligase) (SEQ ID NOs:3 or 4; 23 or 24); a gene encoding a polypeptide that can synthesize a mono-methyl branched chain fatty acid from 2-methylbutyryl-CoA (e.g., fatty acid synthase (FAS) (SEQ ID NOs:5, 6, 7, 8, 9, 10, 11, or 12; 25, 26, 27, 28, 29, 30, 31, or 32); genes encoding polypeptides for the oxidation of mono-methyl branched chain fatty acids to a dicarboxylic acid (e.g., cytochrome P450 monooxygenase (SEQ ID NOs:1, 47, 48, 50, and 51; 21, 41, 42, 44, and 45) cytochrome P450 reductase (SEQ ID NOs:2, 49, and 52; 22, 43, and 46)); a gene encoding a polypeptide capable of activating a dicarboxylic acid to produce a dicarboxylic acid-CoA molecule (e.g., Acyl-CoA synthase); and a gene encoding a polypeptide capable of synthesizing I-muscone from a dicarboxylic acid can produce I-muscone and/or one or more I-muscone precursors in vivo and/or in vitro. The skilled worker will appreciate that these genes can be endogenous to the host provided that at least one (and in some embodiments, all) of these genes is a recombinant gene introduced into the recombinant host cell.

In some embodiments, a recombinant host comprises a nucleic acid encoding a polypeptide capable of attaching a CoA group to (S)-2-methylbutyric acid. For example, Humulus lupulus (HlCCL4) (SEQ ID NO:3; 23) and Solanum tuberosom (StCCL) (SEQ ID NO:4; 24).

In some embodiments, a recombinant host comprises a nucleic acid encoding a polypeptide capable of synthesizing 14-methylhaxadecanoic acid from (S)-2-methylbutyryl-CoA. For example, fatty acid synthase wildtype (SEQ ID NO:5; 25) or the FAS1 mutants fas1 mut1 (I483A) (SEQ ID NOs:6; 26), fas1 mut2 (F427A), (SEQ ID NOs:7; 27), fas1 mut 3 (F427A, I483A), (SEQ ID NOs:8; 28), fas1 mut 4 (I234A F427S), (SEQ ID NOs:9; 29), fas1 mut 5 (Q163A F427A), (SEQ ID NOs:10; 30), fas1 mut 6 (I306A), (SEQ ID NOs:11; 31) and fas1 mut 7 (I306A I483A), (SEQ ID NOs:12; 32).

In some embodiments, a recombinant host cell comprises nucleic acids encoding polypeptides capable of synthesizing 3-methylhexadecanedioic acid from 14-methylhexadecanoic acid or hexadecanedioic acid from palmitic acid. For example, cytochrome P450 monooxygenase (SEQ ID NOs: 1, 47, 48, 50, and 51; 21, 41, 42, 44, and 45) cytochrome P450 reductase (SEQ ID NOs:2, 49, and 52; 22, 43, and 46).

In some embodiments, a recombinant host cell comprises a nucleic acid encoding a polypeptide capable of CoA activation of 3-methylhexadecanedioic acid to form 3-methylhexadecanedioic acid-CoA or hexadecanedioic acid-CoA from hexadecanedioic acid (SEQ ID NO:13; 33).

Nor-Muscone Biosynthetic Pathway

In one embodiment, nor-muscone and nor-muscone precursor production can be produced via a recombinant host comprising the nor-muscone biosynthetic pathway which includes the production of palmitic acid. Palmitic acid is then oxidized to form a dicarboxylic acid, such as hexadecanedioic acid. The dicarboxylic acid intermediate is then activated by the addition of a CoA molecule to form a dicarboxylic acid-CoA molecule. Lastly, nor-muscone is produced via a cyclisation and decarboxylation of a CoA activated dicarboxylic acid (see FIGS. 1B and 1C-1K).

In another embodiment, I-muscone and I-muscone precursor production can be achieved via the I-muscone biosynthetic pathway which includes the production of (S)-2-methylbutyryl acid-CoA which can then be used as a priming unit, or substrate for acyl-CoA ligase, to form a monomethyl branched chain fatty acid (MMBCFA) or an anteiso fatty acid molecule (see FIGS. 1B and 1C-1K). Nor-muscone is subsequently produced via a Dieckmann condensation reaction with a dicarboxylic acid acting as a substrate.

In some embodiments, the nor-muscone-producing recombinant host comprises a gene encoding a polypeptide capable of synthesizing malonyl CoA from acetyl CoA (E.C. 6.2.1.3) (e.g., acetyl CoA carboxylase) (SEQ ID NOs:19; 39); a gene encoding a polypeptide capable of synthesizing palmitic acid from malonyl CoA (e.g., fatty acid synthase) (SEQ ID NOs:5; 25). Palmitic acid produced from the nor-muscone-producing recombinant hosts acts as the starting substrate for the production of nor-muscone (see FIG. 1A). The skilled worker will appreciate that these genes can be endogenous to the host provided that at least one (and in some embodiments, all) of these genes is a recombinant gene introduced into the recombinant host cell.

In one embodiment, the nor-muscone-producing recombinant host further comprises a gene encoding a cytochrome P450 monooxygenase (SEQ ID NOs:1, 47, 48, 50, and 51; 21, 41, 42, 44, and 45) and a gene encoding a cytochrome P450 reductase (SEQ ID NOs:2, 49, and 52; 22, 43, and 46) for the synthesis of hexadecanedioic acid from palmitic acid (see FIGS. 2-6).

Figure 7:
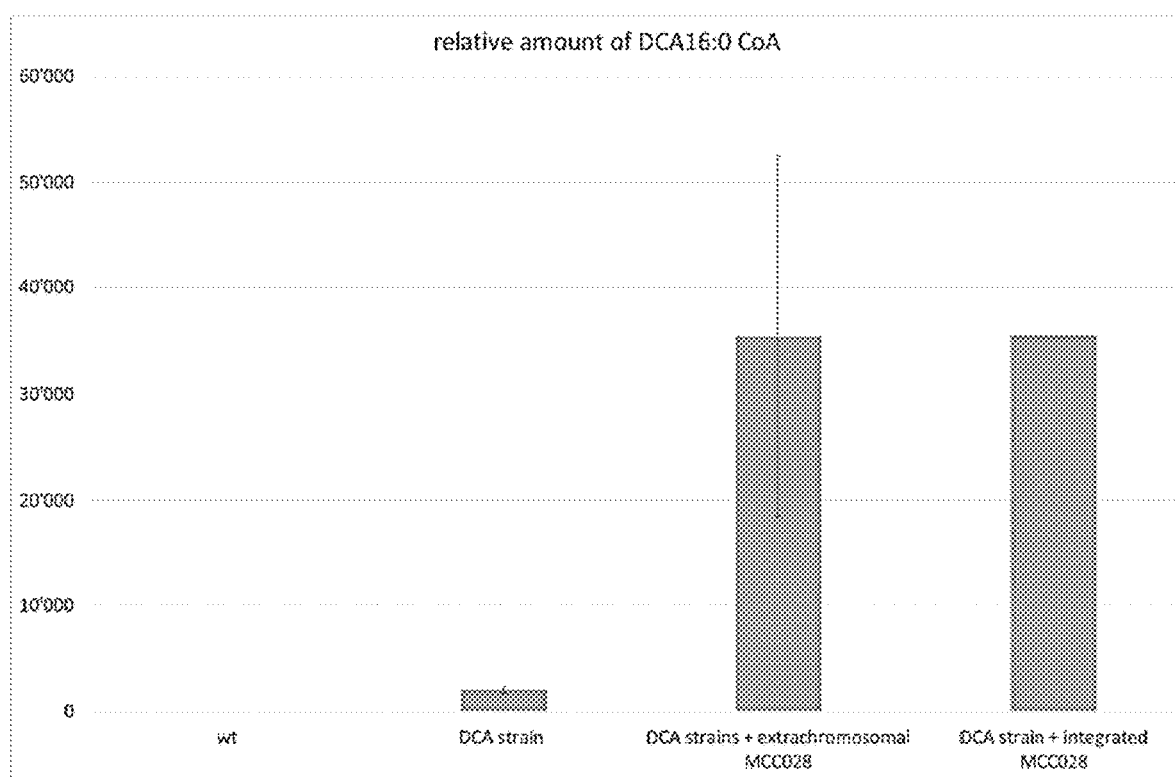
FIG. 7 shows relative amount of hexadecanedioic acid-CoA under extrachromosomal and integrated expression of Acyl CoA synthase (MCC028).

In one embodiment, the nor-muscone-producing recombinant host can further comprise a gene encoding a polypeptide capable of synthesizing hexadecanedioic acid-CoA from hexadecanedioic acid (e.g., Acyl CoA synthetase) (SEQ ID NOs:13; 33) (see FIG. 7).

In one embodiment, the nor-muscone-producing recombinant host can further comprise overexpression of endogenously expressed Acyl CoA synthetase (e.g., Fatty acid activation gene 1 (Faa1), fatty acid activation gene 4 (Faa4), fatty acid transporter (Fat1), fatty acid transport protein 2 (fat2p)). Overexpression of such endogenous CoA synthetases can result in increased production of CoA-activated DCAs such as hexadecanedioic acid-CoA. Faa1 and faa4 are long chain fatty acyl CoA synthetases that have a preference from C12-C16 chain lengths, fat1 has a preference for fatty acids longer than C20, and fat2p is an acyl CoA synthetase involved in beta oxidation of fatty acids (see FIG. 12).

In another embodiment, the nor-muscone-producing recombinant host can comprise a gene encoding a polypeptide capable of synthesizing nor-muscone from a dicarboxylic acid.

In one embodiment, the nor-muscone-producing recombinant host can further comprise a gene encoding a polypeptide capable of synthesizing malonyl CoA from acetyl CoA (e.g., acetyl CoA carboxylase) (SEQ ID NOs:19; 39); a gene encoding a polypeptide capable of synthesizing palmitic acid from malonyl CoA (e.g., fatty acid synthase) (SEQ ID NOs:5; 25); a gene encoding a cytochrome P450 monooxygenase (SEQ ID NOs:1, 47, 48, 50, and 51; 21, 41, 42, 44, and 45) a gene encoding a cytochrome P450 reductase (SEQ ID NOs:2, 49, and 52; 22, 43, and 46) for the synthesis of hexadecanedioic acid from palmitic acid; and a gene encoding a polypeptide capable of synthesizing nor-muscone from a dicarboxylic acid.

In some embodiments, nor-muscone and/or nor-muscone precursors are produced in vivo through expression in a recombinant host of one or more enzymes capable of reactions found in the nor-muscone biosynthetic pathway. For example, a nor-muscone-producing recombinant host expressing a gene encoding a polypeptide capable of synthesizing malonyl CoA from acetyl CoA (e.g., acetyl CoA carboxylase (SEQ ID NOs:19; 39)); a gene encoding a polypeptide capable of synthesizing palmitic acid from malonyl CoA (e.g., fatty acid synthase); a gene encoding a cytochrome P450 monooxygenase (SEQ ID NOs:1;21) and a gene encoding a cytochrome P450 reductase (SEQ ID NOs:2; 22) for the synthesis of hexadecanedioic acid from palmitic acid; a gene encoding a acyl-CoA synthase (SEQ ID NOs:13; 33) for the synthesis of hexdecanedioic acid-CoA from hexadecanedioic acid; and a gene encoding a polypeptide capable of synthesizing nor-muscone from (S)-(+)-3-methylhexadecanoic acid.

In some embodiments, I- and/or nor-muscone and/or muscone precursors are produced through contact of a muscone precursor with one or more enzymes involved in the muscone pathway in vitro. For example, contacting 3-methylhexadecanedioic acid with a Acyl CoA synthase polypeptide can result in production of a 3-methylhexadecanedioic acid-CoA in vitro. In some embodiments, a muscone precursor is produced through contact of an upstream muscone precursor with one or more enzymes involved in the muscone pathway in vitro. For example, contacting 2-methylbutyric acid with a polypeptide capable of synthesizing 2-methylbutyryl-CoA from 2-methylbutyric acid (e.g., Acyl CoA ligase) can result in production of 2-methylbutyryl-CoA in vitro.

In some embodiments, I- and/or nor-muscone and/or muscone precursors are produced through contact of a muscone precursor with one or more enzymes involved in the muscone pathway in vitro. For example, contacting hexadecanedioic acid with a Acyl CoA synthase polypeptide can result in production of a hexadecanedioic acid-CoA in vitro. In some embodiments, a muscone precursor is produced through contact of an upstream muscone precursor with one or more enzymes involved in the muscone pathway in vitro. For example, contacting palmitic acid with a set of polypeptides capable of synthesizing hexadecanedioic acid from palmitic acid (e.g., cytochrome P450 monooxygenase/reductase) can result in production of hexadecanedioic acid in vitro.

In some embodiments, I- and/or nor-muscone or a muscone precursor is produced by whole cell bioconversion. For whole cell bioconversion to occur, a host cell expressing one or more enzymes involved in either or both the I-muscon oer nor-muscone biosynthetic pathway takes up and modifies a muscone precursor in the cell; following modification in vivo, muscone remains in the cell and/or is excreted into the culture medium. For example, a host cell expressing a gene encoding a P450 monoxoygenase/reductase complex polypeptide can take up palmitic acid; following oxidation in vivo, a dicarboxylic acid such as hexadecanedioic acid can be excreted into the culture medium. In some embodiments, the cell is permeabilized to take up a substrate to be modified and/or to excrete a modified product. In another example, a recombinant host cell expressing a gene encoding a fatty acid synthase polypeptide can take up (S)-2-methylbutyryl-CoA and synthesize 14-methylhexadecanoic acid; following synthesis in vitro, a 14-methylhexadecanoic acid, or another anteiso fatty acid, can be excreted into the cell culture medium. A permeabilized recombinant host cell can then be added to the cell culture medium to take up the excreted anteiso fatty acid to be further modified and to excrete a further modified product.

For example, a host cell expressing a gene encoding an acyl CoA synthase polypeptide can take up 3-methylhexadecanedioic acid and activate 3-methylhexadecanedioic acid in the cell; following activation in vivo, the cell is permeabilized to take up a substrate to be modified or to excrete a modified product. In another example, a recombinant host cell expressing genes encoding a cytochrome P450 monooxygenase and a cytochrome P450 reductase polypeptide can take up palmitic acid and oxidize palmitic acid in the cell; following oxidation in vivo, a hexadecanedioic acid can be excreted into the cell culture medium. In some embodiments, muscone or a muscone precursor is produced through contact of an upstream muscone precursor with one or more enzymes involved in either the I- or nor-muscone pathway in vivo. For example, contacting 2-methylbutyric acid with a polypeptide capable of synthesizing 2-methyl-butyryl-CoA from 2-methylbutyric acid (e.g., Acyl CoA ligase can result in production of 2-methylbutyryl-CoA in vivo. A permeabilized recombinant host cell can then be added to the cell culture medium to take up the excreted muscone precursor to be further modified and to excrete a further modified product.

In some embodiments, muscone, civetone and/or one or more precursors thereof are produced by co-culturing of two or more hosts. In some embodiments, one or more hosts, each expressing one or more enzymes involved in the I- and/or nor-muscone biosynthetic pathway, produce muscone, and one or more muscone precursors. For example, a host comprising a gene encoding a polypeptide capable of synthesizing 3-methyl-2-oxopentanoate from L-isoleucine (e.g., transaminase (e.g., branched-chain amino-acid transaminase (BAT1/BAT2)) (SEQ ID NO:14 or 15; 34 or 35), a gene encoding a polypeptide capable of synthesizing (S)-2-methylbutanal from (S)-3-methyl-2-oxopentanaoate (e.g., transaminated amino acid decarboxylase (ARO10)) (SEQ ID NOs:16; 36); a gene encoding a polypeptide capable of synthesizing (S)-2-methylbutyric acid from (S)-2-methylbutanal (e.g., aldehyde dehydrogenase (ALD2/ALD5)) (SEQ ID NO: 17 or 18; 37, or 38); a gene encoding a polypeptide capable of synthesizing (S)-2-methylbutyryl-CoA from (S)-2-methylbutyric acid (e.g., CoA ligase) (SEQ ID NOs:3 or 4; 23 or 24); a gene encoding a polypeptide that can synthesize a mono-methyl branched chain fatty acid from 2-methylbutyryl-CoA (e.g., fatty acid synthase (FAS) (SEQ ID NOs:5, 6, 7, 8, 9, 10, 11, or 12; 25, 26, 27, 28, 29, 30, 31, or 32); genes encoding polypeptides for the oxidation of mono-methyl branched chain fatty acids to a dicarboxylic acid (e.g. cytochrome P450 monooxygenase (SEQ ID NOs: 1, 47, 48, 50, and 51; 21, 41, 42, 44, and 45) cytochrome P450 reductase (SEQ ID NOs:2, 49, and 52; 22, 43, and 46)); a gene encoding a polypeptide capable of activating a dicarboxylic acid to produce a dicarboxylic acid-CoA molecule (e.g., Acyl-CoA synthase) (SEQ ID NOs:13; 33); and a gene encoding a polypeptide capable of synthesizing nor-muscone from a dicarboxylic acid.

Functional Homologs

Functional homologs of the polypeptides described above are also suitable for use in producing muscone, civetone, and/or precursors thereof in a recombinant host. A functional homolog is a polypeptide that has sequence similarity to a reference polypeptide, and that carries out one or more of the biochemical or physiological function(s) of the reference polypeptide. A functional homolog and the reference polypeptide can be a natural occurring polypeptide, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs.

The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of muscone precursor biosynthesis polypeptides. Sequence analysis can involve BLAST, Reciprocal BLAST, or PS I-BLAST analysis of non-redundant databases using a UGT amino acid sequence as the reference sequence. Amino acid sequence is, in some instances, deduced from the nucleotide sequence. Those polypeptides in the database that have greater than 40% sequence identity are candidates for further evaluation for suitability as a muscone precursor biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in muscone biosynthesis polypeptides, e.g., conserved functional domains. In some embodiments, nucleic acids and polypeptides are identified from transcriptome data based on expression levels rather than by using BLAST analysis.

Conserved regions can be identified by locating a region within the primary amino acid sequence of a muscone biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer etal., Nucl. Acids Res., 26:320-322 (1998); Sonnhammer et al., Proteins, 28:405-420 (1997); and Bateman et al., Nucl. Acids Res., 27:260-262 (1999). Conserved regions also can be determined by aligning sequences of the same or related polypeptides from closely related species. Closely related species preferably are from the same family. In some embodiments, alignment of sequences from two different species is adequate to identify such homologs.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, polypeptides suitable for producing muscone (e.g., l- and nor-) and/or l-and nor-muscone precursors in a recombinant host include functional homologs of cytochrome P450 monooxygenases.

Methods to modify the substrate specificity of, for example, cytochrome P450 monooxygenase, are known to those skilled in the art, and include without limitation site-directed/rational mutagenesis approaches, random directed evolution approaches and combinations in which random mutagenesis/saturation techniques are performed near the active site of the enzyme.

A candidate sequence typically has a length that is from 80% to 250% of the length of the reference sequence, e.g., 82, 85, 87, 89, 90, 93, 95, 97, 99, 100, 105, 110, 115, 120, 130, 140, 150, 160, 170, 180, 190, 200, 210, 220, 230, 240, or 250% of the length of the reference sequence. A functional homolog polypeptide typically has a length that is from 95% to 105% of the length of the reference sequence, e.g., 90, 93, 95, 97, 99, 100, 105, 110, 115, or 120% of the length of the reference sequence, or any range between. A % sequence identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using the computer program Clustal Omega (version 1.2.1, default parameters), which allows alignments of nucleic acid or polypeptide sequences to be carried out across their entire length (global alignment). Chenna et al., 2003, Nucleic Acids Res. 31(13):3497-500.

Clustal Omega calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The Clustal Omega output is a sequence alignment that reflects the relationship between sequences. Clustal Omega can be run, for example, at the Baylor College of Medicine Search Launcher site on the World Wide Web (searchlauncher.bcm.tmc.edu/multi-align/multi-align.html) and at the European Bioinformatics Institute site at www.ebi.ac.uk/Tools/msa/clustalo/.

To determine a % sequence identity of a candidate nucleic acid or amino acid sequence to a reference sequence, the sequences are aligned using Clustal Omega, the number of identical matches in the alignment is divided by the length of the reference sequence, and the result is multiplied by 100. It is noted that the % sequence identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that functional CoA ligase, FAS, and cytochrome P450 monooxygenase/reductase proteins can include additional amino acids that are not involved in the enzymatic activities carried out by the enzymes. In some embodiments, CoA ligase, FAS, and cytochrome P450 monooxygenase/reductase proteins are fusion proteins. The terms "chimera," "fusion polypeptide," "fusion protein," "fusion enzyme," "fusion construct," "chimeric protein," "chimeric polypeptide," "chimeric construct," and "chimeric enzyme" can be used interchangeably herein to refer to proteins engineered through the joining of two or more genes that code for different proteins.

In some embodiments, a chimeric enzyme is constructed by joining the C-terminal of a first polypeptide ProteinA to the N-terminal of a second polypeptide ProteinB through a linker "b," i.e., "ProteinA-b-ProteinB." In some aspects, the linker of a chimeric enzyme can be the amino acid sequence "KLVK." In some aspects, the linker of a chimeric enzyme can be the amino acid sequence "RASSTKLVK." In some aspects, the linker of a chimeric enzyme can be the amino acid sequence "GGGGS." In some aspects, the linker of a chimeric enzyme can be two repeats of the amino acid sequence "GGGGS" (i.e., "GGGGSGGGGS"). In some aspects, the linker of a chimeric enzyme can be three repeats of the amino acid sequence "GGGGS." In some aspects, the linker of a chimeric enzyme is a direct bond between the C-terminal of a first polypeptide and the N-terminal of a second polypeptide. In some embodiments, a chimeric enzyme is constructed by joining the C-terminal of a first polypeptide ProteinA to the N-terminal of a second polypeptide ProteinB through a linker "b," i.e., "ProteinA-b-ProteinB" and by joining the C-terminal of the second polypeptide ProteinB to the N-terminal of a third polypeptide ProteinC through a second linker "d," i.e., "ProteinA-b-ProteinB-d-ProteinC.

In some embodiments, a nucleic acid sequence encoding a cytochrome P450 monooxygenase or a Acyl CoA ligase polypeptide can include a tag sequence that encodes a "tag" designed to facilitate subsequent manipulation (e.g., to facilitate purification or detection), solubility, secretion, or localization of the encoded polypeptide. Tag sequences can be inserted in the nucleic acid sequence encoding the polypeptide such that the encoded tag is located at either the carboxyl or amino terminus of the polypeptide. Non-limiting examples of encoded tags include green fluorescent protein (GFP), human influenza hemagglutinin (HA), glutathione S transferase (GST), polyhistidine-tag (HIS tag), disulfide oxidoreductase (DsbA), maltose binding protein (MBP), N-utilization substance (NusA), small ubiquitin-like modifier (SUMO), and Flag™ tag (Kodak, New Haven, Conn.). Other examples of tags include a chloroplast transit peptide, a mitochondrial transit peptide, an amyloplast peptide, signal peptide, or a secretion tag. In some embodiments, a tag is attached to the polypeptide.

In some embodiments, a fusion protein is a protein altered by domain swapping. As used herein, the term "domain swapping" is used to describe the process of replacing a domain of a first protein with a domain of a second protein. In some embodiments, the domain of the first protein and the domain of the second protein are functionally identical or functionally similar. In some embodiments, the structure and/or sequence of the domain of the second protein differs from the structure and/or sequence of the domain of the first protein. In some embodiments, a P450 monooxygenase or an Acyl CoA ligase polypeptide is altered by domain swapping.

Macrocyclic Ketone and Macrocyclic Ketone Precursor Biosynthetic Nucleic Acids

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. "Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also can include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region can be present, e.g., introns, enhancers, upstream activation regions, transcription terminators, and inducible elements.

One or more genes can be combined in a recombinant nucleic acid construct in "modules" useful for a discrete aspect of (I-and nor) muscone and (I-and nor) muscone precursor production. Combining a plurality of genes in a module, particularly a polycistronic module, facilitates the use of the module in a variety of species. For example, an I-musco pnreecursor biosynthesis gene cluster, can be combined in a polycistronic module such that, after insertion of a suitable regulatory region, the module can be introduced into a wide variety of species. As another example, an acyl-CoA gene cluster can be combined such that each acyl-CoA coding sequence is operably linked to a separate regulatory region, to form an acyl-CoA module. Such a module can be used in those species for which monocistronic expression is necessary or desirable. In addition to genes useful for (I- and nor-)muscone and (I- and nor-) muscone precursor production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

In some cases, it is desirable to inhibit one or more functions of an endogenous polypeptide in order to divert metabolic intermediates towards muscone or muscone precursor biosynthesis. For example, it can be desirable to downregulate synthesis of sterols in a yeast strain in order to further increase muscone or muscone precursor production, e.g., by downregulating squalene epoxidase. As another example, it can be desirable to inhibit degradative functions of certain endogenous gene products, e.g., glycohydrolases that remove glucose moieties from secondary metabolites or phosphatases as discussed herein. In such cases, a nucleic acid that overexpresses the polypeptide or gene product can be included in a recombinant construct that is transformed into the strain. Alternatively, mutagenesis can be used to generate mutants in genes for which it is desired to increase or enhance function.

Macrocyclic Ketone Compositions

In some embodiments, the recombinant host cell s and methods described herein can provide compositions of macrocyclic ketones and macrocyclic ketone precursors wherein the relative levels of macrocyclic ketone in the composition correspond to the relative levels of macrocyclic ketone in the recombinant host cell, e.g., the relative levels of macrocyclic ketone in the composition are within 10%, or 9%, or 8%, or 7%, or 6%, or 5%, or 4%, or 3%, or 2%, or 1% of the relative levels of macrocyclic ketone in the recombinant host cell.

The amount of an individual macrocyclic ketones (e.g., I-muscone, nor-muscone, or civetone) accumulated can be from about 1 to about 7,000 mg/L, e.g., about 1 to about 10 mg/L, about 3 to about 10 mg/L, about 5 to about 20 mg/L, about 10 to about 50 mg/L, about 10 to about 100 mg/L, about 25 to about 500 mg/L, about 100 to about 1,500 mg/L, or about 200 to about 1,000 mg/L, at least about 1,000 mg/L, at least about 1,200 mg/L, at least about at least 1,400 mg/L, at least about 1,600 mg/L, at least about 1,800 mg/L, at least about 2,800 mg/L, or at least about 7,000 mg/L. In some aspects, the amount of individual macrocyclic ketones (e.g., I-muscone, nor-muscone, or civetone) can exceed 7,000 mg/L. The amount of a combination of macrocyclic ketones (e.g., I-muscone, nor-muscone, and civetone) accumulated can be from about 1 mg/L to about 7,000 mg/L, e.g., about 200 to about 1,500, at least about 2,000 mg/L, at least about 3,000 mg/L, at least about 4,000 mg/L, at least about 5,000 mg/L, at least about 6,000 mg/L, or at least about 7,000 mg/L. In some aspects, the amount of a combination of macrocyclic ketones can exceed 7,000 mg/L. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce muscone and/or muscone precursors. For example, a first microorganism can comprise one or more biosynthesis genes for producing a muscone precursor, while a second microorganism comprises muscone biosynthesis genes. The product produced by the second, or final microorganism is then recovered. It will also be appreciated that in some embodiments, a recombinant microorganism is grown using nutrient sources other than a culture medium and utilizing a system other than a fermenter.

Macrocyclic ketones and compositions obtained by the methods disclosed herein can be used to make fragrance compositions.

For example, substantially macrocyclic ketones such as I-muscone and nor-muscone can be included in fragrances. A mixture of macrocyclic ketones can be made by culturing recombinant microorganisms separately, each producing a macrocyclic ketone or a macrocyclic ketone precursor, recovering the macrocyclic ketone or macrocyclic ketone precursor from each microorganism and then combining the compounds to obtain a mixture comprising each compound in the desired proportion.

Alternatively, the two or more microorganisms each can be grown in a separate culture medium and the product of the first culture medium, e.g., hexadecanedioic acid, can be introduced into second culture medium to be converted into a subsequent intermediate, or into an end product such as a macrocyclic ketone, I-muscone, nor-muscone, or civetone. The product produced by the second, or final microorganism is then recovered. It will also be appreciated that in some embodiments, a recombinant microorganism is grown using nutrient sources other than a culture medium and utilizing a system other than a fermenter.

Host Microorganisms

Recombinant hosts can be used to express polypeptides for the production of muscone, civetone and/or precursors thereof, including, but not limited to, a plant cell, comprising a plant cell that is grown in a plant, a mammalian cell, an insect cell, a fungal cell, an algal cell, or a bacterial cell.

A number of prokaryotes and eukaryotes are also suitable for use in constructing the recombinant microorganisms described herein, e.g., gram-negative bacteria, yeast, and fungi. A species and strain selected for use as a muscone production strain is first analyzed to determine which production genes are endogenous to the strain and which genes are not present. Genes for which an endogenous counterpart is not present in the strain are advantageously assembled in one or more recombinant constructs, which are then transformed into the strain in order to supply the missing function(s).

Typically, the recombinant microorganism is grown in a fermenter at a temperature(s) for a period of time, wherein the temperature and period of time facilitate production of muscone. The constructed and genetically engineered microorganisms provided by the invention can be cultivated using conventional fermentation processes, including, inter alia, chemostat, batch, fed-batch cultivations, semi-continuous fermentations such as draw and fill, continuous perfusion fermentation, and continuous perfusion cell culture. Depending on the particular microorganism used in the method, other recombinant genes such as (I- and nor-)

muscone biosynthesis genes can also be present and expressed. Levels of substrates and intermediates, e.g., (S)-methylbutyryl-CoA, palmitic acid, 14-methylhexadecanoic acid, and hexadecanedioic acid, can be determined by extracting samples from culture media for analysis according to published methods.

Carbon sources of use in the instant method include any molecule that can be metabolized by the recombinant host cell to facilitate growth and/or production of muscone and/or muscone precursors. Examples of suitable carbon sources include, but are not limited to, sucrose (e.g., as found in molasses), fructose, xylose, ethanol, glycerol, glucose, cellulose, starch, cellobiose or other glucose-comprising polymer. In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

After the recombinant microorganism has been grown in culture for the period of time, wherein the temperature and period of time facilitate production of muscone and/or muscone precursor can then be recovered from the culture using various techniques known in the art. In some embodiments, a permeabilizing agent can be added to aid the feedstock entering into the host and product getting out. For example, a crude lysate of the cultured microorganism can be centrifuged to obtain a supernatant. The resulting supernatant can then be applied to a chromatography column, e.g., a C-18 column, and washed with water to remove hydrophilic compounds, followed by elution of the compound(s) of interest with a solvent such as methanol. The compound(s) can then be further purified by preparative HPLC.

It will be appreciated that the various genes and modules discussed herein can be present in two or more recombinant hosts rather than a single host. When a plurality of recombinant hosts is used, they can be grown in a mixed culture to accumulate muscone and/or muscone precursors.

Alternatively, the two or more hosts each can be grown in a separate culture medium and the product of the first culture medium, e.g., 14-methylhexadecanoic acid can be introduced into second culture medium to be converted into a subsequent intermediate, or into an end product such as, for example, 3-methylhexadecanedioic acid. The product produced by the second, or final host is then recovered. It will also be appreciated that in some embodiments, a recombinant host is grown using nutrient sources other than a culture medium and utilizing a system other than a fermenter.

Exemplary prokaryotic and eukaryotic species are described in more detail below. However, it will be appreciated that other species can be suitable to express polypeptides for the producing (l- and nor-) muscone and/or (l- and nor-) muscone precursors. For example, suitable species can be in a genus such as *Agaricus, Aspergillus, Bacillus, Candida, Corynebacterium, Eremothecium, Escherichia, Fusarium/Gibberella, Kluyveromyces, Laetiporus, Lentinus, Phaffia, Phanerochaete, Pichia* (formally known as Hansuela), *Scheffersomyces, Physcomitrella, Rhodoturula, Saccharomyces, Schizosaccharomyces, Sphaceloma, Xanthophyllomyces, Humicola, Issatchenkia, Brettanomyces, Yamadazyma, Lachancea, Zygosaccharomyces, Komagataella, Kazachstania, Xanthophyllomyces, Geotrichum, Blakeslea, Dunaliella, Haematococcus, Chlorella, Undaria, Sargassum, Laminaria, Scenedesmus, Pachysolen, Trichosporon, Acremonium, Aureobasidium, Cryptococcus, Corynascus, Chrysosporium, Filibasidium, Fusarium, Magnaporthe, Monascus, Mucor, Myceliophthora, Mortierella, Neocallimastix, Neurospora, Paecilomyces, Penicillium, Piromyces, Pachysolen, Phanerochaete, Podospora, Pycnoporus, Rhizopus, Schizophyllum, Sordaria, Talaromyces, Rasmsonia, Thermoascus, Thielavia, Tolypocladium, Kloeckera, Pachysolen, Schwanniomyces, Trametes, Trichoderma, Acinetobacter, Nocardia, Xanthobacter, Streptomyces, Erwinia, Klebsiella, Serratia, Pseudomonas, Salmonella, Choroflexus, Chloronema, Chlorobium, Pelodictyon, Chromatium, Rhode-spirillum, Rhodobacter, Rhodomicrobium,* or *Yarrowia.*

Exemplary species from such genera include *Lentinus tigrinus, Laetiporus sulphureus, Phanerochaete chrysosporium, Pichia pastoris, Pichia kudriavzevii, Cyberlindnera jadinii, Physcomitrella patens, Rhodoturula glutinis, Rhodoturula mucilaginosa, Phaffia rhodozyma, Xanthophyllomyces dendrorhous, Issatchenkia orientalis, Saccharomyces cerevisiae, Saccharomyces bayanus, Saccharomyces pastorianus, Saccharomyces carlsbergensis, Hansuela polymorpha, Brettanomyces anomalus, Yamadazyma philogaea, Fusarium fujikuroil Gibberella fujikuroi, Candida utilis, Candida glabrata, Candida krusei, Candida revkaufi, Candida pulcherrima, Candida tropicalis, Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla, Candida albicans, Bacillus subtilis, Bacillus amyloliquefaciens, Bacillius licheniformis, Bacillus puntis, Bacillius megaterium, Bacillius halofurans, Bacillus punilus, Serratia marcessans, Pseudomonas aeruginosa, Salmonella typhimurium, Blakeslea trispora, Dunaliella sauna, Haematococcus pluvialis, Chlorella* sp., *Undaria pinnatifida, Sargassum, Laminaria japonica, Scenedesmus almeriensis, Salmonella typhi, Choroflexus aurantiacus, Chloronema gigateum, Chlorobium limicola, Pelodictyon luteolum, Chromatium Rhodespirillum rubrum, Rhodobacter spaeroides, Rhodobacter capsulatus, Rhodomicrobium vanellii, Pachysolen tannophilus, Trichosporon beigelii,* and *Yarrowia lipolytica.*

In some embodiments, a microorganism can be a prokaryote such as *Escherichia* bacteria cells, for example, *Escherichia coli* cells; *Lactobacillus* bacteria cells; *Lactococcus* bacteria cells; *Cornebacterium* bacteria cells; *Acetobacter* bacteria cells; *Acinetobacter* bacteria cells; or *Pseudomonas* bacterial cells.

In some embodiments, a microorganism can be an algal cell such as *Blakeslea trispora, Dunaliella salina, Haematococcus pluvialis, Chlorella* sp., *Undaria pinnatifida, Sargassum, Laminaria japonica, Scenedesmus almeriensis* species.

In some embodiments, a microorganism can be a fungi from the genera including but not limited to *Acremonium, Arxula, Agaricus, Aspergillus, Agaricus, Aureobasidium, Brettanomyces, Candida, Cryptococcus, Corynascus, Chrysosporium, Debaromyces, Filibasidium, Fusarium, Gibberella, Humicola, Magnaporthe, Monascus, Mucor, Myceliophthora, Mortierella, Neocallimastix, Neurospora, Paecilomyces, Penicillium, Piromyces, Phanerochaete Podospora, Pycnoporus, Rhizopus, Schizophyllum, Schizosaccharomyces, Sordaria, Scheffersomyces, Talaromyces, Rhodotorula, Rhodosporidium, Rasmsonia, Zygosaccharomyces, Thermoascus, Thielavia, Trichosporon, Tolypocladium , Trametes,* and *Trichoderma.* Fungal species include, but are not limited to, *Aspergillus niger, Aspergillus oryzae, Aspergillus fumigatus, Penicillium chrysogenum, Penicil-*

*lium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla.*

In some embodiments, a microorganism can be an Ascomycete such as *Gibberella fujikuroi, Kluyveromyces lactis, Schizosaccharomyces pombe, Geotrichum Aspergillus niger, Yarrowia lipolytica, Ashbya gossypii, Yamadazyma philogaea, Lachancea kluyveri, Kodamaea ohmeri,* or *S. cerevisiae.*

*Agaricus, Gibberella,* and *Phanerochaete* spp.

*Agaricus, Gibberella,* and *Phanerochaete* spp. are fungi genera commonly used in the production of edible composition.

*Arxula adeninivorans (Blastobotrys adeninivorans)*

*Arxula adeninivorans* is a dimorphic yeast (it grows as budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Rhodotorula* sp.

*Rhodotorula* is unicellular, pigmented yeast. The oleaginous red yeast, *Rhodotorula glutinis*, has been shown to produce lipids and carotenoids from crude glycerol (Saenge et al., 2011, *Process Biochemistry* 46(1):210-8). *Rhodotorula toruloides* strains have been shown to be an efficient fed-batch fermentation system for improved biomass and lipid productivity (Li et al., 2007, *Enzyme and Microbial Technology* 41:312-7).

*Schizosaccharomyces* spp.

*Schizosaccharomyces* is a genus of fission yeasts. Similar to *S. cerevisiae, Schizosaccharomyces* is a model organism in the study of eukaryotic cell biology. It provides an evolutionary distant comparison to *S. cerevisiae.* Species include but are not limited to *S. cryophilius* and *S. pombe.* (See Hoffman et al., 2015, Genetics. 201(2):403-23).

*Humicola* spp.

*Humicola* is a genus of filamentous fungi. Species include but are not limited to *H. alopallonella* and *H. siamensis.*

*Brettanomyces* spp.

*Brettanomyces* is a non-spore forming genus of yeast. It is from the Saccharomycetaceae family and commonly used in the brewing and wine industries. *Brettanomyces* produces several sensory compounds that contribute to the complexity of wine, specifically red wine. *Brettanomyces* species include but are not limited to *B. bruxellensis* and *B. claussenii.* See, e.g., Fugelsang et al., 1997, Wine Microbiology.

*Trichosporon* spp.

*Trichosporon* is a genus of the fungi family. *Trichosporon* species are yeast commonly isolated from the soil, but can also be found in the skin microbiota of humans and animals. Species include, for example but are not limited to, *T. aquatile, T. beigelii,* and *T. dermatis.*

*Debaromyces* spp.

*Debaromyces* is a genus of the ascomycetous yeast family, in which species are characterized as a salt-tolerant marine species. Species include but are not limited to *D. hansenii* and *D. hansenius.*

*Physcomitrella* spp.

*Physcomitrella* mosses, when grown in suspension culture, have characteristics similar to yeast or other fungal cultures. This genera can be used for producing plant secondary metabolites, which can be difficult to produce in other types of cells.

*Saccharomyces* spp.

*Saccharomyces* is a widely used chassis organism in synthetic biology, and can be used as the recombinant microorganism platform. For example, there are libraries of mutants, plasmids, detailed computer models of metabolism and other information available for *S. cerevisiae*, allowing for rational design of various modules to enhance product yield. Methods are known for making recombinant microorganisms. Examples of *Saccharomyces* species include *S. casteffii,* also known as *Naumovozyma eastern.*

*Zmosaccharomvces* spp.

*Zygosaccharomyces* is a genus of yeast. Originally classified under the *Saccharomyces* genus it has since been reclassified. It is widely known in the food industry because several species are extremely resistant to commercially used food preservation techniques. Species include but are not limited to *Z. bisporus* and *Z. cidri.* (See Barnett et al, Yeasts: Characteristics and Identification, 1983).

*Geotrichum* spp.

*Geotrichum* are fungi commonly found in soil, water and sewage worldwide. It's often identified in plants, cereal and dairy products. Species include, for example but are not limited to, *G. candidum* and *G. klebahnii* (see Carmichael et al., Mycologica, 1957, 49(6):820-830.)

*Kazachstania* sp

*Kazachstania* is a yeast genus in the family Sacchromycetaceae.

*Torulaspora* spp.

*Torulaspora* is a genus of yeasts and species include but are not limited to *T. franciscae* and *T. globosa.*

*Aspergillus* spp.

*Aspergillus* species such as *A. oryzae, A. niger* and *A. sojae* are widely used microorganisms in food production and can also be used as the recombinant microorganism platform. Nucleotide sequences are available for genomes of *A. nidulans, A. fumigatus, A. oryzae, A. clavatus, A. flavus, A. niger,* and *A. terreus,* allowing rational design and modification of endogenous pathways to enhance flux and increase product yield. Metabolic models have been developed for *Aspergillus*, as well as transcriptomic studies and proteomics studies.

*Yarrowia lipolytica*

*Yarrowia lipolytica* is a dimorphic yeast (see *Arxula adeninivorans*) and belongs to the family Hemiascomycetes. The entire genome of *Yarrowia lipolytica* is known. *Yarrowia* species is aerobic and considered to be non-pathogenic. *Yarrowia* is efficient in using hydrophobic substrates (e.g., alkanes, fatty acids, and oils) and can grow on sugars. It has a high potential for industrial applications and is an oleaginous microorganism. *Yarrowia lipolytica* can accumulate lipid content to approximately 40% of its dry cell weight and is a model organism for lipid accumulation and remobilization. See e.g., Nicaud, 2012, Yeast 29(10):409-18; Beopoulos et al., 2009, *Biochimie* 91(6):692-6; Bankar et al., 2009, *Appl Microbiol Biotechnol.* 84(5):847-65.

*Rhodosporidium toruloides*

*Rhodosporidium toruloides* is an oleaginous yeast and useful for engineering lipid-production pathways (See e.g. Zhu et al., 2013, *Nature Commun.* 3:1112; Ageitos et al., 2011, *Applied Microbiology and Biotechnology* 90(4):1219-27).

*Candida boidinii*

*Candida boidinii* is a methylotrophic yeast (it can grow on methanol). Like other methylotrophic species such as *Han-* senula polymorpha and *Pichia pastoris*, it provides an excellent platform for producing heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. See, e.g., Mattanovich et al., 2012, *Methods Mol Biol.* 824:329-58; Khoury et al., 2009, *Protein Sci.* 18(10):2125-38.

Hansenula polymorpha (*Pichia anqusta*)

*Hansenula polymorpha* is a methylotrophic yeast (see *Candida boidinii*). It can furthermore grow on a wide range of other substrates; it is thermo-tolerant and can assimilate nitrate (see also, *Kluyveromyces lactis*). It has been applied to producing hepatitis B vaccines, insulin and interferon alpha-2a for the treatment of hepatitis C, furthermore to a range of technical enzymes. See, e.g., Xu et al., 2014, *Virol Sin.* 29(6):403-9.

Candida krusei (*Issatchenkia orientalis*)

*Candida krusei* (scientific name, *Issatchenkia orientalis*), is widely used in chocolate production. *C. krusei* is used to remove the bitter taste of and break down cacao beans. In addition to this species involvement in chocolate production, *C. krusei* is commonly found in the immunocompromised as a fungal nosocomial pathogen (see Mastromarino et al., *New Microbiolgica*, 36:229-238; 2013)

Kluyveromyces lactis

*Kluyveromyces lactis* is a yeast regularly applied to the production of kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale. See, e.g., van Ooyen et al., 2006, *FEMS Yeast Res.* 6(3):381-92.

Pichia pastoris

*Pichia pastoris* is a methylotrophic yeast (see *Candida boidinii* and *Hansenula polymorpha*). It is also commonly referred to as *Komagataella pastoris*. It provides an efficient platform for producing foreign proteins. Platform elements are available as a kit and it is worldwide used in academia for producing proteins. Strains have been engineered that can produce complex human N-glycan (yeast glycans are similar but not identical to those found in humans). See, e.g., Piirainen et al., 2014, *N Biotechnol.* 31(6):532-7.

Scheffersomyces stipitis

*Scheffersomyces stipitis* (also known as *Pichia stipites*) is a homothallic yeast found in haploid form. Commonly used instead of *S. cerevisiae* due to its enhanced respiratory capacity that results from and alternative respiratory system. (See Papini et al., Microbial Cell Factories, 11:136 (2012)).

In some embodiments, a microorganism can be an insect cell such as *Drosophila*, specifically, *Drosophilia melanogaster*.

In some embodiments, a microorganism can be an algal cell such as, for example but not limited to, *Blakeslea trispora, Dunaliella salina, Haematococcus pluvialis, Chlorella* sp.

In some embodiments, a microorganism can be a cyanobacterial cell such as, for example but not limited to, *Blakeslea trispora, Dunaliella salina, Haematococcus pluvialis, Chlorella* sp., *Undaria pinnatifida, Sargassum, Laminaria japonica*, and *Scenedesmus almeriensis*.

In some embodiments, a microorganism can be a bacterial cell. Examples of bacteria include, but are not limited to, the genenera *Bacillus* (e.g., *B. subtilis, B. amyloliquefaciens, B. licheniformis, B. puntis, B. megaterium, B. halodurans, B. pumilus*), *Acinetobacter, Nocardia, Xanthobacter, Escherichia* (e.g., *E. coli*), *Streptomyces, Erwinia, Klebsiella, Serratia* (e.g., *S. marcessans*), *Pseudomonas* (e.g., *P. aeruginosa*), *Salmonella* (e.g., *S. typhimurium*, and *S. typhi*). Bacterial cells can also include, but are not limited to, photosynthetic bacteria (e.g., green non-sulfur bacteria (e.g., *Choroflexus* bacteria (e.g., *C. aurantiacus*), *Chloronema* (e.g., *C. gigateum*), green sulfur bacteria (e.g., *Chlorobium* bacteria (e.g., *C. limicola*), *Pelodictyon* (e.g., *P. luteolum*), purple sulfur bacteria (e.g., *Chromatium* (e.g., *C. okenii*)), and purple non-sulfur bacteria (e.g., *Rhode-spirillum* (e.g., *R. rubrum*), *Rhodobacter* (e.g., *R. sphaeroides, R. capsulatus*), and *Rhodomicrobium* bacteria (e.g., *R. vanellii*)).

E. coli

*E. coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

It can be appreciated that the recombinant host cell disclosed herein can comprise a plant cell, comprising a plant cell that is grown in a plant, a mammalian cell, an insect cell, a fungal cell from *Aspergillus* genus; a yeast cell from *Saccharomyces* (e.g., *S. cerevisiae, S. bayanus, S. pastorianus*, and *S. carlsbergensis*), *Schizosaccharomyces* (e.g., *S. pombe*), *Yarrowia* (e.g., *Y. lipolytica*), *Candida* (e.g., *C. glabrata, C. albicans, C. krusei, C. revkaufi, C. pulcherrima, Candida tropicalis, C. utilis*, and *C. boidinii*), *Ashbya* (e.g., *A. gossypii*), *Cyberlindnera* (e.g., *C. jadinii*), *Pichia* (e.g., *P. pastoris* and *P. kudriavzevii*), *Kluyveromyces* (e.g., *K. lactis*), *Hansenual* (e.g., *H. polymorpha*), *Arxula* (e.g., *A. adeninivorans*), *Xanthophyllomyces* (e.g., *X. dendrorhous*), *Issatchenkia* (e.g., *I. orientali*), *Torulaspora* (e.g., *T. franciscae* and *T. globosa*), *Geotrichum* (e.g., *G. candidum* and *G. klebahni*), *Zygosaccharomyces* (e.g., *Z. bisporus* and *Z. cidri*), *Yamadazyma* (e.g., *Y. philogaea*), *Lanchancea* (e.g., *L. kluyveri*), *Kodamaea* (e.g., *K. ohmen*), *Brettanomyces* (e.g., *B. anomalus*), *Trichosporon* (e.g., *T. aquatile, T. beigelii*, and *T. dermatis*), *Debaromyces* (e.g., *D. hansenuis* and *D. hansenii*), *Scheffersomyces* (e.g., *S. stipis*), *Rhodosporidium* (e.g., *R. toruloides*), *Pachysolen* (e.g., *P. tannophilus*), and *Physcomitrella, Rhodotorula, Kazachstania, Gibberella, Agaricus*, and *Phanerochaete genera*; an insect cell including, but not limited to, *Drosophilia melanogaster*, an algal cell including, but not limited to, *Blakeslea trispora, Dunaliella salina, Haematococcus pluvialis, Chlorella* sp., *Undaria pinnatifida, Sargassum, Laminaria japonica*, and *Scenedesmus almeriensis* species; or a bacterial cell from *Bacillus* genus (e.g., *B. subtilis, B. amyloliquefaciens, B. licheniformis, B. puntis, B. megaterium, B. halodurans*, and *B. pumilus*) *Acinetobacter, Nocardia, Xanthobacter genera, Escherichia* (e.g., *E. coli*), *Streptomyces, Erwinia, Klebsiella, Serratia* (e.g., *S. marcessans*), *Pseudomonas* (e.g., *P. aeruginosa*), *Salmonella* (e.g., *S. typhimurium* and *S. typhi*), and further including, *Choroflexus* bacteria (e.g., *C. aurantiacus*), *Chloronema* (e.g., *C. gigateum*), green sulfur bacteria (e.g., *Chlorobium* bacteria (e.g., *C. limicola*), *Pelodictyon* (e.g., *P. luteolum*)), purple sulfur bacteria (e.g., *Chromatium* (e.g., *C. okenii*)), and purple non-sulfur bacteria (e.g., *Rhode-spirillum* (e.g., *R. rubrum*), *Rhodobacter* (e.g., *R. sphaeroides* and *R. capsulatus*), and *Rhodomicrobium* bacteria (e.g., *R. vanellii*)).

The invention will be further described in the following examples, which do not limit the scope of the invention described in the claims.

EXAMPLES

The Examples that follow are illustrative of specific embodiments of the invention, and various uses thereof. They are set forth for explanatory purposes only, and are not to be taken as limiting the invention.

Example 1: (Ultra Performance) LC-MS Analytical Procedure

LC-MS analyses were performed on a Waters ACQUITY UPLC (Ultra Performance Liquid Chromatography system; Waters Corporation) with a Waters ACQUITY UPLC (Ultra Performance Liquid Chromatography system. Quantification of compounds by UPLC-MS: 5 µl of extract was injected on a Waters Acquity ultra performance liquid chromatography system coupled to a Waters Xevo G2 XS T of mass detector (Milford, Mass., USA). Separation of the compounds was achieved on a Waters Acquity UPLC® HSS T3 C18 column (1.7 µm, 2.1 mm×50 mm) kept at 50° C. Mobile phases were 1% acetonitrile, 99% water, 5 mM ammonium acetate (A), and 10% acetonitrile, 90% isopropanol, 5 mM ammonium acetate (B). An elution gradient from 100% A to 90% A within 1 minute, followed by a ramp to 0% A within another 1 minute at a flow rate of 0.5 ml/min was used. The mass analyzer was equipped with an electrospray source and operated in negative mode. Capillary voltage was 1.0 kV; the source was kept at 150° C. and the desolvation temperature was 500° C. Desolvation and cone gas flow were 800 l/h and 100 l/h, respectively. Compounds of interest were tracked by calculating extracted ion chromatograms of the respective [M–H]-ions within a mass window of 0.05 Da. Peak areas of each compound were calculated and compounds were quantified using a linear calibration curve with authentic standards (ranging from 0.03125 mg/l to 4 mg/l).

Example 2: GC-MS Analytical Procedure

The organic extracts of pellet and supernatant were subjected to gas chromatography/mass spectrometry (GC/MS) analysis using an Agilent 7890A GC system with an Agilent 5975C MSD and equipped with a Restek Rxi-5 ms column 25 m×250 µm×0.25 µm). The program used for GC analysis was as follows: initial hold at 45° C. for 3 min; ramp to 50° C. at 5° C./min and hold for 3 min; ramp to 300° C. at 100° C./min and hold for 3 min. Helium was used as the carrier gas and ran at a constant pressure of 7.14 psi. The injector was maintained at 250° C. and the ion source temperature was set to 230° C. The injection volume was 1.0 µL in splitless mode.

Relevant GC peaks were identified by comparing with the retention times and mass spectra of fatty-acyl methyl ester standards and/or comparison of mass spectra with published data (NIST/EPA/NIH Mass Spectral Library Version 2.0g). Data analysis was performed using Agilent Enhanced Data Analysis and MassFinder 4 (Dr. Hochmuth Scientific Consulting) software.

Establishment of a pathway for the production of dicarboxylic acid (DCA) is essential for the production of muscone and muscone precursors in yeast, specifically hexadecanedioic. Expression of heterologous and species specific P450 monooxygenases and their corresponding reductase allow for the synthesis of hexadecanedioic acid from palmitic acid.

Example 3: Analysis of DCA and DCA-CoA

In Vivo Samples

Following in vivo production of DCA and DCA-CoA molecules, fatty acid chain length and concentration was analyzed. Final $OD_{600}$ of a 1:50 dilution was measured and cells equivalent to 100 OD units were harvested. DCA and DCA-CoAs were extracted by adding 500 µl of methanol to the pellet and incubating this suspension for 10 minutes at 60° C. After centrifugation at 4000 g for 5 minutes, the supernatant was subjected to UPLC-MS analysis.

In Vitro Samples

Following in vivo production of DCA and DCA-CoA molecules, fatty acid chain length and concentration was analyzed. 100 µl in vitro assay samples were extracted by adding 100 µl methanol. Supernatant was recovered by quick centrifugation at 12000× g and placed in injection vials prior to analysis.

Example 4: Qualitative Analysis of Long Chain Branched and Unbranched Fatty Acid Methyl Esters from In Vivo Samples Several long chain branched and unbranched fatty acid methyl ester molecules were produced. To determine the types of fatty acids produced, analysis was conduction on in vivo samples. Final $OD_{600}$ of a 1:50 dilution was measured and yeast cells equivalent to 100 OD units were harvested by centrifuging at 6000 rpm for 10 min. The supernatant was discarded. 1 mL 10% hydrochloric acid-methanol (v/v) was added to the remaining cell pellet, vortexed for 1 min and incubated at 62° C. for 3 hours to methylate the FAs. After cooling to room temperature, the reaction mixture was centrifuged for 4 min at 14 k rpm. The cell pellet was removed and the resulting fatty acid methyl esters were subsequently extracted (twice) from the supernatant by vortexing for 1 min with 1 mL hexane. The top organic phases were removed and combined, washed with 1 mL of MQ-water and dried over sodium sulphate.

The organic extracts were then subjected to gas chromatography/mass spectrometry (GC/MS) analysis using an Agilent 7890A GC system with an Agilent 5975C MSD and equipped with a Restek Rxi-5 ms column (25 m ×250 µm×0.25 µm). The program used for GC analysis was as follows: initial hold at 80° C. for 2 min; ramp to 200° C. at 100° C./min; ramp to 270° C. at 5° C./min; ramp to 300° C. at 100° C./min and hold for 3 min. Helium was used as the carrier gas and ran at a constant pressure of 7.14 psi. The injector was maintained at 250° C. and the ion source temperature was set to 230° C. The injection volume was 1.0 µL in splitless mode. Relevant GC peaks were identified by comparing with the retention times and mass spectra of fatty-acyl methyl ester standards and/or comparison of mass spectra with published data (NIST/EPA/NIH Mass Spectral Library Version 2.0g). Data analysis was performed using Agilent Enhanced Data Analysis and MassFinder 4 (Dr. Hochmuth Scientific Consulting) software.

Example 5: Qualitative Analysis of Short Chain Fatty Acid Methyl Esters from In Vivo Samples Yeast cells were harvested as described in Example 4. Pellets and supernatant were analyzed for the presence of short chain fatty acids (SCFA). Pellets were treated as described in Example 4. The supernatant was kept and 1 mL of supernatant was diluted with 1.1 mL of 10% hydrochloric acid-methanol (v/v), vortexed for 1 min and incubated at 62° C. for 3 hours to methylate the SCFAs. Methylation reaction supernatants were subsequently extracted (twice) by vortexing for 1 min with 1 mL hexane. The top organic phases were removed and combined, washed with 1 mL of MQ-water and dried over sodium sulphate. SCFA methyl esters in the organic phase were concentrated by evaporating the solvent using a gentle stream of nitrogen.

The organic extracts of pellet and supernatant were subjected to gas chromatography/mass spectrometry (GC/MS) analysis using an Agilent 7890A GC system with an Agilent 5975C MSD and equipped with a Restek Rxi-5 ms column 25 m×250 μm×0.25 μm). The program used for GC analysis was as follows: initial hold at 45° C. for 3 min; ramp to 50° C. at 5° C./min and hold for 3 min; ramp to 300° C. at 100° C./min and hold for 3 min. Helium was used as the carrier gas and ran at a constant pressure of 7.14 psi. The injector was maintained at 250° C. and the ion source temperature was set to 230° C. The injection volume was 1.0 μL in splitless mode. Relevant GC peaks were identified by comparing with the retention times and mass spectra of fatty-acyl methyl ester standards and/or comparison of mass spectra with published data (NIST/EPA/NIH Mass Spectral Library Version 2.0g). Data analysis was performed using Agilent Enhanced Data Analysis and MassFinder 4 (Dr. Hochmuth Scientific Consulting) software.

Example 6: α, ω-dicarboxylic Acid (DCA) Formation in Yeast Strains

DCA formation in the civetone, I- and nor-muscone pathways allow for the downstream production of civetone, I- and nor-muscone end products. A recombinant SC288C yeast strain was co-transformed with plasmids containing autonomously replicating sequences (ARS) and a yeast centromere (CEN) (ARS-CEN plasmid) with coexpression of different species specific genes encoding P450 monooxygenases (e.g., C. maltose CYP52A3-A (SEQ ID NO: 47; 41), C. maltosa CYP52A9, C. bombicola CYP52N1 (SEQ ID NO:48; 42), C. tropicalis CYP52A1 (SEQ ID NO:50; 44), and C. tropicalis CYP52A17 (SEQ ID NO:51; 45)) and their corresponding reductases (C. maltose NCP1, S. bombicola NCPI, C. tropicalis NCPI ((SEQ ID NO:52; 46), and S. bombicola CPR (SEQ ID NO:49; 43)) (Table 1). The genes were under the control of a constitutive promoter, glycerol-3-phosphate dehydrogenase-1 GPD1.

In parallel to the production of the yeast strain containing the genes encoding the enzymes above, a recombinant yeast strain was engineered which contained a pox1Δ0 deletion. The pox1Δ0 deletion in the yeast diminished β-oxidation of the muscone precursors.

Selective SC media without supplementation of Leucine (LEU) or Uracil (URA), containing 2% glucose was used for culturing the yeast for the formation of dicarboxylic acid. Cultures were then grown for 24 hours in 250 mL shake flasks without baffles and cell pellet extracts were analyzed using LC/MS as described above.

Civetone may also be produced using the following yeast strains:

EVST26088; EVST27922; EVST26088/pEV25942/pEV24136 (FAS1 wt; FAS2 wt) cl.1;

EVST26088/pEV25942/pEV24136 (FAS1 wt; FAS2 wt) cl.2;
EVST26088/pEV25942/pEV24136 (FAS1 wt; FAS2 wt) cl.3;
EVST26088/pEV25944/pEV24136 (fas1 mut2; FAS2 wt) cl.1;
EVST26088/pEV25944/pEV24136 (fas1 mut2; FAS2 wt) cl.2;
EVST26088/pEV25944/pEV24136 (fas1 mut2; FAS2 wt) cl.3;
EVST26088/pEV25946/pEV24136 (fas1 mut4; FAS2 wt) cl.1;
EVST26088/pEV25946/pEV24136 (fas1 mut4; FAS2 wt) cl.2;
EVST26088/pEV25946/pEV24136 (fas1 mut4; FAS2 wt) cl.3;
EVST27922/pEV25942/pEV24136 (FAS1 wt; FAS2 wt) cl.1;
EVST27922/pEV25942/pEV24136 (FAS1 wt; FAS2 wt) cl.2;
EVST27922/pEV25942/pEV24136 (FAS1 wt; FAS2 wt) cl.3;
EVST27922/pEV25944/pEV24136 (fas1 mut2; FAS2 wt) cl.1;
EVST27922/pEV25944/pEV24136 (fas1 mut2; FAS2 wt) cl.2;
EVST27922/pEV25944/pEV24136 (fas1 mut2; FAS2 wt) cl.3;
EVST27922/pEV25946/pEV24136 (fas1 mut4; FAS2 wt) cl.1;
EVST27922/pEV25946/pEV24136 (fas1 mut4; FAS2 wt) cl.2; and
EVST27922/pEV25946/pEV24136 (fas1 mut4; FAS2 wt) cl.3
(see e.g., yeast strains listed in Tables 3a and 3b).

DCA Formation in Yeast Controls

Figure 2:
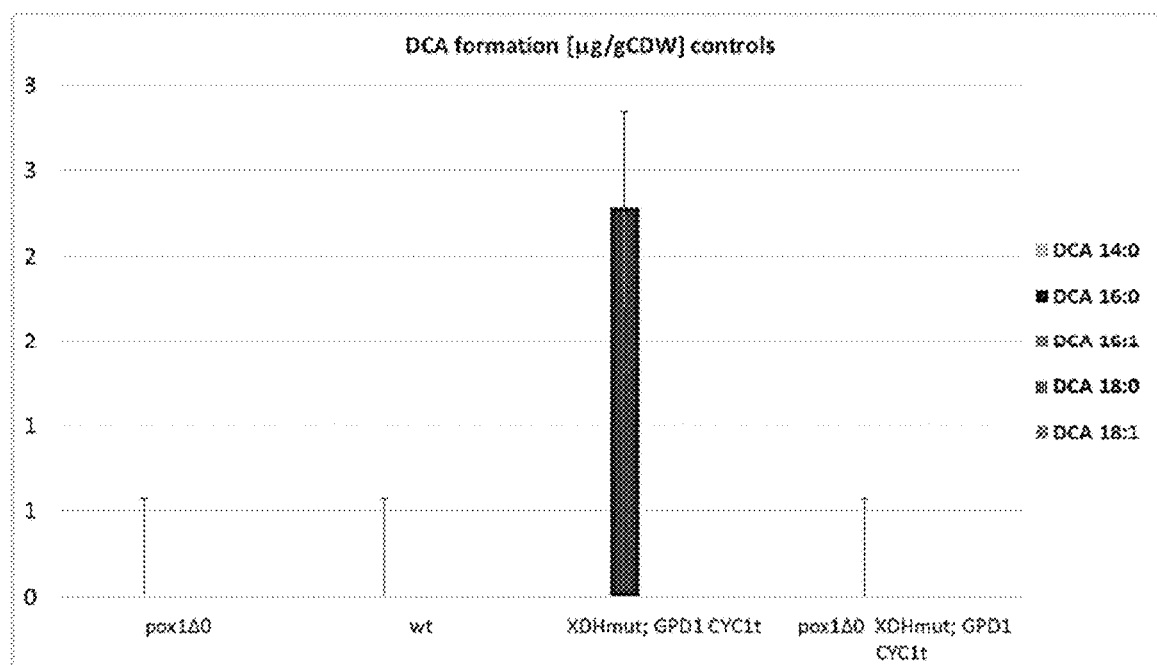
FIG. 2 shows dicarboxylic acid (DCA) formation in *S. cerevisiae* strains expressing only endogenous P450 monooxygenases.

DCA formation was observed in a single instance out of multiple experiments just at the edge of detection limits in control yeast strains with a pox1Δ0 deletion, wildtype, xanthine dehydrogenase (XDH) mut GPD1 CYClt, or a pox1Δ0 deletion and XDH mut GPD1 CYClt. This result is believed to be a false positive and is not considered significant compared to strains consistently producing 200 times greater DCA than the false positive reading. The highest DCA 16:0 formation was seen in the yeast strain expressing XDH mut GPD1 CYClt (2.7 μg/gCDW), while undetectable amounts of DCA was observed in the other conditions (FIG. 2).

DCA Formation in Yeast Expressing C. tropicalis CYP52 Genes

Figure 3:
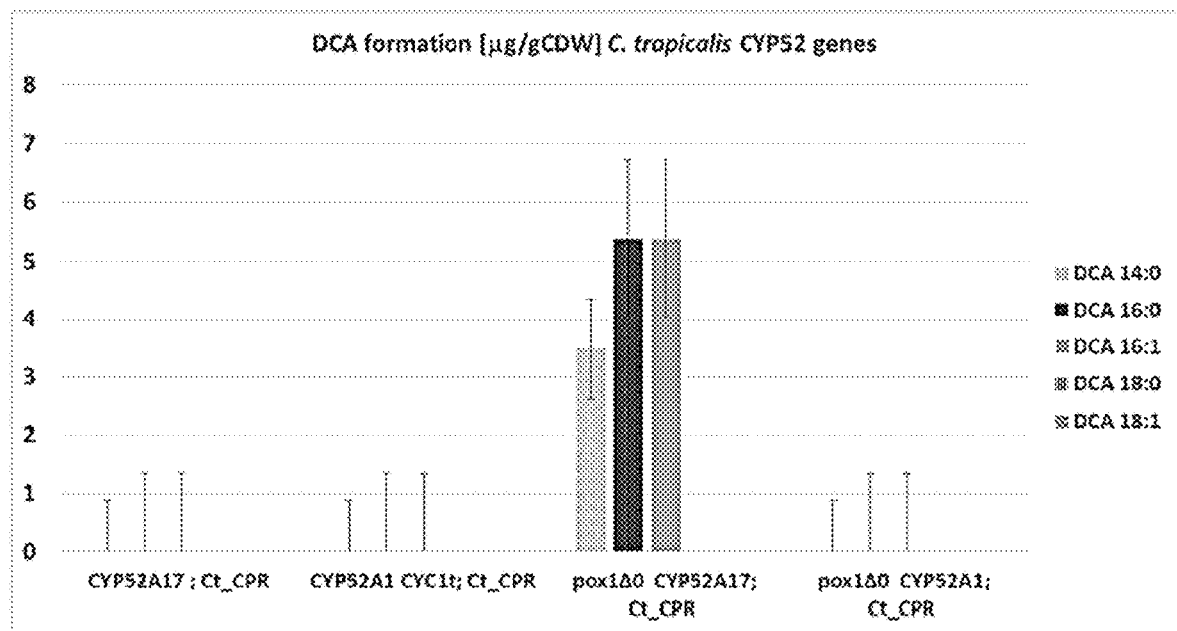
FIG. 3 shows DCA formation in *S. cerevisiae* strains expressing *C. tropicalis* cytochrome p450 (CYP52) genes.

Expression of the various genes encoding the P450 monooxygenases in Table 1 resulted in different levels of DCA formation. DCA formation in yeast engineered with a pox1Δ0 deletion, and C. tropicalis CYP52 genes (CYP52A17 or CYP52A1) and C. tropicalis_CPR genes produced the highest amount of DCA 14:0, DCA 16:0 (hexadecanedioic acid), and DCA 16:1 fatty acids. There was little to no expression of other DCAs; DCA 18:0 (octadecanedioic) and DCA 18:1 (octadecenedioic acid). The yeast strain with a pox1Δ0 deletion and expressing CYP52A17 and its corresponding reductase produced less than 5 μg/gCDW of DCA 14:0, DCA 16:0, and DCA 16:1. Undetectable amounts of DCAs were seen in other conditions (FIG. 3).

DCA Formation in Yeast Expressing S. bombicola CYP52 Genes

Figure 4:
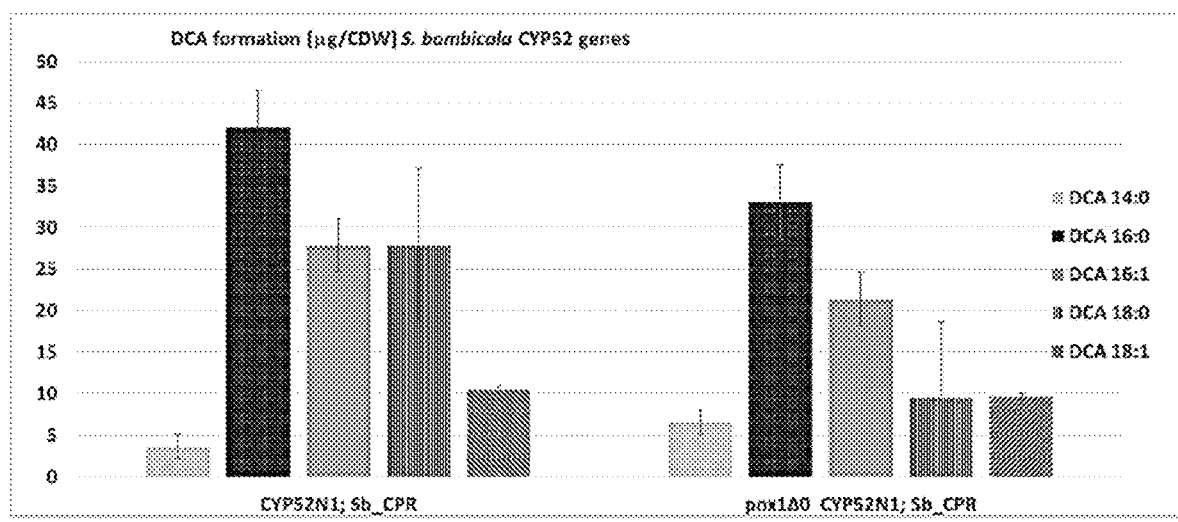
FIG. 4 shows DCA formation in *S. cerevisiae* strains expressing *S. bombicola* CYP52 genes.

DCA formation in yeast engineered with POX1 wildtype or pox1Δ0 deletion, S. bombicola CYP52 genes (CYP52N1) and S. bombicola_CPR resulted in the production of DCA 14:0, DCA 16:0, DCA 16:1, DCA 18:0, DCA 18;1. Yeast strains engineered with and without a deletion of pox1Δ0 both exhibited increased production of DCA 16:0 (~40 μg/CDW and 32 μg/CDW, respectively) followed by the formation of DCA 16:1 (~28 μg/CDW and ~20 μg/CDW, respectively). Formation of DCA 14:0 in both yeast strains was ~5 μg/CDW (FIG. 4).

DCA Formation in Yeast Expressing C. maltosa CYP52 Genes

Figure 5:
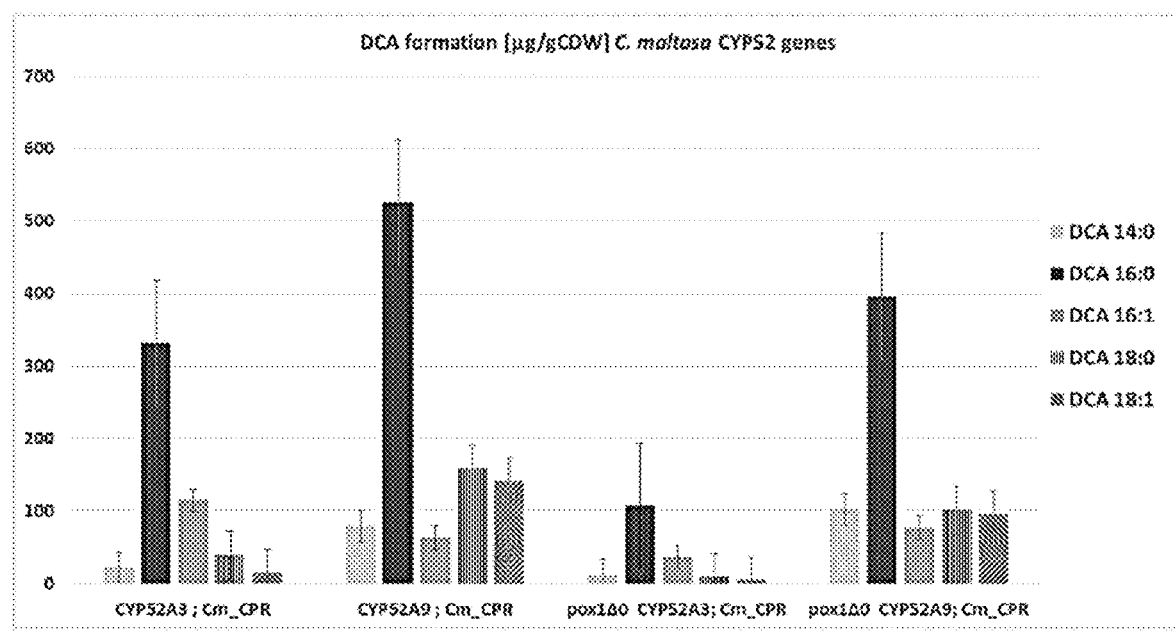
FIG. 5 shows DCA formation in *S. cerevisiae* strains expressing *C. maltosa* CYP52 genes.

DCA formation in yeast engineered with POX1 wildtype or pox1Δ0 deletion, C. maltosa CYP52 genes (CYP52A3 or CYP52A9), and C. maltosa_CPR resulted in the production of DCA 14:0, DCA 16:0, DCA 16:1, DCA 18:0, DCA 18;1. DCA 16:0 was the highest under each condition. Co-expression of CYP52A3 and Cm_CPR produced ~300 μg/gCDW of DCA 16:0, CYP52A9 and Cm_CPR produced ~500 µg/gCDW. Under pox1Δ0 deletion, co-expression of CYP52A3 and Cm_CPR resulted in the predominant formation of ~100 µg/gCDW of DCA 16:0 and co-expression of CYP52A9 and Cm_CPR resulted in the formation of ~400 µg/gCDW of DCA 16:0 (FIG. 5).

DCAs C16:0, C17:0 ante iso, and C18:1 may be the preferable DCAs for the production of nor-muscone, l-muscone and civetone, respectively.

Example 7: DCA Pathway Integrated in *S. cerevisiae*

To produce various DCAs, the DCA pathway can be integrated into yeast, for example *S. cerevisiae*. The production of DCA16:0 (hexadecanedioic acid) is the upstream molecule needed for the downstream production of muscone.

CYP52A9 and reductase genes were cloned into stable yeast integration vector harboring a bidirectional expression cassette. The P450 monooxygenase (CYP52A9) was driven by a TEF1 promoter while expression of CPR was driven by a PGK1 promoter. The expression cassette contained flanking regions for specific integration into the yeast genome. Yeast cells were selected for positive clones where the homologous sequences targeted the construct to the appropriate locus in the genome. Stable integration was performed in both POX1 wildtype and pox1Δ0 deleted strains. Formation of hexadecanedioic acid was detected by LC-MS.

Figure 6A:
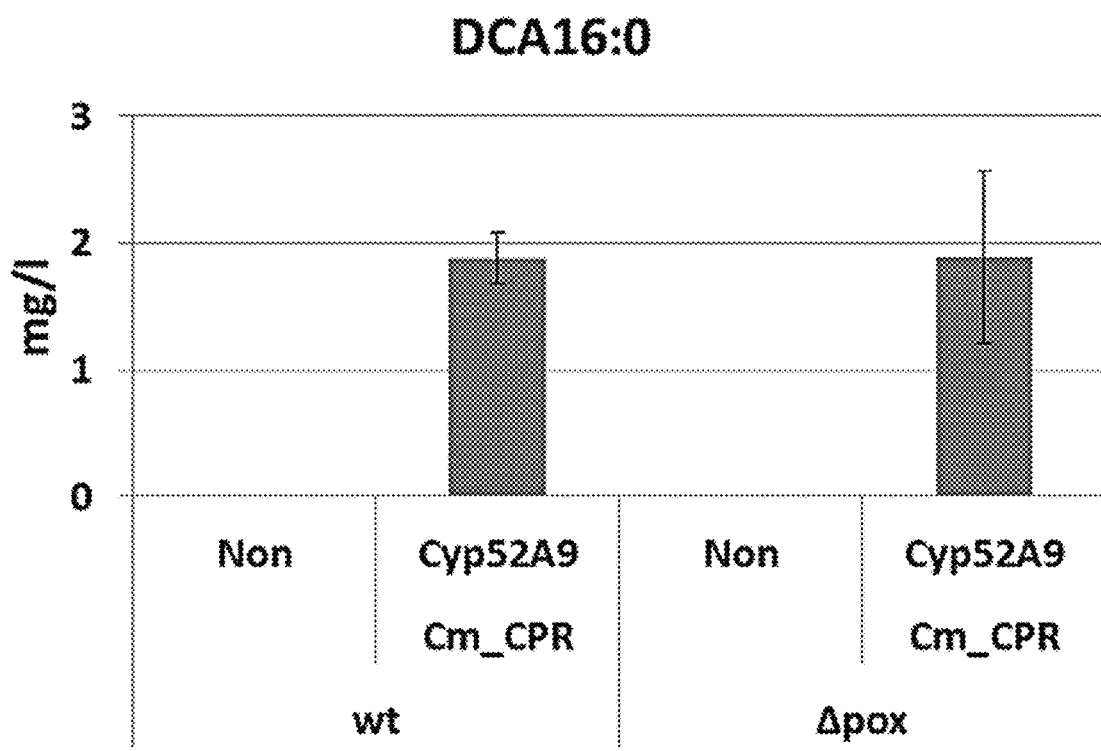
FIG. 6A shows DCA16:0 formation at 24 hours in mg/L in *S. cerevisiae*.
Figure 6B:
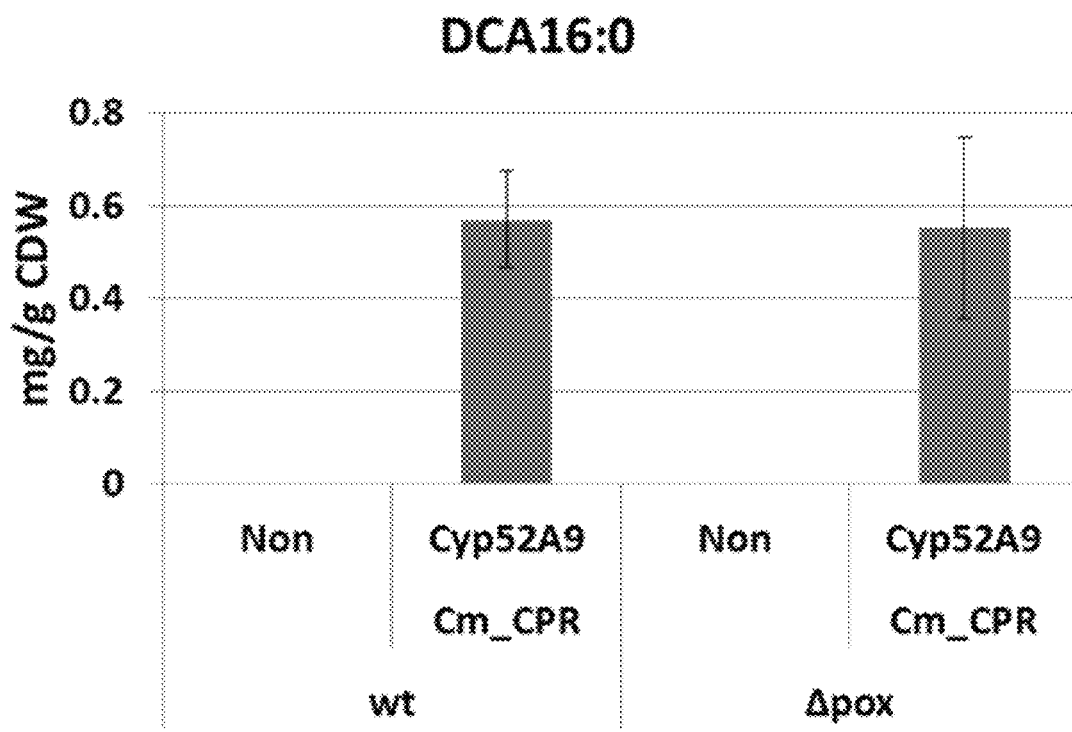
FIG. 6B shows DCA16:0 formation at 24 hours mg/g CDW in *S. cerevisiae*.

DCA pathway integration was functional as evidence by the production of hexadecanedioic acid. POX1 wt and pox1Δ0 deleted yeast strains integrated with CYP52A9 and Cm_CPR produced ~1.75 mg/L and ~0.55 mg/gCDW of hexadecanedioic acid (FIG. 6).

Example 8: CoA Activation of DCA

A dicarboxylic acid molecule must be CoA activated in order to be utilized as a substrate for the formation of l- and nor-muscone production. Synthesis of hexdecanedioic acid-CoA from hexadecanedioic acid requires activation with a CoA molecule.

The yeast strain which stably produced DCA was transformed additionally with an integrative plasmid harboring homologues flanking regions for genomic integration and a dominant selection marker. The integration construct constitutively expressed a cloned gene MCC028 of *Ondatra zibethicus* which was annotated to the murine Acyl CoA synthase ACBG1. The recombinant strain was then grown for 24 hrs at 30° C. in 250 mL shake flask cultures with selective medium. Cultures were then analyzed by LC-MS to evaluate the difference in DCA-CoA formation and compared to strains that expressed extrachromosomal CoA ligase in the same genetic background.

The DCA strain that expressed extrachromosomal MCC028 and the DCA strain with an integrated MCC028 produced the same amount of hexadecanedioic acid-CoA (~35,000 relative peak area) (FIG. 7).

TABLE 1

P450 Monooxygenase and Reductase genes.

| Enzyme (class) | Gene | Native Origin | Uniprot |
|---|---|---|---|
| P450 MO (1.14.14.—) | P450Cm1 (CYP52A3-A) | *Candida maltosa* | P16496 - CP52C_CANMA |
| P450 MO (1.14.14.—) | P450Alk5 (CYP52A9) | *C. maltosa* | Q12586 - CP52I_CANMA |
| CPR (EC: 1.6.2.4) | NCP1 | *C. maltodsa Starmerella bombicola* | P50126 - NCPR_CANMA |
| P450 MO (1.14.14.—) | CYP52N1 | *Candida bombicola* | B8QHP5 - B8QHP5_9ASCO |
| CPR (1.6.2.4) | CPR | *Starmerella bombicola* | A5Y0M3 - A5Y0M3_9ASCO |
| P450 MO (1.14.14.—) | P450alk1 (CYP52A1) | *C. tropicalis* | P10615 - CP52A_CANTR |
| P450 MO (1.14.14.—) | CYP52A17 | *C. tropicalis* | Q874I9 - Q874I9_CANTR |
| NADPH-CYP P450 reductases (1.6.2.4) | NCP1 | *C. tropicalis* | P37201 - NCPR_CANTR |

Example 9: Production of (S)-2-methylbutyryl-CoA in Yeast Strains

The formation of (S)-2-methylbutyryl-CoA from 2-methylbutyric acid by CoA ligase activity allows for a priming unit, or starting material, for the downstream fatty acid synthase (FAS) activity.

Recombinant POX1 wt and pox1Δ0 deletion-bearing *S. cerevisiae* strains for the production of Mono-Methyl-Branched Fatty Acids were engineered by incorporating recombinant genes encoding for Acyl CoA ligases either from *Humulus lupulus* (HICCL4) (hops) (SEQ ID NO:3) or *Solanum tuberosum* (StCCL) (potato) (SEQ ID NO:4). DCA producing yeast strains were transformed with extrachromosomal plasmids containing ARS-CEN plasmids and expression cassettes for the heterologous CoA ligases from HICCL4 (SEQ ID NO:3) or StCCL (SEQ ID NO:4). The genes in the ARS-CEN plasmid were placed under the control of the constitutive promoter TEF1. An additional selection marker for restoring leucine auxotrophy was added after transformation which allowed for the analysis of prototrophic strains.

Selective SC media without Leucine (LEU) supplement containing 2% glucose was used for culturing. Cultures were grown for 24 hours at 30° C. in 250 ml shake flask without baffles and cell pellet extracts have been analyzed. Formation of 2-(S)-methylbutyryl CoA was detected using LC/MS.

Figure 8:
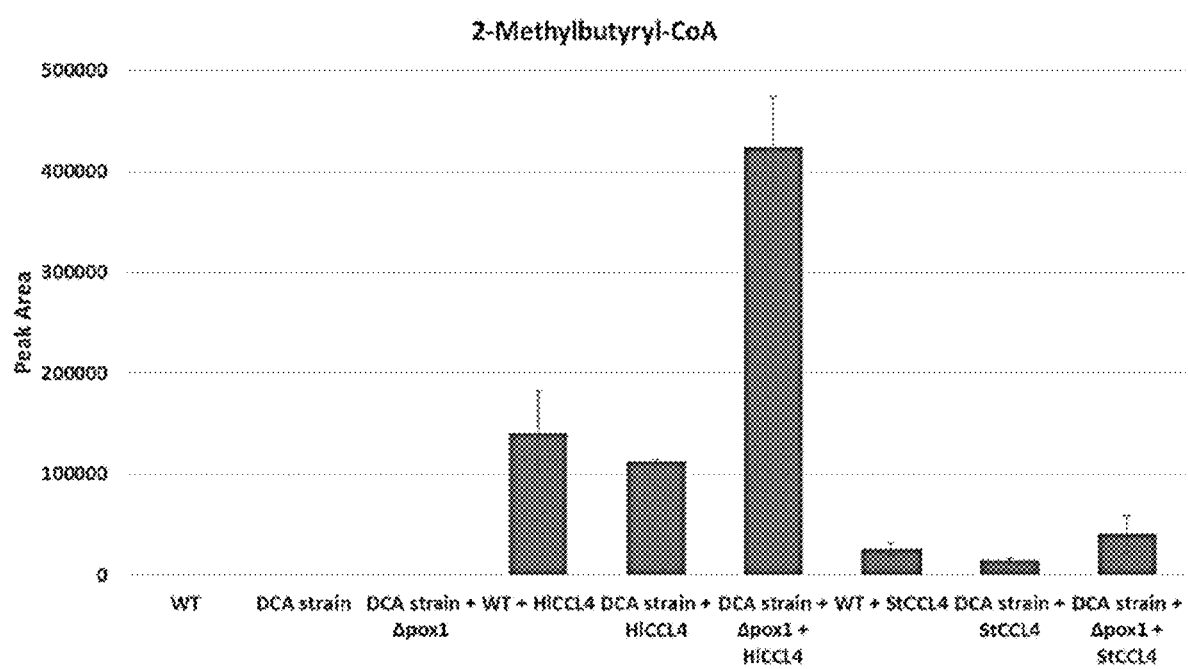
FIG. 8 shows (S)-2-methylbutyryl-CoA production in *S. cerevisiae* DCA producing strain expressing a *Humulus lupulus* (HICCL4) CoA ligase, and having a peroxisomal acyl-CoA oxidase (POX1) gene deletion.

The heterologous expression of CoA ligase from HICCL4 (SEQ ID NO:3) led to a significant production of the branched priming unit for a targeted synthesis of branched fatty acids in yeast. In contrast the in vivo expression of the ligase of StCCI (SEQ ID NO:4) in parallel was less effective. For example, the DCA producing strain with a pox1Δ0 deletion that expressed HICCL4 produced ~40,000 relative peak area 2-methylbutyryl-CoA while the strain that expressed StCCI produced less than 50,000 relative peak area of 2-methylbutyryl-CoA (FIG. 8).

Example 10: Engineering of a Stable (S)-2-Methylbutyryl-CoA Producing Yeast Strains The capability to produce 2-(S)-methylbutyryl CoA, which does not naturally occur endogenously in *S. cerevisiae*, was achieved by engineer a yeast strain which stably expresses these genes in a fas1 deleted background. The absence of FAS1 was the first step for further modifications and integrations of additional genes to establish a Mono-Methyl-Branched fatty acid building pathway in yeast.

HICCL4 (SEQ ID NO:3) and StCCI (SEQ ID NO:4) were cloned into expression cassettes of stable yeast integration vectors which contain constitutive TEF1 promoters and Eno2 terminators. These expression cassettes contained flanking regions for specific integration into the yeast genome by homologous recombination after transformation. Due to the presence of dominant selection markers, transformed yeast cells were selected for positive clones in which the homologous sequences targeted the integration construct to the appropriate locus in the genome. Analytical 250 ml shake flask screenings of the resulting strains and pox1Δ0 deleted derivatives was performed in media with selective conditions and confirmed the presence of the priming unit.

Restoration of FAS1 activity in fas1 mutants that stably expressed the CoA ligase from HICCL4 resulted in the production of 14-methylhexadecanoic acid (C17 anteiso FA). Specifically, the expression of fas1 mut 2 and FAS2 wt led to the highest formation of C17 anteiso FA (~0.31 mg/L) (FIG. 9; Table 2).

TABLE 2

C17:0 FA Species Distribution.

|  | 15-methylhexdecanoic acid (%) | 14-methylhexadecanoic acid (%) | Heptadecanoic acid (%) |
|---|---|---|---|
| FAS1 wt | 0.0 +/− 0.0 | 2.5 +/− 3.5 | 97.5 +/− 3.5 |
| FAS1 mut 2 | 7.1 +/− 0.6 | 62.0 +/− 1.6 | 30.9 +/− 2.2 |
| FAS1 mut 3 | 10.3 +/− 1.1 | 48.8 +/− 2.4 | 38.7 +/− 3.5 |
| FAS1 mut 4 | 7.3 +/− 0.5 | 54.0 +/− 2.2 | 38.7 +/− 1.7 |
| FAS1 mut 5 | 6.1 +/− 1.0 | 51.7 +/− 2.9 | 42.2 +/− 3.8 |

Example 11: Production of Monomethyl Branched Chain Fatty Acid (MMBCFA) in FAS1 Mutant Yeast Yeast strains with a fas1 deleted background generating 2-(S)-methylbutyryl CoA as a priming unit for the route of odd chain fatty acid synthesis were chosen for introduction of several plasmids harboring in silico designed S. cerevisiae fatty acid synthase mutants. Modifications of the FAS1 gene were conducted to evaluate the best acceptance and binding properties of the alternative priming unit and the ability to produce FFA C17:0.

Specific amino acid sequences of the yeast FAS1 were defined in which mutations were introduced by PCR. The appropriate recombinant strains capable to produce the odd chain priming unit were transformed with a series of extra-chromosomal 2 micron plasmids encoding GPD1 driven yeast fatty acid synthase wildtype (SEQ ID NO:5) or the FAS1 mutants fas1 mut (I483A) (SEQ ID NO:6), fas1 mut 2 (F427A), (SEQ ID NO:7), fas1 mut 3 (F427A, I483A), (SEQ ID NO:8), fas1 mut 4 (I234A F427S), (SEQ ID NO:9), fas1 mut 5 (Q163A F427A), (SEQ ID NO:10), fas1 mut 6 (I306A), (SEQ ID NO:11) and fas1 mut 7 (I306A I483A), (SEQ ID NO:12). All mutant variants were co-transformed with a 2 micron plasmid encoding FAS2 wt under the control of the same constitutive promoter to ensure that sufficient supply of synthesized fatty acids was generated. Subsequent selection was performed for the transformed markers, such that Histidine and Leucine prototrophic strains allowed isolation of the positive clones. Additionally 1 mM myristic acid was added to the media to support growth and selection of the transformed cells because the fas1 null phenotype perse exhibited severe inhibitory (lethal) effects on cell growth.

Screening under selective conditions allowed for characterization and isolation of the best performing fas1 mutant in respect to production of odd chain fatty acids. For this, 250 ml shake flask cultures with appropriate selection media were grown for 24 hours at 30° C. and subsequently analyzed by LC/MS. S. cerevisiae strains that expressed these modified FAS1 mutants were able to utilize the endogenously produced 2-methylbutyryl-CoA to form different levels of FFA C17:0. The detection of these odd chain FA in LC/MS and the distribution of diverse species were characterized in detailed by GC-analysis (Table 3).

Three species of C17:0 were identified from GC-analysis. The expression of FAS1 mut2 resulted in the highest production of 14-methylhexadecanoic acid (~62%), while FAS1 wt expression led to the lowest production of 14-methylhexadecanoic acid (~2.5%) (FIG. 10).

Example 12: Stable DCA Pathway Integration in S. cerevisiae Strains Producing Monomethyl Branched Chain Fatty Acids (MMBCFA)

To produce MMBCFAs, a DCA-producing pathway was integrated into S. cerevisiae. A combination of P450 monooxygenase/reductase complex and fas 1 mutants was incorporated into the yeast strain to produce significant amounts of DCAs.

Earlier identification of a suitable cytochrome P450 monooxygenase/reductase complex of the CYP52 family was used to engineer S. cerevisiae strains with the best performing fas1 mutants (fas1 mut 2 (F427A), (SEQ ID NO:7) and fas1 mut 4 (I234A F427S), (SEQ ID NO:9)), producing highest amounts of 3-Methylhexadecanedioic acid. Therefore the Cyp52A9 genes (SEQ ID NOs:1; 21) were cloned into a stable yeast integration vector harboring the bidirectional expression cassette whereby the P450 Monooxygenase is placed under the control of a TEF1 promoter and a PGK1 promoter drives the expression of the reductase Cm_CPR. Recombinant yeast strains stably producing 14-Methylhexadecanoic acid were then transformed with the integrative plasmid. The expression cassette contained flanking regions for a specific integration into the yeast genome by homologous recombination after transformation. Due to the presence of a selectable marker on the construct, yeast cells were then selected for positive clones in which the homologous sequences targeted the integration construct to the appropriate locus in the genome.

Analytical 250 ml shake flask screenings with the resulting strains were performed and the formation of methyl branched hexadecanedioic acid was detected by LC/MS (see FIG. 10) and investigated in more detail using GC analysis (see Table 3a and 3b).

Figure 11:
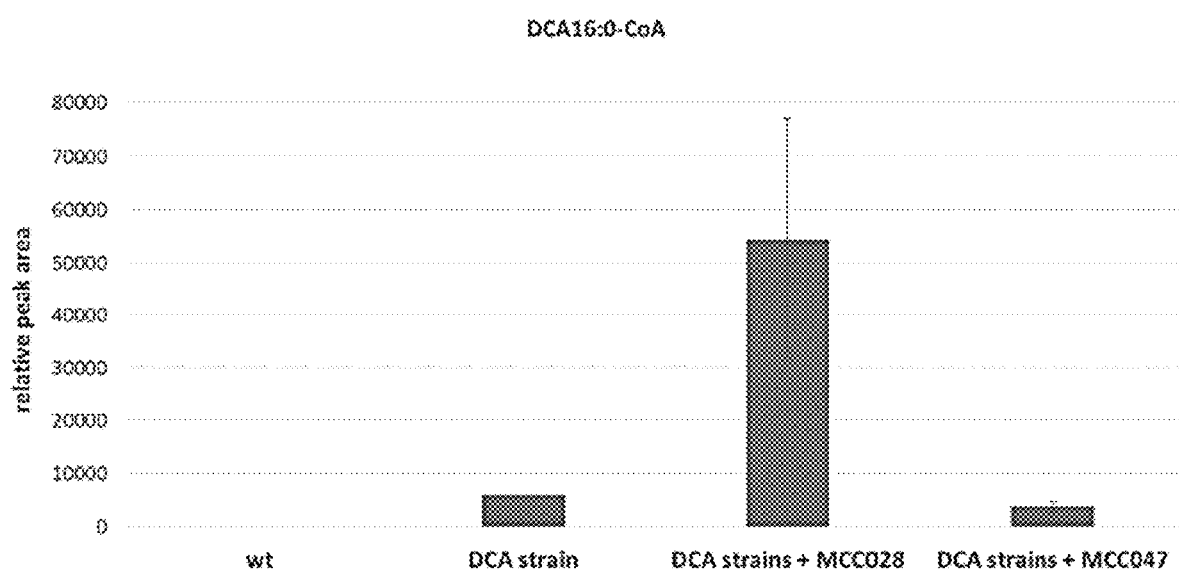
FIG. 11 shows hexadecanedioic acid-CoA production in a *S. cerevisiae* strain expressing genes encoding acyl-CoA synthases.

Fas1 mut4/FAS2 expression in a stable HICCL4 and CYP52A9 expressing yeast strain produced the highest amount of DCA 17:0 (~0.40 µg/OD600), while expression of fas1 mut2/FAS2 produced ~0.37 µg/OD600 of DCA 17:0 (FIG. 11).

TABLE 3a

GC Analysis of DCA from Methyl Branched Hexadecanedioic Acid Producing Yeast Strain

| | DCA C18:0 n | DCA C18:1 n | DCA C18:0 iso' | DCA C17:0 n | DCA C17:0 anteiso' | DCA C17:0 iso' | DCA C16:0 n | DCA C16:0 iso' | DCA C15:0 n | DCA C14:0 n | DCA C12:0 n |
|---|---|---|---|---|---|---|---|---|---|---|---|
| branching | none | none | 2-Me | none | 3-Me | 2-Me | none | 2-Me | none | none | none |
| r.t | 13,279 | 12,936 | 12,385 | 12,005 | 11,23 | | 10,786 | 9,984 | 9,658 | 8,641 | 6,988 |
| RI | 2458 | 2431 | 2387 | 2354 | 2294 | | 2255 | 2184 | 2153 | 2053 | 1849 |
| r.t. | 33,892 | 33,293 | 31,255 | 29,469 | 26,073 | 25,816 | 24,195 | 20,959 | 19,574 | 15,653 | 10,102 |
| RI | 2479 | 2453 | 2386 | 2353 | 2290 | 2285 | 2252 | 2184 | 2151 | 2049 | 1848 |
| EVST26088 | | | | | | | | | | | |
| EVST27922 | | | | | | | | | | | |
| EVST26088/pEV25942/pEV24136 (FAS1 wt; FAS2 wt) cl.1 | | | | | | | | | | | |
| EVST26088/pEV25942/pEV24136 (FAS1 wt; FAS2 wt) cl.2 | | | | | | | | | | | |
| EVST26088/pEV25942/pEV24136 (FAS1 wt; FAS2 wt) cl.3 | | | | | | | | | | | |
| EVST26088/pEV25944/pEV24136 (fas1 mut2; FAS2 wt) cl.1 | | | | | | | | | | | |
| EVST26088/pEV25944/pEV24136 (fas1 mut2; FAS2 wt) cl.2 | | | | | | | | | | | |
| EVST26088/pEV25944/pEV24136 (fas mut2; FAS2 wt) cl.3 | | | | | | | | | | | |
| EVST26088/pEV25946/pEV24136 (fas mut4; FAS2 wt) cl.1 | | | | | | | | | | | |
| EVST26088/pEV25946/pEV24136 (fas1 mut4; FAS2 wt) cl.2 | | | | | | | | | | | |
| EVST26088/pEV25946/pEV24136 (fas1 mut4; FAS2 wt) cl.3 | | | | | | | | | | | |
| EVST27922/pEV25942/pEV24136 (FAS1 wt; FAS2 wt) cl.1 | y | y | | | trace | | y | | y | y | y |
| EVST27922/pEV25942/pEV24136 (FAS1 wt; FAS2 wt) cl.2 | y | y | | | trace | | y | | y | y | y |

TABLE 3a-continued

GC Analysis of DCA from Methyl Branched Hexadecanedioic Acid Producing Yeast Strain

| | DCA C18:0 n | DCA C18:1 n | DCA C18:0 iso' | DCA C17:0 n | DCA C17:0 anteiso' | DCA C17:0 iso' | DCA C16:0 n | DCA C16:0 iso' | DCA C15:0 n | DCA C14:0 n | DCA C12:0 n |
|---|---|---|---|---|---|---|---|---|---|---|---|
| EVST27922/ pEV25942/ pEV24136 (FAS1 wt; FAS2 wt) cl.3 | y | y | | trace | | | y | | y | y | y |
| EVST27922/ pEV25944/ pEV24136 (fas1 mut2; FAS2 wt) cl.1 | y | y | y | y | trace | trace | y | y | y | y | |
| EVST27922/ pEV25944/ pEV24136 (fas1 mut2; FAS2 wt) cl.2 | y | y | y | y | trace | trace | y | y | y | y | |
| EVST27922/ pEV25944/ pEV24136 (fas1 mut2; FAS2 wt) cl.3 | y | y | y | y | trace | trace | y | y | y | y | |
| EVST27922/ pEV25946/ pEV24136 (fas1 mut4; FAS2 wt) cl.1 | y | y | y | y | trace | trace | y | y | y | y | |
| EVST27922/ pEV25946/ pEV24136 (fas1 mut4; FAS2 wt) cl.2 | y | y | y | y | trace | trace | y | y | y | y | |
| EVST27922/ pEV25946/ pEV24136 (fas1 mut4; FAS2 wt) cl.3 | y | y | y | y | trace | trace | y | y | y | y | |

"none" refers to no chain branching, i.e., straight carbon chain.

TABLE 3b

GC Analysis of FA from Methyl Branched Hexadecanedioic Acid Producing Yeast Strain

| | FA C18:0 n | FA C18:1 n | FA C18:1 n | FA C18:0 iso' | FA C17:0 n | FA C17:0 anteiso | FA C17:0 iso | FA C16:0 n | FA C16:1 n | FA C16:0 iso |
|---|---|---|---|---|---|---|---|---|---|---|
| branching | none | none | none | 16-Me | none | 14-Me | 15-Me | none | none | 14-Me |
| r.t. | 9,374 | 9,203 | 9,155 | 9 | 8,39 | 8,144 | 8,058 | 7,534 | 7,406 | 7,251 |
| RI | 2126 | 2110 | 2106 | 2090 | 2027 | 1999 | 1990 | 1999 | 1908 | 1887 |
| r.t. | 18,488 | 17,697 | 17,515 | 17,039 | 14,776 | 13,883 | 13,61 | 11,856 | 11,465 | 10,947 |
| RI | 2125 | 2107 | 2102 | 2090 | 2024 | 1998 | 1988 | 1924 | 1909 | 1888 |
| EVST26088 | y | | | | trace | | | y | (y) | |
| EVST27922 | y | | | | trace | | | y | (y) | |
| EV5T26088/ pEV25942/ pEV24136 (FAS1 wt; FAS2 wt) cl.1 | y | y | y | | y | | | y | y | |
| EVST26088/ pEV25942/ pEV24136 (FAS1 wt; FAS2 wt) cl.2 | y | y | y | | y | | | y | y | |

TABLE 3b-continued

GC Analysis of FA from Methyl Branched Hexadecanedioic Acid Producing Yeast Strain

| | FA C18:0 n | FA C18:1 n | FA C18:1 n | FA C18:0 iso' | FA C17:0 n | FA C17:0 anteiso | FA C17:0 iso | FA C16:0 n | FA C16:1 n | FA C16:0 iso |
|---|---|---|---|---|---|---|---|---|---|---|
| EVST26088/ pEV25942/ pEV24136 (FAS1 wt; FAS2 wt) cl.3 | y | y | y | | y | | | y | y | |
| EVST26088/ pEV25944/ pEV24136 (fas1 mut2; FAS2 wt) cl.1 | y | y | y | y | y | y | y | y | y | y |
| EVST26088/ pEV25944/ pEV24136 (fas1 mut2; FAS2 wt) cl.2 | y | y | y | y | y | y | y | y | y | y |
| EVST26088/ pEV25944/ pEV24135 (fas1 mut2; FAS2 wt) cl.3 | y | y | y | y | y | y | y | y | y | y |
| EVST26088/ pEV25946/ pEV24136 (fas1 mut4; FAS2 wt) cl.1 | y | y | y | y | y | y | y | y | y | y |
| EVST26088/ pEV25946/ pEV24136 (fas1 mut4; FAS2 wt) cl.2 | y | y | y | y | y | y | y | y | y | y |
| EVST26088/ pEV25946/ pEV24136 (fas1 mut4; FAS2 wt) cl.3 | y | y | y | y | y | y | y | y | y | y |
| EVST27922/ pEV25942/ pEV24136 (FAS1 wt; FAS2 wt) cl.1 | y | y | y | | y | | | y | y | |
| EVST27922/ pEV25942/ pEV24136 (FAS1 wt; FAS2 wt) cl.2 | y | y | y | | y | | | y | y | |
| EVST27922/ pEV25942/ pEV24136 (FAS1 wt; FAS2 wt) cl.3 | y | y | y | | y | | | y | y | |
| EVST27922/ pEV25944/ pEV24136 (fas1 mut2; FAS2 wt) cl.1 | y | y | y | y | y | y | trace | y | y | y |
| EVST27922/ pEV25944/ pEV24136 (fas1 mut2; FAS2 wt) cl.2 | y | y | y | y | y | y | trace | y | y | y |

TABLE 3b-continued

GC Analysis of FA from Methyl Branched Hexadecanedioic Acid Producing Yeast Strain

| | FA C18:0 n | FA C18:1 n | FA C18:1 n | FA C18:0 iso' | FA C17:0 n | FA C17:0 anteiso | FA C17:0 iso | FA C16:0 n | FA C16:1 n | FA C16:0 iso |
|---|---|---|---|---|---|---|---|---|---|---|
| EVST27922/ pEV25944/ pEV24136 (fas1 mut2; FAS2 wt) cl.3 | y | y | y | y | y | y | trace | y | y | y |
| EVST27922/ pEV25946/ pEV24136 (fas1 mut4; FAS2 wt) cl.1 | y | y | y | y | y | y | trace | y | y | y |
| EVST27922/ pEV25946/ pEV24136 (fas1 mut4; FAS2 wt) cl.2 | y | y | y | y | y | y | trace | y | y | y |
| EVST27922/ pEV25946/ pEV24136 (fas1 mut4; FAS2 wt) cl.3 | y | y | y | y | y | y | trace | y | y | y |

"none" refers to no chain branching, i.e., straight carbon chain.

Example 13: MCCO28 Expression Increased CoA Activation of DCAs

Increased produced of the upstream muscone intermediate DCA16:0-CoA can result in enhanced production of the final product, muscone.

DCA control yeast strains and DCA yeast strains expressing MCC028 or MCC047 (Acyl CoA synthases) were evaluated based on their ability to produce DCA16:0-CoA.

Figure 12:
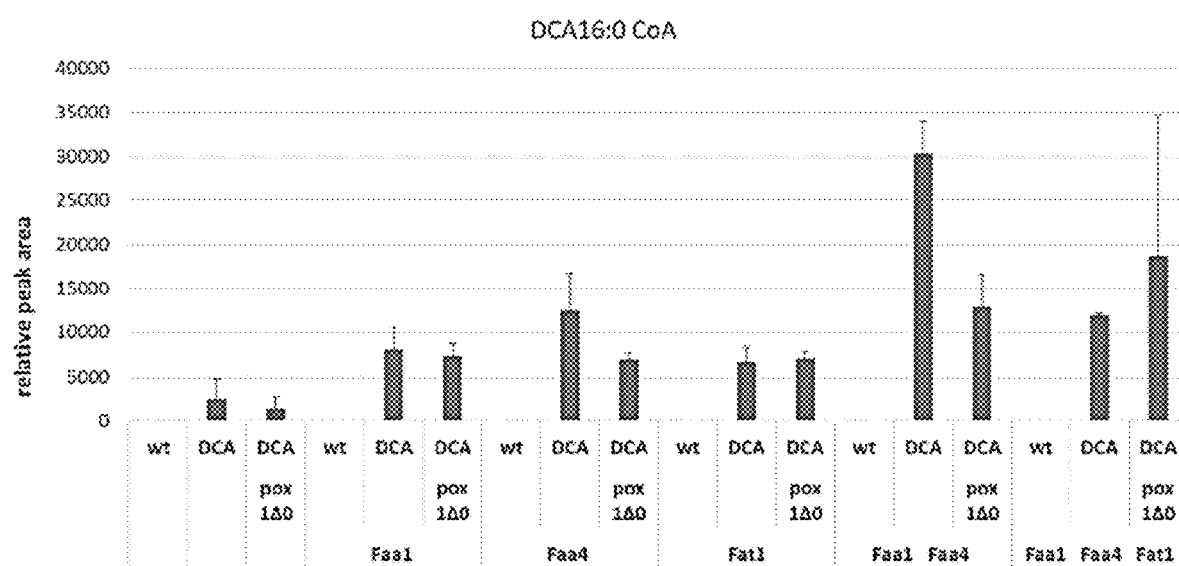
FIG. 12 shows dicarboxylic acid-CoA (DCA-CoA) production in a *S. cerevisiae* strain overexpressing endogenous acyl-CoA synthases.

DCA16:0 production in the wildtype control strain was undetectable, while the DCA strain expressing MCC047 and DCA strain alone produced similar amounts of DCA16:0-CoA (~5000 relative peak area). In contrast, when the DCA strain expressed MCC028, there was significant production of DCA16:0-CoA (~50,000 relative peak area). This was more than 10 times the production of DCA16:0-CoA observed in the other experiments detailed herein (FIG. 12).

Example 14: DCA Formation in Yeast Strains Overexpressing Endogenous Acyl-CoA Synthases There are four endogenous long chain acyl-CoA synthase enzymes in S. cerevisiae that are involved in import, activation and metabolism of fatty acids. Determining CoA activation of DCAs in yeast overexpressing endogenous yeast acyl-CoA synthases resulted in differing amounts of DCA 16:0-CoA.

Faa1, Faa4, or a combination of Faa1 and Faa4 were overexpressed in a wildtype yeast strain, a DCA control yeast strain, and a DCA with pox1Δ0 deletion yeast strain. DCA 16:0-CoA formation was highest in the DCA control yeast strain that co-expressed Faa1 and Faa4 (~30000 RPU).

Example 15: Qualitative and Chiral Analysis of Short Branched Chain Fatty Acid (SBCFA) Ethyl Esters in In Vivo Samples Because short branched chain fatty acids, such as (R) and (S)-2-methylbutyric acid, can be used as starting molecules to produce muscone, additional qualitative and chiral analysis was conducted to identify which chiral 2-methylbutyric acid samples produced the highest amounts of 2-methylbutyric acid ethyl ester.

5 μL of each ethyl ester standard was reacted with 500 μL 10% hydrochloric acid-ethanol (v/v). The reaction mixture was then shaken at 1500 rpm at 60° C. for 2 hours to ethylate the SBCFAs. 600 μl n-hexane were added followed by the addition of 600 μl of saturated $KHCO_3$ solution in MQ water. The samples were then vortexed for 1 minute and the organic layer was pipetted off and the extraction was repeated using 600 μl n-hexane. The combined organic phases were washed with 600 μl in MQ water, then pipetted off and dried over sodium sulphate.

Approximately 40 ml of yeast (FAS1 WT cl.2) culture supernatant were extracted twice with 10 ml of ethyl acetate. The organic solvent was collected, dried over sodium sulphate and evaporated using a gentle stream of nitrogen while the sample was cooled by means of an ice bath in order to minimize loss of volatile SBCFA. 500 μl 10% hydrochloric acid-ethanol (v/v) was added to the supernatant extract and the samples were treated as described above.

Yeast (FAS1 WT cl.2) pellets, corresponding to 100 OD units (at 600 nm), were collected. Yeast cells were ruptured using 1 ml ethanol and shaking at 1500 rpm for 1 hour at 60 C. Cell fragments were centrifuged off (14000 rpm, 4 min) and the ethanolic supernatant was collected. 100 μl hydrochloric acid (37%) was added to the pellet extract and the mixture was reacted and treated as described above in Example 5.

The derivatised standard samples and organic extracts of pellet and supernatant were then subjected to gas chromatography/mass spectrometry (GC/MS) for achiral quality control analysis using an Agilent 7890A GC system with an Agilent 5975C MSD equipped with a Restek Rxi-5 ms column 25 m×250 μm×0.25 μm). The program used for GC analysis was as follows: initial hold at 45° C. for 3 minutes; ramp to 50° C. at 5° C./minute and hold for 3 min; ramp to 300° C. at 100° C./min and hold for 3 min. Helium was used as the carrier gas and ran at a constant pressure of 7.14 psi. The injector was maintained at 250° C. and the ion source temperature was set to 230° C. The injection volume was 1.0 μl in splitless mode. Relevant GC peaks were identified by comparing with the retention times and mass spectra of fatty-acyl methyl ester standards and/or comparison of mass spectra with published data (NIST/EPA/NIH Mass Spectral Library Version 2.0g). Data analysis was performed using Agilent Enhanced Data Analysis and MassFinder 4 (Dr. Hochmuth Scientific Consulting) software.

After quality control, derivatised samples were then subjected to chiral gas chromatography using an Shimadzu GC-2010 GC system with a flame ionization detector (FID) equipped with a Restek Rt-β-DEX325 column (30 m×0.25 mm I.D.×0.25 μm). The program used for GC analysis was as follows: initial hold at 50° C. for 1 minute; ramp to 55° C. at 0.20° C./minute; ramp to 100° C. at 3.00° C./minute; ramp to 250° C. at 60° C./minute and finally hold at 250° C. for 1 minute. Helium was used as the carrier gas (column inlet pressure: 100.0 kPa). The injector was held at 250° C. The flame ionization detector (FID) was kept at 250° C. (H$_2$ flow: 40 ml/minute, Make up: 30 ml/minute (N2), Air flow: 400 ml/minute).

From quantification of (S) and (R)-2-Methylbutyric acid ethyl esters the enantiomeric purity (% ee) was calculated (Table 4). The measured values for (S)-2-Methylbutyric acid ethyl ester showed at least 80% ee in the yeast supernatant, specifically, 84.8%, and 77.4% for yeast pellet.

TABLE 4

Enantiomeric Purity of Short Branched Chain Fatty Acid

| Chiral GC Samples | Relative amount (%) | | |
|---|---|---|---|
| | (R)-2-Methylbutyric acid ethyl ester | (S)-2-Methylbutyric acid ethyl ester | % ee |
| 50/50 Racemic mixture of (S) and (R)-2-Methylbutyric acid | 49.9 | 50.1 | 0.2 |
| (S)-2-Methylbutyric acid | 0.5 | 99.5 | 99 |
| Yeast supernatant | 7.6 | 92.4 | 84.8 |
| Yeast pellet | 11.3 | 88.7 | 77.4 |

Example 15: Production of L-Muscone from (R)-(+)-3-methylhexadecanoic Acid

Several methods are known for producing macrocylic compounds, such as muscone, from dicarboxylic acids, such as described in Terunuma et al. (J. Org. Chem., Vol 52, No.8 1987,1630-1632). One such method is the Dieckmann condensation reaction. By careful provision or selection of specific dicarboxylic substrates in the condensation reaction, various species of valuable macrocyclic ketones can be produced.

A solution of (R)-(+)-3-methylhexadecanedioic acid in absolute ethanol is refluxed for 1-6 hours in the presence of POCl$_3$ to afford the ethyl ester. After evaporation of the solvent, a suitable solvent such as diethyl ether, ethyl acetate or dichloromethane is added to the residue and the obtained solution is washed with a NaHCO$_3$ saturated aqueous solution and water. The solution is then dried with Na$_2$SO$_4$ or MgSO$_4$ prior to evaporation. Pure (R)-(+)-Diethyl 3-Methylhexadecanoate is obtained by flash chromatography or distillation.

A Dieckmann cyclization of (R)-(+)-Diethyl 3-methylhexadecanoate is carried out under a nitrogen atmosphere by using a high-dilution method in the presence of [(CH$_3$)$_3$Si]$_2$NLi (LiHMDS) or [(CH$_3$)$_3$Si]$_2$NNa (NaHMDS). A modified version of the apparatus of Leonard et al. is employed (J. Am. Chem. Soc. 1952, 74, 1704) to achieve high dilution. A solution of (R)-(+)-Dimethyl 3-Methylhexadecanoate in dry tetrahydrofurane (THF) is then added to a gently refluxing solution of [(Me$_3$Si)$_2$NNa] or [(Me$_3$Si)$_2$NLi] in dry THF over a period of 4-8 hours, with vigorous stirring under inert atmosphere. After this addition is complete, the mixture is refluxed for an additional 0.25-3 hours. After the addition of acetic acid to the mixture, the solution is washed with water and then dried over Na$_2$SO$_4$ or MgSO$_4$. Evaporation and isolation of the products with thin layer chromatography or flash chromatography produces a mixture of ethyl (4R)-4-methyl-2-oxocyclopentadecane-1-carboxylate and ethyl (2R)-2-methyl-15-oxocyclopentadecane-1-carboxylate.

A mixture of ethyl (4R)-4-methyl-2-oxocyclopentadecane-1-carboxylate and ethyl (2R)-2-methyl-15-oxocyclopentadecane-1-carboxylate, Me$_2$SO$_4$, and water is maintained for 2-8 hours under an inert atmosphere at 140-186° C. with agitation (Tetrahedron Letters, 1973, No. 12, pp 957-960). After cooling, water is added to the mixture and the mixture is extracted with a hydrocarbon solvent such as pentane, heptane or cyclohexane. The combined extracts are then dried over Na$_2$SO$_4$ or MgSO$_4$. Evaporation and isolation by distillation or flash chromatography results in the production of l-muscone.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention (FIG. 13).

TABLE 4

Sequences disclosed herein.

Candida maltosa

SEQ ID NO: 1

```
atgatcgacg aaatcttgcc aaagttggtc caatactggt atatcgtttt gccaaccttg    60
ttgatcatca agcacgttgt ttcttacatc aacacccaaa gattgatgag aaagtttaga   120
gccaagccag ttaccaacgt tttgaatgat ggtttcttcg gtattccaaa cggtatcaag   180
gctatcaaag aaaagaacaa aggtagagcc caagaataca acgacgaaaa atttgctgct   240
ggtccaaaac ctaaagtcgg tacttatttg ttcaagttgt tcaccaagga tgtcttggtt   300
accaaagatc cagaaaacat taaggctatt ttggccaccc aattcgaaga tttttcattg   360
ggtaagagat tggacttctt caagccatta ttgggttacg gtattttcac cttggatggt   420
gaaggttgga aacattctag agctatgtta agaccacaat tcgccagaga caagttggt    480
catgttaagt tgattgaacc acacttccaa tcttttgaaga agcacatcat taagaacaag   540
ggtcaattct tcgacatcca agaattattc ttcagattca ccgttgattc cgccaccgaa   600
```

TABLE 4-continued

Sequences disclosed herein.

```
ttttttgtttg gtgaatcagt tgaatccttg aaggacgaat ctatcggtta tgaccaacaa    660
gactttgatt tcgacggtag aaagaatttt gctgaagcct ttaacaaggc tcaagaatac    720
ttgggtacta gagcaatctt gcaatctttc tactggttgg ttaatggtgc cgatttcaaa    780
aagtctgttg ccgaagttca taagttcacc gattactatg ttcaaaaggc tttggatgct    840
accccagaag aattggaaaa acattccggt tacatttttct tgtacgaatt ggtccaacaa    900
accagagatc caaaggtttt gagagatcaa tcattgaaca ttttgttggc cggtagagat    960
acaactgctg gtttattgtc tttcgccttg tttgaattgg ctagaaatcc agaagtttgg   1020
tccagattga gagaagaaat tggtgataag ttcggtttgg atgaagatgc taccatcgaa   1080
ggtatttctt tcgaatcctt aaagcaatgc gaatacttga aggccgttgt taacgaatgt   1140
ttgagaatgt atccatccgt cccaagaaac tttagaattg ctacaaagca cactaccttg   1200
ccaagaggtg gtggtcctga tggtaaagat ccaattttca tcaaaaaggg tgccgttgtt   1260
tcctacggta ttaactctac tcacttggac ccaatgtatt acggtccaga tgctagatta   1320
ttcaacccag atagatggtc taagccagaa acaaaaaagt tgggttgggc ttttttgcca   1380
ttcaatggtg gtccaagaat atgcttgggt caacaatttg ctttgacaga agctagttac   1440
gtcttggtca gaatgatcca aaacttcaaa gaattagaat tgactccaaa caccgtctac   1500
ccaccaagaa gattgactaa tttgaccatg tccttgtacg atggtgctta cattaaggtc   1560
aactaa                                                              1566
```

*Candida maltosa*

SEQ ID NO: 2
```
atggccttgg acaagttgga cttgtacgtt attatagttt tggctgttgc tgttgccgct     60
tactttgcta agaatcaatt tttggatcaa ccacaagaca ctggtttctt gtctaatgat    120
actgctggtg gtaactccag agatattttg gaaactttga agaagaacaa caagaacacc    180
ttgttgttgt tcggttctca aactggtact gctgaagatt acgctaacaa gttgtccaga    240
gaaatccatt ctagattcgg tttgaaaact atggttgctg atttcgctga ttacgattgg    300
gataactttg tgatattcc aaacgacatc ttggttttct tcatcgttgc tacttatggt    360
gaaggtgaac ctactgataa cgccgatgaa tttcatactt ggttgactga tgaagccgat    420
actttgtcta ctttgagata cactgttttc ggtttgggta actctaccta cgaatttttac    480
aacgccattg gtagaaagtt cgatagatta ttggaagaaa agggtggtga agatttgcc    540
gattacggtg aaggtgatga tggtactggt actttggatg aagatttctt gacttggaag    600
gacaacgttt cgataccttt gaagaacgac ttgaacttcg aagaaagaga attgaagtac    660
gaacctaacg tcaagttgac cgaaagagat gatttgaccg ttgatgattc cgaagtttct    720
ttgggtgaac ctaacaagaa gtacatccaa tccgaagaga ttgacttgac taagggtcca    780
ttcgatcata ctcatccata cttggctaag atcagtaaga ccagagaatt attcgcctcc    840
aaagaaagaa actgcgttca cgttgaattt gatgtctccg aatctaactt gaagtacact    900
actggtgatc atttggcagt ttggccatct aattctgacg aaaacattgc caagttcatc    960
aagtgctttg gttttgatga taagatcaac accgttttcg aattgaaggc tttggattcc   1020
acttaccaaa ttccattccc aaacccaatt acttacggtg ctgttgttag acatcacttg   1080
gaaatttctg gtccagtctc tagacaattc ttcttggcta ttgctggttt tgctccagac   1140
gaagaaacta agaaaacttt caccagaatc ggtaacgaca agcaagaatt tgctaacaag   1200
atcaccagaa aaaagttgaa cgttgctgac gctttgttgt ttgcttctaa tggtagacct   1260
tggtctgatg tcccattcga atttatcatt gaaaacgtcc cacacttgca acctagatat   1320
tactctatct cctcctcctc attgtctgaa aagcaaacca ttaacattac cgccgttgtt   1380
gaagtagaag aagaagctga cggtagagct gttactggtg ttgttactaa tttgttgaag   1440
aacatcgaaa ttgaacaaaa caagaccggt gaaaagccag ttgttcatta tgatttgtct   1500
ggtccaagaa acaagtttaa caaattcaag ttgccagtcc acgtcagaag atccaatttt   1560
aagttgccaa agaacactac caccccagtt atttttgattg gtccaggtac aggtgttgct   1620
ccattgagag gttttgttag agaaaagagtt caacaagtta agaacggtgt taacgttggt   1680
aagaccgttt tgttttacgg ttgcagaaac gaacacgacg atttcttgta caaacaagaa   1740
tggtctgaat acgcctccgt tttaggtgaa aacttcgaaa tgtttaccgc cttctcaaga   1800
caagacccta ctaaaaaagt ttacgtccaa gataagatcg ccgaaaactc taaggttgtt   1860
aacgacttat tgaacgaagg tgccattatc tacgtttgtg gtgatgcttc aagaatggct   1920
agagatgttc aatctaccat tgctaagatc gttgccaagc acagagaaat tcaagaagat   1980
aaggctgtcg aattggtcaa gtcttggaaa gttcaaaaca gataccaaga gatgtttgg   2040
t                                                                   2041
```

*Humulus lupulus*

SEQ ID NO: 3
```
atggaagatc tgaagccgag accagccagc tcctctccac tcacccctct ggggtttctg     60
gaaagagccg ccaccgttta tggcgactgt acctccgtcg tttacgacgc cgtttcatac    120
acctgtccc agactcaccg ccgctgtctc tgtcttgcct cctccatcgc ctcactcggc    180
atcgaaaacg gccatgtcgt ctccgtcctc gcccccaaacg tccccaaat gtacgagctt    240
cacttcgccg ttcccatggc cggcgccatc ctcaacgccg tcaacctccg tctcgatgcc    300
cgcaccatct ccatcctcct ccatcacagc gaatcgaaac tcatcttcgt cgatcatctc    360
tctcgtgatc tcatcctcga agccatcgct ctgttccgca aacaagcccc tgttcctcgc    420
ctcgtttta tggcggacga gtctgaatcg gtaatagttc agagttggg gaaagaattc    480
ttctgcagtt ataaggatct gatcgataga gggaccccgg atttcaagtg gtcatgcct    540
aaaagcgagt gggacccgat gattcttaac tacacttctg gaacgacgtc atcgccgaaa    600
ggggttgtcc attgtcaccg gggaatattt ataatgacag tcgactctct catcgattgg    660
ggagttccta acagccagt ttatctatgg actctgccca tgtttcacgc caatgggtgg    720
agctatcctt ggggtatggc ggcggtcggc gggaccaata tctgcctgcg taaattcgac    780
tctgaaataa tttacgatat gataaaacgg cacggcgtga cccacatgtg cggagccccc    840
gttgtactca acatgctctc caacgcgccg ggatcggaac cgctgaaaac aacggttcag    900
atcatgactg caggagctcc gccgccctcg gcggtgcttt tccggaccga tcgctgggc    960
ttcgcggtga gccacggcta cgggcttacc gaaacggcgg ggttagtggt gtcgtgcgcg   1020
tggaagaaag agtggaacca tctcccggcg acggagagag cgaggctcaa gtcgagacaa   1080
ggggtgggga cggtgatgca gaccaaaatc gatgtcgttg acccggtgac cggagccgcc   1140
gtgaagcgag acggatcaac gttgggcgag gttgttctga gaggcgggtc ggtcatgctc   1200
```

TABLE 4-continued

Sequences disclosed herein.

```
gggtacctaa aagacccaga aggaacggcg aaatccatga ccgcagacgg gtggttctac  1260
accggggacg ttggagtcat gcacccagat gggtatttgg agatcaaaga ccggtccaag  1320
gacgtcatca tcagcggcgg agagaatttg agcagcgtcg aggtggagtc aattctgtac  1380
agtcacccgg atattctgga ggcggcggtt gtggcccggc cagacgagtt ctgggggag   1440
acgccgtgtg ctttcgtgag cttgaagaaa ggtttaacga agaagccgac ggagaaggag  1500
atcgtggagt attgtcggag taagttgccg cgttacatgg tacccaaaac ggtggtgttt  1560
aaggaggagc ttcccaagac atcgactggg aaggttcaga aatttatact gagagatatg  1620
gccagaggta tgggctctgc aactgctgga gcgagccgga gccgaatgtg a           1671
```

*Solanum tuberosom*

SEQ ID NO: 4
```
atggatgagc taaagccaac gccaccaaat tcaagtcctc ttactccat  taccttcttg   60
gaaagagctg ctactatcta tgccgattgc ccttccatcg tctacaacaa cacaactcac  120
aattggtccc aaacccattc tcgttgccta aaagttgctt catccattgc atctttggt   180
attcaaagaa atcatgttgt ctccgttgtt gcccctaata tccctgccat gtatgagctt  240
cattttgctg ttcccatggc tggtgctgta ctcaacacca ttaatctccg tcttgatgca  300
cgtactatct ctgtactcct ccgtcacagc gaatctaaac tcctcttcgt tgattgtcaa  360
tccaaatccc taattctcga agctctgtcc ttatttccgc ctgaattcca ccgtccggtt  420
ctcgttctta tcgaggacga cgaattccca attccaaaaa ctgatgaatt tatcgctact  480
tatgaggaat tggttgaaag aggggattcg ggtttcaatt ggattcgccc gaaaagtgaa  540
tttgatccga ttgctatgaa ttacacttct ggaactacat ctgctccgaa aggtgtggtt  600
catagccata ggggtatttt cgttgtttcg ttggattcgt tgattgaatg gtccgttccg  660
aaacagccgg tttatttatg gacgctacct atgtttcatg caaacggatg gagttatcca  720
tggggaatgg ctgctgttgg tggaacgaat atctgtttga gaaaattcga tgccggaatc  780
atttatgact cgatcaacaa acatggtgtt actcatatct gcgctgctcc agtggtactc  840
aacatgttgt cgaattcccc tgacagtaag ccattaaaac ccctgttta  tataatgaca   900
gcaggatccc caccccctgc tgctgtcctg tttcgaacag agtccctgg  atttgtagtc   960
catcatggtt atggacttac agaaactggt ggattagtta tttcttgtac atggaaaaat 1020
cactggaata aatttccagc aaatgaaaga gcaaggctga aatcaagaca aggggttagg 1080
acattaggga tggcggaagt ggacgtggtg gatccagaat caggagtcag tgttaaacgg 1140
gacggatcaa cattaggaga aattgttcta aagggtgcct gtgtcatgtt gggttacttt 1200
aaagacccgg aaggaacgtc gaaatgcatg aaagatgatg gttggtttta cacaggggat 1260
gtggcagtta tgcatcctga tggatactta gaaattaaag acagatcaaa ggacgtgatc 1320
ataagtggtg gagagaattt gagcagtgta gaagtgaat  cagtgttgta tacccatcca 1380
gcgattaacg aagcagcagt agtggcacgg ccagatgaat tctggggcga aacaccgtgt 1440
gcatttgtta gtctgaatgg aaaacacaag gcgagtgaaa aagacattat tgagtttgt  1500
agagccaaat tgccacatta tatggtacca aagactgtca taattaaaca agagcttcca 1560
aagacatcaa cagggaaaat tcagaagttc gtgcttagag acattgctaa aagtatgggg 1620
aaaagcaata gcagcaagaa ggtgagcaga atgtag                            1656
```

*Saccharomyces cerevisiae*

SEQ ID NO: 5
```
atggacgctt actccacaag accattaacc ctatctcacg gttctttaga gcacgtgctt   60
ctggtaccaa ccgcttcatt tttcattgct tcgcaattac aagaacaatt taataaaatt  120
ttgcccgaac ccactgaagg gtttgctgca gatgacgagc ctaccacacc tgctgaacta  180
gtggggaaat tccttggcta cgtatcttct ctagtcgaac cttccaaggt cggtcaattc  240
gatcaggtct tgaaccttg cttaacagaa tttgaaaact gttatttaga aggcaatgac  300
attcacgcct tggctgctaa actattacag gaaaacgaca caactttgt  gaagactaaa   360
gaactaatta aaaattatat taccgccaga ataatggcta agagaccatt tgacaaaaaa  420
tccaactctg ctctttttag ggccgtcggc gagggtaacg cacaattggt agccatttc   480
ggtggtcaag gtaacaccga cgactacttt gaagaattgc gtgatctata tcaaacttat  540
catgtcttag tgggagattt aatcaagttc tccgctgaaa ctttaagtag actgattaga  600
actactttag atgctgaaaa agtcttact caaggtttaa acatattgga atggttggag   660
aaccttcaa atacccccaga caaggactat ttactttcca ttccaatttc atgcccctta  720
attggtgtca ttcaattggc tcactacgta gttactgcca agcttttggg tttcactcca  780
ggtgagttaa gatcttactt aaaaggtgct acaggtcact ctcaaggttt ggttactgct  840
gtcgccatag ctgagacgga ttcctgggaa tccttcttcg tctccgtaag aaaagcaatt  900
actgtattat tcttcatcgg tgttcgttgt tacgaagcat acccaaacac ttccctacca  960
ccatccatct ggaagattcc cttggaaaac aatgaaggtg ttccatctcc aatgttgtcc 1020
atttccaatc taactcaaga acaagttcaa gactatgtaa ataagactaa ctctcatttg 1080
ccagctggta aacaagttga aatttctcta gtcaatggtg gaagaatct agtcgtatcg 1140
ggcccaccac aatcattata tggttttaaac ttgactttaa gaaaggccaa ggccccatct 1200
ggactgaatc aatcaagaat cccattcagc gaaagaaaat tgaagttctc caataggttc 1260
ttacctgttg catcaccatt ccattcccat ctattggttc cagcttcaga tttgattaac 1320
aaagacttag tcaaaaacaa tgtcagcttt aacgctaaaa ccccgtttac 1380
gacacttttg atggttcaga tctaaagtcc ctttcaggtt ccatttccga gagaatcgtc 1440
gactgcatca ttagattacc tgtcaaatgg gaaactacta cacaattcaa agccaccac  1500
atattagact ttggtccagg tggagcttcc ggtttaggtg ttttaaccca tcgtaataaa 1560
gatggtactg tgttcgtgt tatcgttgcc ggtactctcg acattaaccc agatgatgat 1620
tacggattca agcaagaaat ctttgatgtt actagtaatg gtttgaagaa aaatccaaac 1680
tggttggaag aataccatcc aaaattaatt aagaacaaat caggcaaaat ttttgtcgaa 1740
acaaattttt ctaaattaat cggtagacca ccttttattgg ttcctggtat gacaccatgt 1800
actgtttctc cagatttcgt agctgctacc acaaatgctg gttataccat tgagtggcc  1860
ggtggtggtt acttttccgc agcaggtatg accgccgcta ttgattctgt ggttctcag  1920
atagaaaagg gtagtacctt cggtatcaac ttgatctacg tcaatccatt tatgttacaa 1980
tggggtattc cattaatcaa ggaactaaga agcaaaggtt atccaattca attcttgacc 2040
attggtgctg gtgtcccatc attggaagtt gctagtgaat acatagagac attaggtttg 2100
aagtacttgg gtttgaaacc aggttccatt gatgctattt cgcaagttat aaacattgct 2160
```

TABLE 4-continued

Sequences disclosed herein.

```
aaagcacatc caaacttccc aatagcttta caatggaccg gtggtagagg tggtggtcat   2220
cattctttcg aagatgccca cactccaatg ttacaaatgt actccaagat tagaagacat   2280
ccaaacatta tgttgatatt cggttctggt ttcggttctg ctgatgacac ttacccatac   2340
ttaaccggtg aatggtccac aaaattcgat tatccaccaa tgccattcga tggtttccta   2400
tttggttcga gggtcatgat tgctaaggaa gttaaaactt ctcctgatgc taagaagtgt   2460
attgctgctt gtactggtgt tcctgatgat aaatgggaac aaacctacaa gaagccaact   2520
ggtggtattg tcactgttcg ctctgaaatg ggtgaaccaa ttcacaaaat tgccactcgt   2580
ggtgttatgc tatggaagga attcgacgaa accatcttca acttaccaaa gaataagttg   2640
gtaccaactt tggaagcaaa gagagattac attatctcaa gattgaacgc cgatttccaa   2700
aaaccatggt ttgctaccgt caacggtcaa gcccgtgacc tagccacaat gacatacgaa   2760
gaagttgcaa agagattggt ggaattaatg ttcatcagat ctaccaactc ttggtttgat   2820
gtcacatgga gaacctttac tggtgatttc ctacgtcgtg tcgaagaacg tttcactaaa   2880
agtaagacat tgtctttaat ccaatcctat tctctactag acaagcctga tgaagctatt   2940
gaaaaagtat ttaatgctta tcctgccgct agggaacagt tcttgaatgc gcaagatatt   3000
gatcactttt tgagcatgtg tcaaaatcca atgcaaaaac cagtgccttt tgttccagtt   3060
ttggatcgta gattcgagat tttttttcaaa aaagattcgt tatggcaatc tgagcacttg   3120
gaagccgtcg tcgaccaaga cgttcaaaga acatgtatcc tacatggacc tgttgcagca   3180
caattcacta aagtcatcga tgaaccaatt aagagcatta tggatggtat tcacgatggt   3240
cacatcaaaa agttactaca tcaatattac ggtgacgatg agtcaaagat tccagcagtt   3300
gagtactttg gtggtgaaag ccctgtagac gtacaaagtc aagttgattc ttcctctgta   3360
tctgaagact cagctgtttt taaggcaaca tcctctactg atgaagaaag ctggtttaag   3420
gctttggcgg gatccgaaat taactggaga catgcaagtt tcttatgttc ctttatcact   3480
caagataaaa tgtttgtttc taaccaatt agaaaagttt tcaagccaag ccaaggaatg   3540
gttgttgaga tttccaacgg caatacttct tcaaagactg ttgtcactct ttcagaacct   3600
gttcaaggtg aattgaaacc aactgttatt ttgaagttgt tgaaggagaa cataatccaa   3660
atggaaatga ttgagaacag aactatggat ggtaagcccg tcagcttgcc attgttgtac   3720
aacttcaacc cagataatgg ttttgctcca atctctgagg ttatggagga cagaaaccaa   3780
agaattaagg aaatgtactg gaaattatgg attgatgagc ctttcaattt ggactttgac   3840
ccaagagatg tcattaaggg caaagatttc gagatcaccg ctaaagaagt ttatgacttt   3900
acacacgctg ttggaaacaa ttgtgaagac ttcgtttcta gacctgatag aacgatgttg   3960
gccccaatgg actttgctat tgttgtcgga tggagagcca tcatcaaggc cattttccct   4020
aatacggtcg atggtgactt attgaagttg gttcatttgt ctaacggcta caagtgatt   4080
cctggcgcta agccactgca agttggtgat gttgtttcaa ctactgctgt tattgaatct   4140
gtcgtcaacc aacctacagg aaagattgtc gatgtggtag gtacattatc gagaaatggc   4200
aagcctgtca tggaagtcac ctcctcattc ttctacagag gcaactatac tgactttgaa   4260
aacactttcc aaaagactgt tgaacctgtt tatcaaatgc acatcaaaac ttctaaagat   4320
atagctgtct tgcgctctaa ggagtggttc caattggacg atgaagactt cgatctgtta   4380
aacaaaactt tgactttcga aactgaaact gaagttactt tcaagaatgc taacatcttc   4440
tcttcagtga aatgttttgg cccaattaaa gttgaattgc caaccaaaga aaccgtggag   4500
atcggtattg tcgattacga agccggtgcc tctcacggta accctgttgt tgatttcttg   4560
aagagaaacg gttccacatt ggaacaaaag gtcaatctag aaaatcctat tccaattgca   4620
gtacttgatt cgtacactcc aagtaccaac gaaccatacg ctagagtttc tggtgatttg   4680
aatccaattc acgtttcacg tcattttgcc tcttacgcaa acttgccagg tactatcacg   4740
cacggtatgt tttcttctgc ttccgtccgt gctttgattg aaaactgggc tctgacagt   4800
gtttcatcca gggtacgtgg ctacacttgt caatttgttg acatggtttt gcctaacact   4860
gctttgaaaa catcgattca acatgttggt atgatcaatg gtagaaaatt gataaagttt   4920
gaaactagaa atgaagatga cgttgtagtt ttgactggtg aagccgaaat tgaacaacct   4980
gttactacct tcgttttcac tggtcaaggt tcacaagaac aaggtatgag tatgaactta   5040
tacaaaactt ctaaagctgc tcaagatgtt tggaatagag ctgacaacca tttcaaggac   5100
acttatggtt tctctatctt agacattgtc attaacaacc cagttaactt aacaattcac   5160
ttcggtggtg aaaagggtaa gaggatcaga gaaaactatt ctgctatgat ctttgagact   5220
atcgtggatg gaaaattgaa gactgaaaaa atttttcaagg aaattaatga gcacagtact   5280
tcttacacat ttagatctga aaaaggttta ttgtctgcta ctcaatttac acaaccagct   5340
ttaactttga tggaaaaagc tgctttcgaa gacttgaaat ctaaaggttt gatcccagcc   5400
gatgctactt tgctggtcaa ctcctttaggt gagtatgctg ctttggcctc tttggctgat   5460
gttatgtcta tcgaatcttt agttgaagtt gtgttctaca gaggtatgac tatgcaagtt   5520
gctgttccaa gagatgagtt gggcagatcc aactatggta tgattgccat taacccaggt   5580
agagtcgctg catcattctc tcaagaagct ttgcaatatg ttgttgagag agttggtaag   5640
agaaccggct ggtggttga aatcgtcaac tacaacgttg aaaaccaaca atatgttgca   5700
gctggtgatc taagagcttt agacaccgtt accaatgttc taaacttcat caaattacaa   5760
aaaattgata ttattgaact acaaaagtcc ttatctttgg aagaagttga aggtcatttg   5820
tttgagatca ttgacgaagc ttccaagaaa tctgctgtca agcctcgccc acttaaattg   5880
gagagaggtt tgcttgtat cccattagtt ggtatttctg ttcctttcca ttccacctac   5940
ttgatgaatg gtgttaaacc attcaagagt ttcttgaaga agaatatcat aaaagaaaat   6000
gtgaaggttg ctagattggc cggaaagtac attccaaact tgactgcaaa accattccag   6060
gttactaagg aatatttcca ggacgtttat gatttgactg gctccgaacc tatcaaggaa   6120
atcatcgaca actgggaaaa gtatgaacaa tcctaa                              6156
```

Saccharomyces cerevisiae

SEQ ID NO: 6

```
atggacgctt actccacaag accattaacc ctatctcacg gttctttaga gcacgtgctt    60
ctggtaccaa ccgcttcatt tttcattgct tcgcaattac aagaacaatt taataaaatt   120
ttgcccgaac ccactgaagg gtttgctgca gatgacgagc ctaccacacc tgctgaacta   180
gtggggaaat tccttggcta cgtatcttct ctagtcgaac cttccaaggt cggtcaattc   240
gatcaggtct tgaaccttg cttaacagaa tttgaaaact gttatttaga aggcaatgac   300
attcacgcct tggctgctaa actattacag gaaaacgaca caactttagt gaagactaaa   360
gaactaatta aaaattatat taccgccaga ataatggcta agagaccatt tgacaaaaaa   420
tccaactctg ctctttttag ggccgtcggc gagggtaacg cacaattggt agccattttc   480
```

TABLE 4-continued

Sequences disclosed herein.

```
ggtggtcaag gtaacaccga cgactacttt gaagaattgc gtgatctata tcaaacttat   540
catgtcttag tgggagattt aatcaagttc tccgctgaaa ctttaagtga actgattaga   600
actactttag atgctgaaaa agtctttact caaggtttaa acatattgga atggttggag   660
aaccctccaa ataccccaga caaggactat ttactttcca ttccaatttc atgcccctta   720
attggtgtca ttcaattggc tcactacgta gttactgcca agcttttggg tttcactcca   780
ggtgagttaa gatcttactt aaaaggtgct acaggtcact ctcaaggttt ggttactgct   840
gtcgccatag ctgagacgga ttcctgggaa tccttcttcg tctccgtaag aaaagcaatt   900
actgtattat tcttcatcgg tgttcgttgt tacgaagcat acccaaacac ttccctacca   960
ccatccatct tggaagattc cttggaaaac aatgaaggtg ttccatctcc aatgttgtcc  1020
atttccaatc taactcaaga acaagttcaa gactatgtaa ataagactaa ctctcatttg  1080
ccagctggta aacaagttga aatttctcta gtcaatggcg cgaagaatct agtcgtatcg  1140
ggcccaccac aatcattata tggtttaaac ttgactttaa gaaaggccaa ggccccatct  1200
ggactggatc aatcaagaat cccattcagc gaaagaaaat tgaagttctc caataggttc  1260
ttacctgttg catcaccatt ccattcccat ctattggttc cagcttcaga tttgattaac  1320
aaagacttag tcaaaaacaa tgtcagcttt aacgctaaaa atattcaaat ccccgtttac  1380
gacacttttg atggttcaga tctaagagtc ctttcaggtt ccatttccga gagaatcgtc  1440
gactgcgcaa ttagattacc tgtcaaatgg gaaactacta cacaattcaa agccaccac   1500
atattagact ttggtccagg tggagcttcc ggtttaggtg ttttaaccca tcgtaataaa  1560
gatggtactg gtgttcgtgt tatcgttgcc ggtactctcg acattaaccc agatgatgat  1620
tacggattca agcaagaaat ctttgatgtt actagtaatg gtttgaagaa aaatccaaac  1680
tggttggaag aataccatcc aaaattaatt aagaacaaat caggcaaaat ttttgtcgaa  1740
acaaaatttt ctaaattaat cggtagacca cctttattgg ttcctggtat gacaccatgt  1800
actgtttctc cagatttcgt agctgctacc acaaatgctg gttataccat tgagttggcc  1860
ggtggtggtt acttttccgc agcaggtatg accgccgcta ttgattctgt ggtttctcag  1920
atagaaaagg gtagtacctt cggtatcaac ttgatctacg tcaatccatt tatgttacaa  1980
tggggtattc cattaatcaa ggaactaaga agcaaaggtt atccaattca attcttgacc  2040
attggtgctg gtgtcccatc attggaagtt gctagtgaat acatagagac attaggtttg  2100
aagtacttgg gtttgaaacc aggttccatt gatgctattt cgcaagttat aaacattgct  2160
aaagcacatc caaacttccc aatagcttta caatggaccg gtggtagagg tggtggtcat  2220
cattctttcg aagatgccca cactccaatg ttacaaatgt actccaagat tagaagacat  2280
ccaaacatta tgttgatatt cggttctggt ttcggttctg ctgatgacac ttacccatac  2340
ttaaccggtg aatggtccac aaaattcgat tatccaccaa tgccattcga tggtttccta  2400
tttggttcga gggtcatgat tgctaaggaa gttaaaactt ctcctgatgc taagaagtgt  2460
attgctgctt gtactggtgt tcctgatgat aaatgggaac aaacctacaa gaagccaact  2520
ggtggtattg tcactgttcg ctctgaaatg ggtgaaccaa ttcacaaaat tgccactcgt  2580
ggtgttatgc tatggaagga aaattcgacgaa accatcttca attaccaaa gaataagttg  2640
gtaccaactt tggaagcaaa agagagattac attatctcaa gattgaacgc cgatttccaa  2700
aaaccatggt ttgctaccgt caacggtcaa gcccgtgacc tagccacaat gacatacgaa  2760
gaagttgcaa agagattggt ggaattaatg ttcatcagat ctaccaactc ttggtttgat  2820
gtcacatgga gaacctttac tggtgatttc ctacgtcgtg tcgaagaacg tttcactaaa  2880
agtaagacat tgtctttaat ccaatcctat tctctactag acaagcctga tgaagctatt  2940
gaaaagtat ttaatgctta tcctgccgct agggaacagt tcttgaatgc gcaagatatt  3000
gatcacttt tgagcatgtg tcaaaatcca atgcaaaaac cagtgccttt tgttccagtt  3060
ttggatcgta gattcgagat ttttttcaaa aaagattcgt tatggcaatc tggcacttg  3120
gaagccgtcg tcgaccaaga cgttcaaaga acatgtatcc tacatggacc tgttgcagca  3180
caattcacta aagtcatcga tgaaccaatt aagagcatta tggatggtat tcacgatggt  3240
cacatcaaaa agttactaca tcaatattac ggtgacgatg agtcaaagat tccagcagtt  3300
gagtactttg gtggtgaaag ccctgtagac gtacaaagtc aagttgattc ttcctctgta  3360
tctgaagact cagctgtttt taaggcaaca tcctctactg atgaagaaag ctggtttaag  3420
gctttggcgg gatccgaaat taactggaga catgcaagtt tcttatgttc ctttatcact  3480
caagataaaa tgtttgtttc taacccaatt agaaagtttt tcaagccaag ccaaggaatg  3540
gttgttgaga tttccaacgg caatacttct tcaaagactg ttgtcactct ttcagaacct  3600
gttcaaggtg aattgaaacc aactgttatt ttgaagttgt tgaaggagaa cataatccaa  3660
atggaaatga ttgagaacag aactatggat ggtaagcccg tcagcttgcc attgttgtac  3720
aacttcaacc cagataatgg ttttgctcca atctctgaag ttatggagga cagaaaccaa  3780
agaattaagg aaatgtactg gaaattatgg attgatgagc ctttcaattt ggactttgac  3840
ccaagagatg tcattaaggg caaagatttc gagatcaccg ctaaagaagt ttatgacttt  3900
acacacgctg ttggaaacaa ttgtgaagac ttcgttccta gacctgatag aacgatgttg  3960
gccccaatgg actttgctat tgtgtcgga tggagagcca tcatcaaggc catttttccct  4020
aatacgtcg atggtgactt attgaagttg gttcattttgt ctaacggcta caagatgatt  4080
cctggcgcta agccactgca agttggtgat gttgttcaa cttggtttct tattgaatct  4140
gtcgtcaacc aacctacagg aaagattgtc gatgtggtag gtacattatc gagaaatggc  4200
aagcctgtca tggaagtcac ctccctcattc ttctacagag gcaactatac tgactttgaa  4260
aacactttcc aaaagactgt tgaacctgtt tatcaaatgc acatcaaaac ttctaaagat  4320
atagctgtct tgcgctctaa ggagtggttc caattggacg atgaagactt cgatctgtta  4380
aacaaaactt tgactttcga aactgaaact gaagttactt tcaagaatgc taacatcttc  4440
tcttcagtga atgttttgg cccaattaaa gttgaattgc caaccaaaga aaccgtggag  4500
atcggtattg tcgattacga agccggtgcc tctcacggta accctgttgt tgatttcttg  4560
aagagaaagg gttccacatt ggaacaaaag gtcaatctag aaaatcctat tccaattgca  4620
gtacttgatt cgtacactcc aagtaccaac gaaccatacg ctagagtttc tggtgatttg  4680
aatccaattc acgtttcacg tcattttgcc tcttacgcaa acttgccagg tactatcacg  4740
cacggtatgt tttcttctgc ttccgtccgt gctttgattg aaaactgggc tgctgacagt  4800
gtttcatcca gggtacgtgg ctacacttgt caatttgtg acgtggtttt gcctaacact  4860
gctttgaaaa catcgattca acatgttggt atgatcaatg gtagaaaatt gataaagttt  4920
gaaactagaa atgaagatga cgttgtagtt ttgactggtg aagccgaaat tgaacaacct  4980
gttactacct tcgttttcac tggtcaaggt tcacaagaac aaggtatggg tatggactta  5040
tacaaaactt ctaaagctgc tcaagatgtt tggaatagag ctgacaacca tttcaaggac  5100
acttatggtt tctctctatctt agacattgtc attaacaacc cagttaactt aacaattcac  5160
```

TABLE 4-continued

Sequences disclosed herein.

```
ttcggtggtg aaaagggtaa gaggatcaga gaaaactatt ctgctatgat ctttgagact    5220
atcgtggatg gaaaattgaa gactgaaaaa attttcaagg aaattaatga gcacagtact    5280
tcttacacat ttagatctga aaaaggttta ttgtctgcta ctcaatttac acaaccagct    5340
ttaactttga tggaaaaagc tgctttcgaa gacttgaaat ctaaaggttt gatcccagcc    5400
gatgctactt ttgctggtca ctctttaggt gagtatgctg ctttggcctc tttggctgat    5460
gttatgtcta tcgaatcttt agttgaagtt gtgttctaca gaggtatgac tatgcaagtt    5520
gctgttccaa gagatgagtt gggcagatcc aactatggta tgattgccat taacccaggt    5580
agagtcgctg catcattctc tcaagaagct ttgcaatatg ttgttgagag agttggtaag    5640
agaaccggct ggttggttga aatcgtcaac tacaacgttg aaaaccaaca atatgttgca    5700
gctggtgatc taagagcttt agacaccgtt accaatgttc taaacttcat caaattacaa    5760
aaaattgata ttattgaact acaaaagtcc ttatcttttgg aagaagttga aggtcatttg    5820
tttgagatca ttgacgaagc ttccaagaaa tctgctgtca agcctcgccc acttaaattg    5880
gagagaggtt ttgcttgtat cccattagtt ggtatttctg ttcctttcca ttccacctac    5940
ttgatgaatg gtgttaaacc attcaagagt ttcttgaaga agaatatcat aaaagaaaat    6000
gtgaaggttg ctagattggc cggaaagtac atttccaaact tgactgcaaa accattccag    6060
gttactaagg aatatttcca ggacgtttat gatttgactg gctccgaacc tatccaaggaa   6120
atcatcgaca actgggaaaa gtatgaacaa tcctaa                              6156
```

*Saccharomyces cerevisiae*

SEQ ID NO: 7

```
atggacgctt actccacaag accattaacc ctatctcacg gttctttaga gcacgtgctt      60
ctggtaccaa ccgcttcatt tttcattgct tcgcaattac aagaacaatt taataaaatt    120
ttgcccgaac ccactgaagg gtttgctgca gatgacgagc ctaccacacc tgctgaacta    180
gtggggaaat tccttggcta cgtatcttct ctagtcgaac cttccaaggt cggtcaattc    240
gatcaggtct tgaaccttttg cttaacagaa tttgaaaact gttatttaga aggcaatgac    300
attcacgcct tggctgctaa actattcagg gaaaacgaca caactttagt gaagactaaa    360
gaactaatta aaaattatat taccgccaga ataatggcta agagaccatt tgacaaaaaa    420
tccaactctg ctctttttag ggccgtcggc gagggtaacg cacaattggt agccattttc    480
ggtggtcaag gtaacaccga cgactacttt gaagaattgc gtgatctata tcaaacttat    540
catgtcttag tgggagattt aatcaagttc tccgctgaaa ctttaagtga actgattaga    600
actactttag atgctgaaaa agtctttact caaggtttaa acatattgga atggttggag    660
aacccttcaa atacccccaga caaggactat ttacttttcca ttccaattc atgccccta    720
attggtgtca ttcaattggc tcactacgta gttactgcca agcttttggg tttcactcca    780
ggtgagttaa gatcttactt aaaaggtgct acaggtcact ctcaaggttt ggttactgct    840
gtcgccatag ctgagacgga ttcctgggaa tccttcttcg tctccgtaag aaaagcaatt    900
actgtattat tcttcatcgg tgttcgttgt tacgaagcat acccaaacac ttccctacca    960
ccatccatct tggaagattc cttggaaaac aatgaaggtg ttccatctcc aatgttgtcc    1020
atttccaatc taactcaaga acaagttcaa gactatgtaa ataagactaa ctctcatttg    1080
ccagctggta acaagttgaa aatttctcta gtcaatggtc gaagaatctt agtcgtatcg    1140
ggcccaccac aatcattata tggtttaaac ttgactttaa gaaaggccaa ggccccatct    1200
ggactggatc aatcaagaat cccattcagc gaaagaaaat tgaagttctc caataggttc    1260
ttacctgttg catcaccagc acattccat ctattggttc cagcttcaga tttgattaac    1320
aaagacttag tcaaaacaa tgtcagcttt aacgctaaag atattcaaat cccgttac      1380
gacactttg atggtttcaga tctaagagtc ctttcaggtt ccatttccga gagaatcgtc    1440
gactgcatca ttagattacc tgtcaaatgg gaaactacta cacaattcaa agccaccgtt    1500
atattagact tggtccagg tggagcttgg ggtttaggtg tttaaccca tcgtaataaa      1560
gatggtactg tgttcgtgt tatcgttgcc ggtactctcg acattaaccc agatgatgat     1620
tacggattca agcaagaaat cttttgatgtt actagtaatg gtttgaagaa aatccaaac    1680
tggttggaag aataccatcc aaaattaatt aagaacaaat caggcaaat ttttgtcgaa     1740
acaaaattt ctaaattaat cggtagacca ccttattatgg ttcctggtat gacaccatgt   1800
actgtttctc cagatttcgt agctgctacc acaaatgctg ttataccat tgagttggcc    1860
ggtggtggtt actttccgc agcaggtatg accgccgcta ttgattcgt ggttctcag      1920
atagaaaagg gtagtacctt cggtatcaac ttgatctacg tcaatccatt tatgttacaa    1980
tggggtattc cattaatcaa ggaactaaga agcaaaggtt atccaattca attcttgacc    2040
attggtgctg gtgtcccatc attggaagtt gctagtaaat acatagagac attaggtttg    2100
aagtacttgg gttttgaaacc aggttccatt gatgctattt cgcaagttat aaacattgct    2160
aaagcacatc caaacttccc aatagcttta caatggaccg gtggtagagg tggtgtcat    2220
cattctttcg aagatgccca cactccaatg ttacaaatgt actccaagaa tagaagacat    2280
ccaaacatta tgttgatatt cggttctggt ttcggttctg ctgatgacac ttacccatac    2340
ttaaccggtg aatggtccac aaaattcgat tatccaccaa tgccattcga tggtttccta    2400
tttggttcga gggtcatgat tgctaaggaa gttaaaactt ctcctgatgc taagaagtgt    2460
attgctgctt gtactggtgt tcctgatgat aaatgggaac aaacctacaa gaagccaact    2520
ggtggtattg tcactgttcg ctctgaaatg ggtgaaccaa ttcacaaaat tgccactcgt    2580
ggtgttatgc tatggaagga attcgacgaa accatcttca acttaccaaa gaataagttg    2640
gtaccaactt tggaagcaaa gagagattac attatctcaa gattgaagcc cgatttccaa    2700
aaaccatggt ttgctaccgt caacggtcaa gcccgtgacc tagccacaat gacatacgaa    2760
gaagttgcaa agagattggt ggaattaatg ttcatcagat ctaccaactc ttggtttgat    2820
gtcacatgga gaacctttac tggtgatttc ctacgtcgtg tcgaagaacg tttcactaaa    2880
agtaagacat tgtctttaat ccaatcctat tctctactag acaagcctga tgaagctctt    2940
gaaaaagtat ttaatgctta tcctgccgct agggaacagt tcttgaatgc gcaagatatt    3000
gatcactttt tgagcatgtg tcaaaatcca atgcaaaaac cagtgccttt tgttccagtt    3060
ttggatcgta gattcgagat tttttcaaa aagattcgt tatggcaatc tgagcacttg      3120
gaagccgtcg tcgaccaaga cgttcaaaga acatgtatcc tacatggacc tgttcgagca    3180
caattcacta aagtcatcga tgaaccaatt aagagcatta tggatggtat tcacgatggt    3240
cacatcaaaa agttactaca tcaatattac ggtgacgatg agtcaaagat tccagcagtt    3300
gagtactttg tgtggtgaaag ccctgtagac gtacaaagtc aagttgattc ttcctctgta   3360
tctgaagact cagctgtttt taaggcaaca tcctctactg atgaagaaag ctggtttaag    3420
gctttggcgg gatccgaaat taactggaga catgcaagtt tcttatgttc ctttatcact    3480
```

TABLE 4-continued

Sequences disclosed herein.

```
caagataaaa tgtttgtttc taacccaatt agaaaagttt tcaagccaag ccaaggaatg   3540
gttgttgaga tttccaacgg caatacttct tcaaagactg ttgtcactct ttcagaacct   3600
gttcaaggtg aattgaaacc aactgttatt ttgaagttgt tgaaggagaa cataatccaa   3660
atggaaatga ttgagaacag aactatggat ggtaagcccg tcagcttgcc attgttgtac   3720
aacttcaacc cagataatgg ttttgctcca atctctgaag ttatgaagga cagaaaccaa   3780
agaattaagg aaatgtactg gaaattatgg attgatgagc ctttcaattt ggactttgac   3840
ccaagagatg tcattaaggg caaagatttc gagatcaccg ctaaagaagt ttatgacttt   3900
acacacgctg ttggaaacaa ttgtgaagac ttcgtttcta gacctgatag aacgatgttg   3960
gccccaatgg actttgctat tgttgtcgga tggagagcca tcatcaaggc cattttccct   4020
aatacggtcg atggtgactt attgaagttg gttcatttgt ctaacggcta caagatgatt   4080
cctggcgcta agccactgca agttggtgat gttgtttcaa ctactgctgt tattgaatct   4140
gtcgtcaacc aacctacagg aaagattgtc gatgtggtag gtacattatc gagaaatggc   4200
aagcctgtca tggaagtcac ctcctcattc ttctacagag gcaactatac tgactttgaa   4260
aacactttca aaagactgt tgaacctgtt tatcaaatgc acatcaaaac ttctaaagat   4320
atagctgtct tgcgctctaa ggagtggttc caattggcag atgaagactt cgatctgtta   4380
aacaaaactt tgactttcga aactgaaact gaagttactt tcaagaatgc taacatcttc   4440
tcttcagtga aatgttttgg cccaattaaa gttgaattgc caaccaaaga aaccgtggag   4500
atcggtattg tcgattacga agccggtgcc tctcacggta accctgttgt tgatttcttg   4560
aagagaaacg gttccacatt ggaacaaaag gtcaatctag aaaatcctat tccaattgca   4620
gtacttgatt cgtacactcc aagtaccaac gaaccatacg ctagagtttc tggtgatttg   4680
aatccaattc acgtttcacg tcattttgcc tcttacgcaa acttgccagg tactatcacg   4740
cacggtatgt tttcttctgc ttccgtccgt gctttgattg aaaactgggc tgctgacagt   4800
gtttcatcca gggtacgtgg ctacacttgt caatttgttg acgttttt gcctaacact   4860
gctttgaaaa catcgattca acatgttggt atgatcaatg gtagaaaatt gataaagttt   4920
gaaactagaa atgaagatga cgttgtagtt ttgactggtg aagccgaaat tgaacaacct   4980
gttactacct tcgttttcac tggtcaaggt tcacaagaac aaggtatggg tatggactta   5040
tacaaaactt ctaaagctgc tcaagatgtt tggaatagag ctgacaacca tttcaaggac   5100
acttatggtt tctctatctt agacattgtc attaacaacc cagttaactt aacaattcac   5160
ttcggtggtg aaaagggtaa gaggatcaga gaaaactatt ctgctatgat ctttgagact   5220
atcgtggatg gaaaattgaa gactgaaaaa attttcaagg aaattaatga gcacagtact   5280
tcttacacat ttagatctga aaaaggttta ttgtctgcta ctcaatttac acaaccagct   5340
ttaactttga tggaaaaagc tgctttcgaa gacttgaaat ctaaaggttt gatcccagcc   5400
gatgctactt ttgctggtca ctcttttaggt gagtatgctg ctttggcctc tttggctgat   5460
gttatgtcta tcgaatcttt agttgaagtt gtgttctaca gaggtatgac tatgcaagtt   5520
gctgttccaa gagatgagtt gggcagatcc aactatggta tgattgccat taacccaggt   5580
agagtcgctg catcattctc tcaagaagct ttgcaatatg ttgttgagag agttggtaag   5640
agaaccggct ggttggttga aatcgtcaac tacaacgttg aaaaccaaca atatgttgca   5700
gctggtgatc taagagcttt agacaccgtt accaatgttc taaacttcat caaattacaa   5760
aaaattgata ttattgaact acaaaagtcc ttatctttgg aagaagttga aggtcatttg   5820
tttgagatca ttgacgaagc ttccaagaaa tctgctgtca agcctcgccc acttaaattg   5880
gagagaggtt ttgcttgtat cccattagtt ggtatttctg ttcctttcca ttccacctac   5940
ttgatgaatg gtgttaaacc attcaagagt ttccttgaaga agaatatcat aaaagaaaat   6000
gtgaaggttg ctagattggc cggaaagtac attccaaact tgactgcaaa accattccag   6060
gttactaagg aatatttcca ggacgtttat gatttgactg gctccgaacc tatcaaggaa   6120
atcatcgaca actgggaaaa gtatgaacaa tcctaa                             6156
```

*Saccharomyces cerevisiae*

SEQ ID NO: 8
```
atggacgctt actccacaag accattaacc ctatctcacg gttctttaga gcacgtgctt     60
ctggtaccaa ccgcttcatt tttcattgct tcgcaattac aagaacaatt taataaaatt    120
ttgcccgaac ccactgaagg gtttgctgca gatgacgagc ctaccacacc tgctgaacta    180
gtggggaaat tccttggcta cgtatctct ctagtcgaac cttccaaggt cggtcaattc    240
gatcaggtct tgaacctttg cttaacagaa tttgaaaact gttatttaga aggcaatgac    300
attcacgcct tggctgctaa actattacag gaaaacgaca caactttagt gaagactaaa    360
gaactaatta aaaattatat taccgccaga ataatgctta agagaccatt tgacaaaaaa    420
tccaactctg ctctttttag ggccgtcggc gagggtaacg cacaattggt agccattttc    480
ggtggtcaag gtaacaccga cgactacttt gaagaattgc gtgatctata tcaaacttat    540
catgtcttag tgggagattt aatcaagttc tccgctgaaa ctttaagtga actgattaga    600
actactttag atgctgaaaa agtctttact caaggtttaa acatattgga atggttggag    660
aacccttcaa atacccccaga caaggactat ttacttttcca ttccaatttc atgccccctta    720
attggtgtca ttcaattggc tcactacgta gttactgcca agcttttttgg tttccactcca    780
ggtgagttaa gatcttactt aaaaggtgct acaggtcact ctcaaggttt ggttactgct    840
gtcgccatag ctgagacgga ttccctgggaa tccttcttcg tctccgtaag aaaagcaatt    900
actgtattat tcttcatcgg tgttcgttgt tacgaagcat acccaaacac ttccctacca    960
ccatccatct tggaagattc cttgaaaaac aatgaaggtg ttccatctcc aatgttgtcc   1020
atttccaatc taactcaaga acaagttcaa gactatgtaa ataagactaa ctctcatttg   1080
ccagctggta aacaagttga aatttctcta gtcaatggtg cgaagaatct agtcgtatcg   1140
ggcccaccac aatcattata tggttaaaac ttgactttaa gaaaggccaa ggccccatct   1200
ggactggatc aatcaagaat cccattcagc gaaagaaaat tgaagttctc caataggttc   1260
ttacctgttg catcaccagc acattccatt ctattggttc cagcttcaga tttgattaac   1320
aaagactaag tcaaaacaa tgtcagcttt aacgctaaag atattcaaat cccgtttac   1380
gacactttg atggttcaga tctaagagtc ctttcaggtt ccatttccga gagaatcgtc   1440
gactgccgaa ttagattacc tgtcaaatgg gaaactacta cacaattcaa agcacaccac   1500
atattagact ttggtccagg tggagcttcc ggtttaggtg ttttaaccca tcgtaataaa   1560
gatggtactg tgttcgtgt tatcgttgcc ggtactctcg acattaaccc agatgatgat   1620
tacgattcca agcaagaaat ctttgatgtt actagtaatg gttgaagaa aaatccaaac   1680
tggttggaag aataccatcc aaaattaatt aagaacaaat caggcaaaat ttttgtcgaa   1740
acaaaatttt ctaaattaat cggtagacca cctttattgg ttcctggtat gacaccatgt   1800
```

TABLE 4-continued

Sequences disclosed herein.

```
actgtttctc cagatttcgt agctgctacc acaaatgctg gttataccat tgagttggcc  1860
ggtggtggtt acttttccgc agcaggtatg accgccgcta ttgattctgt ggtttctcag  1920
atagaaaagg gtagtacctt cggtatcaac ttgatctacg tcaatccatt tatgttacaa  1980
tgggtattc cattaatcaa ggaactaaga agcaaaggtt atccaattca attcttgacc  2040
attggtgctg gtgtcccatc attggaagtt gctagtgaat acatagagac attaggtttg  2100
aagtacttgg gtttgaaacc aggttccatt gatgctattt cgcaagttat aaacattgct  2160
aaagcacatc caaacttccc aatagcttta caatggaccg gtggtagagg tggtggtcat  2220
cattcttttcg aagatgccca cactccaatg ttacaaatgt actccaagat tagaagacat  2280
ccaaacatta tgttgatatt cggttctggt ttcggttctg ctgatgacac ttacccatac  2340
ttaaccggtg aatggtccac aaaattcgat tatccaccaa tgccattcga tggtttccta  2400
tttggttcga gggtcatgat tgctaaggaa gttaaaactt ctcctgatgc taagaagtgt  2460
attgctgctt gtactggtgt tcctgatgat aaatgggaac aaacctacaa gaagccaact  2520
ggtggtattg tcactgttcg ctctgaaatg ggtgaaccaa ttcacaaaat tgccactcgt  2580
ggtgttatgc tatggaagga attcgacgaa accatcttca acttaccaaa gaataagttg  2640
gtaccaactt tggaagcaaa gagagattac attatctcaa gattgaacgc cgatttccaa  2700
aaaccatggt ttgctaccgt caacggtcaa gcccgtgacc tagccacaat gacatacgaa  2760
gaagttgcaa agagattggt ggaattaatg ttcatcagat ctaccaactc ttggtttgat  2820
gtcacatgga gaacctttac tggtgatttc ctacgtcgtg tcgaagaacg tttcactaaa  2880
agtaagacat tgtctttaat ccaatcctat tctctactag acaagcctga tgaagctatt  2940
gaaaaagtat ttaatgctta tcctgccgct agggaacagt tcttgaatgc gcaagatatt  3000
gatcacttttt tgagcatgtg tcaaaatcca atgcaaaaac cagtgccttt tgttccagtt  3060
ttggatcgta gattcgagat tttttttcaaa aaagattcgt tatggcaatc tgagcacttg  3120
gaagccgtcg tcgaccaaga cgttcaaaga acatgtatcc tacatggacc tgttgcagca  3180
caattcacta aagtcatcga tgaaccaatt aagagcatta tggatggtat tcacgatgct  3240
cacatcaaaa agttactaca tcaatattac ggtgacgatg agtcaaagat tccagcagtt  3300
gagtactttg tggtgaaag ccctgtagac gtacaaagtc aagttgattc ttcctctgta  3360
tctgaagact cagctgttttt taaggcaaca tcctctactg gtgaagaaag ctggtttaag  3420
gctttggcgg gatccgaaat taactggaga catgcaagtt tcttatgttc ctttatcact  3480
caagataaaa tgtttgtttc taacccaatt agaaaagttt tcaagccaag ccaaggaatg  3540
gttgttgaga tttccaacgg caatacttct tcaaagactg ttgtcactct ttcagaacct  3600
gttcaaggtg aattgaaacc aactgttatt ttgaagttgt tgaaggagaa cataatccaa  3660
atggaaatga ttgagaacag aactatggat ggtaagcccg tcagcttgcc attgttgtac  3720
aacttcaacc cagataatgg ttttgctcca atctctgaag ttatggagga cagaaaccaa  3780
agaattaagg aaatgtactg gaaattatgg attgatgagc cttttcaattt ggactttgac  3840
ccaagagatg tcattaaggg caaagatttc gagatcaccg ctaagaagt ttatgactttt  3900
acacacgttg ttggaaacaa ttgtgaagac ttcgtttcta gacctgatag aacgatgttg  3960
gccccaatgg actttgctat tgttgtcgga tggagagcca tcatcaaggc cattttccct  4020
aatacggtcg atggtgactt attgaagttg gttcatttgt ctaacggcta caagatgatt  4080
cctggcgcta agccactgca agttggtgat gttgtttcaa ctactgctgt tattgaatct  4140
gtcgtcaacc aacctacagg aaagattgtc gatgtggtca gacattatc gagaaatgat  4200
aagcctgtca tggaagtcac ctcctcattc ttctacagag gcaactatac tgactttgaa  4260
aacacttttcc aaaagactgt tgaacctgtt tatcaaatgc acatcaaaac ttctaaagat  4320
atagctgtct tgcgctctaa ggagtggttc caattggacg atgaagactt cgatctgtta  4380
aacaaaactt tgactttcga aactgaaact gaagttactt tcaagaatgc taacatcttc  4440
tcttcagtga aatgttttgg cccaattaaa gttgaattgc caaccaaaga aaccgttggag  4500
atcggtattg tcgattacga agccggtgcc tctcacggta accctgttgt tgatttcttg  4560
aagagaaacg gttccacatt ggaacaaaag gtcaatctag aaaatcctat tccaattgca  4620
gtacttgatt cgtacactcc aagtaccaac gaaccatacg ctagagtttc tggtgatttg  4680
aatccaattc acgtttcacg tcatttttgcc tcttacgcaa acttgccagg tactatcacg  4740
cacggtatgt tttcttctgc ttccgtccgt gctttgattg aaaactgggc tgctgacagt  4800
gtttcatcca gggtacgtgg ctacacttgt caatttgttg acatggtttt gcctaacact  4860
gctttgaaaa catcgattca acatgttggt atgatcaatg gtagaaaatt gataaagttt  4920
gaaactagaa atgaagatga cgttgtagtt ttgactggtg aagccgaaat tgaacaacct  4980
gttactacct tcgttttcac tggtcaaggt tcacaagaac aaggtatggg tatggactta  5040
tacaaaactt ctaaagctgc tcaagatgtt tggaatagag ctgacaacca tttcaaggac  5100
acttatggtt tctctatctt agacattgtc attaacaacc cagttaactt aacaattcac  5160
ttcggtggtg aaaagggtaa gaggatcaga gaaaactatt ctgctatgat ctttgagact  5220
atcgtggatg gaaaattgaa gactgaaaaa atttttcaagg aaattaatga gcacagtact  5280
tcttacacat ttagatctga aaaaggttta ttgtctgcta ctcaatttac acaaccagct  5340
ttaactttga tggaaaaagc tgctttcgaa gacttgaaat ctaaaggttt gatcccagcc  5400
gatgctactt ttgctggtca ctcttttaggt gagtatgctg ctttggcctc tttggctgaa  5460
gttatgtcta tcgaatcttt agttgaagtt gtgttctaca gaggtatgac tatgcaagtt  5520
gctgttccaa gagatgagtt gggcagatcc aactatggta tgattgccat taacccaggt  5580
agagtcgctg catcattctc tcaagaagct ttgcaatatg ttgttgagag agttggtaag  5640
agaaccggct ggttggttga aatcgtcaac tacaacgttg aaaaccaaca atatgttgca  5700
gctggtgatc taagagcttt agacaccgtt accaatgttc taaacttcat caaattacaa  5760
aaaattgata ttattgaact acaaaagtcc ttatctttgg aagaagttga aggtcatttg  5820
tttgagatca ttgacgaagc ttccaagaaa tctgctgtca agcctcgccc acttaaattg  5880
gagagaggtt ttgcttgtat cccattagtt gtatttctg ttccttttcca ttccacctac  5940
ttgatgaatg gtgttaaacc attcaagagt ttcttgaaga agaatatcat aaaagaaaat  6000
gtgaaggttg ctagattggc cggaaagtac attccaaact tgactcaaaa accattccag  6060
gttactaagg aatatttcca ggacgtttat gatttgactg ctccgaacc tatcaaggaa  6120
atcatcgaca actgggaaaa gtatgaacaa tcctaa                            6156
```

*Saccharomyces cerevisiae*

SEQ ID NO: 9

```
atggacgctt actccacaag accattaacc ctatctcacg gttctttaga gcacgtgctt    60
ctggtaccaa ccgcttcatt tttcattgct tcgcaattac aagaacaatt taataaaatt   120
```

TABLE 4-continued

Sequences disclosed herein.

```
ttgcccgaac ccactgaagg gtttgctgca gatgacgagc ctaccacacc tgctgaacta   180
gtggggaaat tccttggcta cgtatcttct ctagtcgaac cttccaaggt cggtcaattc   240
gatcaggtct tgaacctttg cttaacagaa tttgaaaact gttatttaga aggcaatgac   300
attcacgcct tggctgctaa actattacag gaaaacgaca caactttagt gaagactaaa   360
gaactaatta aaaattatat taccgccaga ataatggcta agagaccatt tgacaaaaaa   420
tccaactctg ctcttttag ggccgtcggc gagggtaacg cacaattggt agccattttc   480
ggtggtcaag gtaacaccga cgactacttt gaagaattgc gtgatctata tcaaacttat   540
catgtcttag tgggagattt aatcaagttc tccgctgaaa ctttaagtga actgattaga   600
actacttag atgctgaaaa agtctttact caaggtttaa acatattgga atggttggag   660
aaccctcaa ataccccaga caaggactat ttactttccg ctccaatttc atgcccctta   720
attggtgtca ttcaattggc tcactacgta gttactgcca agcttttggg tttcactcca   780
ggtgagttaa gatcttactt aaaaggtgct acaggtcact ctcaaggttt ggttactgct   840
gtcgccatag ctgagacgga ttcctgggaa tccttcttcg tctccgtaag aaaagcaatt   900
actgtattat tcttcatcgg tgttcgttgt tacgaagcat acccaaacac ttccctacca   960
ccatccatct tggaagattc cttggaaaac aatgaaggtg ttccatctcc aatgttgtcc  1020
atttccaatc taactcaaga acaagttcaa gactatgtaa ataagactaa ctctcatttg  1080
ccagctggta aacaagttga aatttctcta gtcaatggtg cgaagaatct agtcgtatcg  1140
ggcccaccac aatcattata tggtttaaac ttgactttaa gaaaggccaa ggccccatct  1200
ggactggatc aatcaagaat cccattcagc gaaagaaaat tgaagttctc caataggttc  1260
ttacctgttg catcaccatc ccattccat ctattggttc cagcttcaga tttgattaac  1320
aaaagactag tcaaaaacaa tgtcagcttt aacgctaaag atattcaaat cccgtttac   1380
gacacttttg atggttcaga tctaagagtc ctttcaggtt ccatttccga gagaatcgtc  1440
gactgcatca ttagattacc tgtcaaatgg gaaactacta cacaattcaa agcaacccac  1500
atattagact ttggtccagg tggagcttcc ggtttaggtg ttttaaccca tcgtaataaa  1560
gatggtactg tgttcgtgt tatcgttgcc ggtactctcg acattaaccc agatgatgat  1620
tacgattca agcaagaaat ctttgatgtt actagtaatg gtttgaagaa aaatccaaac  1680
tggttggaag aataccatcc aaaattaatt aagaacaaat caggcaaaat ttttgtcgaa  1740
acaaaatttt ctaaattaat cggtagacca cctttattgg ttcctggtat gacaccatgt  1800
actgtttctc cagatttcgt agctgctacc acaaatgctg gttataccat tgagttggcc  1860
ggtggtggtt acttttccgc agcaggtatg accgccgcta ttgattctgt ggtttctcag  1920
atagaaaagg gtagtacctt cggtatcaac ttgatctacg tcaatccatt tatgttacaa  1980
tggggtattc cattaatcaa ggaactaaga agcaaaggtt atccaattca attcttgacc  2040
attggtgctc gtgtcccatc attggaagtt gctagtgaat acatagagac attaggttg   2100
aagtacttgg gtttgaaacc aggttccatt gatgctattt cgcaagttat aaacattgct  2160
aaagcacatc caaacttccc aatagcttta caatggaccg tggtagagg tggtggtcat  2220
cattcttcg aagatgccca cactccaatg ttacaaatgt actccaagat tagaagacat  2280
ccaaacatta tgttgatatt cggttctggt ttcggttctg ctgatgacac ttacccatac  2340
ttaaccggtg aatggtccac aaaattcgat tatccaccaa tgccattcga tggtttccta  2400
tttggttcga gggtcatgat tgctaaggaa gttaaaactt ctcctgatgc taagaagtgt  2460
attgctgctt gtactggtgt tcctgatgat aaatgggaac aaacctacaa gaagccaact  2520
ggtggtattg tcactgttcg ctctgaaatg ggtgaaccaa ttcacaaaat tgccactcgt  2580
ggtgttatgc tatggaagga attcgacgaa accatcttca acttaccaaa gaataagttg  2640
gtaccaactt ggaagcaaa gagagattac attatctcaa gattgaacgc cgatttccaa  2700
aaccatggt ttgctaccgt caacggtcaa gcccgtgaac tagccacaat gacatacgaa  2760
gaagttgcaa agagattggt ggaattaatg ttcatcagat ctaccaactc ttggtttgat  2820
gtcacatgga gaaccttac tggtgattc ctacgtcgtg tcgaagaacg tttcactaaa  2880
agtaagacat tgtctttaat ccaatcctat tctctactag acaagcctga tgaagctatt  2940
gaaaaagtat ttaatgctta tcctgccgct agggaacagt tcttgaatgc gcaagatatt  3000
gatcactttt tgagcatgtg tcaaaatcca atgcaaaaac cagtgccttt tgttccagtt  3060
ttggatcgta gattcgagat ttttttcaaa aaagattcgt tatggcaatc tgagcacttg  3120
gaagccgtcg tcgaccaaga cgttcaaaga acatgtatcc tacatggacc tgttgcagca  3180
caattcacta aagtcatcga tgaaccaatt aagagcatta tggatggtat tcacgattga  3240
cacatcaaaa agttactaca tcaatattac ggtgacgatg agtcaaagat tccagcagtt  3300
gagtactttg tggtgaaag ccctgtagac gtacaaagtc aagttgattc ttcctctgta  3360
tctgaagact cagctgtttt taaggcaaca tcctctactg atgaagaaag ctggtttaag  3420
gctttggcgg gatccgaaat taactggaga catgcaagtt tcttatgttc cttatcact   3480
caagataaaa tgtttgtttc taaccaatt agaaaagttt caagccaag ccaaggaatg   3540
gttgttgaga tttccaacgg caatacttct tcaaagactg ttgtcactct ttcagaacct  3600
gttcaaggtg aattgaaacc aactgttatt ttgaagttgt tgaaggagaa cataatccaa  3660
atggaaatga ttgagaacag aactatggat ggtaagcccg tcagcttgcc attgttgtac  3720
aacttcaacc cagataatgg ttttgctcca atctctgaag ttatggagga cagaaaccaa  3780
agaattaagg aaatgtactg gaaattatgg attgatgagc ctttcaattt ggactttgac  3840
ccaagagatg tcattaaggg caaagatttc gagatcaccg ctaaagaagt ttatgactt   3900
acacgctg ttggaaacaa ttgtgaagac ttcgtttcta gacctgatag aacgatgttg   3960
gccccaatgg acttgtctat tgttgtcgga tggagagcca ttcaaggc cattttccct   4020
aatacggtcg atggtgactt attgaagttg gttcatttgt ctaacggcta caagatgatt  4080
cctggcgcta agccactgca agttggtgat ttgtttcaa ctactgctgt tattgaatct   4140
gtcgtcaacc aacctacagg aaagattgtc gatgtggtag gtacattatc gagaaatggc  4200
aagcctgtca tggaagtcac ctcctcattc ttctacagag gcaactatac tgactttgaa  4260
aacactttcc aaaagactgt tgaacctgtt tatcaaatgc acatcaaaac ttctaaagat  4320
atagctgtct tgcgctctaa ggagtggttc caattggacg atgaagactt cgatctgtta  4380
aacaaaactt tgactttcga aactgaaact gaagttactt tcaagaatgc taacatcttc  4440
tcttcagtga aatgtttggg cccaattaaa gttgaattgc caaccaaaga aacgtgagg   4500
atcggtattg tcgattacga agccggtgcc tctcacggta accctgttgt tgatttcttg  4560
aagagaaacg gttccacatt ggaacaaaag gtcaatctag aaaatcctat tccaattgca  4620
gtacttgatt cgtacactcc aagtaccaac gaaccatacg ctagagttc tggtgatttg   4680
aatccaattc acgtttcacg tcatttttgcc tcttacgcaa acttgccagg tactatcacg  4740
cacggtatgt ttcttctgc ttccgtccgt gctttgattg aaaactgggc tgctgacagt  4800
```

TABLE 4-continued

Sequences disclosed herein.

```
gtttcatcca gggtacgtgg ctacacttgt caatttgttg acatggtttt gcctaacact    4860
gctttgaaaa catcgattca acatgttggt atgatcaatg gtagaaaatt gataaagttt    4920
gaaactagaa atgaagatga cgttgtagtt ttgactggtg aagccgaaat tgaacaacct    4980
gttactacct tcgttttcac tggtcaaggt tcacaagaac aaggtatggg tatggactta    5040
tacaaaactt ctaaagctgc tcaagatgtt tggaatagaa ctgacaacca tttcaaggac    5100
acttatggtt tctctatctt agacattgtc attaacaacc cagttaactt aacaattcac    5160
ttcggtggtg aaaagggtaa gaggatcaga gaaaactatt ctgctatgat ctttgagact    5220
atcgtggatg gaaaattgaa gactgaaaaa attttcaagg aaattaatga gcacagtact    5280
tcttacacat ttagatctga aaaaggttta ttgtctgcta ctcaatttac acaaccagct    5340
ttaactttga tggaaaaagc tgctttcgaa gacttgaaat ctaaaggttt gatcccagcc    5400
gatgctactt ttgctggtca ctctttaggt gagtatgctg ctttggcctc tttggctgat    5460
gttatgtcta tcgaatcttt agttgaagtt gtgttctaca gaggtatgac tatgcaagtt    5520
gctgttccaa gagatgagtt gggcagatcc aactatggta tgattgccat taacccaggt    5580
agagtcgctg catcattctc tcaagaagct ttgcaatatg ttgttgagag agttggtaag    5640
agaaccggct ggttggttga aatcgtcaac tacaacgttg aaaaccaaca atatgttgca    5700
gctggtgatc taagagcttt agacaccgtt accaatgttc taaacttcat caaattacaa    5760
aaaattgata ttattgaact acaaaagtcc ttatctttgg aagaagttga aggtcatttg    5820
tttgagatca ttgacgaagc ttccaagaaa tctgctgtca agcctcgccc acttaaattg    5880
gagagaggtt ttgcttgtat cccattagtt ggtatttctg ttcctttcca ttccacctac    5940
ttgatgaatg gtgttaaacc attcaagagt ttcttgaaga agaatatcat aaaagaaaat    6000
gtgaaggttg ctagattggc cggaaagtac attccaaact tgactgcaaa accattccag    6060
gttactaagg aatatttcca ggacgtttat gatttgactg gctccgaacc tatcaaggaa    6120
atcatcgaca actgggaaaa gtatgaacaa tcctaa                              6156
```

Saccharomyces cerevisiae

SEQ ID NO: 10

```
atggacgctt actccacaag accattaacc ctatctcacg gttctttaga gcacgtgctt      60
ctggtaccaa ccgcttcatt tttcattgct tcgcaattac aagaacaatt taataaaatt     120
ttgcccgaac ccactgaagg gtttgctgca gatgacgagc ctaccacacc tgctgaacta     180
gtggggaaat tccttggcta cgtatcttct ctagtcgaac cttccaaggt cggtcaattc     240
gatcaggtct tgaaccttgt cttaacagaa tttgaaaact gttatttaga aggcaatgac     300
attcacgcct tggctgctaa actattacag gaaaacgaca caactttagt tgagactaaa     360
gaactaatta aaaattatat taccgccaga ataatggcta agagaccatt tgacaaaaaa     420
tccaactctg ctcttttag ggccgtcggc gagggtaacg cacaattggt agccatttc      480
ggtggtgcag gtaacaccga cgactacttt gaagaattgc gtgatctata tcaaactat      540
catgtcttag tgggagattt aatcaagttc tccgctgaaa actgattaga                600
actactttag atgctgaaaa agtcttact caaggtttaa acatattgga atggttggag     660
aaccttcaa ataccccaga caaggactat ttactttcca ttcaatttc atgcccctta      720
attggtgtca ttcaattggc tcactacgta gttactgcca agcttttggg tttcactcca     780
ggtgagttaa gatcttactt aaaaggtgct acaggtcact ctcaaggttt ggttactgct     840
gtcgccatag ctgagacgga ttcctgggaa tccttcttcg tctccgtaag aaaagcaatt     900
actgtattat tcttcatcgg tgttcgttgt tacgaagcat acccaaacac ttccctacca     960
ccatccatct tggaagattc cttggaaaac aatgaaggtg ttccatctcc aatgttgtcc    1020
atttccaatc taactcaaga acaagttcaa gactatgtaa ataagactaa ctctcatttg    1080
ccagctggta aacaagttga aatttctcta gtcaatggtc cgaagaatct agtcgtatcg    1140
ggcccaccac aatcattata tggttttaaac ttgactttaa gaaaggccaa ggccccatct   1200
ggactggatc aatcaagaat cccattcagc gaaagaaat tgaagttctc caataggttc    1260
ttacctgttg ctcaccagc acattccat ctattggttc cagcttcaga tttgattaac    1320
aaagacttag tcaaaacaa tgtcagcttt aacgctaaag atattcaaat ccccgtttac    1380
gacacttttg atggttcaga tctaagagtc ctttcaggtt ccatttccga gagaatcgtc    1440
gactgcatca ttagattacc tgtcaaatgg gaaactacta cacaattcaa agccacccac    1500
atattagact ttggtccagg tggagcttcc ggttaggtg ttttaaccca tcgtaataaa    1560
gatgctactg gtgttcgtgt tatcgttgcc ggtactctcg acattaaccc agatgatgat    1620
tacggattca agcaagaat ctttgatgtt actagtaatg gttgaagaa aaatccaaac     1680
tggttggaag aataccatcc aaaattaatt aagaacaaat caggcaaaat ttttgtcgaa    1740
acaaaatttt ctaaattaat cggtagacca ccttttattgg ttcctggtat gacaccatgt    1800
actgtttctc cagatttcgt agctgctacc acaaatgctg ttataccat tgagttggcc    1860
ggtggtggtt acttttccgc agcaggtatg accgccgcta ttgattctgt ggttttctcag   1920
atagaaaagg gtagtacctt cggtatcaac ttgatctacg tcaatccatt tatgttacaa    1980
tggggtattc cattaatcaa ggaactaaga agcaaaggtt atccaattca attcttgacc    2040
attggtgctg gtgtcccatc atttgaagtt gctagtgaat acatagagac attaggttg    2100
aagtacttgg gtttgaaacc aggttccatt gatgctattt cgcaagttat aaacattgct    2160
aaagcacatc caaacttccc aatagcttta caatggaccg tggtagagg tgttggtcat    2220
cattctttcg aagatgccca cactccaatg ttacaaatgt actccaagat tagaagacat    2280
ccaaacatta tgttgatatt cggttctggt tcggttctg ctgatgacac ttacccatac    2340
ttaaccggtg aatggtccac aaaattcgat tatccaccaa tgccattcga tggtttccta    2400
tttggttcga gggtcatgat tgctaaggaa gttaaaactt ctcctgatgc taagaagtgt    2460
attgctgctt gtactggtgt tcctgatgat aaatgggaac aaacctacaa gaagccaact    2520
ggtgtgtcg tcactgttcg ctctgaaatg gtgaaccaa ttcacaaaat tgccactcgt     2580
ggtgttatgc tatggaagga attcgacgaa accatcttca acttaccaaa gaataagttga   2640
gtaccaactt tggaagcaaa gagagatac attatctcaa gattgaacgc cgatttccaa    2700
aaaccatggt ttgctaccgt caacggtcaa gcccgtgacc tagccacaat gacatacgaa    2760
gaagttgcaa agagattggt ggaataatg ttcatcagat ctaccaactc ttggtttgat   2820
gtcacatgga gaacctttac tggtgatttc ctacgtcgtg tcgaagaacg tttcactaaa    2880
agtaagacat tgtctttaat ccaatcctat tctctactag acaagcctga tgaagctat    2940
gaaaagtgta ttaatgctta tcctgccgct agggaacagt tcttgaatgc gcaagatatt    3000
gatcacttt tgagcatgtg tcaaaatcca atgcaaaaac cagtgccttt tgttccagtt    3060
ttggatcgta gattcgagat ttttttcaaa aaagattcgt tatggcaatc tgagcacttg    3120
```

TABLE 4-continued

Sequences disclosed herein.

```
gaagccgtcg tcgaccaaga cgttcaaaga acatgtatcc tacatggacc tgttgcagca   3180
caattcacta aagtcatcga tgaaccaatt aagagcatta tggatggtat tcacgatggt   3240
cacatcaaaa agttactaca tcaatattac ggtgacgatg agtcaaagat tccagcagtt   3300
gagtactttg gtggtgaaag ccctgtagac gtacaaagtc aagttgattc ttcctctgta   3360
tctgaagact cagctgtttt taaggcaaca tcctctactg atgaagaaag ctggtttaag   3420
gctttggcgg gatccgaaat taactggaga catgcaagtt tcttatgttc ctttatcact   3480
caagataaaa tgtttgtttc taacccaatt agaaaagttt tcaagccaag ccaaggaatg   3540
gttgttgaga tttccaacgg caatacttct tcaaagactg ttgtcactct ttcagaacct   3600
gttcaaggtg aattgaaacc aactgttatt ttgaagttgt tgaaggagaa cataatccaa   3660
atggaaatga ttgagaacag aactatggat ggtaagcccg tcagcttgcc attgttgtac   3720
aacttcaacc cagataatgg ttttgctcca atctctgaag ttatggagga cagaaaccaa   3780
agaattaagg aaatgtactg gaaattatgg attgatgagc ctttcaattt ggactttgac   3840
ccaagagatg tcattaaggg caaagatttc gagatcaccg ctaaagaagt ttatgacttt   3900
acacacgctg ttggaaacaa ttgtgaagac ttcgtttcta gacctgatag aacgatgttg   3960
gccccaatgg actttgctat tgttgtcgga tggagagcca tcatcaaggc cattttccct   4020
aatacggtcg atggtgactt attgaagttg gttcatttgt ctaacggcta caagatgatt   4080
cctggcgcta agccactgca agttggtgat gttgtttcaa ctactgctgt tattgaatct   4140
gtcgtcaacc aacctacagg aaagattgtc gatgtggtag gtacattatc gagaaatggc   4200
aagcctgtca tggaagtcac ctcctcattc ttctacagag gcaactatac tgactttgaa   4260
aacactttcc aaaagactgt tgaacctgtt tatcaaatgc acatcaaaac ttctaaagat   4320
atagctgtct tgcgctctaa ggagtggttc caattggacg atgaagactt cgatctgtta   4380
aacaaaactt tgactttcga aactgaaact gaagttactt tcaagaatgc taacatcttc   4440
tcttcagtga aatgttttgg cccaattaaa gttgaattgc caaccaaaga aaccgtggag   4500
atcggtattg tcgattacga agccggtgcc tctcacggta accctgttgt tgatttcttg   4560
aagagaaacg gttccacatt ggaacaaaag gtcaatctag aaaatcctat tccaattgca   4620
gtacttgatt cgtacactcc aagtaccaac gaaccatacg ctagagtttc tggtgatttg   4680
aatccaattc acgtttcacg tcattttgcc tcttacgcaa acttgccagg tactatcacg   4740
cacggtatgt tttcttctgc ttccgtccgt gctttgattg aaaactgggc tgctgacagt   4800
gtttcatcca gggtacgtgg ctacacttgt caatttgttg acatggtttt gcctaacact   4860
gctttgaaaa catcgattca acatgttggt atgatcaatg gtagaaaatt gataaagttt   4920
gaaactagaa atgaagatga cgttgtagtt ttgactggtg aagccgaaat tgaacaacct   4980
gttactacct tcgttttcac tggtcaaggt tcacaagaac aaggtatggg tatggactta   5040
tacaaaactt ctaaagctgc tcaagatgtt tggaatagag ctgacaacca tttcaaggac   5100
acttatggtt tctctatctt agacattgtc attaacaacc cagttaactt aacaattcac   5160
ttcggtggtg aaaagggtaa gaggatcaga gaaaactatc tgctatgat ctttgagact   5220
atcgtggatg gaaaattgaa gactgaaaaa atttcaagg aaattaatga gcacagtact   5280
tcttacacat ttagatctga aaaaggtttaa ttgtctgcta ctcaatttac acaaccagct   5340
ttaactttga tggaaaaagc tgctttcgaa gacttgaaat ctaaaggttt gatcccagcc   5400
gatgctactt ttgctggtca ctctttaggt gagtatgctg ctttggcctc tttggctgat   5460
gttatgtcta tcgaatcttt agttgaagtt gtgttctaca gaggtatgac tatgcaagtt   5520
gctgttccaa gagatgagtt gggcagatcc aactatgta tgattgccat taacccaggt   5580
agagtcgctg catcattctc tcaagaagct ttgcaatatg ttgttgagag agttggtaag   5640
agaaccggct ggttggttga aatcgtcaac tacaacgttg aaaaccaaca atatgttgca   5700
gctggtgatc taagagcttt agacaccgtt accaatgttc taaacttcat caaattacaa   5760
aaaattgata ttattgaact acaaaagtcc ttatctttgg aagaagttga aggtcatttg   5820
tttgagatca ttgacgaagc ttccaagaaa tctgctgtca agcctcgccc acttaaattg   5880
gagagaggtt ttgcttgtat cccattagtt ggtatttctg ttcctttcca ttccacctac   5940
ttgatgaatg gtgttaaacc attcaagagt ttettgaaga agaatatcat aaaagaaaat   6000
gtgaaggttg ctagattggc cggaaagtac attccaaact tgactgcaaa accattccag   6060
gttactaagg aatatttcca ggacgtttat gatttgactg gctccgaacc tatcaaggaa   6120
atcatcgaca actgggaaaa gtatgaacaa tcctaa                              6156
```

*Saccharomyces cerevisiae*

SEQ ID NO: 11
```
atggacgctt actccacaag accattaacc ctatctcacg gttctttaga gcacgtgctt     60
ctggtaccaa ccgcttcatt tttcattgct tcgcaattac aagaacaatt taataaaatt    120
ttgcccgaac ccactgaagg gtttgctgca gatgacgatg ctaccacacc tgctgaacta    180
gtggggaaat tccttggcta cgtatcttct ctagtcgaac cttccaaggt cggtcaattc    240
gatcaggtct tgaaccttg cttaacagaa tttgaaaact gttatttaga aggcaatgac    300
attcacgcct tggctgctaa actattacag gaaaacgaca caactttagt gaagactaaa    360
gaactaatta aaaattatat taccgccaga ataatggcta agagaccatt tgacaaaaaa    420
tccaactctg ctcttttag ggccgtcggc gagggtaacg cacaattggt agccattttc    480
ggtggtcaag gtaacaccga cgactacttt gaagaattgc gtgatctata tcaaacttat    540
catgtcttag tgggagattt aatcaagttc tccgctgaaa ctttaagtga actgattaga    600
actactttag atgctgaaaa agtctttact caaggtttaa acatattgga atggttggag    660
aacccttcaa atacccccaga caaggactat ttactttcca ttccaatttc atgcccctta    720
attggtgtca ttcaattggc tcactacgta gttactgcca agcttttggg tttcactcca    780
ggtgagttaa gatcttactt aaaaggtgct acaggtcact ctcaaggttt ggttactgct    840
gtcgccatag ctgagacgga ttcctgggaa tccttcttcg tctccgtaag aaaagcaatt    900
actgtattat tcttcgcagg tgttcgttgt tacgaagcat acccaaacac ttccctacca    960
ccatccatct tggaagattc cttggaaaac aatgaaggtg ttcatctccc aatgttgtcc   1020
atttccaatc taactcaaga acaagttcaa gactatgtaa ataagactaa ctctcatttg   1080
ccagctggta aacaagttga aatttctcta gtcaatggtg cgaagaatct atcgtatcg   1140
ggcccaccac aatcattata tggtttaaac ttgacttta gaaaggccaa ggccccatct   1200
ggactggatc aatcaagaat cccattcagc gaaagaaaat tgaagttctc caataggttc   1260
ttacctgttg catcaccatt ccattcccat ctattggttc cagcttcaga tttgattaac   1320
aaagacttag tcaaaacaa tgtcagcttt aacgctaaag atattcaaat cccgtttac    1380
gacacttttg atggttcaga tctaagagtc ctttcaggtt ccatttccga gagaatccgtc   1440
```

TABLE 4-continued

Sequences disclosed herein.

```
gactgcatca ttagattacc tgtcaaatgg gaaactacta cacaattcaa agccacccac 1500
atattagact ttggtccagg tggagcttcc ggtttaggtg ttttaaccca tcgtaataaa 1560
gatggtactg gtgttcgtgt tatcgttgcc ggtactctcg acattaaccc agatgatgat 1620
tacggattca agcaagaaat ctttgatgtt actagtaatg gtttgaagaa aaatccaaac 1680
tggttggaag aataccatcc aaaattaatt aagaacaaat caggcaaaat ttttgtcgaa 1740
acaaaatttt ctaaattaat cggtagacca ccttttattgg ttcctggtat gacaccatgt 1800
actgttttctc cagatttcgt agctgctacc acaaatgctg gttataccat tgagttggcc 1860
ggtggtggtt acttttccgc agcaggtatg accgccgcta ttgattctgt ggtttctcag 1920
atagaaaagg gtagtacctt cggtatcaac ttgatctacg tcaatccatt tatgttacaa 1980
tggggtattc cattaatcaa ggaactaaga agcaaaggtt atccaattca attcttgacc 2040
attggtgctg gtgtcccatc attggaagtt gctagtgaat acatagagac attaggtttg 2100
aagtacttgg gtttgaaacc aggttccatt gatgctattt cgcaagttat aaacattgct 2160
aaaagcacatc caaacttccc aatagcttta caatggaccg tggtagagg tggtggtcat 2220
cattctttcg aagatgccca cactccaatg ttacaaatgt actccaagat tagaagacat 2280
ccaaacatta tgttgatatt cggttctggt ttcggttctg ctgatgacac ttacccatac 2340
ttaaccggtg aatggtccac aaaattcgat tatccaccaa tgccattcga tggtttccta 2400
tttggttcga gggtcatgat tgctaaggaa gttaaaactt ctcctgatgc taagaagtgt 2460
attgctgctt gtactggtgt tcctgatgat aaatgggaac aaacctacaa gaagccaact 2520
ggtggtattg tcactgttcg ctctgaaatg ggtgaaccaa ttcacaaaat tgccactcgt 2580
ggtgttatgc tatggaagga attcgacgaa accatcttca acttaccaaa gaataagttg 2640
gtaccaactt tggaagcaaa gagagattac attatctcaa gattgaacgc cgatttccaa 2700
aaaccatggt ttgctaccgt caacggtcaa gcccgtgacc tagccacaat gacatacgaa 2760
gaagttgcaa agagattggt ggaattaatg ttcatcagat ctaccaactc ttggtttgat 2820
gtcacatgga aacctttac tggtgatttc ctacgtcgtg tcgaagaacg tttcactaaa 2880
agtaagacat tgtctttaat ccaatcctat tctctactag acaagcctga tgaagctatt 2940
gaaaaagtat ttaatgctta tcctgccgct agggaacagt tcttgaatgc gcaagatatt 3000
gatcacttttt tgagcatgtg tcaaaatcca atgcaaaaac cagtgccttt tgttccagtt 3060
ttggatcgta gattcgagat ttttttcaaa aaagattcgt tatggcaatc tgagcacttg 3120
gaagccgtcg tcgaccaaga cgttcaaaga acatgtatcc tacatggacc tgttgcagca 3180
caattcacta aagtcatcga tgaaccaatt aagagcatta tggatggtat tcacgatggt 3240
cacatcaaaa agttactaca tcaatattac ggtgacgatg agtcaaagat tccagcagtt 3300
gagtactttg gtggtgaaag ccctgtagac gtacaaagtc aagttgattc ttcctcgtga 3360
tctgaagact cagctgtttt taaggcaaca tcctctactg atgaagaaag ctggtttaag 3420
gctttggcgg gatccgaaat taactggaga catgcaagtt tcttatgttc ctttatcact 3480
caagataaaa tgttttgtttc taaccaattg agaaaagttt tcaagccaag ccaaggaatg 3540
gttgttgaga tttccaacgg caatacttct tcaaagactg ttgtcactct ttcagaacct 3600
gttcaaggtg aattgaaacc aactgttatt ttgaagttgt tgaaggagaa cataatccaa 3660
atggaaatga ttgagaacag aactatggat ggtaagcccg tcagcttgcc attgttgtac 3720
aacttcaacc cagataatgg ttttgctcca atctctgaag ttatggagga cagaaaccaa 3780
agaattaagg aaatgtactg gaaattatgg attgatgaac ctttcaattt ggactttgac 3840
ccaagagatg tcattaaggg caaagattttc gagatcaccg ctaaagaagt ttatgacttt 3900
acacacgctg ttgaaacaa ttgtgaagac ttcgtttcta gacctgatag aacgatgttg 3960
gccccaatgg actttgctat tgttgtcgga tggagagcca tcatcaaggc cattttccct 4020
aatacggtcg atggtgactt attgaagttg gttcatttgt ctaacggcta caagatgatt 4080
cctggcgcta agccactgca agttggtgat gttgtttcaa ctactgctgt tattgaatct 4140
gtcgtcaacc aactacagg aaagattgtc gatgtggtag gtacattatc gagaaatggc 4200
aagcctgtca tggaagtcac ctcctcattc ttctacagag gcaactatac tgactttgaa 4260
aacactttcc aaaagactgt tgaacctgtt tatcaaatgc acatcaaaac ttctaaagat 4320
atagctgtct tgcgctctaa ggagtggttc caattggacg atgaagactt cgatctgtta 4380
aacaaaactt tgacttttcga aactgaaact gaagttactt tcaagaatgc taacatcttc 4440
tcttcagtga aatgttttgg cccaattaaa gttgaattgc caaccaaaga aaccgtggag 4500
atcggtattg tcgattacga agccggtgcc tctcacggta accctgttgt tgatttcttg 4560
aagagaaacg gttccacatt ggaacaaaag gtcaatctag aaaatcctat tccaattgca 4620
gtacttgatt cgtacactcc aagtaccaac gaaccatacg ctagagtttc tggtgatttg 4680
aatccaattc acgtttcacg tcattttgcc tcttacgcaa acttgccagg tactatcacg 4740
cacggtatgt tttcttctgc ttccgtccgt gctttgattg aaaactgggc tgctgacagt 4800
gtttcatcca gggtacgtgg ctacacttgt caatttgttg acatggtttt gcctaacact 4860
gctttgaaaa catcgattca acatgttggt atgatcaatg gtagaaaatt gataaagttt 4920
gaaactagaa atgaagatga cgttgtagtt ttgactggtg aagccgaaat tgaacaacct 4980
gttactacct tcgtttttcac tggtcaaggt tcacaagaac aaggtatggg tatggactta 5040
tacaaaactt ctaaagctgc tcaagatgtt tggaatagaa ctgacaacca tttcaaggac 5100
acttatggtt tctctatctt agacattgtc attaacaacc cagttaactt aacaattcac 5160
ttcggtggtg aaaagggtaa gaggatcaga gaaaactatt ctgctatgat ctttgagact 5220
atcgtggatg gaaaattgaa gactgaaaaa attttcaagg aaattaatga gcacagtact 5280
tcttacacat ttagatctga aaaaggttta ttgtctgcta ctcaatttac acaaccagct 5340
ttaactttga tggaaaaagc tgcttttcgaa gacttgaaat ctaaaggttt gatcccagcc 5400
gatgctactt ttgctggtca ctctttaggt gagtatgctg ctttggcctc tttggctgat 5460
gttatgtcta tcgaatcttt agttgaagtt gtgttctaca gaggtatgac tatgcaagtt 5520
gctgttccaa gagatgagtt gggcagatcc aactatggta tgattgccat taacccaggt 5580
agagtcgctg catcattctc tcaagaagct ttgcaatatg ttgttgagag agttggtaag 5640
agaaccgct ggttggttga aatcgtcaac tacaacgttg aaaaccaaca atatgttgca 5700
gctggtgatc taagagcttt agacaccgtt accaatgttc taaacttcat caaattacaa 5760
aaaattgata ttattgaact acaaaagtcc ttatctttgg aagaagttga aggtcatttg 5820
tttgagatca ttgacgaagc ttccaagaaa tctgctgtca agcctcgccc acttaaattg 5880
gagagaggtt ttgcttgtat cccattagtt ggtatttctg ttccttttcca ttccacctac 5940
ttgatgaatg gtgttaaacc attcaagagt ttcttgaaga agaatatcat aaaagaaaat 6000
```

TABLE 4-continued

Sequences disclosed herein.

```
gtgaaggttg ctagattggc cggaaagtac attccaaact tgactgcaaa accattccag   6060
gttactaagg aatatttcca ggacgtttat gatttgactg gctccgaacc tatcaaggaa   6120
atcatcgaca actgggaaaa gtatgaacaa tcctaa                             6156
```

*Saccharomyces cerevisiae*

SEQ ID NO: 12

```
atggacgctt actccacaag accattaacc ctatctcacg gttctttaga gcacgtgctt     60
ctggtaccaa ccgcttcatt tttcattgct tcgcaattac aagaacaatt taataaaatt    120
ttgcccgaac ccactgaagg gtttgctgca gatgacgagc ctaccacacc tgctgaacta    180
gtggggaaat tccttggcta cgtatcttct ctagtcgaac cttccaaggt cggtcaattc    240
gatcaggtct tgaacctttg cttaacagaa tttgaaaact gttatttaga aggcaatgac    300
attcacgcct tggctgctaa actattacag gaaaacgaca caactttagt gaagactaaa    360
gaactaatta aaaattatat taccgccaga ataatggcta agagaccatt tgacaaaaaa    420
tccaactctg ctcttttag ggccgtcggc gagggtaacg cacaattggt agccattttc     480
ggtggtcaag gtaacaccga cgactacttt gaagaattgc gtgatctata tcaaacttat    540
catgtcttag tgggagattt aatcaagttc tccgctgaaa ctttaagtga actgattaga    600
actactttag atgctgaaaa agtctttact caaggtttaa acatattgga atggttggag    660
aacccttcaa atacccccaga caaggactat ttactttcca ttccaatttc atgcccctta   720
attggtgtca ttcaattggc tcactacgta gttactgcca agcttttggg tttcactcca    780
ggtgagttaa gatcttactt aaaaggtgct acaggtcact ctcaaggttt ggttactgct    840
gtcgccatag ctgagacgga ttcctgggaa tccttcttcg tctccgtaag aaaagcaatt    900
actgtattat tcttcgcagg tgttcgttgt tacgaagcat acccaaacac ttccctacca    960
ccatccatct tggaagattc cttggaaaac aatgaaggta ttccatctcc aatgttgtcc   1020
atttccaatc taactcaaga acaagttcaa gactatgtaa ataagactaa ctctcatttg   1080
ccagctggta aacaagttga aatttctcta gtcaatggtg cgaagaatct agtcgtatcg   1140
ggcccaccac aatcattata tggtttaaac ttgactttaa gaaaggccaa ggccccatct   1200
ggactggatc aatcaagaat cccattcagc gaaagaaaat tgaagttctc caataggttc   1260
ttacctgttg catccaccat tccattccat ctattggttc cagcttcaga tttgattaac   1320
aaagacttag tcaaaaacaa tgtcagcttt aacgctaaag atattcaaat cccgtttac    1380
gacactttg atggttcaga tctaagagtc ctttcaggtt ccatttccga gagaatcgtc    1440
gactgcgcaa ttagattacc tgtcaaatgg gaaactacta cacaattcaa agccacccac   1500
atattagact ttggtccagg tggagcttcc ggttagttg tttaaccca tcgtaataaa     1560
gatggtactg tgttcgtgt tatcgttgcc ggtactctcg acattaaccc agatgatgat    1620
tacggattca agcaagaaat ctttgatgtt actagtaatg gtttgaagaa aaatccaaac   1680
tggttggaag aataccatcc aaaattaatt aagaacaaat caggcaaaat ttttgtcgaa   1740
acaaaatttt ctaaattaat cggtagacca cctttattgg ttcctggtat gacaccatgt   1800
actgtttctc cagatttcgt agctgctacc acaaatgctg gttataccat tgagttggcc   1860
ggtggtggtt acttttccgc agcaggtatg accgccgcta ttgattctgt ggtttctcag   1920
atagaaaagg gtagtacctt cggtatcaac ttgatctacg tcaatccatt tatgttacaa   1980
tggggtattc cattaatcaa ggaactaaga agcaaaggtt atccaattca attcttgacc   2040
attggtgctg tgtcccatc attggaagtt gctagtgaat acatagagac attaggtttg    2100
aagtacttgg gtttgaaacc aggttccatt gatgctattt cgcaagttat aaacattgct   2160
aaaagcacatc caaacttccc aatagcttta caatggaccg tggtagagg tggtggtcat   2220
cattctttcg aagatgccca cactccaatg ttacaaatgt actccaagat tagaagacat   2280
ccaaacatta tgttgatatt cggttctggt ttcggttctg ctgatgacac ttacccatac   2340
ttaaccggtg aatggtccac aaaattcgat tatccaccaa tgccattcga tggtttccta   2400
tttggttcga gggtcatgat tgctaaggaa gttaaaactt ctcctgatgc taagaagtgt   2460
attgctgctt gtactggtgt tcctgatgat aaatgggaac aaacctacaa gaagccaact   2520
ggtggtattg tcactgttcg ctctgaaatg ggtgaaccaa ttcacaaaat tgccactcgt   2580
ggtgttatgc tatggaagga attcgacgaa accatcttca acttaccaaa gaataagttg   2640
gtaccaactt ggaagcaaa gagagattac attatctcaa gattgaacgc cgatttccaa   2700
aaaccatggt ttgctaccgt caacggtcaa gcccgtgaac tagccacaat gacatacgaa   2760
gaagttgcaa agagattggt ggaattaatg ttcatcagat ctaccaactc ttggtttgat   2820
gtcacatgga gaacctttac tggtgatttc ctacgtcgtg tcgaagaacg tttcactaaa   2880
agtaagacat tgtctttaat ccaatcctat tctctactag acaagcctga tgaagctatt   2940
gaaaagtat ttaatgctta tcctgccgct agggaacagt tcttgaatgc gcaagatatt   3000
gatcactttt tgagcatgtg tcaaaatcca atgcaaaaac cagtgccttt tgttccagtt   3060
ttggatcgta gattcgagat tttttcaaa aaagattcgt tatggcaatc tgagcacttg   3120
gaagccgtcg tcgaccaaga cgttcaaaga acatgtatcc tacatggacc tgttgcagca   3180
caattcacta agtcatcga tgaccaatt aagagcatta tggatggtat tcacgatggt    3240
cacatcaaaa agttactaca tcaatattac ggtgacgatg agtcaaagat tccagcagtt   3300
gagtactttg gtggtaaag ccctgtagac gtacaaagtc aagttgattc ttcctctgta    3360
tctgaagact cagctgtttt taaggcaaca tcctctactg atgaagaaag ctggtttaag   3420
gctttggcgg gatccgaat taactggaga catgcaagtt tcttatgttc ctttatcact    3480
caagataaa tgtttgtttc taacccaatt agaaaagttt tcaagccaag ccaaggaatg    3540
gttgttgaga tttccaacgg caatacttct tcaaagactg ttgtcactct ttcagaacct   3600
gttcaaggtg aattgaaacc aactgttatt ttgaagttgt tgaaggagaa cataatccaa   3660
atggaaatga ttgagaacag aactatggat ggtaagcccg tcagcttgcc attgttgtac   3720
aacttcaacc cagataatgg ttttgctcca atctctgagg ttatggagga cagaaaccaa   3780
agaattaagg aaatgtactg gaaattatgg attgatgagc ctttcaattt ggactttgac   3840
ccaagagatg tcattaaggg caaagatttc gagatcaccg ctaaagaagt ttatgacttt   3900
acacacgctg ttggaaacaa ttgtgaagac ttcgttctta gacctgatag aacgatgttg   3960
gccccaatgg actttgctat tgttgtcgga tggaagaccca tcatcaaggc cattttccct   4020
aatacggctc atggtgactt attgaagttg gttcatttgt ctaacggcta caagatgatt   4080
cctggcgcta agccactgca agttggtgat gttgtttcaa ctactgctgt tattgaatct   4140
gtcgtcaacc aacctacagg aaagattgtc gatgtggtag gtacattatc gagaaatggc   4200
aagcctgtca tggaagtcac ctcctcattc ttctacagag gcaactatac tgactttgaa   4260
aacacttccc aaaagactgt tgaacctgtt tatcaaatgc acatcaaaac ttctaaagat   4320
```

TABLE 4-continued

Sequences disclosed herein.

```
atagctgtct tgcgctctaa ggagtggttc caattggacg atgaagactt cgatctgtta   4380
aacaaaactt tgactttcga aactgaaact gaagttactt tcaagaatgc taacatcttc   4440
tcttcagtga aatgtttggg cccaattaaa gttgaattgc caaccaaaga aaccgtggag   4500
atcggtattg tcgattacga agccggtgcc tctcacggta accctgttgt tgatttcttg   4560
aagagaaacg gttccacatt ggaacaaaag gtcaatctag aaaatcctat tccaattgca   4620
gtacttgatt cgtacactcc aagtaccaac gaaccatacg ctagagtttc tggtgatttg   4680
aatccaattc acgtttcacg tcatttttgcc tcttacgcaa acttgccagg tactatcacg   4740
cacggtatgt tttcttctgc ttccgtccgt gctttgattg aaaactgggc tgctgacagt   4800
gtttcatcca gggtacgtgg ctacacttgt caatttgttg acatggtttt gcctaacact   4860
gctttgaaaa catcgattca acatgttggt atgatcaatg gtagaaaatt gataaagttt   4920
gaaactagaa atgaagatga cgttgtagtt ttgactggtg aagccgaaat tgaacaacct   4980
gttactacct tcgtttttcac tggtcaaggt tcacaagaac aaggtatggg tatgggactta   5040
tacaaaactt ctaaagctgc tcaagatgtt tggaatagaa ctgacaacca tttcaaggac   5100
acttatggtt tctctatctt agacattgtc attaacaacc cagttaactt aacaattcac   5160
ttcggtggtg aaaagggtaa gaggatcaga gaaaactatt ctgctatgat ctttgagact   5220
atcgtggatg gaaaattgaa gactgaaaaa attttcaagg aaattaatga gcacagtact   5280
tcttacacat ttagatctga aaaaggttta ttgtctgcta ctcaatttac acaaccagct   5340
ttaactttga tggaaaaagc tgctttcgaa gacttgaaat ctaaaggttt gatcccagcc   5400
gatgctactt ttgctggtca ctcttttaggt gagtatgctg ctttggcctc tttggctgat   5460
gttatgtcta tcgaatcttt agttgaagtt gtgttctaca gaggtatgac tatgcaagtt   5520
gctgttccaa gagatgagtt gggcagatcc aactatggta tgattgccat taacccaggt   5580
agagtcgctc atcattctc tcaagaagct ttgcaatatg ttgttgagag agttggtaag   5640
agaaccggct ggttggttga aatcgtcaac tacaacgttg aaaaccaaca atatgttgca   5700
gctggtgatc taagagcttt agacaccgtt accaatgttc taaacttcat caaattacaa   5760
aaaattgata ttattgaact acaaaagtcc ttatctttgg aagaagttga aggtcatttg   5820
tttgagatca ttgacgaagc ttccaagaaa tctgctgtca agcctcgccc acttaaattg   5880
gagagaggtt ttgcttgtat cccattagtt ggtatttctg ttcctttcca ttccacctac   5940
ttgatgaatg gtgttaaacc attcaagagt ttcttgaaga agaatatcat aaaagaaaat   6000
gtgaaggttg ctagattggc cggaaagtac attccaaact tgactgcaaa accattccag   6060
gttactaagg aatatttcca ggacgtttat gatttgactg gctccgaacc tatcaaggaa   6120
atcatcgaca actgggaaaa gtatgaacaa tcctaa                             6156
```

*Ondatra zibethicus*

SEQ ID NO: 13
```
atgccagagg cgctgcttct caggtctgcc agctccatcc tgaggactgt gttcttaagc    60
agactgctac caggtgggcc tgggtgtgtt cgaaaactta gtttgaacct gcagtaccag   120
caaggaataa ggccgaatgt acaaagcagc tccttaactg atgggcgaac actctccaaa   180
gagtcctcaa ctccatggcct tgagttctca gctccagaga aggcctcacc gccagacacc   240
gcagaggaag cactctggac agctcgggca gatggaagag tgcgcctgcg cagggaaccc   300
ttctgcacgc agcctcccta tactgtgcac cggatgtct acgaggccct ggataagtac   360
gggagcctca gtgctctggg tgtcaagcgc agaaacaagt gggaacgcat ctcttactac   420
cagtactacg agattgcccg caaagtcgcc agaggcttcc tgaagcttgg cctgagcga    480
gcccacagcg tggggatcct cggcttcaac tccccagagt ggttcttctc tgcagtgggc   540
acagtgttcg caggggcat tgtcactggc atctcacaca ctagctccct tgaagcctgc   600
cagtacatcg cccacgactg ccgtgccaac gtcattgtgg ttgacacaca gaagcagctg   660
gagaagatac tgaagatctg gaaagacttg ccacacctca aagcagtggt aatataccaa   720
gaaccccttc caaagaagat ggtcaacgtg tacacgatgg aagaactcat agaactggga   780
caagaagtgc ctgaggaggc cctggacacc atcattgaca cccagcagcc caaccagtgt   840
tgcgtgctgg tctacacatc cggcaccacc ggaaacccca agggcgtgat gttgagtcaa   900
gacaatatca catggacagc acggtacggc agtcaggctg gggacatcca gccagcagaa   960
gtccagcagg aggtagtagt cagctacttg cccctcagcc acattgctgc ccagatctac  1020
gacctgtgga ccggcatcca gtggggagcc caggtctgct ttgcagatcc tgatgcccta  1080
aaggggagcc tggtgaacac actgcgggag gtggagccca catcccacat ggggggtgcct  1140
cgtgtgtggg agaagatcat ggaagggatc caggaggtgg cggctcagtc tggcttcatc  1200
cggcgcaaga tgctgctatg ggccatgtca gtgaccttgg aacagaacct cacttgccct  1260
agcaatgacc tgaagccctt cacaagcaga ctggcggatt acctagtatt agccaaggtc  1320
cgtcaggctc tgggcttttgc caagtgtcag aagaacttct acggagcagc ccccatgact  1380
gcagaaacac agcgcttctt tctgggcctt aacatccgcc tgtacgcagg ctacggcctc  1440
agcgagagca caggccccca cttcatgtcc agccccctaca actaccgact gtacagttct  1500
ggcaagttga tccctggctg ccgggtgaag ctggtcaatc aggatgccaa cggcatcggt  1560
gagatctgcc tgtggggccg aaccatcttc atgggctatc tgaacatgga ggacaaaacg  1620
tgtgaggcca ttgactcgga aggctggcta cacacaggtg acatgggccg tctgattcc   1680
gatggcttcc tctacatcac tggcgcctc aaagagttaa tcatcactgc gggtgggag    1740
aatgtgcccc cagtgcccat tgaggaggct gtgaagacgg agctgcccat catcagtagt  1800
gccatgctga tagggacca gaggaagttc ctgtccatgc tgctaactct gaagtgcacg  1860
ctggacccag agacatctga gccgacagac aacctgacag agcaagctgt ggagttctgc  1920
cagagggtgg gcagcggggc cagcaccgta tccgagattg tggggcagag agatgaggct  1980
gtgtatcagg ccatccagga agggatccag agggtgaacg cgaatgcagc agcccggccc  2040
taccacatcc agaagtgggc cattctcaaa cgtgacttct ccatttctgg tggagaactg  2100
ggccctacca tgaaactgaa acggctcaca gttctggaga agtacaaaga tatcatcgat  2160
tccttttatc aagagcaaaa acagtag                                      2187
```

*Saccharomyces cerevisiae*

SEQ ID NO: 14
```
atgttgcaga gacattcctt gaagttgggg aaattctcca tcagaacact cgctactggt    60
gccccattag atgcatccaa actaaaaatt actagaaacc caaatccatc caagccaaga   120
ccaaatgaag aattagtgtt cggccagaca ttcaccgatc atatgttgac cattccttgg   180
tcagccaaag aagggtgggg cactccacac atcaagcctt acggtaatct ttctcttgac   240
```

TABLE 4-continued

Sequences disclosed herein.

```
ccatctgctt gtgtattcca ttatgcattt gaattatttg aaggtttgaa agcctacaga    300
actcctcaaa atactatcac catgttccgt ccggataaga acatggcccg tatgaacaag    360
tctgccgcta gaatttgttt gccaactttc gaatctgaag aattgatcaa acttaccggg    420
aaattgatcg aacaagataa acacttggtt cctcaaggta atggttactc attatacatc    480
agaccaacaa tgattggtac atccaagggt ttaggtgttg gcactccctc cgaggctctt    540
ctttatgtta ttacttctcc agtcggtcct tattataaga ctggtttcaa agccgtacgt    600
cttgaagcaa cagactatgc tacaagagct tggccaggtg gtgttggcga caaaaaattg    660
ggtgctaact atgccccatg catcttacct caactacaag ctgccaaaag agggtaccaa    720
caaaatctat ggttgttcgg cccagaaaag aacatcactg aggttggtac tatgaacgtg    780
ttcttcgttt cctcaacaa agtcactggc aagaaggaat tggttaccgc tccattagat     840
ggtaccattt tagaaggtgt taccagagac tctgttttaa cattggctcg tgacaaacta    900
gatcctcaag aatgggacat caacgagcgt tattacacta ttactgaagt cgccactaga    960
gcaaaacaag gtgaactatt agaagccttc ggttctggta ctgctgctgt cgtttcacct   1020
atcaaggaaa ttggctggaa caacgaagat attcatgttc cactattgcc tggtgaacaa   1080
tgtggtgcat tgaccaagca agttgctcaa tggattgctg atatccaata cggtagagtc   1140
aattatggta actggtcaaa aactgttgcc gacttgaact aa                      1182
```

*Saccharomyces cerevisiae*

SEQ ID NO: 15
```
atgaccttgg cacccctaga cgcctccaaa gttaagataa ctaccacaca acatgcatct    60
aagccaaaac cgaacagtga gttagtgttt ggcaagagct tcacggacca catgttaact   120
gcggaatgga cagctgaaaa agggtggggt accccagaga ttaaaccta tcaaaatctg    180
tctttagacc cttccgcggt ggttttccat tatgcttttg agctattcga agggatgaag   240
gcttacagaa cggtgacaa caaaattaca atgtttcgtc cagatatgaa tatgaagcgc    300
atgaataagt ctgctcagag aatctgtttg ccaacgttcg acccagaaga gttgattacc    360
ctaattggga aactgatcca gcaagataag tgcttagttc ctgaaggaaa aggttactct    420
ttatatatca ggcctacatt aatcggcact acggccggtt taggggtttc cacgcctgat    480
agagccttgc tatatgtcat ttgctgccct gtgggtcctt attacaaaac tggatttaag    540
gcggtcagac tggaagccac tgattatgcc acaagagctt ggccaggagg ctgtggtgac    600
aagaaactag gtgcaaacta cgcccccctgc gtcctgccac aattgcaagc tgcttcaagg    660
ggttaccaac aaaatttatg gctatttggt ccaaataaca acattactga agtcggcacc    720
atgaatgctt ttttcgtgtt taaagatagt aaaacgggca agaaggaact agttactgct    780
ccactagacg gtaccatttt ggaaggtgtt actagggatt ccattttaaa tcttgctaaa    840
gaaagactcg aaccagtgaa atggaccatt agtgaacgct acttcactat aggcgaagtt    900
actgagagat ccaagaacgg tgaactactt gaagcctttg gttctggtac tgctgcgatt    960
gttctctcca ttaaggaaat cggctggaaa ggcgaacaaa ttaatattcc gttgttgccc   1020
ggcgaacaaa ccggtccatt ggccaaagaa gttgcacaat ggattaatgg aatccaatat   1080
ggcgagactg agcatggcaa ttggtcaagg gttgttactg atttgaactg a            1131
```

*Saccharomyces cerevisiae*

SEQ ID NO: 16
```
atggcacctg ttacaattga aaagttcgta aatcaagaag aacgacacct tgtttccaac    60
cgatcagcaa caattccgtt tggtgaatac atatttaaaa gattgttgtc catcgatacg   120
aaatcagttt tcggtgttcc tggtgacttc aacttatctc tattagaata tctctattca    180
cctagtgttg aatcagctgg cctaagatgg gtcggcacgt gtaatgaact gaacgccgct    240
tatgcggccg acggatattc ccgttactct aataagattg gctgtttaat aaccacgtat    300
ggcgttggtg aattaagcgc cttgaacggt atagccggtt cgttcgctga aaatgtcaaa    360
gttttgcaca ttgttggtgt ggccaagtcc atagattcgc gttcaagtaa ctttagtgat    420
cggaacctac atcatttggt cccacagcta catgattcaa attttaaagg gccaaatcat    480
aaagtatatc atgatatggt aaaagataga gtcgcttgct cggtagccta cttggaggat    540
attgaaactg catgtgacca agtcgataat gttatccgcg atatttacaa gtattctaaa    600
cctggttata tttttgttcc tgcagatttt gcggatatgt ctgttacatg tgataatttg    660
gttaatgttc cacgtatatc tcaacaagat tgtatagtat acccttctga aaaccaattg    720
tctgacataa tcaacaagat tactagttgg atatattcca gtaaaacacc tgcgatcctt    780
ggagacgtac tgactgatag gtatggtgtg agtaactttt tgaacaagct tatctgcaaa    840
actgggattt ggaattttc cactgttatg ggaaaatctg taattgatga gtcaaaccca    900
acttatatgg gtcaatataa tggtaaagaa ggtttaaaac aagtctatga aacttttgaa    960
ctgtgcgact tggtcttgca ttttggagtc gacatcaatg aaattaataa tgggcattat   1020
actttactt ataaaccaaa tgctaaaatc attcaatttc atccgaatta tattcgcctt    1080
gtggacacta ggcagggcaa tgagcaaatg ttcaaaggaa tcaattttgc ccctatttta   1140
aaagaactat acaagcgcat tgacgttctt aaactttctt tgcaatatga ttcaaatgta   1200
actcaatata cgaacgaaac aatgcggtta gaagatccta ccaatggaca atcaagcatt   1260
attacacaag ttcacttaca aaagacgatg cctaaatttt tgaaccctgg tgatgttgtc   1320
gtttgtgaaa caggctcttt tcaattctct gttcgtgatt tcgcgtttcc ttcgcaatta   1380
aaatatatat cgcaaggatt tttccttttcc attggcatgg cccttcctgc cgccctaggt   1440
gttggaattg ccatgcaaga ccactcaaac gctcacatca atggtggcaa cgtaaaagag   1500
gactataagc caagattaat tttgtttgaa ggtgacggtg cagcacagat gacaatccaa   1560
gaactgagca ccattctgaa gtgcaatatt ccactagaag ttatcatttg gaacaataac   1620
ggctacacta ttgaaagagc catcatgggc cctaccagtc cgtataacga cgttatgtct   1680
tggaaatgga ccaaactatt tgaagcattc ggagacttcg acggaaagta tactaatagc   1740
actctcattc aatgtccctc taaattagca ctgaaattgg aggagcttaa gaattcaaac   1800
aaaagaagcg ggatagaact tttagaagtc aaattaggcg aattggattt ccccgaacag   1860
ctaaagtgca tggttgaagc agcggcactt aaaagaaata aaaaatag               1908
```

*Saccharomyces cerevisiae*

SEQ ID NO: 17
```
atgcctacct tgtatactga tatcgaaatc ccacaattga aaatctcttt aaagcaaccg    60
ctagggttgt ttatcaacaa tgagttttgt ccatcatcag atgaaagac catcgaaact    120
```

TABLE 4-continued

Sequences disclosed herein.

```
gtgaacccag ctactggcga accgataaca tccttccaag cagctaacga aaaggatgta    180
gacaaagctg tgaaagctgc cagggctgct tttgataacg tttggtcgaa gacatcttct    240
gagcaacgtg gtatttatct ttcaaactta ttaaaactta ttgaggagga gcaagacaca    300
cttgccgcat tagagacttt agacgctgga aagccttacc attcaaatgc caaaggtgat    360
ttggcacaaa ttttacagct taccagatat tttgctggt  ccgctgataa gtttgacaaa    420
ggtgcaacca taccattgac ttttaacaag tttgcatata ctctaaaagt tcctttggc     480
gttgttgctc aaatcgttcc atggaattat cctctagcta tggcttgttg gaaattgcaa    540
ggtgccttag cagccggtaa cacgttatc  atcaaacctg ctgagaatac ctctctatct    600
ctactttatt ttgctacttt aattaaaaaa gcaggttttc cacctggtgt tgtcaatatc    660
gttcctggtt atggatcact tgtaggccaa gccctagcat ctcacatgga tatcgacaaa    720
atatctttta cgggaagcac caaggtcggt ggatttgtgt tggaagcttc cggccaatcg    780
aaccttaaag acgttacact agaatgcggt ggtaagtctc ctgctctcgt atttgaagat    840
gcagaccttg ataaggctat cgattggata gcagctggca ttttctacaa ttcaggacag    900
aattgtaccg caaactcaag agtttatgtt caaagttcga tctacgacaa gtttgttgaa    960
aagtttaaag aaactgcaaa gaaggagtgg gatgttgcag gaaaatttga tccgtttgat   1020
gagaaatgca tcgttggtcc agttatatca agtacacagt atgaccgcat caaaagttac   1080
atagaacgtg gtaaaaggga ggaaaagttg gacatgttcc agacctctga atttcctatt   1140
ggtggagcta aaggctactt cattcccca  accatcttca ctgatgtccc gcaaacatcg   1200
aaactgttac aggatgagat attttggcccg gttgtggttg ttagcaagtt cacaaattat   1260
gatgacgctc tgaagctggc taatgatact tgctacgggc tcgcctctgc ggtcttcaca   1320
aaagatgtca agaaagcgca catgtttgct cgcgatatta aagcaggaac tgtttggatc   1380
aactcatcta acgatgaaga tgttaccgtt ccttttggcg ggtttaaaat gagtggtatt   1440
ggtagagaac tggggcaaag tggtgttgat acctatcttc aaacaaaagc agttcacata   1500
aatctctctt tggacaacta a                                             1521

Saccharomyces cerevisiae
                                                            SEQ ID NO: 18
atgcttttctc gcacaagagc tgcagctccg aattccagaa tattcactag aagcttgtta    60
cgtcttttatt ctcaagcacc attacgcgtt ccaattactc tttccaaatgg tttcacctac   120
gaacagccaa cagggttatt catcaatggt gaatttgttg cctcgaagca aaagaaaacg    180
tttgacgtga tcaatccatc taacgaagaa aagataacaa ctgtatacaa ggctatggaa    240
gatgatgttg atgaagccgt tgcagcggct aaaaaagctt ttgaaacgaa gtggtctatt    300
gtagagccgg aggttcgcgc taaagcttta ttcaatctcg ctgacttggt tgagaaacac    360
caagaaaacac tggctgccat tgagtcaatg gataatggta agtcattgtt ttgtgcgcgc    420
ggtgacgtcg ctttagtatc taaatacttg cgttcttgcg gtggttgggc agataaaatc    480
tacggtaacg ttattgacac aggtaaaaac cattttacct actcaattaa ggaaccatta    540
ggcgttttgcg gccaaataat cccttggaac ttcccttttat tgatgtggtc atggaaaatt    600
gggcctgctc tggctacagg taacaccgtc gtattgaaac ccgctgaaac aacaccttta    660
tctgcccttt tcgcttccca gttgtgtcag gaagcaggca tacccgctgg tgtagtcaat    720
atccttccgg gttccggtag agttgttgga gaaagattgg gtgcacaccc agacgtgaag    780
aagattgctt ttacaggctc tactgccacc ggccgccata ttatgaaggt cgctgccgat    840
actgtcaaga aagtcacttt ggagctggga ggtaaatcac caaatattgt gtttgctgac    900
gctgatctag ataaagccgt caagaacatt gccttcggta tttttttacaa ctctggtgaa    960
gtttgctgcg ctggttccag aatatacatt caagatacag tatacgagga ggtgttgcaa   1020
aaactaaagg attacaccga gtcactaaag gtcggtgacc catttgatga ggaagttttc   1080
caaggtgctc aaacatctga caaacagctg cataaaattt tagactatgt cgatgtagca   1140
aaatcagagg gggctcgtct tgtgactgga ggggccagac atggcagtaa aggttatttt   1200
gtcaagccaa cagtgtttgc tgatgtcaaa gaagatatga gaattgttaa ggaggaagtg   1260
tttggtccca ttgtaactgt atccaagttt tctactgttg atgaagtgat tgctatggca   1320
aatgattctc aatatgggtt agccgcaggt attcacacta acgatattaa caaggctgtt   1380
gatgtgtcca aaagagtgaa agctggtact gtttgggataa atacctataa caacttccac   1440
caaaatgttc ctttcggtgg cttcggccag tcaggtattg gccgtgaaat gggtgaggct   1500
gctttaagta actacactca aacaaaatct gtcagaattg ccattgacaa gccaattcgt   1560
tga                                                                 1563

Saccharomyces cerevisiae
                                                            SEQ ID NO: 19
atgagcgaag aaagcttatt cgagtcttct ccacagaaga tggagtacga aattacaaac    60
tactcagaaa gacatacaga acttccaggt catttcattg gcctcaatac agtagataaa    120
ctagaggagt ccccgttaag ggactttgtt aagagtcacg gtggtcacac ggtcatatcc    180
aagatcctga tagcaaataa tggtattgcc gccgtgaaga aaattagatc cgtcagaaaa    240
tgggcatacg agacgttcgg cgatgacaga accgtccaat tcgtcgccat ggccaccca    300
gaagatctgg aggccaacgc agaatatatc cgtatggccg atcaatacat tgaagtgcca    360
ggtggtacta ataataacaa ctacgctaac gtagacttga tcgtagacat cgccgaaaga    420
gcagacgtag acgccgtatg ggctggctgg ggtcacgcct ccgagaatcc actattgcct    480
gaaaaattgt cccagtctaa gaggaaagtc atctttattg ggcctccagg taacgccatg    540
aggtcttag  gtgataaaat ctcctctacc attgtcgctc aaagtgctaa agtcccatgt    600
attccatggt ctggtaccgg tgttgacacc gttcacgtgg acgagaaaac cggtctggtc    660
tctgtcgacg atgacatcta tcaaaagggt tgttgtacct ctcctgaaga tggtttacaa    720
aaggccaagc gtattggttt tcctgtcatg attaaggcat ccgaaggtgg tggtggtaaa    780
ggtatcagac aagttgaacg tgaagaagat ttcatcgctt tataccacca ggcagccaac    840
gaaattccga gctccccat  tttcatcatg aagttggccg gtagagcgcg tcacttggaa    900
gttcaactgc tagcagatca gtacgtaca  aatatttcct tgttcggtag agctgttcc    960
gttcagagac gtcatcaaaa aattatcgaa gaagcaccga ttacaattgc caaggctgaa    1020
acatttcacg agatggaaaa ggctggcgtc agactgggga aactagtcgg ttatgtctct   1080
gccggtaccg tggagtatct atattctcat gatgatggaa aattctactt tttagaattg   1140
aacccaagat tacaagtcga gcatccaaca acggaaatgg tctccggtgt taacttacct   1200
gcagctcaat tacaaatcgc tatgggtatc cctatgcata gaataagtga cattagaact   1260
```

TABLE 4-continued

Sequences disclosed herein.

```
ttatatggta tgaatcctca ttctgcctca gaaatcgatt tcgaattcaa aactcaagat 1320
gccaccaaga aacaaagaag acctattcca aagggtcatt gtaccgcttg tcgtatcaca 1380
tcagaagatc caaacgatgg attcaagcca tcgggtggta cttttgcatga actaaacttc 1440
cgttcttcct ctaatgtttg gggttacttc tccgtgggta acaatggtaa tattcactcc 1500
ttttcggact ctcagttcgg ccatatttt gcttttggtg aaaatagaca agcttccagg 1560
aaacacatgg ttgttgccct gaaggaattg tccattaggg gtgatttcag aactactgtg 1620
gaatacttga tcaaactttt ggaaactgaa gatttcgagg ataacactat taccaccggt 1680
tggttggacg atttgattac tcataaaatg accgctgaaa agcctgatcc aactcttgcc 1740
gtcatttgcg gtgccgctac aaaggcttc ttagcatctg aagaagcccg ccacaagtat 1800
atcgaatcct tacaaaaggg acaagttcta tctaaagacc tactgcaaac tatgttccct 1860
gtagatttta tccatgaggg taaaagatac aagttcaccg tagctaaatc cggtaatgac 1920
cgttacacat tatttatcaa tggttctaaa tgtgatatca tactgcgtca actatctgat 1980
ggtggtcttt tgattgccat aggcggtaaa tcgcatacca tctattggaa agaagaagtt 2040
gctgctacaa gattatccgt tgactctatg actactttgt tggaagttga aaacgatcca 2100
acccagttgc gtactccatc ccctgataaa ttggttaaat tcttggtgga aaatggtaaa 2160
cacattatca agggccaacc atatgcagaa attgaagtta tgaaaatgca aatgcctttg 2220
gtttctcaag aaaatggtat cgtccagtta ttaaagcaac ctggttctac cattgttgca 2280
ggtgatatca tggctattat gactcttgac gatccatcca aggtcaagca cgctctacca 2340
tttgaaggta tgctgccaga ttttggttct ccagttatcg agggaaccaa acctgcctat 2400
aaattcaagt cattagtgtc tactttggaa aacattttga agggtatga caaccaagtt 2460
attatgaacg cttccttgca acaattgata gaggttttga gaaatccaaa actgccttac 2520
tcagaatgga aactacacat ctctgcttta cattcaagat gcctgctaa gctagatgaa 2580
caaatggaag agttagttgc acgttctttg agacgtggtg ctgttttccc agctagacaa 2640
ttaagtaaat tgattgatat ggccgtgaag aatcctgaat acaacccga caaattgctg 2700
ggcgccgtcg tggaaccatt ggcggatatt gctcataagt actctaacgg gttagaagcc 2760
catgaacatt ctatatttgt ccatttcttg gaagaatatt acgaagttga aaagttattc 2820
aatggtccaa atgttcgtga ggaaaatatc atttctgaaa tgcgtgatga aaaccctaaa 2880
gatctagata aagttgcgct aactgttttg tctcattcga aagtttcagc gaagaataac 2940
ctgatcctag ctatcttgaa acattatcaa ccattgtgca agttatcttc taaagtttct 3000
gccattttct ctactcctct acaacatatt gttgaactag aatctaaggc taccgctaag 3060
gtcgctctac aagcaagaga aattttgatt caaggcgctt taccttcggt caaggaaaga 3120
actgaacaaa ttgaacatat cttaaaatcc tctgttgtga aggttgccta tggctcatcc 3180
aatccaaagc gctctgaacc agattgaat atcttgaagg acttgatcga ttctaattac 3240
gttgtgttcg atgttttact tcaattccta acccatcaag acccagttgt gactgctgca 3300
gctgctcaag tctatattcg tcgtgcttat cgtgcttaca ccataggaga tattagagtt 3360
cacgaaggtg tcacagttcc aattgttgaa tggaaattcc aactacctc agctgcgttc 3420
tccacctttc caactgttaa atctaaaatg ggtatgaaca gggctgtttc tgtttcagat 3480
ttgtcatatg ttgcaaacag tcagtcatct ccgttaagag aaggtatttt gatggctgtg 3540
gatcatttag atgatgttga tgaaatttg tcacaaagtt tggaagttat tcctcgtcac 3600
caatcttctt ctaacggacc tgctcctgat cgttctggta gctccgcatc gttgagtaat 3660
gttgctaatg tttgtgttgc ttctacagaa ggtttcgaat ctgaagagga aattttggta 3720
aggttgagag aaattttgga tttgaataag caggaattaa tcaatgcttc tatccgtcgt 3780
atcacattta tgttcggttt taaagatggg tcttatccaa agtattatac ttttaacggt 3840
ccaaattata acgaaaatga aacaattcgt cacattgagc ggcttttggc cttccaactg 3900
gaattaggaa gattgtccaa cttcaacatt aaaccaattt tcactgataa tagaaacatc 3960
catgtctacg aagctgttag taagacttct ccattggata agagattctt tacaagaggt 4020
attattagaa cgggtcatat ccgtgatgac atttctattc aagaatatct gacttctgaa 4080
gctaacagat tgatgagtga tatattggat aatttagaag tcaccgacac ttcaaattct 4140
gatttgaatc atatcttcat caacttcatt gcggtgtttg atatctctcc agaagatgtc 4200
gaagccgcct tcggtggttt cttagaaaga tttggtaaga gattgttgag attgcgtgtt 4260
tcttctgccg aaattagaat catcatcaaa gatcctcaaa caggtgcccc agtaccattg 4320
cgtgccttga tcaataacgt ttctggttat gttatcaaaa cgaaatgta caccgaagtc 4380
aagaacgcaa aaggtgaatg ggtatttaag tctttgggta aacctggatc catgcatttta 4440
agacctattg ctactccta ccctgttaag aatggttgc aaccaaaacg ttataaggca 4500
cacttgatgg gtaccacata tgtctatgac ttcccagaat tattccgcca agcatcgtca 4560
tcccaatgga aaaatttctc tgcagatgtt aagttaacag atgatttctt tatttccaac 4620
gagttgatta aagatgaaaa cggcgaatta actgaggtgg aaagagaacc tggtgccaac 4680
gctattggta tggttgcctt taagattact gtaaagactc ctgaatatcc aagaggccgt 4740
caatttgttg ttgttgctaa cgatatcaca ttcaagatcg gttcctttgg tccacaagaa 4800
gacgaattct tcaataaggt tactgaatat gctagaaagc gtggtatccc aagaatttac 4860
ttggctgcaa actcaggtgc cagaattggt atggctgaag agattgttcc actatttcaa 4920
gttgcatgga atgatgctgc caatccggac aagggcttcc aatacttata cttaacaagt 4980
gaaggtatgg aaactttaaa gaaatttgac aaagaaaatt ctgttctcac tgaacgtact 5040
gttataaacg gtgaagaaag atttgtcatc aagacaatta ttggttctga agatgggtta 5100
ggtgtcgaat gtctacgtgg atctggttta attgctggtg caacgtcaag ggcttaccac 5160
gatatcttca ctatcacctt agtcacttgt agatccgtcg gtatcggtgc ttatttggtt 5220
cgtttgggtc aaagagctat tcaggtcgaa ggccagccaa ttattttaac tggtgctcct 5280
gcaatcaaca aaatgctggg tagagaagtt tatacttcta acttacaatt gggtggtact 5340
caaatcatgt ataacaacgg tgtttcacat ttgactgctg ttgacgattt agctggtgta 5400
gagaagattg ttgaatggat gtcttatgtt ccagccaagc gtaatatgcc agttcctatc 5460
ttggaaacta aagacacatg ggatagacca gttgatttca ctccaactaa tgatgaaact 5520
tacgatgtaa gatggatgat tgaaggtcgt gagactgaaa gtggatttga atatggtttg 5580
tttgataaag gtctttctct tgaaactttg tcaggatggg ccaaaggtgt tgtcgttgga 5640
agagcccgtc ttggtggtat tccactgggt gttattggtg ttgaaacaag aactgtcgag 5700
aacttgattc ctgctgatcc agctaatcca aatagtgctg aaacattaat tcaagaacct 5760
ggtcaagttt ggcatccaaa ctccgccttc aagactgctc aagctatcaa tgactttaac 5820
aacggtgaac aattgccaat gatgattttg gccaactgga gaggtttctc tggtggtcaa 5880
cgtgatatgt tcaacgaagt cttgaagtat ggttcgttta ttgttgacgc attggtggat 5940
```

TABLE 4-continued

Sequences disclosed herein.

```
tacaaacaac caattattat ctatatccca cctaccggtg aactaagagg tggttcatgg  6000
gttgttgtcg atccaactat caacgctgac caaatggaaa tgtatgccga cgtcaacgct  6060
agagctggtg ttttggaacc acaaggtatg gttggtatca agttccgtag agaaaaattg  6120
ctggacacca tgaacagatt ggatgacaag tacagagaat tgagatctca attatccaac  6180
aagagtttgg ctccagaagt acatcagcaa atatccaagc aattagctga tcgtgagaga  6240
gaactattgc caatttacgg acaaatcagt cttcaatttg ctgatttgca cgataggtct  6300
tcacgtatgg tggccaaggg tgttatttct aaggaactgg aatggaccga ggcacgtcgt  6360
ttcttcttct ggagattgag aagaagattg aacgaagaat atttgattaa aaggttgagc  6420
catcaggtag gcgaagcatc aagattagaa aagatcgcaa gaattagatc gtggtaccct  6480
gcttcagtgg accatgaaga tgataggcaa gtcgcaacat ggattgaaga aaactacaaa  6540
actttggacg ataaactaaa gggtttgaaa ttagagtcat tcgctcaaga cttagctaaa  6600
aagatcagaa gcgaccatga caatgctatt gatggattat ctgaagttat caagatgtta  6660
tctaccgatg ataaagaaaa attgttgaag actttgaaat aa                      6702
```

*Saccharomyces cerevisiae*

SEQ ID NO: 20

```
atgaagccgg aagttgagca agaattagct catattttgc taactgaatt gttagcttat    60
caatttgcct ctcctgtgag atggattgaa actcaagatg tttttttgaa ggattttaac   120
actgaaaggg ttgttgaaat cggtccttct ccaacttttg ctgggatggc tcaaagaacc   180
ttgaagaata aatacgaatc ttacgatgct gctctgtctt tacatagaga aatcttatgc   240
tattcgaagg atgccaaaga gatttattat accccagatc catccgaact agctgcaaag   300
gaagagcccg ctaaggaaga agctcctgct ccaactccag ctgctagtgc tcctgctcct   360
gcagcagcag ccccagctcc cgtcgcggca gcagccccag cagcagcagc tgctgagatt   420
gccgatgaac ctgtcaaggc ttccctattg ttgcacgttt tggttgctca caagttgaag   480
aagtcgttag attccattcc aatgtccaag acaatcaaag acttggtcgg tggtaaatct   540
acagtccaaa atgaaatttt gggtgattta ggtaaagaat ttggtactac tcctgaaaaa   600
ccagaagaaa ctccattaga agaattggca gaaactttcc aagataccct ctctggagca   660
ttgggtaagc aatcttcctc gttattatca agattaatct catctaagat gcctggtggg   720
tttactatta ctgtcgctag aaaatactta caaactcgct ggggactacc atctggtaga   780
caagatggtg tccttttggt agctttatct aacgagcctg ctgctcgtct aggttctgaa   840
gctgatgcca aggcttttctt ggactccatg gctcaaaaat acgcttccat tgttggtgtt   900
gacttatcat cagctgctag cgctagtggt gctgccggtg caggtgctgc tgccggtgca   960
gctatgatcg atgctggcgc tctggaagaa ataaccaaag accacaaggt tttggcgcgt  1020
caacaactgc aagtattggc tcgttatcta aaaatggact tggataacgg tgaaagaaag  1080
ttcttgaaag aaaaggacac tgttgctgaa cttcaagctc agttggatta cttgaatgcc  1140
gaattaggtg aattctttgt taacggtgtt gctacttctt tctctagaaa aaaggccaga  1200
accttcgatt cttcctggaa ctgggctaaa caatctttat tatcattata ctttgagata  1260
attcatggtg tcttgaaaaa cgttgataga gaggttgtta gtgaagctat caatatcatg  1320
aacagatcta acgatgcttt gattaaattc atggaatacc atatctctaa cactgatgaa  1380
acaaaaggtg aaaactatca attggttaaa actcttggtg agcagttgat tgaaaactgt  1440
aaacaagttt tggatgttga tccagtttac aaagatgttg ctaagcctac cggtccaaaa  1500
actgctattg acaagaacgg taacattaca tactcagaag agccaagaga aaaggttagg  1560
aaattatctc aatacgtaca agaaatggcc cttggtggtc aatcaccaa agaatctcaa  1620
cctactattg aagaggattt gactcgtgtt tacaaggcaa tcagtgctca agctgataaa  1680
caagatattt ccagctccac cagggttgaa tttgaaaaac tatatagtga tttgatgaag  1740
ttcttggaaa gctccaaaga aatcgatcct tctcaaacaa cccaaattgg cggtatggat  1800
gttgaggatg ctttggacaa agattccacc aaagaagttg cttcttttgcc aaacaaatct  1860
accatttcta agacggtatc ttcaactatt ccaagagaaa ctattccgtt cttacatttg  1920
agaaagaaga ctcctgccgg agattggaaa tatgaccgcc aattgtcttc tctttttctta  1980
gatggtttag aaaaggctgc cttcaacggt gtcaccttca aggacaaata cgtcttgatc  2040
actggtgctg taagggttc tattggtgct gaagtcttgc aaggttttgtt acaaggtggt  2100
gctaaggttg ttgttaccac ctctcgtttc tctaagcaag ttacagacta ctaccaatcc  2160
atttacgcca aatatggtgc taaggttct actttgattg ttgttccatt caaccaaggt  2220
tctaagcaag acgttgaagc tttgattgaa tttatctacg acactgaaaa gaatggtggt  2280
ttaggttggg atctagatgc tattattcca ttcgcggcca ttccagaaca aggtattgaa  2340
ttagaacata ttgattctaa gtctgaattt gctcatagaa tcatgttgac caatatctta  2400
agaatgatgg gttgtgtcaa gaagcaaaaa tctgcaagag tgattgaaac aagaccagct  2460
caagtcattc taccaatgtc tccaaaccat ggtactttcg gtggtgatgg tatgtattca  2520
gaatccaagt tgtctctgga acttttgttc aacagatggc actctgaatc ctgggccaat  2580
caattaaccg tttgcggtgc tattattggt tggactagag tactggtttt aatgagcgct  2640
aataacatca ttgctgaagg cattgaaaag atggggtatc tgactttctc tcaaaaggaa  2700
atggctttca acttattggg tctattgact ccagaagtcg tagaattgtg ccaaaaatca  2760
cctgttatgc ctgacttgaa tggtggtttg caatttgttc ctgaattgaa ggaattcact  2820
gctaaattgc gtaagagtt ggttgaaact tctgaagtta gaaaggcagt ttccatcgaa  2880
actgctttgg agcataaggt tgtcaatggc aatagcgctg atgctgcatc tgctcaagtc  2940
gaaattcaac caagagctaa cattcaactg gacttcccag aattgaaacc atacaaacag  3000
gttaaacaaa ttgctcccgc tgagcttgaa ggttgttgg atttgaaag agttattgta  3060
gttaccggtt ttgctgaagt cggcccatgg ggttcggcca aacaagatg ggaaatgaa  3120
gcttttggtg aattttcgtt ggaaggttgc gttgaaatgg cctggattat gggcttcatt  3180
tcataccata acgttaattt gaagggtcgt ccatacactg gttgggttga ttccaaaaca  3240
aaagaaccag ttgatgacaa ggacgttaag gccaagtatg aaacatcaat cctagaacac  3300
agtggtatca gattgatcga accagagtta ttcaatggtt acaacccaga aagaaggaa  3360
atgattcaag acgtcattgt cgaagaagac ttggaaccat tggccttc gaaggaaact  3420
gccgaacaat ttaaacacca acatggtgac aaagtggata tcttcgaaat cccagaaaca  3480
ggagagtact ctgttaagtt actaaaggt gccactttat acattccaaa ggctttgaga  3540
tttgaccgtt tggttgcagg tcaaattcca actggttgga atgctaagac ttatggtatc  3600
tctgatgata tcatttctca ggttgaccca atcacattat tcgttttggt ctctgttgtg  3660
gaagcattta ttgcatctgg tatcaccgac ccatacgaaa tgtacaaaata cgtacatgtt  3720
```

TABLE 4-continued

Sequences disclosed herein.

```
tctgaggttg gtaactgttc tggttctggt atgggtggtg tttctgcctt acgtggtatg   3780
tttaaggacc gtttcaagga tgagcctgtc caaaatgata ttttacaaga atcatttatc   3840
aacaccatgt ccgcttgggt taatatgttg ttgatttcct catctggtcc aatcaagaca   3900
cctgttggtg cctgtgccac atccgtggaa tctgttgaca ttggtgtaga aaccatcttg   3960
tctggtaagg ctagaatctg tattgtcggt ggttacgatg atttccaaga agaaggctcc   4020
tttgagttcg gtaacatgaa ggccacttcc aacactttgg aagaatttga acatggtcgt   4080
accccagcgg aaatgtccag acctgccacc actacccgta acggttttat ggaagctcaa   4140
ggtgctggta ttcaaatcat catgcaagct gatttagctt tgaagatggg tgtgccaatt   4200
tacggtattg ttgccatggc tgctaccgcc accgataaga ttggtagatc tgtgccagct   4260
ccaggtaagg gtattttaac cactgctcgt gaacaccact ccagtgttaa gtatgcttca   4320
ccaaacttga acatgaagta cagaaagcgc caattggttc ctcgtgaagc tcagattaaa   4380
gattgggtag aaaacgaatt ggaagctttg aagttggagg ccgaagaaat tccaagcgaa   4440
gaccaaaacg agttcttact tgaacgtacc agagaaatcc acaacgaagc tgaaagtcaa   4500
ttgagagctg cacaacaaca atgggtaac gacttctaca gagggaccc acgtattgct   4560
ccattgagag gagcactggc tacttacggt ttaactattg atgactttggg tgtcgcttca   4620
ttccacggta catccacaaa ggctaatgac aagaacgaat ctgccacaat taatgaaatg   4680
atgaagcatt tgggtagatc tgaaggtaat cccgtcattg gtgttttcca aaagttcttg   4740
actggtcatc caaagggtgc tgctggtgca tggatgatga atggtgcttt gcaaattcta   4800
aacagtgtta ttattccagg taaccgtaac gctgataacg tggataagat cttggagcaa   4860
tttgaatacg tcttgtaccc atccaagact ttaaagaccg acggtgtcag agccgtgtcc   4920
atcacttctt tcggttttgg tcaaaagggt ggtcaagcta ttgtggttca tccagactac   4980
ttatacggtg ctatcactga agacagatac aacgagtatg tcgccaaggt tagtgccaga   5040
gagaaagtg cctacaaatt cttccataat ggtatgatct acaacaagtt gttcgtaagt   5100
aaagagcatg ctccatacac tgatgaattg gaagagatg tttacttgga cccattagcc   5160
cgtgtatcta aggataagaa atcaggctcc ttgactttca actctaaaaa catccaaagc   5220
aaggacagtt acatcaatgc taacaccatt gaactgcca agatgattga aaacatgacc   5280
aaggagaaag tctctaacgg tggcgtcggt gtagatgttg aattaatcac tagcatcaac   5340
gttgaaaatg atacttttat cgagcgcaat ttcaccccgc aagaaataga gtactgcagc   5400
gcgcagccta gtgtgcaaag ctctttcgct gggacatggt ccgccaaaga ggctgttttc   5460
aagtccttag gcgtcaagtc cttaggcggt ggtgctgcat tgaaagacat cgaaatcgta   5520
cgcgttaaca aaaacgctcc agccgttgaa ctgcacggta acgccaaaaa ggctgccgaa   5580
gaagctggtg ttaccgatgt gaaggtatct atttctcacg atgacctcca agctgtcgcg   5640
gtcgccgttt ctactaagaa atag                                           5664
```

Candida maltosa

SEQ ID NO: 21
```
MIDEILPKLV QYWYIVLPTL LIIKHVVSYI NTQRLMRKFR AKPVTNVLND GFFGIPNGIK    60
AIKEKNKGRA QEYNDEKFAA GPKPKVGTYL FKLFTKDVLV TKDPENIKAI LATQFEDFSL   120
GKRLDFFKPL LGYGIFTLDG EGWKHSRAML RPQFAREQVG HVKLIEPHFQ SLKKHIIKNK   180
GQFFDIQELF FRFTVDSATE FLFGESVESL KDESIGYDQQ DFDFDGRKNF AEAFNKAQEY   240
LGTRAILQSF YWLVNGADFK KSVAEVHKFT DYYVQKALDA TPEELEKHSG YIFLYELVQQ   300
TRDPKVLRDQ SLNILLAGRD TTAGLLSFAL FELARNPEVW SRLREEIGDK FGLDEDATIE   360
GISFESLKQC EYLKAVNEC LRMYPSVPRN FRIATKHTTL PRGGGPDKGD PIFIKKGAVV   420
SYGINSTHLD PMYYGPDARL FNPDRWSKPE TKKLGWAFLP FNGGPRICLG QQFALTEASY   480
VLVRMIQNFK ELELTPNTVY PPRRLTNLTM SLYDGAYIKV N                       521
```

Candida maltosa

SEQ ID NO: 22
```
MALDKLDLYV IIVLAVAVAA YFAKNQFLDQ PQDTGFLSND TAGGNSRDIL ETLKKNNKNT    60
LLLFGSQTGT AEDYANKLSR EIHSRFGLKT MVADFADYDW DNFGDIPNDI LVFFIVATYG   120
EGEPTDNADE FHTWLTDEAD TLSTLRYTVF GLGNSTYEFY NAIGRKFDRL LEEKGGERFA   180
DYGEGDDGTG TLDEDPLTWK DNVFDTLKND LNFEERELKY EPNVKLTERD DLTVDDSEVS   240
LGEPNKKYIQ SEEIDLTKGP FDHTHPYLAK ISKTRELFAS KERNCVHVEF DVSESNLKYT   300
TGDHLAVWPS NSDENIAKFI KCFGLDDKIN TVFELKALDS TYQIPFPNPI TYGAVVRHHL   360
EISGPVSRQF FLAIAGFAPD EETKKTFTRI GNDKQEFANK ITRKKLNVAD ALLFASNGRP   420
WSDVPFEFII ENVPHLQPRY YSISSSSLSE KQTINITAVV EVEEEADGRA VTGVVTNLLK   480
NIEIEQNKTG EKPVVHYDLS GPRNKFNKFK LPVHVRRSNF KLPKNTTTPV ILIGPGTGVA   540
PLRGFVRERV QQVKNGVNVG KTVLFYGCRN EHDDFLYKQE WSEYASVLGE NFEMFTAFSR   600
QDPSKKVYVQ DKIAENSKVV NDLLNEGAII YVCGDASRMA RDVQSTIAKI VAKHREIQED   660
KAVELVKSWK VQNRYQEDVW                                              680
```

Humulus lupulus

SEQ ID NO: 23
```
MEDLKPRPAS SSPLTPLGFL ERAATVYGDC TSVVYDAVSY TWSQTHRRCL CLASSIASLG    60
IENGHVVSVL APNVPQMYEL HFAVPMAGAI LNAVNLRLDA RTISILLHHS ESKLIFVDHL   120
SRDLILEAIA LFPKQAPVPR LVFMADESES GNSSELGKEF FCSYKDLIDR GDPDFKWVMP   180
KSEWDPMILN YTSGTTSSPK GVVHCHRGIF IMTVDSLIDW GVPKQPVYLW TLPMFHANGW   240
SYPWGMAAVG GTNICLRKFD SEIIYDMIKR HGVTHMCGAP VVLNMLSNAP GSEPLKTTVQ   300
IMTAGAPPPS AVLFRTESLG FAVSHGYGLT ETAGLVVSCA WKKEWNHLPA TERARLKSRQ   360
GVGTVMQTKI DVVDPVTGAA VKRDGSTLGE VVLRGGSVML GYLKDPEGTA KSMTADGWFY   420
TGDVGVMHPD GYLEIKDRSK DVIISGGENL SSVEVESILY SHPDILEAAV VARPDEFWGE   480
TPCAFVSLKK GLTKKPTEKE IVEYCRSKLP RYMVPKTVVF KEELPKTSTG KVQKFILRDM   540
ARGMGSATAG ASRSRM                                                   556
```

Solanum tubersum

SEQ ID NO: 24
```
MEDLKPRPAS SSPLTPLGFL ERAATVYGDC TSVVYDAVSY TWSQTHRRCL CLASSIASLG    60
IENGHVVSVL APNVPQMYEL HFAVPMAGAI LNAVNLRLDA RTISILLHHS ESKLIFVDHL   120
```

TABLE 4-continued

Sequences disclosed herein.

```
SRDLILEAIA LFPKQAPVPR LVFMADESES GNSSELGKEF FCSYKDLIDR GDPDFKWVMP    180
KSEWDPMILN YTSGTTSSPK GVVHCHRGIF IMTVDSLIDW GVPKQPVYLW TLPMFHANGW    240
SYPWGMAAVG GTNICLRKFD SEIIYDMIKR HGVTHMCGAP VVLNMLSNAP GSEPLKTTVQ    300
IMTAGAPPPS AVLFRTESLG FAVSHGYGLT ETAGLVVSCA WKKEWNHLPA TERARLKSRQ    360
GVGTVMQTKI DVVDPVTGAA VKRDGSTLGE VVLRGGSVML GYLKDPEGTA KSMTADGWFY    420
TGDVGVMHPD GYLEIKDRSK DVIISGGENL SSVEVESILY SHPDILEAAV VARPDEFWGE    480
TPCAFVSLKK GLTKKPTEKE IVEYCRSKLP RYMVPKTVVF KEELPKTSTG KVQKFILRDM    540
ARGMGSATAG ASRSRM                                                    556
```

*Saccharomyces cerevisiae*

SEQ ID NO: 25
```
MDAYSTRPLT LSHGSLEHVL LVPTASFFIA SQLQEQFNKI LPEPTEGFAA DDEPTTPAEL     60
VGKFLGYVSS LVEPSKVGQF DQVLNLCLTE FENCYLEGND IHALAAKLLQ ENDTTLVKTK    120
ELIKNYITAR IMAKRPFDKK SNSALFRAVG EGNAQLVAIF GGQGNTDDYF EELRDLYQTY    180
HVLVGDLIKF SAETLSELIR TTLDAEKVFT QGLNILEWLE NPSNTPDKDY LLSIPISCPL    240
IGVIQLAHYV VTAKLLGFTP GELRSYLKGA TGHSQGLVTA VAIAETDSWE SFFVSVRKAI    300
TVLFFIGVRC YEAYPNTSLP PSILEDSLEN NEGVPSPMLS ISNLTQEQVQ DYVNKTNSHL    360
PAGKQVEISL VNGAKNLVVS GPPQSLYGLN LTLRKAKAPS GLDQSRIPFS ERKLKFSNRF    420
LPVASPFHSH LLVPASDLIN KDLVKNNVSF NAKDIQIPVY DTFDGSDLRV LSGSISERIV    480
DCAIRLPVKW ETTTQFKATH ILDFGPGGAS GLGVLTHRNK DGTGVRVIVA GTLDINPDDD    540
YGFKQEIFDV TSNGLKKNPN WLEEYHPKLI KNKSGKIFVE TKFSKLIGRP PLLVPGMTPC    600
TVSPDFVAAT TNAGYTIELA GGGYFSAAGM TAAIDSVVSQ IEKGSTFGIN LIYVNPFMLQ    660
WGIPLIKELR SKGYPIQFLT IGAGVPSLEV ASEYIETLGK KYLGLKPGSI DAISQVINIA    720
KAHPNFPIAL QWTGGRGGGH HSFEDAHTPM LQMYSKIRRH PNIMLIFGSG FGSADDTYPY    780
LTGEWSTKFD YPPMPFDGFL FGSRVMIAKE VKTSPDAKKC IAACTGVPDD KWEQTYKKPT    840
GGIVTVRSEM GEPIHKIATR GVMLWKEFDE TIFNLPKNKL VPTLEAKRDY IISRLNADFQ    900
KPWFATVNGQ ARDLATMTYE EVAKRLVELM FIRSTNSWFD TVWRTFTGDF LRRVEERFTK    960
SKTLSLIQSY SLLDKPDEAI EKVFNAYPAA REQFLNAQDI DHFLSMCQNP MQKPVPFVPV   1020
LDRRFEIFFK KDSLWQSEHL EAVVQDDVQR TCILHGPVAA QFTKVIDEPI KSIMDGIHDG   1080
HIKKLLHQYY GDDESKIPAV EYFGGESPVD VQSQVDSSSV SEDSAVFKAT SSTDEESWFK   1140
ALAGSEINWR HASFLCSFIT QDKMFVSNPI RKVFKPSQGM VVEISNGNTS SKTVVTLSEP   1200
VQGELKPTVI LKLLKENIIQ MEMIENRTMD GKPVSLPLLY NFNPDNGFAP ISEVMEDRNQ   1260
RIKEMYWKLW IDEPFNLDFD PRDVIKGKDF EITAKEVYDF THAVGNNCED FVSRPDRTML   1320
APMDFAIVVG WRAIIKAIFP NTVDGDLLKL VHLSNGYKMI PGAKPLQVGD VVSTTAVIES   1380
VVNQPTGKIV DVVGTLSRNG KPVMEVTSSF FYRGNYTDFE NTFQKTVEPV YQMHIKTSKD   1440
IAVLRSKEWF QLDDEDFDLL NKTLTFETET EVTFKNANIF SSVKCFGPIK VELPTKETVE   1500
IGIVDYEAGA SHGNPVVDFL KRNGSTLEQK VNLENPIPIA VLDSYTPSTN EPYARVSGDL   1560
NPIHVSRHFA SYANLPGTIT HGMFSSASVR ALIENWAADS VSSRVRGYTC QFVDMVLPNT   1620
ALKTSIQHVG MINGRKLIKF ETRNEDDVVV LTGEAEIEQP VTTFVFTGQG SQEQGMGMDL   1680
YKTSKAAQDV WNRADNHFKD TYGFSILDIV INNPVNLTIP FGGEKGKRIR ENYSAMIFET   1740
IVDGKLKTEK IFKEINEHST SYTFRSEKGL LSATQFTQPA LTLMEKAAFE DLKSKGLIPA   1800
DATFAGHSLG EYAALASLAD VMSIESLVEV VFYRGMTMQV AVPRDELGRS NYGMIAINPG   1860
RVAASFSQEA LQYVVERVGK RTGWLVEIVN YNVENQQYVA AGDLRALDTV TNVLNFIKLQ   1920
KIDIIELQKS LSLEEVEGHL FEIIDEASKK SAVKPRPLKL ERGFACIPLV GISVPHSTY    1980
LMNGVKPFKS FLKKNIIKEN VKVARLAGKY IPNLTAKPFQ VTKEYFQDVY DLTGSEPIKE   2040
IIDNWEKYEQ S                                                        2051
```

*Saccharomyces cerevisiae*

SEQ ID NO: 26
```
MDAYSTRPLT LSHGSLEHVL LVPTASFFIA SQLQEQFNKI LPEPTEGFAA DDEPTTPAEL     60
VGKFLGYVSS LVEPSKVGQF DQVLNLCLTE FENCYLEGND IHALAAKLLQ ENDTTLVKTK    120
ELIKNYITAR IMAKRPFDKK SNSALFRAVG EGNAQLVAIF GGQGNTDDYF EELRDLYQTY    180
HVLVGDLIKF SAETLSELIR TTLDAEKVFT QGLNILEWLE NPSNTPDKDY LLSIPISCPL    240
IGVIQLAHYV VTAKLLGFTP GELRSYLKGA TGHSQGLVTA VAIAETDSWE SFFVSVRKAI    300
TVLFFIGVRC YEAYPNTSLP PSILEDSLEN NEGVPSPMLS ISNLTQEQVQ DYVNKTNSHL    360
PAGKQVEISL VNGAKNLVVS GPPQSLYGLN LTLRKAKAPS GLDQSRIPFS ERKLKFSNRF    420
LPVASPAHSH LLVPASDLIN KDLVKNNVSF NAKDIQIPVY DTFDGSDLRV LSGSISERIV    480
DCAIRLPVKW ETTTQFKATH ILDFGPGGAS GLGVLTHRNK DGTGVRVIVA GTLDINPDDD    540
YGFKQEIFDV TSNGLKKNPN WLEEYHPKLI KNKSGKIFVE TKFSKLIGRP PLLVPGMTPC    600
TVSPDFVAAT TNAGYTIELA GGGYFSAAGM TAAIDSVVSQ IEKGSTFGIN LIYVNPFMLQ    660
WGIPLIKELR SKGYPIQFLT IGAGVPSLEV ASEYIETLGK KYLGLKPGSI DAISQVINIA    720
KAHPNFPIAL QWTGGRGGGH HSFEDAHTPM LQMYSKIRRH PNIMLIFGSG FGSADDTYPY    780
LTGEWSTKFD YPPMPFDGFL FGSRVMIAKE VKTSPDAKKC IAACTGVPDD KWEQTYKKPT    840
GGIVTVRSEM GEPIHKIATR GVMLWKEFDE TIFNLPKNKL VPTLEAKRDY IISRLNADFQ    900
KPWFATVNGQ ARDLATMTYE EVAKRLVELM FIRSTNSWFD TVWRTFTGDF LRRVEERFTK    960
SKTLSLIQSY SLLDKPDEAI EKVFNAYPAA REQFLNAQDI DHFLSMCQNP MQKPVPFVPV   1020
LDRRFEIFFK KDSLWQSEHL EAVVQDDVQR TCILHGPVAA QFTKVIDEPI KSIMDGIHDG   1080
HIKKLLHQYY GDDESKIPAV EYFGGESPVD VQSQVDSSSV SEDSAVFKAT SSTDEESWFK   1140
ALAGSEINWR HASFLCSFIT QDKMFVSNPI RKVFKPSQGM VVEISNGNTS SKTVVTLSEP   1200
VQGELKPTVI LKLLKENIIQ MEMIENRTMD GKPVSLPLLY NFNPDNGFAP ISEVMEDRNQ   1260
RIKEMYWKLW IDEPFNLDFD PRDVIKGKDF EITAKEVYDF THAVGNNCED FVSRPDRTML   1320
APMDFAIVVG WRAIIKAIFP NTVDGDLLKL VHLSNGYKMI PGAKPLQVGD VVSTTAVIES   1380
VVNQPTGKIV DVVGTLSRNG KPVMEVTSSF FYRGNYTDFE NTFQKTVEPV YQMHIKTSKD   1440
IAVLRSKEWF QLDDEDFDLL NKTLTFETET EVTEKNANIF SSVKCFGPIK VELPTKETVE   1500
IGIVDYEAGA SHGNPVVDFL KRNGSTLEQK VNLENPIPIA VLDSYTPSTN EPYARVSGDL   1560
NPIHVSRHFA SYANLPGTIT HGMFSSASVR ALIENWAADS VSSRVRGYTC QFVDMVLPNT   1620
ALKTSIQHVG MINGRKLIKF ETRNEDDVVV LTGEAEIEQP VTTFVFTGQG SQEQGMGMDL   1680
YKTSKAAQDV WNRADNHFKD TYGFSILDIV INNPVNLTIH FGGEKGKRIR ENYSAMIFET   1740
```

TABLE 4-continued

Sequences disclosed herein.

```
IVDGKLKTEK IFKEINEHST SYTFRSEKGL LSATQFTQPA LTLMEKAAFE DLKSKGLIPA  1800
DATFAGHSLG EYAALASLAD VMSIESLVEV VFYRGMTMQV AVPRDELGRS NYGMIAINPG  1860
RVAASFSQEA LQYVVERVGK RTGWLVEIVN YNVENQQYVA AGDLRALDTV TNVLNFIKLQ  1920
KIDIIELQKS LSLEEVEGHL FEIIDEASKK SAVKPRPLKL ERGFACIPLV GISVPFHSTY  1980
LMNGVKPFKS FLKKNIIKEN VKVARLAGKY IPNLTAKPFQ VTKEYFQDVY DLTGSEPIKE  2040
IIDNWEKYEQ S                                                      2051
```

*Saccharomyces cerevisiae*

SEQ ID NO: 27

```
MDAYSTRPLT LSHGSLEHVL LVPTASFFIA SQLQEQFNKI LPEPTEGFAA DDEPTTPAEL   60
VGKFLGYVSS LVEPSKVGQF DQVLNLCLTE FENCYLEGND IHALAAKLLQ ENDTTLVKTK  120
ELIKNYITAR IMAKRPFDKK SNSALFRAVG EGNAQLVAIF GGQGNTDDYF EELRDLYQTY  180
HVLVGDLIKF SAETLSELIR TTLDAEKVFT QGLNILEWLE NPSNTPDKDY LLSIPISCPL  240
IGVIQLAHYV VTAKLLGFTP GELRSYLKGA TGHSQGLVTA VAIAETDSWE SFFVSVRKAI  300
TVLFFIGVRC YEAYPNTSLP PSILEDSLEN NEGVPSPMLS ISNLTQEQVQ DYVNKTNSHL  360
PAGKQVEISL VNGAKNLVVS GPPQSLYGLN LTLRKAKAPS GLDQSRIPFS ERKLKFSNRF  420
LPVASPAHSH LLVPASDLIN KDLVKNNVSF NAKDIQIPVY DTFDGSDLRV LSGSISERIV  480
DCIIRLPVKW ETTTQFKATH ILDFGPGGAS GLGVLTHRNK DGTGVRVIVA GTLDINPDDD  540
YGFKQEIFDV TSNGLKKNPN WLEEYHPKLI KNKSGKIFVE TKFSKLIGRP PLLVPGMTPC  600
TVSPDFVAAT TNAGYTIELA GGGYFSAAGM TAAIDSVVSQ IEKGSTFGIN LIYVNPFMLQ  660
WGIPLIKELR SKGYPIQFLT IGAGVPSLEV ASEYIETLGL KYLGLKPGSI DAISQVINIA  720
KAHPNFPIAL QWTGGRGGGH HSFEDAHTPM LQMYSKIRRH PNIMLIFGSG FGSADDTYPY  780
LTGEWSTKFD YPPMPFDGFL FGSRVMIAKE VKTSPDAKKC IAACTGVPDD KWEQTYKKPT  840
GGIVTVRSEM GEPIHKIATR GVMLWKEFDE TIFNLPKNKL VPTLEAKRDY IISRLNADFQ  900
KPWFATVNGQ ARDLATMTYE EVAKRLVELM FIRSTNSWPD VTWRTFTGDF LRRVEERFTK  960
SKTLSLIQSY SLLDKPDEAI EKVFNAYPAA REQFLNAQDI DHFLSMCQNP MQKPVPFVPV 1020
LDRRFEIFFK KDSLWQSEHL EAVVDQDVQR TCILHGPAVA QFTKVIDEPI KSIMDGIHDG 1080
HIKKLLHQYY GDDESKIPAV EYFGGESPVD VQSQVDSSSV SEDSAVFKAT SSTDEESWFK 1140
ALAGSEINWR HASFLCSFIT QDKMFVSNPI RKVFKPSQGM VVEISNGNTS SKTVVTLSEP 1200
VQGELKPTVI LKLLKENIIQ MEMIENRTMD GKPVSLPLLY NFNPDNGFAP ISEVMEDRNQ 1260
RIKEMYWKLW IDEPFNLDFD PRDVIKGKDF EITAKEVYDF THAVGNNCED FVSRPDRTML 1320
APMDFAIVVG WRAIIKAIFP NTVDGDLLKL VHLSNGYKMI PGAKPLQVGD VVSTTAVIES 1380
VVNQPTGKIV DVVGTLSRNG KPVMEVTSSF FYRGNYTDFE NTFQKTVEPV YQMHIKTSKD 1440
IAVLRSKEWF QLDDEDFDLL NKTLTFETET EVTFKNANIF SSVKCFGPIK VELPTKETVE 1500
IGIVDYEAGA SHGNPVVDFL KRNGSTLEQK VNLENPIPIA VLDSYTPSTN EPYARVSGDL 1560
NPIHVSRHFA SYANLPGTIT HGMFSSASVR ALIENWAADS VSSRVRGYTC QFVDMVLPNT 1620
ALKTSIQHVG MINGRKLIKF ETRNEDDVVV LTGEAEIEQP VTTFVFTGQG SQEQGMGMDL 1680
YKTSKAAQDV WNRADNHFKD TYGFSILDIV INNPVNLTIH FGGEKGKRIR ENYSAMIFET 1740
IVDGKLKTEK IFKEINEHST SYTFRSEKGL LSATQFTQPA LTMEKAAFE DLKSKGLIPA 1800
DATFAGHSLG EYAALASLAD VMSIESLVEV VFYRGMTMQV AVPRDELGRS NYGMIAINPG 1860
RVAASFSQEA LQYVVERVGK RTGWLVEIVN YNVENQQYVA AGDLRALDTV TNVLNFIKLQ 1920
KIDIIELQKS LSLEEVEGHL FEIIDEASKK SAVKPRPLKL ERGFACIPLV GISVPFHSTY 1980
LMNGVKPFKS FLKKNIIKEN VKVARLAGKY IPNLTAKPFQ VTKEYFQDVY DLTGSEPIKE 2040
IIDNWEKYEQ S                                                     2051
```

*Saccharomyces cerevisiae*

SEQ ID NO: 28

```
MDAYSTRPLT LSHGSLEHVL LVPTASFFIA SQLQEQFNKI LPEPTEGFAA DDEPTTPAEL   60
VGKFLGYVSS LVEPSKVGQF DQVLNLCLTE FENCYLEGND IHALAAKLLQ ENDTTLVKTK  120
ELIKNYITAR IMAKRPFDKK SNSALFRAVG EGNAQLVAIF GGQGNTDDYF EELRDLYQTY  180
HVLVGDLIKF SAETLSELIR TTLDAEKVFT QGLNILEWLE NPSNTPDKDY LLSIPISCPL  240
IGVIQLAHYV VTAKLLGFTP GELRSYLKGA TGHSQGLVTA VAIAETDSWE SFFVSVRKAI  300
TVLFFIGVRC YEAYPNTSLP PSILEDSLEN NEGVPSPMLS ISNLTQEQVQ DYVNKTNSHL  360
PAGKQVEISL VNGAKNLVVS GPPQSLYGLN LTLRKAKAPS GLDQSRIPFS ERKLKFSNRF  420
LPVASPAHSH LLVPASDLIN KDLVKNNVSF NAKDIQIPVY DTFDGSDLRV LSGSISERIV  480
DCIIRLPVKW ETTTQFKATH ILDFGPGGAS GLGVLTHRNK DGTGVRVIVA GTLDINPDDD  540
YGFKQEIFDV TSNGLKKNPN WLEEYHPKLI KNKSGKIFVE TKFSKLIGRP PLLVPGMTPC  600
TVSPDFVAAT TNAGYTIELA GGGYFSAAGM TAAIDSVVSQ IEKGSTFGIN LIYVNPFMLQ  660
WGIPLIKELR SKGYPIQFLT IGAGVPSLEV ASEYIETLGL KYLGLKPGSI DAISQVINIA  720
KAHPNFPIAL QWTGGRGGGH HSFEDAKTPM LQMYSKIRRH PNIMLIFGSG FGSADDTYPY  780
LTGEWSTKFD YPPMPFDGFL FGSRVMIAKE VKTSPDAKKC IAACTGVPDD KWEQTYKKPT  840
GGIVTVRSEM GEPIHKIATR GVMLWKEFDE TIFNLPKNKL VPTLEAKRDY IISRLNADFQ  900
KPWFATVNGQ ARDLATMTYE EVAKRLVELM FIRSTNSWPD VTWRTFTGDF LRRVEERFTK  960
SKTLSLIQSY SLLDKPDEAI EKVFNAYPAA REQFLNAQDI DHFLSMCQNP MQKPVPFVPV 1020
LDRRFEIFFK KDSLWQSEHL EAVVDQDVQR TCILHGPAVA QFTKVIDEPI KSIMDGIHDG 1080
HIKKLLHQYY GDDESKIPAV EYFGGESPVD VQSQVDSSSV SEDSAVFKAT SSTDEESWFK 1140
ALAGSEINWR HASFLCSFIT QDKMFVSNPI RKVFKPSQGM VVEISNGNTS SKTVVTLSEP 1200
VQGELKPTVI LKLLKENIIQ MEMIENRTMD GKPVSLPLLY NFNPDNGFAP ISEVMEDRNQ 1260
RIKEMYWKLW IDEPFNLDFD PRDVIKGKDF EITAKEVYDF THAVGNNCED FVSRPDRTML 1320
APMDFAIVVG WRAIIKAIFP NTVDGDLLKL VHLSNGYKMI PGAKPLQVGD VVSTTAVIES 1380
VVNQPTGKIV DVVGTLSRNG KPVMEVTSSF FYRGNYTDFE NTFQKTVEPV YQMHIKTSKD 1440
IAVLRSKEWF QLDDEDFDLL NKTLTFETET EVTFKNANIF SSVKCFGPIK VELPTKETVE 1500
IGIVDYEAGA SHGNPVVDFL KRNGSTLEQK VNLENPIPIA VLDSYTPSTN EPYARVSGDL 1560
NPIHVSRHFA SYANLPGTIT HGMFSSASVR ALIENWAADS VSSRVRGYTC QFVDMVLPNT 1620
ALKTSIQHVG MINGRKLIKF ETRNEDDVVV LTGEAEIEQP VTTFVFTGQG SQEQGMGMDL 1680
YKTSKAAQDV WNRADNHFKD TYGFSILDIV INNPVNLTIH FGGEKGKRIR ENYSAMIFET 1740
IVDGKLKTEK IFKEINEHST SYTFRSEKGL LSATQFTQPA LTMEKAAFE DLKSKGLIPA 1800
DATFAGHSLG EYAALASLAD VMSIESLVEV VFYRGMTMQV AVPRDELGRS NYGMIAINPG 1860
```

TABLE 4-continued

Sequences disclosed herein.

```
RVAASFSQEA LQYVVERVGK RTGWLVEIVN YNVENQQYVA AGDLRALDTV TNVLNFIKLQ   1920
KIDIIELQKS LSLEEVEGHL FEIIDEASKK SAVKPRPLKL ERGFACIPLV GISVPFHSTY   1980
LMNGVKPFKS FLKKNIIKEN VKVARLAGKY IPNLTAKPFQ VTKEYFQDVY DLTGSEPIKE   2040
IIDNWEKYEQ S                                                         2051
```

*Saccharomyces cerevisiae*

SEQ ID NO: 29

```
MDAYSTRPLT LSHGSLEHVL LVPTASFFIA SQLQEQFNKI LPEPTEGFAA DDEPTTPAEL     60
VGKFLGYVSS LVEPSKVGQF DQVLNLCLTE FENCYLEGND IHALAAKLLQ ENDTTLVKTK    120
ELIKNYITAR IMAKRPFDKK SNSALFRAVG EGNAQLVAIF GGQGNTDDYF EELRDLYQTY    180
HVLVGDLIKF SAETLSELIR TTLDAEKVFT QGLNILEWLE NPSNTPDKDY LLSAPISCPL    240
IGVIQLAHYV VTAKLLGFTP GELRSYLKGA TGHSQGLVTA VAIAETDSWE SFFVSVRKAI    300
TVLFFIGVRC YEAYPNTSLP PSILEDSLEN NEGVPSPMLS ISNLTQEQVQ DYVNKTNSHL    360
PAGKQVEISL VNGAKNLVVS GPPQSLYGLN LTLRKAKAPS GLDQSRIPFS ERKLKFSNRF    420
LPVASPSHSH LLVPASDLIN KDLVKNNVSF NAKDIQIPVY DTFDGSDLRV LSGSISERIV    480
DCIIRLPVKW ETTTQFKATH ILDFGPGGAS GLGVLTHRNK DGTGVRVIVA GTLDINPDDD    540
YGFKQEIFDV TSNGLKKNPN WLEEYHPKLI KNKSGKIFVE TKFSKLIGRP PLLVPGMTPC    600
TVSPDFVAAT TNAGYTIELA GGGYFSAAGM TAAIDSVVSQ IEKGSTFGIN LIYVNPFMLQ    660
WGIPLIKELR SKGYPIQFLT IGAGVPSLEV ASEYIETLGL KYLGLKPGSI DAISQVINIA    720
KAHPNFPIAL QWTGGRGGGH HSFEDAHTPM LQMYSKIRRH PNIMLIFGSG FGSADDTYPY    780
LTGEWSTKFD YPPMPFDGFL FGSRVMIAKE VKTSPDAKKC IAACTGVPDD KWEQTYKKPT    840
GGIVTVRSEM GEPIHKIATR GVMLWKEFDE TIFNLPKNKL VPTLEAKRDY IISRLNADFQ    900
KPWFATVNGQ ARDLATMTYE EVAKRLVELM FIRSTNSWFD VTWRTFTGDF LRRVEERFTS    960
SKTLSLIQSY SLLDKPDEAI EKVFNAYPAA REQFLNAQDI DHFLSMCQNP MQKPVPFVPV   1020
LDRRFEIFFK KDSLWQSEHL EAVVQDDVQR TCILHGPVAA QFTKVIDEPI KSIMDGIHDG   1080
HIKKLLHQYY GDDESKIPAV EYFGGESPVD VQSQVDSSSV SEDSAVFKAT SSTDEESWFK   1140
ALAGSEINWR HASFLCSFIT QDKMFVSNPI RKVFKPSQGM VVEISNGNTS SKTVVTLSEP   1200
VQGELKPTVI LKLLKENIIQ MEMIENRTMD GKPVSLPLLY NFNPDNGFAP ISEVMEDRNQ   1260
RIKEMYWKLW IDEPFNLDFD PRDVIKGKDF EITAKEVYDF THAVGNNCED FVSRPDRTML   1320
APMDFAIVVG WRAIIKAIFP NTVDGDLLKL VHLSNGYKMI PGAKPLQVGD VVSTTAVIES   1380
VVNQPTGKIV DVVGTLSRNG KPVMEVTSSF FYRGNYTDFE NTFQKTVEPV YQMHIKTSKD   1440
IAVLRSKEWF QLDDEDFDLL NKTLTFETET EVTFKNANIF SSVKCFGPIK VELPTKETVE   1500
IGIVDYEAGA SHGNPVVDFL KRNGSTLEQK VNLENPIPIA VLDSYTPSTN EPYARVSGDL   1560
NPIHVSRHFA SYANLPGTIT HGMFSSASVR ALIENWAADS VSSRVRGYTC QFVDMVLPNT   1620
ALKTSIQHVG MINGRKLIKF ETRNEDDVVV LTGEAEIEQP VTTFVFTGQG SQEQGMGMDL   1680
YKTSKAAQDV WNRADNHFKD TYGFSILDIV INNPVNLTIH FGGEKGKRIR ENYSAMIFET   1740
IVDGKLKTEK IFKEINEHST SYTFRSEKGL LSATQFTQPA LTLMEKAAFE DLKSKGLIPA   1800
DATFAGHSLG EYAALASLAD VMSIESLVEV VFYRGMTMQV AVPRDELGRS NYGMIAINPG   1860
RVAASFSQEA LQYVVERVGK RTGWLVEIVN YNVENQQYVA AGDLRALDTV TNVLNFIKLQ   1920
KIDIIELQKS LSLEEVEGHL FEIIDEASKK SAVKPRPLKL ERGFACIPLV GISVPFHSTY   1980
LMNGVKPFKS FLKKNIIKEN VKVARLAGKY IPNLTAKPFQ VTKEYFQDVY DLTGSEPIKE   2040
IIDNWEKYEQ S                                                         2051
```

*Saccharomyces cerevisiae*

SEQ ID NO: 30

```
MDAYSTRPLT LSHGSLEAVL LVPTASFFIA SQLQEQFNKI LPEPTEGFAA DDEPTTPAEL     60
VGKFLGYVSS LVEPSKVGQF DQVLNLCLTE FENCYLEGND IHALAAKLLQ ENDTTLVKTK    120
ELIKNYITAR IMAKRPFDKK SNSALFRAVG EGNAQLVAIF GGAGNTDDYF EELRDLYQTY    180
HVLVGDLIKF SAETLSELIR TTLDAEKVFT QGLNILEWLE NPSNTPDKDY LLSIPISCPL    240
IGVIQLAHYV VTAKLLGFTP GELRSYLKGA TGHSQGLVTA VAIAETDSWE SFFVSVRKAI    300
TVLFFIGVRC YEAYPNTSLP PSILEDSLEN NEGVPSPMLS ISNLTQEQVQ DYVNKTNSHL    360
PAGKQVEISL VNGAKNLVVS GPPQSLYGLN LTLRKAKAPS GLDQSRIPFS ERKLKFSNRF    420
LPVASPAHSH LLVPASDLIN KDLVKNNVSF NAKDIQIPVY DTFDGSDLRV LSGSISERIV    480
DCIIRLPVKW ETTTQFKATH ILDFGPGGAS GLGVLTHRNK DGTGVRVIVA GTLDINPDDD    540
YGFKQEIFDV TSNGLKKNPN WLEEYHPKLI KNKSGKIFVE TKFSKLIGRP PLLVPGMTPC    600
TVSPDFVAAT TNAGYTIELA GGGYFSAAGM TAAIDSVVSQ IEKGSTFGIN LIYVNPFMLQ    660
WGIPLIKELR SKGYPIQFLT IGAGVPSLEV ASEYIETLGL KYLGLKPGSI DAISQVINIA    720
KAHPNFPIAL QWTGGRGGGH HSFEDAHTPM LQMYSKIRRH PNIMLIFGSG FGSADDTYPY    780
LTGEWSTKFD YPPMPFDGFL FGSRVMIAKE VKTSPDAKKC IAACTGVPDD KWEQTYKKPT    840
GGIVTVRSEM GEPIHKIATR GVMLWKEFDE TIFNLPKNKL VPTLEAKRDY IISRLNADFQ    900
KPWFATVNGQ ARDLATMTYE EVAKRLVELM FIRSTNSWFD VTWRTFTGDF LRRVEERFTS    960
SKTLSLIQSY SLLDKPDEAI EKVFNAYPAA REQFLNAQDI DHFLSMCQNP MQKPVPFVPV   1020
LDRRFEIFFK KDSLWQSEHL EAVVQDDVQR TCILHGPVAA QFTKVIDEPI KSIMDGIHDG   1080
HIKKLLHQYY GDDESKIPAV EYFGGESPVD VQSQVDSSSV SEDSAVFKAT SSTDEESWFK   1140
ALAGSEINWR HASFLCSFIT QDKMFVSNPI RKVFKPSQGM VVEISNGNTS SKTVVTLSEP   1200
VQGELKPTVI LKLLKENIIQ MEMIENRTMD GKPVSLPLLY NFNPDNGFAP ISEVMEDRNQ   1260
RIKEMYWKLW IDEPFNLDFD PRDVIKGKDF EITAKEVYDF THAVGNNCED FVSRPDRTML   1320
APMDFAIVVG WRAIIKAIFP NTVDGDLLKL VHLSNGYKMI PGAKPLQVGD VVSTTAVIES   1380
VVNQPTGKIV DVVGTLSRNG KPVMEVTSSF FYRGNYTDFE NTFQKTVEPV YQMHIKTSKD   1440
IAVLRSKEWF QLDDEDFDLL NKTLTFETET EVTFKNANIF SSVKCFGPIK VELPTKETVE   1500
IGIVDYEAGA SHGNPVVDFL KRNGSTLEQK VNLENPIPIA VLDSYTPSTN EPYARVSGDL   1560
NPIHVSRHFA SYANLPGTIT HGMFSSASVR ALIENWAADS VSSRVRGYTC QFVDMVLPNT   1620
ALKTSIQHVG MINGRKLIKF ETRNEDDVVV LTGEAEIEQP VTTFVFTGQG SQEQGMGMDL   1680
YKTSKAAQDV WNRADNHFKD TYGFSILDIV INNPVNLTIH FGGEKGKRIR ENYSAMIFET   1740
IVDGKLKTEK IFKEINEHST SYTFRSEKGL LSATQFTQPA LTLMEKAAFE DLKSKGLIPA   1800
DATFAGHSLG EYAALASLAD VMSIESLVEV VFYRGMTMQV AVPRDELGRS NYGMIAINPG   1860
RVAASFSQEA LQYVVERVGK RTGWLVEIVN YNVENQQYVA AGDLRALDTV TNVLNFIKLQ   1920
KIDIIELQKS LSLEEVEGHL FEIIDEASKK SAVKPRPLKL ERGFACIPLV GISVPFHSTY   1980
```

TABLE 4-continued

Sequences disclosed herein.

```
LMNGVKPFKS FLKKNIIKEN VKVARLAGKY IPNLTAKPFQ VTKEYFQDVY DLTGSEPIKE  2040
IIDNWEKYEQ S                                                      2051
```

*Saccharomyces cerevisiae*

SEQ ID NO: 31

```
MDAYSTRPLT LSHGSLEHVL LVPTASFFIA SQLQEQFNKI LPEPTEGFAA DDEPTTPAEL   60
VGKFLGYVSS LVEPSKVGQF DQVLNLCLTE FENCYLEGND IHALAAKLLQ ENDTTLVKTK  120
ELIKNYITAR IMAKRPFDKK SNSALFRAVG EGNAQLVAIF GGQGNTDDYF EELRDLYQTY  180
HVLVGDLIKF SAETLSELIR TTLDAEKVFT QGLNILEWLE NPSNTPDKDY LLSIPISCPL  240
IGVIQLAHYV VTAKLLGFTP GELRSYLKGA TGHSQGLVTA VAIAETDSWE SFFVSVRKAI  300
TVLFFAGVRC YEAYPNTSLP PSILEDSLEN NEGVPSPMLS ISNLTQEQVQ DYVNKTNSHL  360
PAGKQVEISL VNGAKNLVVS GPPQSLYGLN LTLRKAKAPS GLDQSRIPFS ERKLKFSNRF  420
LPVASPFHSH LLVPASDLIN KDLVKNNVSF NAKDIQIPVY DTFDGSDLRV LSGSISERIV  480
DCIIRLPVKW ETTTQFKATH ILDFGPGGAS GLGVLTHRNK DGTGVRVIVA GTLDINPDDD  540
YGFKQEIFDV TSNGLKKNPN WLEEYHPKLI KNKSGKIFVE TKFSKLIGRP PLLVPGMTPC  600
TVSPDFVAAT TNAGYTIELA GGGYFSAAGM TAAIDSVVSQ IEKGSTFGIN LIYVNPFMLQ  660
WGIPLIKELR SKGYPIQFLT IGAGVPSLEV ASEYIETLGL KYLGLKPGSI DAISQVINIA  720
KAHPNFPIAL QWTGGRGGGH HSFEDAHTPM LQMYSKIRRH PNIMLIFGSG FGSADDTYPY  780
LTGEWSTKFD YPPMPFDGFL FGSRVMIAKE VKTSPDAKKC IAACTGVPDD KWEQTYKKPT  840
GGIVTVRSEM GEPIHKIATR GVMLWKEFDE TIFNLPKNKL VPTLEAKRDY IISRLNADFQ  900
KPWFATVNGQ ARDLATMYE  EVAKRLVELM FIRSTNSWFD VTWRTFTGDF LRRVEERFTK  960
SKTLSLIQSY SLLDKPDEAI EKVFNAYPAA REQFLNAQDI DHFLSMCQNP MQKPVPFVPV 1020
LDRRFEIFFK KDSLWQSEHL EAVVDQDVQR TCILHGPVAA QFTKVIDEPI KSIMDGIHDG 1080
HIKKLLHQYY GDDESKIPAV EYFGGESPVD VQSQVDSSSV SEDSAVFKAT SSTDEESWFK 1140
ALAGSEINWR HASFLCSFIT QDKMFVSNPI RKVFKPSQGM VVEISNGNTS SKTVVTLSEP 1200
VQGELKPTVI LKLLKENIIQ MEMIENRTMD GKPVSLPLLY NFNPDNGFAP ISEVMEDRNQ 1260
RIKEMYWKLW IDEPFNLDFD PRDVIKGKDF EITAKEVYQP THAVGNNCED FVSRPDRTML 1320
APMDFAIVVG WRAIIKAIFP NTVDGDLLKL VHLSNGYKMI PGAKPLQVGD VVSTTAVIES 1380
VVNQPTGKIV DVVGTLSRNG KPVMEVTSSF FYRGNYTDFE NTFQKTVEPV YQMHIKTSKD 1440
IAVLRSKEWF QLDDEDFDLL NKTLTFETET EVTFKNANIF SSVKCFGPIK VELPTKETVE 1500
IGIVDYEAGA SHGNPVVDFL KRNGSTLEQK VNLENPIPIA VLDSYTPSTN EPYARVSGDL 1560
NPIHVSRHFA SYANLPGTIT HGMFSSASVR ALIENWAADS VSSRVRGYTC QFVDMVLPNT 1620
ALKTSIQHVG MINGRKLIKF ETRNEDDVVV LTGEAEIEQP VTTFVFTGQG SQEQGMGMDL 1680
YKTSKAAQDV WNRADNHFKD TYGFSILDIV INNPVNLTIH FGGEKGKRIR ENYSAMIFET 1740
IVDGKLKTEK IFKEINEHST SYTFRSEKGL LSATQFTQPA LTLMEKAAFE DLKSKGLIPA 1800
DATFAGHSLG EYAALASLAD VMSIESLVEV VFYRGMTMQV AVPRDELGRS NYGMIAINPG 1860
RVAASFSQEA LQYVVERVGK RTGWLVEIVN YNVENQQYVA AGDLRALDTV TNVLNFIKLQ 1920
KIDIIELQKS LSLEEVEGHL FETIDEASKK SAVKPRPLKL ERGFACIPLV GISVPFHSTY 1980
LMNGVKPFKS FLKKNIIKEN VKVARLAGKY IPNLTAKPFQ VTKEYFQDVY DLTGSEPIKE 2040
IIDNWEKYEQ S                                                     2051
```

*Saccharomyces cerevisiae*

SEQ ID NO: 32

```
MDAYSTRPLT LSHGSLEHVL LVPTASFFIA SQLQEQFNKI LPEPTEGFAA DDEPTTPAEL   60
VGKFLGYVSS LVEPSKVGQF DQVLNLCLTE FENCYLEGND IHALAAKLLQ ENDTTLVKTK  120
ELIKNYITAR IMAKRPFDKK SNSALFRAVG EGNAQLVAIF GGQGNTDDYF EELRDLYQTY  180
HVLVGDLIKF SAETLSELIR TTLDAEKVFT QGLNILEWLE NPSNTPDKDY LLSIPISCPL  240
IGVIQLAHYV VTAKLLGFTP GELRSYLKGA TGHSQGLVTA VAIAETDSWE SFFVSVRKAI  300
TVLFFAGVRC YEAYPNTSLP PSILEDSLEN NEGVPSPMLS ISNLTQEQVQ DYVNKTNSHL  360
PAGKQVEISL VNGAKNLVVS GPPQSLYGLN LTLRKAKAPS GLDQSRIPFS ERKLKFSNRF  420
LPVASPFHSH LLVPASDLIN KDLVKNNVSF NAKDIQIPVY DTFDGSDLRV LSGSISERIV  480
DCAIRLPVKW ETTTQFKATH ILDFGPGGAS GLGVLTHRNK DGTGVRVIVA GTLDINPDDD  540
YGFKQEIFDV TSNGLKKNPN WLEEYHPKLI KNKSGKIFVE TKFSKLIGRP PLLVPGMTPC  600
TVSPDFVAAT TNAGYTIELA GGGYFSAAGM TAAIDSVVSQ IEKGSTFGIN LIYVNPFMLQ  660
WGIPLIKELR SKGYPIQFLT IGAGVPSLEV ASEYIETLGL KYLGLKPGSI DAISQVINIA  720
KAHPNFPIAL QWTGGRGGGH HSFEDAHTPM LQMYSKIRRH PNIMLIFGSG FGSADDTYPY  780
LTGEWSTKFD YPPMPFDGFL FGSRVMIAKE VKTSPDAKKC IAACTGVPDD KWEQTYKKPT  840
GGIVTVRSEM GEPIHKIATR GVMLWKEFDE TIFNLPKNKL VPTLEAKRDY IISRLNADFQ  900
KPWFATVNGQ ARDLATMYE  EVAKRLVELM FIRSTNSWFD VTWRTFTGDF LRRVEERFTK  960
SKTLSLIQSY SLLDKPDEAI EKVFNAYPAA REQFLNAQDI DHFLSMCQNP MQKPVPFVPV 1020
LDRRFEIFFK KDSLWQSEHL EAVVDQDVQR TCILHGPVAA QFTKVIDEPI KSIMDGIHDG 1080
HIKKLLHQYY GDDESKIPAV EYFGGESPVD VQSQVDSSSV SEDSAVFKAT SSTDEESWFK 1140
ALAGSEINWR HASFLCSFIT QDKMFVSNPI RKVFKPSQGM VVEISNGNTS SKTVVTLSEP 1200
VQGELKPTVI LKLLKENIIQ MEMIENRTMD GKPVSLPLLY NFNPDNGFAP ISEVMEDRNQ 1260
RIKEMYWKLW IDEPFNLDFD PRDVIKGKDF EITAKEVYQP THAVGNNCED FVSRPDRTML 1320
APMDFAIVVG WRAIIKAIFP NTVDGDLLKL VHLSNGYKMI PGAKPLQVGD VVSTTAVIES 1380
VVNQPTGKIV DVVGTLSRNG KPVMEVTSSF FYRGNYTDFE NTFQKTVEPV YQMHIKTSKD 1440
IAVLRSKEWF QLDDEDFDLL NKTLTFETET EVTFKNANIF SSVKCFGPIK VELPTKETVE 1500
IGIVDYEAGA SHGNPVVDFL KRNGSTLEQK VNLENPIPIA VLDSYTPSTN EPYARVSGDL 1560
NPIHVSRHFA SYANLPGTIT HGMFSSASVR ALIENWAADS VSSRVRGYTC QFVDMVLPNT 1620
ALKTSIQHVG MINGRKLIKF ETRNEDDVVV LTGEAEIEQP VTTFVFTGQG SQEQGMGMDL 1680
YKTSKAAQDV WNRADNHFKD TYGFSILDIV INNPVNLTIH FGGEKGKRIR ENYSAMIFET 1740
IVDGKLKTEK IFKEINEHST SYTFRSEKGL LSATQFTQPA LTLMEKAAFE DLKSKGLIPA 1800
DATFAGHSLG EYAALASLAD VMSIESLVEV VFYRGMTMQV AVPRDELGRS NYGMIAINPG 1860
RVAASFSQEA LQYVVERVGK RTGWLVEIVN YNVENQQYVA AGDLRALDTV TNVLNFIKLQ 1920
KIDIIELQKS LSLEEVEGHL FEIIDEASKK SAVKPRPLKL ERGFACIPLV GISVPFHSTY 1980
LMNGVKPFKS FLKKNIIKEN VKVARLAGKY IPNLTAKPFQ VTKEYFQDVY DLTGSEPIKE 2040
IIDNWEKYEQ S                                                     2051
```

TABLE 4-continued

Sequences disclosed herein.

*Ondatra zibethicus*
SEQ ID NO: 33

```
MPEALLLRSA SSILRTVFLS RLLPGGPGCV RKLSLNLQYQ QGIRPNVQSS SLTDGRTLSK    60
ESSTHGLEFS APEKASPPDT AEEALWTARA DGRVRLRREP FCTQPPYTVH RMFYEALDKY   120
GSLSALGVKR RNKWERISYY QYYEIARKVA RGFLKLGLER AHSVGILGFN SPEWFFSAVG   180
TVFAGGIVTG IYTTSSLEAC QYIAHDCRAN VIVVDTQKQL EKILKIWKDL PHLKAVVIYQ   240
EPLPKKMVNV YTMEELIELG QEVPEEALDT IIDTQQPNQC CVLVYTSGTT GNPKGVMLSQ   300
DNITWTARYG SQAGDIQPAE VQQEVVVSYL PLSHIAAQIY DLWTGIQWGA QVCFADPDAL   360
KGSLVNTLRE VEPTSHMGVP RVWEKIMEGI QEVAAQSGFI RRKMLLWAMS VTLEQNLTCP   420
SNDLKPFTSR LADYLVLAKV RQALGFAKCQ KNFYGAAPMT AETQRFFLGL NIRLYAGYGL   480
SESTGPHFMS SPYNYRLYSS GKLIPGCRVK LVNQDANGIG EICLWGRTIF MGYLNMEDKT   540
CEAIDSEGWL HTGDMGRLDS DGFLYITGRL KELIITAGGE NVPPVPIEEA VKTELPIISS   600
AMLIGDQRKF LSMLLTLKCT LDPETSEPTD NLTEQAVEFC QRVGSGASTV SEIVGQRDEA   660
VYQAIQEGIQ RVNANAAARP YHIQKWAILK RDFSISGGEL GPTMKLKRLT VLEKYKDIID   720
SFYQEQKQ                                                          728
```

*Saccharomyces cerevisiae*
SEQ ID NO: 34

```
MLQRHSLKLG KFSIRTLATG APLDASKLKI TRNPNPSKPR PNEELVFGQT FTDHMLTIPW    60
SAKEGWGTPH IKPYGNLSLD PSACVFHYAF ELFEGLKAYR TPQNTITMFR PDKNMARMNK   120
SAARICLPTF ESEELIKLTG KLIEQDKHLV PQGNGYSLYI RPTMIGTSKG LGVGTPSEAL   180
LYVITSPVGP YYKTGFKAVR LEATDYATRA WPGGVGDKKL GANYAPCILP QLQAAKRGYQ   240
QNLWLFGPEK NITEVGTMNV FFVPLNKVTG KKELVTAPLD GTILEGVTRD SVLTLARDKL   300
DPQEWDINER YYTITEVATR AKQGELLEAF GSGTAAVVSP IKEIGWNNED IHVPLLPGEQ   360
CGALTKQVAQ WIADIQYGRV NYGNWSKTVA DLN                                393
```

*Saccharomyces cerevisiae*
SEQ ID NO: 35

```
MTLAPLDASK VKITTTQHAS KPKPNSELVF GKSFTDHMLT AEWTAEKGWG TPEIKPYQNL    60
SLDPSAVVFH YAFELFEGMK AYRTVDNKIT MFRPDMNMKR MNKSAQRICL PTFDPEELIT   120
LIGKLIQQDK CLVPEGKGYS LYIRPTLIGT TAGLGVSTPD RALLYVICCP VGPYYKTGFK   180
AVRLEATDYA TRAWPGGCGD KKLGANYAPC VLPQLQAASR GYQQNLWLFG PNNNITEVGT   240
MNAFFVFKDS KTGKKELVTA PLDGTILEGV TRDSILNLAK ERLEPSEWTI SERYFTIGEV   300
TERSKNGELL EAFGSGTAAI VSPIKEIGWK GEQINIPLLP GEQTGPLAKE VAQWINGIQY   360
GETEHGNWSR VVTDLN                                                  376
```

*Saccharomyces cerevisiae*
SEQ ID NO: 36

```
MAPVTIEKFV NQEERHLVSN RSATIPFGEY IFKRLLSIDT KSVFGVPGDF NLSLLEYLYS    60
PSVESAGLRW VGTCNELNAA YAADGYSRYS NKIGCLITTY GVGELSALNG IAGSFAENVK   120
VLHIVGVAKS IDSRSSNFSD RNLHHLVPQL HDSNFKGPNH KVYHDMVKDR VACSVAYLED   180
IETACDQVDN VIRDIYKYSK PGYIFVPADF ADMSVTCDNL VNVPRISQQD CIVYPSENQL   240
SDIINKITSW IYSSKTPAIL GDVLTDRYGV SNFLNKLICK TGIWNFSTVM GKSVIDESNP   300
TYMGQYNGKE GLKQVYEHFE LCDLVLHFGV DINEINNGHY TFTYKPNAKI IQFHPNYIRL   360
VDTRQGNEQM FKGINFAPIL KELYKRIDVS KLSLQYDSNV TQYTNETMRL EDPTNGQSSI   420
ITQVHLQKTM PKFLNPGDVV VCETGSFQFS VRDPAFPSQL KYISQGFFLS IGMALPAALG   480
VGIAMQDHSN AHINGGNVKE DYKPRLILFE GDGAAQMTIQ ELSTILKCNI PLEVIIWNNN   540
GYTIERAIMG PTRSYNDVMS WKWTKLFEAF GDFDGKYTNS TLIQCPSKLA LKLEELKNSN   600
KRSGIELLEV KLGELDFPEQ LKCMVEAAAL KRNKK                             635
```

*Saccharomyces cerevisiae*
SEQ ID NO: 37

```
MPTLYTDIEI PQLKISLKQP LGLFINNEFC PSSDGKTIET VNPATGEPIT SFQAANEKDV    60
DKAVKAARAA FDNVWSKTSS EQRGIYLSNL LKLIEEEQDT LAALETLDAG KPYHSNAKGD   120
LAQILQLTRY FAGSADFDK GATIPLTFNK FAYTLKVPFG VVAQIVPWNY PLAMACWKLQ   180
GALAAGNTVI IKPAENTSLS LLYFATLIKK AGFPPGVVNI VPGYGSLVGQ ALASHMDIDK   240
ISFTGSTKVG GFVLEASGQS NLKDVTLECG GKSPALVFED ADLDKAIDWI AAGIFYNSGQ   300
NCTANSRVYV QSSIYDKFVE KFKETAKKEW DVAGKFDPFD EKCIVGPVIS STQYDRIKSY   360
IERGKREEKL DMFQTSEFPI GGAKGYFIPP TIFTDVPQTS KLLQDEIFGP VVVVSKFTNY   420
DDALKLANDT CYGLASAVFT KDVKKAHMFA RDIKAGTVWI NSSNDEDVTV PFGGFKMSGI   480
GRELGQSGVD TYLQTKAVHI NLSLDN                                        506
```

*Saccharomyces cerevisiae*
SEQ ID NO: 38

```
MPTLYTDIEI PQLKISLKQP LGLFINNEFC PSSDGKTIET VNPATGEPIT SFQAANEKDV    60
DKAVKAARAA FDNVWSKTSS EQRGIYLSNL LKLIEEEQDT LAALETLDAG KPYHSNAKGD   120
LAQILQLTRY FAGSADFDK GATIPLTFNK FAYTLKVPFG VVAQIVPWNY PLAMACWKLQ   180
GALAAGNTVI IKPAENTSLS LLYFATLIKK AGFPPGVVNI VPGYGSLVGQ ALASHMDIDK   240
ISFTGSTKVG GFVLEASGQS NLKDVTLECG GKSPALVFED ADLDKAIDWI AAGIFYNSGQ   300
NCTANSRVYV QSSIYDKFVE KFKETAKKEW DVAGKFDPFD EKCIVGPVIS STQYDRIKSY   360
IERGKREEKL DMFQTSEFPI GGAKGYFIPP TIFTDVPQTS KLLQDEIFGP VVVVSKFTNY   420
DDALKLANDT CYGLASAVFT KDVKKAHMFA RDIKAGTVWI NSSNDEDVTV PFGGFKMSGI   480
GRELGQSGVD TYLQTKAVHI NLSLDN                                        506
```

TABLE 4-continued

Sequences disclosed herein.

*Saccharomyces cerevisiae*

SEQ ID NO: 39

| | | | | | |
|---|---|---|---|---|---|
| MSEESLFESS | PQKMEYEITN | YSERHTELPG | HFIGLNTVDK | LEESPLRDFV | KSHGGHTVIS | 60 |
| KILIANNGIA | AVKEIRSVRK | WAYETFGDDR | TVQFVAMATP | EDLEANAEYI | RMADQYIEVP | 120 |
| GGTNNNNYAN | VDLIVDIAER | ADVDAVWAGW | GHASENPLLP | EKLSQSKRKV | IPIGPPGNAM | 180 |
| RSLGDKISST | IVAQSAKVPC | IPWSGTGVDT | VHVDEKTGLV | SVDDDIYQKG | CCTSPEDGLQ | 240 |
| KAKRIGFPVM | IKASEGGGGK | GIRQVEREED | FIALYHQAAN | EIPGSPIFIM | KLAGRARHLE | 300 |
| VQLLADQYGT | NISLFGRDCS | VQRRHQKIIE | EAPVTIAKAE | TFHEMEKAAV | RLGKLVGYVS | 360 |
| AGTVEYLYSH | DDGKFYFLEL | NPRLQVEHPT | TEMVSGVNLP | AAQLQIAMGI | PMHRISDIRT | 420 |
| LYGMNPHSAS | EIDFEFKTQD | ATKKQRRPIP | KGHCTACRIT | SEDPNDGFKP | SGGTLHELNF | 480 |
| RSSSNVWGYF | SVGNNGNIHS | FSDSQFGHIF | AFGENRQASR | KHMVVALKEL | SIRGDFRTTV | 540 |
| EYLIKLLETE | DFEDNTITTG | WLDDLITHKM | TAEKPDPTLA | VICGAATKAF | LASEEARHKY | 600 |
| IESLQKGQVL | SKDLLQTMFP | VDFIHEGKRY | KFTVAKSGND | RYTLFINGSK | CDIILRQLSD | 660 |
| GGLLIAIGGK | SHTIYWKEEV | AATRLSVDSM | TTLLEVENDP | TQLRTPSPGK | LVKFLVENGE | 720 |
| HIIKGQPYAE | IEVMKMQMPL | VSQENGIVQL | LKQPGSTIVA | GDIMAIMTLD | DPSKVKHALP | 780 |
| FEGMLPDFGS | PVIEGTKPAY | KFKSLVSTLE | NILKGYDNQV | IMNASLQQLI | EVLRNPKLPY | 840 |
| SEWKLHISAL | HSRLPAKLDE | QMEELVARSL | RRGAVFPARQ | LSKLIDMAVK | NPEYNPDKLL | 900 |
| GAVVEPLADI | AHKYSNGLEA | HEHSIFVHFL | EEYYEVEKLF | NGPNVREENI | ILKLRDENPK | 960 |
| DLDKVALTVL | SHSKVSAKNN | LILAILKHYQ | PLCKLSSKVS | AIFSTPLQHI | VELESKATAK | 1020 |
| VALQAREILI | QGALPSVKER | TEQIEAILKS | SVVKVAYGSS | NPKRSEPDLN | ILKDLIDSNY | 1080 |
| VVFDVLLQFL | THQDPVVTAA | AAQVYIRRAY | RAYTIGDIRV | HEGVTVPIVE | WKFQLPSAAF | 1140 |
| STFPTVKSKM | GMNRAVSVSD | LSYVANSQSS | PLREGILMAV | DHLDDVDEIL | SQSLEVIPRH | 1200 |
| QSSSNGPAPD | RSGSSASLSN | VANVCVASTE | GFESEEEILV | RLREILDLNK | QELINASIRR | 1260 |
| ITFMFGPKDG | SYPKYYTFNG | PNYNENETIR | HIEPALAFQL | ELGRLSNFNI | KPIFTDNRNI | 1320 |
| HVYEAVSKTS | PLDKRFFTRG | IIRTGHIRDD | ISIQEYLTSE | ANRLMSDILD | NLEVTDTSNS | 1380 |
| DLNHIFINFI | AVFDISPEDV | EAAFGGFLER | FGKRLLRLRV | SSAEIRIIIK | DPQTGAPVPL | 1440 |
| RALINNVSGY | VIKTEMYTEV | KNAKGEWVFK | SLGKPGSMHL | RPIATPYPVK | EWLQPKRYKA | 1500 |
| HLMGTTYVYD | FPELFRQASS | SQWKNFSADV | KLTDDFFISN | ELIEDENGEL | TEVEREPGAN | 1560 |
| ALGMVAFKIT | VKTPEYPRGR | QFVVVANDIT | FKIGSFGPQE | DEFFNKVTEY | ARKRGIPRIY | 1620 |
| LAANSGARIG | MAEEIVPLFQ | VAWNDAANPD | KGFQYLYLTS | EGEMTLKKFD | KENSVLTERT | 1680 |
| VINGEERFVI | KTIIGSEDGL | GVECLRGSGL | IAGATSRAYH | DIFTITLVTC | RSVGIGAYLV | 1740 |
| RLGQRAIQVE | GQPIILTGAP | AINKMLGREV | YTSNLQLGGT | QIMYNNGVSH | LTAVDDLAGV | 1800 |
| EKIVEWMSYV | PAKRNMPVPI | LETKDTWDRP | VDFTPTNDET | YDVRWMIEGR | ETESGFEYGL | 1860 |
| FDKGSFFETL | SGWAKGVVVG | RARLGGIPLG | VIGVETRTVE | NLIPADPANP | NSAETLIQEP | 1920 |
| GQVWHPNSAF | KTAQAINDFN | NGEQLPMMIL | ANWRGFSQGP | RDMFNEVLKY | GSFIVDALVD | 1980 |
| YKQPIIIYIP | PTGELRGGSW | VVVDPTINAD | QMEMYADVNA | RAGVLEPQGM | VGIKFRREKL | 2040 |
| LDTMNRLDDK | YRELRSQLSN | KSLAPEVHQQ | ISKQLADRER | ELLPIYGQIS | LQFADLHDRS | 2100 |
| SRMVAKGVIS | KELEWTEARR | FFFWRLRRRL | NEEYLIKRLS | HQVGEASRLE | KIARIRSWYP | 2160 |
| ASVDHEDDRQ | VATWIEENYK | TLDDKLKGLK | LESFAQDLAK | KIRSDHDNAI | DGLSEVIKML | 2220 |
| STDDKEKLLK | TLK | | | | | 2233 |

*Saccharomyces cerevisiae*

SEQ ID NO: 40

| | | | | | |
|---|---|---|---|---|---|
| MKPEVEQELA | HILLTELLAY | QFASPVRWIE | TQDVFLKDFN | TERVVEIGPS | PTLAGMAQRT | 60 |
| LKNKYESYDA | ALSLHREILC | YSKDAKEIYY | TPDPSELAAK | EEPAKEEAPA | PTPAASAPAP | 120 |
| AAAAPAPVAA | APAAAAAEI | ADEPVKASLL | LHVLVAHKLK | KSLDSIPMSK | TIKDLVGGKS | 180 |
| TVQNEILGDL | GKEFGTTPEK | PEETPLEELA | ETFQDTFSGA | LGKQSSSLLS | RLISSKMPGG | 240 |
| FTITVARKYL | QTRWGLPSGR | QDGVLLVALS | NEPAARLGSE | ADAKAFLDSM | AQKYASIVGV | 300 |
| DLSSAASASG | AAGAGAAAGA | AMIDAGALEE | ITKDHKVLAR | QQLQVLARYL | KMDLDNGERK | 360 |
| FLKEKDTVAE | LQAQLDYLNA | ELGEFFVNGV | ATSFSRKKAR | TFDSSWNWAK | QSLLSLYFEI | 420 |
| IHGVLKNVDR | EVVSEAINIM | NRSNDALIKF | MEYHISNTDE | TKGENYQLVK | TLGEQLIENC | 480 |
| KQVLDVDPVY | KDVAKPTGPK | TAIDKNGNIT | YSEEPREKVR | KLSQYVQEMA | LGGPITKESQ | 540 |
| PTIEEDLTRV | YKAISAQADK | QDISSSTRVE | FEKLYSDLMK | FLESSKEIDP | SQTTQLAGMD | 600 |
| VEDALDKDST | KEVASLPNKS | TISKTVSSTI | PRETIPFLFL | RKKTPAGDWK | VDRQLSSLFL | 660 |
| DGLEKAAFNG | VTFKDKYVLI | TGAGKGSIGA | EVLQGLLQGG | AKVVVTTSRF | SKQVTDYYQS | 720 |
| IYAKYGAKGS | TLIVVPFNQG | SKQDVEALIE | FIYDTEKNGG | LGWDLDAIIP | FAAIPEQGIE | 780 |
| LEHIDSKSEF | AHRIMLTNIL | RMMGCVKKQK | SARGIETRPA | QVILPMSPNH | GTFGGDGMYS | 840 |
| ESKLSLETLF | NRWHSESWAN | QLTVCGAIIG | WTRGTGLMSA | NNIIAEGIEK | MGVRTFSQKE | 900 |
| MAFNLLGLLT | PEVVELCQKS | PVMADLNGGL | QFVPELKEFT | AKLRKELVET | SEVRKAVSIE | 960 |
| TALEHKVVNG | NSADAAYAQV | EIQPRANIQL | DFPELKPYKQ | VKQIAPAELE | GLLDLERVIV | 1020 |
| VTGFAEVGPW | GSARTRWEME | AFGEFSLEGC | VEMAWIMGFI | SYHNGNLKGR | PYTGWVDSKT | 1080 |
| KEPVDDKDVK | AKYETSILEH | SGIRLIEPEL | FNGYNPEKKE | MIQEVIVEED | LEPFEASKET | 1140 |
| AEQFKHQHGD | KVDIFEIPET | GEYSVKLLKG | ATLYIPKALR | FDRLVAGQIP | TGWNAKTYGI | 1200 |
| SDDIISQVDP | ITLFVLVSVV | EAFIASGITD | PYEMYKYVHV | SEVGNCSGSG | MGGVSALRGM | 1260 |
| FKDRFKDEPV | QNDILQESFI | NTMSAWVNML | LISSSGPIKT | PVGACATSVE | SVDIGVETIL | 1320 |
| SGKARICIVG | GYDDFQEEGS | FEFGNMKATS | NTLEEFEHGR | TPAEMSRPAT | TTRNGFMEAQ | 1380 |
| GAGIQIIMQA | DLALKMGVPI | YGIVAMAATA | TDKIGRSVPA | PGKGILTTAR | EHKSSVKYAS | 1440 |
| PNLNMKYRKR | QLVTREAQIK | DWVENELEAL | KLEAEEIPSE | DQNEFLLERT | REIHNEAESQ | 1500 |
| LRAAQQQWGN | DFYKRDPRIA | PLRGALATYG | LTIDDLGVAS | FHGTSTKAND | KNESATINEM | 1560 |
| MKHLGRSEGN | PVIGVFQKFL | TGHPKGAAGA | WMMNGALQIL | NSGIIPGNRN | ADNVDKILEQ | 1620 |
| FEYVLYPSKT | LKTDGVRAVS | ITSFGFGQKG | GQAIVVHPDY | LYGAITEDRY | NEYVAKVSAR | 1680 |
| EKSAYKFFHN | GMIYNKLFVS | KEHAPYTDEL | EEDVYLDPLA | RVSKDKKSGS | LTFNSKNIQS | 1740 |
| KDSYINANTI | ETAKMIENMT | KEKVSNGGVG | VDVELITSIN | VENDTFIERN | FTPQEIEYCS | 1800 |
| AQPSVQSSFA | GTWSAKEAVF | KSLGVKSLGG | GAALKDIEIV | RVNKNAPAVE | LHGNAKKAAE | 1860 |
| EAGVTDVKVS | ISHDDLQAVA | VAVSTKK | | | | 1887 |

TABLE 4-continued

Sequences disclosed herein.

*Candida maltosa*

SEQ ID NO: 41
```
MMAIEQIIEE VLPYLTKWYT IIFGAAVTYF LSIALRNKFY EYKLKCENPV YFQDAGLFGI    60
PALIDIIKVR KAGQLADYTD TTFDKYPNLS SYMTVAGVLK IVFTVDPENI KAVLATQFND   120
FALGARHAHF DPLLGDGIFT LDGEGWKHSR AMLRPQFARE QIAHVKALEP HVQILAKQIK   180
LNKGKTFDLQ ELFFRFTVDT ATEFLFGESV HSLYDEKSGI PNDIPGRENV REAFNTSQHY   240
LATRTYSQIF YWLTNPKEFR DCNAKVHKLA QYFVNTALNA TEKEVEEKSK GGYVFLYELV   300
KQTRDPKVLQ DQLLNIMVAG RDTTAGLLSF AMFELARNPK IWNKLREEVE VNFGLGDEAR   360
VDEISFETLK KCEYLKAVLN ETLRMYPSVP INFRTATRDT TLPRGGGKDG NSPIFVPKGS   420
SVVYSVYKTH RLKQFYGEDA YEFRPERWFE PSTRKLGWAY LPFNGGPRIC LGQQFALTEA   480
SYVIARLAQM FEHLESKDET YPPNKCIHLT MNHNEGVFIS AK                    522
```

*Starmerella bombicola*

SEQ ID NO: 42
```
MILYAVLGAF AAFLLYMDVL YPFVIYPLRA RWHKCGYIPR DLSWPLGIPL TLVVLSKLRK    60
DMLLQFMAAQ DLSRPYKTSL RQFLGKWVIA TRDPENIKAV LSTKFNDFSL KERGNRMRHV   120
IGDGIFTQDG APWKHSRDML RPQFTKDQIS RVELLSHHID VLIREIRKSG GNVELQRLFH   180
LMTMDTATHF LFGESVGSLE VSGESKGIEI TDPKTGEIYN TVDFVESYTF ANKFALKKII   240
LNDLEFLADL TEPSYKWHLR RVHTVMDHYV QLALKATEKY DPDDDSEKGE YYFSHELAKL   300
TRDPLSLRDQ LFNILIAGRD TTAATLSYAF HYLTKNPAIY AKVREDVLTV FPNGDASLAT   360
YEDLRKAKYL QMVIKEVLRL APAVPLNTRA AVRDTYLPRG GGPAGNLPVF VPKGTAVNYP   420
TYILHRDPDI YGADAYEFNP ERWRPENKLP NSPMYSWGYI PFNGGPRICI GQQFALTEIA   480
LTMIKLVLEF ERLEPADDFE PNLQDKSSLT VMVGGSGVRV KLS                   523
```

*Starmerella bombicola*

SEQ ID NO: 43
```
MADINFIASV VVALAVVFVA YKYFNGGPDV QSSKAGNSTP FGNSKADEDG DSRDFVALME    60
KNNKNVIVFY GSQTGTAEDL ASKLAKELSS KYGLRTMTAD PENFDFEKLD TPESHLAVF   120
LMASYGDGEP TDNAQDLYSF LGNSPSFSQD GETLENLNFA VFGLGNVLYE FYNKAGKDMH   180
KYLTDLGGHS IGPYGEGDDS KGMLEEDYMA WKDEFLAALV AKWGLTEREA VYEPSISVKE   240
IEEDAHSHDV YLGEPNLKHL QASKAQEIPK GPYNASNPML AKITAARELF TNTDRHCIHM   300
EFDTTGARYT TGDHLAFWFQ NNEEEVQRFV KALGIANPQQ PIAISVLDKT STVRIPSPTT   360
YETIIRHFLE INGPVSRQVL SSIAPFAPSE EVKKATQQLG SNKELFASHV AAKKFNIARL   420
LLHLSGGQPW KNVPFSFVIE TIPHLQPRYY SISSSSVQSP NTVSITAVVE RQTLTGVDHE   480
LRGVATNQIL ALSEALVGHP SMTYRLQQPH DFTNSLSSQD IRVPVHIRHS LFKLPGKPTV   540
PIIMVGPGTG VAPFRGFVHE RASQKAAGKE VGKAMLFTGS RHANEDFLYR DEWKQFSDFL   600
DLETAFSRDS SKKVYVQHKL KERAKDVFAL LNEGAVFYVC GDAGGMSHDV HSALLEIVAQ   660
EGNLSSEDAD KFVRKMRSRN KYQEDVW                                     687
```

*Candida tropicalis*

SEQ ID NO: 44
```
MSSSPSIAQE FLATITPYVE YCQENYTEKWY YFIPLVILSL NLISMLHTKY LERKFKAKPL    60
AVYVQDYTFC LITPLVLIYY KSKGTVMQFA CDLWDKNLIV SDPKAKTIGL KILGIPLIET   120
KDPENVKAIL ATQFNDFSLG TRHDFLYSLL GDGIFTLDGA GWKHSRTMLR PQFAREQVSH   180
VKLLEPHMQV LFKHIRKHHG QTFDIQELFF RLTVDSATEF LLGESAESLR DESVGLTPTT   240
KDFDGRNEFA DAFNYSQTNQ AYRFLLQQMY WILNGSEFRK SIAIVHKFAD HYVQKALELT   300
DEDLEKKEGY VFLFELAKQT RDPKVLRDQL LNILVAGRDT TAGLLSFLFF ELSRNPEIFA   360
KLREEIENKF GLGQDARVEE ISFETLKSCE YLKAVINETL RIYPSVPHNF RVATRNTTLP   420
RGGGEGGLSP IAIKKGQVVM YTILATHRDK DIYGEDAYVF RPERWFEPET RKLGWAYVPF   480
NGGPRICLGQ QFALTEASYV TVRLLQEFGN LKQDPNTEYP PKLQNTLTLS LFEGAEVQMY   540
LIL                                                               543
```

*Candida tropicalis*

SEQ ID NO: 45
```
MIEQLLEYWY VVVPVLYIIK QLLAYTKTRV LMKKLGAAPV TNKLYDNAFG IVNGWKALQF    60
KKEGRAQEYN DYKFDHSKNP SVGTYVSILF GTRIVVTKDP ENIKAILATQ FGDFSLGKRH   120
TLFKPLLGDG IFTLDGEGWK HSRAMLRPQF AREQVAHVTS LEPHFQLLKK HILKHKGEYF   180
DIQELFFRFT VDSATEFLFG ESVHSLKDES IGINQDDIDF AGRKDFAESF NKAQEYLAIR   240
TLVQTFYWLV NNKEFRDCTK SVHKFTNYYV QKALDASPEE LEKQSGYVFL YELVKQTRDP   300
NVLRDQSLNI LLAGRDTTAG LLSFAVFELA RHPEIWAKLR EEIEQQFGLG EDSRVEEITF   360
ESLKRCEYLK AFLNETLRIY PSVPRNFRIA TKNTTLPRGG GSDGTSPILI QKGEAVSYGI   420
NSTHLDPVYY GPDAAEFRPE RWFEPSTKKL GWAYLPFNGG PRICLGQQFA LTEAGYVLVR   480
LVQEFSHVRS DPDEVYPPKR LTNLTMCLQD GAIVKFD                          517
```

*Candida tropicalis*

SEQ ID NO: 46
```
MALDKLDLYV IITLVVAIAA YFAKNQFLDQ QQDTGFLNTD SGDGNSRDIS QALKKNNKNT    60
LLLFGSQTGT AEDYANKLSR ELHSRFGLKT MVADFADYDF ENFGDITEDI LVFFIVATYG   120
EGEPTDNADE FHTWLTEEAD TLSTLKYTVF GLGNSTYEFF NAIGRKFDRL LGEKGGDRFA   180
EYGEGDDTG TLDEDFLAWK DNVFDSLKND LNFEEKELKY EPNVKLTERD DLSGNDPDVS   240
LGEPNVKYIK SEGVDLTKGP FDHTHPFLAR IVKTKELFTS EDRHCVHVEF DISESNLKYT   300
TGDHLAIWPS NSDENIKQFA KCFGLEDKLD TVIELKALDS TYSIPFPNPI TYGAVIRHHL   360
EISGPVSRQF FLSIAGFAPD EETKKSFTRI GGDKQEFASK VTRRKFNIAD ALLFASNNRP   420
WSDVPFEFLI ENVQHLTPRY YSISSSSLSE KQTINVTAVV EAEEEADGRP VTGVVTNLLK   480
NIEIEQNKTG ETPMVHYDLN GPRGKFSKFR LPVHVRRSNF KLPKNSTTPV ILIGPGTGVA   540
```

| | | | | | |
|---|---|---|---|---|---|
| PLRGFVRERV | QQVKNGVNVG | KTVLFYGCRN | SEQDFLYKQE | WSEYASVLGE | NFEMFNAFSR | 600 |
| QDPTKKVYVQ | DKILENSALV | DELLSSGAII | YVCGDASRMA | RDVQAAIAKI | VAKSRDIHED | 660 |
| KAAELVKSWK | VQNRYQEDVW | | | | | 680 |

*Candida maltosa*

SEQ ID NO: 47

| | | | | | |
|---|---|---|---|---|---|
| atgatggcca | tcgaacaaat | catcgaagaa | gtcttgccat | acttgactaa | gtggtacacc | 60 |
| attattttcg | gtgctgctgt | tacttacttc | ttgtccattg | ctttgagaaa | caagtctac | 120 |
| gaatacaagt | tgaagtgcga | aaacccagtt | tactttcaag | atgctggttt | gtttggtatt | 180 |
| ccagccttga | tcgatattat | caaggttaga | aaagctggtc | aattggctga | ttacactgat | 240 |
| accactttg | acaagtaccc | aaacttgtcc | tcttacatga | ctgttgctgg | tgttttgaag | 300 |
| atcgttttca | ctgttgatcc | agaaaacatc | aaagctgttt | tggctaccca | attcaacgat | 360 |
| tttgctttgg | gtgctagaca | tgctcatttt | gatccattat | ggggtgatgg | tatcttcacc | 420 |
| ttggatggtt | aaggttggaa | acattctaga | gctatgttaa | gaccacaatt | cgccagagaa | 480 |
| caaattgctc | atgttaaggc | tttggaacca | cacgttcaaa | ttttggctaa | gcaaatcaag | 540 |
| ttgaacaagg | gtaagacttt | cgacttgcaa | gaattattct | tcagattcac | cgttgatacc | 600 |
| gccaccgaat | ttttgttcgg | tgaatcagtt | cattccttgt | acgacgaaaa | atccggtatt | 660 |
| ccaaatgata | tcccaggtag | agaaaatgtc | agagaagcct | taacacctc | ccaacattat | 720 |
| ttggctacta | gaacctactc | ccaaatcttc | tactggttga | ctaacccaaa | agaatttaga | 780 |
| gattgcaacg | ccaaggttca | taagttggct | caatactttg | ttaacaccgc | tttgaacgct | 840 |
| accgaaaaag | aagttgaaga | aaagtctaag | ggtggttacg | ttttcttgta | cgaattggtt | 900 |
| aagcaaacca | gagatccaaa | ggtattgcaa | gaccaattat | tgaacattat | ggttgccggt | 960 |
| agagatacaa | ctgctggttt | attgtctttc | gccatgtttg | aatggctag | aaacccaaag | 1020 |
| atttggaaca | agttgagaga | agaagtagaa | gtcaatttcg | gtttaggtga | tgaagctaga | 1080 |
| gttgacgaaa | tttccttcga | aaccttgaag | aagtgtgaat | acttgaaggc | cgttttgaac | 1140 |
| gaaactttga | aatgtatcc | atccgtccca | atcaatttca | gaactgctac | tagagatacc | 1200 |
| acattgccaa | gaggtggtgg | taaagatggt | aattctccaa | tttttgtccc | aaagggttcc | 1260 |
| tccgttgttt | actctgttta | caagactcac | agattgaagc | aattctacgg | tgaagatgcc | 1320 |
| tacgaattta | gaccagaaag | atgggtttgaa | ccatccacta | gaaaattggg | ttgggcttat | 1380 |
| ttgcctttta | atggtggtcc | aagaatttgc | ttgggtcaac | aatttgcttt | gactgaagcc | 1440 |
| tcttacgtta | ttgctagatt | ggctcaaatg | tttgaacact | tggaatctaa | ggacgaaact | 1500 |
| tacccaccaa | acaagtgtat | tcatttgacc | atgaaccata | cgaaggtgt | tttcatttcc | 1560 |
| gccaagtaa | | | | | | 1569 |

*Starmerella bombicola*

SEQ ID NO: 48

| | | | | | |
|---|---|---|---|---|---|
| atgatcttgt | acgctgtttt | gggtgctttt | gctgctttt | tgttgtacat | ggatgtcttg | 60 |
| tacccattcg | ttatctatcc | attgagagct | agatggcata | agtgtggtta | tcccaaga | 120 |
| gatttgtctt | ggccattggg | tattccattg | actttggttg | ttttgtccaa | gttgagaaag | 180 |
| gatatgttgt | tgcaattcat | ggctgctcaa | gatttgtcca | gaccatacaa | acatccttg | 240 |
| agacaattct | tgggtaaatg | ggttattgct | accagagatc | cagaaaacat | taaggctgtt | 300 |
| ttgtctacca | agttcaacga | cttctcattg | aaagaaagag | gtaacagaat | gagacacgtt | 360 |
| atcggtgatg | gtatttcac | tcaagatggt | gcaccttgga | acactctag | agatatgtta | 420 |
| agaccacaat | tcaccaagga | ccaaatctcc | agagttgaat | tattgtccca | ccatatcgat | 480 |
| gtcttgatca | gagaaattag | aaagtccggt | ggtaacgtcg | aattgcaaag | attattccac | 540 |
| ttgatgacta | tggataccgc | tacccatttt | tgttcggtg | aatctgttgg | ttccttggaa | 600 |
| gtttctggtg | aatctaaggg | tattgaaatc | actgatccaa | agaccggtga | aatcgttaac | 660 |
| actgttgatt | tcgttgaatc | ctacaccttc | gctaacaagt | ttgccttgaa | aaagatcatc | 720 |
| ttgaacgatt | tggaattttt | ggccgatttg | accgaaccat | cttacaaatg | gcatttgaga | 780 |
| agagttcaca | ccgttatgga | tcactatgtt | caattggctt | tgaaggctac | cgaaaagtat | 840 |
| gatccagatg | atgattctga | aaagggtgaa | tattacttct | cccacgaatt | ggctaagttg | 900 |
| actagagatc | cattgtcctt | gagagttcaa | ttattcaaca | ttttgatcgc | cggtagagat | 960 |
| acaactgctg | ctactttgtc | ttacgctttt | cattacttga | ctaagaaccc | agctatctac | 1020 |
| gctaaggtta | gagaagatgt | tttgaccgtt | tttccaaacg | gtgatgcttc | tttggctact | 1080 |
| tacgaagatt | tgagaaaagc | taagtacttg | caaatggtca | tcaaagaagt | tttgagattg | 1140 |
| gctccagctg | ttccattgaa | cactagagct | gctgttagag | atacttattt | gccaagaggt | 1200 |
| ggtggtccag | ctggtaattt | gccagttttt | gttccaaaag | gtactgccgt | taattaccca | 1260 |
| acttacatct | tgcatagaga | tcctgatatc | tatggtgctg | atgcctacga | atttaatcca | 1320 |
| gaaagatgga | gacctgaaaa | caagttgcca | aattctccaa | tgtattcctg | ggttacatt | 1380 |
| ccattcaatg | tgggtcctag | aatctgcatt | ggtcaacaat | ttgctttgac | tgaaattgcc | 1440 |
| ttgaccatga | tcaagttggt | cttggaattt | gaaagattgg | aaccagccga | tgatttcgaa | 1500 |
| cctaacttgc | aagataagtc | ctccttgact | gttatggttg | gtggttctgg | tgttagagtt | 1560 |
| aagttgtctt | aa | | | | | 1572 |

*Starmerella bombicola*

SEQ ID NO: 49

| | | | | | |
|---|---|---|---|---|---|
| atggccgata | tcaacttcat | tgcctccgtt | gttgttgctt | tggctgttgt | ttttgttgcc | 60 |
| tacaagtact | ttaatggtgg | tccagatgtt | caatcttcta | aggctggtaa | ttctactcca | 120 |
| ttcggtaact | ctaaagctga | tgaagatggt | gattccagag | atttcgttgc | tttgatggaa | 180 |
| aagaacaaca | agaacgtcat | cgttttctac | ggttctcaaa | ctggtactgc | tgaagatttg | 240 |
| gcttctaagt | tggctaaaga | attgtcctct | aagtacggtt | taagaaccat | gactgctgat | 300 |
| ccagaaaact | tcgatttcga | aaagttggat | accttcccag | aatctcattt | ggccgttttt | 360 |
| cttatggctg | cttatggtga | tggtgaacct | actgataatg | ctcaagatt | gtactctttc | 420 |
| ttgggtaact | ctccatcttt | ctcacaagac | ggtgaaactt | tggaaaactt | gaactttgct | 480 |
| gttttcggtt | tgggtaacgt | cttgtacgaa | ttttacaaca | aagccggtaa | ggacatgcat | 540 |
| aagtacttga | ctgatttggg | tggtcattct | attggtccat | acggtgaagg | tgatgattct | 600 |
| aaaggtatgt | tggaagaaga | ttacatggcc | tggaaggatg | aatttttggc | tgctttggtt | 660 |
| gctaaatggg | gtttgactga | aagagaagct | gtttacgaac | catccatctc | cgtcaaagaa | 720 |

TABLE 4-continued

Sequences disclosed herein.

```
attgaagaag atgctcactc tcacgatgtt tatttgggtg aacctaattt gaaacacttg    780
caagcctcaa aggctcaaga aattccaaaa ggtccataca atgcttccaa tccaatgttg    840
gcaaaaatta ccgctgccag agaattattc actaacactg atagacattg catccacatg    900
gaatttgata caactggtgc tagatacact accggtgatc atttggcttt ttggttccaa    960
aacaacgaag aagaagtcca aagattcgtt aaggctttgg gtattgctaa tccacaacaa   1020
cctattgcca tttccgtttt ggataagact tctaccgtta gaataccatc tccaactacc   1080
tacgaaacca tcatcagaca tttcttggaa atcaacggtc cagtttccag acaagtttg    1140
tcatctattg caccatttgc cccatctgaa gaagttaaga aagctactca acaattgggt   1200
tccaacaaag aattatttgc ctctcatgtt gctgccaaga agttcaatat tgccagattg   1260
ttgttacatt tgtccggtgg tcaaccttgg aagaatgttc catttttcctt cgtcattgaa   1320
accatcccac acttacaacc tagatattac tccatctcct cctcatctgt tcaatcccca   1380
aatactgttt ccattactgc cgttgttgaa agacaaactt tgaccggtgt tgatcatgaa   1440
ttgagaggtg ttgctaccaa tcaaattttg gctttgtctg aagccttggt tggtcatcca   1500
tctatgactt atagattgca acaaccacac gacttcacca actcattatc ctctcaagat   1560
atcagagttc cagtccatat tagacacagt ttgtttaagt tgccaggtaa gccaactgtt   1620
ccaattatca tggttggtcc aggtactggt gttgctcctt ttagaggttt tgttcacgaa   1680
agagcttctc aaaaagctgc cggtaaagaa gttggtaagg ctatgttgtt taccggttct   1740
agacatgcta acgaagattt cttgtacaga gatgaatgga agcaattctc cgacttcttg   1800
gatttggaaa ctgccttttc tagagactcc tccaaaaagg tttacgtcca acacaagttg   1860
aaagaaagag ctaaggacgt tttcgccttg ttgaatgaag gtgctgtttt ttacgtttgt   1920
ggtgatgctg gtggtatgtc tcatgatgtt cattctgctt tgttagaaat cgttgcccaa   1980
gaaggtaact tgagttctga agatgctgat aagttcgtca gaaagatgag atcaagaaac   2040
aagtaccaag aagatgtttg gtaa                                         2064
```

*Candida tropicalis*

SEQ ID NO: 50
```
atgtcctcct ccccatctat tgcccaagaa ttttttggcta ctattacccc atacgtcgaa     60
tactgtcaag aaaactacac taagtggtac tacttcatcc cattggtcat cttgtccttg    120
aacttgattt ctatgttgca cactaagtac ttggaaagaa agtttaaggc taagccattg    180
gccgtttacg ttcaagatta caccttctgt ttgatcaccc cattggtttt gatctactac    240
aagtctaagg gtactgttat gcaattcgct tgtgatttgt gggacaagaa cttgatagtt    300
tctgatccaa aggccaagac tatccgtttg aagattttgg gtattccatt gatcgaaact    360
aaggacccag aaaacgttaa ggctatttg gccactcaat tcaacgattt ctcattgggt    420
actagacacg acttcttgta ttcctttgttg ggtgatggta tcttcacttt ggatggtgct    480
ggttggaaac attctagaac tatgttaaga ccacaattcg ccagagaaca agtttcccat    540
gttaagttgt tggaaccaca catgcaagtt ttgttcaagc acatcacgagt acatcacggt    600
caaaccttcg atatccaaga attattcttc agattgaccg ttgattccgc caccgaattt    660
ttgttaggtg aatctgctga atccttgaga gatgaatctg ttggtttgac tccaactacc    720
aaggattttg atggtagaaa cgaatttgct gacgccttca attactccca aactaatcaa    780
gcctacagat tcttgttaca acaaatgtac tggattttga acgttccga atttagaaag    840
tccattgcca tcgttcataa gttcgctgat cactatgttc aaaaggcttt ggaattgacc    900
gacgaagatt tggaaaagaa agaaggttac gttttcttgt tcgaattggc caagcaaact    960
agagatccta aggttttgag agatcaatta ttgaacatct tggttgccgg tagagataca   1020
actgctggtt tgttgtcttt tttgttcttc gaattgtcca gaaaccctga aattttcgcc   1080
aagttgagag aagaaatcga aaacaagttt ggtttgggtc aagatgccag agttgaagaa   1140
atctcttttcg aaaccttgaa gtcctgcgaa tacttgaagg ctgttatcaa cgaaactttg   1200
agaatctacc catccgttcc acataatttc agagttgcta ctagaaacac taccttgcca   1260
agaggtggtg gtgaaggtgg tttatctcca attgctatta agaaaggtca agtcgtcatg   1320
tacactatct tggctactca tagagataag gacatctatg gtgaagatgc ctacgttttt   1380
agaccagaaa gatggtttga accagaaacc agaaaattgg gttgggctta tgttcctttt   1440
aatggtggtc ctagaatttg cttgggtcaa caatttgctt tgactgaagc ctcttacgtt   1500
accgtcagat tattgcaaga atttggtaac ttgaagcaag cccaaacac tgaatatcca   1560
ccaaagttgc aaaacacctt gaccttgtca ttattcgaag gtgctgaagt tcaaatgtat   1620
ttgatcttgt aa                                                       1632
```

*Candida tropicalis*

SEQ ID NO: 51
```
atgatcgaac aattattgga ataactggtac gttgttgtcc cagtcttgta catcatcaag    60
caattattag cttacaccaa gaccagagtc ttgatgaaga aattgggtgc tgctccagtt   120
acaaacaagt tgtacgataa tgctttcggt atcgttaatg gttggaaagc cttgcaattc   180
aagaaagaag gtagagccca agaatacaac gattacaagt ttgaccattc caagaacca   240
tctgttggta cttacgtttc tatcttgttc ggtactagaa tcgttgttac taaggaccca   300
gaaaacatta aggctatttt ggctactcaa ttcggtgact tttcattggg taagagacat   360
actttgttca agcctttgtt gggtgatggt attttcactt ggatggtga aggttggaaa    420
cattccagag ctatgttaag accacaattc gctagagaaa aagttgccca tgtttacatct    480
ttggaaccac acttccaatt attgaagaag cacatcttga agcacaaggg tgaatacttc    540
gatatccaag aattattctt cagattcacc gttgattccg ccaccgaatt tttgtttggt    600
gaatcagttc actccttgaa ggatgaatcc atcggtatca atcaagatga tattgatttc    660
gccggtagaa aggatttcgc tgaatctttt aacaaggcc agaatactt ggccattaga    720
actttggttc aaaccttcta ctggttggtc aacaacaaag aatttagaga ctgcaccaag    780
tccgttcata agttcactaa ttactacgtc caaaaggctt tggatgcttc tccagaagaa   840
ttggaaaaac aatccggtta cgtttttcttg tacgaattgg ttaagcaaac cagagatcca    900
aacgtcctga gagatcaatc cttgaacatt ttgttggctg gtagagatac aactgctggt    960
ttgttgtctt ttgccgtttt tgaattggct agacatccag aaatttggcc caagttgaga   1020
gaagaaatcg aacaacaatt tggtttgggt gaagattcca gagttgaaga aatcaccttc   1080
gaatctttga gagatgcgaa atacttgaag gccttttgga acgaaacctt gagaatctat   1140
ccatccgttc caagaaactt cagaattgct actaagaaca ctaccttgcc aagaggtggt   1200
ggttctgatg gtacttctcc aatttttgatt caaaagggtg aagccgtttc ctacggtatt   1260
```

TABLE 4-continued

Sequences disclosed herein.

```
aactctactc acttagatcc agtttactac ggtccagatg ctgctgaatt tagaccagaa   1320
agatggtttg aaccttccac taagaaatta ggttgggctt acttgccttt taatggtggt   1380
cctagaattt gcttgggtca acaattcgca ttgactgaag ctggttatgt tttggttaga   1440
ttggttcaag aattttccca cgttagatcc gatccagatg aagtttatcc accaaagaga   1500
ttgactaact tgaccatgtg tttacaagat ggtgccatcg ttaagttcga ctaa         1554
```

*Candida tropicalis*

SEQ ID NO: 52

```
atggccttgg acaagttgga cttgtacgtt attatcacct tggttgttgc tattgctgct    60
tacttcgcta agaatcaatt cttggatcaa caacaagaca ctggtttctt gaacactgat   120
tctggtgatg gtaactccag agatatttct caagccttga agaagaacaa caaaaacact   180
ttgttgttgt tcggttccca aactggtact gctgaagatt atgctaacaa gttgtccaga   240
gaattgcact ctagattcgg tttgaaaact atggttgctg atttcgccga ttacgacttt   300
gaaaatttcg gtgacattac cgaagatatt ttggttttct tcatcgttgc tacctacggt   360
gaaggtgaac ctactgataa tgctgatgaa tttcatacct ggttgaccga agaagctgat   420
actttgtcta ctttgaagta caccgttttc ggtttgggta actctaccta cgaattttc    480
aacgccattg gtagaaagtt cgatagatta ttgggtgaaa agggtggtga tagatttgct   540
gaatatggtg aaggtgatga tggtactggt actttggatg aagatttttt ggcttggaag   600
gacaacgttt tcgactcttt gaagaacgac ttgaacttcg aagaaaaaga attgaagtac   660
gaacctaacg tcaagttgac tgaaagagat gatttgtctg gtaacgatcc agatgttcc    720
ttgggtgaac ctaatgttaa gtacatcaag tccgaaggtg ttgatttgac taagggtcca   780
tttgatcata cccatccatt tttggctaga atcgtcaaga ccaaagaatt attcacctcc   840
gaagatagac attgcgttca cgttgaattt gacatctccg aatctaactt gaagtatacc   900
actggtgatc atttggctat ttggccatct aattctgacg aaaacattaa gcaattcgcc   960
aagtgctttg gttggaaga taagttggat accgtcattg aattgaaggc tttggattcc  1020
acttactcca ttccatttcc aaacccaatt acttacggtg ccgttatcag acatcatttg  1080
gaaatttctg gtccagtctc cagacaattc ttcttgtcta ttgctggttt tgccccagac  1140
gaagaaacta agaaatcctt cactagaatt ggtggtgaca acaagaatt tgcctctaag   1200
gttaccagaa gaaagttcaa cattgctgat gccttgttgt ttgcctcaaa caatagacct  1260
tggtctgatg tcccattcga attttttgatt gaaaacgtcc aacacttgac cccaagatat  1320
tactctatct cctcttcctc attgtccgaa aagcaaacta ttaacgttac cgctgttgtt  1380
gaagccgaag aagaagcaga cggtagacca gttactggta ttgttactaa tttgttgaag  1440
aacatcgaaa tcgaacaaaa caagactggt gaaaccccaa tggttcacta tgattttgaat  1500
ggtccaagag gtaagttctc caagtttaga ttgccagttc acgtcagaag atccaatttc  1560
aaaattgccaa agaactctac caccccagtt attttgattg gtccaggtac aggtgttgct  1620
ccattgagag gttttgttag agaaagagtt caacaagtca agaacggtgt taacgttggt  1680
aagaccgttt tgttttacgg ttgcagaaac tccgaacaag acttcttgta taagcaagaa  1740
tggtccgaat acgcttccgt tttaggtgaa aacttcgaaa tgttcaacgc cttctctaga  1800
caagatccta ctaagaaggt ttacgtccaa gacaagattt tggaaaactc cgctttggtt  1860
gacgaattat tgtcatctgg tgccattatc tacgtttgtg gtgatgcttc tagaatggct  1920
agagatgttc aagctgctat tgcaaaaatt gtcgccaagt ctagagatat ccatgaagat  1980
aaggctgccg aattggttaa gtcttggaag gttcaaaaca gataccaaga agatgtctgg  2040
taa                                                                2043
```

---

What is claimed is:

1. A recombinant *Saccharomyces cerevisiae* producing one or more macrocyclic ketone precursors, comprising:
   (a) a polynucleotide encoding a polypeptide having at least 95% sequence identity to SEQ ID NO: 34 or SEQ ID NO: 35 capable of synthesizing 3-methyl oxopentanoate from L-isoleucine;
   (b) a polynucleotide encoding a polypeptide having at least 95% sequence identity to SEQ ID NO: 36 capable of synthesizing (S)-2-methylbutanal from 3-methyl-2-oxopentanoate;
   (c) a polynucleotide encoding a polypeptide having at least 95% sequence identity to SEQ ID NO: 37 or SEQ ID NO: 38 capable of synthesizing (S)-2-methylbutyric acid from (S)-2-methylbutanal;
   (d) a polynucleotide encoding a polypeptide having at least 95% sequence identity to SEQ ID NO: 23 or SEQ ID NO: 24 capable of synthesizing (S)-2-methylbutyryl-CoA from (S)-2-methylbutyric acid;
   (e) a polynucleotide encoding a polypeptide having at least 95% sequence identity to SEQ ID NO:25 capable of synthesizing 14- methylhexadecanoic acid from (S)-2-methylbutyryl-CoA; and
   (f) a polynucleotide encoding a polypeptide having at least 95% sequence identity to SEQ ID NO: 21 capable of synthesizing a 3-methylhexadecanedioic acid from 14-methylhexadecanoic acid;
   wherein at least one of the polynucleotides (a)-(f) is a recombinant polynucleotide, and
   wherein the one or more macrocyclic ketone precursors comprises 3-methylhexadecanedioic acid, 14-methylhexadecanoic acid, or a combination thereof.

2. The recombinant *Saccharomyces cerevisiae* of claim 1, wherein the (S)-2-methylbutyric acid has an optical purity of at least 80% ee.

3. The recombinant *Saccharomyces cerevisiae* of claim 1, wherein:
   (a) the polypeptide capable of synthesizing 3-methyl-2-oxopentanoate from L-isoleucine comprises a polypeptide having at least 99% sequence identity to any one of the amino acid sequences of SEQ ID NOs: 34 or 35;
   (b) the polypeptide capable of synthesizing (S)-2-methylbutanal from 3-methyl-2-oxopentanoate comprises a polypeptide having at least 99% sequence identity to the amino acid sequence of SEQ ID NO: 36;
   (c) the polypeptide capable of synthesizing (S)-2-methylbutyric acid from (S)-2-methylbutanal comprises a polypeptide having at least 99% sequence identity to any one of the amino acid sequences of SEQ ID NOs: 37 or 38;
   (d) the polypeptide capable of synthesizing (S)-2-methylbutyryl-CoA from (S)-2-methylbutyric acid comprises a polypeptide having at least 99% sequence identity to any one of the amino acid sequences of SEQ ID NOs: 23 or 24;

(e) the polypeptide capable of synthesizing the 14-methylhexadecanoic acid from (S)-2-methylbutyryl-CoA comprises a polypeptide having at least 99% sequence identity to the amino acid sequences of SEQ ID NO: 25; and (f) the polypeptide capable of synthesizing the 3-methylhexadecanedioic acid from the 14-methylhexadecanoic acid comprises a polypeptide having at least 99% sequence identity to the amino acid sequence of SEQ ID NO: 21.

4. The recombinant *Saccharomyces cerevisiae* of claim 1, wherein the one or more macrocyclic ketone precursor is 14-methylhexadecanoic acid, (S)-14-methylhexadecanoic acid, or 3-methylhexadecanedioic acid.

5. A method of producing the one or more macrocyclic ketone precursors, in a cell culture, comprising culturing the recombinant *Saccharomyces cerevisiae* of claim 1 in the cell culture, under conditions in which the polynucleotides encoding the polypeptides are expressed;
wherein the one or more macrocyclic ketone precursors is produced by the recombinant *Saccharomyces cerevisiae*, and
wherein the one or more macrocyclic ketone precursors comprises 3-methylhexadecanedioic acid, 14-methylhexadecanoic acid, or a combination thereof.

6. The method of claim 5, wherein the polynucleotides encoding the polypeptides are constitutively expressed or wherein expression of the polynucleotides encoding the polypeptides is induced.

7. The method of claim 5, wherein the recombinant *Saccharomyces cerevisiae* is grown in a fermentor at a temperature for a period of time, wherein the temperature and the period of time facilitate the production of the one or more macrocyclic ketone precursors.

8. A method of producing the one or more macrocyclic ketone precursors comprising whole cell bioconversion of a plant-derived or synthetic L-isoleucine, 3-methyl-2-oxopentanoate, (S)-2-methylbutanal, (S)-2-methylbutyric acid, (S)-2-methylbutyryl-CoA, 14-methylhexadecanoic acid, or 3-methylhexadecanedioic acid in a cell culture of the recombinant Saccharomyces cerevisiae of claim 1 using:
(a) the polypeptide capable of synthesizing 3-methyl-2-oxopentanoate from L-isoleucine, comprising a polypeptide having at least 95% sequence identity to any one of the amino acid sequences of SEQ ID NOs: 34 or 35;
(b) the polypeptide capable of synthesizing (S)-2-methylbutanal from 3-methyl oxopentanoate, comprising a polypeptide having at least 95% sequence identity to amino acid sequence of SEQ ID NO: 36;
(c) the polypeptide capable of synthesizing (S)-2-methylbutyric acid from (S)-2-methylbutanal; comprising a polypeptide having at least 95% sequence identity to any one of the amino acid sequences of SEQ ID NO: 37 or 38;
(d) the polypeptide capable of synthesizing (S)-2-methylbutyryl-CoA from (S)-2-methylbutyric acid, comprising a polypeptide having at least 95% sequence identity to any one of the amino acid sequences of SEQ ID NOs: 23 or 24;
(e) the polypeptide capable of synthesizing 14-methylhexadecanoic acid from (S)-2-methylbutyryl-CoA, comprising a polypeptide having at least 95% sequence identity to amino acid sequence of SEQ ID NO: 25; and
(f) the polypeptide having at least 95% sequence identity to SEQ ID NO: 21 capable of synthesizing -3-methylhexadecanedioic acid from 14-methylhexadecanoic acid; comprising a polypeptide having at least 95% sequence identity to amino acid sequence of SEQ ID NO: 21;
wherein at least one of the polypeptides (a)-(f) is a recombinant polypeptide, and
wherein the one or more macrocyclic ketone precursors comprises 3-methylhexadecanedioic acid, 14-methylhexadecanoic acid, or a combination thereof.

9. The method of claim 8, wherein the one or more macrocyclic ketone precursors is produced in the recombinant *Saccharomyces cerevisiae*, wherein the recombinant *Saccharomyces cerevisiae* is permeabilized and transformed with:
(a) the polynucleotide encoding the polypeptide capable of synthesizing 3-methyl-2-oxopentanoate from L-isoleucine;
wherein the polypeptide comprises a polypeptide having at least 95% sequence identity to any one of the amino acid sequences of SEQ ID NOs: 34 or 35;
(b) the polynucleotide encoding the polypeptide capable of synthesizing (S)-2-methylbutanal from 3-methyl-2-oxopentanoate;
wherein the polypeptide comprises a polypeptide having at least 95% sequence identity to the amino acid sequence of SEQ ID NO: 36;
(c) the polynucleotide encoding the polypeptide capable of synthesizing (S)-2-methylbutyric acid from (S)-2-methylbutanal;
wherein the polypeptide comprises a polypeptide having at least 95% sequence identity to any one of the amino acid sequences of SEQ ID NOs: 37 or 38;
(d) the polynucleotide encoding the polypeptide capable of synthesizing (S)-2-methylbutyryl-CoA from (S)-2-methylbutyric acid;
wherein the polypeptide comprises a polypeptide having at least 95% sequence identity to any one of the amino acid sequences of SEQ ID NOs: 23 or 24;
(e) the polynucleotide encoding the polypeptide capable of synthesizing 14-methylhexadecanoic acid from (S)-2-methylbutyryl-CoA;
wherein the polypeptide comprises a polypeptide having at least 95% sequence identity to the amino acid sequences of SEQ ID NO: 25; and
(f) the polynucleotide encoding the polypeptide capable of synthesizing 3-methylhexadecanedioic acid from 14-methylhexadecanoic acid;
wherein the polypeptide comprises a polypeptide having at least 95% sequence identity to the amino acid sequences of SEQ ID NO: 21.

10. The method of claim 5, wherein the cell culture comprises:
(a) the one or more macrocyclic ketone precursors produced by the recombinant *Saccharomyces cerevisiae* bioconversion of a plant-derived or synthetic L-isoleucine, 3-methyl-2-oxopentanoate, (S)-2-methylbutanal, (S)-2-methylbutyric acid, (S)-2-methylbutyryl-CoA, 14-methylhexadecanoic, or 3-methylhexadecanedioic acid; and
(b) supplemental nutrients comprising trace metals, vitamins, salts, yeast nitrogen base (YNB), and/or amino acids.

11. The method of claim 8, wherein the (S)-2-methylbutyric acid has an optical purity of at least 80% ee.

12. The method of claim 5, further comprising isolating the one or more macrocyclic ketone precursors.

13. The method of claim 12, wherein isolating the one or more macrocyclic ketone precursors comprises (a) separating a liquid phase of the cell culture from a solid phase of the cell culture to obtain a supernatant comprising the produced one or more macrocyclic ketone precursors, and:
  (a) contacting the supernatant with one or more adsorbent resins to obtain at least a portion of the produced one or more macrocyclic ketone precursors; or
  (b) contacting the supernatant with one or more ion exchange or reverse-phase chromatography columns to obtain at least a portion of the produced one or more macrocyclic ketone precursors; or
  (c) crystallizing or extracting the produced one or more macrocyclic ketone precursors;
thereby isolating the produced one or more macrocyclic ketone precursors.

14. The method of claim 5, further comprising recovering the one or more macrocyclic ketone precursors from the cell culture.

15. An in vitro method for producing a one or more macrocyclic ketone precursors comprising adding to a reaction mixture:
  (a) a polypeptide having at least 95% sequence identity to SEQ ID NO: 34 or SEQ ID NO: 35 capable of synthesizing 3-methyl-2-oxopentanoate from L-isoleucine;
  (b) a polypeptide having at least 95% sequence identity to SEQ ID NO: 36 capable of synthesizing (S)-2-methylbutanal from 3-methyl-2-oxopentanoate;
  (c) a polypeptide having at least 95% sequence identity to SEQ ID NO: 37 or SEQ ID NO: 38 capable of synthesizing (S)-2-methylbutyric acid from (S)-2-methylbutanal;
  (d) a polypeptide having at least 95% sequence identity to SEQ ID NO: 23 or SEQ ID NO: 24 capable of synthesizing (S)-2-methylbutyryl-CoA from (S)-2-methylbutyric acid;
  (e) a polypeptide having at least 95% sequence identity to SEQ ID NO: 25 capable of synthesizing 14-methylhexadecanoic acid from (S)-2-methylbutyryl-CoA;
  (f) a polypeptide having at least 95% sequence identity to SEQ ID NO: 21 capable of synthesizing 3-methylhexadecanedioic acid from 14-methylhexadecanoic acid; and
  a plant-derived or synthetic L-isoleucine, 3-methyl-2-oxopentanoate, (S)-2-methylbutanal, (S)-2-methylbutyric acid, (S)-2-methylbutyryl-CoA, 14-methylhexadecanoic acid, or 3-methylhexadecanedioic acid;
  wherein at least one of the polypeptides (a)-(f) is a recombinant polypeptide, and
  wherein the one or more macrocyclic ketone precursors comprises 3-methylhexadecanedioic acid, 14-methylhexadecanoic acid, or a combination thereof.

16. The method of claim 5, wherein the one or more macrocyclic ketone precursor is 14-methylhexadecanoic acid, (S)-14-methylhexadecanoic acid, or 3-methylhexadecanedioic acid.

17. A cell culture comprising:
  (i) the recombinant Saccharomyces cerevisiae of claim 1;
  (ii) the one or more macrocyclic ketone precursors and/or one or more macrocyclic ketones synthesized from the one or more macrocyclic ketone precursors, said one or more macrocyclic ketone precursors and the one or more macrocyclic ketones being produced by the recombinant Saccharomyces cerevisiae; and
  (iii) nutrients comprising trace metals, vitamins, salts, yeast nitrogen base (YNB), and/or amino acids;
  wherein the one or more macrocyclic ketone precursors and/or the one or more macrocyclic ketones are present at a concentration of at least 1 mg/liter of the cell culture.

18. A Saccharomyces cerevisiae cell culture lysate of the cell culture of claim 17.

19. A combination of nucleic acid molecules, each nucleic acid molecule encoding:
  (a) a polypeptide capable of synthesizing 3-methyl-2-oxopentanoate from L-isoleucine and having at least 95% sequence identity to any one of the amino acid sequences of SEQ ID NOs:34 or 35;
  (b) a polypeptide capable of synthesizing (S)-2-methylbutanal from 3-methyl-2-oxopentanoate and having at least 95% sequence identity to the amino acid sequence of SEQ ID NO:36;
  (c) a polypeptide capable of synthesizing (S)-2-methylbutyric acid from (S)-2-methylbutanal and having at least 95% sequence identity to any one of the amino acid sequences of SEQ ID NOs:37 or 38;
  (d) a polypeptide capable of synthesizing (S)-2-methylbutyryl-CoA from (S)-2-methylbutyric acid and having at least 95% sequence identity to any one of the amino acid sequences of SEQ ID NOs:23 or 24;
  (e) a polypeptide capable of synthesizing a 14-methylhexadecanoic acid from (S)-2-methylbutyryl-CoA and having at least 95% sequence identity to the amino acid sequence of SEQ ID NO:25; and
  (f) a polypeptide capable of synthesizing a 3-methylhexadecanedioic acid from the 14-methylhexadecanoic acid and having at least 95% sequence identity to the amino acid sequence of SEQ ID NO: 21.

20. The nucleic acid molecule of claim 19, wherein the nucleic acid molecule is cDNA.

21. A recombinant Saccharomyces cerevisiae producing one or more macrocyclic ketone precursors, comprising:
  (a) a polynucleotide encoding a polypeptide comprising a sequence of SEQ ID NO: 34 or SEQ ID NO: 35 capable of synthesizing 3-methyl-2-oxopentanoate from L-isoleucine;
  (b) a polynucleotide encoding a polypeptide comprising a sequence of SEQ ID NO: 36 capable of synthesizing (S)-2-methylbutanal from 3-methyl-2-oxopentanoate;
  (c) a polynucleotide encoding a polypeptide comprising a sequence of SEQ ID NO: 37 or SEQ ID NO: 38 capable of synthesizing (S)-2-methylbutyric acid from (S)-2-methylbutanal;
  (d) a polynucleotide encoding a polypeptide comprising a sequence of SEQ ID NO:23 or SEQ ID NO:24 capable of synthesizing (S)-2-methylbutyryl-CoA from (S)-2-methylbutyric acid;
  (e) a polynucleotide encoding a polypeptide comprising a sequence of SEQ ID NO:25 capable of synthesizing 14-methylhexadecanoic acid from (S)-2-methylbutyryl-CoA; and
  (f) a polynucleotide encoding a polypeptide comprising a sequence of SEQ ID NO: 21 capable of synthesizing 3-methylhexadecanedioic acid from 14-methylhexadecanoic acid;
  wherein at least one of the polynucleotides (a)-(f) is a recombinant polynucleotides, and
  wherein the one or more macrocyclic ketone precursors comprises 3-methylhexadecanedioic acid, 14-methylhexadecanoic acid, or a combination thereof.

22. The recombinant Saccharomyces cerevisiae of claim 1, further comprising:

(g) a polynucleotide encoding a polypeptide having at least 95% sequence identity to SEQ ID NO: 33 capable of synthesizing hexadecanedioic acid-CoA from hexadecanedioic acid.

23. The recombinant *Saccharomyces cerevisiae* of claim 3, further comprising:
(g) a polynucleotide encoding a polypeptide having at least 99% sequence identity to SEQ ID NO: 33 capable of synthesizing hexadecanedioic acid-CoA from hexadecanedioic acid.

24. The combination of nucleic acid molecules according to claim 19, further comprising a nucleic acid molecule encoding:
(g) a polypeptide capable of synthesizing hexadecanedioic acid-CoA from hexadecanedioic acid and having at least 95% sequence identity to the amino acid sequence of SEQ ID NO: 33.

25. The combination of nucleic acid molecules according to claim 21, further comprising a nucleic acid molecule encoding:
(g) a polypeptide capable of synthesizing hexadecanedioic acid-CoA from hexadecanedioic acid and comprising the amino acid sequence of SEQ ID NO: 33.

* * * * *